(12) United States Patent
Stavenhagen et al.

(10) Patent No.: US 11,787,871 B2
(45) Date of Patent: *Oct. 17, 2023

(54) METHODS FOR THE TREATMENT OF DISEASE USING IMMUNOGLOBULINS HAVING FC REGIONS WITH ALTERED AFFINITIES FOR FCGAMMARACTIVATING AND FEGAMMARINHIBITING

(71) Applicant: MacroGenics, Inc., Rockville, MD (US)

(72) Inventors: Jeffrey B. Stavenhagen, Rockville, MD (US); Scott Koenig, Rockville, MD (US)

(73) Assignee: MacroGenics, Inc., Rockville, MD (US)

( * ) Notice: Subject to any disclaimer, the term of this patent is extended or adjusted under 35 U.S.C. 154(b) by 646 days.

This patent is subject to a terminal disclaimer.

(21) Appl. No.: 16/886,964

(22) Filed: May 29, 2020

(65) Prior Publication Data
US 2020/0392245 A1    Dec. 17, 2020

Related U.S. Application Data

(63) Continuation of application No. 15/621,710, filed on Jun. 13, 2017, now Pat. No. 10,711,069, which is a continuation of application No. 14/156,747, filed on Jan. 16, 2014, now Pat. No. 9,708,408, which is a continuation of application No. 11/952,568, filed on Dec. 7, 2007, now Pat. No. 8,652,466.

(60) Provisional application No. 60/869,254, filed on Dec. 8, 2006.

(51) Int. Cl.
| | | |
|---|---|---|
| C07H 21/02 | (2006.01) |
| C07H 21/04 | (2006.01) |
| C12P 21/06 | (2006.01) |
| C12P 21/04 | (2006.01) |
| C12N 5/02 | (2006.01) |
| C12N 1/20 | (2006.01) |
| C12N 15/00 | (2006.01) |
| C07K 16/30 | (2006.01) |
| C07K 16/28 | (2006.01) |
| C07K 16/00 | (2006.01) |
| A61K 39/00 | (2006.01) |

(52) U.S. Cl.
CPC .......... *C07K 16/30* (2013.01); *C07K 16/2887* (2013.01); *A61K 2039/505* (2013.01); *C07K 2317/71* (2013.01); *C07K 2317/72* (2013.01); *C07K 2317/732* (2013.01); *C07K 2317/734* (2013.01)

(58) Field of Classification Search
None
See application file for complete search history.

(56) References Cited

U.S. PATENT DOCUMENTS

| | | |
|---|---|---|
| 4,179,337 A | 12/1979 | Davis et al. |
| 4,752,601 A | 6/1988 | Hahn |
| 5,024,835 A | 6/1991 | Rao et al. |
| 5,225,539 A | 12/1993 | Winter |
| 5,348,876 A | 9/1994 | Michaelson et al. |
| 5,576,184 A | 11/1996 | Better et al. |
| 5,585,089 A | 12/1996 | Queen et al. |
| 5,624,821 A | 4/1997 | Winter et al. |
| 5,648,260 A | 7/1997 | Winter et al. |
| 5,693,761 A | 12/1997 | Queen et al. |
| 5,693,762 A | 12/1997 | Queen et al. |
| 5,698,449 A | 12/1997 | Baumann et al. |
| 5,711,944 A | 1/1998 | Gilbert et al. |
| 5,723,584 A | 3/1998 | Schatz |
| 5,736,135 A | 4/1998 | Goeddel et al. |

(Continued)

FOREIGN PATENT DOCUMENTS

| | | |
|---|---|---|
| EP | 0 327 378 | 8/1989 |
| EP | 0 332 865 | 9/1989 |

(Continued)

OTHER PUBLICATIONS

US 6,331,391 B1, 12/2001, Wittrup et al. (withdrawn)

(Continued)

*Primary Examiner* — Chun W Dahle

(74) *Attorney, Agent, or Firm* — MEDLER, FERRO, WOODHOUSE & MILLS PLLC

(57) ABSTRACT

The present invention relates to methods of treating or preventing cancer and other diseases using molecules, particularly polypeptides, more particularly immunoglobulins (e.g., antibodies), comprising a variant Fc region, wherein said variant Fc region comprises at least one amino acid modification relative to a wild-type Fc region, which variant Fc region binds an FcγR that activates a cellular effector ("FcγR$_{Activating}$," such as FcγRIIA or FcγRIIIA) and an FcγR that inhibits a cellular effector ("FcγR$_{Inhibiting}$," such as FcγRIIA) with an altered Ratio of Affinities relative to the respective binding affinities of such FcγR for the Fc region of the wild-type immunoglobulin. The methods of the invention are particularly useful in preventing, treating, or ameliorating one or more symptoms associated with a disease, disorder, or infection where either an enhanced efficacy of effector cell function mediated by FcγR is desired (e.g., cancer, infectious disease) or an inhibited effector cell response mediated by FcγR is desired (e.g., inflammation, autoimmune disease).

20 Claims, 55 Drawing Sheets

Figure 1:
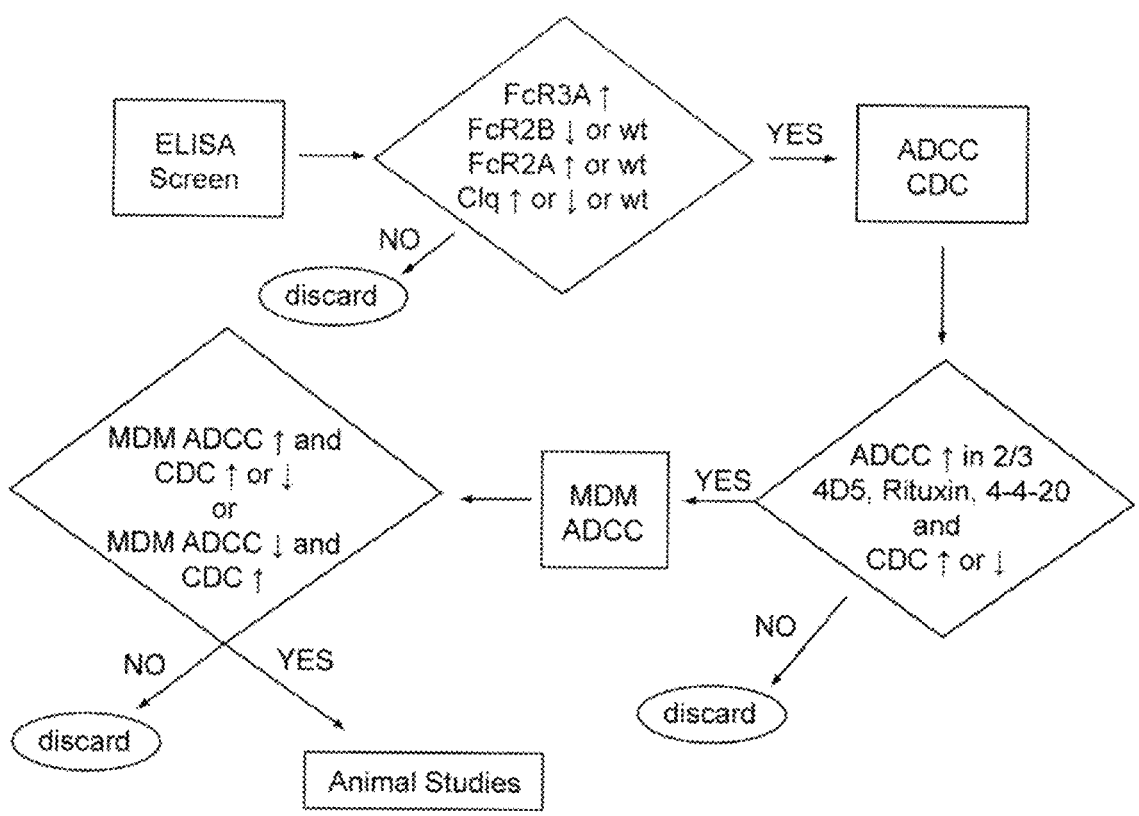

Specification includes a Sequence Listing.

(56) References Cited

U.S. PATENT DOCUMENTS

| | | |
|---|---|---|
| 5,736,137 A | 4/1998 | Anderson et al. |
| 5,837,243 A | 11/1998 | Deo et al. |
| 5,874,239 A | 2/1999 | Schatz |
| 5,877,396 A | 3/1999 | Ravetch et al. |
| 5,888,533 A | 3/1999 | Dunn |
| 5,945,115 A | 3/1999 | Dunn et al. |
| 5,932,433 A | 8/1999 | Schatz |
| 5,985,599 A | 11/1999 | Mckenzie et al. |
| 6,019,968 A | 2/2000 | Platz et al. |
| 6,025,485 A | 2/2000 | Kamb et al. |
| 6,114,147 A | 9/2000 | Frenken et al. |
| 6,132,764 A | 10/2000 | Li et al. |
| 6,132,992 A | 10/2000 | Ledbetter et al. |
| 6,165,745 A | 12/2000 | Ward et al. |
| 6,180,370 B1 | 1/2001 | Queen et al. |
| 6,194,551 B1 | 2/2001 | Idusogie et al. |
| 6,218,149 B1 | 4/2001 | Morrison et al. |
| 6,242,195 B1 | 6/2001 | Idusogie et al. |
| 6,277,375 B1 | 8/2001 | Ward |
| 6,300,065 B1 | 10/2001 | Kieke et al. |
| 6,339,069 B1 | 1/2002 | Meers et al. |
| 6,420,149 B1 | 7/2002 | Fukuda et al. |
| 6,423,538 B1 | 7/2002 | Wittrup et al. |
| 6,455,263 B2 | 9/2002 | Payan |
| 6,472,511 B1 | 10/2002 | Leung et al. |
| 6,528,624 B1 | 3/2003 | Idusogie et al. |
| 6,538,124 B1 | 3/2003 | Idusogie et al. |
| 6,548,640 B1 | 4/2003 | Winter |
| 6,696,550 B2 | 2/2004 | Larosa et al. |
| 6,737,056 B1 | 5/2004 | Presta |
| 6,821,505 B2 | 11/2004 | Ward |
| 6,982,321 B2 | 1/2006 | Winter |
| 7,315,786 B2 | 1/2008 | Dahiyat et al. |
| 7,317,091 B2 | 1/2008 | Lazar et al. |
| 7,355,008 B2 | 4/2008 | Stavenhagen et al. |
| 7,425,619 B2 | 9/2008 | Koenig et al. |
| 7,425,620 B2 | 9/2008 | Koenig et al. |
| 7,632,497 B2 | 12/2009 | Stavenhagen |
| 7,655,229 B2 | 2/2010 | Chan et al. |
| 7,662,925 B2 | 2/2010 | Lazar |
| 7,662,926 B2 | 2/2010 | Chan et al. |
| 7,786,270 B2 | 8/2010 | Johnson et al. |
| 8,652,466 B2 | 2/2014 | Stavenhagen et al. |
| 9,708,408 B2 * | 7/2017 | Stavenhagen et al. |
| 10,711,069 B2 * | 7/2020 | Stavenhagen ......... C07K 16/30 |
| 2001/0036459 A1 | 11/2001 | Ravetch |
| 2002/0004587 A1 | 1/2002 | Miller et al. |
| 2002/0028486 A1 | 3/2002 | Morrison et al. |
| 2003/0077282 A1 | 4/2003 | Bigler et al. |
| 2003/0115614 A1 | 6/2003 | Kanda et al. |
| 2003/0158389 A1 | 8/2003 | Idusogie et al. |
| 2003/0190319 A1 | 10/2003 | Adolf et al. |
| 2003/0207346 A1 | 11/2003 | Arathoon et al. |
| 2004/0002587 A1 | 1/2004 | Watkins et al. |
| 2004/0110226 A1 | 6/2004 | Lazar et al. |
| 2004/0132101 A1 | 7/2004 | Lazar et al. |
| 2004/0185045 A1 | 9/2004 | Koenig et al. |
| 2004/0191244 A1 | 9/2004 | Presta |
| 2004/0220388 A1 | 11/2004 | Mertens et al. |
| 2004/0235065 A1 | 11/2004 | Hansen et al. |
| 2004/0236078 A1 | 11/2004 | Carter et al. |
| 2005/0025764 A1 | 2/2005 | Watkins et al. |
| 2005/0037000 A1 | 2/2005 | Stavenhagen et al. |
| 2005/0054832 A1 | 3/2005 | Lazar et al. |
| 2005/0064514 A1 | 3/2005 | Stavenhagen et al. |
| 2005/0090648 A1 | 4/2005 | Tsurushita et al. |
| 2005/0215767 A1 | 9/2005 | Koenig et al. |
| 2005/0260213 A1 | 11/2005 | Koenig et al. |
| 2006/0013810 A1 | 1/2006 | Johnson et al. |
| 2006/0018899 A1 | 1/2006 | Kao et al. |
| 2006/0024298 A1 | 2/2006 | Lazar et al. |
| 2006/0073142 A1 | 4/2006 | Chan et al. |
| 2006/0134709 A1 | 6/2006 | Stavenhagen et al. |
| 2006/0177439 A1 | 8/2006 | Koenig et al. |
| 2007/0004909 A1 | 1/2007 | Johnson et al. |
| 2007/0036799 A1 | 2/2007 | Stavenhagen et al. |
| 2007/0253948 A1 | 11/2007 | Chan et al. |
| 2008/0044417 A1 | 2/2008 | Johnson et al. |
| 2008/0051563 A1 | 2/2008 | Lazar et al. |
| 2008/0131435 A1 | 6/2008 | Stavenhagen et al. |
| 2008/0138344 A1 | 6/2008 | Stavenhagen et al. |
| 2008/0138349 A1 | 6/2008 | Stavenhagen et al. |
| 2008/0286819 A1 | 11/2008 | Ravetch et al. |
| 2009/0053218 A1 | 2/2009 | Koenig et al. |
| 2009/0098124 A1 | 4/2009 | Stavenhagen et al. |

FOREIGN PATENT DOCUMENTS

| | | |
|---|---|---|
| EP | 0 629 703 | 12/1994 |
| EP | 0 359 096 | 11/1997 |
| EP | 0 953 639 | 11/1999 |
| EP | 1 006 183 | 6/2000 |
| EP | 0 343 950 | 10/2000 |
| WO | WO 1988/007089 | 9/1988 |
| WO | WO 1989/007142 | 8/1989 |
| WO | WO 1992/016562 | 10/1992 |
| WO | WO 1993/022332 | 11/1993 |
| WO | WO 1994/018330 | 8/1994 |
| WO | WO 1994/029351 | 12/1994 |
| WO | WO 1995/005468 | 2/1995 |
| WO | WO 1997/028267 | 8/1997 |
| WO | WO 1997/034631 | 9/1997 |
| WO | WO 1997/044362 | 11/1997 |
| WO | WO 1998/005787 | 2/1998 |
| WO | WO 1998/023289 | 6/1998 |
| WO | WO 1998/052975 | 11/1998 |
| WO | WO 1999/019362 | 4/1999 |
| WO | WO 1999/041285 | 8/1999 |
| WO | WO 1999/043713 | 9/1999 |
| WO | WO 1999/051642 | 10/1999 |
| WO | WO 1999/058572 | 11/1999 |
| WO | WO 2000/009560 | 2/2000 |
| WO | WO 2000/042072 | 7/2000 |
| WO | WO 2001/079299 | 10/2001 |
| WO | WO 2002/002781 | 1/2002 |
| WO | WO 2002/060919 | 8/2002 |
| WO | WO 2002/086070 | 10/2002 |
| WO | WO 2003/035835 | 5/2003 |
| WO | WO 2003/066095 | 8/2003 |
| WO | WO 2003/074679 | 9/2003 |
| WO | WO 2004/016750 | 2/2004 |
| WO | WO 2004/029207 | 4/2004 |
| WO | WO 2004/063351 | 7/2004 |
| WO | WO 2004/065423 | 8/2004 |
| WO | WO 2004/074455 | 9/2004 |
| WO | WO 2004/099249 | 11/2004 |
| WO | WO 2008/009545 | 1/2005 |
| WO | WO 2005/018669 | 3/2005 |
| WO | WO 2005/070963 | 8/2005 |
| WO | WO 2005/110474 | 11/2005 |
| WO | WO 2005/115452 | 12/2005 |
| WO | WO 2006/020114 | 2/2006 |
| WO | WO 2006/028956 | 3/2006 |
| WO | WO 2006/066078 | 6/2006 |
| WO | WO 2006/088494 | 8/2006 |
| WO | WO 2006/113665 | 10/2006 |
| WO | WO 2007/021841 | 2/2007 |
| WO | WO 2007/024249 | 3/2007 |
| WO | WO 2007/106707 | 9/2007 |
| WO | WO 2008/002933 | 1/2008 |
| WO | WO 2008/019199 | 2/2008 |
| WO | WO 2009/083009 | 7/2009 |
| WO | WO 2009/151717 | 9/2009 |

OTHER PUBLICATIONS

Abra et al. The next generation of liposome delivery systems: recent experience with tumor-targeted, sterically-stabilized immunoliposomes and active-loading gradients. J Liposome Res. Feb.-May 2002;12(1-2):1-3.

Alt et al., "Novel Tetravalent and Bispecific IgG-Like Antibody Molecules Combining Single-Chain Diabodies With the Immunoglobin Gamma 1 Fc or CH3 Region," FEBS Letters 454: 90-94, 1999.

(56) References Cited

OTHER PUBLICATIONS

Altman et al., "Phenotypic Analysis of Antigen-Specific T Lymphocytes", Science 274:94-96, 1996.
Amit et al. (1986) Three-dimensional structure of an antigen-antibody complex at 2.8 A resolution.; Science 233:747-753.
Angal et al., "A single amino acid substitution abolishes the heterogeneity of chimeric mouse/human (IgG4) antibody," Mol Immunol 30 :105-108, 1993.
Armour et al., "Differential binding to human FcgammaRIIa and FcgammaRIIb receptors by human IgG wildtype and mutant antibodies," Mol Immunol 40 :585-593, 2003.
Armour et al., "Recombinant human IgG molecules lacking Fcgamma receptor I binding and monocyte triggering activities," Eur J Immunol 29:2613-2624, 1999.
Armour et al., "The contrasting IgG-binding interactions of human and herpes simplex virus Fc receptors," Biochemical Society Transactions 30:495-500, 2002.
Armstrong, S. et al. "Heterogeneity of IgG1 monoclonal anti-Rh(D): an investigation using ADCC and macrophage binding assays," Brit. J. Haematol. 66:257-262 (1987).
Bachmann et al. (2005) "Recall Proliferation of Memory CD8+ T Cells and Antiviral Protection," J. Immunol. 175:4677-4685.
Baggiolini M, Dewald B. "Cellular models for the detection and evaluation of drugs that modulate human phagocyte activity," Experientia. Oct. 15;44(10):841-848, 1988.
Bendas G, Immunoliposomes: a promising approach to targeting cancer therapy. BioDrugs. 2001;15(4):215-24.
Bendig, M.M. (1995) Methods: A Companion to Methods in Enzymology 8:83-93.
Bernard et al. (1986) "A unique epitope on the CD2 molecule defined by the monoclonal antibody 9-1: epitope-specific modulation of the E-rosette receptor and effects on T-cell functions," Hum. Immunol. 17(4):388-405.
Bewarder et al., 1996, "In vivo and in vitro specificity of protein tyrosine kinases for immunoglobulin G receptor (FcgammaRII) phosphorylation," Mol. Cell. Biol. 16 (9):4735-43.
Billadeau et al., ITAMs versus ITIMs: striking a balance during cell regulation, J Clin Invest. Jan. 2002;109(2):161-8.
Boder and Wittrup, "Optimal screening of surface-displayed polypeptide libraries," Biotechnol Prog 14:55-62, 1998.
Boder and Wittrup, "Yeast surface display for directed evolution of protein expression, affinity, and stability," Methods in Enzymology 328:430-444, 2000.
Boder and Wittrup, 1997, "Yeast surface display for screening combinatorial polypeptide libraries", Nature Biotechnology 15:553-557.
Boder et al., "Directed evolution of antibody fragments with monovalent femtomolar antigen-binding affinity," Proc. Natl. Acad. Sci. USA 97:10701-10705, 2000.
Bolland and Ravetch., Inhibitory pathways triggered by ITIM-containing receptors. Adv Immunol. 1999;72:149-177.
Bolland et al., Genetic modifiers of systemic lupus erythematosus in Fc.gamma.RIIB(-/-) mice. J Exp Med. May 6, 2002;195(9):1167-74.
Boruchov et al., "Expression and Modulation of the Inhibitory Fcγ Receptor, FcγRIIB (CD32B), on Human Dendritic Cells (DCs)," Blood 102(11):Abstract #1908, 2003.
Boruchov et al., Activating and inhibitory IgG Fc receptors on human DCs mediate opposing functions. The Journal of Clinical Investigation 115; 10:2914-2923.
Boyer et al. (1999) "Relative cytotoxic activity of immunotoxins reactive with different epitopes on the extracellular domain of the c-erbB-2 (HER-2/neu) gene product p185," Int. J. Cancer. 82(4):525-531.
Brauweiler et al., Partially distinct molecular mechamsms mediate inhibitory Fc.gamma.RIIB signaling in resting and activated B cells. J Immunol, 2001; 167:204-211.

Bredius et al., "Role of neutrophil Fc gamma RIIa (CD32) and Fc gamma RIIIb (CD16) polymorphic forms in phagocytosis of human IgG1-and IgG3-opsonized bacteria and erythrocytes," Immunology 83:624-630, 1994.
Brekke et al., "Human IgG isotype-specific amino acid residues affecting complement-mediated cell lysis and phagocytosis.," Eur J Immunol 24:2542-2547, 1994.
Brekke, O. H. et al. (2003) "Therapeutic Antibodies for Human Diseases at the Dawn of the Twenty-First Century," Nature Reviews 2:52-62.
Brown (2001) "Factors Modifying the Migration of Lymphocytes Across the Blood-Brain Barrier," Int Immunopharmacol. Nov. 2001;1(12):2043-62.
Brown EJ., "In Vitro Assays of Phagocytic Function of Human Peripheral Blood Leukocytes: Receptor Modulation and Signal Transduction," vol. 45 (Microbes as Tools for Cell Biology) in Methods In Cell Biololgy, Russell ed. Academic Press Inc. pp. 147-164, 1994.
Budde et al., Specificity of CD32 mAB for Fc.gamma.RIIa, Fc.gamma.RIIb1, and Fc.gamma.RIIb2 expressed in transfected mouse B cells and BHK-21 cells. Leukocyte Typing V: White cell differentiation antigens. 1995;828-832 (Schlossman, Boumsell, Gilks, Harlan, Kishomoto, eds.).
Burgess et al. (1990) "Possible dissociation of the heparin-binding and mitogenic activities of the heparin-binding (acidic fibroblast) growth factor-1 from its receptor binding activities by site directed mutagenesis of a single lysine residue," J. Cell Biol. 111:2129-2138.
Burlmeister et al., "Crystal structure of the complex of rat neonatal Fc receptor with Fc," Nature 372:379-383, 1994.
Burton and Woof, "Human antibody effector function," Advances in Immunology 51:1-64, 1992.
Burton et al., "Molecular recognition of antibody (IgG) by cellular Fc receptor (FcRI)," Mol Immunol 25:1175-1181, 1988.
Burton, "Immunoglobulin G: functional sites," Mol Immunol 22:161-206, 1985.
Callanan et al., The IgG Fc Receptor, Fc.gamma.RIIB is a target for deregulation by chromosomal translocation in malignant lymphoma. PNAS. Jan. 2000;97(1):309-314.
Cameron et al., Differentiation of the human monocyte cell line, U937, with dibutyryl cyclicAMP induces the expression of the inhibitory Fc receptor, Fc.gamma.RIIb. Immunol Lett. Oct. 1, 2002;83(3):171-9.
Camilleri-Broet et al., Fc.gamma.RIIB is differentially expressed during B cell maturation and in B-cell lymphomas. Br J Haematol. 2004;124(1):55-62.
Campbell et al. (2003) "Monoclonal antibody therapy for lymphoma," Blood Rev. 17(3):143-152.
Canfield and Morrison, "The binding affinity of human IgG for its high affinity Fc receptor is determined by multiple amino acids in the CH2 domain and is modulated by the hinge region," J Exp Med 173:1483-1491, 1991.
Caron et al., "Engineered humanized dimeric forms of IgG are more effective antibodies," J Exp Med 176 :1191-5, 1992.
Carter et al., "Humanization of an anti-p185HER2 antibody for human cancer therapy," Proc. Natl. Acad. Sci. USA 89:4285-4289, 1992.
Cartron et al., "Therapeutic activity of humanized anti-CD20 monoclonal antibody and polymorphism in IgG Fc receptor FcgammaRIIIa gene," Blood 99 :754-758, 2002.
Cassard et al., Modulation of tumor growth by inhibitory Fc.gamma. receptor expressed by human melanoma cells. The J Clin Invest. Nov. 2002;110(10):1549-1557.
Casset et al. (2003) A peptide mimetic of an anti-CD4 monoclonal antibody by rational design, Biochem, Biophs. Res. Commun, 307:198-205.
Cavacini et al. (1995) "Influence of heavy chain constant regions on antigen binding and HIV-1 neutralization by a human monoclonal antibody," J Immunol, 155(7):3638-3644.
Chappel et al., "Identification of a secondary Fc gamma RI binding site within a genetically engineered human IgG antibody," J Biol. Chem 268:25124-25131, 1993.

(56) References Cited

OTHER PUBLICATIONS

Chappel et al., "Identification of the Fc gamma receptor class I binding site in human IgG through the use of recombinant IgG1/IgG2 hybrid and point-mutated antibodies," Proc. Natl. Acad. Sci USA 88:9036-9040, 1991.
Chattergee et al. (1994) "Idiotypic Antibody Immunotherapy of Cancer," Cancer Immuno. Immunother. 38:75-82.
Chen, et al. (1999) "Selection and Analysis of an Optimized Anti-VEGF Antibody: Crystal Structure of an Affinity-Matured Fab in Complex with Antigen," J. Molec. Biol. 293:865-881.
Ciccimarra et al., "Localization of the IgG effector site for monocyte receptors," Proc. Natl. Acad. Sci. U.S.A. 72 :2081-2083, 1975.
Clynes and Ravetch, "Cytotoxic antibodies trigger inflammation through Fc receptors," Immunity 3:21-26, 1995.
Clynes et al., "Fc receptors are required in passive and active immunity to melanoma," Proc. Natl. Acad. Sci USA 95:652-656, 1998.
Clynes et al., "Inhibitory Fc receptors modulate in vivo cytoxicity against tumor targets," Nature Medicine 6 :443-446, 2000.
Clynes et al., "Modulation of immune complex-induced inflammation in vivo by the coordinate expression of activation and inhibitory Fc receptors," J Exp Med 189:179-185, 1999.
Clynes et al., "Uncoupling of immune complex formation and kidney damage in autoimmune glomerulonephritis," Science 279:1052-1054, 1998.
Colman, P.M. (1994) "Effects of amino acid sequence changes on antibody-antigen interactions," Res. Immunol. 145:33-36.
Daeron et al., The Same Tyrosine Based Inhibition Motif, in the Intracytoplasmic Domain of Fc.gamma.RIIB, regulates negatively BCR, TCR-and FcR dependent cell activation. Immunity. Nov. 1995;3: 635-646.
Damle et al., B-cell chronic lymphocytic leukemia cells express a surface membrane phenotype of activated, antigen-experienced B lymphocytes. Blood Jun, 1, 2002;99(11):4087-4093.
Davies et al. (1995) Antibody VH domains as small recognition units, Bio/Technology 13:475-479.
Davies et al., Expression of GnTIII in a recombinant anti-CD20 CHO production cell line: Expression of antibodies with altered glycoforms leads to an increase in ADCC through higher affinity for FC.sub . . . gamma. RIII. Biotechnol Bioeng, Aug. 20, 2001;74(4):288-94.
De Haas, Wien Kin "IgG-Fc receptors and the clinical relevance of their polymorphisms," Wien Klin Wochenscha 113:825-831, 2001.
De Santes et al. (1992) "Radiolabeled Antibody Targeting of the Her-2/neu Oncoprotein," Cancer Res. 52:1916-1923.
Deisenhofer, "Crystallographic refinement and atomic models of a human Fc fragment and its complex with fragment B of protein A from *Staphylococcus aureus* at 2.9-and 2.8-A resolution," Biochem. 20:2361-2370, 1981.
Deo et al., "Clinical significance of IgG Fc receptors and Fc gamma R-directed immunotherapies," Immunology Today 18:127-135, 1997.
DePascalis et al. (2002) "Grafting of Abbreviated Complementarity Determining Regions Containing Specificity Determining Residues Essential for Ligand Contact to Engineer a Less Immunogenic humanized monoclonal antibody," J. Immunol. 169:3076-3084.
Dermer (1994) "Another Anniversary for the War on Cancer," Biotechnology 12:320 (1994).
Ding et al., Inhibition of the function of the Fc.gamma.RIIB by a monoclonal antibody to thymic shared antigen-1, a Ly-6 family antigen. Immunology, Sep. 2001;104(1):28-36.
Dumoulin et al. (2002) Single-domain antibody fragments with high conformational stability, Protein Science 11:500-512.
Duncan and Winter, "Localization of the binding site for the human high-affinity Fc receptor on IgG," Nature 332:563-564, 1988.
Duncan and Winter, "The binding site for C1q on IgG," Nature 332 :738-740, 1988.
Edberg et al., "Modulation of Fcgamma and Complement Receptor Function by the Glycosyl-Phosphatidylinositol-Anchored Form of FcgammaRIII," Journal of Immunology 152: 5826-5835, 1994.

Efferson et al. (2005) "Stimulation of Human T Cells by an Influenza A Vector Expressing a CTL Epitope from the HER-2/neu Protooncogene Results in Higher Numbers of Antigen Specific TCRhi Cells than Stimulation with Peptide," Anticancer Research 25:715-724.
Ellman, J. et al. "Biosynthetic Method for Introducing Unnatural Amino Acids Site-Specifically into Proteins," Methods Enzymol. 202:301-336, 1991.
Eppstein et al., Biological activity of liposome-encapsulated murine interferon .gamma. is mediated by a cell membrane receptor. Proc Natl Acad Sci USA, Jan. 1985;82(11):3688-9.
European Search Report (EP 05778285) dated Apr. 14, 2008.
Extended Search Report EP 05854332.2 (PCT/US2005/045586) (dated 2009).
Extended Search Report EP 05857521.8 (WO 06/088494) (dated 2009).
Extended Search Report EP 07758130.4 (PCT/US2007/063548) (dated 2009).
Extended Search Report EP 07799049 (PCT/US2007/072151) (dated 2010) (7 pages).
Extended Search Report EP 07812341.1 (PCT/US2007/72153) (dated 2009) (9 pages).
Extended Search Report EP 07873826.7 (PCT/US2007/069767) (dated 2009) 8 pages).
Fanger et al., Production and use of anti-FcR bispecific antibodies. Immunomethods. Feb. 1994;4(1):72-81.
Farag, et al., Fc.gamma.RIIIa and Fc.gamma.RIIIa polymorphisms do not predict response to Rituximab in B-cell chronic lymphocytic leukemia. Blood. Oct. 16, 2003 (15 pp.).
Fidler, I. J., Macrophages and metastasis—a biological approach to cancer therapy. Cancer Res. Oct. 1985;45(10):4714-26.
Fleit et al., 1995 "Cross-linking of mAb to FC.gamma.RII results in tyrosine phosphorylation of multiple polypeptides including FC.gamma.RII itself." Leukocyte Typing V: White cell differentiation antigens 826-827 (Schlossman, Boumsell, Gilks, Harlan, Kishomoto, eds.).
Flesch and Neppert, "Functions of the Fc receptors for immunoglobulin G," J Clin Lab Anal 14:141-156, 2000.
Gamberale et al., 2003, "To the Editor: Expression of Fc.gamma. receptors type II (Fc.gamma.RII) in chronic lymphocytic leukemia B cells." Blood (Correspondence) 102(7):2698-2699.
Gerber et al., Stimulatory and inhibitory signals originating from the macrophage Fc.gamma. receptors. Microbes Infect. Feb. 2001;3(2):131-9.
Gergeley et al., "Fc receptors on lymphocytes and K cells," Biochemical Society Transactions 12:739-743, 1984.
Gergely and Sarmay, "The two binding-site models of human IgG binding Fc gamma receptors," FASEB J 4:3275-3283, 1990.
Greenwood and Clark, Effector functions of matched sets of recombinant human IgG subclass antibodies, (final version edited Feb. 11, 1993).
Greenwood et al., "Engineering multiple-domain forms of the therapeutic antibody CAMPATH-1H: effects on complement lysis," Therapeutic Immunology 1:247-255, 1994.
Greenwood et al., "Structural motifs involved in human IgG antibody effector functions," Eur J Immunol 23:1098-1104, 1993.
Gura (1997) "Systems for Identifying New Drugs Are Often Faulty," Science 278:1041-1042.
Hadley et al., "The functional activity of Fc gamma RII and Fc gamma RIII on subsets of human lymphocytes," Immunology 76:446-451, 1992.
Hatta et al., "Association of Fc gamma receptor IIIB, but not of Fc gamma receptor IIA and IIIA polymorphisms with systemic lupus erythematosus in Japanese," Genes and Immunity 1:53-60, 1999.
Hayes, Fc Engineering to Enhance Monoclonal Antibody Effector Functions. (Presentation) Xecor, CA, 2003.
Henry et al. (2004) "A prostate-specific membrane antigen-targeted monoclonal antibody-chemotherapeutic conjugate designed for the treatment of prostate cancer," Cancer Res. 64(21):7995-8001.
Herzenberg et al., "The history and future of the fluorescence activated cell sorter and flow cytometry: a view from Stanford," Clinical Chem. 2002:48:1819-1827, 2002.
Heyman, "Regulation of antibody responses via antibodies, complement, and Fc receptors," Annu Rev Immunol 18:709-737, 2000.

(56) References Cited

OTHER PUBLICATIONS

Hogarth et al., "Characterization of FcR Ig-binding sites and epitope mapping," Immunomethods 4 :17-24, 1994.
Holler et al., "In vitro evolution of a T cell receptor with high affinity for peptide/MHC," Proc. Natl. Acad. Sci. U.S.A. 97 :5387-92, 2000.
Holliger, P. (1993) "Diabodies: Small bivalent and bispecific antibody fragments," Proc. Natl. Acad. Sci. (U.S.A.) 90(14):6444-6448.
Holm et al, (2007) "Functional Mapping and Single Chain Construction of the Anti-Cytokeratin 8 Monoclonal Antibody TS1," Molecular Immunology 44:1075-1084.
Holmberg L.A. & Sandmaier M. (2001) Theratope® vaccine (STn-KLH), Expert Opin Biol Ther 1(5):881-891.
Holmes et al., Alleles of the Ly-17 alloantigen define polymorphisms of the murine IgG Fc receptor. Proc Natl Acad Sci USA. Nov. 1985;82(22):7706-10.
Holt, L.J. (2003) "Domain Antibodies: Proteins for Therapy," TRENDS in Biochemistry 21(11)484-490.
Hulett et al., "Chimeric Fc receptors identify functional domains of the murine high affinity receptor for IgG," J Immunol 147 :1863-1868, 1991.
Hulett et al., "Identification of the IgG binding site of the human low affinity receptor for IgG Fc gamma RII. Enhancement and ablation of binding by site-directed mutagenesis," J. Biol. Chem. 269:15287-15293, 1994.
Hulett et al., "Multiple regions of human Fc gamma RII (CD32) contribute to the binding of IgG," J. Biol. Chem. 270:21188-21194, 1995.
Hwang et al., Hepatic uptake and degradation of unilamellar sphingomyelin/cholesterol liposomes: a kinetic study. Proc Natl Acad Sci U S A. Jul. 1980;77(7):4030-4.
Ibragimova et al. (1999) "Stability of the beta-sheet of the WW domain: A molecular dynamics simulation study," Biophys. J. 77(4):2191-2198.
Idusogie et al., "Engineered antibodies with increased activity to recruit complement," J Immunol 166 :2571-2575, 2001.
Idusogie et al., "Mapping of the C1q binding site on rituxan, a chimeric antibody with a human IgG1 Fc," J Immunol 164: 4178-4184, 2000.
International Preliminary Report on Patentability PCT/US04/000643 (WO04/063351) (dated 2007).
International Preliminary Report on Patentability PCT/US05/024645(WO06/088494) (dated 2007).
International Preliminary Report on Patentability PCT/US05/12798 (WO06/088494) (dated 2005).
International Preliminary Report on Patentability PCT/US06/031201(WO07/021841) (dated 2008).
International Preliminary Report on Patentability PCT/US07/069767 (WO08/105886) (dated 2008)(7 pages).
International Preliminary Report on Patentability PCT/US07/086793 (WO08/140603) (dated 2008).
International Preliminaiy Report on Patentability PCT/US07/72153 (WO08/019199) (dated 2008).
International Search Report and Written Opinion PCT/US2009/68577 (dated 2010) (14 pages).
International Search Report; PCT/US04/000643 (WO04/063351) (dated 2004).
International Search Report; PCT/US05/024645 (WO06/088494) (dated 2007).
International Search Report; PCT/US05/12798 (WO06/088494) (dated 2005).
International Search Report; PCT/US06/031201 (WO07/021841) (dated 2008).
International Search Report; PCT/US07/069767 (WO08/105886) (dated 2008) (4pages).
International Search Report; PCT/US07/086793 (WO08/140603) (dated 2008).
International Search Report; PCT/US07/72153 (WO08/019199) (dated 2008).
International Search Report; PCT/US09/38201 (WO09/123894) (dated 2009) (11 pages).

Isaacs et al., "A therapeutic human IgG4 monoclonal antibody that depletes target cells in humans," Clin Exp Immunol 106 :427-433, 1996.
Isaacs et al., "Therapy with monoclonal antibodies. An in vivo model for the assessment of therapeutic potential," J Immunol 148 :3062-3071, 1992.
Isaacs et al., "Therapy with monoclonal antibodies. II. The contribution of Fc gamma receptor binding and the influence of C(H)1 and C(H)3 domains on in vivo effector function," J Immunol 161 :3862-3869, 1998.
Jain et al. "Barriers to Drug Delivery in Solid Tumors," Scientific American Jul. 1994:58-65.
Jassal et al., "Remodeling glycans on IgG by genetic re-engineering," Biochem Soc Trans 26 :S113, 1998.
Jefferis and Lund, "Interaction sites on human IgG-Fc for FcgammaR: current models," Immunology Letters 82 :57-65, 2002.
Jefferis et al., "IgG-Fc-mediated effector functions: molecular definition of interaction sites for effector ligands and the role of glycosylation," Immunol Rev 163:59-76, 1998.
Jefferis et al., "Molecular definition of interaction sites on human IgG for Fc receptors (huFc gamma R)," Mol Immunol 27 :1237-1240, 1990.
Jefferis et al., "Recognition sites on human IgG for Fc gamma receptors: the role of glycosylation," Immunol Lett 44 :111-7, 1995.
Jendeberg et al., "Engineering of Fc(1) and Fc(3) from human immunoglobulin G to analyse subclass specificity for staphylococcal protein A," J Immunological Methods 201 :25-34, 1997.
Jiang et al. (Epub Nov. 9, 2004) "A novel peptide isolated from a phage display peptide library with trastuzumab can mimic antigen epitope of HER-2," J Biol Chem. 280(6):4656-4662.
Kadar et al., "Modulatory effect of synthetic human IgG Fc peptides on the in vitro immune response of murine spleen cells," Int J Immunpharmacol 13 :1147-55, 1991.
Kadar et al., "Synthetic peptides comprising defined sequences of CH-2 and CH-3 domains of human IgG1 induce prostaglandin E2 production from human peripheral blood mononuclear cells," Immunol Lett 32:59-63, 1992.
Kagari et al., Essential Role of Fc.gamma. Receptors in anti-type II collagen antibody induced arthritis. J. Immunol, Apr. 2003;170:4318-24.
Kang, C.Y. et al. (1988) "Inhibition of Self-Binding Antibodies (Autobodies) by a VH-Derived Peptide," Science 240(4855):1034-1036.
Kato et al., "Structural basis of the interaction between IgG and Fcy receptors," J Mol Biol 295:213-224, 2000.
Keler et al., "Differential effect of cytokine treatment on Fc alpha receptor I-and Fc gamma receptor I-mediated tumor cytotoxicity by monocyte-derived macrophages," J. of Immunol. 164:5746-52, 2000.
Kepley et al. "Co-aggregation of FcgammaRII with FcepsilonRI on human mast cells inhibits antigeninduced secretion and involves SHIP-Grb2-Dok complexes" J. Biol. Chem. 279(34) 35139-35149.
Kieke et al., "Selection of functional T cell receptor mutants from a yeast surface-display library," Proc. Natl. Acad. Sci. U.S.A. 96 :5651-56, 1999.
Kim et al. (2002) "Both the epitope specificity and isotype are important in the antitumor effect of monoclonal antibodies against Her-2/neu antigen," Int. J. Cancer, 102(4):428-434.
Kim et al., "Analysis of FcγRIII and IgG Fc polymorphism reveals functional and evolutionary implications of protein-protein interaction," J Mol Evol 53:1-9, 2001.
Kimura et al. (1981) "A new mouse cell-surface antigen (Ly-m20) controlled by a gene linked to Mls locus and defined by monoclonal antibodies," Immunogenetics. 14(1-2):3-14.
Kipps et al. (1985) "Importance of Immunoglobin Isotype in Human Antibody-Dependent, Cell-Mediated Cytotoxicity Directed by Murine Monoclonal Antbodies," J. Exper. Med. 161:1-17.
Klein et al., "Expression of biological effector functions by immunoglobulin G molecules lacking the hinge region," Proc. Natl. Acad. Sci. U.S.A. 78 :524-528, 1981.
Koene et al., "Fc gammaRIIIa-158V/F polymorphism influences the binding of IgG by natural killer cell Fc gammaRIIIa, independently of the Fc gammaRIIIa-48L/R/H phenotype," Blood 90 :1109-1114, 1997.

(56) References Cited

OTHER PUBLICATIONS

Kounalakis N. & Goydos J.S. (2005) Tumor Cell and Circulating Markers in Melanoma: Diagnosis, Prognosis, and Management, Curr Oncol Reports 7:377-382.
Kranz et al., "Mechanisms of ligand binding by monoclonal anti-fluorescyl antibodies," J. Biol. Chem. 257:6987-6995, 1982.
Kumamaru W. et al. (2004) T-Cell Receptor Vβ Gene Usage by T Cells Reactive with the Tumor-Rejection Antigen SART-1 in Oral Squamous Cell Carcinoma, Int. J. Cancer: 108:686-695.
Kumpel, B.M. Brit. "Human monoclonal anti-D antibodies," J. Haematol. 71:415-420 (1989).
Kurlander et al., 1986, "Comparison of intravenous gamma globulin and a monoclonal anti-Fc receptor antibody as inhibitors of immune clearance in vivo in mice." J. Clin. Invest. 77(6):2010-2018.
Lazar et al. (1988) Transforming growth factor a: mutation of aspartic acid 47 and leucine 48 results in different biological activities, Molec. Cell. Biol. 8:1247-1252.
Le Gall, F. et al. (Epub May 4, 2004) "Effect Of Linker Sequences Between The Antibody Variable Domains On The Formation, Stability And Biological Activity Of A Bispecific Tandem Diabody," Protein Eng Des Sel. 17(4):357-366.
Lehmann et al., "Phagocytosis: measurement by flow cytometry," J Immunol Methods. 243(1-2):229-42, 2000.
Lehrnbecher et al., "Variant genotypes of the low-affinity Fcgamma receptors in two control populations and a review of low-affinity Fcgamma receptor polymorphisms in control and disease populations," Blood 94:4220-4232, 1999.
Lewis et al. (1993) "Differential responses of human tumor cell lines to anti-p185HER2 monoclonal antibodies," Cancer Immunol Immunother. 37(4):255-263.
Li et al. (2007) Regeneration of nigrostriatal dopaminergic axons by degradation of chondroitin sulfate is accompanied by elimination of the fibrotic scar and glia limitans in the lesion site. J. Neurosci. Res. 85:636-547.
Li et al., "Reconstitution of human Fc gamma RIII cell type specificity in transgenic mice," J Exp Med 183 :1259-1263, 1996.
Lifely et al., Glycosylation and biological activity of CAMPATH-1H expressed in different cell lines and grown under different culture conditions. Glycobiology. Dec. 1995;5(8):813-22.
Lin et al., Colony-stimulating factor 1 promotes progression of mammary tumors to malignancy. J Exp Med. 2001;193(6):727-739.
Lin et al., The macrophage growth factor CSF-1 in mammary gland development and tumor progression, J Mammary Gland Biol Neoplasia. 2002;7(2):147-62.
Liu et al., "Production of a mouse-human chimeric monoclonal antibody to CD20 with potent Fc-dependent biologic activity," J. Immunol. 139:3521-3526, 1987.
Looney et al., 1986, "Human Monocytes and U(#& Cells Bear Two Distinct Fc Receptors for IgG." J. Immunol. 136(5):1641-1647.
Lu, D. et al. (2003) "Di-Diabody: A Novel Tetravalent Bispecific Antibody Molecule by Design." J. Immunol. Meth. 279:219-232.
Lund et al., "Expression and characterization of truncated forms of humanized L243 IgG1. Architectural features can influence synthesis of its oligosaccharide chains and affect superoxide production triggered through human Fcgamma receptor I," Eur J Biochem 267 :7246-57, 2000.
Lund et al., "Human Fc gamma RI and Fc gamma RII interact with distinct but overlapping sites on human IgG," J Immunol 147 :2657-62, 1991.
Lund et al., "Multiple binding sites on the CH2 domain of IgG for mouse Fc gamma R11," Molecular Immunology 29:53-59, 1992.
Lund et al., "Multiple interactions of IgG with its core oligosaccharide can modulate recognition by complement and human Fc gamma receptor I and influence the synthesis of its oligosaccharide chains," J Immunol 157 :4963-4969, 1996.
Lund et al., "Oligosaccharide-protein interactions in IgG can modulate recognition by Fc gamma receptors," FASEB J 9 :115-119, 1995.
Lyden et al., The Fc receptor for IgG expressed in the villus endothelium of human placenta is Fc.gamma. RIIb2. J Immunol. Mar. 15, 2001;166(6):3882-9.
MacCallum et al. (1996) "Antibody-Antigen Interactions: Contact Analysis and Binding Site Topography," J. Molec. Biol. 262:732-745.
Maenaka et al., "The human low affinity Fcgamma receptors IIa, IIb, and III bind IgG with fast kinetics and distinct thermodynamic properties," J Biol Chem 48 :44898-904, 2001.
Malbec et al., Fcs receptor I-associated lyn-dependent phosphorylation of Fc.gamma. receptor IIB during negative regulation of mast cell activation, J Immunol. Feb. 15, 1998;160(4):1647-58.
Maresco et al . . . , 1999, "The SH2-Containing 5'-Inositol Phosphatase (SHIP) Is Tyrosine Phosphorylated after Fc.gamma. Receptor Clustering in Monocytes." J. Immunol. 162:6458-6465.
Maruyama K, In vivo targeting by liposomes. Biol Pharm Bull. Jul. 2000;23(7):791-9.
Masui et al. (1986) "Mechanism of antitumor activity in mice for anti-epidermal growth factor receptor monoclonal antibodies with different isotypes.," Canc. Res. 46:5592-5598.
McDevitt et al. "An alpha-particle emitting antibody ([213Bi]J591) for radioimmunotherapy of prostate cancer.," Cancer Res. 60(21):6095-6100.
Melero et al. (1998) The frequent expansion of a subpopulation of B cells that express RF-associated cross-reactive idiotypes: evidence from analysis of a panel autoreactive monoclonal antibodies; Scand. J. Immunol. 48:152-158 1998.
Metcalfe, Mast Cells, Physiol Rev. Oct. 1997;77(4):1033-79.
Michaelsen et al., "One disulfide bond in front of the second heavy chain constant region is necessary and sufficient for effector functions of human IgG3 without a genetic hinge," Immunolgy 91 :9243-9247, 1994.
Micklem et al., Different isoforms of human FcRII distinguished by CDw32 antibodies. J Immunol. Mar. 1990;144:2295-2303.
Morgan et al., "The N-terminal end of the CH2 domain of chimeric human IgG1 anti-HLA-DR is necessary for C1q, Fc gamma RI and Fc gamma RIII binding," Immunology 86 :319-324, 1995.
Morrison et al., "Structural determinants of IgG structure," Immunologist 2 :119-124, 1994.
Munn et al., "Phagocytosis of tumor cells by human monocytes cultured in recombinant macrophage colony-stimulating factor," J Exp Med. 172(1):231-7, 1990.
Nagarajan et al., "Ligand binding and phagocytosis by CD16 (Fc gamma receptor III) isoforms. Phagocytic signaling by associated zeta and gamma subunits in Chinese hamster ovary cells," J Biol Chem 270 :25762-25770, 1995.
Nakamura et al., Fc.gamma. receptor IIB-deficient mice develop Goodpasture's Syndrome upon immunization with Type IV collagen: a novel murine model for Autoimmune Glomerular Basement Membrane Disease. J. Exp. Med. Mar. 6, 2000;191(5):899-905.
Neuberger et al., "Recombinant antibodies possessing novel effector functions," Nature 312 :604-608, 1984.
Norderhaug et al., "Chimeric mouse human IgG3 antibodies with an IgG4-like hinge region induce complement-mediated lysis more efficiently than IgG3 with normal hinge," Eur J Immunol 21:2379-84, 1991.
Noren, C.J. et al. "A General Method for Site-Specific Incorporation of Unnatural Amino Acids into Proteins," Science 244:182-188, 1989.
Norris et al., A naturally occurring mutation in Fc.gamma.RIIA: A Q to K.sup.127 change confers unique IgG binding properties to the R.sup.131 allelic form of the receptor. Blood. Jan. 15, 1998;91(2):656-662.
Nose and Leanderson, "Substitution of asparagine324 with aspartic acid in the Fc portion of mouse antibodies reduces their capacity for C1q binding," Eur J Immunol 19 :2179-81, 1989.
Okazaki et al., "Fucose depletion from human IgG1 oligosaccharide enhances binding enthalpy and association rate between IgG1 and FcgammaRIIIa," J Mol Biol 336 :1239-1249, 2004.
Orfao and Ruiz-Arguelles, "General concepts about cell sorting techniques," Clinical Biochem. 29:5-9, 1996.

(56) References Cited

OTHER PUBLICATIONS

Ott et al., Downstream of Kinase, p62.sup.dok, Is a mediator of Fc.gamma.RIIB inhibition of Fc.epsilon.RI signaling. J. of Immunol. 2002;168:4430-9.
Ott, V.L. et al. "FcgammaRIIB as a potential molecular target for intravenous gamma globulin therapy," J. Allergy Clin Immunol. Oct. 2001:895-98.
Panka et al. (1988) Variable region framework differences result in decreased or increased affinity of variant anti-digoxin antibodies. Proc. Natl. Acad. Sci. USA 85:30803084.
Pardridge et al., Blood-brain barrier drug targeting: The future of brain drug development. Molecular Interventions. 2003, 3;2:90-105, See particularly pp. 91-96.
Park et al., Immunoliposomes for cancer treatment. Adv Pharmacol. 1997;40:399-435.
Park YS, Tumor-directed targeting of liposomes. Biosci Rep. Apr. 2002;22(2):267-81.
Partridge et al., "The use of anti-IgG monoclonal antibodies in mapping the monocyte receptor site on IgG," Mol Immunol. 23(12):1365-72, 1986.
Paul, William E, (1993) "Fundamental Microbiology, 3 Ed." pf. 242, 292-296.
Pereira et al. (1998) Cardiolipin Binding a light Chain from Lupus-prone Mice; Biochem. 37:1460-1437.
Perussia "Human Natural Killer Cell Protocols" in Methods Molecular Biology, vol. 121 (Campbell et al. eds.) Humana Press Inc., Totowa, NJ. 179-92, 2000.
Pettersen et al. (1999) "CD47 Signals T Cell Death," J. Immunol. 162(12):7031-7040.
Pluckthun, A. et al. (1997) "New protein engineering approaches to multivalent and bispecific antibody fragments," Immunotechnology 3(2):83-105.
Polson, A.G. et al. (Epub Mar. 20, 2007) "Antibody-Drug Conjugates Targeted To CD79 For The Treatment Of Non-Hodgkin Lymphoma, " Blood. 110(2):616-623.
Presta LG, Engineering antibodies for therapy. Curr Pharm Biotechnol. Sep. 2002;3(3):237-56.
Presta, L.G. et al. (2005) "Selection, Design and Engineering of Therapeutic Antibodies," J. Allergy Clin. Immunol. 116(4):731-736.
Pricop et al., differential modulation of stimulatory and inhibitory Fc.gamma. receptors on human monocytes by Th1 and Th2 cytokines. J Immunol. Jan, 1, 2001;166(1):531-7.
Pulford et al., 1995 "M6.5: The immunocytochemical distribution of CD16, CD32, and CD64 antigens." Leukocyte Typing V: White cell differentiation antigens 817-821 (Schlossman, Boumsell, Gilks, Harlan, Kishomoto, eds.) pp. 817-821.
Pulford et al., A new monoclonal antibody (KB61) recognizing a novel antigen which is selectively expressed on a subpopulation of human B lymphocytes. Immunology, Jan. 1986;57(1):71-6.
Qin et al., Fc.gamma. receptor IIB on follicular dendritic cells regulates the B cell recall response. J Immunol. 2000;164:6268-6275.
Radaev and Sun, "Recognition of immunoglobulins by Fcgamma receptors," Molecular Immunology 38 :1073-1083, 2001.
Ragupathi G. et al. (2005) Antibody Inducing Polyvalent Cancer Vaccines. In: Khleif S.N. (eds) Tumor Immunology and Cancer Vaccines. Cancer Treatment and Research, vol. 123. Springer, Boston, MA.
Rankin, et al., "CD32B, the human inhibitory Fc-γ receptor IIB, as a target for monoclonal antibody therapy of B-cell lymphoma", Blood, American Society of Hematology, Oct. 1, 2006, vol. 108, No. 7, pp. 2384-2389.
Ravetch and Bolland, "IgG Fc receptors," Annu Rev Immunol 19:275-90, 2001.
Ravetch and Clynes, "Divergent roles for Fc receptors and complement in vivo," Annu Rev Immunol 16:421-432, 1998.
Ravetch and Kinet, "Fc receptors," Annu Rev Immunol 9:457-492, 1991.
Ravetch et al., Fc receptors: rubor redux. Cell. Aug. 26, 1994;78(4):553-60.
Ravetech and Lanier, "Immune inhibitoiy receptors," Science 290:84-89, 2000.
Reali et al., IgEs targeted on tumor cells: therapeutic activity and potential in the design of tumor vaccines. Cancer Res. 2001;61(14): 5517-22.
Redpath et al., "The influence of the hinge region length in binding of human IgG to human Fcgamma receptors," Hum Immunol 59 :720-727, 1998.
Reff et al., "A review of modifications to recombinant antibodies: attempt to increase efficacy in oncology applications," Critical Reviews in Oncology/Hematology 40: 25-35; 2001.
Reff et al., "Depletion of B cells in vivo by a chimeric mouse human monoclonal antibody to CD20," Blood 83:435-445, 1994.
Riechmann et al., "Reshaping human antibodies for therapy," Nature. 332(6162):323-7, 1988.
Riemer et al. (Epub Jan. 8, 2005) "Matching of trastuzumab (Herceptin) epitope mimics onto the surface of Her-2/neu—a new method of epitope definition,," Mol Immunol. 42(9):1121-1124.
Routledge et al., The effect of aglycosylation on the immunogenicity of a humanized therapeutic CD3 monoclonal antibody. Transplantation. Oct. 27, 1995;60(8):847-53.
Rudikoff et al. (1982) "Single amino acid substitution altering antigen-binding specificity" Proc. Natl. Acad. Sci. USA 79:1979-1983.
Samsom et al. (2005) Fc gamma RIIB regulates nasal and oral tolerance: a role for dendritic cells Immunol. 174:5279-5287.
Samuelsson et al., Anti-inflammatory activity of IVIG mediated through the inhibitory Fc receptor. Science. Jan. 19, 2001; 291:484-486.
Sarkar et al., Negative signaling via Fc.gamma.RIIB1 in B cells blocks phospholipase C.sub . . . gamma.2 tyrosine phosphorylation but not Syk or Lyn activation, J Biol Chem. Aug. 16, 1996;271(33):20182-6.
Sarmay et al., "Ligand inhibition studies on the role of Fc receptors in antibody-dependent cell-mediated cytotoxicity," Mol Immunol 21 :43-51, 1984.
Sarmay et al., "Mapping and comparison of the interaction sites on the Fc region of IgG responsible for triggering antibody dependent cellular cytotoxicity (ADCC) through different types of human Fc gamma receptor," Mol Immunol 29 :633-639, 1992.
Sarmay et al., "The effect of synthetic peptides corresponding to Fc sequences in human IgG1 on various steps in the B cell activation pathway," Eur J Immunol 18 :289-294, 1988.
Santes-Fridman et al., "Fc gamma receptors: a magic link with the outside world," ASHI Quarterley, 4th Quarter: 148-151, 2003.
Schaffner et al., "Chimeric interleukin 2 receptor alpha chain antibody derivatives with fused mu and gamma chains permit improved recruitment of effector functions," Mol Immunol 32 :9-20, 1995 (Erratum in 32 :1299, 1995).
Schatz et al., "Use of peptide libraries to map the substrate specificity of a peptide-modifying enzyme: a 13 residue consensus peptide specifies biotinylation in *Escherichia coli*," Bio/Technology 11:1138-1143, 2000.
Scholl et al., Is colony-stimulating factor-1 a key mediator of breast cancer invasion and metastasis? Mol Carcinog. 7(4):207-11.
Schrama D. et al. (2006) "Antibody targeted drugs as cancer therapeutics," Nature 5:147-159.
Schuna et al., 2000, "New Drugs for the treatment of rheumatoid arthritis." Am J. Health Syst. Phar, 57:225-237.
Seaver (1994) "Monoclonal Antibodies in Industry: More Difficult than Originally Thought," Genetic Engineering News 14(14):10, 21.
Sensei et al., "Amino acid differences in the N-terminus of C(H)2 influence the relative abilities of IgG2 and IgG3 to activate complement," Molecular Immunology 34:1019-1029, 1997.
Shields et al., "High resolution mapping of the binding site on human IgG1 for Fc gamma RI, Fc gamma RII, Fc gamma RIII, and FcRn and design of IgG1 variants with improved binding to the Fc gamma R," J Biol Chem 276 :6591-6604, 2001.

(56) References Cited

OTHER PUBLICATIONS

Shields et al., Lack of fucose on human IgG1 N-linked oligosaccharide improves binding to human Fc.gamma. RIII and antibody-dependent cellular toxicity. J Biol Chem. Jul. 26, 2002;277(30):26733-40.
Shim, H. (2011) "One target, different effects: a comparison of distinct therapeutic antibodies against the same targets," Experimental and Mol. Med. 43(10):539-549.
Shopes et al., "Recombinant human IgG1-murine IgE chimeric Ig. Construction, expression, and binding to human Fc gamma receptors," J Immunol 145 :3842-3848, 1990.
Shopes, "A genetically engineered human IgG mutant with enhanced cytolytic activity," J Immunol 148 :2918-2922, 1992.
Shopes, "A genetically engineered human IgG with limited flexibility fully initiates cytolysis via complement," Molecular Immunology 30 :603-609, 1993.
Shusta et al., "Directed evolution of a stable scaffold for T-cell receptor engineering," Nature Biotechnology 18:754-759, 2000.
Shusta et al., "Increasing the secretory capacity of *Saccharomyces cerevisiae* for production of single-chain antibody fragments," Nature Biotechnology 16:773-777, 1998.
Shusta et al., "Yeast polypeptide fusion surface display levels predict thermal stability and soluble secretion efficiency," J Mol Biol 292:949-956, 1999.
Siberil, S. et al. (2006) "Molecular Aspects of Human FcgammaR Interactions with IgG: Functional and Therapeutic Consequences," Immunol. Lett. 106:111-118 (2006).
Singapore Search Report SG 200607186-4 dated Nov. 5, 2008.
Skolnick et al. (2000) From Genes to Protein Stmeture and Function: Novel Aspects of Computational Approaches in the Genomic Era, Trends in Biotechnology 18:34-39.
Sleister et al., "Subtractive Immunization; A tool for the generation of discriminatory antibodies to proteins of similar sequence," Journal of Immunological Methods 261: 213-220, (2002).
Smith and Morrison, "Recombinant polymeric IgG: an approach to engineering more potent antibodies," Bio/Technology 12:683-688, 1994.
Sondermann and Oosthuizen, "The structure of Fc receptor/Ig complexes: considerations on stoichiometry and potential inhibitors," Immunology Letters, 82:51-56, 2002.
Sondermann et al., "Crystal structure of the soluble form of the human fcgamma-receptor IIb: a new member of the immunoglobulin superfamily at 1.7 A resolution," EMBO J 18:1095-1103, 1999.
Sondermann et al., "Molecular basis for immune complex recognition: a comparison of Fc-receptor structures," J. Mol. Biol. 309:737-749, 2001.
Sondermann et al., "The 3.2-A crystal structure of the human IgG1 Fc fragment-Fc gammaRIII complex," Nature 406:267-273, 2000.
Stancovski et al. (1991) "Mechanistic aspects of the opposing effects of monoclonal antibodies to the ERBB2 receptor on tumor growth," Proc Natl Acad Sci U S A. 88(19):8691-8695.
Steeg P.S. et al. (2011) "Brain metastases as preventive and therapeutic targets," Nature Reviews 11:352-363.
Steplewski et al., "Biological activity of human-mouse IgG1, IgG2, IgG3, and IgG4 chimeric monoclonal antibodies with antitumor specificity," Proc. Natl. Acad. Sci. U.S.A. 85:4852-4856, 1988.
Strohmeier et al., "Role of the Fc gamma R subclasses Fc gamma RII and Fc gamma RIII in the activation of human neutrophils by low and high valency immune complexes," J Leukocyte Biol 58:415-422, 1995.
Su et al., Expression profile of Fc.gamma.RIIB on leukocytes and its dysregulation in systemic lupus erythematosus. J. Immunol. 178:3272-3280, 2007.
Sylvestre and Ravetch, "A dominant role for mast cell Fc receptors in the Arthus reaction," Immunity 5:387-390, 1996.
Sylvestre and Ravetch, "Fc receptors initiate the Arthus reaction: redefining the inflammatory cascade," Science 265:1095-1098, 1994.
Takai et al., "Augmented humoral and anaphylactic responses in Fc gamma RII-deficient mice," Nature 379:346-349, 1996.

Takai et al., "FcR gamma chain deletion results in pleiotrophic effector cell defects," Cell 76 :519-529, 1994.
Takai, "Roles of Fc receptors in autoimmunity," Nature Reviews 2:580-592, 2002.
Tam et al., A bispecific antibody against human IgE and human Fc.gamma.RII that inhibits antigen-induced histamine release by human mast cells and basophils. Allergy 2004;59:772-780.
Tamm et al., "The IgG binding site of human FcγRIIIB receptor involves CC' and FG loops of the membrane-proximal domain," J Biol Chem 271:3659-3666, 1996.
Tao and Morrison, Studies of aglycosylated chimeric mouse-human IgG. Role of carbohydrate in the structure and effector functions mediated by the human IgG constant region. J Immunol. Oct. 15, 1989;143(8):2595-601.
Tao et al., "Structural features of human immunoglobulin G that determine isotype-specific differences in complement activation," J Exp Med 178:661-667, 1993.
Tao et al., "The differential ability of human IgG1 and IgG4 to activate complement is determined by the COOH-terminal sequence of the CH2 domain," J Exp Med 173:1025-1028, 1991.
Todorovska et al., Design and application of diabodies, triabodies and tetrabodies for cancer targeting. J Immunol Methods. Feb. 1, 2001;248(1-2):47-66.
Tridandapandi et al., "Regulated Expression and Inhibitory Function of FcgammaRIIB in Human Monocytic Cells," Journal of Biological Chemistiy 277(7): 5082-5089, 2002.
Umana et al., Engineered glycoforms of an antineuroblastoma IgG1 with optimized antibody-dependent cellular cytotoxic activity. Nat Biotechnol. Feb. 1999;17(2):176-80.
Vajdos et al. (2002) "Comprehensive Functional Maps of the Antigen-Binding Site of an Anti-ErbB2 Antibody Obtained with Shotgun Scanning Mutagenesis," J. Molec. Biol. 320:415-428.
Van Antwerp and Wittrup, "Fine affinity discrimination by yeast surface display and flow cytometry," Biotechnol Prog 16:31-37, 2000.
Van De Winkel et al., 1995, "CD32 cluster workshop report." Leukocyte Typing V: White Cell differentiation antigens 823-825 (Schlossman, Boumsell, Gilks, Harlan, Kishomoto, eds.).
Van den Beuken et al. (2001) Building novel binding ligands to B7.1 and B7.2 based on human antibody single variable light chain domains; J. Molec. Biol. 310:591-601.
Van Nguyen et al., Colony stimulating factor-1 is required to recruit macrophages into the mammary gland to facilitate mammary ductal outgrowth. Dev Biol. 2002;247(1):11-25.
Van Sorge et al., "FcgammaR polymorphisms: Implications for function, disease susceptibility and immunotherapy," Tissue Antigens 61:189-202, 2003.
Vely et al., 1997, "A new set of monoclonal antibodies against human Fc gamma RII (CD32) and Fc gamma RIII (CD16): characterization and use in various assays." Hybridoma 16(6):519-28.
Veri, M.C. et al. (2007) "Monoclonal antibodies capable of discriminating the human inhibitory Fcgamma-receptor IIb (CD32B) from the activating Fcgamma-receptor IIA (CD32A): biochemical, biological and functional characterization," Immunology 121(3):392-404.
Vidarte, "Serine 132 is the C3 covalent attachment point on the CH1 domain of human IgG1," J Biol Chem 276:38217-38233, 2001.
Vingerhoeds et al., Immunoliposomes in vivo. Immunomethods. Jun. 1994;4(3):259-72.
Vitetta, E.S. et al. (2006) "Immunology. Cnsidering Therapeutic Antibodies," Science 313:308-309.
Vuist et al. (1990) "Two distinct mechanisms of antitumor activity mediated by the combination of interleukin 2 and monoclonal antibodies," Canc. Res. 50:5767-5772.
Wallick et al., Glycosylation of a VH residue of a monoclonal antibody against {acute over (.alpha.)} (1.fwdarw.6) dextran increases its affinity for antigen, J Exp Med. Sep. 1, 1988;168(3):1099-109.
Ward and Ghetie, "The effector functions of immunoglobulins: implications for therapy," Therapeutic Immunology 2:77-94, 1995.
Ward et al. (1989) Building Activities of a repertoire of single immunoglobulin variable domains secreted from *Escherichia coli*, Nature 341:544-546 (1989).

(56) References Cited

OTHER PUBLICATIONS

Warmerdam et al., Molecular basis for a polymorphism of human Fc gamma receptor II (CD32). J Exp Med. Jul. 1, 1990;172(1):19-25.
Warren, HS et al.(1999) "NK cells and apoptosis," Immunol. Cell Biol. 77(1):64-75.
Weinrich, V. et al. "Epitope Mapping of New Monoclonal Antibodies Recognizing Distinct Human FCRII (CD32) Isoforms," Hybridoma 15(2):109-116.
Weng and Levy, "Two immunoglobulin G fragment C receptor polymorphisms independently predict response to rituximab in patients with follicular lymphoma," J Clin Oncol 21:3940-3947, 2003.
Wheeler, "Preventive Vaccines for Cervical Cancer," Salud Publica d Mexico, 1997, vol. 39, pp. 1-9.
Wiener, E. et al. "Differences between the activities of human monoclonal IgG1 and IgG3 anti-D antibodies of the Rh blood group system in their abilities to mediate effector functions of monocytes," Immunol. 65:159-163 (1988).
Wing et al., "Mechanism of first-dose cytokine-release syndrome by CAMPATH 1-H: Involvement ofCD16 (FcγRIII) and CD11a/CD18 (LFA-1) on NK cells," J Clin Invest 98 :2819-2826, 1996.
Wingren et al., "Comparison of surface properties of human IgA, IgE, IgG and IgM antibodies with identical and different specificities," Scand J Immunol 44:430-436, 1996.
Wittrup, "The single cell as a microplate well," Nat Biotechnol 18:1039-1040, 2000.
Witttrup, "Protein engineering by cell-surface display," Curr, Opin. Biotechnol. 12:395-399, 2001.
Woof et al., "Localisation of the monocyte-binding region on human immunoglobulin G," Mol Immunol 23 :319-330, 1986.
Wright and Morrison, Effect of glycosylation on antibody function: implications for genetic engineering. Trends Biotechnol. Jan. 1997;15(1):26-32.
Wu et al. (2001) "Multimerization of a chimeric anti-DC20 Single-Chain Fv-Fc fusion protein is mediated through variable domain exchange," Protein Engineering 14(2): 1025-1033.
Wu et al., "A novel polymorphism of FcγRIIIa (CD16) alters receptor function and predisposes to autoimmune disease," J Clin Invst 100 :1059-1070, 1997.
Wu et al., "Humanization of a Murine Monoclonal Antibody by Simultaneous Optimization of Framework and CDR Residues," Journal of Molecular Biology, 1999, vol. 294, pp. 151-162.
Xu et al. (1993) "Antibody-induced growth inhibition is mediated through immunochemically and functionally distinct epitopes on the extracellular domain of the c-erbB-2 (HER-2/neu) gene product p185," Int. J. Cancer. 53(3):401-408.
Xu et al., "Residue at position 331 in the IgG1 and IgG4 CH2 domains contributes to their differential ability to bind and activate complement," J Biol Chem 269 :3469-3474, 1994.
Xu et al., Fc.gamma.Rs Modulate Cytotoxicity of Anti-Fas Antibodies: Implications for Agonistic Antibody Based Therapeutics. J Immunol. 2003;171:562-68.
Yeung and Wittrup, "Quantitative screening of yeast surface-displayed polypeptide libraries by magnetic bead capture," Biotechnol Prog 18:212-220, 2002.
Zeidler et al., "The Fc-region of a new class of intact bispecific antibody mediates activation of accessory cells and NK cells and induces direct phagocytosis of tumour cells," British J Cancer 83:261-266, 2000.
Zola et al., 2000, "CD32 (FcgammaRII)." J Biol Regul Homeost Agents 14(4):311-6.
Zuckier et al., "Chimeric human-mouse IgG antibodies with shuffled constant region exons demonstrate that multiple domains contribute to in vivo half-life," Cancer Res 58 :3905-3908, 1998.
Boehm, B.E. et al. (2023) "*Biomarkers of Aggressive Prostate Cancer at Diagnosis*," Int. J. Mol. Sci. 24(3):2185:1-18.
Egloff, A.M. et al. (2006) "*Cyclin B1 And Other Cyclins As Tumor Antigens In Immunosurveillance And Immunotherapy Of Cancer*," Cancer Res. 66(1):6-9.
Holmberg, L.A. et al. (2001) "*Theratope Vaccine (sTn-KLH)*," Expert Opin. Biol. Ther. 1(5):881-891.
Medic, S. et al. (2007) "*Molecular Markers Of Circulating Melanoma Cells*," Pigment Cell Res. 20(2):80-91.
Rajasekaran, A.K. et al. (2005) "*Is Prostate-Specific Membrane Antigen A Multifunctional Protein*"? Am. J. Physiol. Cell. Physiol. 288(5):C975-C981.
Shichijo, S. et al. (1998) "*A Gene Encoding Antigenic Peptides Of Human Squamous Cell Carcinoma Recognized By Cytotoxic T Lymphocytes*," J. Exp. Med 187(3):277-288.

\* cited by examiner

8B5.3.4 VH nucleotide/amino acid sequence

```
gaa gtg aag ctt gag gag tct gga gga ggc ttg gtg caa cct gga gga    48
Glu Val Lys Leu Glu Glu Ser Gly Gly Gly Leu Val Gln Pro Gly Gly
 1               5                  10                  15 tcc atg aaa ctc tct tgt gaa gcc tct gga ttc act ttt agt gac gcc    96
Ser Met Lys Leu Ser Cys Glu Ala Ser Gly Phe Thr Phe Ser Asp Ala
             20                  25                  30

CDR1
tgg atg gac tgg gtc cgt cag tct cca gag aag ggg ctt gag tgg gtt   144
Trp Met Asp Trp Val Arg Gln Ser Pro Glu Lys Gly Leu Glu Trp Val
         35                  40                  45

CDR2
gct gaa att aga aac aaa gct aaa aat cat gca aca tac tat gct gag   192
Ala Glu Ile Arg Asn Lys Ala Lys Asn His Ala Thr Tyr Tyr Ala Glu
         50                  55                  60 tct gtg ata ggg agg ttc acc atc tca aga gat gat tcc aaa agt agt   240
Ser Val Ile Gly Arg Phe Thr Ile Ser Arg Asp Asp Ser Lys Ser Ser
 65                  70                  75                  80 gtc tac ctg caa atg aac agc tta aga gct gaa gac act ggc att tat   288
Val Tyr Leu Gln Met Asn Ser Leu Arg Ala Glu Asp Thr Gly Ile Tyr
             85                  90                  95

CDR3
tac tgt ggg gct ctg ggc ctt gac tac tgg ggc caa ggc acc act ctc   336
Tyr Cys Gly Ala Leu Gly Leu Asp Tyr Trp Gly Gln Gly Thr Thr Leu
            100                 105                 110 aca gtc tcc tcg                                                    348
Thr Val Ser Ser
        115
```

FIG. 2

8B5.3.4 VL nucleotide/amino acid sequence

```
gac att cag atg aca cag tct cca tcc tcc cta ctt gcg gcg ctg gga    48
Asp Ile Gln Met Thr Gln Ser Pro Ser Ser Leu Leu Ala Ala Leu Gly
 1               5                  10                  15

┌─────────── CDR1 ───────────
gaa aga gtc agt ctc act tgt cgg gca agt cag gaa att agt ggt tac    96
Glu Arg Val Ser Leu Thr Cys Arg Ala Ser Gln Glu Ile Ser Gly Tyr
             20                  25                  30

─────────┐
tta agc tgg ctt cag cag aaa cca gat gga act att aaa cgc ctg atc   144
Leu Ser Trp Leu Gln Gln Lys Pro Asp Gly Thr Ile Lys Arg Leu Ile
         35                  40                  45

┌─── CDR2 ────────────────────────────────┐
tac gcc gca tcc act tta gat tct ggt gtc cca aaa agg ttc agt ggc   192
Tyr Ala Ala Ser Thr Leu Asp Ser Gly Val Pro Lys Arg Phe Ser Gly
         50                  55                  60 agt gag tct ggg tca gat tat tct ctc acc atc agc agt ctt gag tct   240
Ser Glu Ser Gly Ser Asp Tyr Ser Leu Thr Ile Ser Ser Leu Glu Ser
 65                  70                  75                  80

┌─── CDR3 ───────────────────
gaa gat ttt gca gac tat tac tgt cta caa tat ttt agt tat ccg ctc   288
Glu Asp Phe Ala Asp Tyr Tyr Cys Leu Gln Tyr Phe Ser Tyr Pro Leu
             85                  90                  95

─────┐
acg ttc ggt gct ggg acc aag ctg gag ctg aaa                       321
Thr Phe Gly Ala Gly Thr Lys Leu Glu Leu Lys
             100                 105
```

FIG. 3

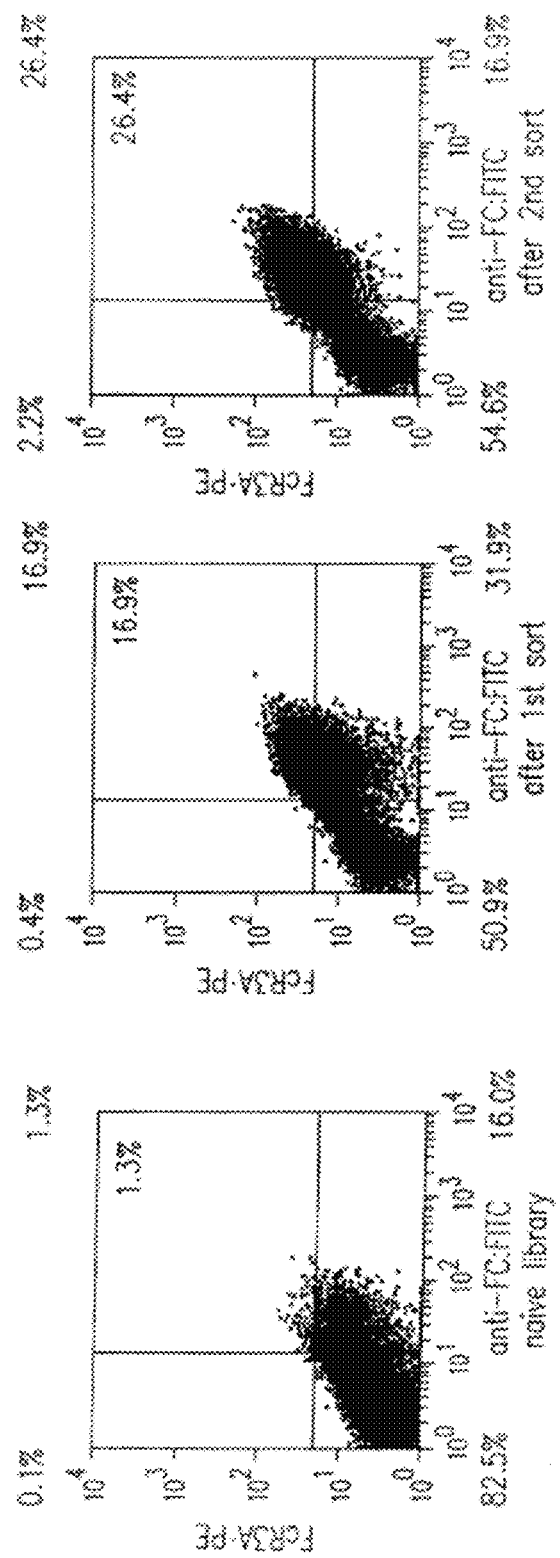

PCD64 Day 0

PCD64 Day 8
Condition 1

PCD64 Day 8
Condition 2

CD32A Day 0

CD32A Day 8
Condition 1

CD32A Day 8
Condition 2

CD32B Day 0

CD32B Day 8
Condition 1

CD32B Day 8
Condition 2

CD16 Day 0

**CD16 Day 8
Condition 1**

**CD16 Day 8
Condition 2**

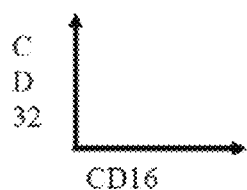
FIG. 15M
Day 0
Condition 1
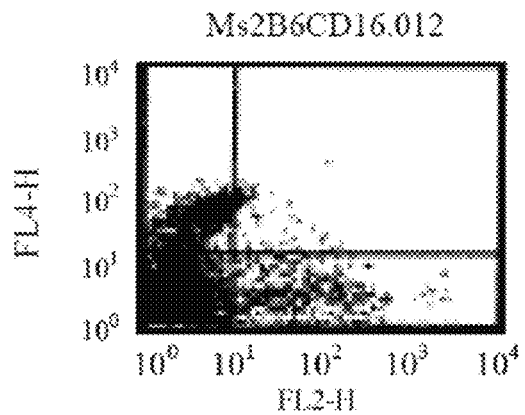
FIG. 15N
Day 8
Condition 1
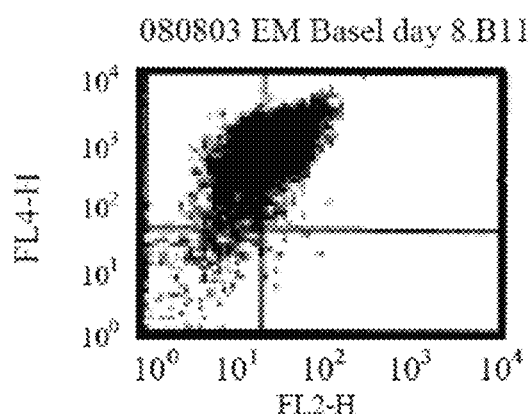
FIG. 15O
Day 8
Condition 1
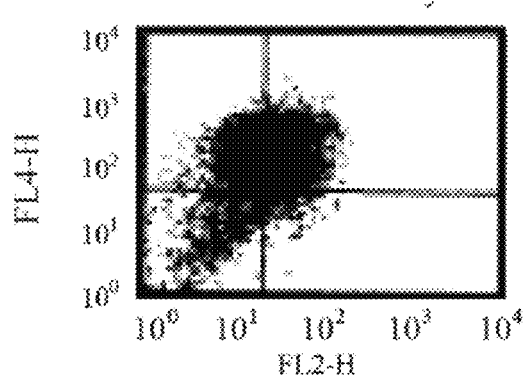

SEQUENCE LISTING

<160> NUMBER OF SEQ ID NOS: 44

<210> SEQ ID NO 1
<211> LENGTH: 121
<212> TYPE: PRT
<213> ORGANISM: Artificial
<220> FEATURE:
<223> OTHER INFORMATION: Humanized heavy chain variable region

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Ile His Trp Val Arg Gln Ala Pro Gly Gln Gly Leu Glu Trp Met
            35                  40                  45

Gly Val Ile Asp Pro Ser Asp Thr Tyr Pro Asn Tyr Asn Lys Lys Phe
        50                  55                  60

Lys Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Gly Asp Ser Asp Tyr Tyr Ser Gly Met Asp Tyr Trp Gly
                100                 105                 110

Gln Gly Thr Thr Val Thr Val Ser Ser
            115                 120

<210> SEQ ID NO 2

```
<211> LENGTH: 121
<212> TYPE: PRT
<213> ORGANISM: Artificial
<220> FEATURE:
<223> OTHER INFORMATION: humanized heavy chain variable region H2B6VH-A

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Ile
        35                  40                  45

Gly Val Ile Asp Pro Ser Asp Thr Tyr Pro Asn Tyr Asn Lys Lys Phe
    50                  55                  60

Lys Gly Arg Val Thr Met Thr Val Val Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Gly Asp Ser Asp Tyr Tyr Ser Gly Met Asp Tyr Trp Gly
            100                 105                 110

Gln Gly Thr Thr Val Thr Val Ser Ser
        115                 120

<210> SEQ ID NO 3
<211> LENGTH: 121
<212> TYPE: PRT
<213> ORGANISM: Artificial
<220> FEATURE:
<223> OTHER INFORMATION: Humanized heavy chain variable region H2B6VH-3

<400> SEQUENCE: 3

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Ile
        35                  40                  45

Gly Val Ile Asp Pro Ser Asp Thr Tyr Pro Asn Tyr Asn Lys Lys Phe
    50                  55                  60

Lys Gly Arg Val Thr Met Thr Val Asp Thr Ser Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Gly Asp Ser Asp Tyr Tyr Ser Gly Met Asp Tyr Trp Gly
            100                 105                 110

Gln Gly Thr Thr Val Thr Val Ser Ser
        115                 120

<210> SEQ ID NO 4
<211> LENGTH: 107
<212> TYPE: PRT
<213> ORGANISM: Artificial
<220> FEATURE:
<223> OTHER INFORMATION: Humanized 2B6 Light Chain Variable Region-
      Hu2B6VL-1

<400> SEQUENCE: 4

Glu Ile Val Leu Thr Gln Ser Pro Asp Phe Gln Ser Val Thr Pro Lys
1               5                   10                  15
```

Glu Lys Val Thr Ile Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Asn Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys
                100                 105

<210> SEQ ID NO 5
<211> LENGTH: 107
<212> TYPE: PRT
<213> ORGANISM: Artificial
<220> FEATURE:
<223> OTHER INFORMATION: Humanized 2B6 light chain variable region-
      Hu2B6VL-2

<400> SEQUENCE: 5

Glu Ile Val Leu Thr Gln Ser Pro Asp Phe Gln Ser Val Thr Pro Lys
1               5                   10                  15

Glu Lys Val Thr Ile Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys
                100                 105

<210> SEQ ID NO 6
<211> LENGTH: 107
<212> TYPE: PRT
<213> ORGANISM: Artificial
<220> FEATURE:
<223> OTHER INFORMATION: Humanized 2B6 light chain variable region-
      Hu2B6VL-3

<400> SEQUENCE: 6

Glu Ile Val Leu Thr Gln Ser Pro Asp Phe Gln Ser Val Thr Pro Lys
1               5                   10                  15

Glu Lys Val Thr Ile Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Tyr Ala Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

```
Thr Phe Gly Gly Gly Thr Lys Val Glu Ile Lys
                100                 105

<210> SEQ ID NO 7
<211> LENGTH: 107
<212> TYPE: PRT
<213> ORGANISM: Mus sp.
<220> FEATURE:
<221> NAME/KEY: MISC_FEATURE
<222> LOCATION: (1)..(107)
<223> OTHER INFORMATION: mouse 3H7 Light Chain Variable Region

<400> SEQUENCE: 7

Asp Ile Gln Met Thr Gln Ser Pro Ser Ser Leu Ser Ala Ser Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Arg Arg Leu Ile
        35                  40                  45

Tyr Ala Ala Ser Thr Leu Asp Ser Gly Val Pro Lys Arg Phe Ser Gly
    50                  55                  60

Ser Trp Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Val Ser Tyr Pro Tyr
                85                  90                  95

Thr Phe Gly Gly Gly Thr Lys Leu Glu Ile Lys
                100                 105

<210> SEQ ID NO 8
<211> LENGTH: 107
<212> TYPE: PRT
<213> ORGANISM: Artificial
<220> FEATURE:
<223> OTHER INFORMATION: Humanized light chain variable region - H2B6VL-
      5

<400> SEQUENCE: 8

Glu Ile Val Leu Thr Gln Ser Pro Asp Phe Gln Ser Val Thr Pro Lys
1               5                   10                  15

Glu Lys Val Thr Phe Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Glu Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
65                  70                  75                  80

Glu Asp Ala Ala Thr Tyr Tyr Cys Gln Gln Ser Asn Thr Trp Pro Phe
                85                  90                  95

Thr Phe Gly Gly Gly Thr Lys Val Glu Ile Lys
                100                 105

<210> SEQ ID NO 9
<211> LENGTH: 116
<212> TYPE: PRT
<213> ORGANISM: Artificial
<220> FEATURE:
<223> OTHER INFORMATION: Human Variable Heavy Chain Domain 8B5.3.4 VH

<400> SEQUENCE: 9
```

```
Glu Val Lys Leu Glu Glu Ser Gly Gly Gly Leu Val Gln Pro Gly
1               5                   10                  15

Ser Met Lys Leu Ser Cys Glu Ala Ser Gly Phe Thr Phe Ser Asp Ala
            20                  25                  30

Trp Met Asp Trp Val Arg Gln Ser Pro Glu Lys Gly Leu Glu Trp Val
            35                  40                  45

Ala Glu Ile Arg Asn Lys Ala Lys Asn His Ala Thr Tyr Tyr Ala Glu
        50                  55                  60

Ser Val Ile Gly Arg Phe Thr Ile Ser Arg Asp Asp Ser Lys Ser Ser
65                  70                  75                  80

Val Tyr Leu Gln Met Asn Ser Leu Arg Ala Glu Asp Thr Gly Ile Tyr
                85                  90                  95

Tyr Cys Gly Ala Leu Gly Leu Asp Tyr Trp Gly Gln Gly Thr Thr Leu
            100                 105                 110

Thr Val Ser Ser
        115
```

```
<210> SEQ ID NO 10
<211> LENGTH: 107
<212> TYPE: PRT
<213> ORGANISM: Artificial
<220> FEATURE:
<223> OTHER INFORMATION: Human Variable Light Chain Domain 8B5.3.4 VL

<400> SEQUENCE: 10
```

```
Asp Ile Gln Met Thr Gln Ser Pro Ser Ser Leu Leu Ala Ala Leu Gly
1               5                   10                  15

Glu Arg Val Ser Leu Thr Cys Arg Ala Ser Gln Glu Ile Ser Gly Tyr
            20                  25                  30

Leu Ser Trp Leu Gln Gln Lys Pro Asp Gly Thr Ile Lys Arg Leu Ile
            35                  40                  45

Tyr Ala Ala Ser Thr Leu Asp Ser Gly Val Pro Lys Arg Phe Ser Gly
        50                  55                  60

Ser Glu Ser Gly Ser Asp Tyr Ser Leu Thr Ile Ser Ser Leu Glu Ser
65                  70                  75                  80

Glu Asp Phe Ala Asp Tyr Tyr Cys Leu Gln Tyr Phe Ser Tyr Pro Leu
                85                  90                  95

Thr Phe Gly Ala Gly Thr Lys Leu Glu Leu Lys
            100                 105
```

```
<210> SEQ ID NO 11
<211> LENGTH: 321
<212> TYPE: DNA
<213> ORGANISM: Artificial
<220> FEATURE:
<223> OTHER INFORMATION: Human variable light chain domain 8B5.3.4 VL

<400> SEQUENCE: 11
```

```
gacattcaga tgacacagtc tccatcctcc ctacttgcgg cgctgggaga aagagtcagt      60
ctcacttgtc gggcaagtca ggaaattagt ggttacttaa gctggcttca gcagaaacca     120
gatggaacta ttaaacgcct gatctacgcc gcatccactt tagattctgg tgtcccaaaa     180
aggttcagtg cagtgagtc tgggtcagat tattctctca ccatcagcag tcttgagtct     240
gaagattttg cagactatta ctgtctacaa tattttagtt atccgctcac gttcggtgct     300
gggaccaagc tggagctgaa a                                              321
```

```
<210> SEQ ID NO 12
```

```
<211> LENGTH: 348
<212> TYPE: DNA
<213> ORGANISM: Artificial
<220> FEATURE:
<223> OTHER INFORMATION: Human variable heavy chain domain 8B5.3.4 VH

<400> SEQUENCE: 12
gaagtgaagc ttgaggagtc tggaggaggc ttggtgcaac ctggaggatc catgaaactc      60
tcttgtgaag cctctggatt cacttttagt gacgcctgga tggactgggt ccgtcagtct     120
ccagagaagg ggcttgagtg ggttgctgaa attagaaaca aagctaaaaa tcatgcaaca     180
tactatgctg agtctgtgat agggaggttc accatctcaa gagatgattc caaaagtagt     240
gtctacctgc aaatgaacag cttaagagct gaagacactg catttatta ctgtggggct      300 ctgggccttg actactgggg ccaaggcacc actctcacag tctcctcg                  348

<210> SEQ ID NO 13
<211> LENGTH: 121
<212> TYPE: PRT
<213> ORGANISM: Mus sp.
<220> FEATURE:
<221> NAME/KEY: MISC_FEATURE
<222> LOCATION: (1)..(121)
<223> OTHER INFORMATION: Mouse 2B6 heavy chain variable region

<400> SEQUENCE: 13

Gln Val Gln Leu Gln Gln Pro Val Thr Glu Leu Val Arg Pro Gly Ala
1               5                   10                  15

Ser Val Met Leu Ser Cys Lys Ala Ser Asp Tyr Pro Phe Thr Asn Tyr
            20                  25                  30

Trp Ile His Trp Val Lys Gln Arg Pro Gly Gln Gly Leu Glu Trp Ile
        35                  40                  45

Gly Val Ile Asp Pro Ser Asp Thr Tyr Pro Asn Tyr Asn Lys Lys Phe
    50                  55                  60

Lys Gly Lys Ala Thr Leu Thr Val Val Ser Ser Thr Ala Tyr
65                  70                  75                  80

Met Gln Leu Ser Ser Leu Thr Ser Asp Asp Ser Ala Val Tyr Tyr Cys
                85                  90                  95

Ala Arg Asn Gly Asp Ser Asp Tyr Tyr Ser Gly Met Asp Tyr Trp Gly
            100                 105                 110

Gln Gly Thr Ser Val Thr Val Ser Ser
        115                 120

<210> SEQ ID NO 14
<211> LENGTH: 107
<212> TYPE: PRT
<213> ORGANISM: Mus sp.
<220> FEATURE:
<221> NAME/KEY: MISC_FEATURE
<222> LOCATION: (1)..(107)
<223> OTHER INFORMATION: Mouse 2B6 light chain variable region

<400> SEQUENCE: 14

Asp Ile Leu Leu Thr Gln Ser Pro Ala Ile Leu Ser Val Ser Pro Gly
1               5                   10                  15

Glu Arg Val Ser Phe Ser Cys Arg Thr Ser Gln Ser Ile Gly Thr Asn
            20                  25                  30

Ile His Trp Tyr Gln Gln Arg Thr Asn Gly Phe Pro Arg Leu Leu Ile
        35                  40                  45

Lys Asn Val Ser Glu Ser Ile Ser Gly Ile Pro Ser Arg Phe Ser Gly
    50                  55                  60
```

```
Ser Gly Ser Gly Thr Asp Phe Ile Leu Ser Ile Asn Ser Val Glu Ser
65                  70                  75                  80

Glu Asp Ile Ala Asp Tyr Tyr Cys Gln Gln Ser Asn Thr Trp Pro Phe
                85                  90                  95

Thr Phe Gly Gly Gly Thr Lys Leu Glu Ile Lys
            100                 105

<210> SEQ ID NO 15
<211> LENGTH: 5
<212> TYPE: PRT
<213> ORGANISM: Artificial
<220> FEATURE:
<223> OTHER INFORMATION: 2B6 Heavy Chain Variable Region-CDR1

<400> SEQUENCE: 15

Asn Tyr Trp Ile His
1               5

<210> SEQ ID NO 16
<211> LENGTH: 5
<212> TYPE: PRT
<213> ORGANISM: Artificial
<220> FEATURE:
<223> OTHER INFORMATION: 3H7 Heavy Chain Variable region - CDR1

<400> SEQUENCE: 16

Asp Ala Trp Met Asp
1               5

<210> SEQ ID NO 17
<211> LENGTH: 17
<212> TYPE: PRT
<213> ORGANISM: Artificial
<220> FEATURE:
<223> OTHER INFORMATION: 2B6 Heavy chain variable region - CDR2

<400> SEQUENCE: 17

Val Ile Asp Pro Ser Asp Thr Tyr Pro Asn Tyr Asn Lys Lys Phe Lys
1               5                   10                  15

Gly

<210> SEQ ID NO 18
<211> LENGTH: 19
<212> TYPE: PRT
<213> ORGANISM: Artificial
<220> FEATURE:
<223> OTHER INFORMATION: 3H7 Heavy Chain Variable region - CDR2

<400> SEQUENCE: 18

Glu Ile Arg Asn Lys Ala Asn Asn Leu Ala Thr Tyr Tyr Ala Glu Ser
1               5                   10                  15

Val Lys Gly

<210> SEQ ID NO 19
<211> LENGTH: 12
<212> TYPE: PRT
<213> ORGANISM: Artificial
<220> FEATURE:
<223> OTHER INFORMATION: 2B6 Heavy chain variable region - CDR3

<400> SEQUENCE: 19

Asn Gly Asp Ser Asp Tyr Tyr Ser Gly Met Asp Tyr
1               5                   10
```

<210> SEQ ID NO 20
<211> LENGTH: 6
<212> TYPE: PRT
<213> ORGANISM: Artificial
<220> FEATURE:
<223> OTHER INFORMATION: 2B6 Light chain variable region - CDR1

<400> SEQUENCE: 20

```
Tyr Ser Pro Phe Ala Tyr
1               5
```

<210> SEQ ID NO 21
<211> LENGTH: 11
<212> TYPE: PRT
<213> ORGANISM: Artificial
<220> FEATURE:
<223> OTHER INFORMATION: 2B6 Light chain variable region - CDR1

<400> SEQUENCE: 21

```
Arg Thr Ser Gln Ser Ile Gly Thr Asn Ile His
1               5                   10
```

<210> SEQ ID NO 22
<211> LENGTH: 11
<212> TYPE: PRT
<213> ORGANISM: Artificial
<220> FEATURE:
<223> OTHER INFORMATION: 3H7 Light Chain Variable region - CDR1

<400> SEQUENCE: 22

```
Arg Ala Ser Gln Glu Ile Ser Gly Tyr Leu Ser
1               5                   10
```

<210> SEQ ID NO 23
<211> LENGTH: 7
<212> TYPE: PRT
<213> ORGANISM: Artificial
<220> FEATURE:
<223> OTHER INFORMATION: 2B6 Light chain variable region - CDR2

<400> SEQUENCE: 23

```
Asn Val Ser Glu Ser Ile Ser
1               5
```

<210> SEQ ID NO 24
<211> LENGTH: 7
<212> TYPE: PRT
<213> ORGANISM: Artificial
<220> FEATURE:
<223> OTHER INFORMATION: 2B6 Light chain variable region - CDR2

<400> SEQUENCE: 24

```
Tyr Val Ser Glu Ser Ile Ser
1               5
```

<210> SEQ ID NO 25
<211> LENGTH: 7
<212> TYPE: PRT
<213> ORGANISM: Artificial
<220> FEATURE:
<223> OTHER INFORMATION: 2B6 Light chain variable region - CDR2

<400> SEQUENCE: 25

```
Tyr Ala Ser Glu Ser Ile Ser
1               5
```

```
<210> SEQ ID NO 26
<211> LENGTH: 7
<212> TYPE: PRT
<213> ORGANISM: Artificial
<220> FEATURE:
<223> OTHER INFORMATION: 3H7 Light Chain Variable region - CDR2

<400> SEQUENCE: 26

Ala Ala Ser Thr Leu Asp Ser
1               5

<210> SEQ ID NO 27
<211> LENGTH: 9
<212> TYPE: PRT
<213> ORGANISM: Artificial
<220> FEATURE:
<223> OTHER INFORMATION: 2B6 Light chain variable region - CDR3

<400> SEQUENCE: 27

Gln Gln Ser Asn Thr Trp Pro Phe Thr
1               5

<210> SEQ ID NO 28
<211> LENGTH: 9
<212> TYPE: PRT
<213> ORGANISM: Artificial
<220> FEATURE:
<223> OTHER INFORMATION: 3H7 Light Chain Variable region - CDR3

<400> SEQUENCE: 28

Leu Gln Tyr Val Ser Tyr Pro Tyr Thr
1               5

<210> SEQ ID NO 29
<211> LENGTH: 451
<212> TYPE: PRT
<213> ORGANISM: Artificial
<220> FEATURE:
<223> OTHER INFORMATION: humanized 2B6 antibody heavy chain

<400> SEQUENCE: 29

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
                20                  25                  30

Trp Ile His Trp Val Arg Gln Ala Pro Gly Gln Gly Leu Glu Trp Ile
            35                  40                  45

Gly Val Ile Asp Pro Ser Asp Thr Tyr Pro Asn Tyr Asn Lys Lys Phe
    50                  55                  60

Lys Gly Arg Val Thr Met Thr Val Asp Thr Ser Thr Ser Thr Ala Tyr
65                  70                  75                  80

Met Glu Leu Arg Ser Leu Arg Ser Asp Thr Ala Val Tyr Tyr Cys
                85                  90                  95

Ala Arg Asn Gly Asp Ser Asp Tyr Ser Gly Met Asp Tyr Trp Gly
                100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
```

```
            165                 170                 175
Val Leu Gln Ser Ser Gly Leu Tyr Ser Leu Ser Ser Val Val Thr Val
            180                 185                 190

Pro Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Leu Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Arg Glu Glu Gln Tyr Asn Ser Thr Leu
290                 295                 300

Arg Val Val Ser Ile Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
            325                 330                 335

Glu Lys Thr Ile Ser Lys Ala Lys Gly Gln Pro Arg Glu Pro Gln Val
        340                 345                 350

Tyr Thr Leu Pro Pro Ser Arg Asp Glu Leu Thr Lys Asn Gln Val Ser
    355                 360                 365

Leu Thr Cys Leu Val Lys Gly Phe Tyr Pro Ser Asp Ile Ala Val Glu
370                 375                 380

Trp Glu Ser Asn Gly Gln Pro Glu Asn Asn Tyr Lys Thr Thr Pro Leu
385                 390                 395                 400

Val Leu Asp Ser Asp Gly Ser Phe Phe Leu Tyr Ser Lys Leu Thr Val
            405                 410                 415

Asp Lys Ser Arg Trp Gln Gln Gly Asn Val Phe Ser Cys Ser Val Met
        420                 425                 430

His Glu Ala Leu His Asn His Tyr Thr Gln Lys Ser Leu Ser Leu Ser
    435                 440                 445

Pro Gly Lys
    450

<210> SEQ ID NO 30
<211> LENGTH: 214
<212> TYPE: PRT
<213> ORGANISM: Artificial
<220> FEATURE:
<223> OTHER INFORMATION: Humanized 2B6 antibody Light Chain

<400> SEQUENCE: 30

Glu Ile Val Leu Thr Gln Ser Pro Asp Phe Gln Ser Val Thr Pro Lys
1               5                   10                  15

Glu Lys Val Thr Phe Thr Cys Arg Thr Ser Gln Ser Ile Gly Thr Asn
            20                  25                  30

Ile His Trp Tyr Gln Gln Lys Pro Asp Gln Ser Pro Lys Leu Leu Ile
        35                  40                  45

Lys Glu Val Ser Glu Ser Ile Ser Gly Val Pro Ser Arg Phe Ser Gly
    50                  55                  60

Ser Gly Ser Gly Thr Asp Phe Thr Leu Thr Ile Asn Ser Leu Glu Ala
```

```
            65                  70                  75                  80
Glu Asp Ala Ala Thr Tyr Tyr Cys Gln Gln Ser Asn Thr Trp Pro Phe
                    85                  90                  95

Thr Phe Gly Gly Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 31
<211> LENGTH: 1255
<212> TYPE: PRT
<213> ORGANISM: Artificial
<220> FEATURE:
<223> OTHER INFORMATION: Her2/neu receptor

<400> SEQUENCE: 31

Met Glu Leu Ala Ala Leu Cys Arg Trp Gly Leu Leu Leu Ala Leu Leu
1               5                   10                  15

Pro Pro Gly Ala Ala Ser Thr Gln Val Cys Thr Gly Thr Asp Met Lys
                20                  25                  30

Leu Arg Leu Pro Ala Ser Pro Glu Thr His Leu Asp Met Leu Arg His
            35                  40                  45

Leu Tyr Gln Gly Cys Gln Val Val Gln Gly Asn Leu Glu Leu Thr Tyr
        50                  55                  60

Leu Pro Thr Asn Ala Ser Leu Ser Phe Leu Gln Asp Ile Gln Glu Val
65                  70                  75                  80

Gln Gly Tyr Val Leu Ile Ala His Asn Gln Val Arg Gln Val Pro Leu
                85                  90                  95

Gln Arg Leu Arg Ile Val Arg Gly Thr Gln Leu Phe Glu Asp Asn Tyr
                100                 105                 110

Ala Leu Ala Val Leu Asp Asn Gly Asp Pro Leu Asn Asn Thr Thr Pro
            115                 120                 125

Val Thr Gly Ala Ser Pro Gly Gly Leu Arg Glu Leu Gln Leu Arg Ser
        130                 135                 140

Leu Thr Glu Ile Leu Lys Gly Gly Val Leu Ile Gln Arg Asn Pro Gln
145                 150                 155                 160

Leu Cys Tyr Gln Asp Thr Ile Leu Trp Lys Asp Ile Phe His Lys Asn
                165                 170                 175

Asn Gln Leu Ala Leu Thr Leu Ile Asp Thr Asn Arg Ser Arg Ala Cys
            180                 185                 190

His Pro Cys Ser Pro Met Cys Lys Gly Ser Arg Cys Trp Gly Glu Ser
        195                 200                 205

Ser Glu Asp Cys Gln Ser Leu Thr Arg Thr Val Cys Ala Gly Gly Cys
```

```
             210                 215                 220
Ala Arg Cys Lys Gly Pro Leu Pro Thr Asp Cys Cys His Glu Gln Cys
225                 230                 235                 240

Ala Ala Gly Cys Thr Gly Pro Lys His Ser Asp Cys Leu Ala Cys Leu
                245                 250                 255

His Phe Asn His Ser Gly Ile Cys Glu Leu His Cys Pro Ala Leu Val
                260                 265                 270

Thr Tyr Asn Thr Asp Thr Phe Glu Ser Met Pro Asn Pro Glu Gly Arg
                275                 280                 285

Tyr Thr Phe Gly Ala Ser Cys Val Thr Ala Cys Pro Tyr Asn Tyr Leu
                290                 295                 300

Ser Thr Asp Val Gly Ser Cys Thr Leu Val Cys Pro Leu His Asn Gln
305                 310                 315                 320

Glu Val Thr Ala Glu Asp Gly Thr Gln Arg Cys Glu Lys Cys Ser Lys
                325                 330                 335

Pro Cys Ala Arg Val Cys Tyr Gly Leu Gly Met Glu His Leu Arg Glu
                340                 345                 350

Val Arg Ala Val Thr Ser Ala Asn Ile Gln Glu Phe Ala Gly Cys Lys
                355                 360                 365

Lys Ile Phe Gly Ser Leu Ala Phe Leu Pro Glu Ser Phe Asp Gly Asp
                370                 375                 380

Pro Ala Ser Asn Thr Ala Pro Leu Gln Pro Glu Gln Leu Gln Val Phe
385                 390                 395                 400

Glu Thr Leu Glu Glu Ile Thr Gly Tyr Leu Tyr Ile Ser Ala Trp Pro
                405                 410                 415

Asp Ser Leu Pro Asp Leu Ser Val Phe Gln Asn Leu Gln Val Ile Arg
                420                 425                 430

Gly Arg Ile Leu His Asn Gly Ala Tyr Ser Leu Thr Leu Gln Gly Leu
                435                 440                 445

Gly Ile Ser Trp Leu Gly Leu Arg Ser Leu Arg Glu Leu Gly Ser Gly
                450                 455                 460

Leu Ala Leu Ile His His Asn Thr His Leu Cys Phe Val His Thr Val
465                 470                 475                 480

Pro Trp Asp Gln Leu Phe Arg Asn Pro His Gln Ala Leu Leu His Thr
                485                 490                 495

Ala Asn Arg Pro Glu Asp Glu Cys Val Gly Glu Gly Leu Ala Cys His
                500                 505                 510

Gln Leu Cys Ala Arg Gly His Cys Trp Gly Pro Gly Pro Thr Gln Cys
                515                 520                 525

Val Asn Cys Ser Gln Phe Leu Arg Gly Gln Glu Cys Val Glu Glu Cys
                530                 535                 540

Arg Val Leu Gln Gly Leu Pro Arg Glu Tyr Val Asn Ala Arg His Cys
545                 550                 555                 560

Leu Pro Cys His Pro Glu Cys Gln Pro Gln Asn Gly Ser Val Thr Cys
                565                 570                 575

Phe Gly Pro Glu Ala Asp Gln Cys Val Ala Cys Ala His Tyr Lys Asp
                580                 585                 590

Pro Pro Phe Cys Val Ala Arg Cys Pro Ser Gly Val Lys Pro Asp Leu
                595                 600                 605

Ser Tyr Met Pro Ile Trp Lys Phe Pro Asp Glu Glu Gly Ala Cys Gln
                610                 615                 620

Pro Cys Pro Ile Asn Cys Thr His Ser Cys Val Asp Leu Asp Asp Lys
625                 630                 635                 640
```

```
Gly Cys Pro Ala Glu Gln Arg Ala Ser Pro Leu Thr Ser Ile Ile Ser
                645                 650                 655

Ala Val Val Gly Ile Leu Leu Val Val Leu Gly Val Val Phe Gly
                660                 665                 670

Ile Leu Ile Lys Arg Arg Gln Gln Lys Ile Arg Lys Tyr Thr Met Arg
                675                 680                 685

Arg Leu Leu Gln Glu Thr Glu Leu Val Glu Pro Leu Thr Pro Ser Gly
                690                 695                 700

Ala Met Pro Asn Gln Ala Gln Met Arg Ile Leu Lys Glu Thr Glu Leu
705                 710                 715                 720

Arg Lys Val Lys Val Leu Gly Ser Gly Ala Phe Gly Thr Val Tyr Lys
                725                 730                 735

Gly Ile Trp Ile Pro Asp Gly Glu Asn Val Lys Ile Pro Val Ala Ile
                740                 745                 750

Lys Val Leu Arg Glu Asn Thr Ser Pro Lys Ala Asn Lys Glu Ile Leu
                755                 760                 765

Asp Glu Ala Tyr Val Met Ala Gly Val Gly Ser Pro Tyr Val Ser Arg
                770                 775                 780

Leu Leu Gly Ile Cys Leu Thr Ser Thr Val Gln Leu Val Thr Gln Leu
785                 790                 795                 800

Met Pro Tyr Gly Cys Leu Leu Asp His Val Arg Glu Asn Arg Gly Arg
                805                 810                 815

Leu Gly Ser Gln Asp Leu Leu Asn Trp Cys Met Gln Ile Ala Lys Gly
                820                 825                 830

Met Ser Tyr Leu Glu Asp Val Arg Leu Val His Arg Asp Leu Ala Ala
                835                 840                 845

Arg Asn Val Leu Val Lys Ser Pro Asn His Val Lys Ile Thr Asp Phe
850                 855                 860

Gly Leu Ala Arg Leu Leu Asp Ile Asp Glu Thr Glu Tyr His Ala Asp
865                 870                 875                 880

Gly Gly Lys Val Pro Ile Lys Trp Met Ala Leu Glu Ser Ile Leu Arg
                885                 890                 895

Arg Arg Phe Thr His Gln Ser Asp Val Trp Ser Tyr Gly Val Thr Val
                900                 905                 910

Trp Glu Leu Met Thr Phe Gly Ala Lys Pro Tyr Asp Gly Ile Pro Ala
                915                 920                 925

Arg Glu Ile Pro Asp Leu Leu Glu Lys Gly Glu Arg Leu Pro Gln Pro
930                 935                 940

Pro Ile Cys Thr Ile Asp Val Tyr Met Ile Met Val Lys Cys Trp Met
945                 950                 955                 960

Ile Asp Ser Glu Cys Arg Pro Arg Phe Arg Glu Leu Val Ser Glu Phe
                965                 970                 975

Ser Arg Met Ala Arg Asp Pro Gln Arg Phe Val Val Ile Gln Asn Glu
                980                 985                 990

Asp Leu Gly Pro Ala Ser Pro Leu Asp Ser Thr Phe Tyr Arg Ser Leu
                995                 1000                1005

Leu Glu Asp Asp Asp Met Gly Asp Leu Val Asp Ala Glu Glu Tyr
                1010                1015                1020

Leu Val Pro Gln Gln Gly Phe Phe Cys Pro Asp Pro Ala Pro Gly
                1025                1030                1035

Ala Gly Gly Met Val His His Arg His Arg Ser Ser Ser Thr Arg
                1040                1045                1050
```

```
Ser Gly Gly Gly Asp Leu Thr Leu Gly Leu Glu Pro Ser Glu Glu
    1055                1060                1065

Glu Ala Pro Arg Ser Pro Leu Ala Pro Ser Glu Gly Ala Gly Ser
    1070                1075                1080

Asp Val Phe Asp Gly Asp Leu Gly Met Gly Ala Ala Lys Gly Leu
    1085                1090                1095

Gln Ser Leu Pro Thr His Asp Pro Ser Pro Leu Gln Arg Tyr Ser
    1100                1105                1110

Glu Asp Pro Thr Val Pro Leu Pro Ser Glu Thr Asp Gly Tyr Val
    1115                1120                1125

Ala Pro Leu Thr Cys Ser Pro Gln Pro Glu Tyr Val Asn Gln Pro
    1130                1135                1140

Asp Val Arg Pro Gln Pro Pro Ser Pro Arg Glu Gly Pro Leu Pro
    1145                1150                1155

Ala Ala Arg Pro Ala Gly Ala Thr Leu Glu Arg Pro Lys Thr Leu
    1160                1165                1170

Ser Pro Gly Lys Asn Gly Val Val Lys Asp Val Phe Ala Phe Gly
    1175                1180                1185

Gly Ala Val Glu Asn Pro Glu Tyr Leu Thr Pro Gln Gly Gly Ala
    1190                1195                1200

Ala Pro Gln Pro His Pro Pro Ala Phe Ser Pro Ala Phe Asp
    1205                1210                1215

Asn Leu Tyr Tyr Trp Asp Gln Asp Pro Pro Glu Arg Gly Ala Pro
    1220                1225                1230

Pro Ser Thr Phe Lys Gly Thr Pro Thr Ala Glu Asn Pro Glu Tyr
    1235                1240                1245

Leu Gly Leu Asp Val Pro Val
    1250                1255

<210> SEQ ID NO 32
<211> LENGTH: 120
<212> TYPE: PRT
<213> ORGANISM: Mus sp.
<220> FEATURE:
<221> NAME/KEY: MISC_FEATURE
<222> LOCATION: (1)..(120)
<223> OTHER INFORMATION: Murine Amino Acid Sequence of antibody 4d5
      (heavy chain)

<400> SEQUENCE: 32

Gln Val Gln Leu Gln Gln Ser Gly Pro Glu Leu Val Lys Pro Gly Ala
1               5                   10                  15

Ser Leu Lys Leu Ser Cys Thr Ala Ser Gly Phe Asn Ile Lys Asp Thr
            20                  25                  30

Tyr Ile His Trp Val Lys Gln Arg Pro Glu Gln Gly Leu Glu Trp Ile
        35                  40                  45

Gly Arg Ile Tyr Pro Thr Asn Gly Tyr Thr Arg Tyr Asp Pro Lys Phe
    50                  55                  60

Gln Asp Lys Ala Thr Ile Thr Ala Asp Thr Ser Ser Asn Thr Ala Tyr
65                  70                  75                  80

Leu Gln Val Ser Arg Leu Thr Ser Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Ala Ser Val Thr Val Ser Ser
        115                 120
```

-continued

<210> SEQ ID NO 33
<211> LENGTH: 109
<212> TYPE: PRT
<213> ORGANISM: Mus sp.
<220> FEATURE:
<221> NAME/KEY: MISC_FEATURE
<222> LOCATION: (1)..(109)
<223> OTHER INFORMATION: Murine Amino Acid Sequence of antibody 4d5
      (light chain)

<400> SEQUENCE: 33

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Asn Thr Ala
            20                  25                  30

Val Ala Trp Tyr Gln Gln Lys Pro Gly His Ser Pro Lys Leu Leu Ile
        35                  40                  45

Tyr Ser Ala Ser Phe Arg Tyr Thr Gly Val Pro Asp Arg Phe Thr Gly
    50                  55                  60

Asn Arg Ser Gly Thr Asp Phe Thr Phe Thr Ile Ser Ser Val Gln Ala
65                  70                  75                  80

Ala Asp Leu Ala Val Tyr Tyr Cys Gln Gln His Tyr Thr Thr Pro Pro
                85                  90                  95

Thr Phe Gly Gly Gly Thr Lys Leu Glu Ile Lys Arg Ala
            100                 105

<210> SEQ ID NO 34
<211> LENGTH: 120
<212> TYPE: PRT
<213> ORGANISM: Homo sapiens
<220> FEATURE:
<221> NAME/KEY: MISC_FEATURE
<222> LOCATION: (1)..(120)
<223> OTHER INFORMATION: Humanized Amino Acid Sequence of antibody 4d5
      (heavy chain)

<400> SEQUENCE: 34

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 35
<211> LENGTH: 109
<212> TYPE: PRT
<213> ORGANISM: Homo sapiens
<220> FEATURE:
<221> NAME/KEY: MISC_FEATURE
<222> LOCATION: (1)..(109)

<223> OTHER INFORMATION: Humanized Amino Acid Sequence of antibody
      4d5(light chain)

<400> SEQUENCE: 35

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Val Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr
            100                 105

<210> SEQ ID NO 36
<211> LENGTH: 5
<212> TYPE: PRT
<213> ORGANISM: Artificial
<220> FEATURE:
<223> OTHER INFORMATION: 4D5 Heavy Chain Variable Region - CDR1

<400> SEQUENCE: 36

Asp Thr Tyr Ile His
1               5

<210> SEQ ID NO 37
<211> LENGTH: 16
<212> TYPE: PRT
<213> ORGANISM: Artificial
<220> FEATURE:
<223> OTHER INFORMATION: 4D5 Heavy Chain Variable Region - CDR2

<400> SEQUENCE: 37

Arg Ile Tyr Pro Thr Asn Gly Tyr Thr Arg Tyr Asp Pro Lys Phe Gln
1               5                   10                  15

<210> SEQ ID NO 38
<211> LENGTH: 11
<212> TYPE: PRT
<213> ORGANISM: Artificial
<220> FEATURE:
<223> OTHER INFORMATION: 4D5 Heavy Chain Variable Region - CDR3

<400> SEQUENCE: 38

Trp Gly Gly Asp Gly Phe Tyr Ala Met Asp Tyr
1               5                   10

<210> SEQ ID NO 39
<211> LENGTH: 11
<212> TYPE: PRT
<213> ORGANISM: Artificial
<220> FEATURE:
<223> OTHER INFORMATION: 4D5 Light Chain Variable Region - CDR1

<400> SEQUENCE: 39

Lys Ala Ser Gln Asp Val Asn Thr Ala Val Ala
1               5                   10

```
<210> SEQ ID NO 40
<211> LENGTH: 7
<212> TYPE: PRT
<213> ORGANISM: Artificial
<220> FEATURE:
<223> OTHER INFORMATION: 4D5 Light Chain Variable Region - CDR2

<400> SEQUENCE: 40

Ser Ala Ser Phe Arg Tyr Thr
1               5

<210> SEQ ID NO 41
<211> LENGTH: 9
<212> TYPE: PRT
<213> ORGANISM: Artificial
<220> FEATURE:
<223> OTHER INFORMATION: 4D5 Light Chain Variable Region - CDR3

<400> SEQUENCE: 41

Gln Gln His Tyr Thr Thr Pro Pro Thr
1               5

<210> SEQ ID NO 42
<211> LENGTH: 451
<212> TYPE: PRT
<213> ORGANISM: Artificial
<220> FEATURE:
<223> OTHER INFORMATION: humanized 2B6 antibody heavy chain

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Trp Ile His Trp Val Arg Gln Ala Pro Gly Gln Gly Leu Glu Trp Ile
        35                  40                  45

Gly Val Ile Asp Pro Ser Asp Thr Tyr Pro Asn Tyr Asn Lys Lys Phe
    50                  55                  60

Lys Gly Arg Val Thr Met Thr Val Val Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Asn Gly Asp Ser Asp Tyr Tyr Ser Gly Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240
```

Gly Pro Ser Val Phe Leu Leu Pro Pro Lys Pro Lys Asp Thr Leu Met
            245                 250                 255

Ile Ser Arg Thr Pro Glu Val Thr Cys Val Val Val Asp Val Ser His
        260                 265                 270

Glu Asp Pro Glu Val Lys Phe Asn Trp Tyr Val Asp Gly Val Glu Val
    275                 280                 285

His Asn Ala Lys Thr Lys Pro Pro Glu Glu Gln Tyr Asn Ser Thr Leu
290                 295                 300

Arg Val Val Ser Ile Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Leu
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 43
<211> LENGTH: 1356
<212> TYPE: DNA
<213> ORGANISM: Artificial
<220> FEATURE:
<223> OTHER INFORMATION: humanized 2B6 antibody heavy chain

<400> SEQUENCE: 43
caggttcagc tggtgcagtc tggagctgag gtgaagaagc ctggggcctc agtgaaggtc      60
tcctgcaagg cttctggtta cacctttacc aactactgga tacactgggt gcgacaggcc     120
cctggacaag ggcttgagtg gattggagtg attgatcctt ctgatactta tccaaattac     180
aataaaaagt tcaagggcag agtcaccatg accgtagaca tccacgagca cagcctac      240 atggagctga ggagcctgag atctgacgac acggccgtgt attactgtgc gagaaacggt     300
gattccgatt attactctgg tatggactac tgggggcaag gaccacggt caccgtctcc     360 tcagcctcca ccaagggccc atcggtcttc cccctggcac cctcctccaa gagcacctct     420
gggggcacag cggccctggg ctgcctggtc aaggactact tccccgaacc ggtgacggtg     480
tcgtggaact caggcgccct gaccagcggc gtgcacacct tcccggctgt cctacagtcc     540
tcaggactct actccctcag cagcgtggtg accgtgccct ccagcagctt gggcacccag     600
acctacatct gcaacgtgaa tcacaagccc agcaacacca aggtggacaa gagagttgag     660
cccaaatctt gtgacaaaac tcacacatgc ccaccgtgcc cagcacctga actcctgggg     720
ggaccgtcag tcttcctctt ccccccaaaa cccaaggaca ccctcatgat ctcccggacc     780

-continued

```
cctgaggtca catgcgtggt ggtggacgtg agccacgaag accctgaggt caagttcaac      840
tggtacgtgg acggcgtgga ggtgcataat gccaagacaa agccgccgga ggagcagtac      900
aacagcacgc tccgtgtggt cagcatcctc accgtcctgc accaggactg gctgaatggc      960
aaggagtaca agtgcaaggt ctccaacaaa gccctcccag cccccatcga gaaaaccatc     1020
tccaaagcca aagggcagcc ccgagaacca caggtgtaca ccctgccccc atcccgggat     1080
gagctgacca gaaccaggt cagcctgacc tgcctggtca aaggcttcta tcccagcgac     1140
atcgccgtgg agtgggagag caatgggcag ccggagaaca actacaagac cacgcctctc     1200
gtgctggact ccgacggctc cttcttcctc tacagcaagc tcaccgtgga caagagcagg     1260
tggcagcagg ggaacgtctt ctcatgctcc gtgatgcatg aggctctgca caaccactac     1320
acgcagaaga gcctctccct gtctccgggt aaatga                               1356
```

<210> SEQ ID NO 44
<211> LENGTH: 645
<212> TYPE: DNA
<213> ORGANISM: Artificial
<220> FEATURE:
<223> OTHER INFORMATION: humanized 2B6 antibody light chain

<400> SEQUENCE: 44

```
gaaattgtgc tgactcagtc tccagacttt cagtctgtga ctccaaagga gaaagtcacc       60
ttcacctgca ggaccagtca gagcattggc acaaacatac actggtacca gcagaaacca      120
gatcagtctc caaagctcct catcaaggag gtttctgagt ctatctctgg agtcccatcg      180
aggttcagtg gcagtggatc tgggacagat ttcacccctca ccatcaatag cctggaagct      240
gaagatgctg caacgtatta ctgtcaacaa agtaatacct ggccgttcac gttcggcgga      300
gggaccaagg tggagatcaa acgaactgtg gctgcaccat ctgtcttcat cttcccgcca      360
tctgatgagc agttgaaatc tggaactgcc tctgttgtgt gcctgctgaa taacttctat      420
cccagagagg ccaaagtaca gtggaaggtg gataacgccc tccaatcggg taactcccag      480
gagagtgtca cagagcagga cagcaaggac agcacctaca gcctcagcag caccctgacg      540
ctgagcaaag cagactacga gaaacacaaa gtctacgcct gcgaagtcac ccatcagggc      600
ctgagctcgc ccgtcacaaa gagcttcaac aggggagagt gttag                      645
```

METHODS FOR THE TREATMENT OF DISEASE USING IMMUNOGLOBULINS HAVING FC REGIONS WITH ALTERED AFFINITIES FOR FCGAMMARACTIVATING AND FEGAMMARINHIBITING

1. CROSS REFERENCE TO RELATED APPLICATIONS

This application is a continuation of U.S. application Ser. No. 15/621,710, filed on Jun. 13, 2017, which is a continuation of U.S. application Ser. No. 14/156,747, filed on Jan. 16, 2014, which issued as U.S. Pat. No. 9,708,408, which is a continuation of U.S. application Ser. No. 11/952,568, filed on Dec. 7, 2007, which issued as U.S. Pat. No. 8,652,466, which applications claim benefit to U.S. Patent Application Ser. No. 60/869,254, filed on Dec. 8, 2006, which applications are all incorporated herein by reference in their entireties and to which priority is claimed.

2. REFERENCE TO SEQUENCE LISTING

This application includes one or more Sequence Listings pursuant to 37 C.F.R. 1.821 et seq., which are disclosed in computer-readable media (file name: sequencelisting_ST25, created May 28, 2020, and having a size of 47,136 bytes), which file is herein incorporated by reference in its entirety.

3. FIELD OF THE INVENTION

The present invention relates to methods of treating or preventing cancer and other diseases using molecules, particularly polypeptides, more particularly immunoglobulins (e.g., antibodies), comprising a variant Fc region, wherein said variant Fc region comprises at least one amino acid modification relative to a wild-type Fc region, which variant Fc region binds an FcγR that activates a cellular effector ("FcγR$_{Activating}$," such as FcγRIIA or FcγRIIIA) and an FcγR that inhibits a cellular effector ("FcγR$_{Inhibiting}$," such as FcγRIIA) with an altered Ratio of Affinities relative to the respective binding affinities of such FcγR for the Fc region of the wild-type immunoglobulin. The methods of the invention are particularly useful in preventing, treating, or ameliorating one or more symptoms associated with a disease, disorder, or infection where an enhanced efficacy of effector cell function (e.g., ADCC) mediated by FcγR is desired, e.g., cancer, infectious disease. The methods of the invention are also of use in enhancing the therapeutic efficacy of therapeutic antibodies the effect of which is mediated by ADCC. Conversely, the methods of the invention are particularly useful in preventing, treating, or ameliorating one or more symptoms associated with a disease or disorder in which decreased efficacy of effector cell function mediated by FcγR is desired, e.g., inflammation, etc. The methods of the invention are thus also of use in enhancing the therapeutic efficacy of therapeutic antibodies which attenuate inflammatory processes.

4. BACKGROUND OF THE INVENTION 4.1 Fc Receptors and their Roles in the Immune System
The interaction of antibody-antigen complexes with cells of the immune system results in a wide array of responses, ranging from effector functions such as antibody-dependent cytotoxicity, mast cell degranulation, and phagocytosis to immunomodulatory signals such as regulating lymphocyte proliferation and antibody secretion. All these interactions are initiated through the binding of the Fc domain of antibodies or immune complexes to specialized cell surface receptors on hematopoietic cells. The diversity of cellular responses triggered by antibodies and immune complexes results from the structural heterogeneity of Fc receptors. Fc receptors share structurally related ligand binding domains which presumably mediate intracellular signaling.

The Fc receptors, members of the immunoglobulin gene superfamily of proteins, are surface glycoproteins that can bind the Fc portion of immunoglobulin molecules. Each member of the family recognizes immunoglobulins of one or more isotypes through a recognition domain on the a chain of the Fc receptor. Fc receptors are defined by their specificity for immunoglobulin subtypes. Fc receptors for IgG are referred to as FcγR, for IgE as RR, and for IgA as FcαR. Different accessory cells bear Fc receptors for antibodies of different isotype, and the isotype of the antibody determines which accessory cells will be engaged in a given response (reviewed by Ravetch J. V. et al. 1991, Annu. Rev. Immunol. 9: 457-92; Gerber J. S. et al. 2001 Microbes and Infection, 3: 131-139; Billadeau D. D. et al. 2002, The Journal of Clinical Investigation, 2(109): 161-1681; Ravetch J. V. et al. 2000, Science, 290: 84-89; Ravetch J. V. et al., 2001 Annu. Rev. Immunol. 19:275-90; Ravetch J. V. 1994, Cell, 78(4): 553-60). The different Fc receptors, the cells that express them, and their isotype specificity is well known in the art, see, e.g., Immunobiology: The Immune System in Health and Disease, 4$^{th}$ed. 1999, Elsevier Science Ltd/Garland Publishing, New York, which is hereby incorporated by reference in its entirety.

Fcγ Receptors
Each member of this family is an integral membrane glycoprotein, possessing extracellular domains related to a C2-set of immunoglobulin-related domains, a single membrane spanning domain and an intracytoplasmic domain of variable length. There are three known FcγRs, designated FcγRI (CD64), FcγRII (CD32), and FcγRIII (CD16). The three receptors are encoded by distinct genes; however, the extensive homology between the three family members suggest they arose from a common progenitor perhaps by gene duplication.

FcγRII (CD32)
FcγRII proteins are 40 KDa integral membrane glycoproteins which bind only the complexed IgG due to a low affinity for monomeric Ig ($10^6$ M$^{-1}$). This receptor is the most widely expressed FcγR, present on all hematopoietic cells, including monocytes, macrophages, B cells, NK cells, neutrophils, mast cells, and platelets. FcγRII has only two immunoglobulin-like regions in its immunoglobulin binding chain and hence a much lower affinity for IgG than FcγRI. There are three human FcγRII genes (FcγRII-A, FcγRII-B, FcγRII-C), all of which bind IgG in aggregates or immune complexes.

Distinct differences within the cytoplasmic domains of FcγRII-A and FcγRII-B create two functionally heterogenous responses to receptor ligation. The fundamental difference is that the A isoform initiates intracellular signaling leading to cell activation such as phagocytosis and respiratory burst, whereas the B isoform initiates inhibitory signals, e.g., inhibiting B-cell activation.

Signaling Through FcγRs
Both activating and inhibitory signals are transduced through the FcγRs following ligation. These diametrically opposing functions result from structural differences among the different receptor isoforms. Two distinct domains within the cytoplasmic signaling domains of the receptor called immunoreceptor tyrosine based activation motifs (ITAMs)

or immunoreceptor tyrosine based inhibitory motifs (IT-IMS) account for the different responses. The recruitment of different cytoplasmic enzymes to these structures dictates the outcome of the FcγR-mediated cellular responses. ITAM-containing FcγR complexes include FcγRI, FcγRIIA, FcγRIIIA, whereas ITIM-containing complexes only include FcγRIIB.

Human neutrophils express the FcγRIIA gene. FcγRIIA clustering via immune complexes or specific antibody cross-linking serves to aggregate ITAMs along with receptor-associated kinases which facilitate ITAM phosphorylation. ITAM phosphorylation serves as a docking site for Syk kinase, activation of which results in activation of downstream substrates (e.g., $PI_3K$). Cellular activation leads to release of proinflammatory mediators.

The FcγRIIB gene is expressed on B lymphocytes; its extracellular domain is 96% identical to FcγRIIA and binds IgG complexes in an indistinguishable manner. The presence of an ITIM in the cytoplasmic domain of FcγRIIB defines this inhibitory subclass of FcγR. Recently the molecular basis of this inhibition was established. When colligated along with an activating FcγR, the ITIM in FcγRIIB becomes phosphorylated and attracts the SH2 domain of the inositol polyphosphate 5'-phosphatase (SHIP), which hydrolyzes phophoinositol messengers released as a consequence of ITAM-containing FcγR-mediated tyrosine kinase activation, consequently preventing the influx of intracellular $Ca^{++}$. Thus crosslinking of FcγRIIB dampens the activating response to FcγR ligation and inhibits cellular responsiveness. B cell activation, B cell proliferation and antibody secretion is thus aborted.

4.2 Diseases of Relevance 4.2.1 Cancer

A neoplasm, or tumor, is a neoplastic mass resulting from abnormal uncontrolled cell growth which can be benign or malignant. Benign tumors generally remain localized. Malignant tumors are collectively termed cancers. The term "malignant" generally means that the tumor can invade and destroy neighboring body structures and spread to distant sites to cause death (for review, see Robbins and Angell, 1976, *Basic Pathology*, 2d Ed., W.B. Saunders Co., Philadelphia, pp. 68-122). Cancer can arise in many sites of the body and behave differently depending upon its origin. Cancerous cells destroy the part of the body in which they originate and then spread to other part(s) of the body where they start new growth and cause more destruction.

More than 1.2 million Americans develop cancer each year. Cancer is the second leading case of death in the United States and if current trends continue, cancer is expected to be the leading cause of the death by the year 2010. Lung and prostate cancer are the top cancer killers for men in the United States. Lung and breast cancer are the top cancer killers for women in the United States. One in two men in the United States will be diagnosed with cancer at some time during his lifetime. One in three women in the United States will be diagnosed with cancer at some time during her lifetime.

A cure for cancer has yet to be found. Current treatment options, such as surgery, chemotherapy and radiation treatment, are oftentimes either ineffective or present serious side effects.

Cancer Therapy

Currently, cancer therapy may involve surgery, chemotherapy, hormonal therapy and/or radiation treatment to eradicate neoplastic cells in a patient (See, for example, Stockdale, 1998, "Principles of Cancer Patient Management", in *Scientific American: Medicine*, vol. 3, Rubenstein and Federman, eds., Chapter 12, Section IV). Recently, cancer therapy could also involve biological therapy or immunotherapy. All of these approaches pose significant drawbacks for the patient. Surgery, for example, may be contraindicated due to the health of the patient or may be unacceptable to the patient. Additionally, surgery may not completely remove the neoplastic tissue. Radiation therapy is only effective when the neoplastic tissue exhibits a higher sensitivity to radiation than normal tissue, and radiation therapy can also often elicit serious side effects. Hormonal therapy is rarely given as a single agent and although can be effective, is often used to prevent or delay recurrence of cancer after other treatments have removed the majority of the cancer cells. Biological therapies/immunotherapies are limited in number and may produce side effects such as rashes or swellings, flu-like symptoms, including fever, chills and fatigue, digestive tract problems or allergic reactions.

With respect to chemotherapy, there are a variety of chemotherapeutic agents available for treatment of cancer. A significant majority of cancer chemotherapeutics act by inhibiting DNA synthesis, either directly, or indirectly by inhibiting the biosynthesis of the deoxyribonucleotide triphosphate precursors, to prevent DNA replication and concomitant cell division (See, for example, Gilman et al., Goodman and Gilman's: *The Pharmacological Basis of Therapeutics*, Eighth Ed. (Pergamom Press, New York, 1990)). These agents, which include alkylating agents, such as nitrosourea, anti-metabolites, such as methotrexate and hydroxyurea, and other agents, such as etoposides, campathecins, bleomycin, doxorubicin, daunorubicin, etc., although not necessarily cell cycle specific, kill cells during S phase because of their effect on DNA replication. Other agents, specifically colchicine and the *vinca* alkaloids, such as vinblastine and vincristine, interfere with microtubule assembly resulting in mitotic arrest. Chemotherapy protocols generally involve administration of a combination of chemotherapeutic agents to increase the efficacy of treatment.

Despite the availability of a variety of chemotherapeutic agents, chemotherapy has many drawbacks (See, for example, Stockdale, 1998, "Principles Of Cancer Patient Management" in *Scientific American Medicine*, vol. 3, Rubenstein and Federman, eds., ch. 12, sect. 10). Almost all chemotherapeutic agents are toxic, and chemotherapy causes significant, and often dangerous, side effects, including severe nausea, bone marrow depression, immunosuppression, etc. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even those agents that act by mechanisms different from the mechanisms of action of the drugs used in the specific treatment; this phenomenon is termed pleiotropic drug or multidrug resistance. Thus, because of drug resistance, many cancers prove refractory to standard chemotherapeutic treatment protocols.

There is a significant need for alternative cancer treatments, particularly for treatment of cancer that has proved refractory to standard cancer treatments, such as surgery, radiation therapy, chemotherapy, and hormonal therapy. A promising alternative is immunotherapy, in which cancer cells are specifically targeted by cancer antigen-specific antibodies. Major efforts have been directed at harnessing the specificity of the immune response, for example, hybridoma technology has enabled the development of tumor selective monoclonal antibodies (See Green M. C. et al., 2000 *Cancer Treat Rev.*, 26: 269-286; Weiner L M, 1999 *Semin Oncol.* 26 (suppl. 14):43-51), and in the past few years, the Food and Drug Administration has approved the first MAbs for cancer therapy: Rituxin (anti-CD20) for non-Hodgkin's Lymphoma and Herceptin [anti-(c-erb-2/HER-2)] for metastatic breast cancer (Suzanne A. Eccles, 2001, *Breast Cancer Res.*, 3: 86-90). However, the potency of antibody effector function, e.g., to mediate antibody dependent cellular cytotoxicity ("ADCC") is an obstacle to such treatment. Methods to improve the efficacy of such immunotherapy are thus needed.

4.2.2 Inflammatory Diseases and Autoimmune Diseases

Inflammation is a process by which the body's white blood cells and chemicals protect our bodies from infection by foreign substances, such as bacteria and viruses. It is usually characterized by pain, swelling, warmth and redness of the affected area. Chemicals known as cytokines and prostaglandins control this process, and are released in an ordered and self-limiting cascade into the blood or affected tissues. This release of chemicals increases the blood flow to the area of injury or infection, and may result in the redness and warmth. Some of the chemicals cause a leak of fluid into the tissues, resulting in swelling. This protective process may stimulate nerves and cause pain. These changes, when occurring for a limited period in the relevant area, work to the benefit of the body.

In autoimmune and/or inflammatory disorders, the immune system triggers an inflammatory response when there are no foreign substances to fight and the body's normally protective immune system causes damage to its own tissues by mistakenly attacking self. There are many different autoimmune disorders which affect the body in different ways. For example, the brain is affected in individuals with multiple sclerosis, the gut is affected in individuals with Crohn's disease, and the synovium, bone and cartilage of various joints are affected in individuals with rheumatoid arthritis. As autoimmune disorders progress destruction of one or more types of body tissues, abnormal growth of an organ, or changes in organ function may result. The autoimmune disorder may affect only one organ or tissue type or may affect multiple organs and tissues. Organs and tissues commonly affected by autoimmune disorders include red blood cells, blood vessels, connective tissues, endocrine glands (e.g., the thyroid or pancreas), muscles, joints, and skin. Examples of autoimmune disorders include, but are not limited to, Hashimoto's thyroiditis, pernicious anemia, Addison's disease, type 1 diabetes, rheumatoid arthritis, systemic lupus erythematosus, dermatomyositis, Sjogren's syndrome, dermatomyositis, lupus erythematosus, multiple sclerosis, autoimmune inner ear disease myasthenia gravis, Reiter's syndrome, Graves disease, autoimmune hepatitis, familial adenomatous polyposis and ulcerative colitis.

Rheumatoid arthritis (RA) and juvenile rheumatoid arthritis are types of inflammatory arthritis. Arthritis is a general term that describes inflammation in joints. Some, but not all, types of arthritis are the result of misdirected inflammation. Besides rheumatoid arthritis, other types of arthritis associated with inflammation include the following: psoriatic arthritis, Reiter's syndrome, ankylosing spondylitis arthritis, and gouty arthritis. Rheumatoid arthritis is a type of chronic arthritis that occurs in joints on both sides of the body (such as both hands, wrists or knees). This symmetry helps distinguish rheumatoid arthritis from other types of arthritis. In addition to affecting the joints, rheumatoid arthritis may occasionally affect the skin, eyes, lungs, heart, blood or nerves.

Rheumatoid arthritis affects about 1% of the world's population and is potentially disabling. There are approximately 2.9 million incidences of rheumatoid arthritis in the United States. Two to three times more women are affected than men. The typical age that rheumatoid arthritis occurs is between 25 and 50. Juvenile rheumatoid arthritis affects 71,000 young Americans (aged eighteen and under), affecting six times as many girls as boys.

Rheumatoid arthritis is an autoimmune disorder where the body's immune system improperly identifies the synovial membranes that secrete the lubricating fluid in the joints as foreign. Inflammation results, and the cartilage and tissues in and around the joints are damaged or destroyed. In severe cases, this inflammation extends to other joint tissues and surrounding cartilage, where it may erode or destroy bone and cartilage and lead to joint deformities. The body replaces damaged tissue with scar tissue, causing the normal spaces within the joints to become narrow and the bones to fuse together. Rheumatoid arthritis creates stiffness, swelling, fatigue, anemia, weight loss, fever, and often, crippling pain. Some common symptoms of rheumatoid arthritis include joint stiffness upon awakening that lasts an hour or longer; swelling in a specific finger or wrist joints; swelling in the soft tissue around the joints; and swelling on both sides of the joint. Swelling can occur with or without pain, and can worsen progressively or remain the same for years before progressing.

The diagnosis of rheumatoid arthritis is based on a combination of factors, including: the specific location and symmetry of painful joints, the presence of joint stiffness in the morning, the presence of bumps and nodules under the skin (rheumatoid nodules), results of X-ray tests that suggest rheumatoid arthritis, and/or positive results of a blood test called the rheumatoid factor. Many, but not all, people with rheumatoid arthritis have the rheumatoid-factor antibody in their blood. The rheumatoid factor may be present in people who do not have rheumatoid arthritis. Other diseases can also cause the rheumatoid factor to be produced in the blood. That is why the diagnosis of rheumatoid arthritis is based on a combination of several factors and not just the presence of the rheumatoid factor in the blood.

The typical course of the disease is one of persistent but fluctuating joint symptoms, and after about 10 years, 90% of sufferers will show structural damage to bone and cartilage. A small percentage will have a short illness that clears up completely, and another small percentage will have very severe disease with many joint deformities, and occasionally other manifestations of the disease. The inflammatory process causes erosion or destruction of bone and cartilage in the joints. In rheumatoid arthritis, there is an autoimmune cycle of persistent antigen presentation, T-cell stimulation, cytokine secretion, synovial cell activation, and joint destruction. The disease has a major impact on both the individual and society, causing significant pain, impaired function and disability, as well as costing millions of dollars in healthcare expenses and lost wages. (See, for example, the NIH website and the NIAID website).

Currently available therapy for arthritis focuses on reducing inflammation of the joints with anti-inflammatory or immunosuppressive medications. The first line of treatment of any arthritis is usually anti-inflammatories, such as aspirin, ibuprofen and Cox-2 inhibitors such as celecoxib and rofecoxib. "Second line drugs" include gold, methotrexate and steroids. Although these are well-established treatments for arthritis, very few patients remit on these lines of treatment alone. Recent advances in the understanding of the pathogenesis of rheumatoid arthritis have led to the use of methotrexate in combination with antibodies to cytokines or recombinant soluble receptors. For example, recombinant soluble receptors for tumor necrosis factor (TNF)-α have been used in combination with methotrexate in the treatment of arthritis. However, only about 50% of the patients treated with a combination of methotrexate and anti-TNF-α agents such as recombinant soluble receptors for TNF-α show clinically significant improvement. Many patients remain refractory despite treatment. Difficult treatment issues still remain for patients with rheumatoid arthritis. Many current treatments have a high incidence of side effects or cannot completely prevent disease progression. So far, no treatment is ideal, and there is no cure. Novel therapeutics are needed that more effectively treat rheumatoid arthritis and other autoimmune disorders.

4.2.3 Infectious Diseases

Infectious agents that cause disease fall into five groups: viruses, bacteria, fungi, protozoa, and helminths (worms). The remarkable variety of these pathogens has caused the natural selection of two crucial features of adaptive immunity. First, the advantage of being able to recognize a wide range of different pathogens has driven the development of receptors on B and T cells of equal or greater diversity. Second, the distinct habitats and life cycles of pathogens have to be countered by a range of distinct effector mechanisms. The characteristic features of each pathogen are its mode of transmission, its mechanism of replication, its pathogenesis or the means by which it causes disease, and the response it elicits.

The record of human suffering and death caused by smallpox, cholera, typhus, dysentery, malaria, etc. establishes the eminence of the infectious diseases. Despite the outstanding successes in control afforded by improved sanitation, immunization, and antimicrobial therapy, the infectious diseases continue to be a common and significant problem of modern medicine. The most common disease of mankind, the common cold, is an infectious disease, as is the feared modern disease AIDS. Some chronic neurological diseases that were thought formerly to be degenerative diseases have proven to be infectious. There is little doubt that the future will continue to reveal the infectious diseases as major medical problems.

An enormous number of human and animal diseases result from virulent and opportunistic infections from any of the above mentioned infectious agents (see Belshe (Ed.) 1984 *Textbook of Human Virology*, PSG Publishing, Littleton, Mass.).

One category of infectious diseases are viral infections for example. Viral diseases of a wide array of tissues, including the respiratory tract, CNS, skin, genitourinary tract, eyes, ears, immune system, gastrointestinal tract, and musculoskeletal system, affect a vast number of humans of all ages (see Table 328-2 In: Wyngaarden and Smith, 1988, *Cecil Textbook of Medicine*, $18^{th}$ Ed., W.B. Saunders Co., Philadelphia, pp. 1750-1753). Although considerable effort has been invested in the design of effective anti-viral therapies, viral infections continue to threaten the lives of millions of people worldwide. In general, attempts to develop anti-viral drugs have focused on several stages of viral life cycle (See e.g., Mitsuya et al., 1991, *FASEB J.* 5:2369-2381, discussing HIV). However, a common drawback associated with using of many current anti-viral drugs is their deleterious side effects, such as toxicity to the host or resistance by certain viral strains.

5. SUMMARY OF THE INVENTION

The invention relates to methods of treating or preventing cancer and other diseases, disorders and infections using molecules, preferably polypeptides, and more preferably immunoglobulins (e.g., antibodies), comprising a variant Fc region, having one or more amino acid modifications (e.g., substitutions, but also including insertions or deletions) in one or more regions, which modification(s) alter (relative to a wild-type Fc region) the Ratio of Affinities of the variant Fc region to an activating FcγR (such as FcγRIIA or FcγRIIIA) relative to an inhibiting FcγR (such as FcγRIIB):

Ratio of Affinities=

$$\frac{\text{Wild-Type to Variant Change in Affinity to } Fc\gamma R_{Activating}}{\text{Wild-Type to Variant Change in Affinity to } Fc\gamma R_{Inhibiting}}$$

Of particular interest are Ratios of Affinities in which either FcγRIIIA or FcγRIIA is the $Fc\gamma R_{Activating}$ and FcγRIIB is the $Fc\gamma R_{Inhibiting}$. Where an Fc variant has a Ratio of Affinities greater than 1, the methods of the invention have particular use in providing a therapeutic or prophylactic treatment of a disease, disorder, or infection, or the amelioration of a symptom thereof, where an enhanced efficacy of effector cell function (e.g., ADCC) mediated by FcγR is desired, e.g., cancer or infectious disease. Such an increased Ratio of Affinities may result from the Fc region of the molecule having (relative to a wild type Fc) an increase in affinity to an $Fc\gamma R_{Activating}$ (e.g., FcγRIIIA or FcγRIIA) coupled with either an unchanged affinity to an $Fc\gamma R_{Inhibiting}$ (e.g., FcγRIIB) or a decrease in affinity to such $Fc\gamma R_{Inhibiting}$. Alternatively, an increased Ratio of Affinities may result from the Fc region of such molecule exhibiting an increase in affinity to both an $Fc\gamma R_{Activating}$ and an $Fc\gamma R_{Inhibiting}$ (relative to a wild-type Fc), provided that the increase in affinity to the $Fc\gamma R_{Activating}$ exceeds the increase in affinity to the $Fc\gamma R_{Inhibiting}$, or may result from the Fc region of such molecule exhibiting a decreased affinity to both the $Fc\gamma R_{Activating}$ and an $Fc\gamma R_{Inhibiting}$ (relative to a wild-type Fc), provided that the decrease in affinity to the $Fc\gamma R_{Activating}$ is less than the decrease in affinity to the $Fc\gamma R_{Inhibiting}$, or may result from an unchanged affinity to an $Fc\gamma R_{Activating}$ coupled with a decrease in affinity to an $Fc\gamma R_{Inhibiting}$.

Where an Fv variant has a Ratio of Affinities less than 1, the methods of the invention have particular use in providing a therapeutic or prophylactic treatment of a disease or disorder, or the amelioration of a symptom thereof, where a decreased efficacy of effector cell function mediated by FcγR is desired, e.g., autoimmune or inflammatory disorders. Such a decreased Ratio of Affinities may result from the Fc region of the molecule having (relative to a wild type Fc) a decrease in affinity to an $Fc\gamma R_{Activating}$ (e.g., FcγRIIIA or FcγRIIA) coupled with either an unchanged affinity to an $Fc\gamma R_{Inhibiting}$ (e.g., FcγRIIB) or an increase in affinity to such $Fc\gamma R_{Inhibiting}$. Alternatively, a decreased Ratio of Affinities may result from the Fc region of such molecule exhibiting a decrease in affinity to both an $Fc\gamma R_{Activating}$ and an $Fc\gamma R_{Inhibiting}$ (relative to a wild-type Fc), provided that the decrease in affinity to the $Fc\gamma R_{Activating}$ exceeds the decrease in affinity to the $Fc\gamma R_{Inhibiting}$, or may result from the Fc region of such molecule exhibiting an increased affinity to both an $Fc\gamma R_{Activating}$ and an $Fc\gamma R_{Inhibiting}$ (relative to a wild-type Fc), provided that the increase in affinity to the $Fc\gamma R_{Activating}$ is less than the increase in affinity to the FcγR$_{Inhibiting}$, or may result from an unchanged affinity to an FcγR$_{Activating}$ coupled with an increase in affinity to an FcγR$_{Inhibiting}$.

Current approaches to optimize the Fc region function (e.g., antibody-dependent cell mediated cytotoxicity (ADCC), complement dependent cytotoxicity (CDC) activity) in therapeutic monoclonal antibodies and soluble polypeptides fused to Fc regions have focused on a limited number of single amino acid changes based on structural analysis and/or computer aided designs. Alternative approaches in engineering Fc regions have focused on the glycosylation of the Fc region to optimize Fc region function. The validity of using an Fc variant's Ratio of Affinities to assess its therapeutic potential has been suggested with respect to Fc variants whose sequences were derived using computer algorithms to search sequence-structure space (Lazar, G. A. et al. Proc. Natl. Acad. Sci. (USA) 103:4005-4010 (2006)). This approach identified four Fc variants: (1) S239D; (2) I322E; (3) S239D and I322E; and (4) S239D, I332E and A330L, all of which bound FcγRIIIa as well as FcγRIIb with greater affinity than wild-type (Lazar, G. A. et al. Proc. Natl. Acad. Sci. (USA) 103:4005-4010 (2006). In contrast, the present invention is based, in part, on selecting desired variant Fc-containing molecules that exhibit an altered Ratio of Affinities for FcγRIII and FcγRII, from an unbiased library of Fc variants. This approach enabled the identification of a larger universe of desired Fc variants, as well as variants having Ratios of Affinities far in excess of those reported by Lazar, G. A. et al. (Proc. Natl. Acad. Sci. (USA) 103:4005-4010 (2006)). The present invention encompasses methods for engineering Fc regions and identification and screening of novel Fc variants outside the expected regions identified by structural studies. Expected regions as used herein refer to those regions that based on structural and/or biochemical studies are in contact with an Fc ligand.

The therapeutic or prophylactic molecules that are used in accordance with the methods of the invention thus comprise variant Fc regions comprising one or more amino acid modifications that exhibit an altered Ratio of Affinities, especially wherein the FcγR$_{Activating}$ is either FcγRIIA or FcγRIIIA and the FcγR$_{Inhibiting}$ is FcγRIIB. In a preferred embodiment, the molecules of the invention further specifically bind FcγRIIB (via the Fc region) with a lower affinity than a comparable molecule (i.e., having the same amino acid sequence as the molecule of the invention except for the one or more amino acid modifications in the Fc region) comprising the wild-type Fc region binds FcγRIIB. In some embodiments, the invention encompasses molecules with variant Fc regions, having one or more amino acid modifications, which modifications increase the affinity of the variant Fc region for FcγRIIIA and/or FcγRIIA and enhance the affinity of the variant Fc region for FcγRIIB relative to a comparable molecule with a wild type Fc region. In other embodiments, the invention encompasses molecules with variant Fc regions, having one or more amino acid modifications, which modifications increase the affinity of the variant Fc region for FcγRIIIA and/or FcγRIIA but do not alter the affinity of the variant Fc regions for FcγRIIB relative to a comparable molecule with a wild type Fc region. A preferred embodiment is a variant Fc region that has enhanced affinity for FcγRIIIA and FcγRIIA but reduced affinity for FcγRIIB relative to a comparable molecule with a wild type Fc region.

The Fc variants of the present invention may be combined with other Fc modifications, including but not limited to modifications that alter effector function. The invention encompasses combining an Fc variant of the invention with other Fc modifications to provide additive, synergistic, or novel properties in antibodies or Fc fusions. Preferably, the Fc variants of the invention enhance the phenotype of the modification with which they are combined. For example, if an Fc variant of the invention is combined with a mutant known to bind FcγRIIIA with a higher affinity than a comparable molecule comprising a wild type Fc region; the combination with a mutant of the invention results in a greater fold enhancement in FcγRIIIA affinity.

In one embodiment, the Fc variants of the present invention may be combined with other known Fc variants such as those disclosed in Duncan et al, 1988, Nature 332:563-564; Lund et al., 1991, J. Immunol 147:2657-2662; Lund et al, 1992, Mol Immunol 29:53-59; Alegre et al, 1994, Transplantation 57:1537-1543; Hutchins et al; 1995, Proc Natl. Acad Sci USA 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:49634969; Armour et al, 1999, Eur J Immunol 29:2613-2624; Idusogie et al, 2000, J Immunol 164:41784184; Reddy et al, 2000, J Immunol 164:1925-1933; Xu et al., 2000, Cell Immunol 200:16-26; Idusogie et al, 2001, J Immunol 166:2571-2575; Shields et al., 2001, J Biol Chem 276:6591-6604; Shields et al, 2002, J Biol Chem 277:26733-26740; Jefferis et al, 2002, Immunol Lett 82:57-65; Presta et al., 2002, Biochem Soc Trans 30:487-490); Lazar, G. A. et al. Proc. Natl. Acad. Sci. (USA) 103:4005-4010 (2006); U.S. Pat. Nos. 5,624,821; 5,885,573; 6,194,551; PCT WO 00/42072; PCT WO 99/58572; PCT WO 04/063351; U.S. Patent Application Publication 2005/0037000; and U.S. Patent Application Publication 2005/0064514; each of which is incorporated herein by reference in its entirety. In certain embodiments, the Fc variants of the present invention may be combined with one or more of the Fc variants, i.e., amino acid modifications relative to a wild-type Fc region, presented in tables 4, 5, 9, and 10, infra.

The invention encompasses molecules that are homodimers or heterodimers of Fc regions. Heterodimers comprising Fc regions refer to molecules where the two Fc chains have the same or different sequences. In some embodiments, in the heterodimeric molecules comprising variant Fc regions, each chain has one or more different modifications from the other chain. In other embodiments, in the heterodimeric molecules comprising variant Fc regions, one chain contains the wild-type Fc region and the other chain comprises one or more modifications. Methods of engineering heterodimeric Fc containing molecules are known in the art and encompassed within the invention.

In some embodiments, the invention encompasses molecules comprising a variant Fc region, wherein said variant Fc region comprises at least one amino acid modification relative to a wild type Fc region, which variant Fc region binds an FcγR$_{Activating}$ but does not bind an FcγR$_{Inhibiting}$ or binds an FcγR$_{Inhibiting}$ with a reduced affinity, relative to a comparable molecule comprising the wild-type Fc region, as determined by standard assays (e.g., in vitro assays) known to one skilled in the art. In an alternative embodiment, the invention encompasses molecules comprising a variant Fc region, wherein said variant Fc region comprises at least one amino acid modification relative to a wild type Fc region, which variant Fc region binds an FcγR$_{Inhibiting}$, does not bind an FcγR$_{Activating}$ or binds an an FcγR$_{Activating}$ with reduced affinity, relative to a comparable molecule comprising the wild-type Fc region, as determined by standard assays (e.g., in vitro assays) known to one skilled in the art. In a specific embodiment, the invention encompasses molecules comprising a variant Fc region, wherein said variant Fc region comprises at least one amino acid modification relative to a wild type Fc region, which variant Fc region only binds one FcγR, wherein said FcγR is FcγIIIA. In another specific embodiment, the invention encompasses molecules comprising a variant Fc region, wherein said variant Fc region comprises at least one amino acid modification relative to a wild type Fc region, which variant Fc region only binds one FcγR, wherein said FcγR is FcγRIIA. In yet another embodiment, the invention encompasses molecules comprising a variant Fc region, wherein said variant Fc region comprises at least one amino acid modification relative to a wild type Fc region, which variant Fc region only binds one FcγR, wherein said FcγR is FcγRIIB.

The affinities and binding properties of the molecules of the invention for an FcγR are initially determined using in vitro assays (biochemical or immunological based assays) known in the art for determining Fc-FcγR interactions, i.e., specific binding of an Fc region to an FcγR including but not limited to ELISA assay, surface plasmon resonance assay, immunoprecipitation assays (See Section 6.2). Preferably, the binding properties of the molecules of the invention are also characterized by in vitro functional assays for determining one or more FcγR mediator effector cell functions (See Section 6.2.2). In most preferred embodiments, the molecules of the invention have similar binding properties in in vivo models (such as those described and disclosed herein) as those in in vitro based assays. However, the present invention does not exclude molecules of the invention that do not exhibit the desired phenotype in in vitro based assays but do exhibit the desired phenotype in vivo.

In a specific embodiment, the invention encompasses a molecule comprising a variant Fc region, wherein said variant Fc region comprises at least one amino acid modification relative to a wild-type Fc region and exhibits a Ratio of Affinities greater than 1, provided that said variant Fc region does not solely have a substitution at any one of positions 329, 331, or 332, or does not include, or is not solely a substitution of, any one of: (1) alanine at any of positions 256, 290, 298, 312, 333, 334, 359, 360, 326, or 430; (2) a lysine at position 330; (3) a threonine at position 339; (4) a methionine at position 320; (5) a serine at position 326; (6) an asparagine at position 326; (7) an aspartic acid at position 326; (8) a glutamic acid at position 326; (9) a glutamine at position 334; (10) a glutamic acid at position 334; (11) a methionine at position 334; (12) a histidine at position 334; (13) a valine at position 334; (14) a leucine at position 334; (15) a lysine at position 335, or (16) solely a glutamic acid at position 332; (17) solely a glutamic acid at position 332 and an aspartic acid at position 239; (18) solely a glutamic acid at position 332, an aspartic acid at position 239, and a leucine at position 330.

The invention particularly concerns a molecule having such a variant Fc region, wherein said variant Fc region is additionally characterized in possessing at least one amino acid modification relative to a wild-type Fc region at position 243, 247, 255, 270, 284, 292, 300, 305, 316, 370, 392, 396, 416, 419 and/or 421.

The invention further concerns such molecules wherein the variant Fc regions are additionally characterized in possessing substitutions at at least the two positions: (a) 235 and 243; (b) 243 and 292; (c) 243 and 300; (d) 243 and 305; (e) 243 and 396; (f) 247 and 270; (g) 247 and 421; (h) 255 and 270; (i) 255 and 396; (j) 270 and 316; (k) 270 and 396; (l) 270 and 416; (m) 270 and 421; (n) 292 and 300; (o) 292 and 305; (p) 292 and 396; (q) 300 and 396; (r) 305 and 396; (s) 316 and 416; (t) 392 and 270; (u) 392 and 396; (v) 419 and 270; or (w) 419 and 396.

The invention further concerns such molecules wherein the variant Fc regions are additionally characterized in possessing substitutions at at least the three positions: ((a) 243, 247 and 421; (b) 243, 292 and 300; (c) 243, 292 and 305; (d) 243, 292 and 396; (e) 243 300 and 396; (0 243, 305 and 396; (g) 247, 270 and 421; (h) 255, 270 and 396; (i) 270, 316 and 416; (j) 270, 392 and 396; (k) 270, 396 and 419; (1) 292 300 and 396; or (m) 292, 305 and 396.

The invention additionally concerns the above-described methods wherein the variant Fc region possesses at least amino acid modifications relative to a wild-type Fc region at positions: 243, 292 and 300 and at least one additional modification at position 234, 235, or 396. The invention concerns the embodiment of the above-described methods wherein the variant Fc region possesses at least amino acid modifications relative to a wild-type Fc region at positions: L234, F243, R292 and Y300 (and especially the modifications: L234F, F243L, R292P and Y300L). The invention also concerns the embodiment of the above-described methods wherein the variant Fc region possesses at least amino acid modifications relative to a wild-type Fc region at positions: L235, F243, R292 and Y300. The invention also concerns the embodiment of such methods wherein the variant Fc region possesses at least the following amino acid modifications relative to a wild-type Fc region: F243L, R292P and Y300L (and particularly, the modifications: L235I, L235Q, L235V or L235P). The invention also concerns the embodiment of such methods wherein the variant Fc region possesses at least amino acid modifications relative to a wild-type Fc region at positions: 235, 243, 292, 300 and 396. The invention also concerns the embodiment of such methods wherein the variant Fc region possesses at least the following amino acid modifications relative to a wild-type Fc region: F243L, R292P, Y300L and P396L (especially wherein the variant Fc region also possesses L235V or L235P).

The invention further concerns such molecules wherein the variant Fc regions exhibit a Ratio of Affinities greater than 1, and wherein such variant Fc regions have at least any of the following substitutions: (a) F243L; (b) D270E; (c) R292G; or (d) R292P.

The invention further concerns such molecules wherein the variant Fc regions exhibit a Ratio of Affinities greater than 1, and wherein such variant Fc regions have at least any of the following pairs of substitutions: (a) F243L and R292P; (b) F243L and Y300L; (c) F243L and P396L; (d) D270E and P396L; (e) R292P and Y300L; (f) R292P and V305I; (g) R292P and P396L; (h) Y300L and P396L; and (i) P396L and Q419H.

The invention further concerns such molecules wherein the variant Fc regions exhibit a Ratio of Affinities greater than 1, and wherein such variant Fc regions have at least any of the following trios of substitutions: (a) F243L, P247L and N421K; (b) F243L, R292P and Y300L; (c) F243L, R292P and Y300L; (d) F243L, R292P and V305I; (e) F243L, R292P and P396L; (f) F243L, Y300L and P396L; (g) P247L, D270E and N421K; (h) R255L, D270E and P396L; (i) D270E, G316D and R416G; (j) D270E, K392T and P396L; (k) D270E, P396L and Q419H; (1) V284M, R292L and K370N or (m) R292P, Y300L and P396L.

The invention further concerns such molecules wherein the variant Fc regions exhibit a Ratio of Affinities greater than 1, and wherein such variant Fc regions have at least any of the following tetrads of substitutions: (a) L234F, F243L, R292P and Y300L; (b) L235I, F243L, R292P and Y300L;

(c) L235Q, F243L, R292P and Y300L; (d) F243L, R292P, Y300L, and P396L; (e) F243L, P247L, D270E and N421K; (f) F243L, R255L, D270E and P396L; (g) F243L, D270E, G316D and R416G; (h) F243L, D270E, K392T and P396L; (i) F243L, D270E, P396L and Q419H; (j) F243L, R292P, V305I and P396L; (k) D270E, G316D, P396L and R416G; (1) P247L, D270E, Y300L and N421K; (m) R255L, D270E, R292G and P396L; or (n) R255L, D270E, Y300L and P396L.

The invention further concerns such molecules wherein the variant Fc regions exhibit a Ratio of Affinities greater than 1, and wherein such variant Fc regions have at least any of the following pentads of substitutions: ((a) L235V, F243L, R292P, Y300L and P396L; (b) L235P, F243L, R292P, Y300L and P396L; (c) F243L, R292P, V305I, Y300L and P396L; or (d) F243L, R292P, Y300L, V305I and P396L.

The invention further concerns such molecules wherein the variant Fc regions exhibit a Ratio of Affinities less than 1, and wherein such variant Fc regions have at least any of the following substitutions: (a) P396L or (b) Y300L.

The invention further concerns such molecules wherein the variant Fc regions exhibit a Ratio of Affinities less than 1, and wherein such variant Fc regions have at least any of the following pairs of substitutions: (a) F243L and P396L; (b) P247L and N421K; (c) R255L and P396L; (d) R292P and V305I; (e) K392T and P396L; or (f) P396L and Q419H.

The invention further concerns such molecules wherein the variant Fc regions exhibit a Ratio of Affinities less than 1, and wherein such variant Fc regions have at least the following three substitutions: F243L, R292P and V305I.

In another specific embodiment, the invention encompasses a molecule comprising a variant Fc region, wherein said variant Fc region comprises at least one amino acid modification relative to a wild-type Fc region, such that said polypeptide specifically binds FcγRIIA with a greater affinity than a comparable molecule comprising the wild-type Fc region binds FcγRIIA, provided that the one or more amino acid modifications do not include or are not solely substitution with an alanine at any of positions 256, 290, 326, 255, 258, 267, 272, 276, 280, 283, 285, 286, 331, 337, 268, 272, or 430; an asparagine at position 268; a glutamine at position 272; a glutamine, serine, or aspartic acid at position 286; a serine at position 290; a methionine, glutamine, glutamic acid, or arginine at position 320; a glutamic acid at position 322; a serine, glutamic acid, or aspartic acid at position 326; a lysine at position 330; a glutamine at position 335; or a methionine at position 301.

In a preferred specific embodiment, the invention encompasses a molecule comprising a variant Fc region, wherein said variant Fc region comprises at least one amino acid modification relative to a wild-type Fc region, such that said molecule has an altered affinity for an FcγR, provided that said variant Fc region does not have a substitution at positions that make a direct contact with FcγR based on crystallographic and structural analysis of Fc-FcγR interactions such as those disclosed by Sondermann et al., (2000 Nature, 406: 267-273, which is incorporated herein by reference in its entirety). Examples of positions within the Fc region that make a direct contact with FcγR are amino acids 234-239 (hinge region), amino acids 265-269 (B/C loop), amino acids 297-299 (C'/E loop), and amino acids 327-332 (F/G) loop. In some embodiments, the molecules of the invention comprising variant Fc regions comprise modification of at least one residue that does not make a direct contact with an FcγR based on structural and crystallographic analysis, e.g., is not within the Fc-FcγR binding site.

In another preferred embodiment, the invention encompasses a molecule comprising a variant Fc region, wherein said variant Fc region comprises at least one amino acid modification relative to a wild-type Fc region, such that said molecule binds an FcγR (via its Fc region) with an altered affinity relative to a molecule comprising a wild-type Fc region, provided that said at least one amino acid modification do not include or are not solely a substitution at any of positions 255, 256, 258, 267, 268, 269, 270, 272, 276, 278, 280, 283, 285, 286, 289, 290, 292, 293, 294, 295, 296, 298, 300, 301, 303, 305, 307, 309, 312, 320, 322, 326, 329, 330, 332, 331, 333, 334, 335, 337, 338, 339, 340, 359, 360, 373, 376, 416, 419, 430, 434, 435, 437, 438, 439. In a specific embodiment, the invention encompasses a molecule comprising a variant Fc region, wherein said variant Fc region comprises at least one amino acid modification relative to a wild-type Fc region, such that said molecule binds an FcγR (via its Fc region) with an altered affinity relative to a molecule comprising a wild-type Fc region, provided that said variant Fc region does not include or are not solely a substitution at any of positions 255, 258, 267, 269, 270, 276, 278, 280, 283, 285, 289, 292, 293, 294, 295, 296, 300, 303, 305, 307, 309, 322, 329, 332, 331, 337, 338, 340, 373, 376, 416, 419, 434, 435, 437, 438, 439 and does not have an alanine at any of positions 256, 290, 298, 312, 333, 334, 359, 360 326, or 430; a lysine at position 330; a threonine at position 339; a methionine at position 320; a serine at position 326; an asparagine at position 326; an aspartic acid at position 326; a glutamic acid at position 326; a glutamine at position 334; a glutamic acid at position 334; a methionine at position 334; a histidine at position 334; a valine at position 334; or a leucine at position 334; a lysine at position 335 an asparagine at position 268; a glutamine at position 272; a glutamine, serine, or aspartic acid at position 286; a serine at position 290; a methionine, glutamine, glutamic acid, or arginine at position 320; a glutamic acid at position 322; a serine, glutamic acid, or aspartic acid at position 326; a lysine at position 330; a glutamine at position 335; or a methionine at position 301.

In a specific embodiment, the invention encompasses a molecule comprising a variant Fc region, wherein said variant Fc region does not include or are not solely a substitution at any of positions 268, 269, 270, 272, 276, 278, 283, 285, 286, 289, 292, 293, 301, 303, 305, 307, 309, 331, 333, 334, 335, 337, 338, 340, 360, 373, 376, 416, 419, 430, 434, 435, 437, 438 or 439 and does not have a histidine, glutamine, or tyrosine at position 280; a serine, glycine, threonine or tyrosine at position 290, a leucine or isoleucine at position 300; an asparagine at position 294, a proline at position 296; a proline, asparagine, aspartic acid, or valine at position 298; a lysine at position 295. In yet another preferred embodiment, the invention encompasses a molecule comprising a variant Fc region, wherein said variant Fc region comprises at least one amino acid modification relative to a wild-type Fc region, such that said molecule binds an FcγR (via its Fc region) with a reduced affinity relative to a molecule comprising a wild-type Fc region provided that said variant Fc region does not have or are not solely have a substitution at any of positions 252, 254, 265, 268, 269, 270, 278, 289, 292, 293, 294, 295, 296, 298, 300, 301, 303, 322, 324, 327, 329, 333, 335, 338, 340, 373, 376, 382, 388, 389, 414, 416, 419, 434, 435, 437, 438, or 439. In yet another preferred embodiment, the invention encompasses a molecule comprising a variant Fc region, wherein said variant Fc region comprises at least one amino acid modification relative to a wild-type Fc region, such that said molecule binds an FcγR (via its Fc region) with an enhanced affinity relative to a molecule comprising a wild-type Fc region provided that said variant Fc region does not have or are not solely a substitution at any of positions 280, 283, 285, 286, 290, 294, 295, 298, 300, 301, 305, 307, 309, 312, 315, 331, 333, 334, 337, 340, 360, 378, 398, or 430.

In a specific embodiment, the invention encompasses a molecule comprising a variant Fc region, wherein said variant Fc region does not include a substitution or does not solely have a substitution at any of positions 330, 243, 247, 298, 241, 240, 244, 263, 262, 235, 269, or 328 and does not have a leucine at position 243, an asparagine at position 298, a leucine at position 241, and isoleucine or an alanine at position 240, a histidine at position 244, a valine at position 330, or an isoleucine at position 328.

In a specific embodiment, molecules of the invention comprise a variant Fc region having one or more amino acid modifications (e.g., substitutions), which modifications increase the affinity of the variant Fc region for FcγRIIIA and/or FcγRIIA by at least 2-fold, relative to a comparable molecule comprising a wild-type Fc region. In certain embodiments, molecules of the invention comprise a variant Fc region having one or more amino acid modifications (e.g., substitutions), which modifications increase the affinity of the variant Fc region for FcγRIIIA and/or FcγRIIA by greater than 2-fold, at least 4-fold, at least 5-fold, at least 6-fold, at least 8-fold, or at least 10-fold relative to a comparable molecule comprising a wild-type Fc region. In other embodiments of the invention, molecules of the invention comprising a variant Fc region specifically bind FcγRIIIA and/or FcγRIIA with at least 65%, at least 75%, at least 85%, at least 95%, at least 100%, at least 150%, at least 200% greater affinity relative to a molecule comprising a wild-type Fc region. Such measurements are preferably in vitro assays.

The invention encompasses molecules with altered affinities for the activating and/or inhibitory Fcγ receptors. In particular, the invention contemplates molecules with variant Fc regions, having one or more amino acid modifications, which modifications increase the affinity of the variant Fc region for FcγRIIB but decrease the affinity of the variant Fc region for FcγRIIIA and/or FcγRIIA, relative to a comparable molecule with a wild-type Fc region. In other embodiments, the invention encompasses molecules with variant Fc regions, having one or more amino acid modifications, which modifications decrease the affinity of the variant Fc region for FcγRIIB and also decrease the affinity of the variant Fc regions for FcγRIIIA and/or FcγRIIA relative to a comparable molecule with a wild-type Fc region. In yet other embodiments, the invention encompasses molecules with variant Fc regions, having one or more amino acid modifications, which modifications increase the affinity of the variant Fc region for FcγRIIB and also increase the affinity of the variant Fc regions for FcγRIIIA and/or FcγRIIA relative to a comparable molecule with a wild-type Fc region. In yet other embodiments, the invention encompasses molecules with variant Fc regions, which modifications decrease the affinity of the variant Fc region for FcγRIIIA and/or FcγRIIA but do not alter the affinity of the variant Fc region for FcγRIIB relative to a comparable molecule with a wild-type Fc region. In yet other embodiments, the invention encompasses molecules with variant Fc regions, which modifications increase the affinity of the variant Fc region for FcγRIIIA and/or FcγRIIA but reduce the affinity of the variant Fc region for FcγRIIB relative to a comparable molecule with a wild-type Fc region.

In a specific embodiment, the molecules of the invention comprise a variant Fc region, having one or more amino acid modifications (e.g., substitutions), which one or more modifications increase the affinity of the variant Fc region for FcγRIIIA and decrease the affinity of the variant Fc region for FcγRIIB, relative to a comparable molecule comprising a wild-type Fc region which binds FcγRIIIA and FcγRIIB with wild-type affinity. In a certain embodiment, the one or more amino acid modifications are not a substitution with alanine at any of positions 256, 298, 333, or 334.

In another specific embodiment, the molecules of the invention comprise a variant Fc region, having one or more amino acid modifications (e.g., substitutions), which one or more modifications increase the affinity of the variant Fc region for FcγRIIA and decrease the affinity of the variant Fc region for FcγRIIB, relative to a comparable molecule comprising a wild-type Fc region which binds FcγRIIA and FcγRIIB with wild-type affinity. In a certain embodiment, the one or more amino acid modifications is not a substitution with arginine at position 320.

In most preferred embodiments, the molecules of the invention with altered affinities for activating and/or inhibitory receptors having variant Fc regions, have one or more amino acid modifications, wherein said one or more amino acid modification is a substitution at position 288 with asparagine, at position 330 with serine and at position 396 with leucine (MgFc10) (See Tables 4 & 5); or a substitution at position 334 with glutamic acid, at position 359 with asparagine, and at position 366 with serine (MgFc13); or a substitution at position 316 with aspartic acid, at position 378 with valine, and at position 399 with glutamic acid (MgFc27); or a substitution at position 392 with threonine, and at position 396 with leucine (MgFc38); or a substitution at position 221 with glutamic acid, at position 270 with glutamic acid, at position 308 with alanine, at position 311 with histidine, at position 396 with leucine, and at position 402 with aspartic acid (MgFc42); or a substitution at position 240 with alanine, and at position 396 with leucine (MgFc52); or a substitution at position 410 with histidine, and at position 396 with leucine (MgFc53); or a substitution at position 243 with leucine, at position 305 with isoleucine, at position 378 with aspartic acid, at position 404 with serine, and at position 396 with leucine (MgFc54); or a substitution at position 255 with isoleucine, and at position 396 with leucine (MgFc55); or a substitution at position 370 with glutamic acid and at position 396 with leucine (MgFc59); or a substitution at position 243 with leucine, at position 292 with proline, at position 300 with leucine, at position 305 with isoleucine, and at position 396 with leucine (MgFc88); or a substitution at position 243 with leucine, at position 292 with proline, at position 300 with leucine, and at position 396 with leucine (MgFc88A); or a substitution at position 243 with leucine, at position 292 with proline, and at position 300 with leucine (MgFc155); or a substitution at position 243 with leucine, at position 292 with proline, and at position 300 with leucine; or a substitution at position 243 with leucine, at position 292 with proline, and at position 396 with leucine; or a substitution at position 243 with leucine, and at position 292 with proline; or a substitution at position 243 with leucine; or a substitution at position 273 with phenylalanine; or a substitution at position 247 with leucine, at position 270 with glutamic acid, and at position 421 with lysine. In a related embodiment, the variant Fc region further comprises one or more amino acid modifications disclosed in tables 4, 5, 9, and 10 infra.

In certain embodiments, the invention encompasses methods for screening and identifying therapeutic and/or prophylactic molecules comprising variant Fc regions with altered FcγR affinities (e.g., enhanced FcγRIIIA affinity) using yeast surface display technology (for review see Boder and Wittrup, 2000, Methods in Enzymology, 328: 430-444, which is incorporated herein by reference in its entirety). Yeast surface display of the mutant Fc containing polypeptides of the invention may be performed in accordance with any of the techniques known to those skilled in the art or described herein (see, e.g., U.S Patent application Publications 2005/0037000 and 2005/0064514, and International Patent Application Publication WO 04/063351, each of which is hereby incorporated by reference in its entirety). Yeast display offers the advantage of utilizing actual binding to a desired receptor to identify variant Fc regions that have enhanced binding to that receptor.

In certain embodiments, the invention encompasses methods for screening and identifying therapeutic and/or prophylactic molecules comprising variant Fc regions with altered FcγR affinities (e.g., enhanced FcγRIIIA affinity) using yeast display technology known in the art or described herein in combination with one or more biochemical based assays, preferably in a high throughput manner. The one or more biochemical assays can be any assay known in the art for identifying Fc-FcγR interaction, i.e., specific binding of an Fc region to an FcγR, including, but not limited to, an ELISA assay, surface plasmon resonance assays, immunoprecipitation assay, affinity chromatography, and equilibrium dialysis. In some embodiments, screening and identifying molecules comprising variant Fc regions with altered FcγR affinities (e.g., enhanced FcγRIIIA affinity) are done using the yeast display technology as described herein in combination with one or more functional based assays, preferably in a high throughput manner. The functional based assays can be any assay known in the art for characterizing one or more FcγR mediated effector cell function such as those described herein in Section 6.2.2. Non-limiting examples of effector cell functions that can be used in accordance with the methods of the invention, include but are not limited to, antibody-dependent cell mediated cytotoxicity (ADCC), antibody-dependent phagocytosis, phagocytosis, opsonization, opsonophagocytosis, cell binding, rosetting, C1q binding, and complement dependent cell mediated cytotoxicity. In some embodiments, screening and identifying molecules comprising variant Fc regions with altered FcγR affinities (e.g., enhanced FcγRIIIA affinity) are done using the yeast display technology as described herein or known in the art in combination with one or more biochemical based assays in combination or in parallel with one or more functional based assays, preferably in a high throughput manner.

In preferred embodiments, the invention encompasses methods for screening and characterizing FcγR-Fc interaction using biochemical assays developed by the inventors and disclosed in U.S Patent application Publications 2005/0037000 and 2005/0064514, and International Patent Application Publication WO 04/063351, each of which is hereby incorporated by reference in its entirety. The disclosed assays allow detection and quantitation of the FcγR-Fc interaction, despite the inherently weak affinity of the receptor for its ligand, e.g., in the micromolar range for FcγRIIB and FcγRIIIA. The method involves the formation of an FcγR complex (e.g., FcγRIIIA, FcγRIIB) that has an improved avidity for an Fc region, relative to an uncomplexed FcγR.

The invention encompasses the use of the immune complexes formed according to the methods described above for determining the functionality of molecules comprising an Fc region in cell-based or cell-free assays.

In preferred embodiments, molecules of the invention (e.g., immunoglogulins or fragments thereof) comprising the variant Fc regions are further characterized in an animal model for interaction with an FcγR or in an animal model of disease state. Preferred animal models for use in the methods of the invention are, for example, transgenic mice expressing human FcγRs, e.g., any mouse model described in U.S. Pat. Nos. 5,877,397, and 6,676,927 which are incorporated herein by reference in their entirety. Transgenic mice for use in the methods of the invention include, but are not limited to, knockout FcγRIIIA mice carrying human FcγRIIIA; knockout FcγRIIIA mice carrying human FcγRIIA; knockout FcγRIIIA mice carrying human FcγRIIB and human FcγRIIIA; knockout FcγRIIIA mice carrying human FcγRIIB and human FcγRIIA; knockout FcγRIIIA and FcγRIIA mice carrying human FcγRIIIA and FcγRIIA; and knockout FcγRIIIA, FcγRIIA and FcγRIIB mice carrying human FcγRIIIA, FcγRIIA and FcγRIIB. The mouse strain used for knockout studies may be any suitable inbred strain (e.g., B6) as determined routinely in the art. In preferred embodiments, the mouse strain is that of a nude genotype, i.e., immune compromised, to allow xenograft studies (e.g., cancer models). Such nude strains include, but are not limited to FoxN1 and N/N. In other embodiments the mice carrying one or more human FcγRs further comprise one or more additional genetic mutations including one or more knockouts, e.g. RAG1 −/−.

In a specific embodiment, the invention provides modified immunoglobulins comprising a variant Fc region with an enhanced affinity for FcγRIIIA and/or FcγRIIA. Such immunoglobulins include IgG molecules that naturally contain FcγR binding regions (e.g., FcγRIIIA and/or FcγRIIB binding regions), or immunoglobulin derivatives that have been engineered to contain an FcγR binding region (e.g., FcγRIIIA and/or FcγRIIB binding regions). The modified immunoglobulins of the invention include any immunoglobulin molecule that binds, preferably, immunospecifically, i.e., competes off non-specific binding as determined by immunoassays well known in the art for assaying specific antigen-antibody binding, an antigen and contains an FcγR binding region (e.g., a FcγRIIIA and/or FcγRIIB binding region). Such antibodies include, but are not limited to, polyclonal, monoclonal, bi-specific, multi-specific, human, humanized, chimeric antibodies, single chain antibodies, Fab fragments, F(ab')₂ fragments, disulfide-linked Fvs, and fragments containing either a VL or VH domain or even a complementary determining region (CDR) that specifically binds an antigen, in certain cases, engineered to contain or fused to an FcγR binding region.

In certain embodiment, the invention encompasses immunoglobulins comprising a variant Fc region with an enhanced affinity for FcγRIIIA and/or FcγRIIA such that the immunoglobulin has an enhanced effector function, e.g., antibody dependent cell mediated cytotoxicity. The effector function of the molecules of the invention can be assayed using any assay described herein or known to those skilled in the art. In some embodiments, immunoglobulins comprising a variant Fc region with an enhanced affinity for FcγRIIIA and/or FcγRIIA have an enhanced ADCC activity relative to wild-type by at least 2-fold, at least 4-fold, at least 8-fold, at least 10-fold, at least 50-fold, or at least 100-fold.

The invention encompasses engineering human or humanized therapeutic antibodies (e.g., tumor specific monoclonal antibodies) in the Fc region by modification (e.g., substitution, insertion, deletion) of one or more amino acid residues, which modifications modulate the affinity of the therapeutic antibody for an FcγR activating receptor and/or an FcγR inhibitory receptor. In one embodiment, the invention relates to engineering human or humanized therapeutic antibodies (e.g., tumor specific monoclonal antibodies) in the Fc region by modification of one or more amino acid residues, which modifications increase the affinity of the Fc region for FcγRIIIA and/or FcγRIIA. In another embodiment, the invention relates to engineering human or humanized therapeutic antibodies (e.g., tumor specific monoclonal antibodies) in the Fc region by modification of one or more amino acid residues, which modification increases the affinity of the Fc region for FcγRIIIA and/or FcγRIIA and further decreases the affinity of the Fc region for FcγRIIB. The engineered therapeutic antibodies may further have an enhanced effector function, e.g., enhanced ADCC activity, phagocytosis activity, etc., as determined by standard assays known to those skilled in the art.

In a specific embodiment, the invention encompasses engineering a monoclonal antibody specific for Her2/neu protooncogene (amino acid sequence SEQ ID NO:31) (e.g., Ab4D5 antibody as disclosed in Carter et al., 1992, Proc. Natl. Acad. Sci. USA 89:4285-9; U.S. Pat. No. 5,677,171; or International Patent Application Publication WO 01/00245, each of which is hereby incorporated by references in its entirety) by modification (e.g., substitution, insertion, deletion) of at least one amino acid residue which modification increases the affinity of the Fc region for FcγRIIIA and/or FcγRIIA. In another specific embodiment, modification of the humanized Her2/neu monoclonal antibody may also further decrease the affinity of the Fc region for FcγRIIB. In yet another specific embodiment, the engineered humanized monoclonal antibodies specific for Her2/neu may further have an enhanced effector function as determined by standard assays known in the art and disclosed and exemplified herein. In a certain embodiment, the 4D5 antibody is chimeric. In another embodiment, the 4D5 antibody is humanized. In a specific embodiment, the 4D5 antibody to be engineered in accordance with the methods of the invention comprises a heavy chain having the amino acid sequence SEQ ID NO:32. In another specific embodiment, the 4D5 antibody to be engineered in accordance with the methods of the invention comprises a light chain having the amino acid sequence SEQ ID NO:33. In still other embodiments, the 4D5 antibody to be engineered in accordance with the methods of the invention is humanized and comprises a heavy chain having the amino sequence SEQ ID NO:34. In further embodiments, the 4D5 antibody to engineered in accordance with the methods of the invention is humanized and comprises a light chain having the amino sequence SEQ ID NO:35.

In a specific embodiment, the antibodies of the invention bind Her2/neu. The anti-Her2/neu antibodies of the invention may have a heavy chain variable region comprising the amino acid sequence of CDR1 (SEQ ID NO:36) and/or CDR2 (SEQ ID NO:37) and/or CDR3 (SEQ ID NO:38) and/or a light chain variable region comprising the amino acid sequence of CDR1 (SEQ ID NO:39) and/or a CDR2 (SEQ ID NO:40) and/or CDR3 (SEQ ID NO:41).

In a specific embodiment, the invention encompasses a 4D5 antibody (e.g., chimeric, humanized) comprising a variant Fc region having a substitution at position 243 with leucine, at position 292 with proline, at position 300 with leucine, at position 305 with isoleucine, and at position 396 with leucine. In another specific embodiment, the invention encompasses a 4D5 antibody having a leucine at position 243, a proline at position 292, a leucine at position 300, an isoleucine at position 305, and a leucine at position 396. In other embodiments, the invention encompasses a 4D5 antibody comprising a variant Fc region having a substitution at position 243 with leucine, at position 292 with proline, and at position 300 with leucine. In other embodiments, the invention encompasses a 4D5 antibody having a leucine at position 243, a proline at position 292, and a leucine at position 300. In other embodiments, the invention encompasses a 4D5 antibody comprising a variant Fc region having a substitution at position 247 with leucine, at position 270 with glutamic acid, and at position 421 with lysine. In another embodiment, the invention encompasses a 4D5 antibody having a leucine at position 247, a glutamic acid at position 292, and a lysine at position 421.

In another specific embodiment, the invention encompasses engineering an anti-CD20 antibody by modification (e.g., substitution, insertion, deletion) of at least one amino acid residue which modification increases the affinity of the Fc region for FcγRIIIA and/or FcγRIIA. In a related embodiment, the anti-CD20 antibody is mouse human chimeric anti-CD20 monoclonal antibody, 2H7 Further nonlimiting examples of anti-CD20 antibodies that can be used in the methods of the invention are disclosed in U.S. patent application Ser. No. 11/271,140, filed Nov. 10, 2005, hereby incorporated by reference in its entirety. In another specific embodiment, modification of the anti-CD20 monoclonal antibody, 2H7 may also further decrease the affinity of the Fc region for FcγRIIB. In yet another specific embodiment, the engineered anti-CD20 monoclonal antibody, 2H7 may further have an enhanced effector function as determined by standard assays known in the art and disclosed and exemplified herein.

In a specific embodiment, the invention encompasses a 2H7 antibody (e.g., chimeric, humanized) comprising a variant Fc region having a substitution at position 243 with leucine, at position 292 with proline, at position 300 with leucine, at position 305 with isoleucine, and at position 396 with leucine. In another specific embodiment, the invention encompasses a 2H7 antibody having a leucine at position 243, a proline at position 292, a leucine at position 300, an isoleucine at position 305, and a leucine at position 396. In other embodiments, the invention encompasses a 4D5 antibody comprising a variant Fc region having a substitution at position 243 with leucine, at position 292 with proline, and at position 300 with leucine. In other embodiments, the invention encompasses a 2H7 antibody having a leucine at position 243, a proline at position 292, and a leucine at position 300. In other embodiments, the invention encompasses a 2H7 antibody comprising a variant Fc region having a substitution at position 247 with leucine, at position 270 with glutamic acid, and at position 421 with lysine. In another embodiment, the invention encompasses a 2H7 antibody having a leucine at position 247, a glutamic acid at position 292, and a lysine at position 421.

In another specific embodiment, the invention encompasses engineering an anti-FcγRIIB antibody, in particular an anti-FcγRIIB antibody that specifically binds human FcγRIIB, more particularly native human FcγRIIB, by modification (e.g., substitution, insertion, deletion) of at least one amino acid residue which modification increases the affinity of the Fc region for FcγRIIIA and/or FcγRIIA. Non-limiting examples of representative anti-FcγRIIB antibodies are disclosed in U.S. Provisional Application No. 60/403,266 filed on Aug. 12, 2002; U.S. application Ser. No. 10/643,857 filed on Aug. 14, 2003; and U.S Patent Application Publication Numbers: 2004-0185045; 2005-0260213; and 2006-0013810, all of which are hereby incorporated by reference in their entireties. Examples of anti-FcγRIIB antibodies that may be engineered in accordance with the methods of the invention are the monoclonal antibodies produced by clone 2B6, 3H7, 8B5.4.3, 1D5, 2E1, 2H9, 2D11, 8B5 and 1F2 having ATCC accession numbers PTA-4591, PTA-4592, PTA-7610, PTA-5958, PTA-5961, PTA-5962, PTA-5960, PTA-7610 and PTA-5959, respectively (deposited at ATCC, 10801 University Boulevard, Manassas, Va. 02209-2011, all of which are incorporated herein by reference), or chimeric, humanized or other engineered versions thereof.

In a specific embodiment, the invention encompasses engineering a humanized antibody comprising the heavy chain variable domain and/or light chain variable domain of 2B6, 3H7 or 8B5.3.4. In another specific embodiment, the invention encompasses engineering a humanized antibody comprising the CDRs of 2B6, 3H7 or 8B5.3.4. In a specific embodiment, the invention encompasses engineering a humanized antibody comprising the heavy chain variable domain having the amino acid sequence of SEQ ID NO: 1, SEQ ID NO:2 or SEQ ID NO:3 and the light chain variable domain having the amino acid sequence of SEQ ID NO: 4, SEQ ID NO:5, SEQ ID NO:6, SEQ ID NO:7 or SEQ ID NO: 8. In a specific embodiment, the invention encompasses engineering a humanized antibody comprising the heavy chain variable domain having the amino acid sequence of SEQ ID NO:9 and the light chain variable domain having the amino acid sequence of SEQ ID NO:10.

In a specific embodiment, the invention encompasses engineering a humanized 2B6 antibody comprising a heavy chain having the amino acid sequence SEQ ID NO:42. In another specific embodiment, the invention encompasses engineering a humanized 2B6 antibody comprising a heavy chain having the amino acid sequence SEQ ID NO:29. In still other embodiments, the invention encompasses engineering a humanized 2B6 antibody comprising a light chain having the amino acid sequence SEQ ID NO:30. In a preferred embodiment, the invention encompasses engineering a humanized 2B6 antibody comprising a heavy chain containing the amino acid sequence SEQ ID NO:29 and a light chain containing the sequence SEQ ID NO:30. In a specific aspect of the invention, the invention encompasses the use of plasmid pMGx0675, which includes the nucleotide sequences SEQ ID NO:43 and SEQ ID NO:44 that encode the heavy chain amino acid sequence SEQ ID NO:29 and the light chain amino acid sequence SEQ ID NO:30, respectively. Plasmid pMGx0675 been deposited with the American Type Culture Collection (10801 University Blvd., Manassas, Va. 20110-2209) on May 23, 2006 under the provisions of the Budapest Treaty on the International Recognition of the Deposit of Microorganisms for the Purposes of Patent Procedures, and assigned accession number PTA 7609, and is incorporated herein by reference.

In specific embodiments, the invention encompasses engineering antibodies, preferably humanized, that bind the extracellular domain of native human FcγRIIB. The humanized anti-FcγRIIB antibodies encompassed by the invention may have a heavy chain variable region comprising the amino acid sequence of CDR1 (SEQ ID NO:15, SEQ ID NO:16, an amino acid sequence corresponding to amino acids 31-35 as set forth in SEQ ID NO:2, or an amino acid sequence corresponding to amino acids 31-35 as set forth in SEQ ID NO:3) and/or CDR2 (SEQ ID NO:17, SEQ ID NO:18, an amino acid sequence corresponding to amino acids 50-66 as set forth in SEQ ID NO:2, or an amino acid sequence corresponding to amino acids 50-66 as set forth in SEQ ID NO:3) and/or CDR3 (SEQ ID NO:19, SEQ ID NO:20, an amino acid sequence corresponding to amino acids 100-111 as set forth in SEQ ID NO:2, or an amino acid sequence corresponding to amino acids 100-111 as set forth in SEQ ID NO:3) and/or a light chain variable region comprising the amino acid sequence of CDR1 (SEQ ID NO:21, SEQ ID NO:22, or an amino acid sequence corresponding to amino acids 24-34 as set forth in SEQ ID NO:8) and/or a CDR2 (SEQ ID NO:23, SEQ ID NO:24, SEQ ID NO:25, SEQ ID NO:26, or an amino acid sequence corresponding to amino acids 50-56 as set forth in SEQ ID NO:62) and/or CDR3 (SEQ ID NO:27, SEQ ID NO:28, or an amino acid sequence corresponding to amino acids 90-98 as set forth in SEQ ID NO:8).

In a specific embodiment, the invention encompasses a 2B6 antibody comprising a variant Fc region having a substitution at position 243 with leucine, at position 292 with proline, at position 300 with leucine, at position 305 with isoleucine, and at position 396 with leucine. In another specific embodiment, the invention encompasses a 2B6 antibody having a leucine at position 243, a proline at position 292, a leucine at position 300, an isoleucine at position 305, and a leucine at position 396. In other embodiments, the invention encompasses a 2B6 antibody comprising a variant Fc region having a substitution at position 243 with leucine, at position 292 with proline, and at position 300 with leucine. In other embodiments, the invention encompasses a 2B6 antibody having a leucine at position 243, a proline at position 292, and a leucine at position 300. In other embodiments, the invention encompasses a 2B6 antibody comprising a variant Fc region having a substitution at position 247 with leucine, at position 270 with glutamic acid, and at position 421 with lysine. In another embodiment, the invention encompasses a 2B6 antibody having a leucine at position 247, a glutamic acid at position 292, and a lysine at position 421.

In a specific embodiment, modification of the anti-FcγRIIB antibody may also decrease the affinity of the Fc region for FcγRIIB relative to the wild-type antibody. In yet another specific embodiment, the engineered anti-FcγRIIB antibody may further have an enhanced effector function as determined by standard assays known in the art and disclosed and exemplified herein. In a specific embodiment, the anti-FcγRIIB monoclonal antibody comprises a modification at position 334 with glutamic acid, at position 359 with asparagine, and at position 366 with serine (MgFc13); or a substitution at position 316 with aspartic acid, at position 378 with valine, and at position 399 with glutamic acid (MgFc27); or a substitution at position 243 with isoleucine, at position 379 with leucine, and at position 420 with valine (MgFc29); or a substitution at position 392 with threonine and at position 396 with leucine (MgFc38); or a substitution at position 221 with glutamic acid, at position 270 with glutamic acid, at position 308 with alanine, at position 311 with histidine, at position 396 with leucine, and at position 402 with aspartic (MgFc42); or a substitution at position 410 with histidine, and at position 396 with leucine (MgFc53); or a substitution at position 243 with leucine, at position 305 with isoleucine, at position 378 with aspartic acid, at position 404 with serine, and at position 396 with leucine (MgFc54); or a substitution at position 255 with isoleucine, and at position 396 with leucine (MgFc55); or a substitution at position 370 with glutamic acid, and at position 396 with leucine (MgFc59); or a substitution at position 243 with leucine, at position 292 with proline, at position 300 with leucine, at position 305 with isoleucine, and at position 396 with leucine (MgFc88); or a substitution at position 243 with leucine, at position 292 with proline, at position 300 with leucine, and at position 396 with leucine (MgFc88A); or a substitution at position 234 with leucine, at position 292 with proline, and at position 300 with leucine (MgFc155); or a substitution at position 243 with leucine, at position 292 with proline, and at position 300 with leucine; or a substitution at position 243 with leucine, at position 292 with proline, and at position 396 with leucine; or a substitution at position 243 with leucine, and at position 292 with proline; or a substitution at position 243 with leucine; or a substitution at position 273 with phenylalanine; or a substitution at position 247 with leucine, at position 270 with glutamic acid, and at position 421 with lysine. In a related embodiment, the variant Fc region further comprises one or more amino acid modifications disclosed in tables 4, 5, 9, and 10, infra.

In a specific embodiments, the invention encompasses an antibody that binds to CD79a or CD79b (e.g., chimeric, humanized) comprising a variant Fc region and use of the antibodies for treatment of cancer. In specific embodiments, the antibody that binds to CD79b or CD79b has a substitution at position 243 with leucine, at position 292 with proline, at position 300 with leucine, at position 305 with isoleucine, and at position 396 with leucine. In another specific embodiment, the invention encompasses an antibody that binds to CD79a or CD79b having a leucine at position 243, a proline at position 292, a leucine at position 300, an isoleucine at position 305, and a leucine at position 396. In other embodiments, the invention an antibody that binds to CD79a or CD79b receptor comprising a variant Fc region having a substitution at position 243 with leucine, at position 292 with proline, and at position 300 with leucine. In other embodiments, the invention encompasses an antibody that binds to CD79a or CD79b having a leucine at position 243, a proline at position 292, and a leucine at position 300. In other embodiments, the invention encompasses an antibody that binds to CD79a or CD79b comprising a variant Fc region having a substitution at position 247 with leucine, at position 270 with glutamic acid, and at position 421 with lysine. In another embodiment, the invention encompasses an antibody that binds to CD79a or CD79b having a leucine at position 247, a glutamic acid at position 292, and a lysine at position 421.

In a specific embodiments, the invention encompasses an antibody that binds to ErbB1 (e.g., chimeric, humanized) comprising a variant Fc region and use of the antibodies for treatment of cancer. In specific embodiments, the antibody that binds to ErbB1 has a substitution at position 243 with leucine, at position 292 with proline, at position 300 with leucine, at position 305 with isoleucine, and at position 396 with leucine. In another specific embodiment, the invention encompasses an antibody that binds to ErbB1 having a leucine at position 243, a proline at position 292, a leucine at position 300, an isoleucine at position 305, and a leucine at position 396. In other embodiments, the invention an antibody that binds to ErbB1 receptor comprising a variant Fc region having a substitution at position 243 with leucine, at position 292 with proline, and at position 300 with leucine. In other embodiments, the invention encompasses an antibody that binds to ErbB1 having a leucine at position 243, a proline at position 292, and a leucine at position 300. In other embodiments, the invention encompasses an antibody that binds to ErbB1 comprising a variant Fc region having a substitution at position 247 with leucine, at position 270 with glutamic acid, and at position 421 with lysine. In another embodiment, the invention encompasses an antibody that binds to ErbB1 having a leucine at position 247, a glutamic acid at position 292, and a lysine at position 421.

In a specific embodiments, the invention encompasses an antibody that binds to A33, CD5, CD11c, CD19, CD22, CD23, CD27, CD40, CD45, CD103, CTLA4, ErbB3, ErbB4, VEGF receptor, TNF-a receptor, TNF-β receptor, or TNF-γ receptor (e.g., chimeric, humanized) comprising a variant Fc region and use of the antibodies for treatment of cancer. In specific embodiments, the antibody that binds to A33, CD5, CD11c, CD19, CD22, CD23, CD27, CD40, CD45, CD103, CTLA4, ErbB3, ErbB4, VEGF receptor, TNF-a receptor, TNF-β receptor, or TNF-γ receptor has a substitution at position 243 with leucine, at position 292 with proline, at position 300 with leucine, at position 305 with isoleucine, and at position 396 with leucine. In another specific embodiment, the invention encompasses an antibody that binds to A33, CD5, CD11c, CD19, CD22, CD23, CD27, CD40, CD45, CD103, CTLA4, ErbB3, ErbB4, VEGF receptor, TNF-a receptor, TNF-β receptor, or TNF-γ receptor having a leucine at position 243, a proline at position 292, a leucine at position 300, an isoleucine at position 305, and a leucine at position 396. In other embodiments, the invention an antibody that binds to A33, CD5, CD11c, CD19, CD22, CD23, CD27, CD40, CD45, CD103, CTLA4, ErbB3, ErbB4, VEGF receptor, TNF-a receptor, TNF-β receptor, or TNF-γ receptor comprising a variant Fc region having a substitution at position 243 with leucine, at position 292 with proline, and at position 300 with leucine. In other embodiments, the invention encompasses an antibody that binds to A33, CD5, CD11c, CD19, CD22, CD23, CD27, CD40, CD45, CD103, CTLA4, ErbB3, ErbB4, VEGF receptor, TNF-a receptor, TNF-β receptor, or TNF-γ receptor having a leucine at position 243, a proline at position 292, and a leucine at position 300. In other embodiments, the invention encompasses an antibody that binds to A33, CD5, CD11c, CD19, CD22, CD23, CD27, CD40, CD45, CD103, CTLA4, ErbB3, ErbB4, VEGF receptor, TNF-a receptor, TNF-β receptor, or TNF-γ receptor comprising a variant Fc region having a substitution at position 247 with leucine, at position 270 with glutamic acid, and at position 421 with lysine. In another embodiment, the invention encompasses an antibody that binds to A33, CD5, CD11c, CD19, CD22, CD23, CD27, CD40, CD45, CD103, CTLA4, ErbB3, ErbB4, VEGF receptor, TNF-a receptor, TNF-β receptor, or TNF-γ receptor having a leucine at position 247, a glutamic acid at position 292, and a lysine at position 421.

The present invention also includes polynucleotides that encode a molecule of the invention, including polypeptides and antibodies, identified by the methods of the invention. The polynucleotides encoding the molecules of the invention may be obtained, and the nucleotide sequence of the polynucleotides determined, by any method known in the art. The invention relates to an isolated nucleic acid encoding a molecule of the invention. The invention also provides a vector comprising said nucleic acid. The invention further provides host cells containing the vectors or polynucleotides of the invention.

The invention further provides methods for the production of the molecules of the invention. The molecules of the invention, including polypeptides and antibodies, can be produced by any method known to those skilled in the art, in particular, by recombinant expression. In a specific embodiment, the invention relates to a method for recombinantly producing a molecule of the invention, said method comprising: (i) culturing in a medium a host cell comprising a nucleic acid encoding said molecule, under conditions suitable for the expression of said molecule; and (ii) recovery of said molecule from said medium.

The molecules identified in accordance with the methods of the invention are useful in preventing, treating, or ameliorating one or more symptoms associated with a disease, disorder, or infection. The molecules of the invention are particularly useful for the treatment or prevention of a disease or disorder where an enhanced efficacy of effector cell function (e.g., ADCC) mediated by FcγR is desired, e.g., cancer, infectious disease, and in enhancing the therapeutic efficacy of therapeutic antibodies the effect of which is mediated by ADCC.

In one embodiment, the invention encompasses a method of treating cancer in a patient having a cancer characterized by a cancer antigen, said method comprising administering a therapeutically effective amount of a therapeutic antibody that binds the cancer antigen, which has been engineered in accordance with the methods of the invention. In a specific embodiment, the invention encompasses a method for treating cancer in a patient having a cancer characterized by a cancer antigen, said method comprising administering a therapeutically effective amount of a therapeutic antibody that specifically binds said cancer antigen, said therapeutic antibody comprising a variant Fc region, wherein said variant Fc region comprises at least one amino acid modification relative to a wild-type Fc region, such that said therapeutic antibody specifically binds FcγRIIIA via its Fc region with a greater affinity than the therapeutic antibody comprising the wild-type Fc region binds FcγRIIIA, provided that said variant Fc region does not have a substitution at positions 329, 331, or 332, and does not have an alanine at any of positions 256, 290, 298, 312, 333, 334, 359, 360, or 430; a lysine at position 330; a threonine at position 339; a methionine at position 320; a serine at position 326; an asparagine at position 326; an aspartic acid at position 326; a glutamic acid at position 326; a glutamine at position 334; a glutamic acid at position 334; a methionine at position 334; a histidine at position 334; a valine at position 334; or a leucine at position 334. In another specific embodiment, the invention encompasses a method for treating cancer in a patient having a cancer characterized by a cancer antigen, said method comprising administering a therapeutically effective amount of a therapeutic antibody that specifically binds a cancer antigen, said therapeutic antibody comprising a variant Fc region, wherein said variant Fc region comprises at least one amino acid modification relative to a wild-type Fc region such that said therapeutic antibody specifically binds FcγRIIIA via its Fc region with a greater affinity than a therapeutic antibody comprising the wild-type Fc region binds FcγRIIIA, and said therapeutic antibody further specifically binds FcγRIIB with a lower affinity than a therapeutic antibody comprising the wild-type Fc region binds FcγRIIB, provided that said variant Fc region does not have an alanine at any of positions 256, 298, 333, or 334. The invention encompasses a method for treating cancer in a patient characterized by a cancer antigen, said method comprising administering a therapeutically effective amount of a therapeutic antibody that specifically binds said cancer antigen and said therapeutic antibody comprises a variant Fc region so that the antibody has an enhanced ADCC activity.

The invention encompasses a method of treating an autoimmune disorder and/or inflammatory disorder in a patient in need thereof, said method comprising administering to said patient a therapeutically effective amount of a molecule comprising a variant Fc region, wherein said variant Fc region comprises at least one amino acid modification relative to a wild type Fc region, such that said molecule specifically binds FcγRIIB via its Fc region with a greater affinity than a comparable molecule comprising the wild type Fc region, and said molecule further specifically binds FcγRIIIA via its Fc region with a lower affinity than a comparable molecule comprising the wild type Fc region, and said molecule binds an immune complex (e.g., an antigen/antibody complex). The invention encompasses a method of treating an autoimmune disorder and/or inflammatory disorder further comprising administering one or more additional prophylactic or therapeutic agents, e.g., immunomodulatory agents, anti-inflammatory agents, used for the treatment and/or prevention of such diseases.

The invention also encompasses methods for treating or preventing an infectious disease in a subject comprising administering a therapeutically or prophylactically effective amount of one or more molecules of the invention that bind an infectious agent or cellular receptor therefor. Infectious diseases that can be treated or prevented by the molecules of the invention are caused by infectious agents including but not limited to viruses, bacteria, fungi, protozae, and viruses.

According to one aspect of the invention, molecules of the invention comprising variant Fc regions have an enhanced antibody effector function towards an infectious agent, e.g., a pathogenic protein, relative to a comparable molecule comprising a wild-type Fc region. In a specific embodiment, molecules of the invention enhance the efficacy of treatment of an infectious disease by enhancing phagocytosis and/or opsonization of the infectious agent causing the infectious disease. In another specific embodiment, molecules of the invention enhance the efficacy of treatment of an infectious disease by enhancing ADCC of infected cells causing the infectious disease.

In some embodiments, the molecules of the invention may be administered in combination with a therapeutically or prophylactically effective amount of one or additional therapeutic agents known to those skilled in the art for the treatment and/or prevention of an infectious disease. The invention contemplates the use of the molecules of the invention in combination with antibiotics known to those skilled in the art for the treatment and or prevention of an infectious disease.

The invention provides pharmaceutical compositions comprising a molecule of the invention, e.g., a polypeptide comprising a variant Fc region, an immunoglobulin comprising a variant Fc region, a therapeutic antibody engineered in accordance with the invention, and a pharmaceutically acceptable carrier. The invention additionally provides pharmaceutical compositions further comprising one or more additional therapeutic agents, including but not limited to anti-cancer agents, anti-inflammatory agents, immunomodulatory agents.

5.1 Definitions

As used herein, the term "Fc region" is used to define a C-terminal region of an IgG heavy chain. Although the boundaries may vary slightly, the human IgG heavy chain Fc region is defined to stretch from Cys226 to the carboxy terminus. The Fc region of an IgG comprises two constant domains, CH2 and CH3. The CH2 domain of a human IgG Fc region (also referred to as "Cγ2" domain) usually extends from amino acid 231 to amino acid 338. The CH3 domain of a human IgG Fc region usually extends from amino acids 342 to 447. The CH2 domain is unique in that it is not closely paired with another domain. Rather, two N-linked branched carbohydrate chains are interposed between the two CH2 domains of an intact native IgG.

Throughout the present specification, the numbering of the residues in an IgG heavy chain is that of the EU index as in Kabat et al., *Sequences of Proteins of Immunological Interest*, 5$^{th}$ Ed. Public Health Service, NHI, MD (1991), expressly incorporated herein by references. The "EU index as in Kabat" refers to the numbering of the human IgG1 EU antibody.

The "hinge region" is generally defined as stretching from Glu216 to Pro230 of human IgG1. Hinge regions of other IgG isotypes may be aligned with the IgG1 sequence by placing the first and last cysteine residues forming inter-heavy chain S—S bonds in the same positions.

As used herein, the terms "antibody" and "antibodies" refer to monoclonal antibodies, multispecific antibodies, human antibodies, humanized antibodies, synthetic antibodies, chimeric antibodies, polyclonal antibodies, camelized antibodies, single-chain Fvs (scFv), single chain antibodies, Fab fragments, F(ab') fragments, disulfide-linked bispecific Fvs (sdFv), intrabodies, and anti-idiotypic (anti-Id) antibodies (including, e.g., anti-Id and anti-anti-Id antibodies to antibodies of the invention), and epitope-binding fragments of any of the above. In particular, antibodies include immunoglobulin molecules and immunologically active fragments of immunoglobulin molecules, i.e., molecules that contain an antigen binding site. Immunoglobulin molecules can be of any type (e.g., IgG, IgE, IgM, IgD, IgA and IgY), class (e.g., IgG$_1$, IgG$_2$, IgG$_3$, IgG$_4$, IgA$_1$ and IgA$_2$) or subclass.

As used herein, the term "variant Fc region" is intended to denote an Fc region that has been modified, by substitution, insertion or deletion of one or more amino acid residues relative to the Fc region of the unmodified molecule (i.e., the "wild-type" immunoglobulin). The present invention relates to molecules that possess Fc regions having an altered Ratio of Affinities for an FcγR that activates a cellular effector function (i.e., "an FcγR$_{Activating}$," such as FcγRIIA or FcγRIIIA) relative to an FcγR that inhibits a cellular effector function (i.e., "an FcγR$_{Inhibiting}$," such as FcγRIIB):

$$\text{Ratio of Affinities} = \frac{\text{Wild-Type to Variant Change in Affinity to } Fc\gamma R_{Activating}}{\text{Wild-Type to Variant Change in Affinity to } Fc\gamma R_{Inhibiting}}$$

Thus, for any particular molecule having a variant Fc region, the molecule's Ratio of Affinities is determined by calculating the difference in affinity of the variant Fc region of the molecule to an FcγR$_{Activating}$ (for example, to FcγRIIA or to FcγRIIIA), relative to the affinity of a wild-type immunoglobulin to such FcγR$_{Activating}$ (e.g., Affinity$_{FcγRIIIA}$ of the variant Fc region—Affinity$_{FcγRIIIA}$ of the wild-type immunoglobulin), and dividing such difference by the difference in affinity to an FcγR$_{Inhibiting}$ (for example, FcγRIIB) of the variant Fc region of the molecule, relative to the affinity of a wild-type immunoglobulin to such FcγR$_{Inhibiting}$ (e.g., Affinity$_{FcγRIIB}$ of the variant Fc region—Affinity$_{FcγRIIB}$ of the wild-type immunoglobulin). An increased Ratio of Affinities may result from the Fc region of the molecule having (relative to a wild type Fc) an increase in affinity to an FcγR$_{Activating}$ (for example, to FcγRIIA or to FcγRIIIA) coupled with either an unchanged affinity to an FcγR$_{Inhibiting}$ (for example, FcγRIIB) or a decrease in affinity to such FcγR$_{Inhibiting}$. Alternatively, an increased Ratio of Affinities may result from the Fc region of such molecule exhibiting an increase in affinity to both an FcγR$_{Activating}$ and an FcγR$_{Inhibiting}$ (relative to a wild-type Fc), provided that the increase in affinity to the FcγR$_{Activating}$ exceeds the increase in affinity to the FcγR$_{Inhibiting}$ (i.e., binding to the FcγR$_{Activating}$ is "greatly" increased compared to binding to the FcγR$_{Inhibiting}$, which is merely increased), or may result from the Fc region of such molecule exhibiting a decreased affinity to both an FcγR$_{Activating}$ and an FcγR$_{Inhibiting}$ (relative to a wild-type Fc), provided that the decrease in affinity to the FcγR$_{Activating}$ is less than the decrease in affinity to an FcγR$_{Inhibiting}$ (i.e., binding to the FcγR$_{Inhibiting}$ is "greatly" decreased compared to binding to the FcγR$_{Activating}$, which is merely decreased), or may result from an unchanged affinity to an FcγR$_{Activating}$ coupled with a decrease in affinity to an FcγR$_{Inhibiting}$. A decreased Ratio of Affinities may result from the Fc region of the molecule having (relative to a wild type Fc) a decrease in affinity to an FcγR$_{Activating}$ coupled with either an unchanged affinity to an FcγR$_{Inhibiting}$ or an increase in affinity to an FcγR$_{Inhibiting}$. Alternatively, a decreased Ratio of Affinities may result from the Fc region of such molecule exhibiting a decrease in affinity to both an FcγR$_{Activating}$ and an FcγR$_{Inhibiting}$ (relative to a wild-type Fc), provided that the decrease in affinity to the FcγR$_{Activating}$ exceeds the decrease in affinity to the FcγR$_{Inhibiting}$ (i.e., binding to the FcγR$_{Activating}$ is "greatly" decreased compared to binding to the FcγR$_{Inhibiting}$, which is merely decreased), or may result from the Fc region of such molecule exhibiting an increased affinity to both an FcγR$_{Activating}$ and an FcγR$_{Inhibiting}$ (relative to a wild-type Fc), provided that the increase in affinity to the FcγR$_{Activating}$ is less than the increase in affinity to the an FcγR$_{Inhibiting}$ (i.e., binding to the FcγR$_{Inhibiting}$ is "greatly" increased compared to binding to he FcγR$_{Activating}$, which is merely increased), or may result from an unchanged affinity to an FcγR$_{Activating}$ coupled with an increase in affinity to an FcγR$_{Inhibiting}$.

As used herein, the term "derivative" in the context of polypeptides or proteins refers to a polypeptide or protein that comprises an amino acid sequence which has been altered by the introduction of amino acid residue substitutions, deletions or additions. The term "derivative" as used herein also refers to a polypeptide or protein which has been modified, i.e., by the covalent attachment of any type of molecule to the polypeptide or protein. For example, but not by way of limitation, an antibody may be modified, e.g., by glycosylation, acetylation, pegylation, phosphorylation, amidation, derivatization by known protecting/blocking groups, proteolytic cleavage, linkage to a cellular ligand or other protein, etc. A derivative polypeptide or protein may be produced by chemical modifications using techniques known to those of skill in the art, including, but not limited to specific chemical cleavage, acetylation, formylation, metabolic synthesis of tunicamycin, etc. Further, a derivative polypeptide or protein derivative possesses a similar or identical function as the polypeptide or protein from which it was derived.

As used herein, the term "derivative" in the context of a non-proteinaceous derivative refers to a second organic or inorganic molecule that is formed based upon the structure of a first organic or inorganic molecule. A derivative of an organic molecule includes, but is not limited to, a molecule modified, e.g., by the addition or deletion of a hydroxyl, methyl, ethyl, carboxyl or amine group. An organic molecule may also be esterified, alkylated and/or phosphorylated.

As used herein, the terms "disorder" and "disease" are used interchangeably to refer to a condition in a subject. In particular, the term "autoimmune disease" is used interchangeably with the term "autoimmune disorder" to refer to a condition in a subject characterized by cellular, tissue and/or organ injury caused by an immunologic reaction of the subject to its own cells, tissues and/or organs. The term "inflammatory disease" is used interchangeably with the term "inflammatory disorder" to refer to a condition in a subject characterized by inflammation, preferably chronic inflammation. Autoimmune disorders may or may not be associated with inflammation. Moreover, inflammation may or may not be caused by an autoimmune disorder. Thus, certain disorders may be characterized as both autoimmune and inflammatory disorders.

As used herein, the term "cancer" refers to a neoplasm or tumor resulting from abnormal uncontrolled growth of cells. As used herein, cancer explicitly includes leukemias and lymphomas. In some embodiments, cancer refers to a benign tumor, which has remained localized. In other embodiments, cancer refers to a malignant tumor, which has invaded and destroyed neighboring body structures and spread to distant sites. In some embodiments, the cancer is associated with a specific cancer antigen.

As used herein, the term "immunomodulatory agent" and variations thereof refer to an agent that modulates a host's immune system. In certain embodiments, an immunomodulatory agent is an immunosuppressant agent. In certain other embodiments, an immunomodulatory agent is an immunostimulatory agent. Immunomodatory agents include, but are not limited to, small molecules, peptides, polypeptides, fusion proteins, antibodies, inorganic molecules, mimetic agents, and organic molecules.

As used herein, the term "epitope" refers to a fragment of a polypeptide or protein or a non-protein molecule having antigenic or immunogenic activity in an animal, preferably in a mammal, and most preferably in a human. An epitope having immunogenic activity is a fragment of a polypeptide or protein that elicits an antibody response in an animal. An epitope having antigenic activity is a fragment of a polypeptide or protein to which an antibody immunospecifically binds as determined by any method well-known to one of skill in the art, for example by immunoassays. Antigenic epitopes need not necessarily be immunogenic.

As used herein, the term "fragment" refers to a peptide or polypeptide comprising an amino acid sequence of at least 5 contiguous amino acid residues, at least 10 contiguous amino acid residues, at least 15 contiguous amino acid residues, at least 20 contiguous amino acid residues, at least 25 contiguous amino acid residues, at least 40 contiguous amino acid residues, at least 50 contiguous amino acid residues, at least 60 contiguous amino residues, at least 70 contiguous amino acid residues, at least contiguous 80 amino acid residues, at least contiguous 90 amino acid residues, at least contiguous 100 amino acid residues, at least contiguous 125 amino acid residues, at least 150 contiguous amino acid residues, at least contiguous 175 amino acid residues, at least contiguous 200 amino acid residues, or at least contiguous 250 amino acid residues of the amino acid sequence of another polypeptide. In a specific embodiment, a fragment of a polypeptide retains at least one function of the polypeptide.

As used herein, the terms "nucleic acids" and "nucleotide sequences" include DNA molecules (e.g., cDNA or genomic DNA), RNA molecules (e.g., mRNA), combinations of DNA and RNA molecules or hybrid DNA/RNA molecules, and analogs of DNA or RNA molecules. Such analogs can be generated using, for example, nucleotide analogs, which include, but are not limited to, inosine or tritylated bases. Such analogs can also comprise DNA or RNA molecules comprising modified backbones that lend beneficial attributes to the molecules such as, for example, nuclease resistance or an increased ability to cross cellular membranes. The nucleic acids or nucleotide sequences can be single-stranded, double-stranded, may contain both single-stranded and double-stranded portions, and may contain triple-stranded portions, but preferably is double-stranded DNA.

As used herein, a "therapeutically effective amount" refers to that amount of the therapeutic agent sufficient to treat or manage a disease or disorder. A therapeutically effective amount may refer to the amount of therapeutic agent sufficient to delay or minimize the onset of disease, e.g., delay or minimize the spread of cancer. A therapeutically effective amount may also refer to the amount of the therapeutic agent that provides a therapeutic benefit in the treatment or management of a disease. Further, a therapeutically effective amount with respect to a therapeutic agent of the invention means the amount of therapeutic agent alone, or in combination with other therapies, that provides a therapeutic benefit in the treatment or management of a disease.

As used herein, the terms "prophylactic agent" and "prophylactic agents" refer to any agent(s) which can be used in the prevention of a disorder, or prevention of recurrence or spread of a disorder. A prophylactically effective amount may refer to the amount of prophylactic agent sufficient to prevent the recurrence or spread of hyperproliferative disease, particularly cancer, or the occurrence of such in a patient, including but not limited to those predisposed to hyperproliferative disease, for example those genetically predisposed to cancer or previously exposed to carcinogens. A prophylactically effective amount may also refer to the amount of the prophylactic agent that provides a prophylactic benefit in the prevention of disease. Further, a prophylactically effective amount with respect to a prophylactic agent of the invention means that amount of prophylactic agent alone, or in combination with other agents, that provides a prophylactic benefit in the prevention of disease.

As used herein, the terms "prevent", "preventing" and "prevention" refer to the prevention of the recurrence or onset of one or more symptoms of a disorder in a subject as result of the administration of a prophylactic or therapeutic agent.

As used herein, the term "in combination" refers to the use of more than one prophylactic and/or therapeutic agents. The use of the term "in combination" does not restrict the order in which prophylactic and/or therapeutic agents are administered to a subject with a disorder. A first prophylactic or therapeutic agent can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second prophylactic or therapeutic agent to a subject with a disorder.

"Effector function" as used herein is meant a biochemical event that results from the interaction of an antibody Fc region with an Fc receptor or ligand. Effector functions include but are not limited to antibody dependent cell mediated cytotoxicity (ADCC), antibody dependent cell mediated phagocytosis (ADCP), and complement dependent cytotoxicity (CDC). Effector functions include both those that operate after the binding of an antigen and those that operate independent of antigen binding.

"Effector cell" as used herein is meant a cell of the immune system that expresses one or more Fc receptors and mediates one or more effector functions. Effector cells include but are not limited to monocytes, macrophages, neutrophils, dendritic cells, eosinophils, mast cells, platelets, B cells, large granular lymphocytes, Langerhans' cells, natural killer (NK) cells, and may be from any organism including but not limited to humans, mice, rats, rabbits, and monkeys.

"Fc ligand" as used herein is meant a molecule, preferably a polypeptide, from any organism that binds to the Fc region of an antibody to form an Fc-ligand complex. Fc ligands include but are not limited to FcγRs, FcγRs, FcγRs, FcRn, C1q, C3, staphylococcal protein A, streptococcal protein G, and viral FcγR. Fc ligands may include undiscovered molecules that bind Fc.

6. BRIEF DESCRIPTION OF THE DRAWINGS

FIG. 1 DECISION TREE FOR SELECTION OF Fc MUTANTS

An exemplary protocol for selecting Fc mutants.

FIG. 2 SCHEMATIC OF SEQUENCE OF 8B5.3.4 VARIABLE HEAVY CHAIN DOMAIN

Depiction of the of the 8B5.3.4 VH nucleotide and amino acid sequence (SEQ ID NOS:12 and 9, respectively).

FIG. 3 SCHEMATIC OF SEQUENCE OF 8B5.3.4 VARIABLE LIGHT CHAIN DOMAIN

Depiction of the 8B5.3.4 VL nucleotide and amino acid sequence (SEQ ID NOS:11 and 10, respectively).

FIG. 4 CAPTURE OF CH 4-4-20 ANTIBODY ON BSA-FITC SURFACE

6 μL of antibody at a concentration of approximately 20 μg/mL was injected at 5 μL/min over a BSA-fluoroscein isothiocyanate (FITC) surface. BIAcore sensogram of the binding of ch 4-4-20 antibodies with mutant Fc regions on the surface of the BSA-FITC immobilized sensor ship is shown. The marker was set on wild-type captured antibody response.

Figure 5:
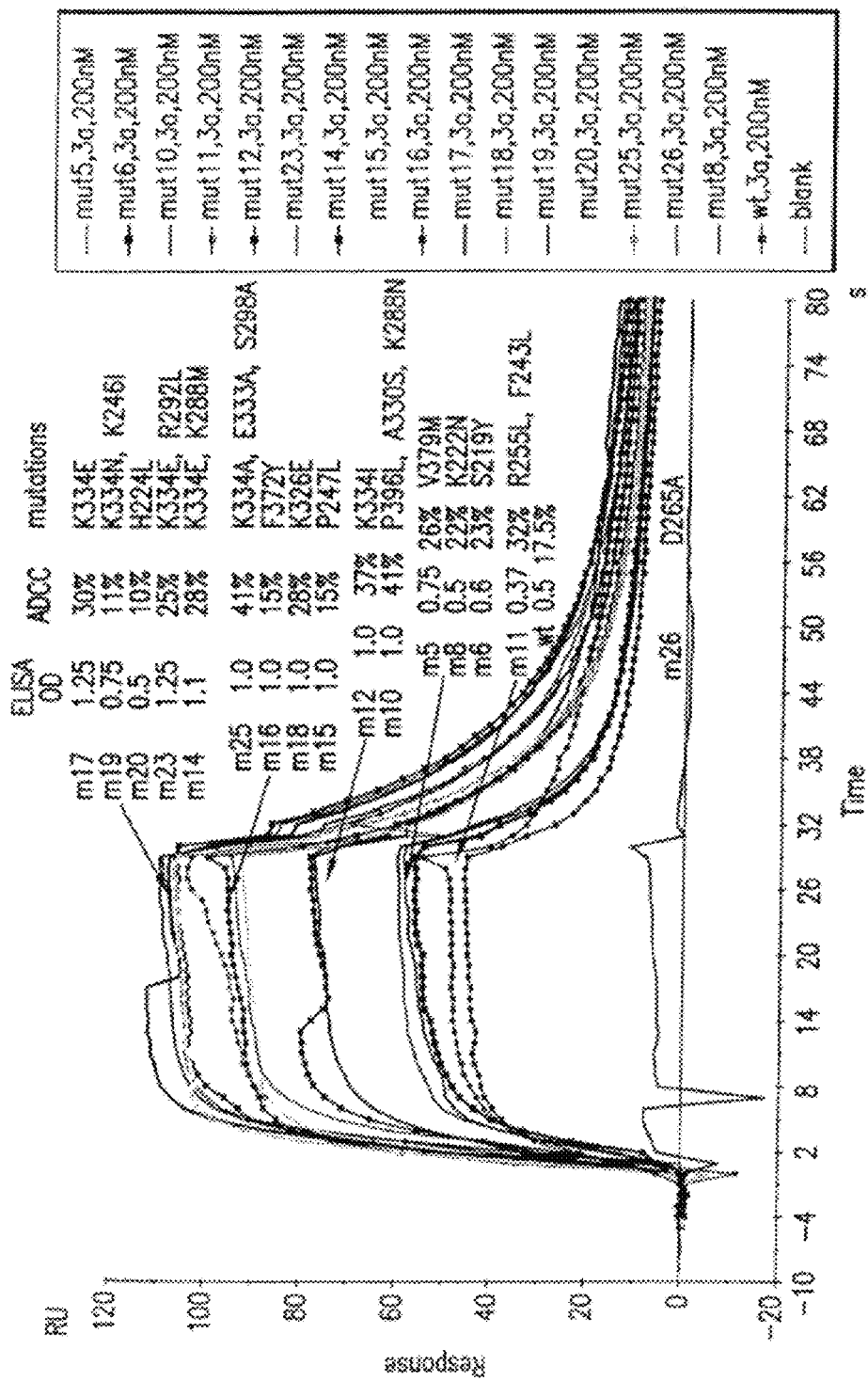
Figure 6A:
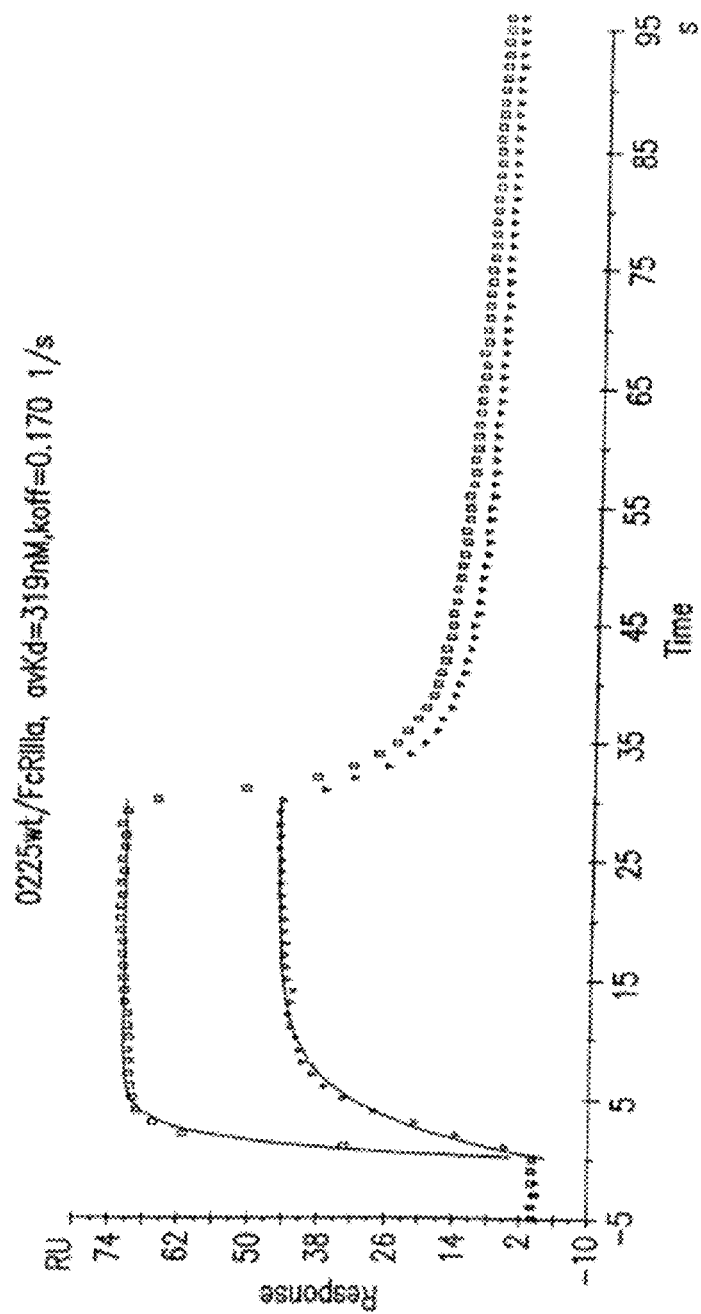
Figure 6B:
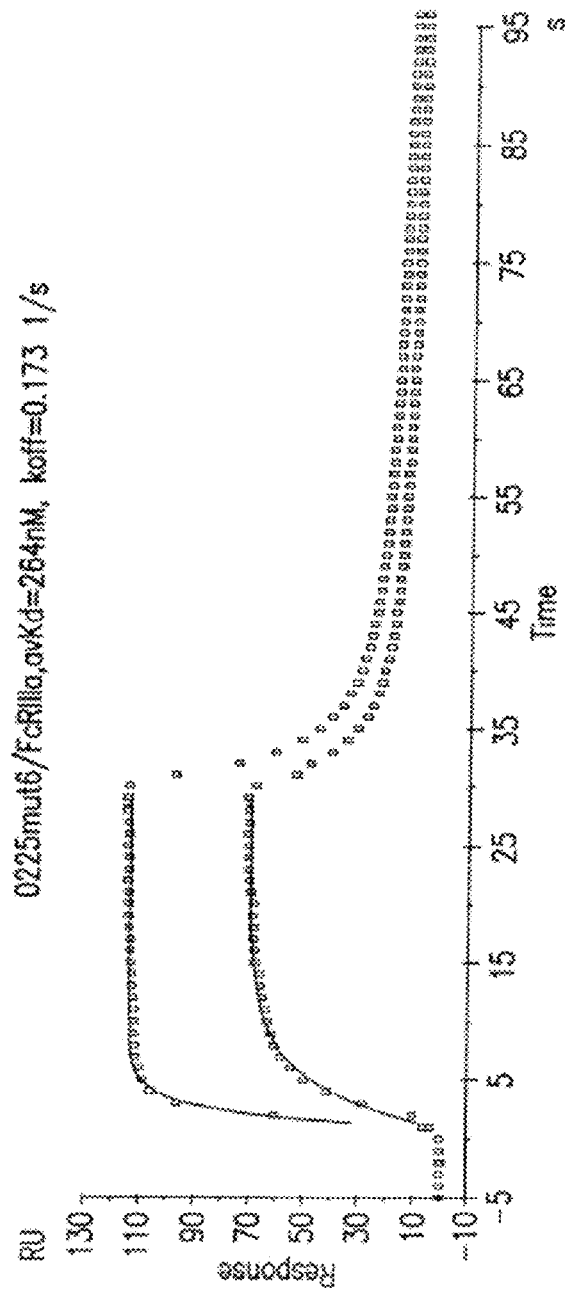
Figure 6C:
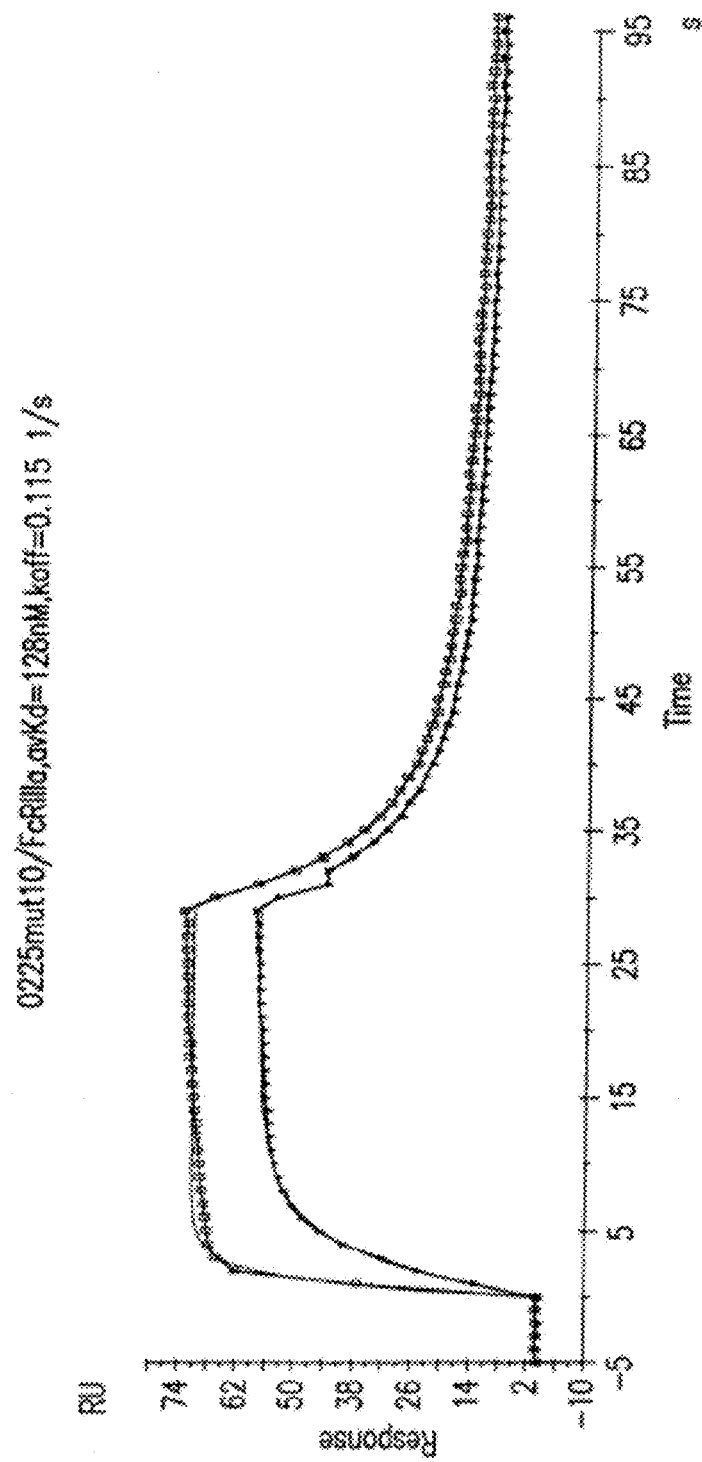
Figure 6D:
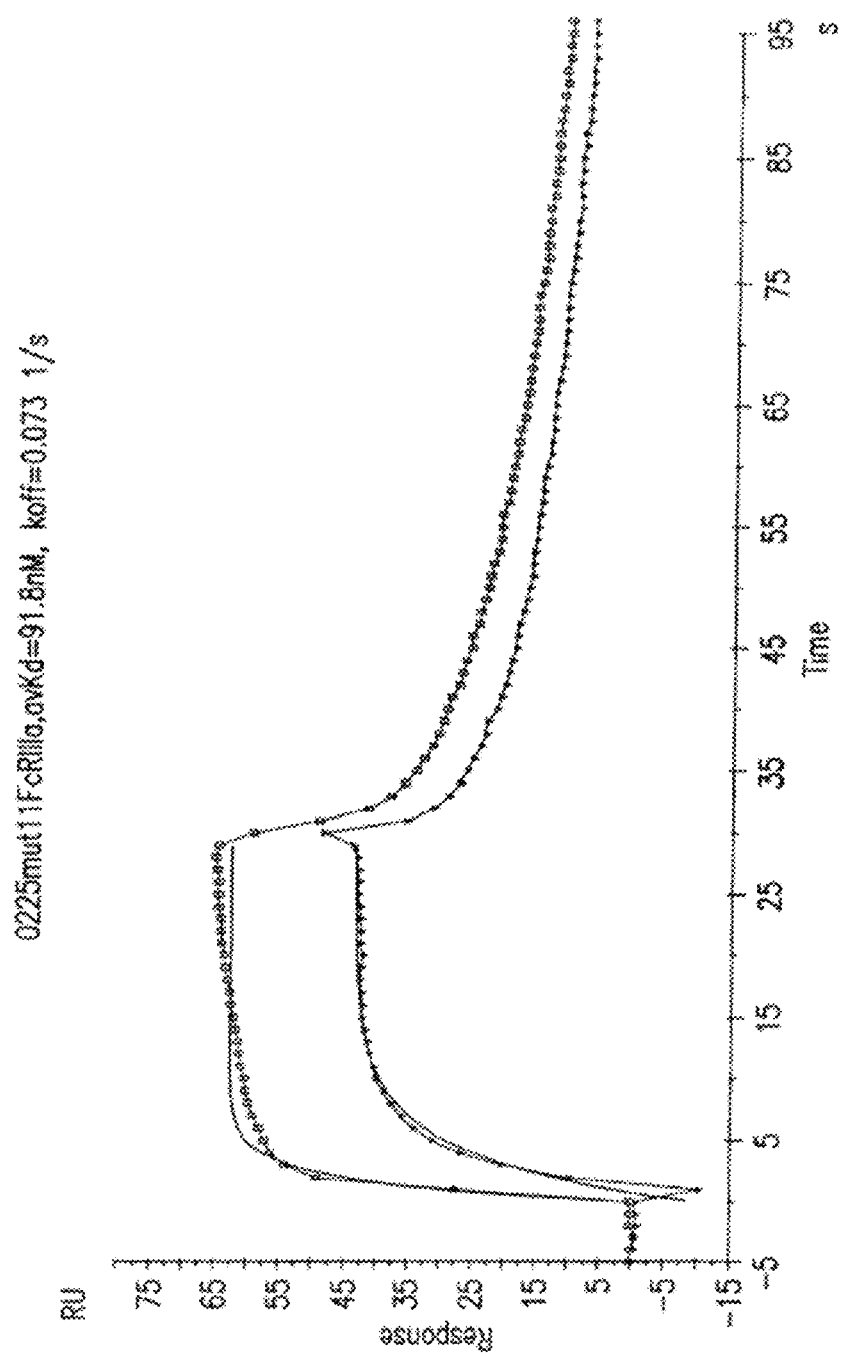
Figure 6E:
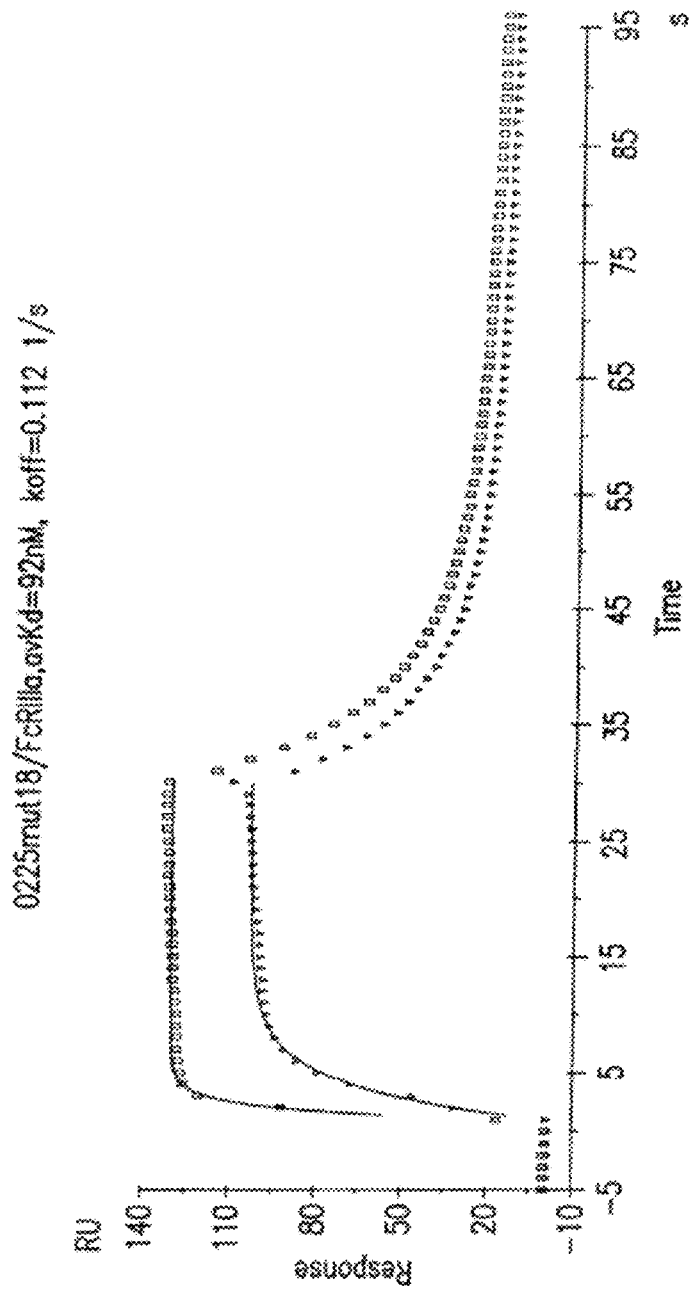
Figure 6F:
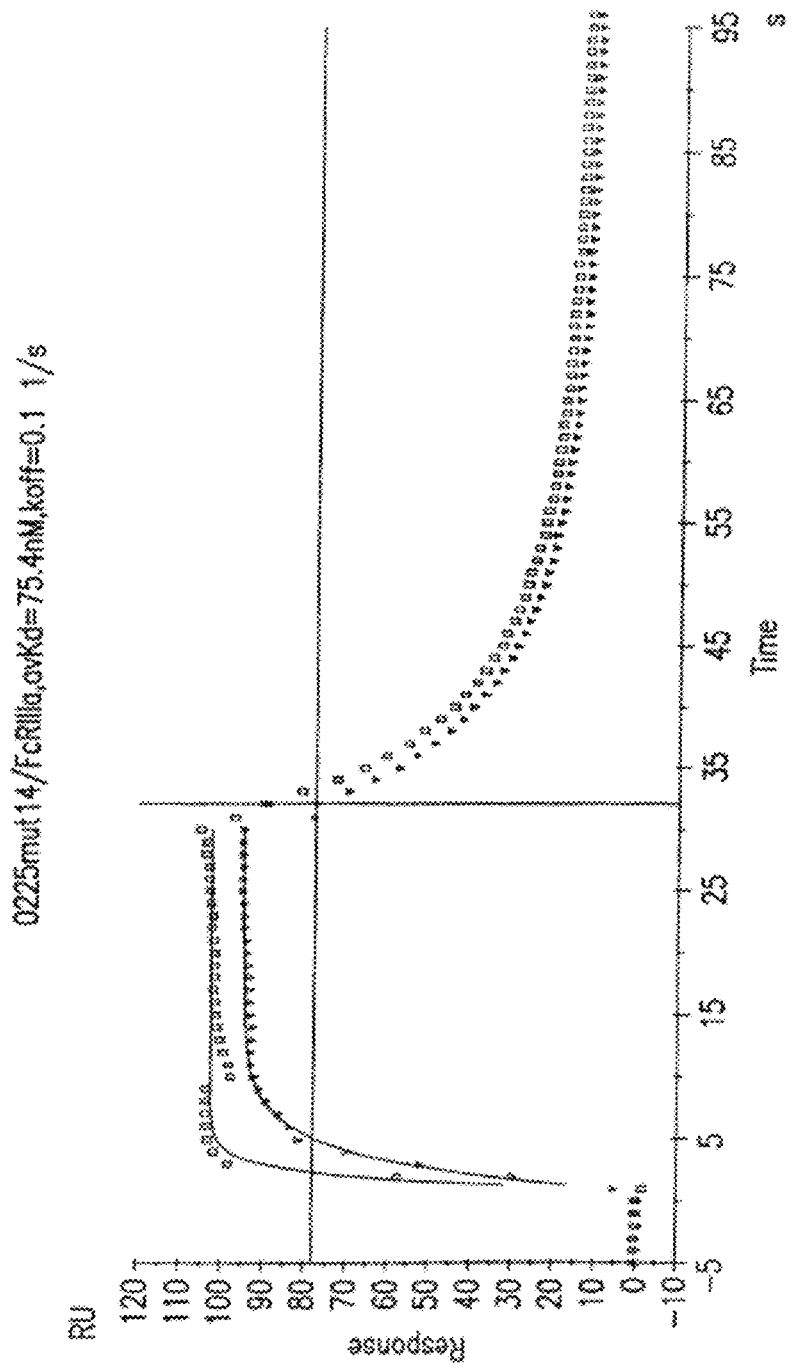
Figure 6G:
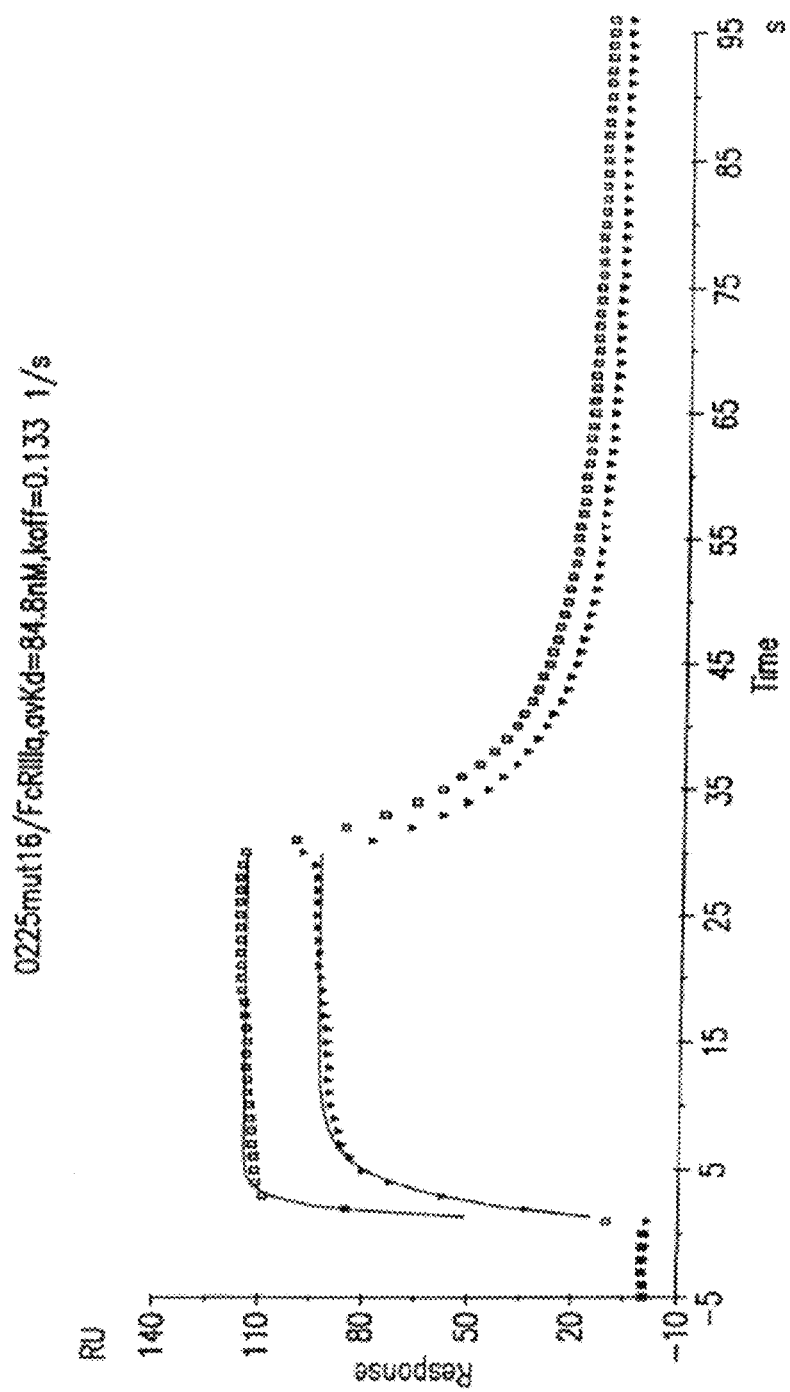
Figure 6H:
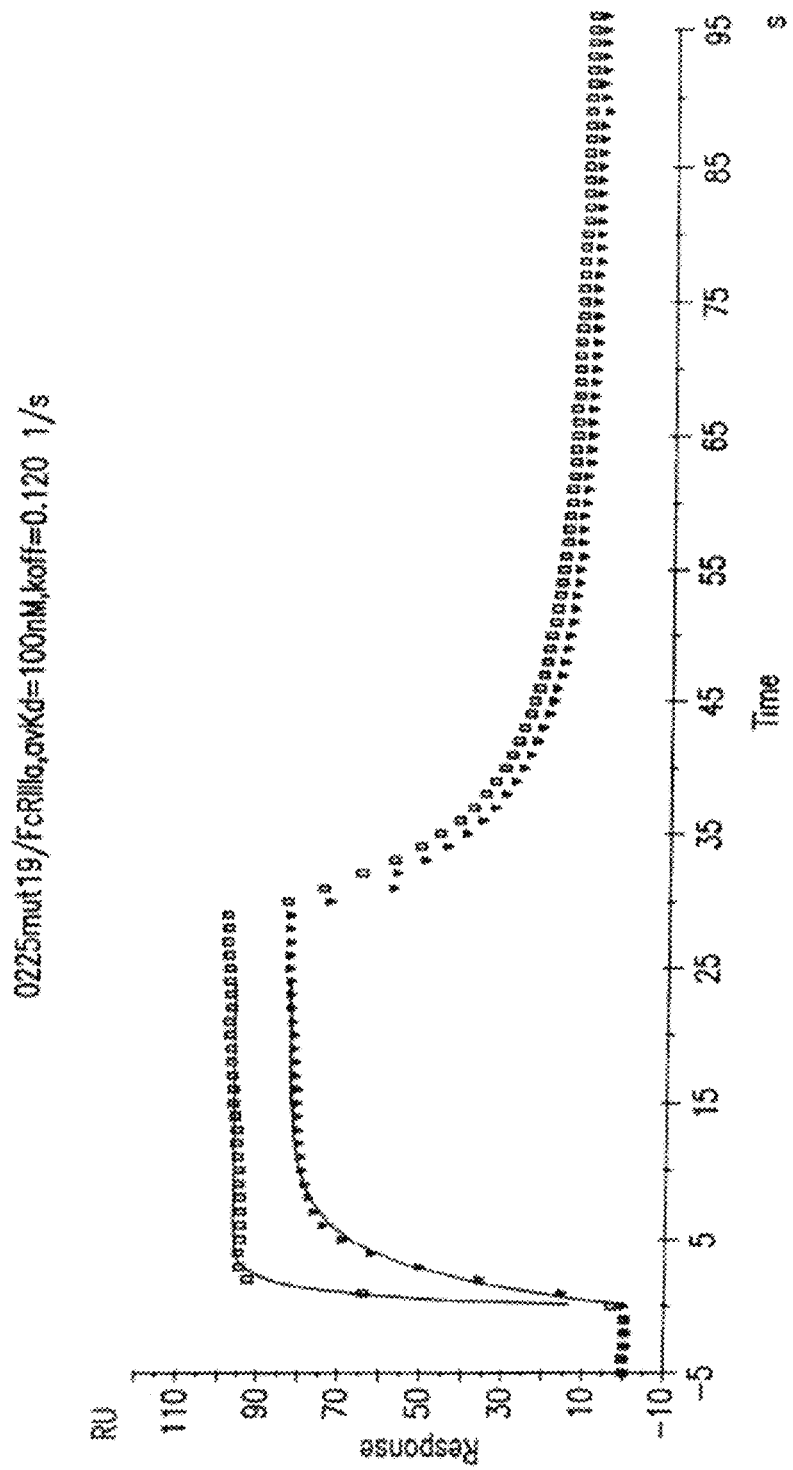

FIG. 5 SENSOGRAM OF REAL TIME BINDING OF FcγRIIIA TO CH 4-4-20 ANTIBODIES CARRYING VARIANT Fc REGIONS

Binding of FcγRIIIA to ch-4-4-20 antibodies carrying variant Fc regions was analyzed at 200 nM concentration. Responses were normalized at the level of ch-4-4-20 antibody obtained for wild-type.

Mutants used were as follows: Mut 6 (S219V), Mut 10 (P396L, A330S, K288N); Mut 18 (K326E); Mut 14 (K334E, K288N); Mut 11 (R255L, F243L); Mut 16 (F372Y); Mut 19 (K334N, K246I).

FIGS. 6A-6H ANALYSIS OF KINETIC PARAMETERS OF FcγRIIIA BINDING TO ANTIBODIES CARRYING VARIANT Fc REGIONS

Kinetic parameters for FcγRIIIA binding to antibodies carrying variant Fc regions were obtained by generating separate best fit curves for 200 nM and 800 nM. Solid line indicates an association fit which was obtained based on the $k_{off}$ values calculated for the dissociation curves in the 32-34 sec interval. $K_d$ and $k_{off}$ values represent the average from two concentrations.

Figure 7:
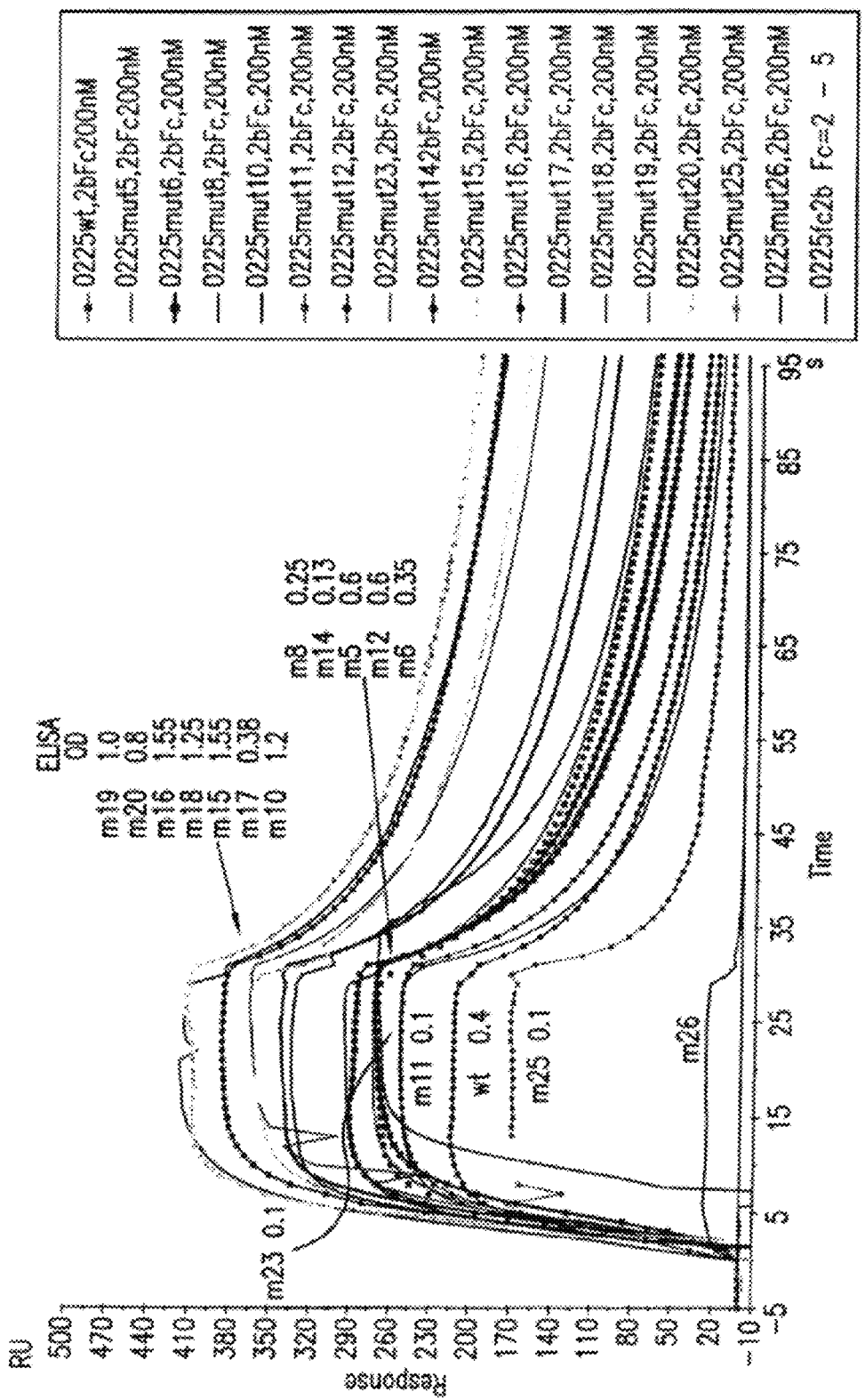

FIG. 7 SENSOGRAM OF REAL TIME BINDING OF FcγRIIB-Fc FUSION PROTEINS TO ANTIBODIES CARRYING VARIANT Fc REGIONS

Binding of FcγRIIB-Fc fusion proteins to ch-4-4-20 antibodies carrying variant Fc regions was analyzed at 200 nM concentration. Responses were normalized at the level of ch-4-4-20 antibody obtained for wild type.

Figure 8A:
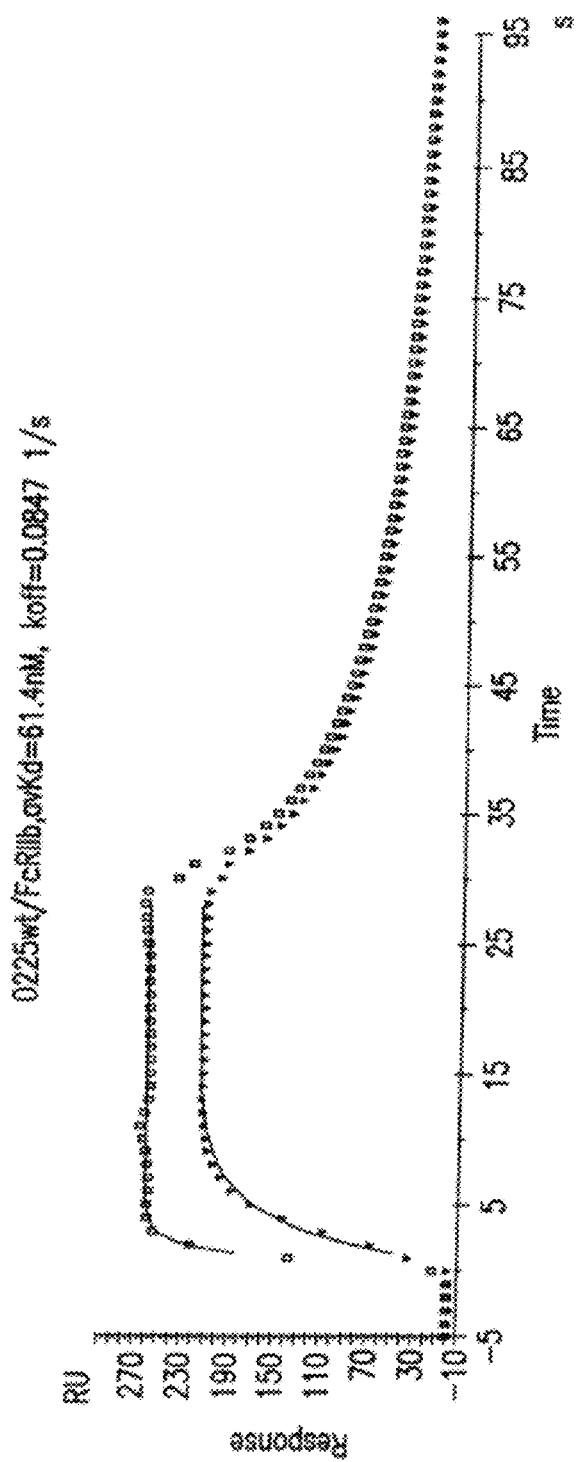
Figure 8B:
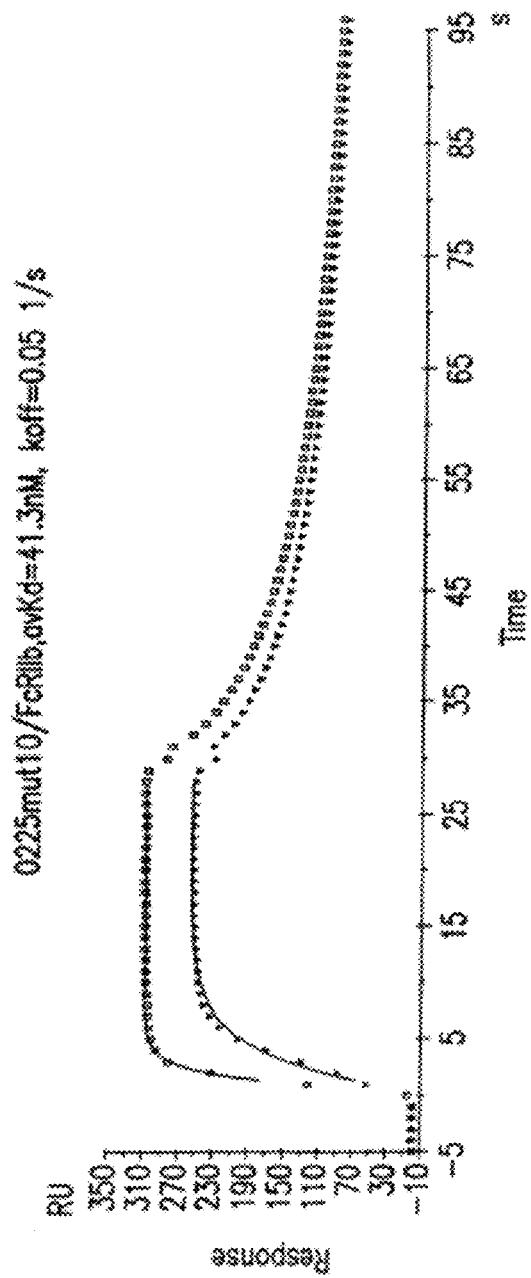
Figure 8C:
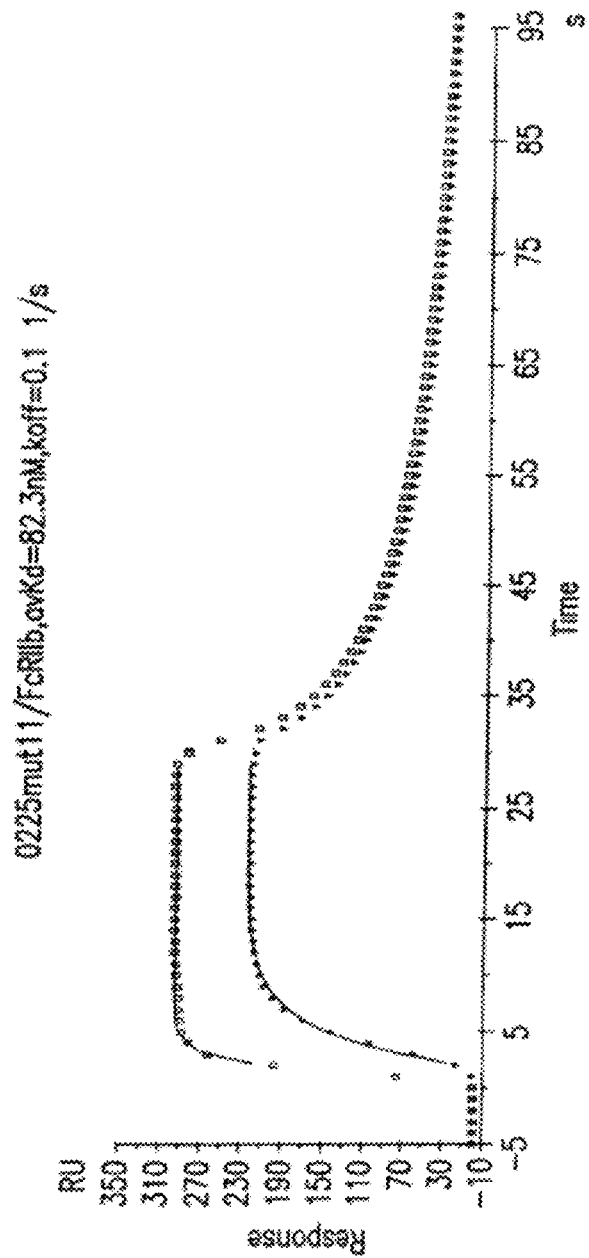

FIGS. 8A-8C ANALYSIS OF KINETIC PARAMETERS FcγRIIB-Fc FUSION PROTEINS TO ANTIBODIES CARRYING VARIANT Fc REGIONS

Kinetic parameters for FcγRIIB-Fc binding to antibodies carrying variant Fc regions were obtained by generating separate best fit curves for 200 nM and 800 nM. Solid line indicates an association fit which was obtained based on the $k_{off}$ values calculated for the dissociation curves in the 32-34 sec. interval. $K_d$ and $K_{off}$ values represent the average from two concentrations.

Mutants used were as follows: Mut 6 (S219V), Mut 10 (P396L, A330S, K288N); Mut 18 (K326E); Mut 14 (K334E, K288N); Mut 11 (R255L, F243L); Mut 16 (F372Y); Mut 19 (K334N, K246I).

Figure 9:
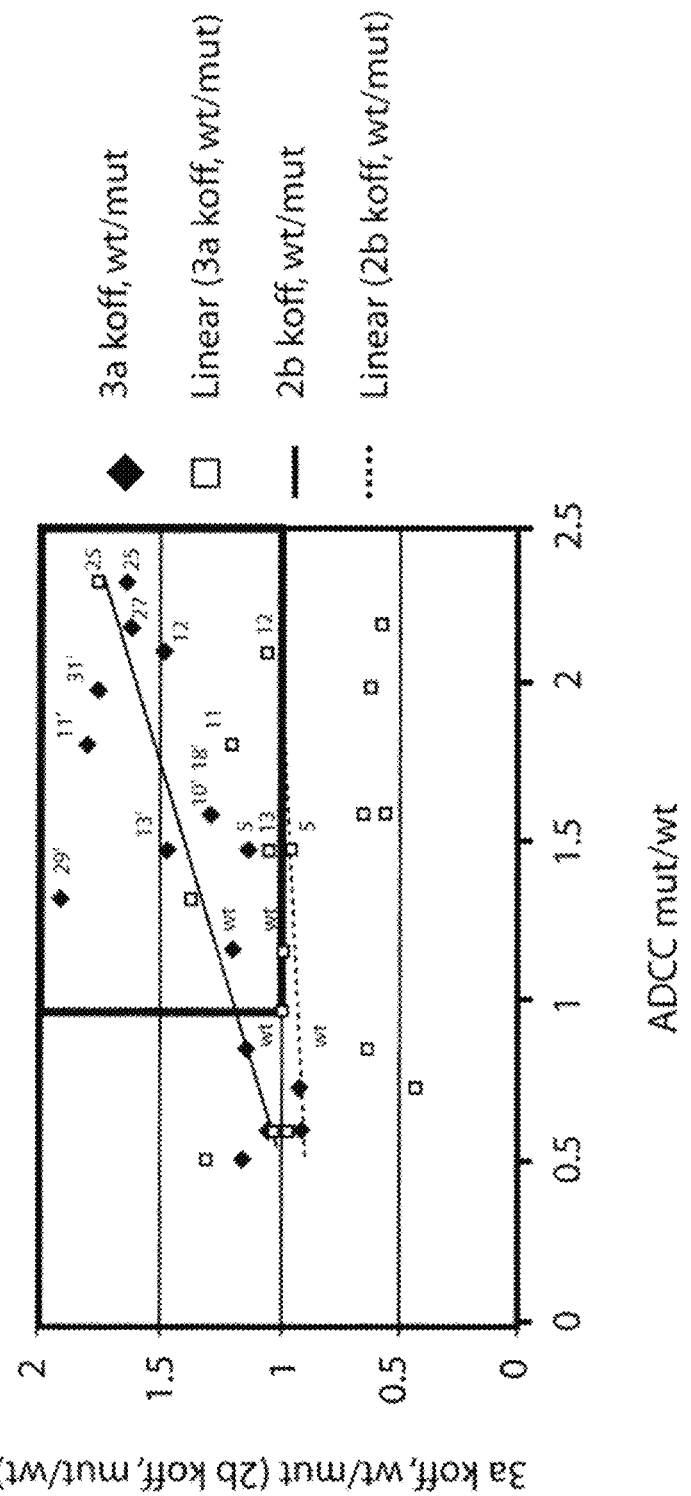

FIG. 9 RATIOS OF $K_{off}$ (WT)/$K_{off}$ (MUT) FOR FcγRIIIA-Fc PLOTTED AGAINST ADCC DATA Numbers higher than one show a decreased dissociation rate for FcγRIIIA binding and increased dissociation rate for FcγRIIB-Fc binding relative to wild-type. Mutants in the box have lower off rate for FcγRIIIA binding and higher off rate for FcγRIIB-Fc binding.

Figure 10:
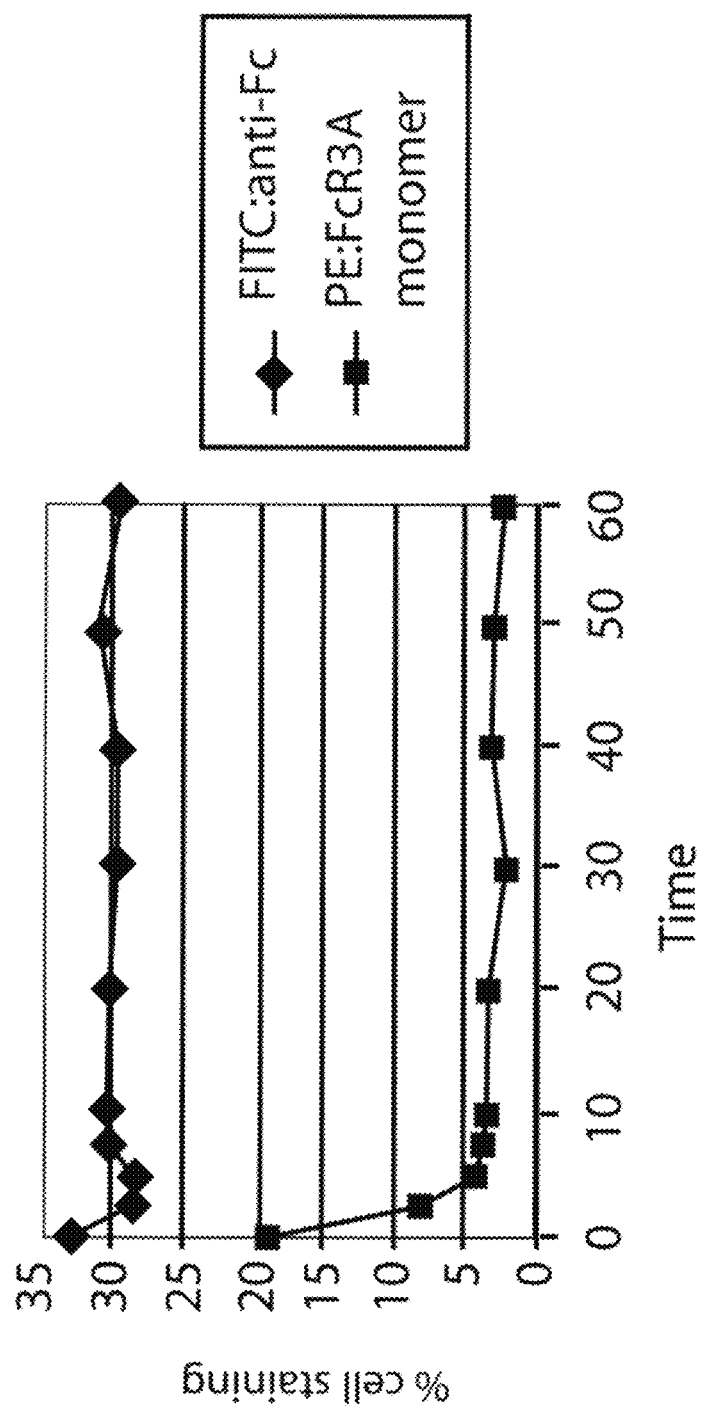
Figure 12A:
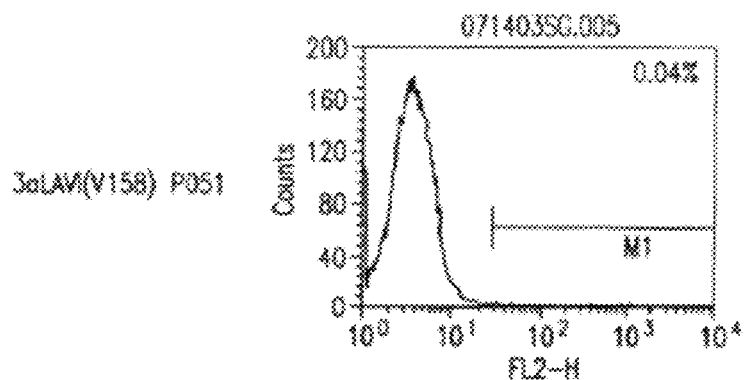
Figure 12B:
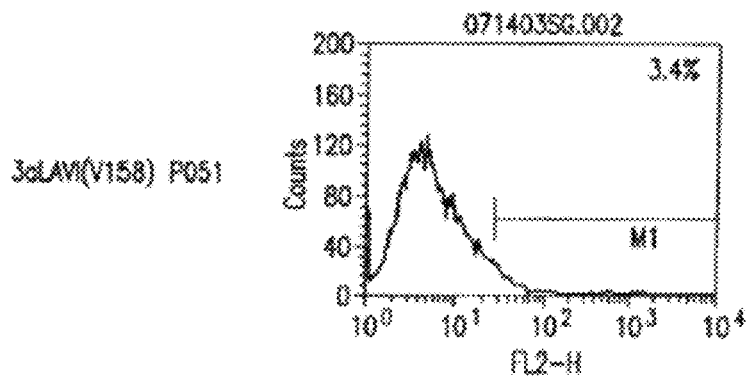
Figure 12C:
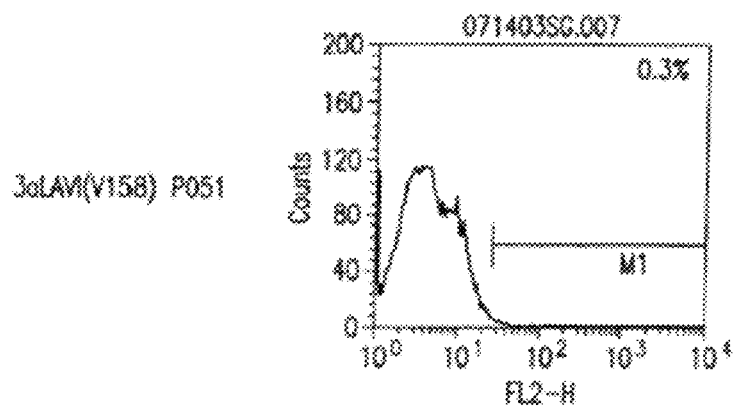
Figure 12D:
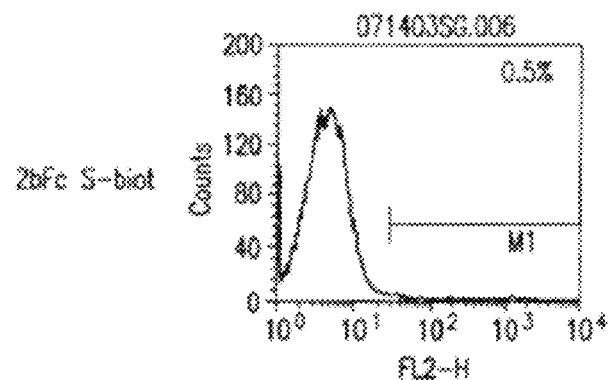
Figure 12E:
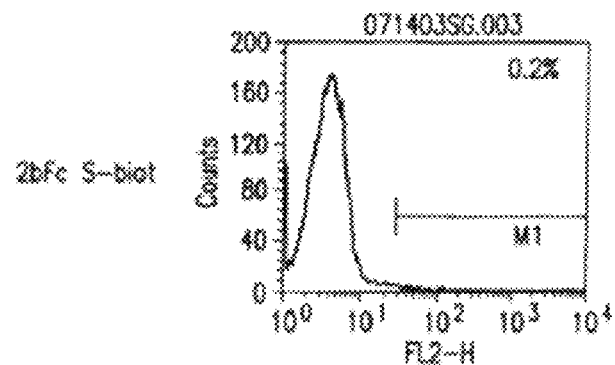
Figure 12F:
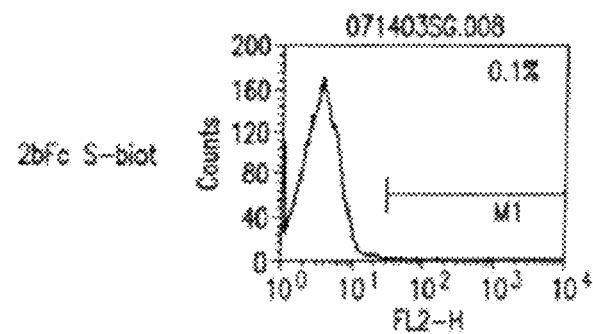
Figure 12G:
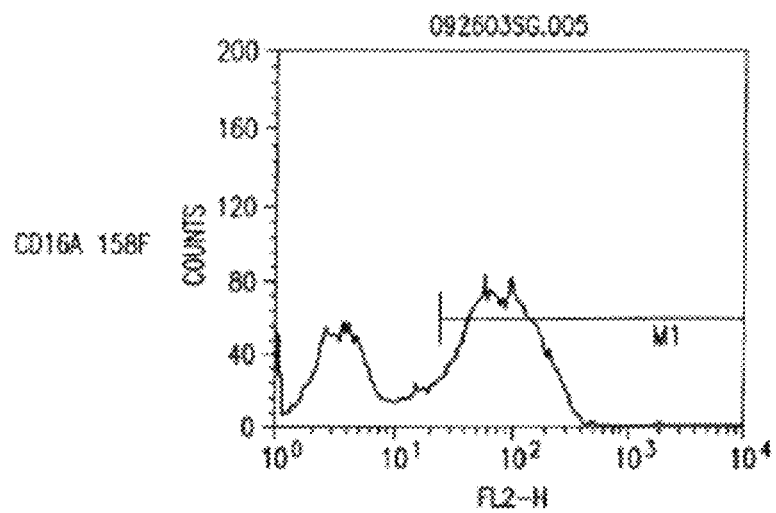
Figure 12H:
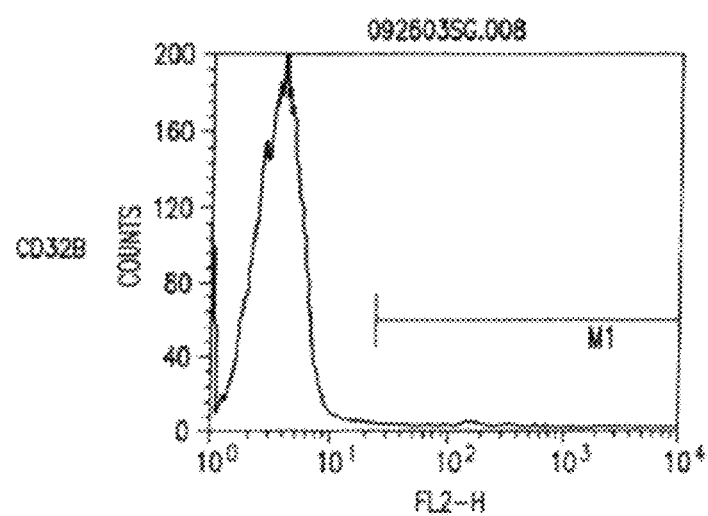
Figure 12I:
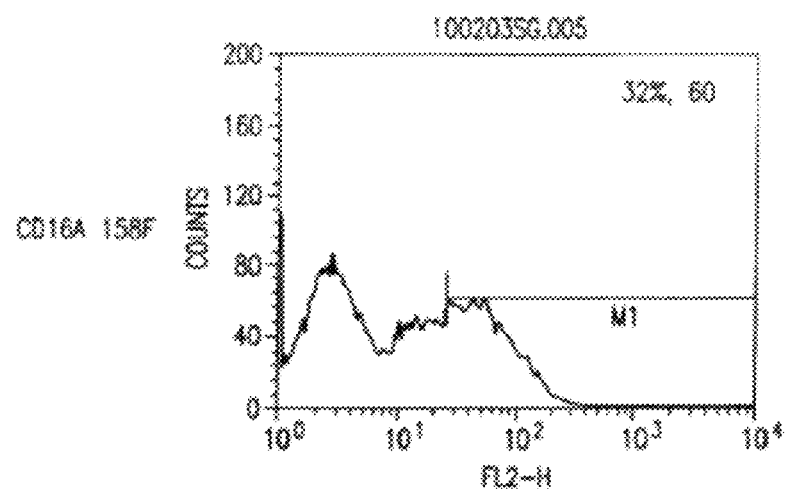
Figure 12J:
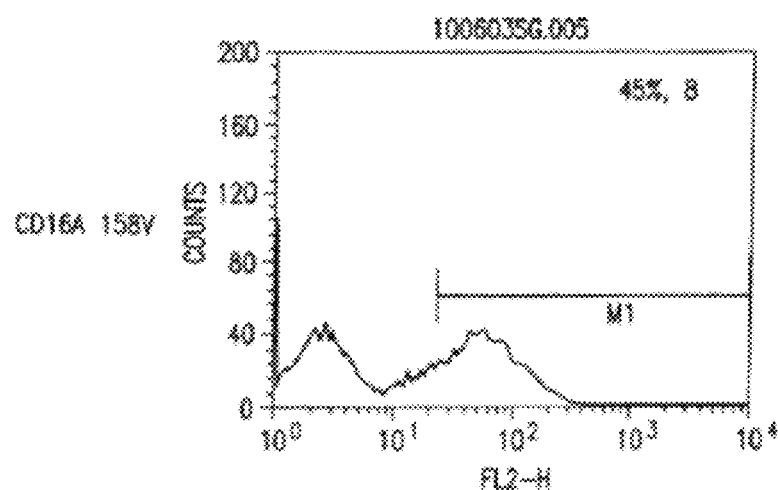
Figure 12K:
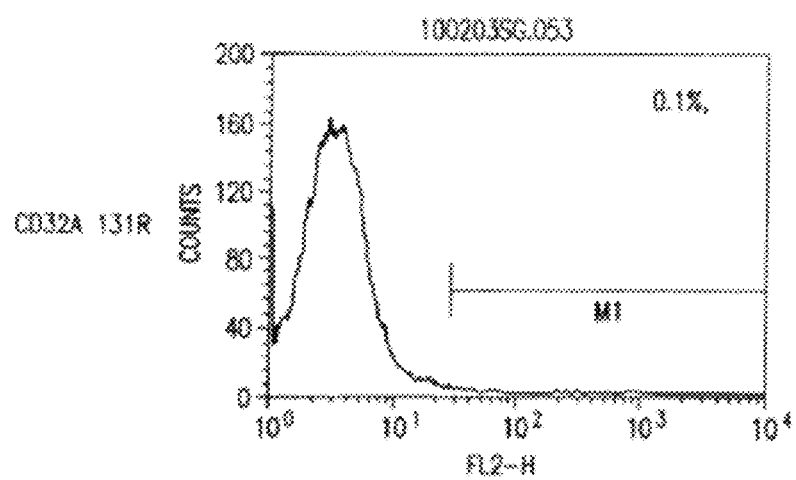
Figure 12L:
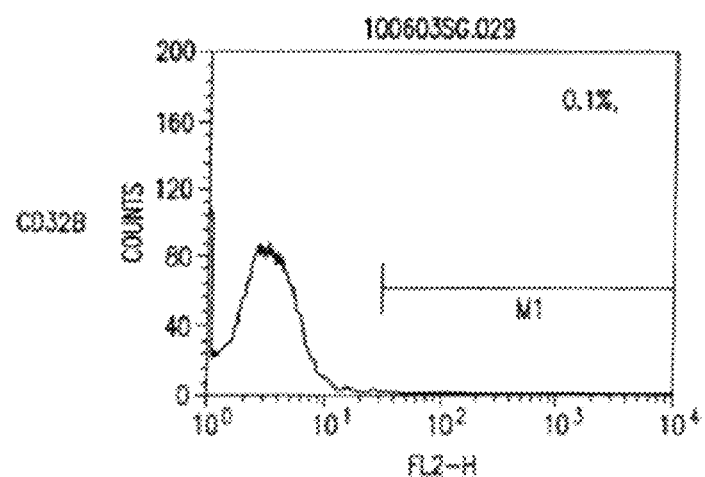

FIG. 10 COMPETITION WITH UNLABELED FcγRIIIA

A kinetic screen was implemented to identify Fc region mutants with improved $K_{off}$ rates for binding FcγRIIIA. A library of Fc region variants containing P396L mutation was incubated with 0.1 μM biotinylated FcγRIIIA-Linker-Avitag for one hour and then washed. Subsequently 0.8 uM unlabeled FcγRIIIA was incubated with the labeled yeast for different time points. Yeast was spun down and unlabeled FcγRIIIA was removed, Receptor bound yease was stained with SA (streptavidin):PE (phycoerythrin) for FACS analysis.

FIGS. 11A-11C FACS ANALYSIS BASED ON THE KINETIC SCREEN

Based on the calculated $K_{off}$ from the data presented in FIG. 22, a one minute time point selection was chosen. A 10-fold excess of library was incubated with 0.1 μM biotinylated FcγRIIIA-Linker-Avitag monomer; cells were washed and incubated with unlabeled ligand for one minute; then washed and labeled with SA:PE. The cells were then sorted by FACS, selecting the top 0.3% binders. The nonselected P396L library was compared to the yeast cells selected for improved binding by FACS. The histograms show the percentage of cells that are costained with both FcγRIIIA/PE and goat anti-human Fc/FITC.

FIGS. 12A-12L SELECTION BASED ON SOLID PHASE DEPLETION OF FcγRIIB Fc BINDERS

A-F. The P396L library was screened based on FcγRIIB depletion and FcγRIIIA selection using magnetic beads. The FcγRIIB depletion by magnetic beads was repeated 5 times. The resulting yeast population was analyzed and found to show greater than 50% cell staining with goat anti-human Fc and a very small percentage of cells stained with FcγRIIIA. Subsequently cells were selected twice by FACS using 0.1 μM biotinylated FcγRIIIA linker-avitag. Yeast cells were analyzed for both FcγRIIIA and FcγRIIB binding after each sort and compared to wild type binding.

G-L. Fc Mutants were selected from the FcγRIIB depleted yeast population using biotinylated FcγRIIIA 158F linker avitag monomer as a ligand. The sort gate was set to select the top 0.25% FcγRIIIA 158F binders. The resulting enriched population was analyzed by FACS for binding to the different FcγRIIIA (158F and 158V), FcγRIIIB and FcγRIIA (131R).

Figure 13:
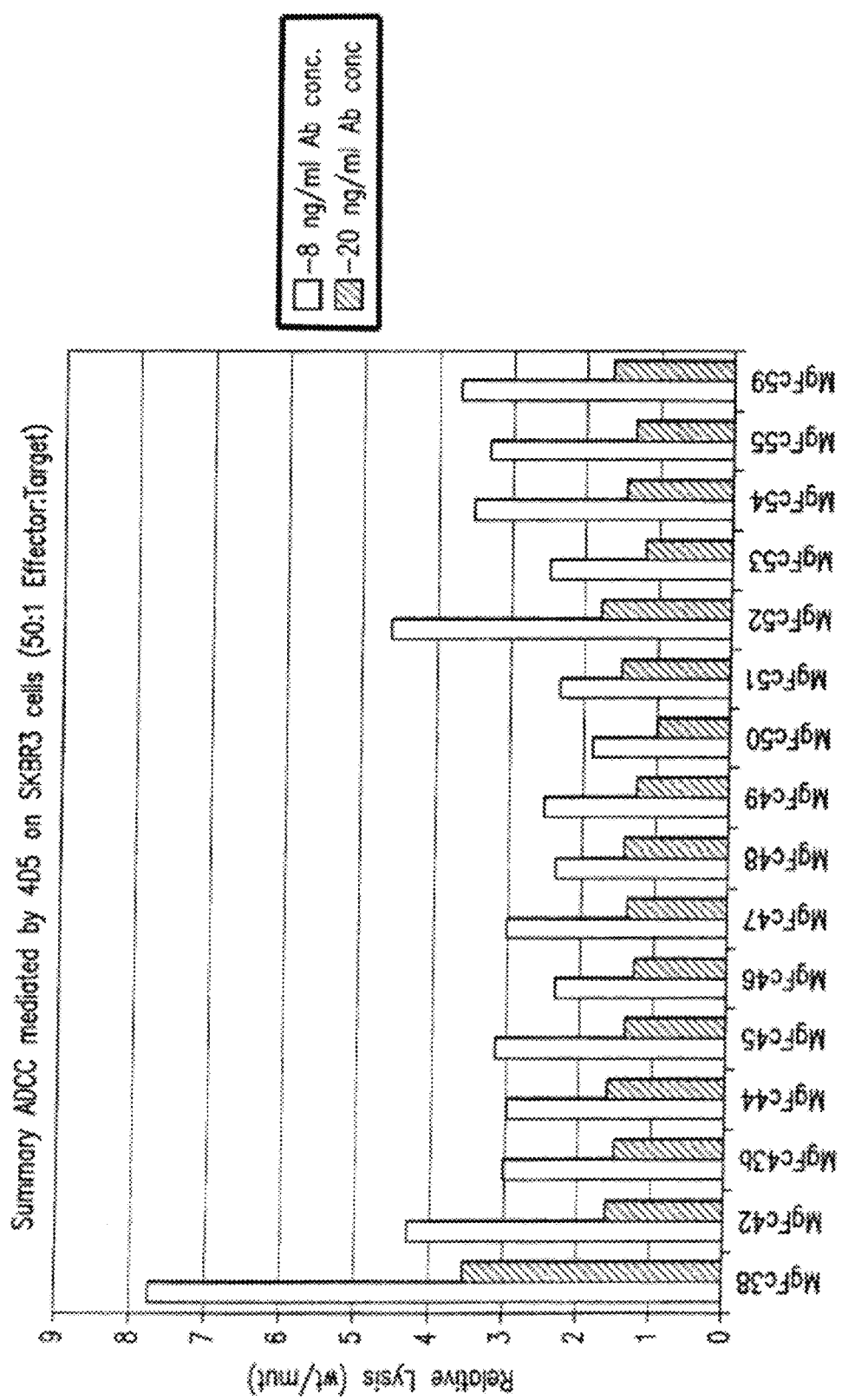

FIG. 13 RELATIVE RATES OF SKBR3 TARGET CELL LYSIS MEDIATED BY CHIMERIC 4D5 HARBORING FC MUTANTS

Relative rates of lysis was calculated for each Fc mutant tested. Lysis rates for 4D5 antibody with Fc mutants were divided by the rate of lysis mediated by wild type 4D5 antibody. Data from at least 2 independent assays were averaged and plotted on the histogram. For each Fc mutant data from two different antibody concentrations are shown. The antibody concentrations were chosen to flank the point along the curve at which lysis was ~50%.

Figure 14:
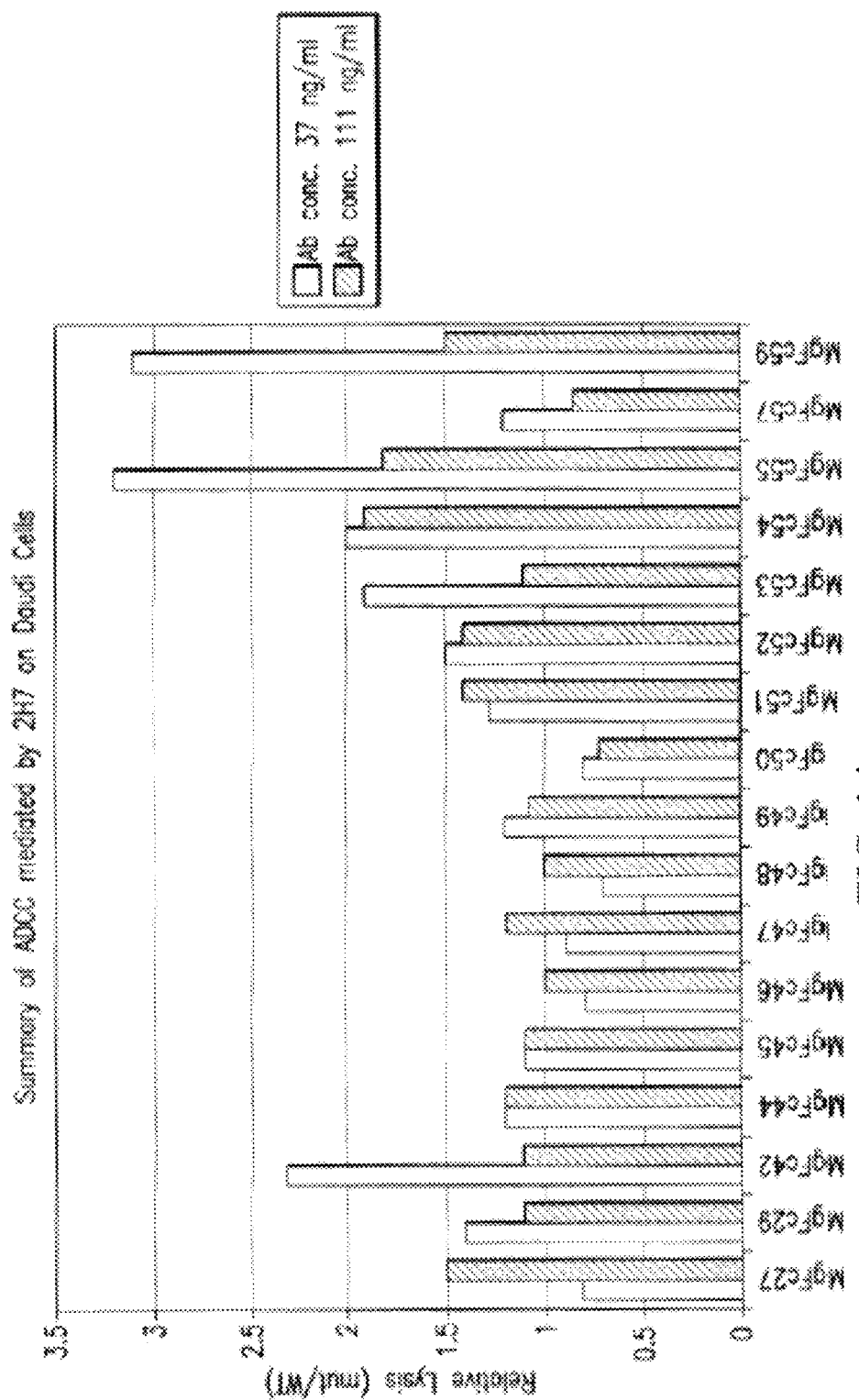

FIG. 14 RELATIVE RATES OF DAUDI CELL LYSIS MEDIATED BY CHIMERIC 2H7 HARBORING FC MUTANTS

Relative rates of lysis was calculated for each Fc mutant tested. Lysis rates for 2H7 antibody with Fc mutants were divided by the rate of lysis mediated by wild type 2H7 antibody. Data from at least 1-2 independent assays were averaged and plotted on the histogram. For each Fc mutant, data from two different antibody concentrations are shown The antibody concentrations were chosen based on the point along the curve at which lysis was ~50%.

Figure 15A:
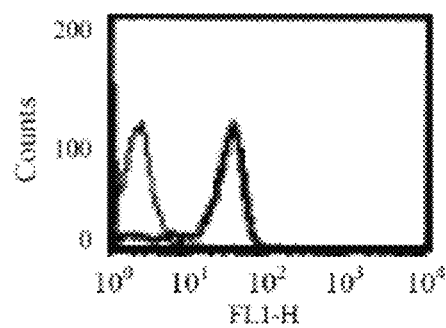
Figure 15B:
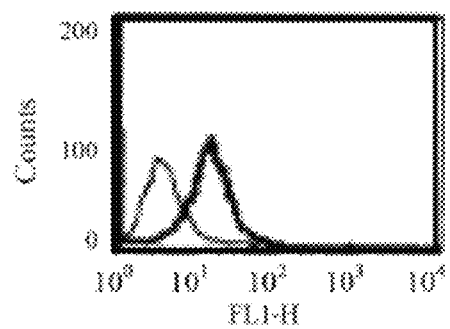
Figure 15C:
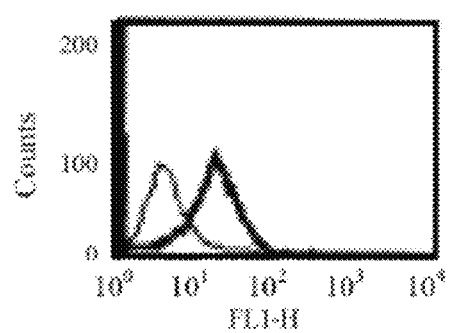
Figure 15D:
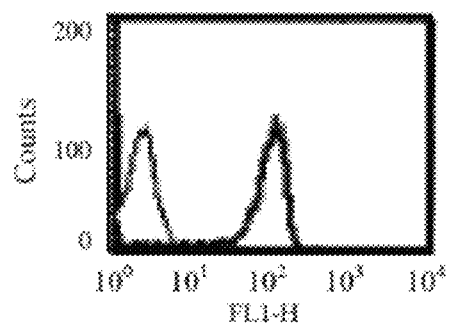
Figure 15E:
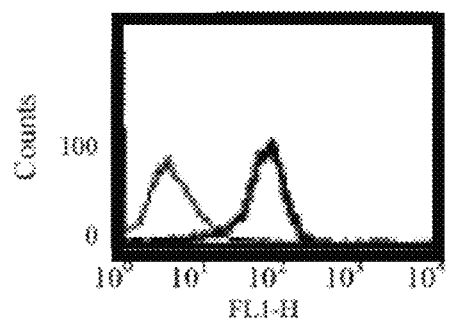
Figure 15F:
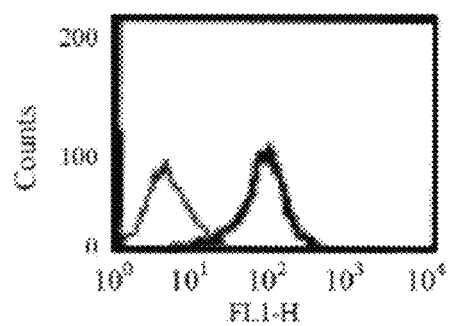
Figure 15G:
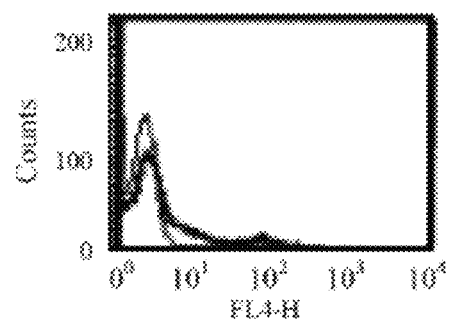
Figure 15H:
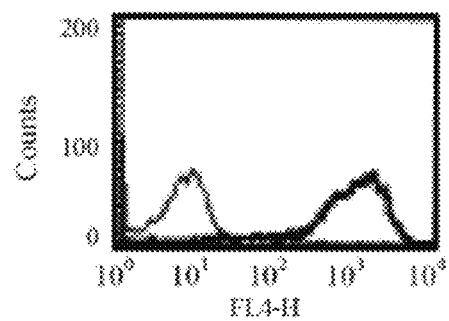
Figure 15I:
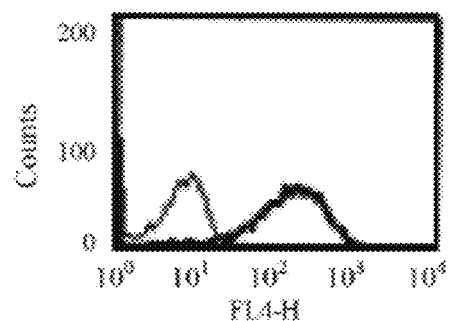
Figure 15J:
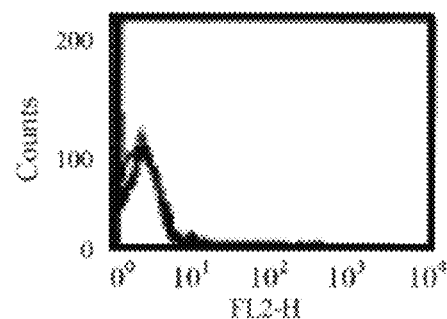
Figure 15K:
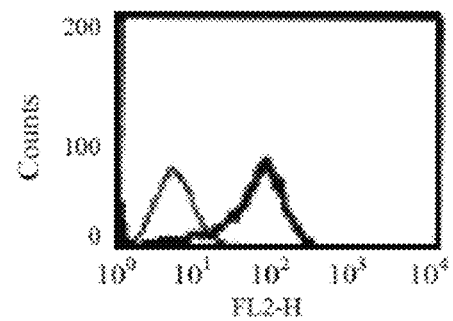
Figure 15L:
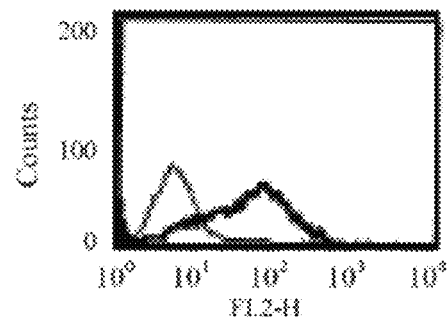

FIG. 15A-15O Fc RECEPTOR PROFILES VIA FACS UPON CYTOKINE TREATMENT OF MONOCYTES.

Cytokine treatment of monocytes increases low affinity Fc receptor expression. Elutriated monocytes were cultured using specific cytokines in serum free media. Fc receptor profiles were assayed using FACS.

Figure 16:
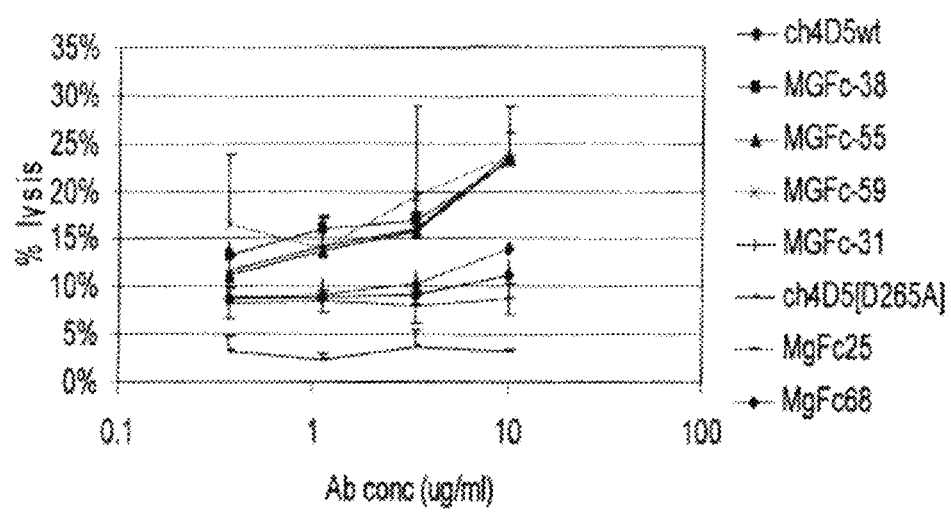

FIG. 16 IMPROVED TUMOR CELL KILLING USING FC MUTANTS IN MACROPHAGE-DERIVED MONOCYTES BASED ADCC.

Ch4D5 MAb concentration over 2 logs was tested using effector:target ratio of 35:1. Percent lysis was calculated as in FIG. 30.

FIG. 17 COMPLEMENT DEPENDENT CYTOTOXICITY ASSAY FLOW CHART.

The flow chart summarizes the CDC assays used.

FIG. 18 COMPLEMENT DEPENDENT CYTOTOXICITY ACTIVITY

Fc mutants that show enhanced binding to FcγRIIIA also showed improved complement activity. Anti-CD20 ChMAb over 3 orders of magnitude was titrated. Percent lysis was calculated as in as in FIG. 30.

Figure 19A:
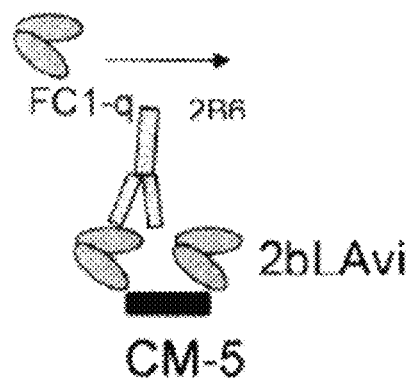
Figure 19B:
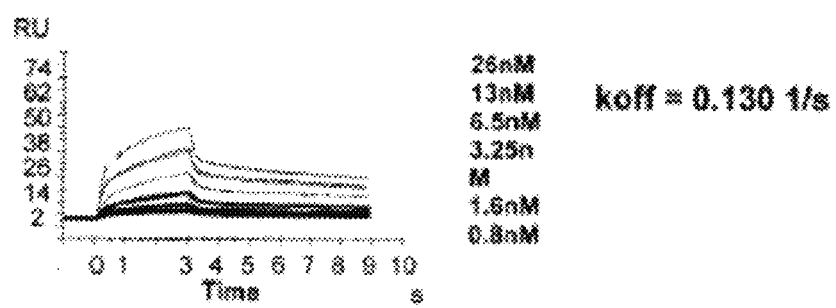
Figure 19C:
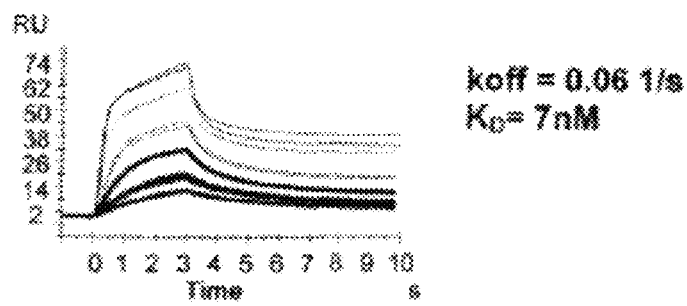
Figure 20A:
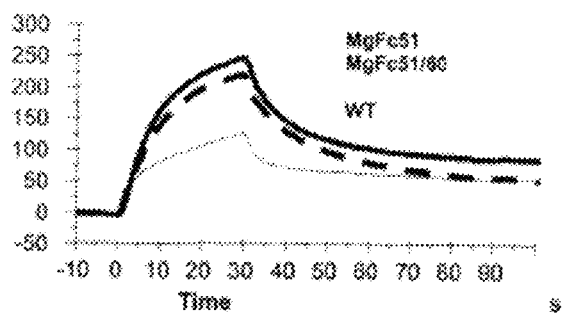
Figure 20B:
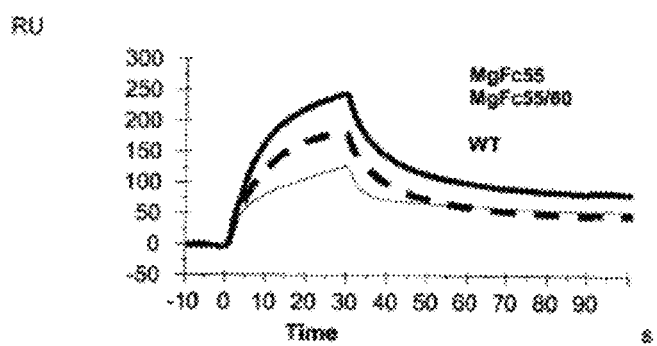
Figure 20C:
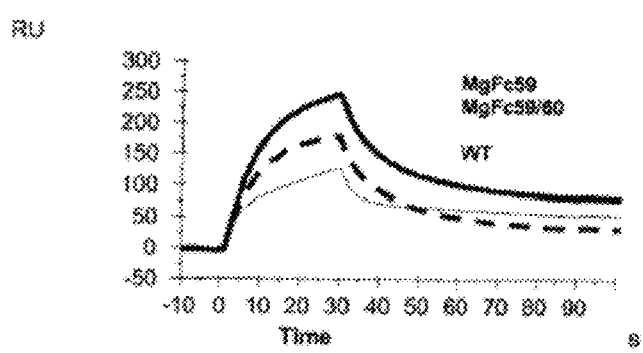
Figure 20D:
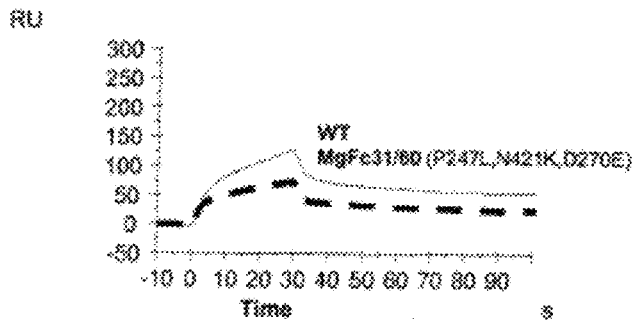
Figure 21A:
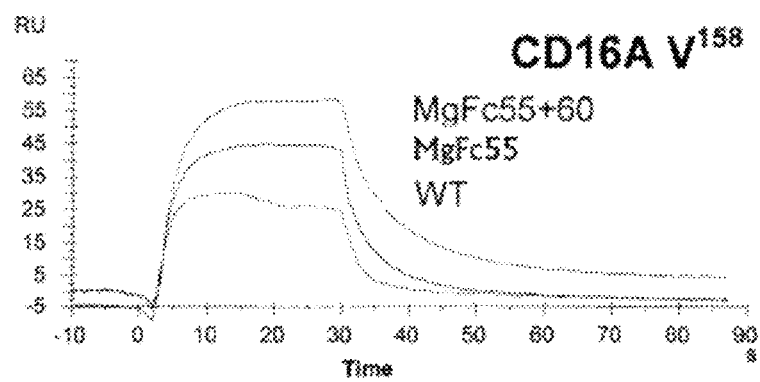
Figure 21B:
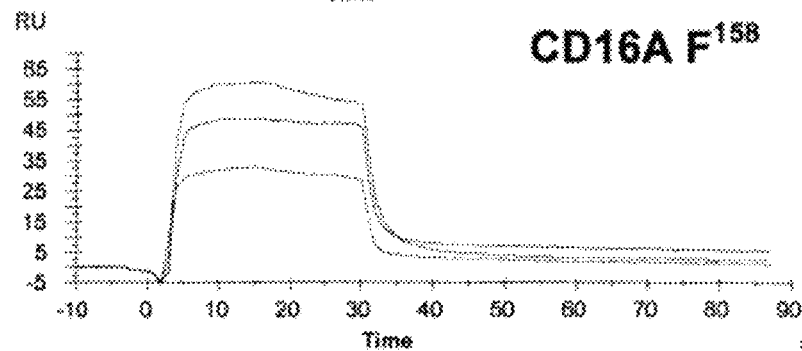
Figure 21C:
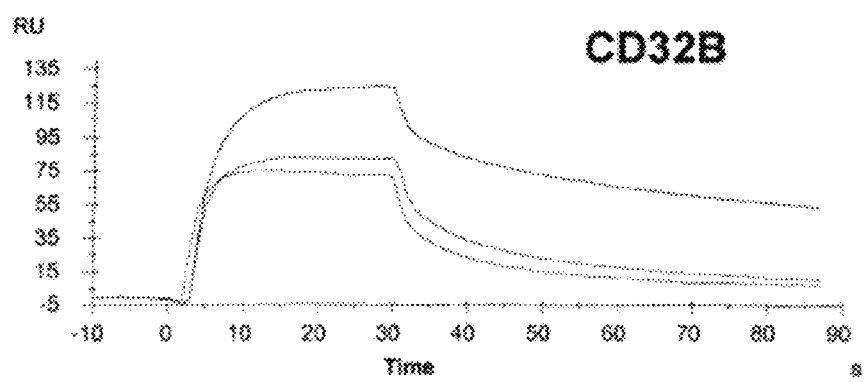
Figure 21D:
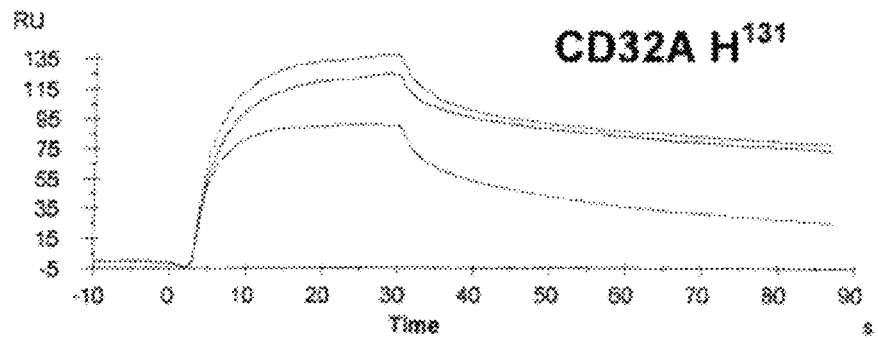
Figure 22A:
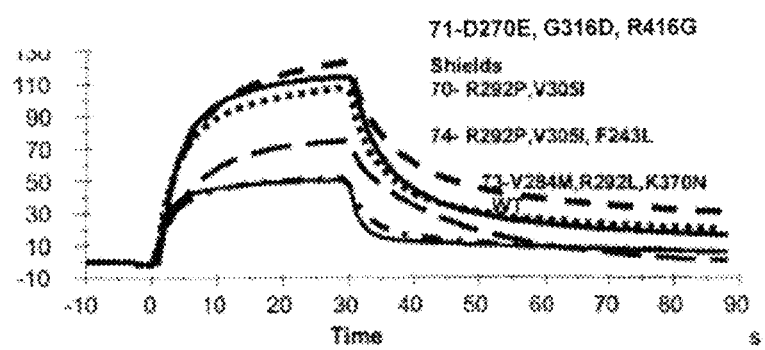
Figure 22B:
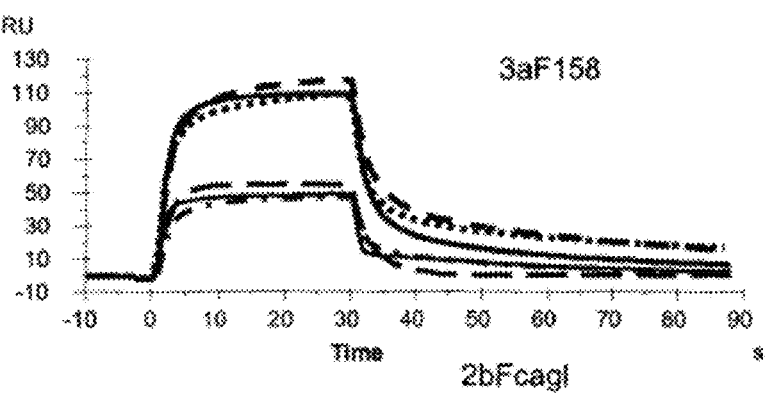
Figure 22C:
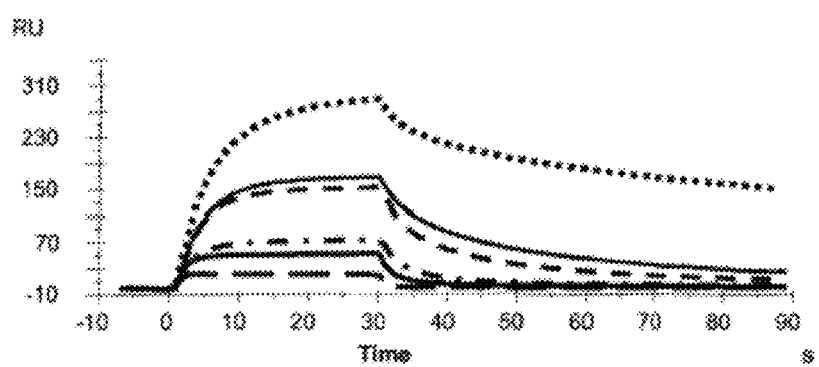
Figure 22D:
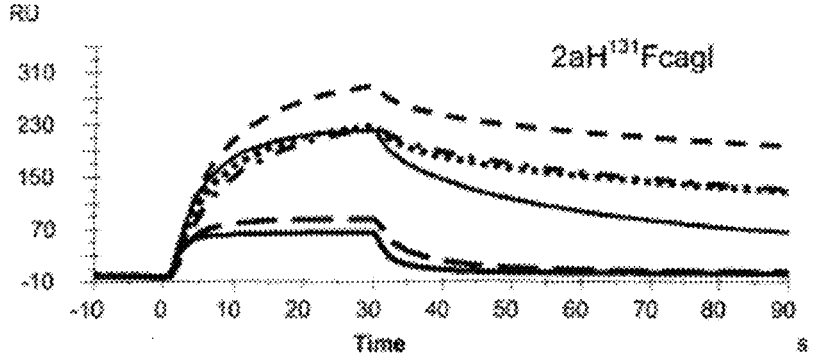

FIG. 19A-19C C1q BINDING TO 2B6 ANTIBODY

A-B. The diagram depicts the BIAcore format for analysis of 2B6 binding to the first component of the complement cascade.

C. Sensogram of real time binding of 2B6 antibody carrying variant Fc regions to C1q.

FIGS. 20A-20D C1q BINDING TO 2B6 MUTANT ANTIBODY.

Sensogram of real time binding of 2B6 mutants to C1q (3.25 nM). Mutants depicted at MgFc51 (Q419H, P396L); MgFc51/60 in Panel A; MgFc55 and MgFc55/60 (Panel B); MgFc59 and MgFc59/60 (Panel C); and MgFc31/60 (Panel D).

FIGS. 21A-21D Fc VARIANTS WITH DECREASED BINDING TO FcγRIIB

Binding of FcR to ch4D5 antibodies to compare effect of D270E (60) on R255L, P396L double mutant (MgFc55). $K_D$ was analyzed at different concentrations of FcR; 400 nM CD16A 158V; 800 nM CD16A 158F; 200 nM CD32B; 200 nM CD32A 131H. Analysis was performed using separate $K_D$ using Biacore 3000 software.

FIGS. 22A-22D KINETIC CHARACTERISTICS OF 4D5 MUTANTS SELECTED FROM FcγRIIB DEPLETIONS/FcγRIIAH131 SELECTION

Binding of FcR to ch4D5 antibodies carrying different Fc mutations selected by CD32B depletion and CD32A H131 screening strategy. $K_D$ was analyzed at different concentrations of FcR; 400 nM CD16A 158V; 800 nM CD16A 158F; 200 nM CD32B; 200 nM CD32A 131H. Analysis was performed using separate $K_D$ using Biacore 3000 software.

Figure 23:
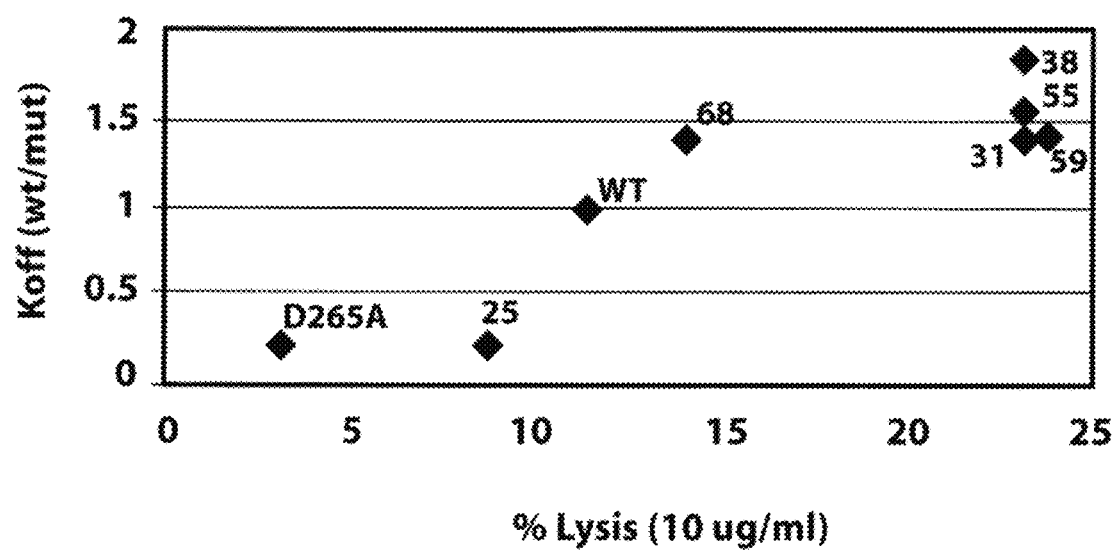

FIG. 23. PLOT OF MDM ADCC DATA AGAINST THE $K_{OFF}$ DETERMINED FOR CD32A 131H BINDING AS DETERMINED BY BIACORE.

The mutants are as follows: MgFc 25 (E333A, K334A, S298A); MgFc68 (D270E); MgFc38 (K392T, P396L); MgFc55 (R255L, P396L); MgFc31 (P247L, N421K); MgFc59 (K370E, P396L).

Figure 24A:
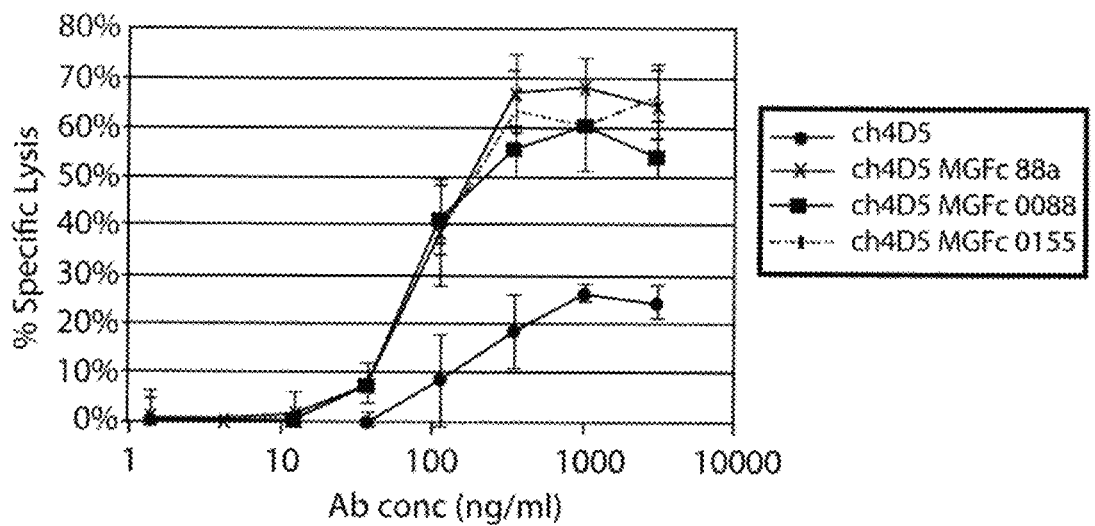
Figure 24B:
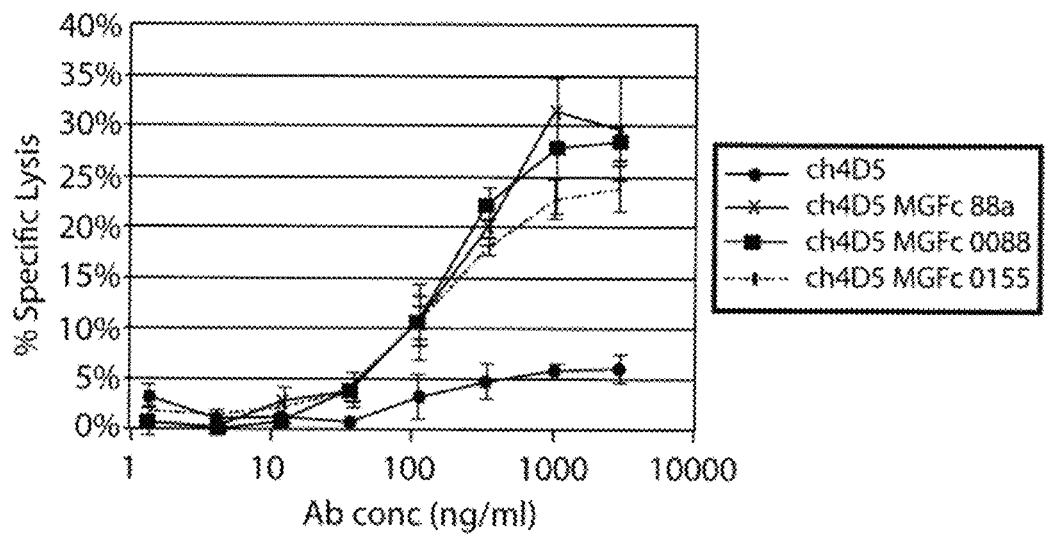

FIGS. 24A-24B. ADCC ACTIVITY OF MUTANTS IN A HER2/NEU CHIMERIC MONOCLONAL ANTIBODY

Chimeric HER2/neu monoclonal antibodies containing mutant Fc regions were assessed, in duplicate, for their ADCC activity and compared to the ADCC activity of the wild type, chimeric Her2/neu antibody. The mutants analyzed are as follows: MGFc88 (F243L, R292P, Y300L, V305I, P396L), MGFc88A (F243L, R292P, Y300L, P396L), MGFc155 (F243L, R292P, Y300L).

Figure 25A:
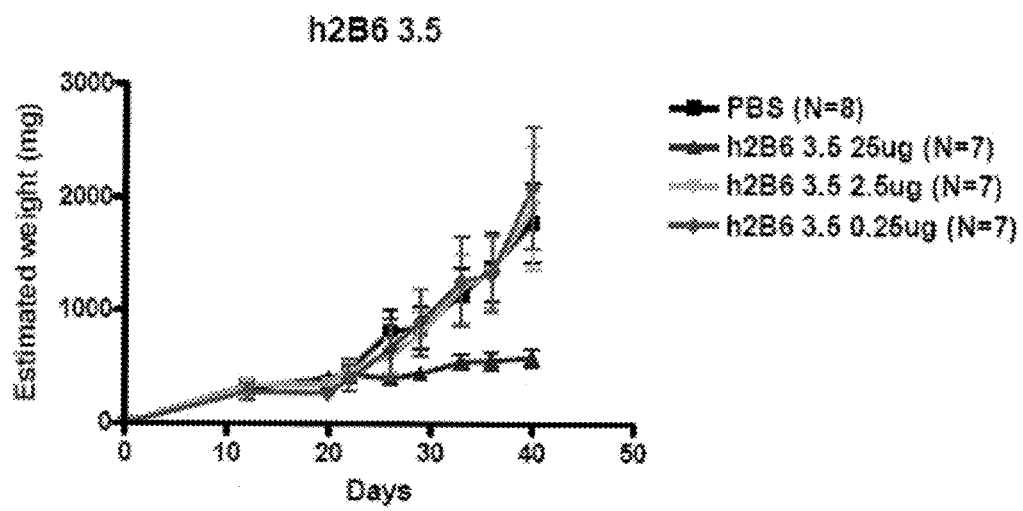
Figure 25B:
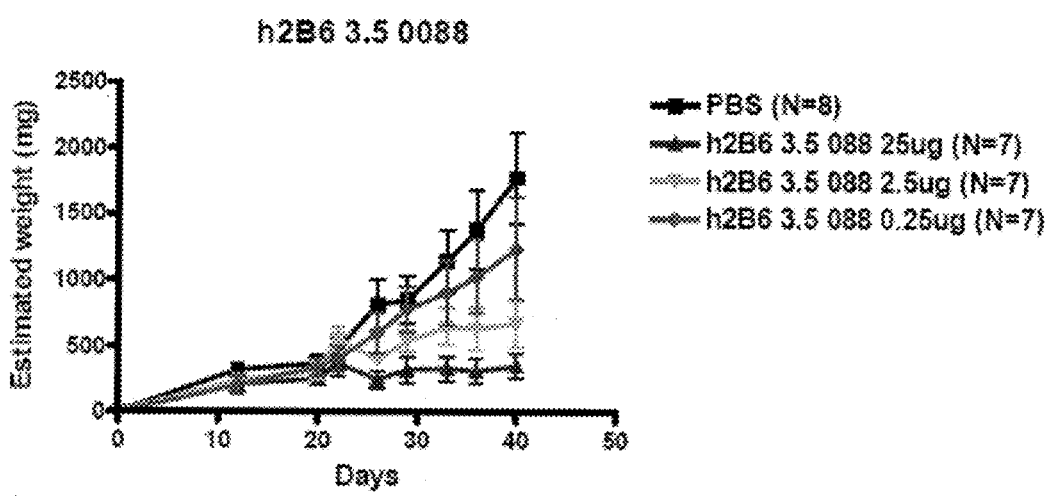

FIGS. 25A-25B. ESTIMATED TUMOR WEIGHT IN MICE TREATED WITH WILD-TYPE OR Fc MUTANT h2B6

Balb/c nude mice were inoculated subcutaneously with Daudi cells and administered 25 µg, 2.5 µg or 0.25 µg weekly doses of either wild-type h2B6 (A) or h2B6 harboring Fc mutant MGFc 0088 (F243L, R292P, Y300L, V305I, P396L) (B). Mice administered buffer alone were used as control. Tumor weight was calculated based on the estimated volume of the subcutaneous tumor according to the formula (width$^2$×length)/2.

Figure 26A:
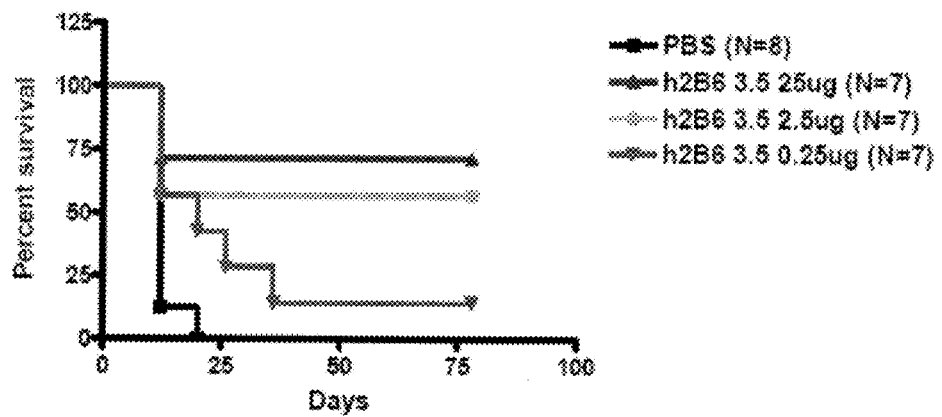
Figure 26B:
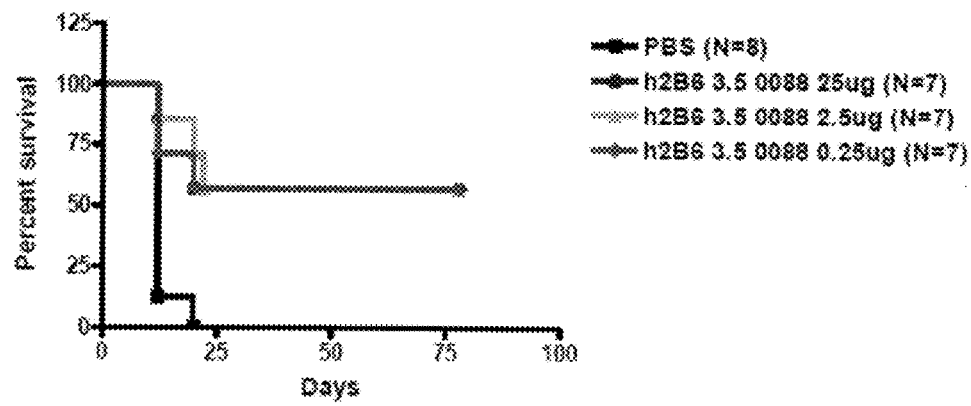

FIGS. 26A-26B. SURVIVAL IN TUMOR BEARING MICE TREATED WITH WILD-TYPE OR Fc MUTANT h2B6

Nude mice were inoculated with Daudi cells and administered 25 µg, 2.5 µg or 0.25 µg weekly doses of either wild-type h2B6 (A) or h2B6 harboring Fc mutant MGFc 0088 (F243L, R292P, Y300L, V305I, P396L) (B). Mice administered buffer alone were used as control.

Figure 27:
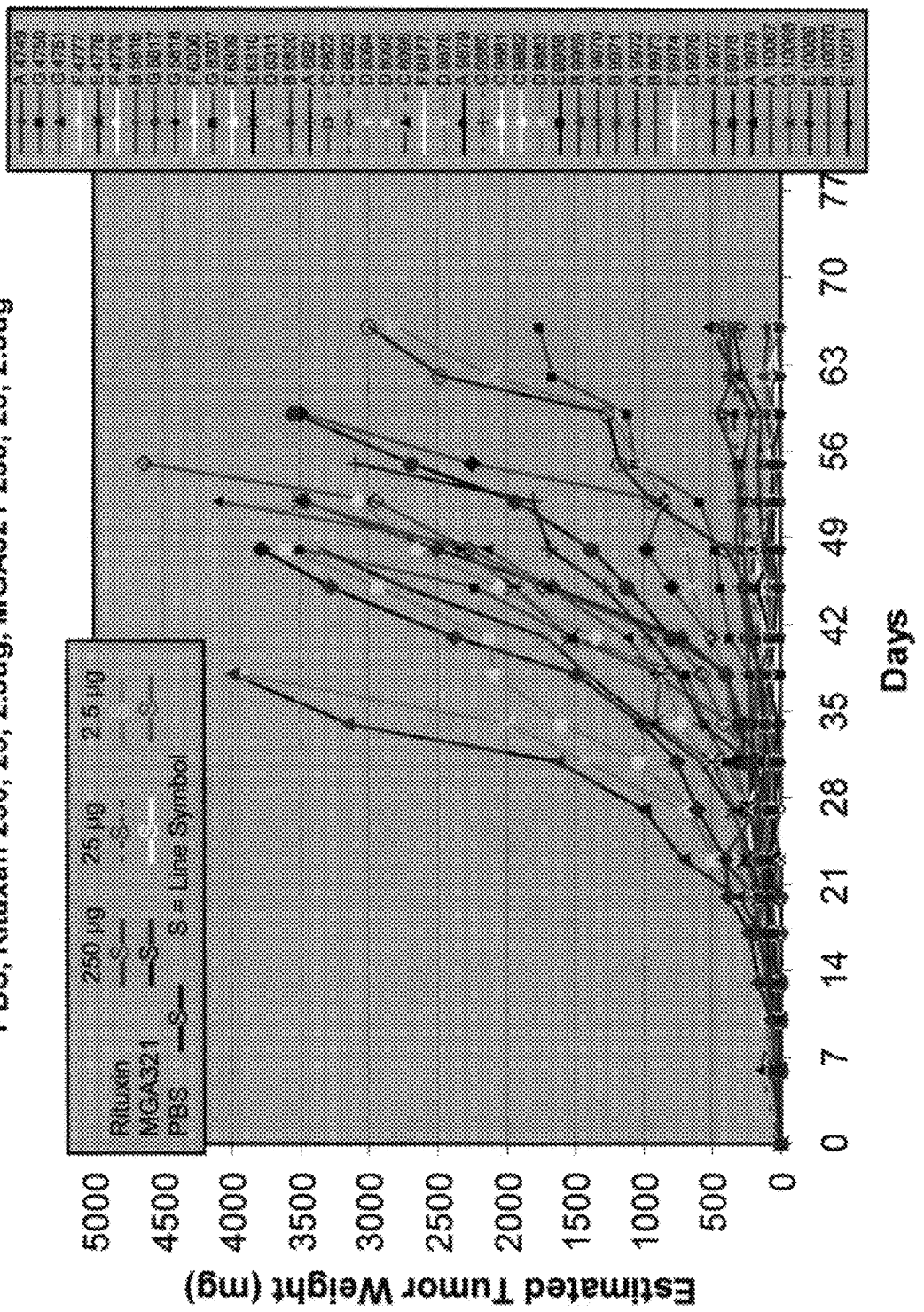

FIG. 27. ESTIMATED TUMOR WEIGHT IN HUMAN Fc RECEPTOR-EXPRESSING TRANSGENIC MICE TREATED WITH WILD-TYPE OR Fc-OPTIMIZED h2B6 0088 mCD16−/− huCD16A+ RAG1−/− C57Bl/6 mice were inoculated subcutaneously with Raji cells and after two weeks were intraperitoneally administered six weekly doses of either buffer alone (PBS), or 250 µg, 25 µg or 2.5 µg of wild-type h2B6 (Rituxan) or h2B6 comprising mutant FcMG0088 (F243L, R292P, Y300L, V305I P396L) (MGA321). Tumor weight was calculated based on the estimated volume of the subcutaneous tumor according to the formula (width$^2$×length)/2. Lines correspond to tumor weight, over time, for each individual mouse tested.

Figure 28:
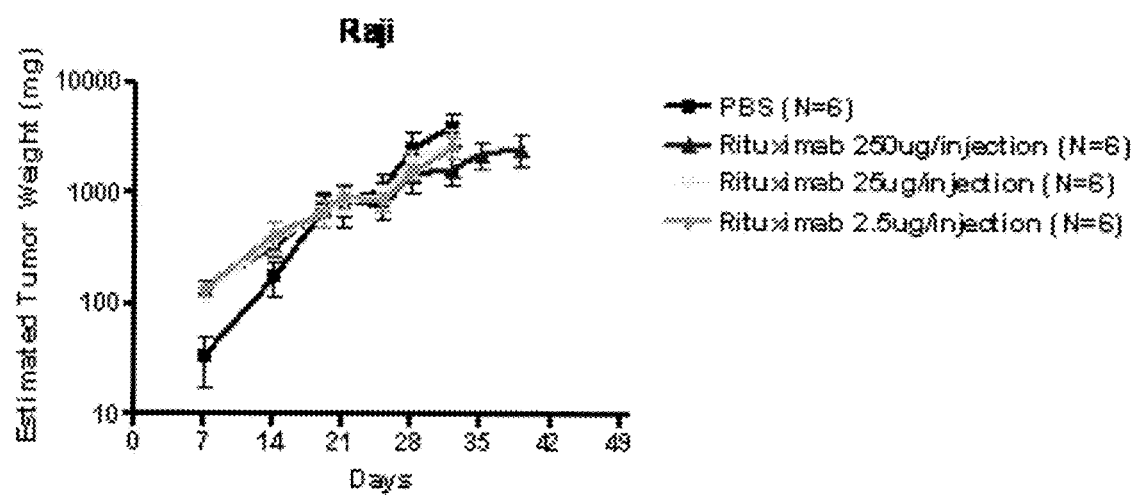
Figure 28B:
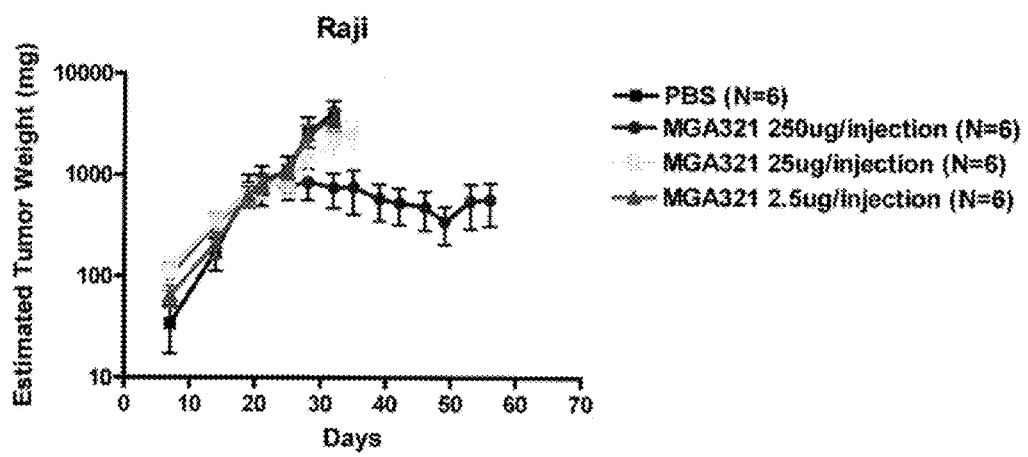

FIGS. 28A-28B. ESTIMATED TUMOR WEIGHT IN HUMAN Fc RECEPTOR-EXPRESSING TRANSGENIC MICE TREATED WITH WILD-TYPE OR Fc-OPTIMIZED h2B6 0088 mCD16−/− huCD16A+ RAG1−/− C57Bl/6 mice were inoculated subcutaneously with Raji cells and after three weeks were intraperitoneally administered five weekly doses of 250 µg, 25 µg or 2.5 µg of wild-type h2B6 (Rituxan "Rituximab") (A) or h2B6 comprising mutant FcMG0088 (F243L, R292P, Y300L, V305I P396L) (h2B6 0088 "MGA321") (B). Tumor weight was calculated based on the estimated volume of the subcutaneous tumor according to the formula (width$^2$×length)/2.

Figure 29:
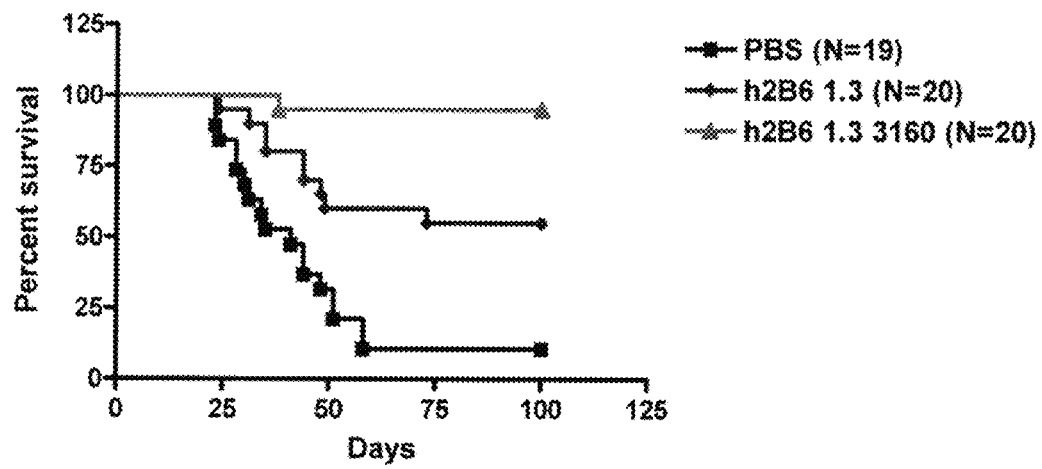

FIG. 29. SURVIVAL IN TUMOR-BEARING HUMAN Fc RECEPTOR-EXPRESSING TRANSGENIC MICE TREATED WITH WILD-TYPE OR Fc-OPTIMIZED h2B6 31/60 mCD16−/− huCD16A+ nude (FoxN1) mice were intraperitoneally inoculated with EL4-CD32B cells and intraperitoneally administered on days 0, 1, 2, 3 and 6 either wild-type h2B6 1.3 or h2B6 1.3 comprising mutant 31/60 (P247L, D270E, N421K) (h2B6 1.3 3160). Mice administered buffer alone (PBS) were used as control.

Figure 30:
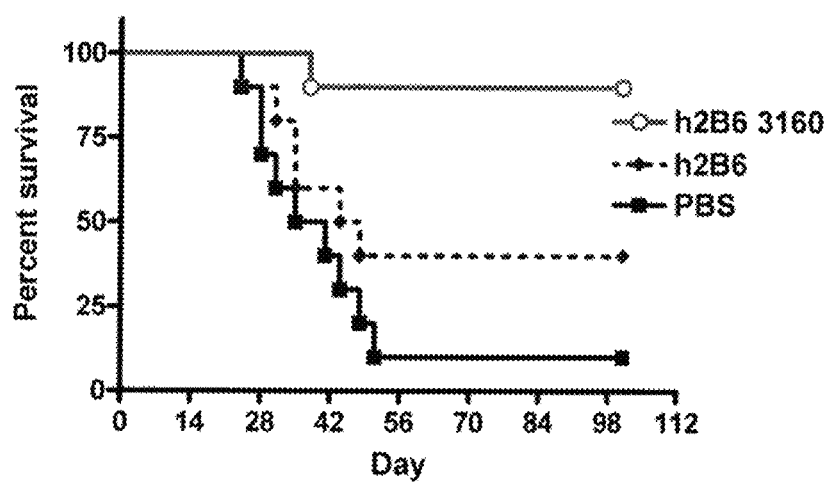

FIG. 30. SURVIVAL IN TUMOR-BEARING HUMAN Fc RECEPTOR-EXPRESSING TRANSGENIC MICE TREATED WITH WILD-TYPE OR Fc-OPTIMIZED h2B6 31/60 mCD16−/− huCD16A+ nude (FoxN1) mice were intraperitoneally inoculated with EL4-CD32B cells and intraperitoneally administered on days 0-3 and 6 doses of 10 µg/g body weight of either h2B6 comprising mutant 31/60 (P247L, D270E, N421K) (h2B6 3160) or wild-type h2B6.

Figure 31A:
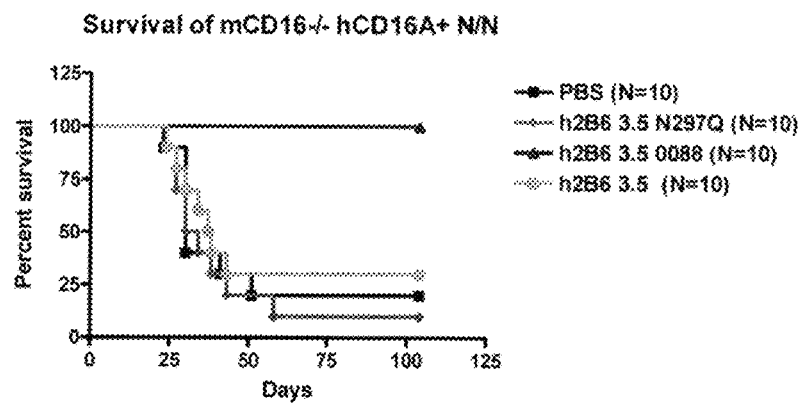
Figure 31B:
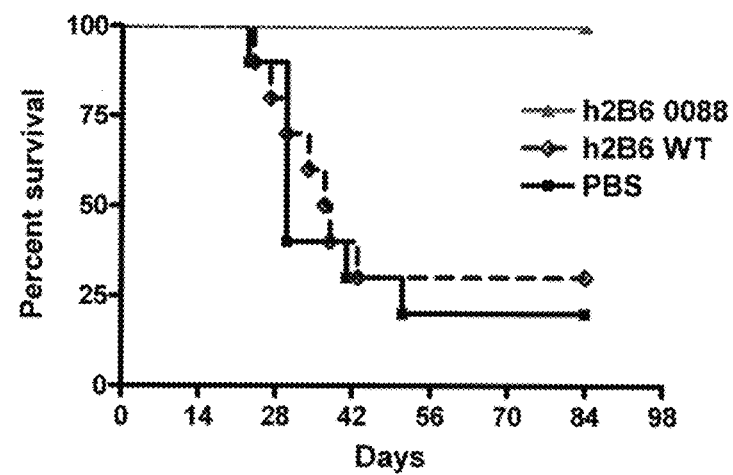

FIGS. 31A-31B. SURVIVAL IN TUMOR-BEARING HUMAN Fc RECEPTOR-EXPRESSING TRANSGENIC MICE TREATED WITH WILD-TYPE OR Fc-OPTIMIZED h2B6 0088

(A) mCD16−/− huCD16A+ nude (FoxN1 or N/N) mice were intraperitoneally inoculated with EL4-CD32B cells and intraperitoneally administered on days 0-3 with doses of either h2B6 3.5 N297Q (negative control), h2B6 3.5 comprising mutant FcMG0088 (F243L, R292P, Y300L, V305I P396L) (h2B6 3.5 0088) or wild-type h2B6 3.5. Mice administered buffer alone (PBS) were used as control. (B) Tumor-bearing mice as in A were intraperitoneally administered on days 0-3 and 6 doses of 4 µg/g body weight of either PBS, h2B6 comprising mutant FcMG0088 (F243L, R292P, Y300L, V305I P396L) (h2B6 0088) or wild-type h2B6.

Figure 32:
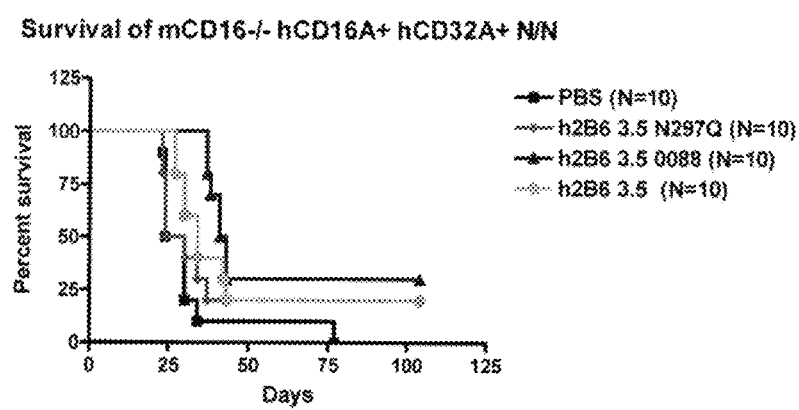

FIG. 32. SURVIVAL IN TUMOR-BEARING HUMAN Fc RECEPTOR-EXPRESSING TRANSGENIC MICE TREATED WITH WILD-TYPE OR Fc-OPTIMIZED h2B6 0088 mCD16−/− huCD16A+ hCD32A+ nude (FoxN1 or N/N) mice were intraperitoneally inoculated with EL4-CD32B cells and intraperitoneally administered on days 0-3 of either h2B6 3.5 N297Q (negative control), h2B6 comprising mutant FcMG0088 (F243L, R292P, Y300L, V305I P396L) (h2B6 3.5 0088) or wild-type h2B6 3.5. Mice administered buffer alone (PBS) were used as control.

Figure 33A:
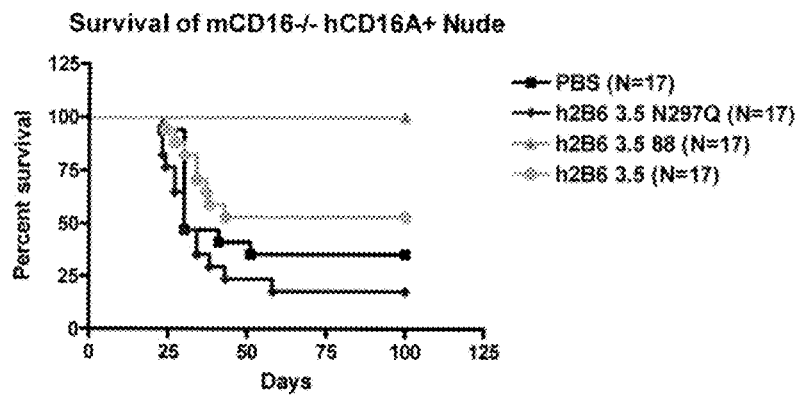
Figure 33B:
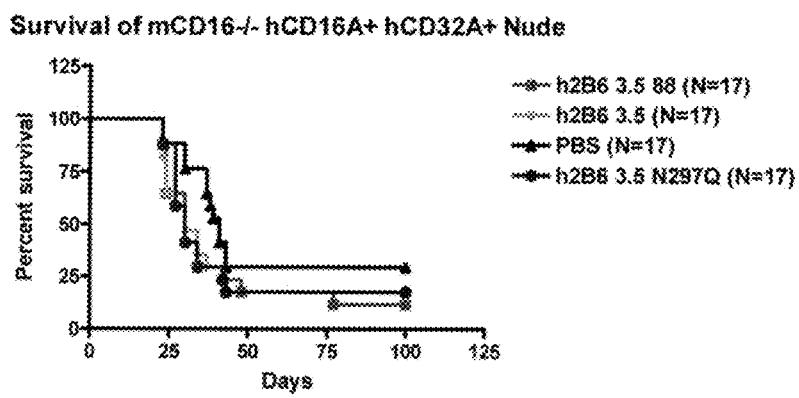
Figure 33C:
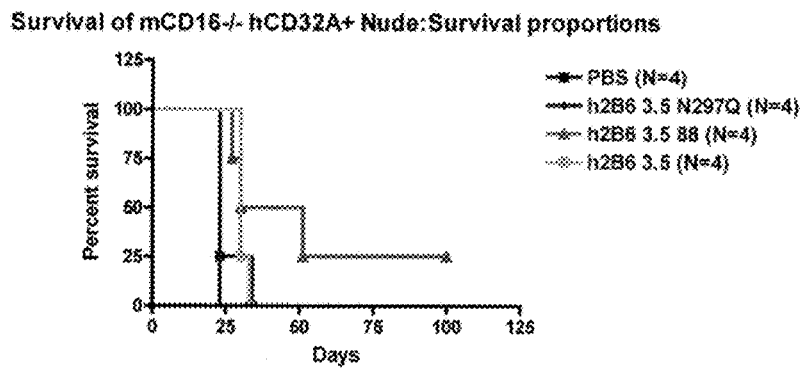

FIGS. 33A-33C. SURVIVAL IN TUMOR-BEARING TRANSGENIC MICE TREATED WITH WILD-TYPE OR Fc-OPTIMIZED h2B6 0088

Nude (FoxN1) mice were intraperitoneally inoculated with EL4-CD32B cells and intraperitoneally administered on days 0-3 of either h2B6 3.5 N297Q (negative control), h2B6 comprising mutant FcMG0088 (F243L, R292P, Y300L, V305I P396L) (h2B6 3.5 88) or wild-type h2B6 3.5. Mice administered buffer alone (PBS) were used as control. The transgenic mice strains examined were (A) mCD16−/− huCD16A+, (B) mCD16−/− huCD16A+ hCD32A+ and (C) mCD16−/− hCD32A+.

Figure 34:
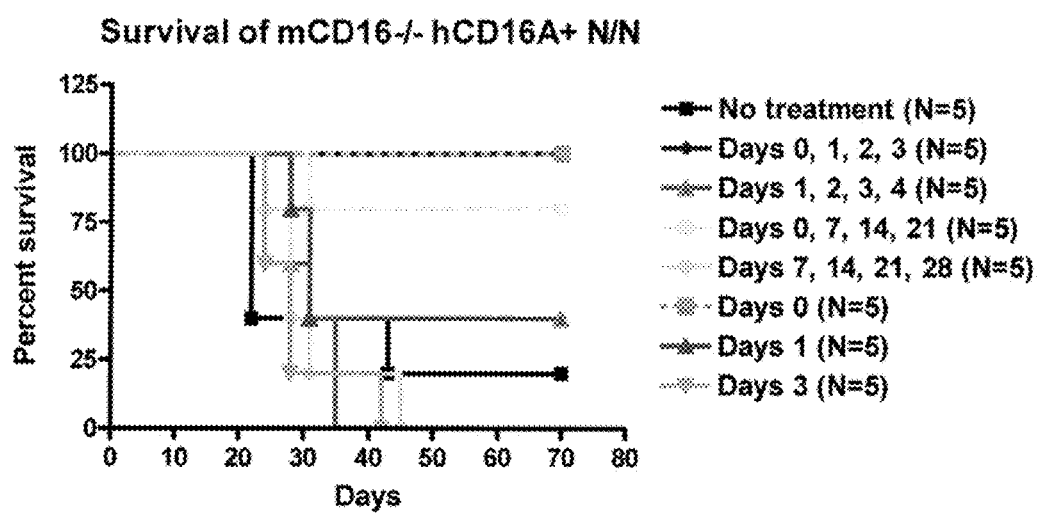

FIG. 34. SURVIVAL IN TUMOR-BEARING HUMAN Fc RECEPTOR-EXPRESSING TRANSGENIC MICE TREATED AT VARYING INTERVALS WITH WILD-TYPE OR Fc-OPTIMIZED h2B6 0088 mCD16−/− huCD16A+ nude (FoxN1 or N/N) mice were intraperitoneally inoculated with EL4-CD32B cells and intraperitoneally treated with h2B6 comprising mutant FcMG0088 (F243L, R292P, Y300L, V305I, P396L) (MGA321) at the indicated time intervals.

Figure 35A:
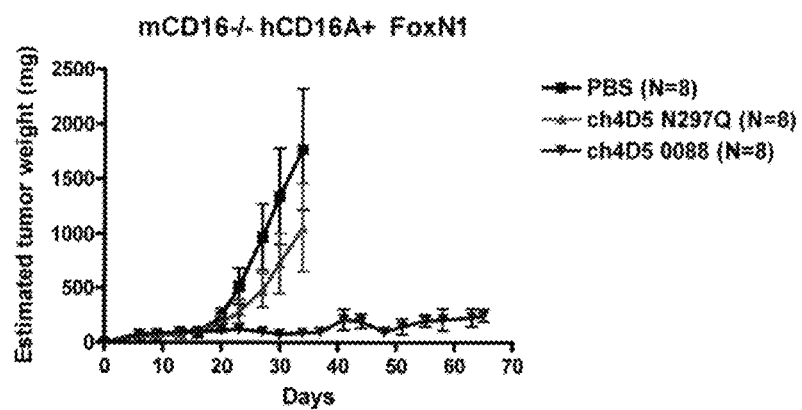
Figure 35B:
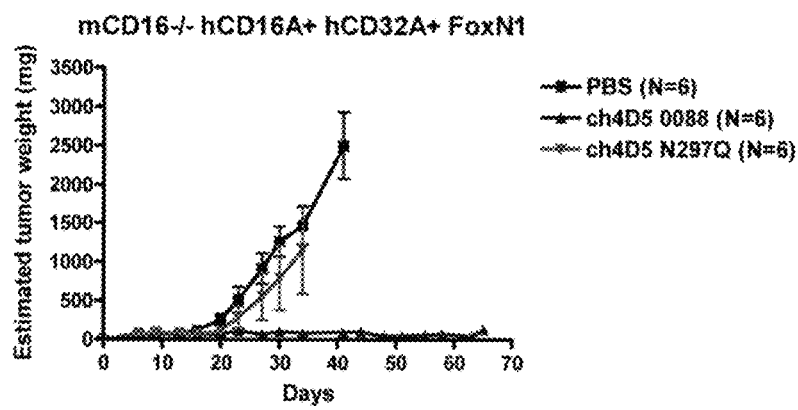

FIGS. 35A-35B. ESTIMATED TUMOR WEIGHT IN HUMAN Fc RECEPTOR-EXPRESSING TRANSGENIC MICE TREATED WITH WILD-TYPE OR Fc-OPTIMIZED ch4D5 0088

Nude (FoxN1) mice with the transgenic genotype mCD16−/− hCD16A+(A) or mCD16−/− hCD16A+ hCD32A+(B) were inoculated subcutaneously with mSCOV3 cells and, starting on day 0, were intraperitoneally administered eight weekly doses of either ch4D5 N297Q (negative control) or ch4D5 comprising mutant FcMG0088 (F243L, R292P, Y300L, V305I, P396L) (ch4D5 0088). Mice administered buffer alone (PBS) were used as control. Tumor weight was calculated based on the estimated volume of the subcutaneous tumor according to the formula (width$^2$×length)/2.

Figure 36A:
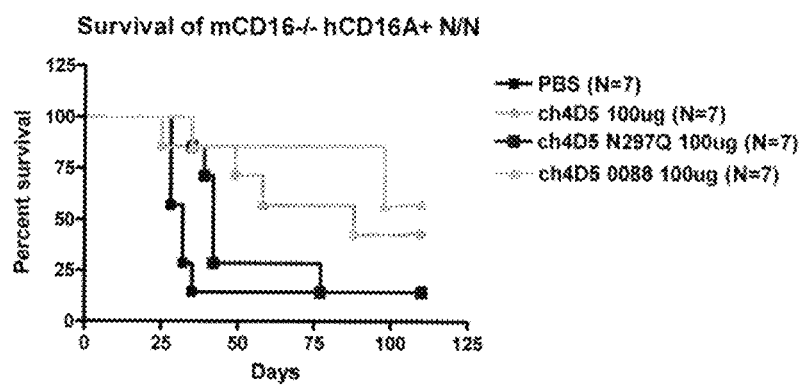
Figure 36B:
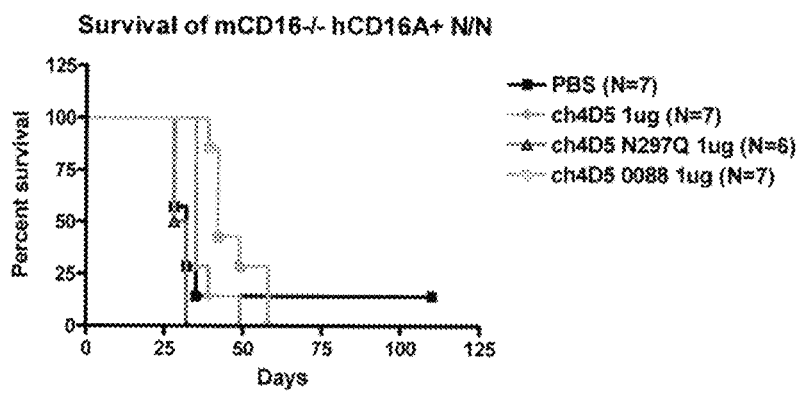

FIGS. 36A-36B. SURVIVAL IN TUMOR-BEARING HUMAN Fc RECEPTOR-EXPRESSING TRANSGENIC MICE TREATED WITH WILD-TYPE OR Fc-OPTIMIZED ch4D5 0088 mCD16−/− huCD16A+ nude (N/N) mice were intraperitoneally inoculated with mSKOV3 cells and, starting on day 0, were intraperitoneally administered six weekly doses of either 100 µg (A) or 1 µg (B) of either wild-type ch4D5, ch4D5 N297Q (negative control) or ch4D5 comprising mutant FcMG0088 (F243L, R292P, Y300L, V305I P396L) (ch4D5 0088). Mice administered buffer alone (PBS) were used as control.

Figure 37A:
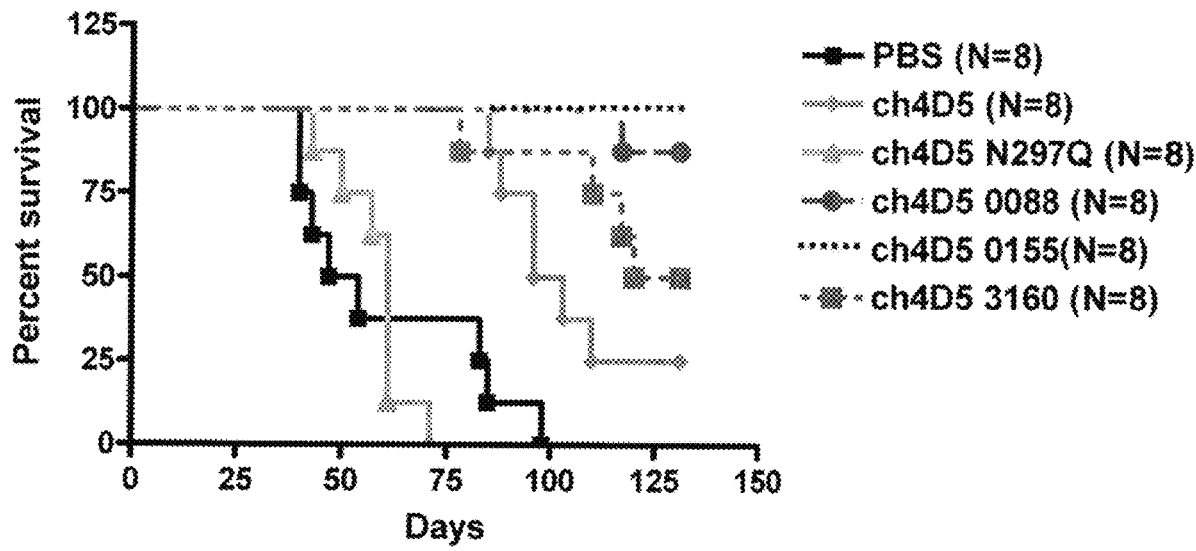
Figure 37B:
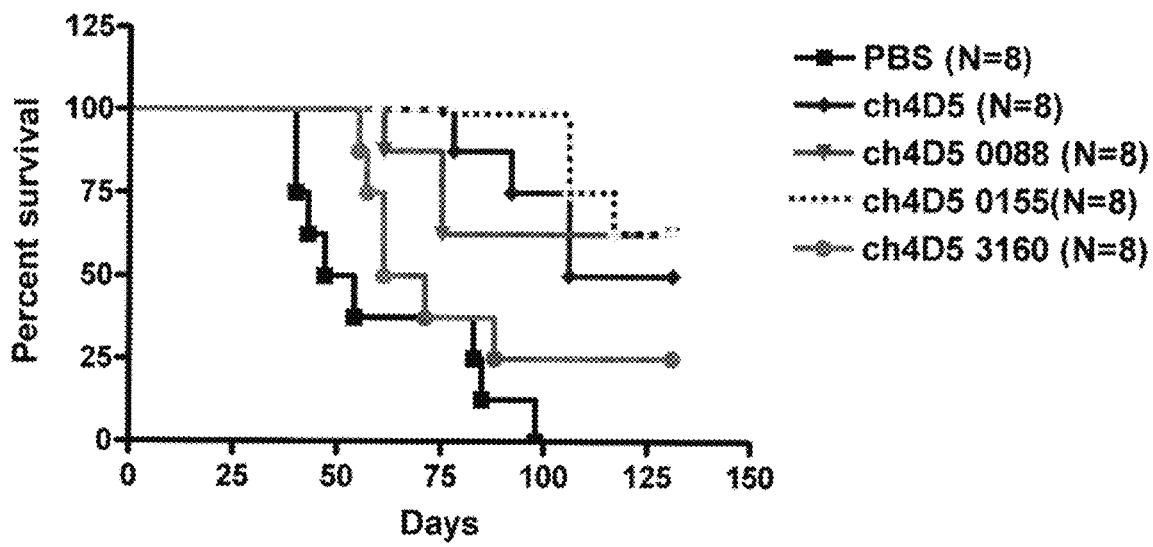

FIGS. 37A-37B. SURVIVAL IN TUMOR-BEARING HUMAN Fc RECEPTOR-EXPRESSING TRANSGENIC MICE TREATED WITH WILD-TYPE OR Fc-OPTIMIZED VARIANTS OF ch4D5 mCD16−/− huCD16A+ nude (N/N) mice were intraperitoneally inoculated with mSKOV3 cells and, starting on day 0, were intraperitoneally administered eight weekly doses of either 100 µg (A) or 10 µg (B) of either wild-type ch4D5, ch4D5 N297Q (negative control), ch4D5 comprising mutant FcMG0088 (F243L, R292P, Y300L, V305I P396L) (ch4D5 0088), ch4D5 mutant MGFc0155 (F243L, R292P, Y300L) (ch4D5 0155) or ch4D5 mutant MCFc3160 (P247L, D270E, N421K) ("ch4D5 3160"). Mice administered buffer alone (PBS) were used as control.

Figure 38A:
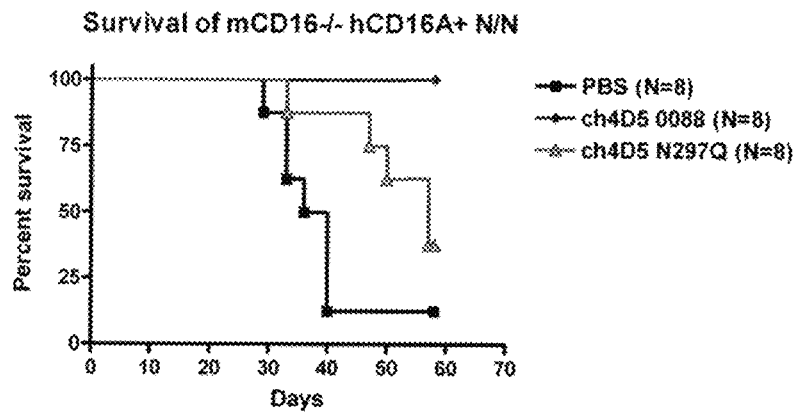
Figure 38B:
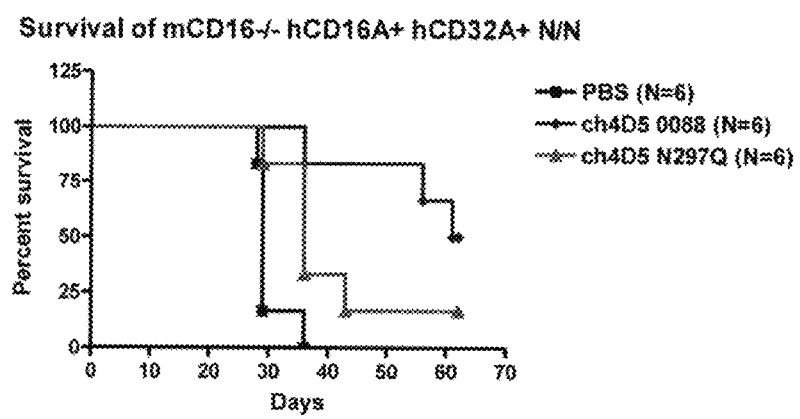

FIGS. 38A-38B. SURVIVAL IN TUMOR-BEARING HUMAN Fc RECEPTOR-EXPRESSING TRANSGENIC MICE TREATED WITH WILD-TYPE OR Fc-OPTIMIZED ch4D5 0088

Nude (N/N) mice with the transgenic genotype mCD16−/− hCD16A+(A) or mCD16−/− hCD16A+ hCD32A+(B) were intraperitoneally inoculated with mSKOV3 cells and, starting on day 0, intraperitoneally administered eight weekly doses of either ch4D5 comprising mutant FcMG0088 (F243L, R292P, Y300L, V305I P396L) (ch4D5 0088) or ch4D5 N297Q (negative control). Mice administered buffer alone (PBS) were used as control.

FIG. 39A-39F. Fc OPTIMIZATION ENHANCES TUMOR-CELL DEPLETION IN VIVO.

(A-D) Enhanced reduction of tumor burden by Fc-engineered hu2B6 treatment of Daudi cell subcutaneous xenografts in Balb/c FoxN1 (nu/nu) mice (6-8 mice/group). Statistical significance between curves was determined by a student T test; WT vs MG12, P=0.431; WT vs MG4, P=0.002; MG4 vs MG12, P=0.002. (E-F) Kaplan-Meier survival plots of mFcγRIII−/− human CD16A+ FoxN1 mice injected intra-peritoneally with CD32B-EL4 cells (10 mice/group) and treated with either WT-Fc hu2B6 or the indicated Fc-engineered forms of hu2B6 (C, 10 µg/g; D, 4 µg/g). Data was analyzed for significance using log-rank analysis.

7. DETAILED DESCRIPTION

The present invention relates to methods of treatment of cancer or other diseases using molecules, preferably polypeptides, and more preferably immunoglobulins (e.g., antibodies), comprising a variant Fc region, having one or more amino acid modifications (e.g., substitutions, but also including insertions or deletions) in one or more regions, which modifications alter, e.g., increase or decrease, the affinity of the variant Fc region for an FcγR. Enhancing the ability of immunoglobulins to mediate antibody-dependent cell-mediated cytotoxicity (ADCC), complement-dependent cytotoxicity (CDC) or antibody-dependent cell-mediated phagocytosis (ADCP) provides an approach for enhancing the therapeutic activity of immunoglobulins against cancers and infectious diseases.

The invention thus encompasses therapeutic antibodies in the treatment or prevention of a disease or disorder, or the amelioration of a symptom thereof, where an enhanced efficacy of effector cell function (e.g., ADCC) mediated by FcγR is desired, e.g., cancer or infectious disease, or where a modulation of effector cell function mediated by FcγR is desired, e.g., autoimmune or inflammatory disorders. In some embodiments, the invention encompasses the use of molecules comprising Fc regions with amino acid modifications including but not limited to any of the modifications disclosed in U.S Patent Application Publications 2005/0037000 and 2005/0064514; and International Patent Application Publication WO 04/063351. Each of the above mentioned applications is incorporated herein by reference in its entirety. In some embodiments, the invention encompasses the use of molecules comprising a variant Fc region, wherein said variant Fc region comprises at least one amino acid modification relative to a wild-type Fc region, which variant Fc region binds FcγRIIIA with a greater affinity, relative to a comparable molecule, i.e., being the same as said molecule with a variant Fc region but not having the one or more amino acid modifications, comprising the wild-type Fc region as determined by methods known to one skilled in the art for determining Fc-FcγR interactions and methods disclosed herein, for example, an ELISA assay or a surface plasmon resonance assay. In yet other embodiments, the invention encompasses molecules comprising a variant Fc region, wherein said variant Fc region comprises at least one amino acid modification relative to a wild-type Fc region, which variant Fc region binds FcγRIIIA with a reduced affinity relative to a comparable molecule comprising the wild-type Fc region. In a preferred embodiment, the molecules of the invention further specifically bind FcγRIIB (via the Fc region) with a lower affinity than a comparable molecule comprising the wild-type Fc region binds FcγRIIB. In some embodiments, the invention encompasses molecules comprising a variant Fc region, wherein said variant Fc region comprises at least one amino acid modification relative to a wild-type Fc region, which variant Fc region binds FcγRIIIA and FcγRIIB with a greater affinity, relative to a comparable molecule comprising the wild-type Fc region. In other embodiments, the invention encompasses molecules comprising a variant Fc region, wherein said variant Fc region comprises at least one amino acid modification relative to a wild-type Fc region, which variant Fc region binds FcγRIIB with a greater affinity, relative to a comparable molecule comprising the wild-type Fc region. In other embodiments, the invention encompasses molecules comprising variant Fc region, wherein said variant Fc region comprises at least one amino acid modification relative to a wild-type Fc region, which variant Fc region binds FcγRIIB with a reduced affinity, relative to a comparable molecule comprising the wild-type Fc region.

In specific embodiments, the invention encompasses therapeutic antibodies that immunospecifically bind FcγRIIB via their variable domains with greater affinity than FcγRIIA, e.g., antibodies derived from mouse monoclonal antibody produced by clone 2B6 or 3H7, having ATCC accession numbers PTA-4591 and PTA-4592, respectively. In other embodiments, the anti-FcγRIIB antibodies of the invention are derived from a mouse monoclonal antibody produced by clone 1D5, 2E1, 2H9, 2D11, or 1F2, having ATCC Accession numbers, PTA-5958, PTA-5961, PTA-5962, PTA-5960, and PTA-5959, respectively. Hybridomas producing antibodies 2B6 and 3H7 have been deposited with the American Type Culture Collection (10801 University Blvd., Manassas, Va. 20110-2209) on Aug. 13, 2002 under the provisions of the Budapest Treaty on the International Recognition of the Deposit of Microorganisms for the Purposes of Patent Procedures, and assigned accession numbers PTA-4591 (for hybridoma producing 2B6) and PTA-4592 (for hybridoma producing 3H7), respectively, and are incorporated herein by reference. Hybridomas producing 1D5, 2E1, 2H9, 2D11, and 1F2 were deposited under the provisions of the Budapest Treaty with the American Type Culture Collection (10801 University Blvd., Manassas, Va. 20110-2209) on May 7, 2004, and assigned accession numbers PTA-5958, PTA-5961, PTA-5962, PTA-5960, and PTA-5959, respectively and are incorporated herein by reference. In preferred embodiments, the anti-FcγRIIB antibodies of the invention (e.g., 2B6) comprise a variant Fc region, wherein said variant Fc region has a substitution at portion at position 243 with leucine, at position 292 with proline, at position 300 with leucine, at position 305 with isoleucine, and at position 396 with leucine. In another embodiment, the invention encompasses a 2B6 antibody having a leucine at position 243, a proline at position 292, a leucine at position 300, an isoleucine at position 305, and a leucine at position 396. In other embodiments, the invention encompasses a 2B6 antibody comprising a variant Fc region having a substitution at position 243 with leucine, at position 292 with proline, and at position 300 with leucine. In other embodiments, the invention encompasses a 2B6 antibody having a leucine at position 243, a proline at position 292, and a leucine at position 300. In other embodiments, the invention encompasses a 2B6 antibody comprising a variant Fc region having a substitution at position 247 with leucine, at position 270 with glutamic acid, and at position 421 with lysine. In another embodiment, the invention encompasses a 2B6 antibody having a leucine at position 247, a glutamic acid at position 292, and a lysine at position 421.

In a specific embodiment, the invention encompasses therapeutic antibodies that bind the Her2/neu protooncogene (amino acid sequence SEQ ID NO:31) (e.g., Ab4D5 antibody as disclosed in Carter et al., 1992, *Proc. Natl. Acad. Sci. USA* 89:4285-9; U.S. Pat. No. 5,677,171; or International Patent Application Publication WO 01/00245, each of which is hereby incorporated by references in its entirety). In a certain embodiment, the 4D5 antibody is chimeric. In another embodiment, the 4D5 antibody is humanized. In a specific embodiment, the 4D5 antibody is engineered to comprise a variant Fc region by modification (e.g., substitution, insertion, deletion) of at least one amino acid residue which modification increases the affinity of the Fc region for FcγRIIIA and/or FcγRIIA and/or decreases the affinity of the Fc region for FcγRIIB and/or modulates the effector function of the antibody relative to a comparable antibody comprising a wild-type Fc region. In certain embodiments, the 4D5 antibody of the invention comprises a variant Fc region having a substitution at position 243 with leucine, at position 292 with proline, at position 300 with leucine, at position 305 with isoleucine, and at position 396 with leucine. In other embodiments, the invention encompasses a 4D5 antibody having a leucine at position 243, a proline at position 292, a leucine at position 300, an isoleucine at position 305, and a leucine at position 396. In yet another embodiment, the invention encompasses a 4D5 antibody comprising a variant Fc region having a substitution at position 243 with leucine, at position 292 with proline, and at position 300 with leucine. In still other embodiments, the invention encompasses a 4D5 antibody having a leucine at position 243, a proline at position 292, and a leucine at position 300. In other embodiments, the invention encompasses a 4D5 antibody comprising a variant Fc region having a substitution at position 247 with leucine, at position 270 with glutamic acid, and at position 421 with lysine. In another embodiment, the invention encompasses a 4D5 antibody having a leucine at position 247, a glutamic acid at position 292, and a lysine at position 421.

In some embodiments, the invention encompasses molecules comprising a variant Fc region, wherein said variant Fc region comprises at least one amino acid modification relative to a wild type Fc region, which variant Fc region does not show a detectable binding to any FcγR (e.g., does not bind FcγRIIA, FcγRIIB, or FcγRIIIA, as determined by, for example, an ELISA assay), relative to a comparable molecule comprising the wild-type Fc region.

In a specific embodiment, the invention encompasses molecules comprising a variant Fc region, wherein said variant Fc region comprises at least one amino acid modification relative to a wild type Fc region, which variant Fc region only binds one FcγR, wherein said FcγR is FcγIIIA. In another specific embodiment, the invention encompasses molecules comprising a variant Fc region, wherein said variant Fc region comprises at least one amino acid modification relative to a wild type Fc region, which variant Fc region only binds one FcγR, wherein said FcγR is FcγRIIA. In yet another embodiment, the invention encompasses molecules comprising a variant Fc region, wherein said variant Fc region comprises at least one amino acid modification relative to a wild type Fc region, which variant Fc region only binds one FcγR, wherein said FcγR is FcγRIIB. The invention particularly relates to the modification of human or humanized therapeutic antibodies (e.g., tumor specific anti-angiogenic or anti-inflammatory monoclonal antibodies) for enhancing the efficacy of therapeutic antibodies by enhancing, for example, the effector function of the therapeutic antibodies, e.g., enhancing ADCC.

The affinities and binding properties of the molecules of the invention for an FcγR are initially determined using in vitro assays (biochemical or immunological based assays) known in the art for determining Fc-FcγR interactions, i.e., specific binding of an Fc region to an FcγR including but not limited to ELISA assay, surface plasmon resonance assay, immunoprecipitation assays (See Section 6.2.2). Preferably, the binding properties of the molecules of the invention are also characterized by in vitro functional assays for determining one or more FcγR mediator effector cell functions (See Section 6.2.2). In most preferred embodiments, the molecules of the invention have similar binding properties in in vivo models (such as those described and disclosed herein) as those in in vitro based assays. However, the present invention does not exclude molecules of the invention that do not exhibit the desired phenotype in in vitro based assays but do exhibit the desired phenotype in vivo.

In some embodiments, the molecules of the invention comprising a variant Fc region comprise at least one amino acid modification in the CH3 domain of the Fc region, which is defined as extending from amino acids 342-447. In other embodiments, the molecules of the invention comprising a variant Fc region comprise at least one amino acid modification in the CH2 domain of the Fc region, which is defined as extending from amino acids 231-341. In some embodiments, the molecules of the invention comprise at least two amino acid modifications, wherein one modification is in the CH3 region and one modification is in the CH2 region. The invention further encompasses amino acid modification in the hinge region. Molecules of the invention with one or more amino acid modifications in the CH2 and/or CH3 domains have altered affinities for an FcγR as determined using methods described herein or known to one skilled in the art.

In a particular embodiment, the invention encompasses amino acid modification in the CH1 domain of the Fc region.

In particularly preferred embodiments, the invention encompasses molecules comprising a variant Fc region wherein said variant has an increased binding to FcγRIIA (CD32A) and/or an increased ADCC activity, as measured using methods known to one skilled in the art and exemplified herein. The ADCC assays used in accordance with the methods of the invention may be NK dependent or macrophage dependent.

The Fc variants of the present invention may be combined with other known Fc modifications including but not limited to modifications which alter effector function and modification which alter FcγR binding affinity. In a particular embodiment, an Fc variant of the invention comprising a first amino acid modification in the CH3 domain, CH2 domain or the hinge region may be combined with a second Fc modification such that the second Fc modification is not in the same domain as the first so that the first Fc modification confers an additive, synergistic or novel property on the second Fc modification. In some embodiments, the Fc variants of the invention do not have any amino acid modification in the CH2 domain.

The Fc variants of the present invention may be combined with any of the known Fc modifications in the art such as those disclosed in Table 1 below.

TABLE 1

| Substitution(s) | | |
|---|---|---|
| V264I/S298A/I332E | K334L | V264A |
| S239D/S298A/I332E | A330K | V264L |
| S239N/S298A/I332E | T335K | V264I |
| S239D/V264I/I332E | A339T | F241W |
| S239D/V264I/S298A/I332E | E333A, K334A | F241L |
| S239D/V264I/A330L/I332E | T256A, S298A | F243W |
| F241L/F243L/V262I/V264I | S298A, E333A | F243L |
| F241W/F243W | T256A | F241L/V262I |
| F241W/F243W/V262A/V264A | K290A | F243L/V264I |
| D265Y/N297D/I332E | K326A | A330L/I332E |
| D265Y/N297D/T299L/I332E | R255A | L328M |
| D265F/N297E/I332E | E258A | L328E |
| F243L/V262I/V264W | S267A | L328F |
| S239D/N297D/I332E | E272A | I332E |
| S239E/N297D/I332E | N276A | L328M/I332E |
| V264I/N297D/I332E | D280A | P244H |
| Y296D/N297D/I332E | E283A | P245A |
| Y296E/N297D/I332E | H285A | P247V |

TABLE 1-continued

| Substitution(s) | | |
|---|---|---|
| Y296N/N297D/I332E | N286A | W313F |
| Y296Q/N297D/I332E | P331A | P244H/P245A/P247V |
| Y296H/N297D/I332E | S337A | P247G |
| Y296T/N297D/I332E | H268A | V264I/I332E |
| N297D/T299V/I332E | E272A | S298A |
| N297D/T299I/I332E | E430A | S298A/I332E |
| N297D/T299L/I332E | A330K | S298A/E333A/K334A |
| N297D/T299F/I332E | R301M | S239E/I332E |
| N297D/T299H/I332E | H268N | S239Q/I332E |
| N297D/T299E/I332E | H268S | S239E |
| N297D/A330Y/I332E | E272Q | D265G |
| N297D/S298A/A330Y/I332E | N286Q | D265N |
| S239D/A330Y/I332E | N286S | S239E/D265G |
| S239N/A330Y/I332E | N286D | S239E/D265N |
| S239D/A330L/I332E | K290S | S239E/D265Q |
| S239N/A330L/I332E | K320M | Y296E |
| S239D/D265V/N297D/I332E | K320Q | Y296Q |
| S239D/D265I/N297D/I332E | K320E | S298T |
| S239D/D265L/N297D/I332E | K320R | S298N |
| S239D/D265F/N297D/I332E | K322E | T299I |
| S239D/D265Y/N297D/I332E | K326S | A327S |
| S239D/D265H/N297D/I332E | K326D | A327N |
| S239D/D265T/N297D/I332E | K326E | S267Q/A327S |
| F241E/F243R/V262E/V264R/I332E | A330K | S267L/A327S |
| S267A, E258A, D280A, R255A | T335E | A327L |
| T256A, D280A, S298A, T307A | S267A, E258A | P329F |
| S298A, E333A, K334A S298A, K334A | S267A, R255A | A330L |
| F241E/F243Q/V262T/V264E/I332E | S267A, D280A | A330Y |
| F241R/F243Q/V262T/V264R/I332E | S267A, E272A | I332D |
| F241E/F243Y/V262T/V264R/I332E | S267A, E293A | N297S |
| F241Y/F243Y/V262T/V264T | P238A | N297D |
| F241E/F243R/V262E/V264R | D265A | N297S/I332E |
| F241E/F243Q/V262T/V264E | E269A | N297D/I332E |
| F241R/F243Q/V262T/V264R | D270A | N297E/I332E |
| F241E/F243Y/V262T/V264R | N297A | L328I/I332E |
| V264I/A330Y/I332E | P329A | L328Q/I332E |
| V264I/A330L/I332E | A327Q | I332N |
| S239E/V264I/I332E | S239A | I332Q |
| S239Q/V264I/I332E | E294A | V264T |
| S239E/V264I/A330Y/I332E | Q295A | V264F |
| S239E/V264I/S298A/A330Y/I332E | V303A | V240I |
| F241Y/F243Y/V262T/V264T/ | K246A | V263I |
| N297D/I332E | I253A | V266I |
| S239N/I332D | T260A | T299A |
| S239N/I332E | K274A | T299S |
| S239N/I332N | V282A | T299V |
| S239N/I332Q | K288A | N325Q |
| S239Q/I332D | Q311A | N325L |
| S239Q/I332E | K317A | N325I |
| S239Q/I332N | E318A | S239D |
| S239Q/I332Q | K338A | S239N |
| K326E | K340A | S239F |
| Y296D | Q342A | S239D/I332D |
| Y296N | R344A | S239D/I332E |
| A330Y/I332E | E345A | S239D/I332N |

| Substitution(s) | | |
|---|---|---|
| L235V | Q347A | S239D/I332Q |
| L235F | R355A | S239E/I332D |
| S239T | E356A | S239E/I332N |
| S239H | M358A | S239E/I332Q |
| S239Y | K360A | L234D |
| V240A | N361A | L234E |
| V240T | Q362A | L234N |
| V240M | Y373A | L234Q |
| V263A | S375A | L234T |
| V263T | D376A | L234H |
| V263M | E380A | L234Y |
| V264M | E382A | L234I |
| V264Y | S383A | L234V |
| V266A | N384A | L234F |
| V266T | Q386A | L235D |
| V266M | E388A | L235S |
| E269H | N389A | L235N |
| E269Y | N390A | L235Q |
| E269F | Y391A | L235T |
| E269R | K392A | L235H |
| Y296S | L398A | L235Y |
| Y296T | S400A | L235I |
| Y296L | D401A | A378L |
| Y296I | D413A | Y391F |
| A298H | K414A | T256A |
| T299H | S415A | K290A |
| A330V | R416A | D312A |
| A330I | Q418A | *K326A |
| A330F | Q419A | S298A |
| A330R | N421A | E333A |
| A330H | V422A | K334A |
| N325D | S424A | E430A |
| N325E | E430A | T359A |
| N325A | H433A | K360A |
| N325T | N434A | E430A |
| N325V | H435A | K320M |
| N325H | Y436A | K326S |
| L328D/I332E | T437A | K326N |
| L328E/I332E | Q438A | K326D |
| L328N/I332E | K439A | K326E |
| L328Q/I332E | S440A | K334Q |
| L328V/I332E | S442A | K334E |
| L328T/I332E | S444A | K334M |
| L328H/I332E | K447A | |
| L328I/I332E | K246M | |
| L328A | K248M | |
| I332T | Y300F | |
| I332H | A330Q | |
| I332Y | K338M | |
| I332A | K340M | |
| K334H | | |
| K334V | | |

In other embodiments, the Fc variants of the present invention may be combined with any of the known Fc modifications in the art such as those disclosed in Tables 2 A and B below.

TABLE 2A

| Starting Variant | Position 300 | Position 298 | Position 296 | Position 295 | Position 294 |
|---|---|---|---|---|---|
| Y300I + → | — | S298N, S298V, S298D, S298P, S298A, S298G, S298T, or S298L. | Y296P, Y296F, or N276Q. | Q295K, Q295L, or Q295A. | E294N, E294A, E294Q, or E294D. |
| Y300L + → | — | S298N, S298V, S298D, S298P, S298A, S298G, S298T, or S298L. | Y296P, Y296F, or N276Q. | Q295K, Q295L, or Q295A. | E294N, E294A, E294Q, or E294D. |

TABLE 2A-continued

| Starting Variant | Position 300 | Position 298 | Position 296 | Position 295 | Position 294 |
|---|---|---|---|---|---|
| S298N + → | Y300I, Y300L, or Y300F. | — | Y296P, Y296F, or N276Q. | Q295K, Q295L, or Q295A. | E294N, E294A, E294Q, or E294D. |
| S298V + → | Y300I, Y300L, or Y300F. | — | Y296P, Y296F, or N276Q. | Q295K, Q295L, or Q295A. | E294N, E294A, E294Q, or E294D. |
| S298D + → | Y300I, Y300L, or Y300F. | — | Y296P, Y296F, or N276Q. | Q295K, Q295L, or Q295A. | E294N, E294A, E294Q, or E294D. |
| S298P + → | Y300I, Y300L, or Y300F. | — | Y296P, Y296F, or N276Q. | Q295K, Q295L, or Q295A. | E294N, E294A, E294Q, or E294D. |
| Y296P + → | Y300I, Y300L, or Y300F. | S298N, S298V, S298D, S298P, S298A, S298G, S298T, or S298L. | — | Q295K, Q295L, or Q295A. | E294N, E294A, E294Q, or E294D. |
| Q295K + → | Y300I, Y300L, or Y300F. | S298N, S298V, S298D, S298P, S298A, S298G, S298T, or S298L. | Y296P, Y296F, or N276Q. | — | E294N, E294A, E294Q, or E294D. |
| Q295L + → | Y300I, Y300L, or Y300F. | S298N, S298V, S298D, S298P, S298A, S298G, S298T, or S298L. | Y296P, Y296F, or N276Q. | — | E294N, E294A, E294Q, or E294D. |
| E294N + → | Y300I, Y300L, or Y300F. | S298N, S298V, S298D, S298P, S298A, S298G, S298T, or S298L. | Y296P, Y296F, or N276Q. | Q295K, Q295L, or Q295A. | — |

** Note that table uses EU numbering as in Kabat.

TABLE 2B

| Starting Variant | Position 334 | Position 333 | Position 324 | Position 286 | Position 276 |
|---|---|---|---|---|---|
| Y300I + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |
| Y300L + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |
| S298N + → | K334A, K334R, K334Q, K334N, K334S, | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |

TABLE 2B-continued

| Starting Variant | Position 334 | Position 333 | Position 324 | Position 286 | Position 276 |
|---|---|---|---|---|---|
| | K334E, K334D, K334M, K334Y, K334W, K334H, K334V, or K334L. | | | | |
| S298V + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |
| S298D + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |
| S298P + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |
| Y296P + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |
| Q295K + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |

TABLE 2B-continued

| Starting Variant | Position 334 | Position 333 | Position 324 | Position 286 | Position 276 |
|---|---|---|---|---|---|
| Q295L + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |
| E294N + → | K334A, K334R, K334Q, K334N, K334S, K334E, K334D, K334M, K334Y, K334W, K334H, K334V, or K334L. | E33A, E333Q, E333N, E333S, E333K, E333R, E333D, or E333G. | S324A, S324N, S324Q, S324K, or S324E. | N286Q, N286S, N286A, or N286D. | N276Q, N276A, or N276K. |

** Note that table uses EU numbering as in Kabat.

In a preferred specific embodiment, the invention encompasses a molecule comprising a variant Fc region, wherein said variant Fc region comprises at least one amino acid modification relative to a wild-type Fc region, such that said molecule has an altered affinity for an FcγR, provided that said variant Fc region does not have a substitution at positions that make a direct contact with FcγR based on crystallographic and structural analysis of Fc-FcγR interactions such as those disclosed by Sondermann et al., 2000 (*Nature*, 406: 267-273 which is incorporated herein by reference in its entirety). Examples of positions within the Fc region that make a direct contact with FcγR are amino acids 234-239 (hinge region), amino acids 265-269 (B/C loop), amino acids 297-299 (C'/E loop), and amino acids 327-332 (F/G) loop. In some embodiments, the molecules of the invention comprising variant Fc regions comprise modification of at least one residue that makes a direct contact with an FcγR based on structural and crystallographic analysis.

The FcγR interacting domain maps to the lower hinge region and select sites within the CH2 and CH3 domains of the IgG heavy chain. Amino acid residues flanking the actual contact positions and amino acid residues in the CH3 domain play a role in IgG/FcγR interactions as indicated by mutagenesis studies and studies using small peptide inhibitors, respectively (Sondermann et al., 2000 *Nature*, 406: 267-273; Diesenhofer et al., 1981, Biochemistry, 20: 2361-2370; Shields et al., 2001, J. Biol. Chem. 276: 6591-6604; each of which is incorporated herein by reference in its entirety). Direct contact as used herein refers to those amino acids that are within at least 1 Å, at least 2, or at least 3 angstroms of each other or within 1 Å, 1.2 Å, 1.5 Å, 1.7 Å or 2 Å Van Der Waals radius. An exemplary list of previously identified sites on the Fc that effect binding of Fc interacting proteins is listed in the Table 3 below. In some embodiments, the invention encompasses Fc variants that do not have any modifications at the sites listed below. In other embodiments, the invention encompasses Fc variants comprising amino acid modifications at one or more sites listed below in combination with other modifications disclosed herein such that such modification has a synergistic or additive effect on the property of the mutant.

TABLE 3

PREVIOUSLY IDENTIFIED SITES ON THE Fc THAT EFFECT BINDING OF Fc INTERACTING PROTEINS

| FcR-Fc | Domain | residue | FcRI | FcRII | FcRIII | C1g | FcRn |
|---|---|---|---|---|---|---|---|
|  | CH2 | 233 | C | C | C |  | C |
| A,B | CH2 | 234 | C | C | C | G | C |
| A,B | CH2 | 235 | C | C | C | G | C |
| A,B | CH2 | 236 | C | C | C |  | C |
| A,B | CH2 | 237 |  |  |  |  |  |
| A,B | CH2 | 238 | D |  |  |  |  |
| A,B | CH2 | 239 |  |  | C |  |  |
| A,B | CH2 | 241 | D |  |  |  |  |
|  | CH2 | 243 | D |  |  |  |  |
|  | CH2 | 246 | D |  |  |  |  |
|  | CH2 | 250 |  |  |  |  | E |
|  | CH2 | 254 |  |  |  |  | C |
|  | CH2 | 255 |  | C |  |  |  |
|  | CH2 | 256 |  | C | C |  |  |
|  | CH2 | 258 |  | C |  |  |  |
| B | CH2 | 265 | C | C | C | F | C |
| B | CH2 | 267 |  | C |  |  |  |
|  | CH2 | 268 |  | C | C |  |  |
| B | CH2 | 269 |  |  | C |  |  |
|  | CH2 | 270 |  | C | C | F |  |
|  | CH2 | 272 |  | C |  |  |  |
|  | CH2 | 276 |  | C |  |  |  |
|  | CH2 | 285 |  | C |  |  |  |
|  | CH2 | 286 |  | C |  |  |  |
|  | CH2 | 288 |  |  |  |  | C |
|  | CH2 | 290 |  | C | C |  |  |
|  | CH2 | 292 |  | C |  |  |  |
|  | CH2 | 293 |  |  | C |  |  |
|  | CH2 | 295 |  | C | C |  |  |
|  | CH2 | 296 |  |  | C |  |  |
| B | CH2 | 297 | X | X | X | X |  |
| B | CH2 | 298 |  |  |  |  |  |
| B | CH2 | 299 |  |  |  |  |  |

TABLE 3-continued

PREVIOUSLY IDENTIFIED SITES ON THE Fc THAT EFFECT BINDING OF Fc INTERACTING PROTEINS

| FcR-Fc | Domain | residue | FcRI | FcRII | FcRIII | C1g | FcRn |
|---|---|---|---|---|---|---|---|
|  | CH2 | 301 | D | C | C |  |  |
|  | CH2 | 311 |  |  |  |  | C |
|  | CH2 | 312 |  |  |  |  | C |
|  | CH2 | 315 |  | C |  |  |  |
|  | CH2 | 317 |  |  |  |  | C |
|  | CH2 | 322 |  | C | C | F |  |
|  | CH2 | 326 |  |  | C | F |  |
| A,B | CH2 | 327 | D,C | C | C |  |  |
| A | CH2 | 328 |  |  |  |  |  |
| A | CH2 | 329 | D,C | C | C | F |  |
| A | CH2 | 330 |  |  |  |  |  |
|  | CH2 | 331 |  | C |  | F |  |
| A | CH2 | 332 |  |  |  |  |  |
|  | CH2 | 333 |  |  | C | F |  |
|  | CH2 | 334 |  |  | C |  |  |
|  | CH2 | 337 |  | C |  |  |  |
|  | CH2 | 338 |  |  | C |  |  |
|  | CH3 | 339 |  |  | C |  |  |
|  | CH3 | 360 |  |  |  |  | C |
|  | CH3 | 362 |  |  |  |  | C |
|  | CH3 | 376 |  |  | C |  |  |
|  | CH3 | 378 |  | C |  |  |  |
|  | CH3 | 380 |  |  |  |  | C |
|  | CH3 | 382 |  |  |  |  | C |
|  | CH3 | 414 |  | C |  |  |  |
|  | CH3 | 415 |  |  |  |  | C |
|  | CH3 | 424 |  |  |  |  | C |
|  | CH3 | 428 |  |  |  |  | E |
|  | CH3 | 430 |  | C |  |  |  |
|  | CH3 | 433 |  |  |  |  | C |
|  | CH3 | 434 |  |  |  |  | C |
|  | CH3 | 435 |  |  |  |  | C |
|  | CH3 | 436 |  |  |  |  | C |

Table 3 lists sites within the Fc region that have previously been identified to be important for the Fc-FcR interaction. Columns labeled FcR-Fc identifies the Fc chain contacted by the FcR. Letters identify the reference in which the data was cited. C is Shields et al., 2001, J. Biol. Chem. 276: 6591-6604; D is Jefferis et al., 1995, Immunol. Lett. 44: 111-7; E is Hinton et al; 2004, J. Biol. Chem. 279(8): 6213-6; F is Idusogie et al., 2000, J. Immunol. 164: 4178-4184; each of which is incorporated herein by reference in its entirety.

In another preferred embodiment, the invention encompasses a molecule comprising a variant Fc region, wherein said variant Fc region comprises at least one amino acid modification relative to a wild-type Fc region, such that said molecule binds an FcγR via the Fc region with an altered affinity relative to a molecule comprising a wild-type Fc region, provided that said variant Fc region does not have or is not solely a substitution at any of positions 255, 256, 258, 267, 268, 269, 270, 272, 276, 278, 280, 283, 285, 286, 289, 290, 292, 293, 294, 295, 296, 298, 300, 301, 303, 305, 307, 309, 312, 320, 322, 326, 329, 330, 332, 331, 333, 334, 335, 337, 338, 339, 340, 359, 360, 373, 376, 416, 419, 430, 434, 435, 437, 438, 439. In a specific embodiment, the invention encompasses a molecule comprising a variant Fc region, wherein said variant Fc region comprises at least one amino acid modification relative to a wild-type Fc region, such that said molecule binds an FcγR via the Fc region with an altered affinity relative to a molecule comprising a wild-type Fc region, provided that said variant Fc region does not have or is not solely a substitution at any of positions 255, 258, 267, 269, 270, 276, 278, 280, 283, 285, 289, 292, 293, 294, 295, 296, 300, 303, 305, 307, 309, 322, 329, 332, 331, 337, 338, 340, 373, 376, 416, 419, 434, 435, 437, 438, 439 and does not have an alanine at any of positions 256, 290, 298, 312, 333, 334, 359, 360 326, or 430; a lysine at position 330; a threonine at position 339; a methionine at position 320; a serine at position 326; an asparagine at position 326; an aspartic acid at position 326; a glutamic acid at position 326; a glutamine at position 334; a glutamic acid at position 334; a methionine at position 334; a histidine at position 334; a valine at position 334; or a leucine at position 334; a lysine at position 335 an asparagine at position 268; a glutamine at position 272; a glutamine, serine, or aspartic acid at position 286; a serine at position 290; a methionine, glutamine, glutamic acid, or arginine at position 320; a glutamic acid at position 322; a serine, glutamic acid, or aspartic acid at position 326; a lysine at position 330; a glutamine at position 335; or a methionine at position 301.

In a specific embodiment, the invention encompasses a molecule comprising a variant Fc region, wherein said variant Fc region does not have or is not solely a substitution at any of positions 268, 269, 270, 272, 276, 278, 283, 285, 286, 289, 292, 293, 301, 303, 305, 307, 309, 331, 333, 334, 335, 337, 338, 340, 360, 373, 376, 416, 419, 430, 434, 435, 437, 438 or 439 and does not have a histidine, glutamine, or tyrosine at position 280; a serine, glycine, threonine or tyrosine at position 290, a leucine or isoleucine at position 300; an asparagine at position 294, a proline at position 296; a proline, asparagine, aspartic acid, or valine at position 298; a lysine at position 295. In yet another preferred embodiment, the invention encompasses a molecule comprising a variant Fc region, wherein said variant Fc region comprises at least one amino acid modification relative to a wild-type Fc region, such that said molecule binds an FcγR via the Fc region with a reduced affinity relative to a molecule comprising a wild-type Fc region provided that said variant Fc region does not have or is not solely a substitution at any of positions 252, 254, 265, 268, 269, 270, 278, 289, 292, 293, 294, 295, 296, 298, 300, 301, 303, 322, 324, 327, 329, 333, 335, 338, 340, 373, 376, 382, 388, 389, 414, 416, 419, 434, 435, 437, 438, or 439. In yet another preferred embodiment, the invention encompasses a molecule comprising a variant Fc region, wherein said variant Fc region comprises at least one amino acid modification relative to a wild-type Fc region, such that said molecule binds an FcγR via the Fc region with an enhanced affinity relative to a molecule comprising a wild-type Fc region provided that said variant Fc region does not have or is not solely a substitution at any of positions 280, 283, 285, 286, 290, 294, 295, 298, 300, 301, 305, 307, 309, 312, 315, 331, 333, 334, 337, 340, 360, 378, 398, or 430.

In a specific embodiment, the invention encompasses a molecule comprising a variant Fc region, wherein said variant Fc region does not include or are not solely a substitution at any of positions 330, 243, 247, 298, 241, 240, 244, 263, 262, 235, 269, or 328 and does not have a leucine at position 243, an asparagine at position 298, a leucine at position 241, and isoleucine or an alanine at position 240, a histidine at position 244, a valine at position 330, or an isoleucine at position 328.

In most preferred embodiments, the molecules of the invention with altered affinities for activating and/or inhibitory receptors having variant Fc regions, have one or more amino acid modifications, wherein said one or more amino acid modification is a substitution at position 288 with asparagine, at position 330 with serine and at position 396 with leucine (MgFc10)(See Tables 4 & 5); or a substitution at position 334 with glutamic acid, at position 359 with asparagine, and at position 366 with serine (MgFc13); or a substitution at position 316 with aspartic acid, at position 378 with valine, and at position 399 with glutamic acid (MgFc27); or a substitution at position 392 with threonine, and at position 396 with leucine (MgFc38); or a substitution at position 221 with glutamic acid, at position 270 with glutamic acid, at position 308 with alanine, at position 311 with histidine, at position 396 with leucine, and at position 402 with aspartic acid (MgFc42); or a substitution at position 240 with alanine, and at position 396 with leucine (MgFc52); or a substitution at position 410 with histidine, and at position 396 with leucine (MgFc53); or a substitution at position 243 with leucine, at position 305 with isoleucine, at position 378 with aspartic acid, at position 404 with serine, and at position 396 with leucine (MgFc54); or a substitution at position 255 with isoleucine, and at position 396 with leucine (MgFc55); or a substitution at position 370 with glutamic acid and at position 396 with leucine (MgFc59); or a substitution at position 243 with leucine, at position 292 with proline, at position 300 with leucine, at position 305 with isoleucine, and at position 396 with leucine (MgFc88); or a substitution at position 243 with leucine, at position 292 with proline, at position 300 with leucine, and at position 396 with leucine (MgFc88A); or a substitution at position 234 with leucine, at position 292 with proline, and at position 300 with leucine (MgFc155); or a substitution at position 243 with leucine, at position 292 with proline, and at position 300 with leucine; or a substitution at position 243 with leucine, at position 292 with proline, and at position 396 with leucine; or a substitution at position 243 with leucine, and at position 292 with proline; or a substitution at position 243 with leucine; or a substitution at position 273 with phenylalanine; or a substitution at position 247 with leucine, at position 270 with glutamic acid, and at position 421 with lysine.

In one specific embodiment, the invention encompasses a molecule comprising a variant Fc region wherein said variant Fc region comprises a substitution at position 396 with leucine, at position 270 with glutamic acid and at position 243 with leucine. In another specific embodiment the molecule further comprises one or more amino acid modification such as those disclosed herein.

In some embodiments, the invention encompasses molecules comprising a variant Fc region having an amino acid modification at one or more of the following positions: 119, 125, 132, 133, 141, 142, 147, 149, 162, 166, 185, 192, 202, 205, 210, 214, 217, 219, 215, 216, 217, 218, 219, 221, 222, 223, 224, 225, 227, 288, 229, 231, 232, 233, 235, 240, 241, 242, 243, 244, 246, 247, 248, 250, 251, 252, 253, 254, 255, 256, 258, 261, 262, 263, 268, 269, 270, 272, 273, 274, 275, 276, 279, 280, 281, 282, 284, 287, 288, 289, 290, 291, 292, 293, 295, 298, 300, 301, 303, 304, 305, 306, 307, 308, 309, 310, 311, 312, 313, 315, 316, 317, 318, 319, 320, 323, 326, 327, 328, 330, 333, 334, 335, 337, 339, 340, 343, 344, 345, 347, 348, 352, 353, 354, 355, 358, 359, 360, 361, 362, 365, 366, 367, 369, 370, 371, 372, 375, 377, 378, 379, 380, 381, 382, 383, 384, 385, 386, 387, 388, 389, 390, 392, 393, 394, 395, 396, 397, 398, 399, 400, 401, 402, 404, 406, 407, 408, 409, 410, 411, 412, 414, 415, 416417, 419, 420, 421, 422, 423, 424, 427, 428, 431, 433, 435, 436, 438, 440, 441, 442, 443, 446, 447. Preferably such mutations result in molecules that have an altered affinity for an FcγR and/or have an altered effector cell mediated function as determined using methods disclosed and exemplified herein and known to one skilled in the art.

The invention encompasses molecules comprising variant Fc regions consisting of or comprising any of the mutations listed in the table below in Table 4.

TABLE 4

EXEMPLARY MUTATIONS

SINGLE SITE MUTANTS

| | | | |
|---|---|---|---|
| S132I | D270E | K334E | V379L |
| A162V | F275Y | K334I | V379M |
| S219Y | V282M | K334N | K392R |
| K222N | K288N | M352L | P396L |
| H224L | R292L | T359N | P396H |
| T225S | R292G | K326E | L398V |
| E233G | R292P | T366N | D401V |
| F243L | S298N | T366S | S400P |
| P247L | N315I | F372Y | S407I |
| K248M | E318K | I377F | K414N |
| V273F | A330S | I377N | |

DOUBLE SITE MUTANTS

| | | | |
|---|---|---|---|
| K210M, P396L | P247L, L398Q | K288N, A330S | Q347H, A339V |
| P217S, P396L | P247L, L406F | K290E, L142P | L358P, P396L |
| P227S, K290E | P247L, N421K | K290T, G371D | K370E, P396L |
| P227S, P396L | P247S, P396L | P291S, P353Q | K370N, S440N |
| P232S, S304G | T250A, P396L | R292L. K334E | S375C, P396L |
| E233D, K334E | L251F, F372L | S298N, W381R | V379M, P396L |
| V240I, V281M | R255L, E318K | S298N, S407R | N384K, P396L |
| V240A, P396L | R255L, P396L | V303I, P396L | K392T, P396L |
| F241L, E258G | R255Q, K326E | V305L, P396L | T394M. V397M |
| L242F, P396L | E258D, N384K | K317N, F423Δ | D399E, G402D |
| F243L, R292P | E258D, P396L | K320E, K326E | D399E, M428L |
| F243L, E318K | V263Q, E272D | V323I, P396L | S400F, P396L |
| F243I, V379L | H268D, E318D | K326E, A330T | K409R, S166N |
| F243L, P396L | H268D, P396L | K326E, G385E | L410H, P396L |
| P244H, P396L | H268N, P396L | K326I, P396L | Q419H, P396L |
| K246T, Y319F | V279L, P395S | K334E, E380D | Q419L, P396L |
| K246I, K334N | V284A, F372L | A330V, Q419H | V427A, P396L |
| K246T, P396H | G285E, P247H | K334E, E308D | |
| P247L, I377F | K288M, K334E | E233D, K334A | |
| P247L, E389G | K288N, K326N | K334N, P396L | |

Δ = Deletion

In yet other embodiments, the invention encompasses molecules comprising variant Fc regions having more than two amino acid modifications. A non-limiting example of such variants is listed in the table below (Table 5). The invention encompasses mutations listed in Table 5 which further comprise one or more amino acid modifications such as those disclosed herein.

TABLE 5

EXEMPLARY COMBINATION VARIANTS

V125L, V215I, S408I
K133M, F149Y, K205E, R214I, K218E, T256N, V262L, S383N, N384K
A141V, H268L, K288E, P291S
K147T, Y202M, F275I, K334N, V348M
V185M, R292L, D399E
S192T, M252L, R301C
K210M, K261N, P396L
K210N, K222I, K320M, P396L
T215P, K274N, A287G, K334N, L365V, P396L
V215I, K290V, P396L
E216D, K334R, S375I
E216D, E345K, S375I
P217S, V305I, I309L, N390H, P396L
P217A, T359A, P396L
P217S, A378V, S408R
K218R, G281D, G385R
S219T, T225K, D270E
S219T, T225K, D270E, K360R
D221Y, M252I, A330G, A339T, T359N, V422I, H433L
D221E, D270E, V308A, Q311H, P396L, G402D
K222E, V263Q, S298N
K222N, T335N, K370E, A378V, T394M
T223I, T256S, L406F
C229Y, A287T, V379M, P396L, L443V
A231V, Q386H, V412M
E233G, P247S, L306P

TABLE 5-continued

EXEMPLARY COMBINATION VARIANTS

L235P, S304G, V305I, V323I, V382M
V240A, D270E, P396L
F243L, S254T, A330V, N361D
F243L, R255L, E318K
F243L, R292P, Y300L
F243L, R292P, Y300L, P396L
F243L, R292P, Y300L, V305I, P396L
F243L, R292P, V305I
F243L, R292P, V305I, P396L
F243L, R292P, V305L
F243L, R292P, P396L
F243L, Y300L, V305I, P396L
F243L, V305I, A378D, P396L, F404S
F243I, V379L, G420V
P244A, K326I, C367R, S375I, K447T
P244H, L358M, V379M, N384K, V397M
K246E, V284M, V308A
K246I, Q362H, K370E
K246N, P396L, Q419R
P247L, D270E, N421K
P247L, A330T, S440G
P247H, G385E
P247L, I253N, K334N
P247L, W313R, E388G
P247L, A431V, S442F
R255L, D270E, P396L
T256S, V305I, K334E, N390S
E258D, T289A, H310Y, Y407V
V263Q, E272D, Q419H
E269K, K290N, Q311R, H433Y
D270E, G316D, R416G
D270E, K370E, P396L
D270E, K392T, P396L
D270E, P396L, Q419H
V273I, K326E, L328I, P396L
F275I, K334N, V348M
F275L, Q362H, N384K, P396L
N276Y, T393N, W417R
D280E, S354F, A431D, L441I
V282L, A330V, H433Y, T436R
V282E, V369I, L406F
V284M, R292L, K370N
V284M, S298N, K334E, R355W
V284M, S298N, K334E, R355W, R416T
K288R, T307A, K344E, P396L
K288N, A330S, P396L
K290E, V369A, T393A, P396L
K290T, N390I, P396L
R292P, V305I, P396L
R292P, V305I
R292L, T359N, P396L
E293V, Q295E, A327T
R301H, K340E, D399E
V303I, V369F, M428L
D312E, K327N, I378S
N315I, V379M, T394M
G316D, A378V, D399E
Y319F, P352L, P396L
K326Q, K334E, T359N, T366S
K326I, S408N, P396L
A330V, G427M, K438R
A330V, H433Q, V427M
K334E, T359N, T366S
K334E, T359N, T366S, Q386R
K334E, E380D, G446V
T335N, P387S, H435Q
P343S, P353L, S375I, S383N
T335N, K370E, A378V, T394M, S424L
T355N, P387S, H435Q
A378V, N390I, V422I
V397M, T411A, S415N

In some embodiments, the molecules, preferably the immunoglobulins of the invention further comprise one or more glycosylation sites, so that one or more carbohydrate moieties are covalently attached to the molecule. Preferably, the antibodies of the invention with one or more glycosylation sites and/or one or more modifications in the Fc region have an enhanced antibody mediated effector function, e.g., enhanced ADCC activity. In some embodiments, the invention further comprises antibodies comprising one or more modifications of amino acids that are directly or indirectly known to interact with a carbohydrate moiety of the antibody, including but not limited to amino acids at positions 241, 243, 244, 245, 245, 249, 256, 258, 260, 262, 264, 265, 296, 299, and 301. Amino acids that directly or indirectly interact with a carbohydrate moiety of an antibody are known in the art, see, e.g., Jefferis et al., 1995 *Immunology Letters*, 44: 111-7, which is incorporated herein by reference in its entirety.

The invention encompasses antibodies that have been modified by introducing one or more glycosylation sites into one or more sites of the antibodies, preferably without altering the functionality of the antibody, e.g., binding activity to FcγR. Glycosylation sites may be introduced into the variable and/or constant region of the antibodies of the invention. As used herein, "glycosylation sites" include any specific amino acid sequence in an antibody to which an oligosaccharide (i.e., carbohydrates containing two or more simple sugars linked together) will specifically and covalently attach. Oligosaccharide side chains are typically linked to the backbone of an antibody via either N- or O-linkages. N-linked glycosylation refers to the attachment of an oligosaccharide moiety to the side chain of an asparagine residue. O-linked glycosylation refers to the attachment of an oligosaccharide moiety to a hydroxyamino acid, e.g., serine, threonine. The antibodies of the invention may comprise one or more glycosylation sites, including N-linked and O-linked glycosylation sites. Any glycosylation site for N-linked or O-linked glycosylation known in the art may be used in accordance with the instant invention. An exemplary N-linked glycosylation site that is useful in accordance with the methods of the present invention, is the amino acid sequence: Asn-X-Thr/Ser, wherein X may be any amino acid and Thr/Ser indicates a threonine or a serine. Such a site or sites may be introduced into an antibody of the invention using methods well known in the art to which this invention pertains. See, for example, "*In Vitro Mutagenesis,*" *Recombinant DNA: A Short Course*, J. D. Watson, et al. W. H. Freeman and Company, New York, 1983, chapter 8, pp. 106-116, which is incorporated herein by reference in its entirety. An exemplary method for introducing a glycosylation site into an antibody of the invention may comprise: modifying or mutating an amino acid sequence of the antibody so that the desired Asn-X-Thr/Ser sequence is obtained.

In some embodiments, the invention encompasses methods of modifying the carbohydrate content of an antibody of the invention by adding or deleting a glycosylation site. Methods for modifying the carbohydrate content of antibodies are well known in the art and encompassed within the invention, see, e.g., U.S. Pat. No. 6,218,149; EP 0 359 096 B1; U.S. Publication No. US 2002/0028486; WO 03/035835; U.S. Publication No. 2003/0115614; U.S. Pat. Nos. 6,218,149; 6,472,511; all of which are incorporated herein by reference in their entirety. In other embodiments, the invention encompasses methods of modifying the carbohydrate content of an antibody of the invention by deleting one or more endogenous carbohydrate moieties of the antibody. In a specific embodiment, the invention encompasses shifting the glycosylation site of the Fc region of an antibody, by modifying position 297 (e.g., from asparagine to a residue without an available amine group, e.g., glutamine) and/or positions adjacent to 297. In a specific embodiment, the invention encompasses modifying position 296 so that position 296 and not position 297 is glycosylated.

7.1 Polypeptides and Antibodies with Variant Fc Regions

It will be appreciated by one skilled in the art that aside from amino acid substitutions, the present invention contemplates other modifications of the Fc region amino acid sequence in order to generate an Fc region variant with one or more altered properties, e.g., altered effector function. The invention contemplates deletion of one or more amino acid residues of the Fc region in order to reduce binding to an FcγR. Preferably, no more than 5, no more than 10, no more than 20, no more than 30, no more than 50 Fc region residues will be deleted according to this embodiment of the invention. The Fc region herein comprising one or more amino acid deletions will preferably retain at least about 80%, and preferably at least about 90%, and most preferably at least about 95%, of the wild type Fc region. In some embodiments, one or more properties of the molecules are maintained such as for example, non-immunogenicity, FcγRIIIA binding, FcγRIIA binding, or a combination of these properties.

In alternate embodiments, the invention encompasses amino acid insertion to generate the Fc region variants, which variants have altered properties including altered effector function. In one specific embodiment, the invention encompasses introducing at least one amino acid residue, for example one to two amino acid residues and preferably no more than 10 amino acid residues adjacent to one or more of the Fc region positions identified herein. In alternate embodiments, the invention further encompasses introducing at least one amino acid residue, for example one to two amino acid residues and preferably no more than 10 amino acid residues adjacent to one or more of the Fc region positions known in the art as impacting FcγR interaction and/or binding.

The invention further encompasses incorporation of unnatural amino acids to generate the Fc variants of the invention. Such methods are known to those skilled in the art such as those using the natural biosynthetic machinery to allow incorporation of unnatural amino acids into proteins, see, e.g., Wang et al., 2002 Chem. Comm. 1: 1-11; Wang et al., 2001, Science, 292: 498-500; van Hest et al., 2001. Chem. Comm. 19: 1897-1904, each of which is incorporated herein by reference in its entirety. Alternative strategies focus on the enzymes responsible for the biosynthesis of amino acyl-tRNA, see, e.g., Tang et al., 2001, J. Am. Chem. 123(44): 11089-11090; Kiick et al., 2001, FEBS Lett. 505 (3): 465; each of which is incorporated herein by reference in its entirety.

The affinities and binding properties of the Fc variants, or fragments thereof, of use in the invention are initially determined using a yeast-display system, preferably combined with in vitro assays (biochemical or immunological based assays) known in the art for determining Fc-FcγR interactions, i.e., specific binding of an Fc region to an FcγR including but not limited to ELISA assay, surface plasmon resonance assay, immunoprecipitation assays (See Section 6.2.1). In certain embodiments, candidate Fc variants identified using the yeast display system are further incorporated into an antibody or fragment thereof for testing in said in vitro assay. Preferably, the binding properties of the molecules of the invention are also characterized by in vitro functional assays for determining one or more FcγR mediator effector cell functions (See Section 6.2.5). Such methods have previously been disclosed by the inventors, see, e.g., U.S Patent Application Publications 2005/0037000 and 2005/0064514, and International Patent Application Publication WO 04/063351, each of which is hereby incorporated by reference in its entirety, and have been used to identify and characterize novel Fc mutations based on binding characteristics to FcγRIIIA and FcγRIIB, see, e.g., Table 6.

TABLE 6

Fc MUTATIONS IDENTIFIED USING YEAST DISPLAY AND ELISA ASSAY

| Clone # | Mutation sites | Domain | IIIA binding | IIB binding |
|---|---|---|---|---|
| 4 | A339V, Q347H | CH2, CH3 | + | + |
| 5 | L251P, S415I | CH2, CH3 | + | + |
| 8 | V185M, K218N, R292L, D399E | CH1, hinge, CH2, CH3 | no change | − |
| 12 | K290E, L142P | CH1, CH2 | + | not tested |
| 16 | A141V, H268L, K288E, P291S | CH1, CH2 | − | not tested |
| 19 | L133M, P150Y, K205E, S383N, N384K | CH1, CH2, CH3 | − | not tested |
| 21 | P396L | CH3 | • | •+ |
| 25 | P396H | CH3 | ••• | •• |
| 6 | K392R | CH3 | no change | no change |
| 15 | R301C, M252L, S192T | CH1, CH2 | − | not tested |
| 17 | N315I | CH2 | no change | not tested |
| 18 | S132I | CH1 | no change | not tested |
| 26 | A162V | CH1 | no change | not tested |
| 27 | V348M, K334N, F275I, Y202M, K147T | CH1, Ch2 | + | + |
| 29 | H310Y, T289A, G337E | CH2 | − | not tested |
| 30 | S119F, G371S, Y407N, E258D | CH1, CH2, CH3 | + | no change |
| 31 | K409R, S166N | CH1, CH3 | no change | not tested |
| 20 | S408I, V215I, V125I | CH1, Hinge, CH3 | + | no change |
| 24 | G385E, P247H | CH2, CH3 | ••• | + |
| 16 | V379M | CH3 | •• | no change |
| 17 | S219Y | Hinge | • | − |
| 18 | V282M | CH2 | • | − |
| 31 | F275I, K334N, V348M | CH2 | + | no change |
| 35 | D401V | CH3 | + | no change |
| 37 | V280L, P395S | CH2 | + | − |
| 40 | K222N | Hinge | • | no change |
| 41 | K246T, Y319F | CH2 | • | no change |
| 42 | F243I, V379L | CH2, CH3 | •+ | − |
| 43 | K334E | CH2 | •+ | − |
| 44 | K246T, P396H | CH2, CH3 | • | ••+ |
| 45 | H268D, E318D | CH2 | •+ | ••••• |
| 49 | K288N, A3305, P396L | CH2, CH3 | ••••• | ••• |
| 50 | F243L, R255L, E318K | CH2 | • | − |
| 53 | K334E, T359N, T3665 | CH2, CH3 | • | no change |
| 54 | I377F | CH3 | •+ | + |
| 57 | K334I | CH2 | • | no change |
| 58 | P244H, L358M, V379M, N384K, V397M | CH2, CH3 | •+ | •+ |
| 59 | K334E, T359N, T366S (independent isolate) | CH2, CH3 | •+ | no change |
| 61 | I377F (independent isolate) | CH3 | ••• | ••+ |
| 62 | P247L | CH2 | •• | ••+ |
| 64 | P217S, A378V, S408R | Hinge, CH3 | •• | •••••+ |
| 65 | P247L, I253N, K334N | CH2 | ••• | ••+ |
| 66 | K288M, K334E | CH2 | ••• | − |
| 67 | K334E, E380D | CH2, CH3 | •+ | − |
| 68 | P247L (independent isolate) | CH2 | + | •••• |
| 69 | T256S, V305I, K334E, N390S | CH2, CH3 | •+ | no change |
| 70 | K326E | CH2 | •+ | ••+ |
| 71 | F372Y | CH3 | + | •••••+ |
| 72 | K326E (independent isolate) | CH2 | + | •• |
| 74 | K334E, T359N, T366S (independent isolate) | CH2, CH3 | •• | no change |
| 75 | K334E (independent isolate) | CH2 | •••+ | no change |
| 76 | P396L (independent isolate) | CH3 | •+ | no change |
| 78 | K326E (independent isolate) | CH2 | •• | •••+ |
| 79 | K246I, K334N | CH2 | • | •••• |
| 80 | K334E (independent isolate) | CH2 | • | no change |
| 81 | T335N, K370E, A378, T394M, S424L | CH2, CH3 | • | no change |
| 82 | K320E, K326E | CH2 | • | • |

TABLE 6-continued

Fc MUTATIONS IDENTIFIED USING YEAST DISPLAY AND ELISA ASSAY

| Clone # | Mutation sites | Domain | IIIA binding | IIB binding |
|---|---|---|---|---|
| 84 | H224L | Hinge | • | ••••• |
| 87 | S375C, P396L | CH3 | •+ | ••••+ |
| 89 | E233D, K334E | CH2 | •+ | no change |
| 91 | K334E (independent isolate) | CH2 | • | no change |
| 92 | K334E (independent isolate) | CH2 | • | no change |
| 94 | K334E, T359N, T366S, Q386R | CH2 | • | no change | relative to comparable molecule with wild-type Fc region, • = 1-fold increase in affinity; + = up to 50% increase in affinity; and − = 1-fold decrease in affinity In most preferred embodiments, the molecules of the invention have similar binding properties in in vivo models (such as those disclosed herein and/or known in the art) as those in in vitro based assays. However, the present invention does not exclude molecules of the invention that do not exhibit the desired phenotype in in vitro based assays but do exhibit the desired phenotype in vivo. A representative flow chart of the screening and characterization of molecules of the invention is described in FIG. 1.

The invention encompasses molecules comprising a variant Fc region that binds with a greater affinity to one or more FcγRs. Such molecules preferably mediate effector function more effectively as discussed infra. In other embodiments, the invention encompasses molecules comprising a variant Fc region that bind with a weaker affinity to one or more FcγRs. Reduction or elimination of effector function is desirable in certain cases for example in the case of antibodies whose mechanism of action involves blocking or antagonism but not killing of the cells bearing a target antigen. Reduction or elimination of effector function would be desirable in cases of autoimmune disease where one would block FcγR activating receptors in effector cells (This type of function would be present in the host cells). In general increased effector function would be directed to tumor and foreign cells.

The Fc variants of the present invention may be combined with other Fc modifications, including but not limited to modifications that alter effector function. The invention encompasses combining an Fc variant of the invention with other Fc modifications to provide additive, synergistic, or novel properties in antibodies or Fc fusions. Preferably the Fc variants of the invention enhance the phenotype of the modification with which they are combined. For example, if an Fc variant of the invention is combined with a mutant known to bind FcγRIIIA with a higher affinity than a comparable molecule comprising a wild type Fc region; the combination with a mutant of the invention results in a greater fold enhancement in FcγRIIIA affinity.

In one embodiment, the Fc variants of the present invention may be combined with other known Fc variants such as those disclosed in Duncan et al, 1988, Nature 332:563-564; Lund et al., 1991, J. Immunol 147:2657-2662; Lund et al, 1992, Mol Immunol 29:53-59; Alegre et al, 1994, Transplantation 57:1537-1543; Hutchins et al; 1995, Proc Natl. Acad Sci USA 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:49634969; Armour et aL, 1999, Eur J Immunol 29:2613-2624; Idusogie et al, 2000, J Immunol 164:41784184; Reddy et al, 2000, J Immunol 164:1925-1933; Xu et al., 2000, Cell Immunol 200:16-26; Idusogie et al, 2001, J Immunol 166:2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. Nos. 5,624,821; 5,885,573; 6,194,551; PCT WO 00/42072; PCT WO 99/58572; each of which is incorporated herein by reference in its entirety.

In some embodiments, the Fc variants of the present invention are incorporated into an antibody or Fc fusion that comprises one or more engineered glycoforms, i.e., a carbohydrate composition that is covalently attached to a molecule comprising an Fc region, wherein said carbohydrate composition differs chemically from that of a parent molecule comprising an Fc region. Engineered glycoforms may be useful for a variety of purposes, including but not limited to enhancing or reducing effector function. Engineered glycoforms may be generated by any method known to one skilled in the art, for example by using engineered or variant expression strains, by co-expression with one or more enzymes, for example DI N-acetylglucosaminyltransferase III (GnTI11), by expressing a molecule comprising an Fc region in various organisms or cell lines from various organisms, or by modifying carbohydrate(s) after the molecule comprising Fc region has been expressed. Methods for generating engineered glycoforms are known in the art, and include but are not limited to those described in Umana et al, 1999, Nat. Biotechnol 17:176-180; Davies et al., 20017 Biotechnol Bioeng 74:288-294; Shields et al, 2002, J Biol Chem 277:26733-26740; Shinkawa et aL, 2003, J Biol Chem 278:3466-3473) U.S. Pat. No. 6,602,684; U.S. Ser. No. 10/277,370; U.S. Ser. No. 10/113,929; PCT WO 00/61739A1; PCT WO 01/292246A1; PCT WO 02/311140A1; PCT WO 02/30954A1; Potillegent™ technology (Biowa, Inc. Princeton, N.J.); GlycoMAb™ glycosylation engineering technology (GLYCART biotechnology AG, Zurich, Switzerland); each of which is incorporated herein by reference in its entirety. See, e.g., WO 00061739; EA01229125; US 20030115614; Okazaki et al., 2004, JMB, 336: 1239-49 each of which is incorporated herein by reference in its entirety.

The Fc variants of the present invention may be optimized for a variety of properties. Properties that may be optimized include but are not limited to enhanced or reduced affinity for an FcγR, enhanced or reduced effector function. In a preferred embodiment, the Fc variants of the present invention are optimized to possess enhanced affinity for a human activating FcγR, preferably FcγR, FcγRIIA, FcγRIIc, FcγRIIIA, and FcγRIIIB, most preferably FcγRIIIA. In an alternate preferred embodiment, the Fc variants are optimized to possess reduced affinity for the human inhibitory receptor FcγRIIB. These preferred embodiments are anticipated to provide antibodies and Fc fusions with enhanced therapeutic properties in humans, for example enhanced effector function and greater anti-cancer potency as described and exemplified herein. These preferred embodiments are anticipated to provide antibodies and Fc fusions with enhanced tumor elimination in mouse xenograft tumor models.

In an alternate embodiment the Fc variants of the present invention are optimized to have reduced affinity for a human FcγR, including but not limited to FcγRI, FcγRIIA, FcγRIIB, FcγRIIc, FcγRIIIA, and FcγRIIIB. These embodiments are anticipated to provide antibodies and Fc fusions with enhanced therapeutic properties in humans, for example reduced effector function and reduced toxicity.

In alternate embodiments the Fc variants of the present invention possess enhanced or reduced affinity for FcγRs from non-human organisms, including but not limited to mice, rats, rabbits, and monkeys. Fc variants that are optimized for binding to a non-human FcγR may find use in experimentation. For example, mouse models are available for a variety of diseases that enable testing of properties such as efficacy, toxicity, and pharmacokinetics for a given drug candidate. As is known in the art, cancer cells can be grafted or injected into mice to mimic a human cancer, a process referred to as xenografting. Testing of antibodies or Fc fusions that comprise Fc variants that are optimized for one or more mouse FcγRs, may provide valuable information with regard to the efficacy of the antibody or Fc fusion, its mechanism of action, and the like. In certain embodiments, molecules of the invention comprising a variant human Fc region are tested in transgenic mice expressing one or more human Fcγ receptors (e.g., FcγRIIIA, FcγRIIA, FcγRIIB).

While it is preferred to alter binding to an FcγR, the instant invention further contemplates Fc variants with altered binding affinity to the neonatal receptor (FcRn). Although not intending to be bound by a particular mechanism of action, Fc region variants with improved affinity for FcRn are anticipated to have longer serum half-lives, and such molecules will have useful applications in methods of treating mammals where long half-life of the administered polypeptide is desired, e.g., to treat a chronic disease or disorder. Although not intending to be bound by a particular mechanism of action, Fc region variants with decreased FcRn binding affinity, on the contrary, are expected to have shorter half-lives, and such molecules may, for example, be administered to a mammal where a shortened circulation time may be advantageous, e.g., for in vivo diagnostic imaging or for polypeptides which have toxic side effects when left circulating in the blood stream for extended periods. Fc region variants with decreased FcRn binding affinity are anticipated to be less likely to cross the placenta, and thus may be utilized in the treatment of diseases or disorders in pregnant women.

In other embodiments, these variants may be combined with other known Fc modifications with altered FcRn affinity such as those disclosed in International Publication Nos. WO 98/23289; and WO 97/34631; and U.S. Pat. No. 6,277,375, each of which is incorporated herein by reference in its entirety.

The invention encompasses any other method known in the art for generating antibodies having an increased half-life in vivo, for example, by introducing one or more amino acid modifications (i.e., substitutions, insertions or deletions) into an IgG constant domain, or FcRn binding fragment thereof (preferably a Fc or hinge-Fc domain fragment). See, e.g., International Publication Nos. WO 98/23289; and WO 97/34631; and U.S. Pat. No. 6,277,375, each of which is incorporated herein by reference in its entirety to be used in combination with the Fc variants of the invention. Further, antibodies of the invention can be conjugated to albumin in order to make the antibody or antibody fragment more stable in vivo or have a longer half-life in vivo. The techniques well-known in the art, see, e.g., International Publication Nos. WO 93/15199, WO 93/15200, and WO 01/77137, and European Patent No. EP 413,622, all of which are incorporated herein by reference in their entirety.

The variant(s) described herein may be subjected to further modifications, often times depending on the intended use of the variant. Such modifications may involve further alteration of the amino acid sequence (substitution, insertion and/or deletion of amino acid residues), fusion to heterologous polypeptide(s) and/or covalent modifications. Such further modifications may be made prior to, simultaneously with, or following, the amino acid modification(s) disclosed herein which results in altered properties such as an alteration of Fc receptor binding and/or ADCC activity.

Alternatively or additionally, the invention encompasses combining the amino acid modifications disclosed herein with one or more further amino acid modifications that alter C1q binding and/or complement dependent cytotoxicity function of the Fc region as determined in vitro and/or in vivo. Preferably, the starting molecule of particular interest herein is usually one that binds to C1q and displays complement dependent cytotoxicity (CDC). The further amino acid substitutions described herein will generally serve to alter the ability of the starting molecule to bind to C1q and/or modify its complement dependent cytotoxicity function, e.g., to reduce and preferably abolish these effector functions. In other embodiments molecules comprising substitutions at one or more of the described positions with improved C1q binding and/or complement dependent cytotoxicity (CDC) function are contemplated herein. For example, the starting molecule may be unable to bind C1q and/or mediate CDC and may be modified according to the teachings herein such that it acquires these further effector functions. Moreover, molecules with preexisting C1q binding activity, optionally further having the ability to mediate CDC may be modified such that one or both of these activities are altered, e.g., enhanced. In some embodiments, the invention encompasses variant Fc regions with altered CDC activity without any alteration in C1q binding. In yet other embodiments, the invention encompasses variant Fc regions with altered CDC activity and altered C1q binding.

To generate an Fc region with altered C1q binding and/or complement dependent cytotoxicity (CDC) function, the amino acid positions to be modified are generally selected from positions 270, 322, 326, 327, 329, 331, 333, and 334, where the numbering of the residues in an IgG heavy chain is that of the EU index as in Kabat et al., Sequences of Proteins of Immunological Interest, 5th Ed. Public Health Service, National Institutes of Health, Bethesda, Md. (199). These amino acid modifications may be combined with one or more Fc modifications disclosed herein to provide a synergistic or additive effect on C1q binding and/or CDC activity. In other embodiments, the invention encompasses Fc variants with altered C1q binding and/or complement dependent cytotoxicity (CDC) function comprising an amino acid substitution at position 396 with leucine and at position 255 with leucine; or an amino acid substitution at position 396 with leucine and at position 419 with histidine; an amino acid substitution at position 396 with leucine and at position 370 with glutamic acid; an amino acid substitution at position 396 with leucine and at position 240 with alanine; an amino acid substitution at position 396 with leucine and at position 392 with threonine; an amino acid substitution at position 247 with leucine and at position 421 with lysine. The invention encompasses any known modification of the Fc region which alters C1q binding and/or complement dependent cytotoxicity (CDC) function such as those disclosed in Idusogie et al., 2001, *J. Immunol.* 166(4) 2571-5; Idusogie et al., J Immunol. 2000 164(8): 4178-4184; each of which is incorporated herein by reference in its entirety.

As disclosed above, the invention encompasses an Fc region with altered effector function, e.g., modified C1q binding and/or FcR binding and thereby altered CDC activity and/or ADCC activity. In specific embodiments, the invention encompasses variant Fc regions with improved C1q binding and improved FcγRIII binding; e.g. having both improved ADCC activity and improved CDC activity. In alternative embodiments, the invention encompasses a variant Fc region with reduced CDC activity and/or reduced ADCC activity. In other embodiments, one may increase only one of these activities, and optionally also reduce the other activity, e.g. to generate an Fc region variant with improved ADCC activity, but reduced CDC activity and vice versa.

7.1.1 Mutants with Enhanced Altered Affinities for FcγRIIIA and/or FcγRIIA

The invention encompasses molecules comprising a variant Fc region, having one or more amino acid modifications (e.g., substitutions) in one or more regions, wherein such modifications alter the affinity of the variant Fc region for an activating FcγR. In some embodiments, molecules of the invention comprise a variant Fc region, having one or more amino acid modifications (e.g., substitutions) in one or more regions, which modifications increase the affinity of the variant Fc region for FcγRIIIA and/or FcγRIIA by at least 2-fold, relative to a comparable molecule comprising a wild-type Fc region. In another specific embodiment, molecules of the invention comprise a variant Fc region, having one or more amino acid modifications (e.g., substitutions) in one or more regions, which modifications increase the affinity of the variant Fc region for FcγRIIIA and/or FcγRIIA by greater than 2 fold, relative to a comparable molecule comprising a wild-type Fc region. In other embodiments of the invention the one or more amino acid modifications increase the affinity of the variant Fc region for FcγRIIIA and/or FcγRIIA by at least 3-fold, 4-fold, 5-fold, 6-fold, 8-fold, or 10-fold relative to a comparable molecule comprising a wild-type Fc region. In yet other embodiments of the invention the one or more amino acid modifications decrease the affinity of the variant Fc region for FcγRIIIA and/or FcγRIIA by at least 3-fold, 4-fold, 5-fold, 6-fold, 8-fold, or 10-fold relative to a comparable molecule comprising a wild-type Fc region. Such fold increases are preferably determined by an ELISA or surface plasmon resonance assays. In a specific embodiment, the one or more amino acid modifications do not include or are not solely a substitution at any one of positions 329, 331, or 322 with any amino acid. In certain embodiments, the one or more amino acid modifications do not include or are not solely a substitution with any one of alanine at positions 256, 290, 298, 312, 333, 334, 359, 360, or 430; with lysine at position 330; with threonine at position 339; with methionine at position 320; with serine, asparagine, aspartic acid, or glutamic acid at position 326 with glutamine, glutamic acid, methionine, histidine, valine, or leucine at position 334. In another specific embodiment, the one or more amino acid modifications do not include or are not solely a substitution at any of positions 280, 290, 300, 294, or 295. In another more specific embodiment, the one or more amino acid modifications do not include or are not solely a substitution at position 300 with leucine or isoleucine; at position 295 with lysine; at position 294 with asparagine; at position 298 with valine; aspartic acid proline, aspargine, or valine; at position 280 with histidine, glutamine or tyrosine; at position 290 with serine, glycine, threonine or tyrosine.

In another specific embodiment, the invention encompasses a molecule comprising a variant Fc region, wherein said variant Fc region comprises at least one amino acid modification relative to a wild-type Fc region, such that said polypeptide specifically binds FcγRIIA via it Fc region with a greater affinity than a comparable molecule comprising the wild-type Fc region binds FcγRIIA, provided that said variant Fc region does not have an alanine at any of positions 256, 290, 326, 255, 258, 267, 272, 276, 280, 283, 285, 286, 331, 337, 268, 272, or 430; an asparagine at position 268; a glutamine at position 272; a glutamine, serine, or aspartic acid at position 286; a serine at position 290; a methionine, glutamine, glutamic acid, or arginine at position 320; a glutamic acid at position 322; a serine, glutamic acid, or aspartic acid at position 326; a lysine at position 330; a glutamine at position 335; or a methionine at position 301. In a specific embodiment, molecules of the invention comprise a variant Fc region, having one or more amino acid modifications (e.g., substitutions) in one or more regions, which modifications increase the affinity of the variant Fc region for FcγRIIA by at least 2-fold, relative to a comparable molecule comprising a wild-type Fc region. In another specific embodiment, molecules of the invention comprise a variant Fc region, having one or more amino acid modifications (e.g., substitutions) in one or more regions, which modifications increase the affinity of the variant Fc region for FcγRIIA by greater than 2 fold, relative to a comparable molecule comprising a wild-type Fc region. In other embodiments of the invention the one or more amino acid modifications increase the affinity of the variant Fc region for FcγRIIA by at least 3-fold, 4-fold, 5-fold, 6-fold, 8-fold, or 10-fold relative to a comparable molecule comprising a wild-type Fc region In a specific embodiment, the invention encompasses molecules, preferably polypeptides, and more preferably immunoglobulins (e.g., antibodies), comprising a variant Fc region, having one or more amino acid modifications (e.g., substitutions but also include insertions or deletions), which modifications increase the affinity of the variant Fc region for FcγRIIIA and/or FcγRIIA by at least 65%, at least 70%, at least 75%, at least 85%, at least 90%, at least 95%, at least 99%, at least 100%, at least 150%, and at least 200%, relative to a comparable molecule comprising a wild-type Fc region.

In a specific embodiment, the one or more amino acid modifications which increase the affinity of the variant Fc region for one or more activating FcγRs comprise a substitution at position 347 with histidine, and at position 339 with valine; or a substitution at position 425 with isoleucine and at position 215 with phenylalanine; or a substitution at position 408 with isoleucine, at position 215 with isoleucine, and at position 125 with leucine; or a substitution at position 385 with glutamic acid and at position 247 with histidine; or a substitution at position 348 with methionine, at position 334 with asparagine, at position 275 with isoleucine, at position 202 with methionine, and at position 147 with threonine; or a substitution at position 275 with isoleucine, at position 334 with asparagine, and at position 348 with methionine; or a substitution at position 279 with leucine and at position 395 with serine; or a substitution at position 246 with threonine and at position 319 with phenylalanine; or a substitution at position 243 with isoleucine and at position 379 with leucine; or a substitution at position 243 with leucine, at position 255 with leucine and at position 318 with lysine; or a substitution at position 334 with glutamic acid, at position 359 with asparagine, and at position 366 with serine; or a substitution at position 288 with methionine and at position 334 with glutamic acid; or a substitution at position 334 with glutamic acid and at position 380 with aspartic acid; or a substitution at position 256 with serine, at position 305 with isoleucine, at position 334 with glutamic acid and at position 390 with serine; or a substitution at position 335 with asparagine, at position 370 with glutamic acid, at position 378 with valine, at position 394 with methionine, and at position 424 with leucine; or a substitution at position 233 with aspartic acid and at position 334 with glutamic acid; or a substitution at position 334 with glutamic acid, at position 359 with asparagine, at position 366 with serine, and at position 386 with arginine; or a substitution at position 246 with threonine and at position 396 with histidine; or a substitution at position 268 with aspartic acid and at position 318 with aspartic acid; or a substitution at position 288 with asparagine, at position 330 with serine, and at position 396 with leucine; or a substitution at position 244 with histidine, at position 358 with methionine, at position 379 with methionine, at position 384 with lysine and at position 397 with methionine; or a substitution at position 217 with serine, at position 378 with valine, and at position 408 with arginine; or a substitution at position 247 with leucine, at position 253 with asparagine, and at position 334 with asparagine; or a substitution at position 246 with isoleucine, and at position 334 with asparagine; or a substitution at position 320 with glutamic acid and at position 326 with glutamic acid; or a substitution at position 375 with cysteine and at position 396 with leucine; or a substitution at position 243 with leucine, at position 292 with proline, at position 300 with leucine, at position 305 with isoleucine, and at position 396 with leucine; or a substitution at position 243 with leucine, at position 292 with proline, at position 300 with leucine, and at position 396 with leucine; or a substitution at position 234 with leucine, at position 292 with proline, and at position 300 with leucine; or a substitution at position 234 with leucine, at position 292 with proline, and at position 396 with leucine; or a substitution at position 234 with leucine, at position 292 with proline, and at position 305 with isoleucine; or a substitution at position 234 with leucine and at position 292 with proline; or a substitution at position 234 with leucine; or a substitution at position 247 with leucine, at position 270 with glutamic acid, and at position 421 with lysine. Examples of other amino acid substitutions that results in an enhanced affinity for FcγRIIIA in vitro are disclosed below and summarized in Table 4.

The invention encompasses a molecule comprising a variant Fc region, wherein said variant Fc region comprises a substitution at position 243 with isoleucine and at position 379 with leucine, such that said molecule binds FcγRIIIA with about a 1.5 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 288 with asparagine, at position 330 with serine, and at position 396 with leucine, such that said molecule binds FcγRIIIA with about a 5 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 243 with leucine and at position 255 with leucine such that said molecule binds FcγRIIIA with about a 1 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 334 with glutamic acid, at position 359 with asparagine, and at position 366 with serine, such that said molecule binds FcγRIIIA with about a 1.5 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 288 with methionine and at position 334 with glutamic acid, such that said molecule binds FcγRIIIA with about a 3 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 316 with aspartic acid, at position 378 with valine, and at position 399 with glutamic acid, such that said molecule binds FcγRIIIA with about a 1.5 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 315 with isoleucine, at position 379 with methionine, and at position 399 with glutamic acid, such that said molecule binds FcγRIIIA with about a 1 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 243 with isoleucine, at position 379 with leucine, and at position 420 with valine, such that said molecule binds FcγRIIIA with about a 2.5 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 247 with leucine, and at position 421 with lysine, such that said molecule binds FcγRIIIA with about a 3 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 392 with threonine and at position 396 with leucine such that said molecule binds FcγRIIIA with about a 4.5 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 293 with valine, at position 295 with glutamic acid, and at position 327 with threonine, such that said molecule binds FcγRIIIA with about a 1.5 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 268 with asparagine and at position 396 with leucine, such that said molecule binds FcγRIIIA with about a 2 fold higher affinity than a comparable molecule comprising the wild type Fc region binds FcγRIIIA, as determined by an ELISA assay. In a specific embodiment, the invention encompasses a molecule comprising a variant Fc region, wherein said variant Fc region comprises a substitution at position 319 with phenylalanine, at position 352 with leucine, and at position 396 with leucine, such that said molecule binds FcγRIIIA with about a 2 fold higher affinity than a comparable molecule comprising the wild type Fc region binds FcγRIIIA, as determined by an ELISA assay.

In a specific embodiment, the invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 396 with histidine. In a specific embodiment, the invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 248 with methionine. The invention encompasses an isolated polypeptide comprising a variant Fc region, wherein said variant Fc region comprises at least one amino acid modification relative to a wild-type Fc region, such that said polypeptide specifically binds FcγRIIIA with a similar affinity than a comparable polypeptide comprising the wild-type Fc region, wherein said at least one amino acid modification comprises substitution at position 392 with arginine. The invention encompasses an isolated polypeptide comprising a variant Fc region, wherein said variant Fc region comprises at least one amino acid modification relative to a wild-type Fc region, such that said polypeptide specifically binds FcγRIIIA with a similar affinity than a comparable polypeptide comprising the wild-type Fc region, wherein said at least one amino acid modification comprises substitution at position 315 with isoleucine. The invention encompasses an isolated polypeptide comprising a variant Fc region, wherein said variant Fc region comprises at least one amino acid modification relative to a wild-type Fc region, such that said polypeptide specifically binds FcγRIIIA with a similar affinity than a comparable polypeptide comprising the wild-type Fc region, wherein said at least one amino acid modification comprises substitution at position 132 with isoleucine. The invention encompasses an isolated polypeptide comprising a variant Fc region, wherein said variant Fc region comprises at least one amino acid modification relative to a wild-type Fc region, such that said polypeptide specifically binds FcγRIIIA with a similar affinity than a comparable polypeptide comprising the wild-type Fc region, wherein said at least one amino acid modification comprises substitution at position 162 with valine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 396 with leucine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 379 with methionine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 219 with tyrosine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 282 with methionine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 401 with valine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 222 with asparagine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 334 with glutamic acid. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 377 with phenylalanine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 334 with isoleucine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 247 with leucine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 326 with glutamic acid. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 372 with tyrosine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 224 with leucine.

The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 275 with tyrosine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 398 with valine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 334 with asparagine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 400 with proline. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 407 with isoleucine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 372 with tyrosine. The invention encompasses an isolated polypeptide comprising a variant Fc region, wherein said variant Fc region comprises at least one amino acid modification relative to a wild-type Fc region, such that said polypeptide specifically binds FcγRIIIA with a similar affinity than a comparable polypeptide comprising the wild-type Fc region, wherein said at least one amino acid modification comprises substitution at position 366 with asparagine. The invention encompasses an isolated polypeptide comprising a variant Fc region, wherein said variant Fc region comprises at least one amino acid modification relative to a wild-type Fc region, such that said polypeptide specifically binds FcγRIIIA with a reduced affinity than a comparable polypeptide comprising the wild-type Fc region, wherein said at least one amino acid modification comprises substitution at position 414 with asparagine. The invention encompasses an isolated polypeptide comprising a variant Fc region, wherein said variant Fc region comprises at least one amino acid modification relative to a wild-type Fc region, such that said polypeptide specifically binds FcγRIIIA with a reduced affinity than a comparable polypeptide comprising the wild-type Fc region, wherein said at least one amino acid modification comprises substitution at position 225 with serine. The invention encompasses an isolated polypeptide comprising a variant Fc region, wherein said variant Fc region comprises at least one amino acid modification relative to a wild-type Fc region, such that said polypeptide specifically binds FcγRIIIA with a reduced affinity than a comparable polypeptide comprising the wild-type Fc region, wherein said at least one amino acid modification comprises substitution at position 377 with asparagine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 243 with leucine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 292 with proline. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 300 with leucine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 305 with isoleucine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 396 with leucine. The invention encompasses an isolated polypeptide comprising a variant Fc region, wherein said variant Fc region comprises at least one amino acid modification relative to a wild-type Fc region, such that said polypeptide specifically binds FcγRIIIA with a greater affinity than a comparable polypeptide comprising the wild-type Fc region, wherein said at least one amino acid modification comprises substitution at position 273 with phenylalanine.

In a specific embodiment, the invention encompasses an isolated polypeptide comprising a variant Fc region, wherein said variant Fc region comprises at least one amino acid modification relative to a wild-type Fc region, such that said polypeptide specifically binds FcγRIIIA with about a 2 fold greater affinity than a comparable polypeptide comprising the wild-type Fc region as determined by an ELISA assay, wherein said at least one amino acid modification comprises substitution at position 379 with methionine. In another specific embodiment, the invention encompasses an isolated polypeptide comprising a variant Fc region, wherein said variant Fc region comprises at least one amino acid modification relative to a wild-type Fc region, such that said polypeptide specifically binds FcγRIIIA with about a 1.5 fold greater affinity than a comparable polypeptide comprising the wild-type Fc region as determined by an ELISA assay, wherein said at least one amino acid modification comprises substitution at position 248 with methionine.

In some embodiments, the molecules of the invention have an altered affintiy for FcγRIIIA and/or FcγRIIA as determined using in vitro assays (biochemical or immunological based assays) known in the art for determining Fc-FcγR interactions, i.e., specific binding of an Fc region to an FcγR including but not limited to ELISA assay, surface plasmon resonance assay, immunoprecipitation assays (See Section 6.2.5.1). Preferably, the binding properties of these molecules with altered affinities for activating FcγR receptors are also correlated to their activity as determined by in vitro functional assays for determining one or more FcγR mediator effector cell functions (See Section 6.2.7), e.g., molecules with variant Fc regions with enhanced affinity for FcγRIIIA have an enhanced ADCC activity. In most preferred embodiments, the molecules of the invention that have an altered binding property for an activating Fc receptor, e.g., FcγRIIIA in an in vitro assay also have an altered binding property in in vivo models (such as those described and disclosed herein). However, the present invention does not exclude molecules of the invention that do not exhibit an altered FcγR binding in in vitro based assays but do exhibit the desired phenotype in vivo.

7.1.2 Mutants with Enhanced Affinity for FcγRIIIa and Reduced or No Affinity for FcγRIIb In a specific embodiment, the molecules of the invention comprise a variant Fc region, having one or more amino acid modifications (i.e., substitutions) in one or more regions, which one or more modifications increase the affinity of the variant Fc region for FcγRIIIA and decreases the affinity of the variant Fc region for FcγRIIB, relative to a comparable molecule comprising a wild-type Fc region which binds FcγRIIIA and FcγRIIB with wild-type affinity. In a certain embodiment, the one or more amino acid modifications do not include or are not solely a substitution with alanine at any of positions 256, 298, 333, 334, 280, 290, 294, 298, or 296; or a substitution at position 298 with asparagine, valine, aspartic acid, or proline; or a substitution 290 with serine. In certain amino embodiments, the one or more amino acid modifications increases the affinity of the variant Fc region for FcγRIIIA by at least 65%, at least 70%, at least 75%, at least 85%, at least 90%, at least 95%, at least 99%, at least 100%, at least 200%, at least 300%, at least 400% and decreases the affinity of the variant Fc region for FcγRIIB by at least 65%, at least 70%, at least 75%, at least 85%, at least 90%, at least 95%, at least 99%, at least 100%, at least 200%, at least 300%, at least 400%.

In a specific embodiment, the molecule of the invention comprising a variant Fc region with an enhanced affinity for FcγRIIIA and a lowered affinity or no affinity for FcγRIIB, as determined based on an ELISA assay and/or an ADCC based assay using ch-4-4-20 antibody, or a surface plasmon resonance assay using a chimeric 4D5 antibody, carrying the variant Fc region comprises a substitution at position 275 with isoleucine, at position 334 with asparagine, and at position 348 with methionine; or a substitution at position 279 with leucine and at position 395 with serine; or a substitution at position 246 with threonine and at position 319 with phenylalanine; or a substitution at position 243 with leucine, at position 255 with leucine, and at position 318 with lysine; or a substitution at position 334 with glutamic acid, at position 359 with asparagine and at position 366 with serine; or a substitution at position 334 with glutamic acid and at position 380 with aspartic acid; or a substitution at position 256 with serine, at position 305 with isoleucine, at position 334 with glutamic acid, and at position 390 with serine; or a substitution at position 335 with asparagine, at position 370 with glutamic acid, at position 378 with valine, at position 394 with methionine and at position 424 with leucine; or a substitution at position 233 with aspartic acid and at position 334 with glutamic acid; or a substitution at position 334 with glutamic acid, at position 359 with asparagine, at position 366 with serine and at position 386 with arginine; or a substitution at position 312 with glutamic acid, at position 327 with asparagine, and at position 378 with serine; or a substitution at position 288 with asparagine and at position 326 with asparagine; or a substitution at position 247 with leucine and at position 421 with lysine; or a substitution at position 298 with asparagine and at position 381 with arginine; or a substitution at position 280 with glutamic acid, at position 354 with phenylalanine, at position 431 with aspartic acid, and at position 441 with isoleucine; or a substitution at position 255 with glutamine and at position 326 with glutamic acid; or a substitution at position 218 with arginine, at position 281 with aspartic acid and at position 385 with arginine; or a substitution at position 247 with leucine, at position 330 with threonine and at position 440 with glycine; or a substitution at position 284 with alanine and at position 372 with leucine; or a substitution at position 335 with asparagine, as position 387 with serine and at position 435 with glutamine; or a substitution at position 247 with leucine, at position 431 with valine and at position 442 with phenylalanine; or a substitution at position 243 with leucine, at position 292 with proline, at position 305 with isoleucine, and at position 396 with leucine; or a substitution at position 243 leucine, at position 292 with proline, and at position 305 with isoleucine; or a substitution at position 292 with proline, at position 305 with isoleucine, and at position 396 with leucine; or a substitution at position 243 with leucine, and at position 292 with proline; or a substitution at position 292 with proline; or a substitution at position 243 with leucine, at position 292 with proline, and at position 396 with leucine; or a substitution at position 243 with leucine, at position 292 with proline, at position 300 with leucine; or a substitution at position 243 with leucine.

In a specific embodiment, the molecule of the invention comprising a variant Fc region with an enhanced affinity for FcγRIIIA and a lowered affinity or no affinity for FcγRIIB as determined based on an ELISA assay and/or an ADCC based assay using ch-4-4-20 antibody carrying the variant Fc region comprises a substitution at position 379 with methionine; at position 219 with tyrosine; at position 282 with methionine; at position 401 with valine; at position 222 with asparagine; at position 334 with isoleucine; at position 334 with glutamic acid; at position 275 with tyrosine; at position 398 with valine. In yet another specific embodiment, the molecule of the invention comprising a variant Fc region with an enhanced affinity for FcγRIIIA and a lowered affinity or no affinity for FcγRIIB as determined based on an ELISA assay and/or an ADCC based assay using ch-4-4-20 antibody, or a surface plasmon resonance assay using a chimeric 4D5 antibody, carrying the variant Fc region comprises a substitution at position 243 with leucine; at position 292 with proline; and at position 300 with leucine.

The invention encompasses an isolated polypeptide comprising a variant Fc region, wherein said variant Fc region comprises at least one amino acid modification relative to a wild-type Fc region, such that said polypeptide specifically binds FcγRIIB with about a 3 fold lower affinity than a comparable polypeptide comprising the wild-type Fc region as determined by an ELISA assay, wherein said at least one amino acid modification comprises substitution at position 288 with asparagine, at position 330 with serine, and at position 396 with leucine. The invention encompasses an isolated polypeptide comprising a variant Fc region, wherein said variant Fc region comprises at least one amino acid modification relative to a wild-type Fc region, such that said polypeptide specifically binds FcγRIIB with about a 10-15 fold lower affinity than a comparable polypeptide comprising the wild-type Fc region as determined by an ELISA assay, wherein said at least one amino acid modification comprises substitution at position 316 with aspartic acid, at position 378 with valine, and at position 399 with glutamic acid. The invention encompasses an isolated polypeptide comprising a variant Fc region, wherein said variant Fc region comprises at least one amino acid modification relative to a wild-type Fc region, such that said polypeptide specifically binds FcγRIIB with about a 10 fold lower affinity than a comparable polypeptide comprising the wild-type Fc region as determined by an ELISA assay, wherein said at least one amino acid modification comprises substitution at position 315 with isoleucine, at position 379 with methionine, and at position 399 with glutamic acid. The invention encompasses an isolated polypeptide comprising a variant Fc region, wherein said variant Fc region comprises at least one amino acid modification relative to a wild-type Fc region, such that said polypeptide specifically binds FcγRIIB with about a 7 fold lower affinity than a comparable polypeptide comprising the wild-type Fc region as determined by an ELISA assay, wherein said at least one amino acid modification comprises substitution at position 243 with isoleucine, at position 379 with leucine, and at position 420 with valine. The invention encompasses an isolated polypeptide comprising a variant Fc region, wherein said variant Fc region comprises at least one amino acid modification relative to a wild-type Fc region, such that said polypeptide specifically binds FcγRIIB with about a 3 fold lower affinity than a comparable polypeptide comprising the wild-type Fc region as determined by an ELISA assay, wherein said at least one amino acid modification comprises substitution at position 392 with threonine and at position 396 with leucine. The invention encompasses an isolated polypeptide comprising a variant Fc region, wherein said variant Fc region comprises at least one amino acid modification relative to a wild-type Fc region, such that said polypeptide specifically binds FcγRIIB with about a 5 fold lower affinity than a comparable polypeptide comprising the wild-type Fc region as determined by an ELISA assay, wherein said at least one amino acid modification comprises substitution at position 268 with asparagine and at position 396 with leucine. The invention also encompasses an isolated polypeptide comprising a variant Fc region, wherein said variant Fc region comprises at least one amino acid modification relative to a wild-type Fc region, such that said polypeptide specifically binds FcγRIIB with about a 2 fold lower affinity than a comparable polypeptide comprising the wild-type Fc region as determined by an ELISA assay, wherein said at least one amino acid modification comprises substitution at position 319 with phenylalanine, at position 352 with leucine, and at position 396 with leucine.

7.1.3 Mutants with Enhanced Affinity to FcγRIIIa and FcγRIIB

The invention encompasses molecules comprising variant Fc regions, having one or more amino acid modifications, which modifications increase the affinity of the variant Fc region for FcγRIIIA and FcγRIIB by at least 65%, at least 70%, at least 75%, at least 85%, at least 90%, at least 95%, at least 99%, at least 100%, at least 200%, at least 300%, at least 400% and decreases the affinity of the variant Fc region for FcγRIIB by at least 65%, at least 70%, at least 75%, at least 85%, at least 90%, at least 95%, at least 99%, at least 100%, at least 200%, at least 300%, at least 400%. In a specific embodiment, the molecule of the invention comprising a variant Fc region with an enhanced affinity for FcγRIIIA and an enhanced affinity for FcγRIIB (as determined based on an ELISA assay and/or an ADCC based assay using ch-4-4-20 antibody, or a surface plasmon resonance assay using a chimeric 4D5 antibody, carrying the variant Fc region as described herein) comprises a substitution at position 415 with isoleucine and at position 251 with phenylalanine; or a substitution at position 399 with glutamic acid, at position 292 with leucine, and at position 185 with methionine; or a substitution at position 408 with isoleucine, at position 215 with isoleucine, and at position 125 with leucine; or a substitution at position 385 with glutamic acid and at position 247 with histidine; or a substitution at position 348 with methionine, at position 334 with asparagine, at position 275 with isoleucine, at position 202 with methionine and at position 147 with threonine; or a substitution at position 246 with threonine and at position 396 with histidine; or a substitution at position 268 with aspartic acid and at position 318 with aspartic acid; or a substitution at position 288 with asparagine, at position 330 with serine and at position 396 with leucine; or a substitution at position 244 with histidine, at position 358 with methionine, at position 379 with methionine, at position 384 with lysine and at position 397 with methionine; or a substitution at position 217 with serine, at position 378 with valine, and at position 408 with arginine; or a substitution at position 247 with leucine, at position 253 with asparagine, and at position 334 with asparagine; or a substitution at position 246 with isoleucine and at position 334 with asparagine; or a substitution at postion 320 with glutamic acid and at position 326 with glutamic acid; or a substitution at positoion 375 with cysteine and at position 396 with leucine; or a substitution at position 343 with serine, at position 353 with leucine, at position 375 with isoleucine, at position 383 with asparagine; or a substitution at position 394 with methionine and at position 397 with methionine; or a substitution at position 216 with aspartic acid, at position 345 with lysine and at position 375 with isoleucine; or a substitution at position 288 with asparagine, at position 330 with serine, and at position 396 with leucine; or a substition at position 247 with leucine and at position 389 with glycine; or a substitution at position 222 with asparagine, at position 335 with asparagine, at position 370 with glutamic acid, at position 378 with valine and at position 394 with methionine; or a substitution at position 316 with aspartic acid, at position 378 with valine and at position 399 with glutamic acid; or a substitution at position 315 with isoleucine, at position 379 with methionine, and at position 394 with methionine; or a substitution at position 290 with threonine and at position 371 with aspartic acid; or a substitution at position 247 with leucine and at position 398 with glutamine; or a substitution at position 326 with glutamine; at position 334 with glutamic acid, at position 359 with asparagine, and at position 366 with serine; or a substitution at position 247 with leucine and at position 377 with phenylalanine; or a substitution at position 378 with valine, at position 390 with isoleucine and at position 422 with isoleucine; or a substitution at position 326 with glutamic acid and at position 385 with glutamic acid; or a substitution at position 282 with glutamic acid, at position 369 with isoleucine and at position 406 with phenylalanine; or a substitution at position 397 with methionine; at position 411 with alanine and at position 415 with asparagine; or a substitution at position 223 with isoleucine, at position 256 with serine and at position 406 with phenylalanine; or a substitution at position 298 with asparagine and at position 407 with arginine; or a substitution at position 246 with arginine, at position 298 with asparagine, and at position 377 with phenylalanine; or a substitution at position 235 with proline, at position 382 with methionine, at position 304 with glycine, at position 305 with isoleucine, and at position 323 with isoleucine; or a substitution at position 247 with leucine, at position 313 with arginine, and at position 388 with glycine; or a substitution at position 221 with tyrosine, at position 252 with isoleucine, at position 330 with glycine, at position 339 with threonine, at position 359 with asparagine, at position 422 with isoleucine, and at position 433 with leucine; or a substitution at position 258 with aspartic acid, and at position 384 with lysine; or a substitution at position 241 with leucine and at position 258 with glycine; or a substitution at position 370 with asparagine and at position 440 with asparagine; or a substitution at position 317 with asparagine and a deletion at position 423; or a substitution at position 243 with isoleucine, at position 379 with leucine and at position 420 with valine; or a substitution at position 227 with serine and at position 290 with glutamic acid; or a substitution at position 231 with valine, at position 386 with histidine, and at position 412 with methionine; or a substitution at position 215 with proline, at position 274 with asparagine, at position 287 with glycine, at position 334 with asparagine, at position 365 with valine and at position 396 with leucine; or a substitution at position 293 with valine, at position 295 with glutamic acid and at position 327 with threonine; or a substitution at position 319 with phenylalanine, at position 352 with leucine, and at position 396 with leucine; or a substitution at position 392 with threonine and at position 396 with leucine; at a substitution at position 268 with asparagine and at position 396 with leucine; or a substitution at position 290 with threonine, at position 390 with isoleucine, and at position 396 with leucine; or a substitution at position 326 with isoleucine and at position 396 with leucine; or a substitution at position 268 with aspartic acid and at position 396 with leucine; or a substitution at position 210 with methionine and at position 396 with leucine; or a substitution at position 358 with proline and at position 396 with leucine; or a substitution at position 288 with arginine, at position 307 with alanine, at position 344 with glutamic acid, and at position 396 with leucine; or a substitution at position 273 with isoleucine, at position 326 with glutamic acid, at position 328 with isoleucine and at position 396 with leucine; or a substitution at position 326 with isoleucine, at position 408 with asparagine and at position 396 with leucine; or a substitution at position 334 with asparagine and at position 396 with leucine; or a substitution at position 379 with methionine and at position 396 with leucine; or a substitution at position 227 with serine and at position 396 with leucine; or a substitution at position 217 with serine and at position 396 with leucine; or a substitution at position 261 with asparagine, at position 210 with methionine and at position 396 with leucine; or a substitution at position 419 with histidine and at position 396 with leucine; or a substitution at position 370 with glutamic acid and at position 396 with leucine; or a substitution at position 242 with phenylalanine and at position 396 with leucine; or a substitution at position 255 with leucine and at position 396 with leucine; or a substitution at position 240 with alanine and at position 396 with leucine; or a substitution at position 250 with serine and at position 396 with leucine; or a substitution at position 247 with serine and at position 396 with leucine; or a substitution at position 410 with histidine and at position 396 with leucine; or a substitution at position 419 with leucine and at position 396 with leucine; or a substitution at position 427 with alanine and at position 396 with leucine; or a substitution at position 258 with aspartic acid and at position 396 with leucine; or a substitution at position 384 with lysine and at position 396 with leucine; or a substitution at position 323 with isoleucine and at position 396 with leucine; or a substitution at position 244 with histidine and at position 396 with leucine; or a substitution at position 305 with leucine and at position 396 with leucine; or a substitution at position 400 with phenylalanine and at position 396 with leucine; or a substitution at position 303 with isoleucine and at position 396 with leucine; or a substitution at position 243 with leucine, at position 305 with isoleucine, at position 378 with aspartic acid, at position 404 with serine and at position 396 with leucine; or a substitution at position 290 with glutamic acid, at position 369 with alanine, at position 393 with alanine and at position 396 with leucine; or a substitution at position 210 with asparagine, at position 222 with isoleucine, at position 320 with methionine and at position 396 with leucine; or a substitution at position 217 with serine, at position 305 with isoleucine, at position 309 with leucine, at position 390 with histidine and at position 396 with leucine; or a substitution at position 246 with asparagine; at position 419 with arginine and at position 396 with leucine; or a substitution at position 217 with alanine, at position 359 with alanine and at position 396 with leucine; or a substitution at position 215 with isoleucine, at position 290 with valine and at position 396 with leucine; or a substitution at position 275 with leucine, at position 362 with histidine, at position 384 with lysine and at position 396 with leucine; or a substitution at position 334 with asparagine; or a substitution at position 400 with proline; or a substitution at position 407 with isoleucine; or a substitution at position 372 with tyrosine; or a substitution at position 366 with asparagine; or a substitution at position 414 with asparagine; or a substitution at position 352 with leucine; or a substitution at position 225 with serine; or a substitution at position 377 with asparagine; or a substitution at position 248 with methionine; or a substitution at position 243 with leucine, at position 292 with proline, at position 300 with leucine, at position 305 with isoleucine, and at position 396 with leucine; or a substitution at position 243 with leucine, at position 292 with proline, at position 300 with leucine, and at position 396 with leucine; or a substitution at position 243 with leucine, and at position 396 with leucine; or at position 292 with proline, and at position 305 with isoleucine.

7.1.4 Mutants that do not Bind any FcγR

In some embodiments, the invention encompasses molecules comprising a variant Fc region, wherein said variant Fc region comprises at least one amino acid modification relative to a wild-type Fc region, which variant Fc region does not bind any FcγR, as determined by standard assays known in the art and disclosed herein, relative to a comparable molecule comprising the wild type Fc region. In a specific embodiment, the one or more amino acid modifications which abolish binding to all FcγRs comprise a substitution at position 232 with serine and at position 304 with glycine; or a substitution at position 269 with lysine, at position 290 with asparagine, at position 311 with arginine, and at position 433 with tyrosine; or a substitution at position 252 with leucine; or a substitution at position 216 with aspartic acid, at position 334 with arginine, and at position 375 with isoleucine; or a substitution at position 247 with leucine and at position 406 with phenylalanine, or a substitution at position 335 with asparagine, at position 387 with serine, and at position 435 with glutamine; or a substitution at position 334 with glutamic acid, at position 380 with aspartic acid, and at position 446 with valine; or a substitution at position 303 with isoleucine, at position 369 with phenylalanine, and at position 428 with leucine; or a substitution at position 251 with phenylalanine and at position 372 with leucine; or a substitution at position 246 with glutamic acid, at position 284 with methionine and at position 308 with alanine; or a substitution at position 399 with glutamic acid and at position 402 with aspartic acid; or a substitution at position 399 with glutamic acid and at position 428 with leucine.

7.1.5 Mutants with Altered FcγR-Mediated Effector Functions

The invention encompasses immunoglobulin comprising Fc variants with altered effector functions. In some embodiments, immunoglobulins comprising Fc variants mediate effector function more effectively in the presence of effector cells as determined using assays known in the art and exemplified herein. In other embodiments, immunoglobulins comprising Fc variants mediate effector function less effectively in the presence of effector cells as determined using assays known in the art and exemplified herein. In specific embodiments, the Fc variants of the invention may be combined with other known Fc modifications that alter effector function, such that the combination has an additive, synergistic effect. The Fc variants of the invention have altered effector function in vitro and/or in vivo.

In a specific embodiment, the immunoglobulins of the invention with enhanced affinity for FcγRIIIA and/or FcγRIIA have an enhanced FcγR-mediated effector function as determined using ADCC activity assays disclosed herein. Examples of effector functions that could be mediated by the molecules of the invention include, but are not limited to, C1q binding, complement-dependent cytotoxicity, antibody-dependent cell mediate cytotoxicity (ADCC), phagocytosis, etc. The effector functions of the molecules of the invention can be assayed using standard methods known in the art, examples of which are disclosed in Section 6.2.6.

In a specific embodiment, the immunoglobulins of the invention comprising a variant Fc region with enhanced affinity for FcγRIIIA and/or FcγRIIA mediate antibody dependent cell mediated cytotoxicity (ADCC) 2-fold more effectively, than an immunoglobulin comprising a wild-type Fc region. In other embodiments, the immunoglobulins of the invention comprising a variant Fc region with enhanced affinity for FcγRIIIA and/or FcγRIIA mediate antibody dependent cell mediated cytotoxicity (ADCC) at least 4-fold, at least 8-fold, at least 10-fold, at least 100-fold, at least 1000-fold, at least $10^4$-fold, at least $10^5$-fold more effectively, than an immunoglobulin comprising a wild-type Fc region. In another specific embodiment, the immunoglobulins of the invention with enhanced affinity for FcγRIIIA and/or FcγRIIA have altered C1q binding activity. In some embodiments, the immunoglobulins of the invention with enhanced affinity for FcγRIIIA and/or FcγRIIA have at least 2-fold, at least 4-fold, at least 8-fold, at least 10-fold, at least 100-fold, at least 1000-fold, at least $10^4$-fold, at least $10^5$-fold higher C1q binding activity than an immunoglobulin comprising a wild-type Fc region. In yet another specific embodiment, the immunoglobulins of the invention with enhanced affinity for FcγRIIIA and/or FcγRIIA have altered complement dependent cytotoxicity. In yet another specific embodiment, the immunoglobulins of the invention with enhanced affinity for FcγRIIIA and/or FcγRIIA have an enhanced complement dependent cytotoxicity than an immunoglobulin comprising a wild-type Fc region. In some embodiments, the immunoglobulins of the invention with enhanced affinity for FcγRIIIA and/or FcγRIIA have at least 2-fold, at least 4-fold, at least 8-fold, at least 10-fold, at least 100-fold, at least 1000-fold, at least $10^4$-fold, at least $10^5$-fold higher complement dependent cytotoxicity than an immunoglobulin comprising a wild-type Fc region.

In certain embodiments, the Fc variants of the invention may be combined with or comprise any of the Fc variants previously identified by the inventors to modulate effector function as disclosed in U.S Patent Application Publications 2005/0037000 and 2005/0064514, and International Patent Application Publication WO 04/063351, each of which is hereby incorporated by reference in its entirety. Examples of such Fc variants previously identified by the authors are provided in Tables 7 and 8 infra.

In other embodiments, immunoglobulins of the invention with enhanced affinity for FcγRIIIA and/or FcγRIIA have enhanced phagocytosis activity relative to an immunoglobulin comprising a wild-type Fc region, as determined by standard assays known to one skilled in the art or disclosed herein. In some embodiments, the immunoglobulins of the invention with enhanced affinity for FcγRIIIA and/or FcγRIIA have at least 2-fold, at least 4-fold, at least 8-fold, at least 10-fold higher phagocytosis activity relative to an immunoglobulin comprising a wild-type Fc region.

TABLE 7

Summary of ADCC Activity of Mutants in ch4D5

| | | | ADCC | | | |
|---|---|---|---|---|---|---|
| | | | 1 µg/ml | | 0.5 µg/ml | |
| Label | Ref | Amino Acid Variation | % Specific Lysis | Normalized | % Specific Lysis | Normalized |
| MGFc-27 | 2C4 | G316D, A378V, D399E | 33% | 2.24 | 22% | 3.60 |
| MGFc-31 | 3B9 | P247L, N421K | 30% | 2.05 | 17% | 2.90 |
| MGFc-10 | 1E1 | K288N, A330S, P396L | 24% | 1.66 | 10% | 1.67 |

TABLE 7-continued

Summary of ADCC Activity of Mutants in ch4D5

| | | | ADCC | | | |
|---|---|---|---|---|---|---|
| | | | 1 µg/ml | | 0.5 µg/ml | |
| Label | Ref | Amino Acid Variation | % Specific Lysis | Normalized | % Specific Lysis | Normalized |
| MGFc-28 | 2C5 | N3151, V379M, T394M | 20% | 1.37 | 10% | 1.69 |
| MGFc-29 | 3D11 | F243I, V379L, G420V | 20% | 1.35 | 7% | 1.17 |
| CH4-4-20 (P54008) | | | 15% | 1.00 | 6 | 1.00 |
| MGFc-35 | 3D2 | R255Q, K326E | 11% | 0.79 | 3% | 0.53 |
| MGFc-36 | 3D3 | K218R, G281D, G385R | 10% | 0.67 | 5% | 0.78 |
| MGFc-30 | 3A8 | F275Y | 9% | 0.64 | 2% | 0.37 |
| MGFc-32 | 3C8 | D280E, 5354F, A431D, L441I | 9% | 0.62 | 4% | 0.75 |
| MGFc-33 | 3C9 | K317N, F4234 | 3% | 0.18 | −1% | −0.22 |
| MGFc-34 | 3B10 | F421L, E258G | −1% | −0.08 | −4% | −0.71 |
| MGFc-26 | | D265A | 1% | 0.08 | −3% | −0.45 |

TABLE 8

SUMMARY OF MUTANTS

| Fc Variant | Amino Acid changes | FcR3A, $K_D$/Koff | FcR2B, $K_D$/$K_{off}$ | ELISA IIIA binding | ELISA IIB binding | Phagocytosis (mutant/WT) | 4-4-20 ADCC (mutant/wt) | Anti-HER2 ADCC (mutant/wt) |
|---|---|---|---|---|---|---|---|---|
| Wt | none | 198/0.170 | 94/.094 | 1 | 1 | 1 | 1 | 1 |
| MGFc 5 | V379M | 160/0.167 | 70/0.10 | 2X | N/C | 0.86 | 2.09 | 1.77 |
| MGFc 9 | P243I, V379L | 99.7/0.105 | 120/0.113 | 1.5X | reduced | ? | 2.25 | 2.04 |
| MGFc 10 | K288N, A330S, P396L | 128/0.115 | 33.4/0.050 | 5X | 3X | 1.2 | 2.96 | 2.50 |
| MGFc 11 | F243L, R255L | 90/0.075 | 74.7/0.09 | 1x | reduced | 0.8 | 2.38 | 1.00 |
| MGFc13 | K334E, T359N, T366S | 55.20.128 | 72/0.11 | 1.5X | N/C | [ | 1.57 | 3.67 |
| MGFc 14 | K288M, K334E | 75.4/0.1 | 95.6/0.089 | 3X | reduced | [ | 1.74 | |
| MGFc 23 | K334E, R292L | 70.2/0.105 | 108/0.107 | | | [ | 2.09 | 1.6 |
| MGFc 27 | G316D, A378V, D399E | 72/0.117 | 46/0.06 | 1.5X | 14X | 1.4 | 3.60 | 6.88 |
| MGFc 28 | N315I, A379M, D399E | | | 1X | 9X | 1.37 | 1.69 | 1.00 |
| MGFc 29 | P243I, V379L, G420V | 108/0.082 | 93.4/.101 | 2.5X | 7X | 0.93 | 1.17 | 1.00 |
| MGFc 31 | P247L, N421K | 62/0.108 | 66/0.065 | 3X | N/C | 1.35 | 2.90 | 1.00 |
| MGFc 37 | K248M | 154/0.175 | 100/0.091 | 1.4X | reduced | 0.98 | 3.83 | 0.67 |
| MGFc 38 | K392T, P396L | 84/0.104 | 50/0.041 | 4.5X | 2.5X | 1.4 | 3.07 | 2.50 |
| MGFc 39 | E293V, Q295E, A327T | 195/0.198 | 86/0.074 | 1.4X | reduced | 1.5 | 4.29 | 0.50 |
| MGFc 40 | K248M | 180/0.186 | 110/0.09 | 1.4X | reduced | 1.14 | 4.03 | |
| MGFc 41 | H268N, P396L | 178/0.159 | 46.6/0.036 | 2.2X | 4.5X | 1.96 | 2.24 | 0.67 |
| MGFc 43 | Y319F, P352L, P396L | 125/0.139 | 55.7/0.041 | 3.5X | 2X | 1.58 | 1.09 | |

In a specific embodiment, the invention encompasses an immunoglobulin comprising a variant Fc region with one or more amino acid modifications, with an enhanced affinity for FcγRIIIA and/or FcγRIIA such that the immunoglobulin has an enhanced effector function, e.g., antibody dependent cell mediated cytotoxicity, or phagocytosis. In a specific embodiment, the one or more amino acid modifications which increase the affinity of the variant Fc region for FcγRIIIA and/or FcγRIIA and increase the ADCC activity of the immunoglobulin comprise a substitution at position 379 with methionine; or a substitution at position 243 with isoleucine and at position 379 with leucine; or a substitution at position 288 with asparagine, at position 330 with serine, and at position 396 with leucine; or a substitution at position 243 leucine and at position 255 with leucine; or a substitution at position 334 with glutamic acid, at position 359 with asparagine, and at position 366 with serine; or a substitution at position 288 with methionine and at position 334 with glutamic acid; or a substitution at position 334 with glutamic acid and at position 292 with leucine; or a substitution at position 316 with aspartic acid, at position 378 with valine, and at position 399 with glutamic acid; or a substitution at position 315 with isoleucine, at position 379 with methionine, and at position 399 with glutamic acid; or a substitution at position 243 with isoleucine, at position 379 with leucine, and at position 420 with valine; or a substitution at position 247 with leucine and at position 421 with lysine; or a substitution at position 248 with methionine; or a substitution at position 392 with threonine and at position 396 with leucine; or a substitution at position 293 with valine, at position 295 with glutamic acid, and at position 327 with threonine; or a substitution at position 268 with asparagine and at position 396 with leucine; or a substitution at position 319 with phenylalanine, at position 352 with leucine, and at position 396 with leucine; or a substitution at position 243 with leucine, at position 292 with proline, at position 300 with leucine, at position 305 with isoleucine, and at position 396 with leucine; or a substitution at position 243 with leucine, at position 292 with proline, at position 300 with leucine, and at position 396 with leucine; or a substitution at position 243 with leucine, at position 292 with proline, and at position 300 with leucine.

In another specific embodiment, the one or more amino acid modifications which increase the ADCC activity of the immunoglobulin is any of the mutations listed below, in table 9.

TABLE 9

AMINO ACID MODIFICATION WHICH INCREASE ADCC

| | |
|---|---|
| E333A, K334A | T250S, P396L |
| R292L, K334E | P247S, P396L |
| V379M | K290E, V369A, T393A, P396L |
| S219Y | K210N, K222I, K320M, P396L |
| V282M | L410H, P396L |
| K222N | Q419L, P396L |
| F243I, V379L | V427A, P396L |
| F243L, R255L, E318K | P217S, V305I, I309L, N390H, P396L |
| K334I | E258D, P396L |
| K334E, T359N, T366S | N384K, P396L |
| K288M, K334E | V323I, P396L |
| K288N, A330S, P396L | K246N, Q419R, P396L |
| K326E | V273I, K326E, L328I, P396L |
| G316D, A378V, D399E | K326I, S408N, P396L |
| N315I, V379M, T394M | K334N, P396L |
| F243I, V379L, G420V | V379M, P396L |
| E293V, Q295E, A327T | P227S, P396L |
| Y319F, P352L, P396L | P217S, P396L |
| K392T, P396L | K261N, K210M, P396L |
| K248M | Q419H, P396L |
| H268N, P396L | K370E, P396L |
| K290T, N390I, P396L | L242F, P396L |
| <u>K326I, P396L</u> | F243L, V305I, A378D, F404S, P396L |
| H268D, P396L | R255L, P396L |
| K210M, P396L | V240A, P396L |
| L358P, P396L | P217A, T359A, P396L |
| K288R, T307A, K344E, P396L | P244H, P396L |
| D270E, G316D, R416G | V215I, K290V, P396L |
| P247L, N421K | F275L, Q362H, N384K, P396L |
| P247L, N421K, D270E | V305L, P396L |
| Q419H, P396L, D270E | S400F, P396L |
| K370E, P396L, D270E | V303I, P396L |

TABLE 9-continued

AMINO ACID MODIFICATION WHICH INCREASE ADCC

| | |
|---|---|
| R255L, P396L, D270E | F243L, R292P, Y300L, V305I, P396L |
| V240A, P396L, D270E | F243L, R292P, Y300L, P396L |
| K392T, P396L, D270E | F243L, R292P, Y300L |

Alternatively or additionally, it may be useful to combine the above amino acid modifications or any other amino acid modifications disclosed herein with one or more further amino acid modifications that alter C1q binding and/or complement dependent cytoxicity function of the Fc region. The starting molecule of particular interest herein is usually one that binds to C1q and displays complement dependent cytotoxicity (CDC). The further amino acid substitutions described herein will generally serve to alter the ability of the starting molecule to bind to C1q and/or modify its complement dependent cytotoxicity function, e.g., to reduce and preferably abolish these effector functions. However, molecules comprising substitutions at one or more of the described positions with improved C1q binding and/or complement dependent cytotoxicity (CDC) function are contemplated herein. For example, the starting molecule may be unable to bind C1q and/or mediate CDC and may be modified according to the teachings herein such that it acquires these further effector functions. Moreover, molecules with preexisting C1q binding activity, optionally further having the ability to mediate CDC may be modified such that one or both of these activities are enhanced.

As disclosed above, one can design an Fc region with altered effector function, e.g., by modifying C1q binding and/or FcR binding and thereby changing CDC activity and/or ADCC activity. For example, one can generate a variant Fc region with improved C1q binding and improved FcγRIII binding; e.g., having both improved ADCC activity and improved CDC activity. Alternatively, where one desires that effector function be reduced or ablated, one may engineer a variant Fc region with reduced CDC activity and/or reduced ADCC activity. In other embodiments, one may increase only one of these activities, and optionally also reduce the other activity, e.g., to generate an Fc region variant with improved ADCC activity, but reduced CDC activity and vice versa.

The invention encompasses specific variants of the Fc region that have been identified using the methods of the invention from a yeast library of mutants after 2nd-4th-round of sorting are listed in Table 10. Table 10 summarizes the various mutants that were identified using the methods of the invention. The mutants were assayed using an ELISA assay for determining binding to FcγRIIIA and FcγRIIB. The mutants were also tested in an ADCC assay, by cloning the Fc variants into a ch 4-4-20 antibody using methods disclosed and exemplified herein. Bolded items refer to experiments, in which the ch4-4-20 were purified prior the ADCC assay. The antibody concentration used was in the range 0.5 µg/mL-1.0 µg/mL.

TABLE 10

MUTATIONS IDENTIFIED IN THE Fc REGION

| Mutations | Domain | Binding FcγRIIIA (ELISA) | Binding to FcγRIIB (ELISA) | Jan. 4, 2020 ADCC (Relative Lysis (Mut/Wt) |
|---|---|---|---|---|
| pYD-CH1 library FACS screen with A tetramer | | | | |
| Q347H, A339V | CH3 | ↑ 0.5x | NT | |
| S415I, L251F | CH2, CH3 | ↑ 0.5x | ↑ .75x | 0.82 |

TABLE 10-continued

MUTATIONS IDENTIFIED IN THE Fc REGION

| Mutations | Domain | Binding FcγRIIIA (ELISA) | Binding to FcγRIIB (ELISA) | Jan. 4, 2020 ADCC (Relative Lysis (Mut/Wt) |
|---|---|---|---|---|
| K392R | CH3 | N/C | NT | |
| D399E; R292L; V185M | CH1, CH2, CH3 | N/C | ↑□ 0.5x | 0.65 0.9 |
| K290E; L142P | CH1, CH2 | N/C | NT | |
| R301C; M252L; S192T | CH1, CH2 | ↓.5x | NT | |
| P291S; K288E; H268L: A141V | CH1, CH2 | ↓.5x | NT | |
| N315I | CH2 | N/C | ↑ .75x | |
| S132I | CH1 | N/C | NT | |
| S383N; N384K; T256N; V262L; K218E. R214I; K205E. F149Y. K133M | All | ↑0.5x | NT | |
| S408I; V215I; V125L | CH1, CH2, CH3 | ↑□ 0.5x | ↑ .75x | 0.62 |
| P396L | CH3 | ↑1x | ↑1x | 0.55 |
| G385E; P247H; | CH2, CH3 | ↑1x | ↑ .75x | 0.44 |
| P396H | CH3 | ↑1x | □ ↑1x | 0.58 |
| A162V | CH1 | N/C | NT | |
| V348M; K334N; F275I; Y202M; K147T | CH1, CH2, CH3 | ↑□ 0.5x | ↑.75x | 0.33 |
| H310Y; T289A; G337E | CH2 | ↑.5x | NT | |
| S119F; G371S; Y407V; E258D | CH1, CH2, CH3 | N/C | N/C | 0.29 |
| K409R; S166N | CH1, CH3 | N/C | NT | |
| in vitro Site Directed mutants | | | | |
| R292L | CH2 | NT | NT | 0.82 |
| T359N | CH3 | NT | NT | 1.06 |
| T366S | CH3 | NT | NT | 0.93 |
| E333A, K334A | CH2 | NT | NT | 1.41 |
| R292L, K334E | CH2 | NT | NT | 1.41; 1.64 |
| R292L, P396L, T359N | CH2, CH3 | NT | NT | 0.89; 1.15 |
| V379L | CH3 | NT | NT | 0.83 |
| K288N | CH2 | NT | NT | 0.78 |
| A330S | CH2 | NT | NT | 0.52 |
| F243L | CH2 | NT | NT | 0.38 |
| E318K | CH2 | NT | NT | 0.86 |
| K288N, A330S | CH2 | NT | NT | 0.08 |
| R255L, E318K | CH2 | NT | NT | 0.82 |
| F243L, E318K | CH2 | NT | NT | 0.07 |
| Mutants in Apr. 4, 2020 mini-library Increased FcγRIIIA binding, decreased or no change to FcγRIIB binding N/C means no change; N/B means no binding; NT means not tested | | | | |
| V379M | CH3 | ↑2x | N/C | 1.47 |
| S219Y | Hinge | ↑1x | ↓ or N/B | 1.28 |
| V282M | CH2 | ↑1x | ↓ or N/B | 1.25; 1 |
| F275I, K334N, V348M | CH2 | ↑0.5x | N/C | |
| D401V | CH3 | ↑ 0.5x | N/C | |
| V279L, P395S | CH2 | ↑ 1x | N/C | |
| K222N | Hinge | ↑ 1x | ↓ or N/B | 1.33; 0.63 |
| K246T, Y319F | CH2 | ↑ 1x | N/C | |
| F243I, V379L | CH2, CH3 | ↑1.5x | ↓ or N/B | 1.86; 1.35 |
| F243L, R255L, E318K | CH2 | ↑ 1x | ↓ or N/B | 1.81; 1.45 |
| K334I | CH2 | ↑ 1x | N/C | 2.1; 1.97 |
| K334E, T359N, T366S | CH2, CH3 | ↑1.5x | N/C | 1.49; 1.45 |
| K288M, K334E | CH2 | ↑ 3x | ↓ or N/B | 1.61; 1.69 |
| K334E, E380D | CH2, CH3 | ↑1.5x | N/C | |
| T256S, V305I, K334E, N390S | CH2, CH3 | ↑1.5x | N/C | |
| K334E | CH2 | ↑2.5x | N/C | 1.75; 2.18 |
| T335N, K370E, A378V, T394M, S424L | CH2, CH3 | ↑0.5x | N/C | |
| E233D, K334E | CH2 | ↑1.5x | N/C | 0.94; 1.02 |
| K334E, T359N, T366S, Q386R | CH2 | ↑ 1x | N/C | |
| Increased Binding to FcγIIIA and FcγRIIB | | | | |
| K246T, P396H | CH2, CH3 | ↑ 1x | ↑ 2.5x | |
| H268D, E318D | CH2 | ↑1.5x | ↑ 5x | |
| K288N, A330S, P396L | CH2, CH3 | ↑ 5x | ↑ 3x | 2.34; 1.66; 2.54 |
| I377F | CH3 | ↑1.5x | ↑0.5x | |
| P244H, L358M, V379M, N384K, V397M | CH2, CH3 | ↑1.75x | ↑1.5x | |
| P217S, A378V, S408R | Hinge, CH3 | ↑ 2x | ↑4.5x | |
| P247L, I253N, K334N | CH2 | ↑ 3x | ↑ 2.5x | |
| P247L | CH2 | ↑0.5x | ↑ 4x | 0.91; 0.84 |
| F372Y | CH3 | ↑0.75x | ↑5.5x | 0.88; 0.59 |

TABLE 10-continued

MUTATIONS IDENTIFIED IN THE Fc REGION

| Mutations | Domain | Binding FcγRIIIA (ELISA) | Binding to FcγRIIB (ELISA) | Jan. 4, 2020 ADCC (Relative Lysis (Mut/Wt) |
|---|---|---|---|---|
| K326E | CH2 | ↑ 2x | ↑ 3.5x | 1.63; 2 |
| K246I, K334N | CH2 | ↑0.5x | ↑ 4x | 0.66; 0.6 |
| K320E, K326E | CH2 | ↑ 1x | ↑ 1x | |
| H224L | Hinge | ↑0.5x | ↑ 5x | 0.55; 0.53 |
| S375C, P396L | CH3 | ↑1.5x | ↑4.5x | |
| D312E, K327N, I378S | CH2, CH3 | ↑0.5x | N/C | |
| K288N, K326N | CH2 | ↑ 1x | N/C | |
| F275Y | CH2 | ↑ 3x | N/C | 0.64 |
| P247L, N421K | CH2, CH3 | ↑ 3x | N/C | 2.0 |
| S298N, W381R | CH2, CH3 | ↑ 2x | N/C | |
| D280E, S354F, A431D, L441I | CH2, CH3 | ↑ 3x | N/C | 0.62 |
| R255Q, K326E | CH2 | ↑ 2x | N/C | 0.79 |
| K218R, G281D, G385R | H, CH2, CH3 | ↑3.5x | N/C | 0.67 |
| L398V | CH3 | ↑1.5x | N/C | |
| P247L, A330T, S440G | CH2, CH3 | ↑0.75x | ↓ 0.25x | |
| V284A, F372L | CH2, CH3 | 1x | N/C | |
| T335N, P387S, H435Q | CH2, CH3 | 1.25x | N/C | |
| P247L, A431V, S442F | CH2, CH3 | 1x | N/C | |
| Increased Binding to FcγRIIIA and FcγRIIB | | | | |
| P343S, P353L, S375I, S383N | CH3 | ↑ 0.5x | ↑ 6x | |
| T394M, V397M | CH3 | ↑0.5x | ↑ 3x | |
| E216D, E345K, S375I | H, CH2, CH3 | ↑ 0.5x | ↑ 4x | |
| K334N, | CH2 | ↑0.5x | ↑ 2x | |
| K288N, A330S, P396L | CH2, CH3 | ↑0.5x | ↑ 9x | |
| P247L, E389G | CH2, CH3 | ↑1.5x | ↑ 9x | |
| K222N, T335N, K370E, A378V, T394M | H, CH2, CH3 | ↑ 1x | ↑ 7x | |
| G316D, A378V, D399E | CH2, CH3 | ↑1.5x | ↑ 14x | 2.24 |
| N315I, V379M, T394M | CH2, CH3 | ↑ 1x | ↑ 9x | 1.37 |
| K290T, G371D, | CH2, CH3 | ↑ 0.25x | ↑ 6x | |
| P247L, L398Q | CH2, CH3 | ↑ 1.25x | ↑ 10x | |
| K326Q, K334E, T359N, T366S | CH2,CH3 | ↑ 1.5x | ↑ 5x | |
| S400P | CH3 | ↑ 1x | ↑ 6x | |
| P247L, I377F | CH2, CH3 | ↑ 1x | ↑ 5x | |
| A378V, N390I, V422I | CH3 | ↑0.5x | ↑ 5x | |
| K326E, G385E | CH2, CH3 | ↑0.5x | ↑15x | |
| V282E, V369I, L406F | CH2, CH3 | ↑ 0.5x | ↑ 7x | |
| V397M, T411A, S415N | CH3 | ↑ 0.25x | ↑5x | |
| T223I, T256S, L406F | H, CH2, CH3 | ↑ 0.25x | ↑ 6x | |
| S298N, S407R | CH2, CH3 | ↑0.5x | ↑ 7x | |
| K246R, S298N, I377F | CH2, CH3 | ↑ 1x | ↑ 5x | |
| S407I | CH3 | ↑ 0.5x | ↑4x | |
| F372Y | CH3 | ↑0.5x | ↑4x | |
| L235P, V382M, S304G, V305I, V323I | CH2, CH3 | ↑ 2x | ↑ 2x | |
| P247L, W313R, E388G | CH2, CH3 | ↑1.5x | ↑1x | |
| D221Y, M252I, A330G, A339T, T359N, V422I, H433L | H, CH2, CH3 | ↑2.5x | ↑ 6x | |
| E258D, N384K | CH2, CH3 | ↑1.25x | ↑4x | |
| F241L, E258G | CH2 | ↑ 2x | ↑ 2.5x | −0.08 |
| K370N, S440N | CH3 | ↑1x | ↑ 3.5x | |
| K317N, F423-deleted | CH2, CH3 | ↑ 2.5x | ↑ 7x | 0.18 |
| F243I, V379L, G420V | CH2, CH3 | ↑ 2.5x | ↑3.5x | 1.35 |
| P227S, K290E | H, CH2 | ↑ 1x | ↑ 0.5x | |
| A231V, Q386H, V412M | CH2, CH3 | ↑1.5x | ↑ 6x | |
| T215P, K274N, A287G, K334N, L365V, P396L | H, CH2, CH3 | ↑2x | ↑ 4x | |
| Increased Binding to FcγRIIB but not FcγRIIIA | | | | |
| K334E, E380D | CH2, CH3 | N/C | ↑4.5x | |
| T366N | CH3 | N/C | ↑ 5x | |
| P244A, K326I, C367R, S375I, K447T | CH2, CH3 | N/C | ↑ 3x | |
| C229Y, A287T, V379M, P396L, L443V | H, CH2, CH3 | ↓ 0.25x | ↑10x | |
| Decreased binding to FcγRIIIA and FcγRIIB | | | | |
| R301H, K340E, D399E | CH2, CH3 | ↓ 0.50x | ↓ 0.25x | |
| K414N | CH3 | ↓ 0.25x | N/B | |
| P291S, P353Q | CH2, CH3 | ↓ 0.50x | ↓ 0.25x | |
| V240I, V281M | CH2 | ↓ 0.25x | ↓ 0.25x | |
| P232S, S304G | CH2 | N/B | N/B | |
| E269K, K290N, Q311R, H433Y | CH2, CH3 | N/B | N/B | |
| M352L | CH3 | N/B | N/B | |
| E216D, K334R, S375I | H, CH2,CH3 | N/B | N/B | |
| P247L, L406F | CH2, CH3 | N/B | N/B | |
| T335N, P387S, H435Q | CH2, CH3 | N/B | N/B | |

TABLE 10-continued

MUTATIONS IDENTIFIED IN THE Fc REGION

| Mutations | Domain | Binding FcγRIIIA (ELISA) | Binding to FcγRIIB (ELISA) | Jan. 4, 2020 ADCC (Relative Lysis (Mut/Wt) |
|---|---|---|---|---|
| T225S | CH2 | ↓ 0.25x | ↓ 0.50x | |
| D399E, M428L | CH3 | ↓ 0.50x | ↓ 0.50x | |
| K246I, Q362H, K370E | CH2, CH3 | N/B | ↓ 0.50x | |
| K334E, E380D, G446V | CH2, CH3 | N/B | N/B | |
| I377N | CH3 | ↓ 0.50x | N/B | |
| V303I, V369F, M428L | CH2, CH3 | N/B | N/B | |
| L251F, F372L | CH2, CH3 | N/B | N/B | |
| K246E, V284M, V308A | CH2, CH3 | N/B | N/B | |
| D399E, G402D | CH3 | N/B | N/B | |
| D399E, M428L | CH3 | N/B | N/B | |
| FcγRIIB depletion/FcγRIIIA selection: Naïve Fc library. | | | | |
| E293V, Q295E, A327T | CH2 | ↑0.4x | ↓ or N/B | 4.29 |
| Y319F, P352L, P396L | CH2, CH3 | ↑3.4x | ↑2x | 1.09 |
| K392T, P396L | CH3 | ↑ 4.5x | ↑ 2.5x | 3.07 |
| K248M | CH2 | ↑0.4x | ↓ or N/B | 4.03 |
| H268N, P396L | CH2, CH3 | ↑ 2.2x | ↑ 4.5x | 2.24 |
| Solution competition 40X FcγRIIB-G2:P396L Library | | | | |
| D221E, D270E, V308A, Q311H, P396L, G402D | | ↑3.6x | ↑0.1x | 3.17 |
| Equilibrium Screen: 0.8 μM FcγRIIIA monomer: P396L library | | | | |
| K290T, N390I, P396L | CH2, CH3 | ☐ ↑2.8x | ↑ 6.1x | 1.93 |
| K326I, P396L | CH2, CH3 | ☐ ↑2.9x | ↑ 5.9x | 1.16 |
| H268D, P396L | CH2, CH3 | ↑3.8x | ↑13.7x | 2.15 |
| K210M, P396L | CH1, CH3 | ↑1.9x | ↑ 4.6x | 2.02 |
| L358P, P396L | CH3 | ↑1.9x | ↑ 4.2x | 1.58 |
| K288R, T307A, K344E, P396L | CH2, CH3 | ↑ 4.1x | ↑ 2.3x | 3.3 |
| V273I, K326E, L328I, P396L | CH2, CH3 | ↑ 1.3x | ↑10.8x | 0.78 |
| K326I, S408N, P396L | CH2, CH3 | ↑4x | ↑ 9.3x | 1.65 |
| K334N, P396L | CH2, CH3 | ↑3.1x | ↑ 3x | 2.43 |
| V379M, P396L | CH3 | ↑1.9x | ↑5.6x | 2.01 |
| P227S, P396L | CH2, CH3 | ↑1.5x | ↑ 4x | 2.01 |
| P217S, P396L | H, CH3 | ↑1.6x | ↑4.5x | 2.04 |
| K261N, K210M, P396L | CH2, CH3 | ↑ 2x | ↑ 4.2x | 2.06 |
| Kinetic Screen: 0.8 μM, 1' with cold 8 μM FcγRIIIA: P396L Library | | | | |
| term is M, P396L | CH3 | ↑1.9x | ↑ 7.2x | 3.09 |
| Q419H, P396L | CH3 | ↑ 2x | ↑ 6.9x | 2.24 |
| K370E, P396L | CH3 | ↑2x | ↑6.6x | 2.47 |
| L242F, P396L | CH2, CH3 | ↑ 2.5x | ↑ 4.1x | 2.4 |
| F243L, V305I, A378D, F404S, P396L | CH2, CH3 | ↑1.6x | ↑5.4x | 3.59 |
| R255L, P396L | CH2, CH3 | ↑1.8x | ↑ 6x | 2.79 |
| V240A, P396L | CH2, CH3 | ↑ 1.3x | ↑ 4.2x | 2.35 |
| T250S, P396L | CH2, CH3 | ↑ 1.5x | ↑6.8x | 1.60 |
| P247S, P396L | CH2, CH3 | ↑ 1.2x | ↑ 4.2x | 2.10 |
| K290E, V369A, T393A, P396L | CH2, CH3 | ↑1.3x | ↑ 6.7x | 1.55 |
| K210N, K222I, K320M, P396L | H, CH2, CH3 | ↑ 2.7x | ↑ 8.7x | 1.88 |
| L410H, P396L | CH3 | ↑ 1.7x | ↑ 4.5x | 2.00 |
| Q419L, P396L | CH3 | ↑ 2.2x | ↑ 6.1x | 1.70 |
| V427A, P396L | CH3 | ↑ 1.9x | ↑4.7x | 1.67 |
| P217S, V305I, I309L, N390H, P396L | H, CH2, CH3 | ↑2x | ↑ 7x | 1.54 |
| E258D, P396L | CH2, CH3 | ↑ 1.9x | ↑ 4.9x | 1.54 |
| N384K, P396L | CH3 | ↑ 2.2x | ↑5.2x | 1.49 |
| V323I, P396L | CH2, CH3 | ↑ 1.1x | ↑ 8.2x | 1.29 |
| K246N, Q419R, P396L | CH2, CH3 | ↑1.1x | ↑ 4.8x | 1.10 |
| P217A, T359A, P396L | H, CH2, CH3 | ↑1.5x | ↑ 4.8x | 1.17 |
| P244H, P396L | CH2, CH3 | ↑2.5x | ↑ 4x | 1.40 |
| V215I, K290V, P396L | H, CH2, CH3 | ↑2.2x | ↑ 4.6x | 1.74 |
| F275L, Q362H, N384K, P396L | CH2, CH3 | ↑ 2.2x | ↑ 3.7x | 1.51 |
| V305L, P396L | CH2, CH3 | ↑1.3x | ↑ 5.5x | 1.50 |
| S400F, P396L | CH3 | ↑1.5x | ↑4.7x | 1.19 |
| V303I, P396L | CH3 | ↑1.1x | ↑ 4x | 1.01 |
| FcγRIIB depletion FcγRIIIA 158V solid phase selection: Naïve Library | | | | |
| A330V, H433Q, V427M | CH2, CH3 | NT | NT | NT |
| V263Q, E272D, Q419H | CH2, CH3 | NT | NT | NT |
| N276Y, T393N, W417R | CH2, CH3 | NT | NT | NT |

TABLE 10-continued

MUTATIONS IDENTIFIED IN THE Fc REGION

| Mutations | Domain | Binding FcγRIIIA (ELISA) | Binding to FcγRIIB (ELISA) | ADCC (Relative Lysis (Mut/Wt) |
|---|---|---|---|---|
| V282L, A330V, H433Y, T436R | CH2, CH3 | NT | NT | NT |
| A330V, Q419H | CH2, CH3 | NT | NT | NT |
| V284M, S298N, K334E, R355W | CH2, CH3 | NT | NT | NT |
| A330V, G427M, K438R | CH2, CH3 | NT | NT | NT |
| S219T, T225K, D270E, K360R | CH2, CH3 | NT | NT | NT |
| K222E, V263Q, S298N | CH2 | NT | NT | NT |
| V263Q, E272D | CH2 | NT | NT | NT |
| R292G | CH2 | NT | NT | NT |
| S298N | CH2 | NT | NT | NT |
| E233G, P247S, L306P | CH2 | NT | NT | NT |
| D270E | CH2 | NT | NT | NT |
| S219T, T225K, D270E | CH2 | NT | NT | NT |
| K326E, A330T | CH2 | NT | NT | NT |
| E233G | CH2 | NT | NT | NT |
| S254T, A330V, N361D, P243L | CH2, CH3 | NT | NT | NT |
| FcγRIIB depletion FcγRIIIA 158F solid phase selection: Naïve Library 158F by FACS top 0.2% | | | | |
| V284M, S298N, K334E, R355W R416T | CH2, CH3 | NT | NT | |
| FcγRIIB depletion FcgRIIA 131H solid phase selection: Naïve Library | | | | |
| R292P, V305I | CH2, CH2 | NT | NT | |
| D270E, G316D, R416G | CH2, CH3 | NT | NT | |
| V284M, R292L, K370N | CH2, CH3 | NT | NT | |
| R292P, V305I, F243L | CH2 | NT | NT | |

In preferred embodiments, the invention provides modified immunoglobulin molecules (e.g., antibodies) with variant Fc regions, having one or more amino acid modifications, which one or more amino acid modifications increase the affinity of the molecule for FcγRIIIA and/or FcγRIIA. Such immunoglobulins include IgG molecules that naturally contain FcγR binding regions (e.g., FcγRIIIA and/or FcγRIIB binding region), or immunoglobulin derivatives that have been engineered to contain an FcγR binding region (e.g., FcγRIIIA and/or FcγRIIB binding region). The modified immunoglobulins of the invention include any immunoglobulin molecule that binds, preferably, immunospecifically, i.e., competes off non-specific binding as determined by immunoassays well known in the art for assaying specific antigen-antibody binding, an antigen and contains an FcγR binding region (e.g., a FcγRIIIA and/or FcγRIIB binding region). Such antibodies include, but are not limited to, polyclonal, monoclonal, bi-specific, multi-specific, human, humanized, chimeric antibodies, single chain antibodies, Fab fragments, F(ab')$_2$ fragments, disulfide-linked Fvs, and fragments containing either a VL or VH domain or even a complementary determining region (CDR) that specifically binds an antigen, in certain cases, engineered to contain or fused to an FcγR binding region.

In some embodiments, the molecules of the invention comprise portions of an Fc region. As used herein the term "portion of an Fc region" refers to fragments of the Fc region, preferably a portion with effector activity and/or FcγR binding activity (or a comparable region of a mutant lacking such activity). The fragment of an Fc region may range in size from 5 amino acids to the entire Fc region minus one amino acid. The portion of an Fc region may be missing up to 10, up to 20, up to 30 amino acids from the N-terminus or C-terminus.

The IgG molecules of the invention are preferably IgG1 subclass of IgGs, but may also be any other IgG subclasses of given animals. For example, in humans, the IgG class includes IgG1, IgG2, IgG3, and IgG4; and mouse IgG includes IgG1, IgG2a, IgG2b, IgG2c and IgG3.

The immunoglobulins (and other polypeptides used herein) may be from any animal origin including birds and mammals. Preferably, the antibodies are human, rodent (e.g., mouse and rat), donkey, sheep, rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example, in U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide or may be specific for heterologous epitopes, such as a heterologous polypeptide or solid support material. See, e.g., PCT publications WO 93/17715; WO 92/08802; WO 91/00360; WO 92/05793; Tuft, et al., *J. Immunol.*, 147:60-69, 1991; U.S. Pat. Nos. 4,474,893; 4,714,681; 4,925,648; 5,573,920; 5,601,819; Kostelny et al., *J. Immunol.*, 148:1547-1553, 1992.

Multispecific antibodies have binding specificities for at least two different antigens. While such molecules normally will only bind two antigens (i.e. bispecific antibodies, BsAbs), antibodies with additional specificities such as trispecific antibodies are encompassed by the instant invention. Examples of BsAbs include without limitation those with one arm directed against a tumor cell antigen and the other arm directed against a cytotoxic molecule.

Methods for making bispecific antibodies are known in the art. Traditional production of full length bispecific antibodies is based on the coexpression of two immunoglobulin heavy chain-light chain pairs, where the two chains have different specificities (Millstein et al., Nature, 305:537-539 (1983); which is incorporated herein by reference in its entirety). Because of the random assortment of immunoglobulin heavy and light chains, these hybridomas (quadromas) produce a potential mixture of 10 different antibody molecules, of which only one has the correct bispecific structure. Purification of the correct molecule, which is usually done by affinity chromatography steps, is rather cumbersome, and the product yields are low. Similar procedures are disclosed in WO 93/08829, and in Traunecker et al., EMBO J., 10:3655-3659 (1991).

According to a different approach, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2, and CH3 regions. It is preferred to have the first heavy-chain constant region (CH1) containing the site necessary for light chain binding, present in at least one of the fusions. DNAs encoding the immunoglobulin heavy chain fusions and, if desired, the immunoglobulin light chain, are inserted into separate expression vectors, and are co-transfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when, the expression of at least two polypeptide chains in equal ratios results in high yields or when the ratios are of no particular significance.

In a preferred embodiment of this approach, the bispecific antibodies are composed of a hybrid immunoglobulin heavy chain with a first binding specificity in one arm, and a hybrid immunoglobulin heavy chain-light chain pair (providing a second binding specificity) in the other arm. It was found that this asymmetric structure facilitates the separation of the desired bispecific compound from unwanted immunoglobulin chain combinations, as the presence of an immunoglobulin light chain in only one half of the bispecific molecule provides for a facile way of separation. This approach is disclosed in WO 94/04690. For further details of generating bispecific antibodies see, for example, Suresh et al., Methods in Enzymology, 121:210 (1986). According to another approach described in WO96/27011, a pair of antibody molecules can be engineered to maximize the percentage of heterodimers which are recovered from recombinant cell culture. The preferred interface comprises at least a part of the CH3 domain of an antibody constant domain. In this method, one or more small amino acid side chains from the interface of the first antibody molecule are replaced with larger side chains (e.g. tyrosine or tryptophan). Compensatory "cavities" of identical or similar size to the large side chain(s) are created on the interface of the second antibody molecule by replacing large amino acid side chains with smaller ones (e.g. alanine or threonine). This provides a mechanism for increasing the yield of the heterodimer over other unwanted end-products such as homodimers.

Bispecific antibodies include cross-linked or "heteroconjugate" antibodies. For example, one of the antibodies in the heteroconjugate can be coupled to avidin, the other to biotin. Such antibodies have, for example, been proposed to target immune system cells to unwanted cells (U.S. Pat. No. 4,676,980), and for treatment of HIV infection (WO 91/00360, WO 92/200373, and EP 03089). Heteroconjugate antibodies may be made using any convenient cross-linking methods. Suitable cross-linking agents are well known in the art, and are disclosed in U.S. Pat. No. 4,676,980, along with a number of cross-linking techniques.

Antibodies with more than two valencies are contemplated. For example, trispecific antibodies can be prepared. See, e.g., Tutt et al. J. Immunol. 147: 60 (1991), which is incorporated herein by reference.

The antibodies of the invention include derivatives that are otherwise modified, i.e., by the covalent attachment of any type of molecule to the antibody such that covalent attachment does not prevent the antibody from binding antigen and/or generating an anti-idiotypic response. For example, but not by way of limitation, the antibody derivatives include antibodies that have been modified, e.g., by glycosylation, acetylation, pegylation, phosphorylation, amidation, derivatization by known protecting/blocking groups, proteolytic cleavage, linkage to a cellular ligand or other protein, etc. Any of numerous chemical modifications may be carried out by known techniques, including, but not limited to, specific chemical cleavage, acetylation, formylation, metabolic synthesis of tunicamycin, etc. Additionally, the derivative may contain one or more non-classical amino acids.

For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a constant region derived from a human immunoglobulin. Methods for producing chimeric antibodies are known in the art. See e.g., Morrison, *Science,* 229:1202, 1985; Oi et al., *BioTechniques,* 4:214 1986; Gillies et al., *J. Immunol. Methods,* 125:191-202, 1989; U.S. Pat. Nos. 5,807,715; 4,816,567; and 4,816,397, which are incorporated herein by reference in their entireties. Humanized antibodies are antibody molecules from non-human species that bind the desired antigen having one or more complementarity determining regions (CDRs) from the non-human species and framework regions and constant domains from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. See, e.g., Queen et al., U.S. Pat. No. 5,585,089; Riechmann et al., Nature, 332:323, 1988, which are incorporated herein by reference in their entireties. Antibodies can be humanized using a variety of techniques known in the art including, for example, CDR-grafting (EP 239,400; PCT publication WO 91/09967; U.S. Pat. Nos. 5,225,539; 5,530, 101 and 5,585,089), veneering or resurfacing (EP 592,106; EP 519,596; Padlan, *Molecular Immunology,* 28(4/5):489-498, 1991; Studnicka et al., *Protein Engineering,* 7(6):805-814, 1994; Roguska et al., *Proc Natl. Acad. Sci. USA,* 91:969-973, 1994), and chain shuffling (U.S. Pat. No. 5,565, 332), all of which are hereby incorporated by reference in their entireties. Humanized antibodies may be generated using any of the methods disclosed in U.S. Pat. No. 5,693, 762 (Protein Design Labs), U.S. Pat. No. 5,693,761, (Protein Design Labs) U.S. Pat. No. 5,585,089 (Protein Design Labs), U.S. Pat. No. 6,180,370 (Protein Design Labs), and U.S. Publication Nos. 20040049014, 200300229208, each of which is incorporated herein by reference in its entirety.

Completely human antibodies are particularly desirable for therapeutic treatment of human patients. Human antibodies can be made by a variety of methods known in the art including phage display methods described above using antibody libraries derived from human immunoglobulin sequences. See U.S. Pat. Nos. 4,444,887 and 4,716,111; and PCT publications WO 98/46645; WO 98/50433; WO 98/24893; WO 98/16654; WO 96/34096; WO 96/33735; and WO 91/10741, each of which is incorporated herein by reference in its entirety.

Human antibodies can also be produced using transgenic mice which are incapable of expressing functional endogenous immunoglobulins, but which can express human immunoglobulin genes. For an overview of this technology for producing human antibodies, see Lonberg and Huszar, *Int. Rev. Immunol.*, 13:65-93, 1995. For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entireties. In addition, companies such as Abgenix, Inc. (Freemont, Calif.), Medarex (NJ) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope (Jespers et al., *Bio/technology*, 12:899-903, 1988).

The invention encompasses engineering human or humanized therapeutic antibodies (e.g., tumor specific monoclonal antibodies) in the Fc region, by modification (e.g., substitution, insertion, deletion) of at least one amino acid residue, which modification increases the affinity of the Fc region for FcγRIIIA and/or FcγRIIA. In another embodiment, the invention relates to engineering human or humanized therapeutic antibodies (e.g., tumor specific monoclonal antibodies) in the Fc region, by modification of at least one amino acid residue, which modification increases the affinity of the Fc region for FcγRIIIA and/or FcγRIIA and further decreases the affinity of the Fc region for FcγRIIB. The engineered therapeutic antibodies may further have an enhanced effector function, e.g., enhanced ADCC activity, phagocytosis activity, etc., as determined by standard assays known to those skilled in the art.

In a specific embodiment, the invention encompasses engineering a humanized monoclonal antibody specific for Her2/neu protooncogene (e.g., Ab4D5 humanized antibody as disclosed in Carter et al., 1992, *Proc. Natl. Acad. Sci. USA* 89:4285-9) by modification (e.g., substitution, insertion, deletion) of at least one amino acid residue which modification increases the affinity of the Fc region for FcγRIIIA and/or FcγRIIA. In another specific embodiment, modification of the humanized Her2/neu monoclonal antibody may also further decrease the affinity of the Fc region for FcγRIIB. In yet another specific embodiment, the engineered humanized monoclonal antibodies specific for Her2/neu may further have an enhanced effector function as determined by standard assays known in the art and disclosed and exemplified herein.

In another specific embodiment, the invention encompasses engineering a mouse human chimeric anti-CD20 monoclonal antibody, 2H7 by modification (e.g., substitution, insertion, deletion) of at least one amino acid residue which modification increases the affinity of the Fc region for FcγRIIIA and/or FcγRIIA. In another specific embodiment, modification of the anti-CD20 monoclonal antibody, 2H7 may also further decrease the affinity of the Fc region for FcγRIIB. In yet another specific embodiment, the engineered anti-CD20 monoclonal antibody, 2H7 may further have an enhanced effector function as determined by standard assays known in the art and disclosed and exemplified herein.

In another specific embodiment, the invention encompasses engineering an antibody that binds A33, CD5, CD11c, CD19, CD20, CD22, CD23, CD27, CD40, CD45, CD79a, CD79b, CD103, CTLA4, ErbB1, ErbB3, ErbB4, VEGF receptor, TNF-α receptor, TNF-β receptor, or TNF-γ receptor (particularly a humanized or chimerized form of the antibody) by modification (e.g., substitution, insertion, deletion) of at least one amino acid residue which modification increases the affinity of the Fc region for FcγRIIIA and/or FcγRIIA. In another specific embodiment, modification of the antibody that binds A33, CD5, CD11c, CD19, CD20, CD22, CD23, CD27, CD40, CD45, CD79a, CD79b, CD103, CTLA4, ErbB1, ErbB3, ErbB4, VEGF receptor, TNF-α receptor, TNF-β receptor, or TNF-γ receptor may also further decrease the affinity of the Fc region for FcγRIIB. In yet another specific embodiment, the antibody that binds A33, CD5, CD11c, CD19, CD20, CD22, CD23, CD27, CD40, CD45, CD79a, CD79b, CD103, CTLA4, ErbB1, ErbB3, ErbB4, VEGF receptor, TNF-α receptor, TNF-β receptor, or TNF-γ receptor may further have an enhanced effector function as determined by standard assays known in the art and disclosed and exemplified herein.

In certain embodiments, the invention encompasses engineering an antibody (or chimeric, humanized or other engineered versions thereof), comprising the heavy chain variable domain and/or light chain variable domain of the monoclonal antibody produced by clone 2B6, 3H7, 8B5.4.3, 1D5, 2E1, 2H9, 2D11 or 1F2 having ATCC accession numbers PTA-4591, PTA-4592, PTA-7610, PTA-5958, PTA-5961, PTA-5962, PTA-5960, and PTA-5959, respectively (deposited at ATCC, 10801 University Boulevard, Manassas, Va. 02209-2011, all of which are incorporated herein by reference). In a specific embodiment, the invention encompasses engineering a humanized antibody comprising the heavy chain variable and/or light chain variable domains of 2B6, 3H7 or 8B5.3.4. In another specific embodiment, the invention encompasses engineering a humanized antibody comprising the CDRs of 2B6, 3H7 or 8B5.3.4. In another specific embodiment, the invention encompasses engineering a humanized antibody comprising the heavy chain variable domain having the amino acid sequence of SEQ ID NO: 1, SEQ ID NO:2 or SEQ ID NO:3 and the light chain variable domain having the amino acid sequence of SEQ ID NO: 4, SEQ ID NO:5, SEQ ID NO:6, SEQ ID NO:7 or SEQ ID NO: 8. In another specific embodiment, the invention encompasses engineering an anti-FcγRIIB antibody comprising the heavy chain variable domain having the amino acid sequence of SEQ ID NO:13 and the light chain variable domain having the amino acid sequence of SEQ ID NO:14.

In another specific embodiment, the invention encompasses engineering a humanized anti-FcγRIIB antibody comprising the heavy chain variable domain having the amino acid sequence of SEQ ID NO:3 and the light chain variable domain having the amino acid sequence of SEQ ID NO:8. In another specific embodiment, the invention encompasses engineering a humanized anti-FcγRIIB antibody comprising the heavy chain variable domain having the amino acid sequence of SEQ ID NO:9 and the light chain variable domain having the amino acid sequence of SEQ ID NO:10.

In another specific embodiment, the invention encompasses engineering an anti-FcγRIIB antibody including but not limited to any of the antibodies disclosed in U.S. Provisional Application No. 60/403,266 filed on Aug. 12, 2002, U.S. application Ser. No. 10/643,857 filed on Aug. 14, 2003, U.S. Provisional Application No. 60/562,804 filed on Apr. 16, 2004, U.S. Provisional Application No. 60/582,044 filed on Jun. 21, 2004, U.S. Provisional Application No. 60/582,045 filed on Jun. 21, 2004, U.S. Provisional Application No. 60/636,663 filed on Dec. 15, 2004 and U.S. application Ser. No. 10/524,134 filed Feb. 11, 2005 by modification (e.g., substitution, insertion, deletion) of at least one amino acid residue which modification increases the affinity of the Fc region for FcγRIIIA and/or FcγRIIA. In another specific embodiment, the invention encompasses engineering a humanized anti-FcγRIIB antibody including but not limited to any of the antibodies disclosed in U.S. Provisional Application No. 60/569,882 filed on May 10, 2004, U.S. Provisional Application No. 60/582,043 filed on Jun. 21, 2004 and U.S. application Ser. No. 11/126,978, filed on May 10, 2005 by modification (e.g., substitution, insertion, deletion) of at least one amino acid residue which modification increases the affinity of the Fc region for FcγRIIIA and/or FcγRIIA. Each of the above mentioned applications is incorporated herein by reference in its entirety. Examples of anti-FcγRIIB antibodies, which may or may not be humanized, that may be engineered in accordance with the methods of the invention are 2B6 monoclonal antibody having ATCC accession number PTA-4591 and 3H7 having ATCC accession number PTA-4592, 1D5 monoclonal antibody having ATCC accession number PTA-5958, 1F2 monoclonal antibody having ATCC accession number PTA-5959, 2D11 monoclonal antibody having ATCC accession number PTA-5960, 2E1 monoclonal antibody having ATCC accession number PTA-5961, 8B5.3.4 having ATCC accession number PTA-7610, and 2H9 monoclonal antibody having ATCC accession number PTA-5962 (all deposited at 10801 University Boulevard, Manassas, Va. 02209-2011), which are incorporated herein by reference. In another specific embodiment, modification of the anti-FcγRIIB antibody may also further decrease the affinity of the Fc region for FcγRIIB. In yet another specific embodiment, the engineered anti-FcγRIIB antibody may further have an enhanced effector function as determined by standard assays known in the art and disclosed and exemplified herein.

In a specific embodiment, the invention encompasses engineering an anti-FcγRIIB antibody according to methods of the present invention that comprises one or more complementarily determining regions (CDRs), preferably all 6 CDRs, of the antibody produced by clone 2B6, 3H7, or 8B5.3.4 with ATCC accession numbers PTA-4591, PTA-4592, and PTA-7610, respectively (e.g., the heavy chain CDR3). In a specific embodiment, an anti-FcγRIIB antibody engineered according to methods of the invention comprises one or more complementarily determining regions (CDRs), preferably all 6 CDRs, of the antibody produced by clone 1D5, 2E1, 2H9, 2D11, and 1F2 having ATCC Accession numbers, PTA-5958, PTA-5961, PTA-5962, PTA-5960, and PTA-5959, respectively (e.g., the heavy chain CDR3). In another embodiment, an anti-FcγRIIB antibody engineered according to methods of the invention binds to the same epitope as the mouse monoclonal antibody produced from clone 2B6, 3H7, or 8B5.3.4 with ATCC accession numbers PTA-4591, PTA-4592, and PTA-7610, respectively and/or competes with the mouse monoclonal antibody produced from clone 2B6, 3H7, or 8B5.3.4 with ATCC accession numbers PTA-4591, PTA-4592, and PTA-7610, respectively as determined, e.g., in an ELISA assay or other appropriate competitive immunoassay, and also binds FcγRIIB with a greater affinity than said antibody or a fragment thereof binds FcγRIIA. In another embodiment, an anti-FcγRIIB antibody engineered according to methods of the invention binds to the same epitope as the mouse monoclonal antibody produced from clone 1D5, 2E1, 2H9, 2D11, and 1F2 having ATCC Accession numbers, PTA-5958, PTA-5961, PTA-5962, PTA-5960, and PTA-5959, respectively, and/or competes with the mouse monoclonal antibody produced from clone 1D5, 2E1, 2H9, 2D11, and 1F2 having ATCC Accession numbers, PTA-5958, PTA-5961, PTA-5962, PTA-5960, and PTA-5959, respectively, as determined, e.g., in an ELISA assay or other appropriate competitive immunoassay, and also binds FcγRIIB, via its variable region, with a greater affinity than said antibody or a fragment thereof binds FcγRIIA.

The present invention also encompasses engineering an anti-FcγRIIB antibody comprising a heavy chain variable domain and/or light chain variable domain amino acid sequence that is at least 45%, at least 50%, at least 55%, at least 60%, at least 65%, at least 70%, at least 75%, at least 80%, at least 85%, at least 90%, at least 95%, or at least 99% identical to the amino acid sequence of the heavy chain variable domain and/or light chain variable domain of the mouse monoclonal antibody produced by clone 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively. The present invention further encompasses the engineering of anti-FcγRIIB antibodies comprising an amino acid sequence of one or more CDRs that is at least 45%, at least 50%, at least 55%, at least 60%, at least 65%, at least 70%, at least 75%, at least 80%, at least 85%, at least 90%, at least 95%, or at least 99% identical to the amino acid sequence of one or more CDRs of the mouse monoclonal antibody produced by clone 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively. The determination of percent identity of two amino acid sequences can be determined by any method known to one skilled in the art, including BLAST protein searches.

The present invention also encompasses the the engineering of one or more anti-FcγRIIB antibodies comprising one or more variable domains encoded by a nucleotide sequence that hybridizes to the nucleotide sequence of one or more variable domains of a mouse monoclonal antibody produced by clone 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively, under stringent conditions. In a preferred embodiment, the invention encompasses engineering one or more anti-FcγRIIB antibodies comprising a variable light chain and/or variable heavy chain domain encoded by a nucleotide sequence that hybridizes under stringent conditions to the nucleotide sequence of the variable light chain and/or variable heavy chain domain of the mouse monoclonal antibody produced by clone 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively, under stringent conditions. In another preferred embodiment, the invention provides engineering anti-FcγRIIB antibodies comprising one or more CDRs encoded by a nucleotide sequence that hybridizes under stringent conditions to the nucleotide sequence of one or more CDRs of the mouse monoclonal antibody produced by clone 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively. Stringent hybridization conditions include, but are not limited to, hybridization to filter-bound DNA in 6× sodium chloride/sodium citrate (SSC) at about 45° C. followed by one or more washes in 0.2×SSC/0.1% SDS at about 50-65° C., highly stringent conditions such as hybridization to filter-bound DNA in 6×SSC at about 45° C. followed by one or more washes in 0.1×SSC/0.2% SDS at about 60° C., or any other stringent hybridization conditions known to those skilled in the art (see, for example, Ausubel, F. M. et al., eds. 1989 Current Protocols in Molecular Biology, vol. 1, Green Publishing Associates, Inc. and John Wiley and Sons, Inc., NY at pages 6.3.1 to 6.3.6 and 2.10.3, incorporated herein by reference).

In a preferred embodiment, the engineered antibodies of the invention are humanized by any method known in the art or described herein and/or comprise the CDR regions of a humanized FcγRIIB specific antibody or humanized CD20 specific antibody, whrein said CDRs are derived from a murine antibody specific for FcγRIIB or CD20, respectively. In some embodiments, the humanized antibodies described herein comprise alterations, including but not limited to amino acid deletions, insertions, modifications, of the acceptor antibody, i.e., human, heavy and/or light chain variable domain framework regions that are necessary for retaining binding specificity of the donor monoclonal antibody. In some embodiments, the framework regions of the humanized antibodies described herein do not necessarily consist of the precise amino acid sequence of the framework region of a natural occurring human antibody variable region, but contains various alterations, including but not limited to amino acid deletions, insertions, modifications that alter the property of the humanized antibody, for example, improve the binding properties of a humanized antibody variable region specific for the same target as the murine FcγRIIB or CD20 specific antibody. In most preferred embodiments, a minimal number of alterations are made to the framework region in order to avoid large-scale introductions of non-human framework residues and to ensure minimal immunogenicity of the humanized antibody of the invention in humans. The donor monoclonal antibody is preferably a monoclonal antibody produced by clones 2B6, 3H7, 8B5.3.4, 1D5, 2E1, 2H9, 2D11, or 1F2 (having ATCC accession numbers PTA-4591, PTA-4592, PTA-7610, PTA-5958, PTA-5961, PTA-5962, PTA-5960, and PTA-5959, respectively) which bind FcγRIIB, or the monoclonal antibody is a CD20 antibody, such as rituximab or 2H7.

In a specific embodiment, the invention encompasses engineering a CDR-grafted antibody that comprises a heavy chain variable region domain comprising framework residues of the recipient antibody and residues from the donor monoclonal antibody, which specifically binds FcγRIIB, e.g., monoclonal antibody produced from clones 2B6, 3H7, 8B5.3.4, 1D5, 2E1, 2H9, 2D11, or 1F2 having ATCC accession numbers PTA-4591, PTA-4592, PTA-7610, PTA-5958, PTA-5961, PTA-5962, PTA-5960, and PTA-5959, respectively. In another specific embodiment, the invention encompasses engineering a CDR-grafted antibody that comprises a light chain variable region domain comprising framework residues of the recipient antibody and residues from the donor monoclonal antibody, which specifically binds FcγRIIB, e.g., monoclonal antibody produced from clones 2B6, 3H7, 8B5.3.4, 1D5, 2E1, 2H9, 2D11, or 1F2.

Preferably the FcγRIIB humanized antibodies bind the extracellular domain of native human FcγRIIB. The humanized anti-FcγRIIB antibodies of the combinations can have a heavy chain variable region comprising the amino acid sequence of CDR1 (SEQ ID NO: 15 or SEQ ID NO: 16) and/or CDR2 (SEQ ID NO:17 or SEQ ID NO:18) and/or CDR3 (SEQ ID NO: 19 or SEQ ID NO:20) and/or a light chain variable region comprising the amino acid sequence of CDR1 (SEQ ID NO:21 or SEQ ID NO:22) and/or a CDR2 (SEQ ID NO:23, SEQ ID NO:24, SEQ ID NO:25, or SEQ ID NO:26) and/or CDR3 (SEQ ID NO:27 or SEQ ID NO:28).

In a specific embodiment, the invention encompasses the engineering of a humanized anti-FcγRIIB antibody with the heavy chain variable domain having the amino acid sequence of SEQ ID NO:1, SEQ ID NO:2, or SEQ ID NO:3 and a light chain variable domain having the amino acid sequence of SEQ ID NO:4, SEQ ID NO:5, SEQ ID NO:6; SEQ ID NO:7 or SEQ ID NO:8.

In one specific embodiment, the invention encompasses engineering a humanized anti-FcγRIIB antibody, wherein the VH region of the FcγRIIB antibody consists of the FR segments from the human germline VH segment VH1-18 (Matsuda et al., 1998, J. Exp. Med. 188:2151062) and JH6 (Ravetch et al., 1981, Cell 27 (3 Pt. 2): 583-91), and one or more CDR regions of a 2B6 VH, having the amino acid sequence of SEQ ID NO: 1, SEQ ID NO:17, or SEQ ID NO:19. In one embodiment, the 2B6 VH has the amino acid sequence of SEQ ID NO:1, SEQ ID NO:3, or SEQ ID NO:29. In another specific embodiment, the humanized anti-FcγRIIB antibody further comprises a VL region, which consists of the FR segments of the human germline VL segment VK-A26 (Lautner-Rieske et al., 1992, Eur. J. Immunol. 22:1023-1029) and JK4 (Hieter et al., 1982, J. Biol. Chem. 257:1516-22), and one or more CDR regions of a 2B6VL, having the amino acid sequence of SEQ ID NO:21, SEQ ID NO:23, SEQ ID NO:24, SEQ ID NO:25, and SEQ ID NO:27. In one embodiment, the 2B6 VL has the amino acid sequence of SEQ ID NO:4, SEQ ID NO:5, SEQ ID NO:6; SEQ ID NO:7, SEQ ID NO:8, or SEQ ID NO:30, and optionally in combination with one of the above-referenced 2B6 VH.

In some embodiments, the anti-FcγRIIB antibody angineered in accordance with the methods of the invention has a VH chain and/or a VH domain comprising the amino acid sequence (H2B6VH-3):

(SEQ ID NO: 3)
QVQLVQSGAEVKKPGASVKVSCKASGYTFTNYWIHWVRQAPGQGLEWIGV

IDPSDTYPNYNKKFKGRVTMTVDTSTSTAYMELRSLRSDDTAVYYCARNG

DSDYYSGMDYWGQGTTVTVSS.

In some embodiments, the anti-FcγRIIB antibody angineered in accordance with the methods of the invention has a VL chain and/or VL domain comprising the amino acid sequence (H2B6VL-5):

(SEQ ID NO: 8)
EIVLTQSPDFQSVTPKEKVTFTCRTSQSIGTNIHWYQQKPDQSPKLLIKE

VSESISGVPSRFSGSGSGTDFTLTINSLEAEDAATYYCQQSNTWPFTFGG

GTKVEIK.

In some embodiments, the anti-FcγRIIB antibody angineered in accordance with the methods of the invention has a VH chain and/or VH domain comprising the amino acid sequence (H2B6VH-3):

(SEQ ID NO: 3)
QVQLVQSGAEVKKPGASVKVSCKASGYTFTNYWIHWVRQAPGQGLEWIGV

IDPSDTYPNYNKKFKGRVTMTVDTSTSTAYMELRSLRSDDTAVYYCARNG

DSDYYSGMDYWGQGTTVTVSS, (SEQ ID NO: 8)
EIVLTQSPDFQSVTPKEKVTFTCRTSQSIGTNIHWYQQKPDQSPKLLIKE

VSESISGVPSRFSGSGSGTDFTLTINSLEAEDAATYYCQQSNTWPFTFGG

GTKVEIK.

and a VL chain and/or VL domain comprising the amino acid sequence (H2B6VL-5)

(SEQ ID NO: 8)
EIVLIQSPDFQSVTPKEKVTFTCRTSQSIGTNIHWYQQKPDQSPKLLIK

EVSESISGVPSRFSGSGSGTDFTLTINSLEAEDAATYYCQQSNTWPFTF

GGGTKVEIK.

In some embodiments, the anti-FcγRIIB antibody angineered in accordance with the methods of the invention has a VH domain and/or VH chain comprising the amino acid sequence (8B5.3.4 VH, see FIG. 2):

(SEQ ID NO: 9)
EVKLEESGGGLVQPGGSMKLSCEASGFTFSDAWMDWVRQSPEKGLEWVAE

IRNKAKNHATYYAESVIGRFTISRDDSKSSVYLQMNSLRAEDTGIYYCGA

LGLDYWGQGTTLTVSS.

In some embodiments, the anti-FcγRIIB antibody angineered in accordance with the methods of the invention has a VL domain and/or VL chain comprising the amino acid sequence (8B5.3.4 VL, see FIG. 3):

(SEQ ID NO: 10)
DIQMTQSPSSLLAALGERVSLTCRASQEISGYLSWLQQKPDGTIKRLIYA

ASTLDSGVPKRFSGSESGSDYSLTISSLESEDFADYYCLQYFSYPLTFGA

GTKLELK.

In some embodiments, the anti-FcγRIIB antibody angineered in accordance with the methods of the invention has a VH domain and/or VH chain comprising the amino acid sequence (8B5.3.4 VH):

(SEQ ID NO: 9, see FIG. 2)
EVKLEESGGGLVQPGGSMKLSCEASGFTFSDAWMDWVRQSPEKGLEWVAE

IRNKAKNHATYYAESVIGRFTISRDDSKSSVYLQMNSLRAEDTGIYYCGA

LGLDYWGQGTTLIVSS, and a VL domain and or VL chain comprising the amino acid sequence (8B5.3.4 VL, see FIG. 3):

(SEQ ID NO: 10)
DIQMTQSPSSLLAALGERVSLICRASQEISGYLSWLQQKPDGTIKRLIY

AASTLDSGVPKRFSGSESGSDYSLTISSLESEDFADYYCLQYFSYPLTF

GAGTKLELK.

In another specific embodiment, the anti-FcγRIIB antibody angineered in accordance with the methods of the invention is a humanized 3H7 antibody, wherein the FcγRIIB VH region consists of the FR segments from a human germline VH segment and the CDR regions of the 3H7 VH, having the amino acid sequence of SEQ ID NO: 37. In another specific embodiment, the humanized 3H7 antibody further comprises a VL region, which consists of the FR segments of a human germline VL segment and the CDR regions of 3H7VL, having the amino acid sequence of SEQ ID NO:7.

In particular, the invention encompasses the engineering of an anti-FcγRIIB antibody wherein the antibody immunospecifically binds to an extracellular domain of native human FcγRIIB, said FcγRIIB antibody comprising (or alternatively, consisting of) CDR sequences of 2B6, 3H7, or 8B5.3.4 in any of the following combinations: a VH CDR1 and a VL CDR1; a VH CDR1 and a VL CDR2; a VH CDR1 and a VL CDR3; a VH CDR2 and a VL CDR1; VH CDR2 and VL CDR2; a VH CDR2 and a VL CDR3; a VH CDR3 and a VH CDR1; a VH CDR3 and a VL CDR2; a VH CDR3 and a VL CDR3; a VH1 CDR1, a VH CDR2 and a VL CDR1; a VH CDR1, a VH CDR2 and a VL CDR2; a VH CDR1, a VH CDR2 and a VL CDR3; a VH CDR2, a VH CDR3 and a VL CDR1, a VH CDR2, a VH CDR3 and a VL CDR2; a VH CDR2, a VH CDR2 and a VL CDR3; a VH CDR1, a VL CDR1 and a VL CDR2; a VH CDR1, a VL CDR1 and a VL CDR3; a VH CDR2, a VL CDR1 and a VL CDR2; a VH CDR2, a VL CDR1 and a VL CDR3; a VH CDR3, a VL CDR1 and a VL CDR2; a VH CDR3, a VL CDR1 and a VL CDR3; a VH CDR1, a VH CDR2, a VH CDR3 and a VL CDR1; a VH CDR1, a VH CDR2, a VH CDR3 and a VL CDR2; a VH CDR1, a VH CDR2, a VH CDR3 and a VL CDR3; a VH CDR1, a VH CDR2, a VL CDR1 and a VL CDR2; a VH CDR1, a VH CDR2, a VL CDR1 and a VL CDR3; a VH CDR1, a VH CDR3, a VL CDR1 and a VL CDR2; a VH CDR1, a VH CDR3, a VL CDR1 and a VL CDR3; a VH CDR2, a VH CDR3, a VL CDR1 and a VL CDR2; a VH CDR2, a VH CDR3, a VL CDR1 and a VL CDR3; a VH CDR2 and a VL CDR3; a VH CDR1, a VH CDR2, a VH CDR3, a VL CDR1 and a VL CDR2; a VH CDR1, a VH CDR2, a VH CDR3, a VL CDR1 and a VL CDR3; a VH CDR1, a VH CDR2, a VL CDR1, a VL CDR2, and a VL CDR3; a VH CDR1, a VH CDR3, a VL CDR1, a VL CDR2, and a VL CDR3; a VH CDR2, a VH CDR3, a VL CDR1, a VL CDR2, and a VL CDR3; or any combination thereof of the VH CDRs and VL CDRs disclosed herein.

In a specific embodiment, the anti-FcγRIIB monoclonal antibody comprises a modification at position 334 with glutamic acid, at position 359 with asparagine, and at position 366 with serine (MgFc13); or a substitution at position 316 with aspartic acid, at position 378 with valine, and at position 399 with glutamic acid (MgFc27); or a substitution at position 243 with isoleucine, at position 379 with leucine, and at position 420 with valine (MgFc29); or a substitution at position 392 with threonine and at position 396 with leucine (MgFc38); or a substitution at position 221 with glutamic acid, at position 270 with glutamic acid, at position 308 with alanine, at position 311 with histidine, at position 396 with leucine, and at position 402 with aspartic (MgFc42); or a substitution at position 410 with histidine, and at position 396 with leucine (MgFc53); or a substitution at position 243 with leucine, at position 305 with isoleucine, at position 378 with aspartic acid, at position 404 with serine, and at position 396 with leucine (MgFc54); or a substitution at position 255 with isoleucine, and at position 396 with leucine (MgFc55); or a substitution at position 370 with glutamic acid, and at position 396 with leucine (MgFc59); or a substitution at position 243 with leucine, at position 292 with proline, at position 300 with leucine, at position 305 with isoleucine, and at position 396 with leucine (MgFc88); or a substitution at position 243 with leucine, at position 292 with proline, at position 300 with leucine, and at position 396 with leucine (MgFc88A); or a substitution at position 234 with leucine, at position 292 with proline, and at position 300 with leucine (MgFc155); or a substitution at position 243 with leucine, at position 292 with proline, and at position 300 with leucine; or a substitution at position 243 with leucine, at position 292 with proline, and at position 396 with leucine; or a substitution at position 243 with leucine, and at position 292 with proline; or a substitution at position 243 with leucine; or a substitution at position 273 with phenylalanine (See Tables 5 & 6).

7.1.6 Polypeptide and Antibody Conjugates

Molecules of the invention (i.e., polypeptides, antibodies) comprising variant Fc regions may be recombinantly fused or chemically conjugated (including both covalently and non-covalently conjugations) to heterologous polypeptides (i.e., an unrelated polypeptide; or portion thereof, preferably at least 10, at least 20, at least 30, at least 40, at least 50, at least 60, at least 70, at least 80, at least 90 or at least 100 amino acids of the polypeptide) to generate fusion proteins. The fusion does not necessarily need to be direct, but may occur through linker sequences.

Further, molecules of the invention (i.e., polypeptides, antibodies) comprising variant Fc regions may be conjugated to a therapeutic agent or a drug moiety that modifies a given biological response. Therapeutic agents or drug moieties are not to be construed as limited to classical chemical therapeutic agents. For example, the drug moiety may be a protein or polypeptide possessing a desired biological activity. Such proteins may include, for example, a toxin such as abrin, ricin A, *pseudomonas* exotoxin (i.e., PE-40), or diphtheria toxin, ricin, gelonin, and pokeweed antiviral protein, a protein such as tumor necrosis factor, interferons including, but not limited to, α-interferon (IFN-α), β-interferon (IFN-β), nerve growth factor (NGF), platelet derived growth factor (PDGF), tissue plasminogen activator (TPA), an apoptotic agent (e.g., TNF-α, TNF-β, AIM I as disclosed in PCT Publication No. WO 97/33899), AIM II (see, PCT Publication No. WO 97/34911), Fas Ligand (Takahashi et al., *J. Immunol.*, 6:1567-1574, 1994), and VEGI (PCT Publication No. WO 99/23105), a thrombotic agent or an anti-angiogenic agent (e.g., angiostatin or endostatin), or a biological response modifier such as, for example, a lymphokine (e.g., interleukin-1 ("IL-1"), interleukin-2 ("IL-2"), interleukin-6 ("IL-6"), granulocyte macrophage colony stimulating factor ("GM-CSF"), and granulocyte colony stimulating factor ("G-CSF"), macrophage colony stimulating factor, ("M-CSF"), or a growth factor (e.g., growth hormone ("GH"); proteases, or ribonucleases.

Molecules of the invention (i.e., polypeptides, antibodies) can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., 1989, *Proc. Natl. Acad. Sci. USA*, 86:821-824, for instance, hexa-histidine provides for convenient purification of the fusion protein. Other peptide tags useful for purification include, but are not limited to, the hemagglutinin "HA" tag, which corresponds to an epitope derived from the influenza hemagglutinin protein (Wilson et al., *Cell*, 37:767 1984) and the "flag" tag (Knappik et al., *Biotechniques*, 17(4):754-761, 1994).

Additional fusion proteins may be generated through the techniques of gene-shuffling, motif-shuffling, exon-shuffling, and/or codon-shuffling (collectively referred to as "DNA shuffling"). DNA shuffling may be employed to alter the activities of molecules of the invention (e.g., antibodies with higher affinities and lower dissociation rates). See, generally, U.S. Pat. Nos. 5,605,793; 5,811,238; 5,830,721; 5,834,252; and 5,837,458, and Patten et al., 1997, *Curr. Opinion Biotechnol.* 8:724-33; Harayama, 1998, *Trends Biotechnol.* 16:76; Hansson, et al., 1999, *J. Mol. Biol.* 287:265; and Lorenzo and Blasco, 1998, *BioTechniques* 24:308 (each of these patents and publications are hereby incorporated by reference in its entirety). Molecules of the invention comprising variant Fc regions, or the nucleic acids encoding the molecules of the invention, may be further altered by being subjected to random mutagenesis by error-prone PCR, random nucleotide insertion or other methods prior to recombination. One or more portions of a polynucleotide encoding a molecule of the invention, may be recombined with one or more components, motifs, sections, parts, domains, fragments, etc. of one or more heterologous molecules.

The present invention also encompasses molecules of the invention comprising variant Fc regions (i.e., antibodies, polypeptides) conjugated to a diagnostic or therapeutic agent or any other molecule for which serum half-life is desired to be increased and/or targeted to a particular subset of cells. The molecules of the invention can be used diagnostically to, for example, monitor the development or progression of a disease, disorder or infection as part of a clinical testing procedure to, e.g., determine the efficacy of a given treatment regimen. Detection can be facilitated by coupling the molecules of the invention to a detectable substance. Examples of detectable substances include various enzymes, prosthetic groups, fluorescent materials, luminescent materials, bioluminescent materials, radioactive materials, positron emitting metals, and nonradioactive paramagnetic metal ions. The detectable substance may be coupled or conjugated either directly to the molecules of the invention or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Such diagnosis and detection can be accomplished by coupling the molecules of the invention to detectable substances including, but not limited to, various enzymes, enzymes including, but not limited to, horseradish peroxidase, alkaline phosphatase, beta-galactosidase, or acetylcholinesterase; prosthetic group complexes such as, but not limited to, streptavidin/biotin and avidin/biotin; fluorescent materials such as, but not limited to, umbelliferone, fluorescein, fluorescein isothiocyanate, rhodamine, dichlorotriazinylamine fluorescein, dansyl chloride or phycoerythrin; luminescent material such as, but not limited to, luminol; bioluminescent materials such as, but not limited to, luciferase, luciferin, and aequorin; radioactive material such as, but not limited to, bismuth ($^{213}$Bi), carbon ($^{14}$C), chromium ($^{51}$Cr), cobalt ($^{57}$Co), fluorine ($^{18}$F), gadolinium ($^{153}$Gd, $^{159}$Gd), gallium ($^{68}$Ga, $^{67}$Ga), germanium ($^{68}$Ge), holmium ($^{166}$Ho), indium ($^{115}$In, $^{113}$In, $^{112}$In, $^{111}$In), iodine ($^{131}$I), $^{125}$I, $^{123}$I, $^{121}$I) lanthanium ($^{140}$La) lutetium ($^{177}$Lu), manganese ($^{54}$Mn), molybdenum ($^{99}$Mo), palladium ($^{103}$Pd), phosphorous ($^{32}$P), praseodymium ($^{142}$Pr), promethium ($^{149}$Pm), rhenium ($^{186}$Re, $^{188}$Re), rhodium ($^{105}$Rh), ruthemium ($^{97}$Ru), samarium ($^{153}$Sm), scandium ($^{47}$Sc), selenium ($^{75}$Se), strontium ($^{85}$Sr), sulfur ($^{35}$S), technetium ($^{99}$Tc), thallium ($^{201}$Ti), tin ($^{113}$Sn, $^{117}$Sn), tritium ($^{3}$H), xenon ($^{133}$Xe), ytterbium ($^{169}$Yb, $^{175}$Yb), yttrium ($^{90}$Y), zinc ($^{65}$Zn); positron emitting metals using various positron emission tomographies, and nonradioactive paramagnetic metal ions.

Molecules of the invention (i.e., antibodies, polypeptides) comprising a variant Fc region may be conjugated to a therapeutic moiety such as a cytotoxin (e.g., a cytostatic or cytocidal agent), a therapeutic agent or a radioactive element (e.g., alpha-emitters, gamma-emitters, etc.). Cytotoxins or cytotoxic agents include any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cisdichlorodiamine platinum (II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC), and anti-mitotic agents (e.g., vincristine and vinblastine).

Moreover, a molecule of the invention can be conjugated to therapeutic moieties such as a radioactive materials or macrocyclic chelators useful for conjugating radiometal ions (see above for examples of radioactive materials). In certain embodiments, the macrocyclic chelator is 1,4,7,10-tetraazacyclododecane-N,N',N'',N'''-tetraacetic acid (DOTA) which can be attached to the antibody via a linker molecule. Such linker molecules are commonly known in the art and described in Denardo et al., 1998, *Clin Cancer Res.* 4:2483-90; Peterson et al., 1999, *Bioconjug. Chem.* 10:553; and Zimmerman et al., 1999, *Nucl. Med. Biol.* 26:943-50 each of which is incorporated herein by reference in their entireties.

Techniques for conjugating such therapeutic moieties to antibodies are well known; see, e.g., Arnon et al., "Monoclonal Antibodies For Immunotargeting Of Drugs In Cancer Therapy", in *Monoclonal Antibodies And Cancer Therapy*, Reisfeld et al. (eds.), 1985, pp. 243-56, Alan R. Liss, Inc.); Hellstrom et al., "Antibodies For Drug Delivery", in *Controlled Drug Delivery* (2nd Ed.), Robinson et al. (eds.), 1987, pp. 623-53, Marcel Dekker, Inc.); Thorpe, "Antibody Carriers Of Cytotoxic Agents In Cancer Therapy: A Review", in *Monoclonal Antibodies '84: Biological And Clinical Applications*, Pinchera et al. (eds.), 1985, pp. 475-506); "Analysis, Results, And Future Prospective Of The Therapeutic Use Of Radiolabeled Antibody In Cancer Therapy", in *Monoclonal Antibodies For Cancer Detection And Therapy*, Baldwin et al. (eds.), 1985, pp. 303-16, Academic Press; and Thorpe et al., *Immunol. Rev.*, 62:119-58, 1982.

In one embodiment, where the molecule of the invention is an antibody comprising a variant Fc region, it can be administered with or without a therapeutic moiety conjugated to it, administered alone, or in combination with cytotoxic factor(s) and/or cytokine(s) for use as a therapeutic treatment. Alternatively, an antibody of the invention can be conjugated to a second antibody to form an antibody heteroconjugate as described by Segal in U.S. Pat. No. 4,676,980, which is incorporated herein by reference in its entirety. Antibodies of the invention may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

7.2 Screening of Molecules with Variant Fc Regions for Enhanced FcγRIII Binding and Characterization of Same In preferred embodiments, screening and identifying molecules comprising variant Fc regions with altered FcγR affinities (e.g., enhanced FcγRIIIA affinity) are done using the yeast display technology in combination with one or more biochemical based assays, preferably in a high throughput manner, as described herein or as disclosed in U.S Patent Application Publications 2005/0037000 and 2005/0064514, and International Patent Application Publication WO 04/063351, each of which is hereby incorporated by reference in its entirety. The one or more biochemical assays can be any assay known in the art for identifying Fc-FcγR interaction, i.e., specific binding of an Fc region to an FcγR, including, but not limited to, an ELISA assay, surface plasmon resonance assays, immunoprecipitation assay, affinity chromatography, and equilibrium dialysis. In some embodiments, screening and identifying molecules comprising variant Fc regions with altered FcγR affinities (e.g., enhanced FcγRIIIA affinity) are done using the yeast display technology as described herein in combination with one or more functional based assays, preferably in a high throughput manner. The functional based assays can be any assay known in the art for characterizing one or more FcγR mediated effector cell functions such as those described herein in Section 6.2.7. Non-limiting examples of effector cell functions that can be used in accordance with the methods of the invention, include but are not limited to, antibody-dependent cell mediated cytotoxicity (ADCC), antibody-dependent phagocytosis, phagocytosis, opsonization, opsonophagocytosis, cell binding, rosetting, C1q binding, and complement dependent cell mediated cytotoxicity. In some embodiments, screening and identifying molecules comprising variant Fc regions with altered FcγR affinities (e.g., enhanced FcγRIIIA affinity) are done using the yeast display technology as described herein in combination with one or more biochemical based assays in combination or in parallel with one or more functional based assays, preferably in a high throughput manner.

The term "specific binding" of an Fc region to an FcγR refers to an interaction of the Fc region and a particular FcγR which has an affinity constant of at least about 150 nM, in the case of monomeric FcγRIIIA and at least about 60 nM in the case of dimeric FcγRIIB as determined using, for example, an ELISA or surface plasmon resonance assay (e.g., a BIAcore™). The affinity constant of an Fc region for monomeric FcγRIIIA may be 150 nM, 200 nM or 300 nM. The affinity constant of an Fc region for dimeric FcγRIIB may be 60 nM, 80 nM, 90 nM, or 100 nM. Dimeric FcγRIIB for use in the methods of the invention may be generated using methods known to one skilled in the art. Typically, the extracellular region of FcγRIIB is covalently linked to a heterologous polypeptide which is capable of dimerization, so that the resulting fusion protein is a dimer, e.g., see, U.S. Application No. 60/439,709 filed on Jan. 13, 2003, which is incorporated herein by reference in its entirety. A specific interaction generally is stable under physiological conditions, including, for example, conditions that occur in a living individual such as a human or other vertebrate or invertebrate, as well as conditions that occur in a cell culture such conditions as used for maintaining and culturing mammalian cells or cells from another vertebrate organism or an invertebrate organism.

In a specific embodiment, screening for and identifying molecules comprising variant Fc regions and altered FcγR affinities comprise: displaying the molecule comprising a variant Fc region on the yeast surface; and characterizing the binding of the molecule comprising the variant Fc region to a FcγR (one or more), using a biochemical assay for determining Fc-FcγR interaction, preferably, an ELISA based assay. Once the molecule comprising a variant Fc region has been characterized for its interaction with one or more FcγRs and determined to have an altered affinity for one or more FcγRs, by at least one biochemical based assay, e.g., an ELISA assay, the molecule maybe engineered into a complete immunoglobulin, using standard recombinant DNA technology methods known in the art, and the immunoglobulin comprising the variant Fc region expressed in mammalian cells for further biochemical characterization. The immunoglobulin into which a variant Fc region of the invention is introduced (e.g., replacing the Fc region of the immunoglobulin) can be any immunoglobulin including, but not limited to, polyclonal antibodies, monoclonal antibodies, bispecific antibodies, multi-specific antibodies, humanized antibodies, and chimeric antibodies. In preferred embodiments, a variant Fc region is introduced into an immunoglobulin specific for a cell surface receptor, a tumor antigen, or a cancer antigen. The immunoglobulin into which a variant Fc region of the invention is introduced may specifically bind a cancer or tumor antigen for example, including, but not limited to, KS 1/4 pan-carcinoma antigen (Perez and Walker, 1990, J. Immunol. 142: 3662-3667; Bumal, 1988, Hybridoma 7(4): 407-415), ovarian carcinoma antigen (CA125) (Yu et al., 1991, Cancer Res. 51(2): 468-475), prostatic acid phosphate (Tailor et al., 1990, Nucl. Acids Res. 18(16): 4928), prostate specific antigen (Henttu and Vihko, 1989, Biochem. Biophys. Res. Comm. 160(2): 903-910; Israeli et al., 1993, Cancer Res. 53: 227-230), melanoma-associated antigen p97 (Estin et al., 1989, J. Natl. Cancer Instit. 81(6): 445-446), melanoma antigen gp75 (Vijayasardahl et al., 1990, J Exp. Med. 171(4): 1375-1380), high molecular weight melanoma antigen (HMW-MAA) (Natali et al., 1987, Cancer 59: 55-63; Mittelman et al., 1990, J. Clin. Invest. 86: 2136-2144), prostate specific membrane antigen, carcinoembryonic antigen (CEA) (Foon et al., 1994, Proc. Am. Soc. Clin. Oncol. 13: 294), polymorphic epithelial mucin antigen, human milk fat globule antigen, colorectal tumor-associated antigens such as: CEA, TAG-72 (Yokata et al., 1992, Cancer Res. 52: 3402-3408), CO17-1A (Ragnhammar et al., 1993, Int. J. Cancer 53: 751-758); GICA 19-9 (Herlyn et al., 1982, Clin. Immunol. 2: 135), CTA-1 and LEA, Burkitt's lymphoma antigen-38.13, CD19 (Ghetie et al., 1994, Blood 83: 1329-1336), human B-lymphoma antigen-CD20 (Reff et al., 1994, Blood 83:435-445), CD33 (Sgouros et al., 1993, J Nucl. Med. 34:422-430), melanoma specific antigens such as ganglioside GD2 (Saleh et al., 1993, J. Immunol., 151, 3390-3398), ganglioside GD3 (Shitara et al., 1993, Cancer Immunol. Immunother. 36:373-380), ganglioside GM2 (Livingston et al., 1994, J. Clin. Oncol. 12: 1036-1044), ganglioside GM3 (Hoon et al., 1993, Cancer Res. 53: 5244-5250), tumor-specific transplantation type of cell-surface antigen (TSTA) such as virally-induced tumor antigens including T-antigen DNA tumor viruses and Envelope antigens of RNA tumor viruses, oncofetal antigen-alpha-fetoprotein such as CEA of colon, bladder tumor oncofetal antigen (Hellstrom et al., 1985, Cancer. Res. 45:2210-2188), differentiation antigen such as human lung carcinoma antigen L6, L20 (Hellstrom et al., 1986, Cancer Res. 46: 3917-3923), antigens of fibrosarcoma, human leukemia T cell antigen-Gp37 (Bhattacharya-Chatterjee et al., 1988, J. of Immun. 141:1398-1403), neoglycoprotein, sphingolipids, breast cancer antigen such as EGFR (Epidermal growth factor receptor), HER2 antigen ($p185^{HER2}$), polymorphic epithelial mucin (PEM) (Hilkens et al., 1992, Trends in Bio. Chem. Sci. 17:359), malignant human lymphocyte antigen-APO-1 (Bernhard et al., 1989, Science 245: 301-304), differentiation antigen (Feizi, 1985, Nature 314: 53-57) such as I antigen found in fetal erythrocytes, primary endoderm I antigen found in adult erythrocytes, preimplantation embryos, I(Ma) found in gastric adenocarcinomas, M18, M39 found in breast epithelium, SSEA-1 found in myeloid cells, VEP8, VEP9, My1, VIM-D5, $D_I$56-22 found in colorectal cancer, TRA-1-85 (blood group H), C14 found in colonic adenocarcinoma, F3 found in lung adenocarcinoma, AH6 found in gastric cancer, Y hapten, $Le^y$ found in embryonal carcinoma cells, TL5 (blood group A), EGF receptor found in A431 cells, $E_1$ series (blood group B) found in pancreatic cancer, FC10.2 found in embryonal carcinoma cells, gastric adenocarcinoma antigen, CO-514 (blood group $Le^a$) found in Adenocarcinoma, NS-10 found in adenocarcinomas, CO-43 (blood group $Le^b$), G49 found in EGF receptor of A431 cells, MH2 (blood group $ALe^b/Le^y$) found in colonic adenocarcinoma, 19.9 found in colon cancer, gastric cancer mucins, $T_5A_7$ found in myeloid cells, $R_{24}$ found in melanoma, 4.2, $G_{D3}$, D1.1, OFA-1, $G_{M2}$, OFA-2, $G_{D2}$, and M1:22:25:8 found in embryonal carcinoma cells, and SSEA-3 and SSEA-4 found in 4 to 8-cell stage embryos. In one embodiment, the antigen is a T cell receptor derived peptide from a Cutaneous Tcell Lymphoma (see, Edelson, 1998, The Cancer Journal 4:62).

The invention particularly concerns the embodiment in which the binding of the Fc variant to an FcγR activates a cellular effector which targets cells that array a cancer antigen such as A33 (a colorectal carcinoma antigen; Almqvist, Y. 2006, Nucl Med Biol. November; 33(8):991-998); B1 (Egloff, A. M. et al. 2006, Cancer Res. 66(1):6-9); BAGE (Bodey, B. 2002 Expert Opin Biol Ther. 2(6):577-84); beta-catenin (Prange W. et al. 2003 J Pathol. 201(2): 250-9); CA125 (Bast, R. C. Jr. et al. 2005 Int J Gynecol Cancer 15 Suppl 3:274-81); CD5 (Calin, G. A. et al. 2006

Semin Oncol. 33(2):167-73; CD19 (Troussard, X. et al. 1998 Hematol Cell Ther. 40(4):139-48); CD20 (Thomas, D. A. et al. 2006 Hematol Oncol Clin North Am. 20(5):1125-36); CD22 (Kreitman, R. J. 2006 AAPS J. 18; 8 (3):E532-51); CD23 (Rosati, S. et al. 2005 Curr Top Microbiol Immunol. 5; 294:91-107); CD25 (Troussard, X. et al. 1998 Hematol Cell Ther. 40(4):139-48); CD27 (Bataille, R. 2006 Haematologica 91(9):1234-40); CD28 (Bataille, R. 2006 Haematologica 91(9):1234-40); CD36 (Ge, Y. 2005 Lab Hematol. 11(1):31-7); CD40/CD154 (Messmer, D. et al. 2005 Ann N Y Acad Sci. 1062:51-60); CD45 (Jurcic, J. G. 2005 Curr Oncol Rep. 7(5):339-46); CD56 (Bataille, R. 2006 Haematologica 91(9):1234-40); CD79a/CD79b (Troussard, X. et al. 1998 Hematol Cell Ther. 40(4):139-48; Chu, P. G. et al. 2001 Appl Immunohistochem Mol Morphol. 9(2):97-106); CD103 (Troussard, X. et al. 1998 Hematol Cell Ther. 40(4):139-48); CDK4 (Lee, Y. M. et al. 2006 Cell Cycle 5(18):2110-4); CEA (carcinoembryonic antigen; Mathelin, C. 2006 Gynecol Obstet Fertil. 34(7-8):638-46; Tellez-Avila, F. I. et al. 2005 Rev Invest Clin. 57(6):814-9); CTLA4 (Peggs, K. S. et al. 2006 Curr Opin Immunol. 18(2):206-13); EGF-R (epidermal growth factor receptor; Adenis, A. et al. 2003 Bull Cancer. 90 Spec No:5228-32); Erb (ErbB1; ErbB3; ErbB4; Zhou, H. et al. 2002 Oncogene 21(57):8732-40; Rimon, E. et al. 2004 Int J Oncol. 24(5):1325-38); GAGE (GAGE-1; GAGE-2; Akcakanat, A. et al. 2006 Int J Cancer. 118(1):123-8); GD2/GD3/GM2 (Livingston, P. O. et al. 2005 Cancer Immunol Immunother. 54(10):1018-25); gp100 (Lotem, M. et al. 2006 J Immunother. 29(6):616-27); HER-2/neu (Kumar, Pal S et al. 2006 Semin Oncol. 33(4): 386-91); human papillomavirus-E6/human papillomavirus-E7 (DiMaio, D. et al. 2006 Adv Virus Res. 66:125-59; KSA (17-1A) (Ragupathi, G. 2005 Cancer Treat Res. 123:157-80); MAGE (MAGE-1; MAGE-3; (Bodey, B. 2002 Expert Opin Biol Ther. 2(6):577-84); MART (Kounalakis, N. et al. 2005 Curr Oncol Rep. 7(5):377-82; MUC-1 (Mathelin, C. 2006 Gynecol Obstet Fertil. 34(7-8):638-46); MUM-1 (Castelli, C. et al. 2000 J Cell Physiol. 182(3):323-31); N-acetylglucosaminyltransferase (Dennis, J. W. 1999 Biochim Biophys Acta. 6; 1473(1):21-34); p15 (Gil, J. et al. 2006 Nat Rev Mol Cell Biol. 7(9):667-77); PSA (prostate specific antigen; Cracco, C. M. et al. 2005 Minerva Urol Nefrol. 57(4):301-11); PSMA (Ragupathi, G. 2005 Cancer Treat Res. 123:157-80); sTn (Holmberg, L. A. 2001 Expert Opin Biol Ther. 1(5):881-91); TNF-receptor (TNF-$\alpha$ receptor, TNF-$\beta$ receptor; or TNF-$\gamma$ receptor; van Horssen, R. et al. 2006 Oncologist. 11(4):397-408; Gardnerova, M. et al. 2000 Curr Drug Targets. 1(4):327-64); or VEGF receptor (O'Dwyer. P. J. 2006 Oncologist. 11(9):992-8). Also of interest are antigens specific to particular infectious agents, e.g., viral agents including, but not limited to human immunodeficiency virus (HIV), hepatitis B virus (HBV), influenza, human papilloma virus (HPV), foot and mouth (coxsackieviruses), the rabies virus, herpes simplex virus (HSV), and the causative agents of gastroenteritis, including rotaviruses, adenoviruses, caliciviruses, astroviruses and Norwalk virus; bacterial agents including, but not limited to E. coli, Salmonella thyphimurium, Pseudomonas aeruginosa, Vibrio cholerae, Neisseria gonorrhoeae, Helicobacter pylori, Hemophilus influenzae, Shigella dysenteriae, Staphylococcus aureus, Mycobacterium tuberculosis and Streptococcus pneumoniae, fungal agents and parasites such as Giardia.

In some embodiments, a variant Fc region of the invention is introduced into an anti-fluoresceine monoclonal antibody, 4-4-20 (Kranz et al., 1982 J. Biol. Chem. 257(12): 6987-6995; which is incorporated herein by reference in its entirety). In other embodiments, a variant Fc region of the invention is introduced into a mouse-human chimeric anti-CD20 monoclonal antibody 2H7, which recognizes the CD20 cell surface phosphoprotein on B cells (Liu et al., 1987, Journal of Immunology, 139: 3521-6; which is incorporated herein by reference in its entirety). In yet other embodiments, a variant Fc region of the invention is introduced into a humanized antibody (Ab4D5) against the human epidermal growth factor receptor 2 (p185 HER2) as described by Carter et al. (1992, Proc. Natl. Acad. Sci. USA 89: 4285-9; which is incorporated herein by reference in its entirety). In yet other embodiments, a variant Fc region of the invention is introduced into a humanized anti-TAG72 antibody (CC49) (Sha et al., 1994 Cancer Biother. 9(4): 341-9). In other embodiments, a variant Fc region of the invention is introduced into Rittman which is used for treating lymphomas.

In another specific embodiment, the invention encompasses engineering an anti-Fc$\gamma$RIIB antibody including but not limited to any of the antibodies disclosed in U.S. Patent Application Publications 2005/02157667; 2004/0185045; 2005/0260213; or 2006/013810; International Patent Application Publications WO 2005/110474 or WO 2005/115452; U.S. patent application Ser. No. 11/305,787 filed Dec. 15, 2005; or Provisional Applications No. 60/809,116; 60/816, 126; or 60/816,688 filed on May 26, 2006, Jun. 23, 2006, or Jun. 26, 2006, respectively by modification (e.g., substitution, insertion, deletion) of at least one amino acid residue which modification increases the affinity of the Fc region for Fc$\gamma$RIIIA and/or Fc$\gamma$RIIA. Each of the above mentioned references is hereby incorporated by reference in their entirety. Examples of anti-Fc$\gamma$RIIB antibodies, which may or may not be humanized, that may be engineered in accordance with the methods of the invention are 2B6 monoclonal antibody having ATCC accession number PTA-4591 and 3H7 having ATCC accession number PTA-4592, 1D5 monoclonal antibody having ATCC accession number PTA-5958, 1F2 monoclonal antibody having ATCC accession number PTA-5959, 2D11 monoclonal antibody having ATCC accession number PTA-5960, 2E1 monoclonal antibody having ATCC accession number PTA-5961 and 2H9 monoclonal antibody having ATCC accession number PTA-5962 (all deposited at 10801 University Boulevard, Manassas, Va. 02209-2011), which are incorporated herein by reference. In another specific embodiment, modification of the anti-Fc$\gamma$RIIB antibody may also further decrease the affinity of the Fc region for Fc$\gamma$RIIB. In yet another specific embodiment, the engineered anti-Fc$\gamma$RIIB antibody may further have an enhanced effector function as determined by standard assays known in the art and disclosed and exemplified herein. In some embodiments, a variant Fc region of the invention is introduced into a therapeutic monoclonal antibody specific for a cancer antigen or cell surface receptor including but not limited to, Erbitux™ (also known as IMC-C225) (ImClone Systems Inc.), a chimerized monoclonal antibody against EGFR; HERCEPTIN® (Trastuzumab) (Genentech, Calif.) which is a humanized anti-HER2 monoclonal antibody for the treatment of patients with metastatic breast cancer; REOPRO® (abciximab) (Centocor) which is an anti-glycoprotein IIb/IIIa receptor on the platelets for the prevention of clot formation; ZENAPAX® (daclizumab) (Roche Pharmaceuticals, Switzerland) which is an immunosuppressive, humanized anti-CD25 monoclonal antibody for the prevention of acute renal allograft rejection. Other examples are a humanized anti-CD18 F(ab')$_2$ (Genentech); CDP860 which is a humanized anti-CD18 F(ab')$_2$ (Celltech, UK); PRO542 which is an anti-HIV gp120 antibody fused with CD4 (Progenics/Genzyme Transgenics); C14 which is an anti-CD14 antibody (ICOS Pharm); a humanized anti-VEGF IgG1 antibody (Genentech); OVAREX™ which is a murine anti-CA 125 antibody (Altarex); PANOREX™ which is a murine anti-17-IA cell surface antigen IgG2a antibody (Glaxo Wellcome/Centocor); IMC-C225 which is a chimeric anti-EGFR IgG antibody (ImClone System); VITAXIN™ which is a humanized anti-αVβ3 integrin antibody (Applied Molecular Evolution/MedImmune); Campath 1H/LDP-03 which is a humanized anti CD52 IgG1 antibody (Leukosite); Smart M195 which is a humanized anti-CD33 IgG antibody (Protein Design Lab/Kanebo); RITUXAN™ which is a chimeric anti-CD20 IgG1 antibody (IDEC Pharm/Genentech, Roche/Zettyaku); LYMPHOCIDE™ which is a humanized anti-CD22 IgG antibody (Immunomedics); Smart ID10 which is a humanized anti-HLA antibody (Protein Design Lab); ONCOLYM™ (Lym-1) is a radiolabelled murine anti-HLA DR antibody (Techniclone); anti-CD11a is a humanized IgG1 antibody (Genetech/Xoma); ICM3 is a humanized anti-ICAM3 antibody (ICOS Pharm); IDEC-114 is a primatized anti-CD80 antibody (IDEC Pharm/Mitsubishi); ZEVALIN™ is a radiolabelled murine anti-CD20 antibody (IDEC/Schering AG); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); MDX-33 is a human anti-CD64 (FcγR) antibody (Medarex/Centeon); rhuMab-E25 is a humanized anti-IgE IgG1 antibody (Genentech/Norvartis/Tanox Biosystems); IDEC-152 is a primatized anti-CD23 antibody (IDEC Pharm); ABX-CBL is a murine anti CD-147 IgM antibody (Abgenix); BTI-322 is a rat anti-CD2 IgG antibody (Medimmune/Bio Transplant); Orthoclone/OKT3 is a murine anti-CD3 IgG2a antibody (ortho Biotech); SIMULECT™ is a chimeric anti-CD25 IgG1 antibody (Novartis Pharm); LDP-01 is a humanized anti-β$_2$-integrin IgG antibody (LeukoSite); Anti-LFA-1 is a murine anti CD18 F(ab')$_2$ (Pasteur-Merieux/Immunotech); CAT-152 is a human anti-TGF-β$_2$ antibody (Cambridge Ab Tech); and Corsevin M is a chimeric anti-Factor VII antibody (Centocor).

The variant Fc regions of the invention, preferably in the context of an immunoglobulin, can be further characterized using one or more biochemical assays and/or one or more functional assays, preferably in a high throughput manner. In some alternate embodiments, the variant Fc regions of the inventions are not introduced into an immunoglobulin and are further characterized using one or more biochemical based assays and/or one or more functional assays, preferably in a high throughput manner. The one or more biochemical assays can be any assay known in the art for identifying Fc-FcγR interactions, including, but not limited to, an ELISA assay, and surface plasmon resonance-based assay for determining the kinetic parameters of Fc-FcγR interaction, e.g., BIAcore assay. The one or more functional assays can be any assay known in the art for characterizing one or more FcγR mediated effector cell function as known to one skilled in the art or described herein. In specific embodiments, the immunoglobulins comprising the variant Fc regions are assayed in an ELISA assay for binding to one or more FcγRs, e.g., FcγRIIIA, FcγRIIA, FcγRIIA; followed by one or more ADCC assays. In some embodiments, the immunoglobulins comprising the variant Fc regions are assayed further using a surface plasmon resonance-based assay, e.g., BIAcore. Surface plasmon resonance-based assays are well known in the art, and are further discussed in Section 6.2.7, and exemplified herein in Example 7.8.

An exemplary high throughput assay for characterizing immunoglobulins comprising variant Fc regions may comprise: introducing a variant Fc region of the invention, e.g., by standard recombinant DNA technology methods, in a 4-4-20 antibody; characterizing the specific binding of the 4-4-20 antibody comprising the variant Fc region to an FcγR (e.g., FcγRIIIA, FcγRIIB) in an ELISA assay; characterizing the 4-4-20 antibody comprising the variant Fc region in an ADCC assay (using methods disclosed herein) wherein the target cells are opsonized with the 4-4-20 antibody comprising the variant Fc region; the variant Fc region may then be cloned into a second immunoglobulin, e.g., 4D5, 2H7, and that second immunoglobulin characterized in an ADCC assay, wherein the target cells are opsonized with the second antibody comprising the variant Fc region. The second antibody comprising the variant Fc region is then further analyzed using an ELISA-based assay to confirm the specific binding to an FcγR.

Preferably, a variant Fc region of the invention binds FcγRIIIA and/or FcγRIIA with a higher affinity than a wild type Fc region as determined in an ELISA assay. Most preferably, a variant Fc region of the invention binds FcγRIIIA and/or FcγRIIA with a higher affinity and binds FcγRIIB with a lower affinity than a wild type Fc region as determined in an ELISA assay. In some embodiments, the variant Fc region binds FcγRIIIA and/or FcγRIIA with at least 2-fold higher, at least 4-fold higher, more preferably at least 6-fold higher, most preferably at least 8 to 10-fold higher affinity than a wild type Fc region binds FcγRIIIA and/or FcγRIIA and binds FcγRIIB with at least 2-fold lower, at least 4-fold lower, more preferably at least 6-fold lower, most preferably at least 8 to 10-fold lower affinity than a wild type Fc region binds FcγRIIB as determined in an ELISA assay.

The immunoglobulin comprising the variant Fc regions may be analyzed at any point using a surface plasmon based resonance based assay, e.g., BIAcore, for defining the kinetic parameters of the Fc-FcγR interaction, using methods disclosed herein and known to those of skill in the art. Preferably, the Kd of a variant Fc region of the invention for binding to a monomeric FcγRIIIA and/or FcγRIIA as determined by BIAcore analysis is about 100 nM, preferably about 70 nM, most preferably about 40 nM; and the Kd of the variant Fc region of the invention for binding a dimeric FcγRIIB is about 80 nM, about 100 nM, more preferably about 200 nM.

In most preferred embodiments, the immunoglobulin comprising the variant Fc regions is further characterized in an animal model for interaction with an FcγR. Preferred animal models for use in the methods of the invention are, for example, transgenic mice expressing human FcγRs, e.g., any mouse model described in U.S. Pat. Nos. 5,877,397, and 6,676,927 which are incorporated herein by reference in their entirety. Transgenic mice for use in the methods of the invention include, but are not limited to, nude knockout FcγRIIIA mice carrying human FcγRIIIA; nude knockout FcγRIIIA mice carrying human FcγRIIA; nude knockout FcγRIIIA mice carrying human FcγRIIB and human FcγRIIIA; nude knockout FcγRIIIA mice carrying human FcγRIIB and human FcγRIIA; nude knockout FcγRIIA and FcγRIIA mice carrying human FcγRIIIA and FcγRIIA and nude knockout FcγRIIIA, FcγRIIA and FcγRIIB mice carrying human FcγRIIIA, FcγRIIA and FcγRIIB.

7.2.1 Design Strategies

The present invention encompasses engineering methods to generate Fc variants including but not limited to computational design strategies, library generation methods, and experimental production and screening methods. These strategies may be applied individually or in various combinations to engineer the Fc variants of the instant invention.

In most preferred embodiments, the engineering methods of the invention comprise methods in which amino acids at the interface between an Fc region and the Fc ligand are not modified. Fc ligands include but are not limited to FcγRs, C1q, FcRn, C3, mannose receptor, protein A, protein G, mannose receptor, and undiscovered molecules that bind Fc. Amino acids at the interface between an Fc region and an Fc ligand is defined as those amino acids that make a direct and/or indirect contact between the Fc region and the ligand, play a structural role in determining the conformation of the interface, or are within at least 3 angstroms, preferably at least 2 angstroms of each other as determined by structural analysis, such as x-ray crystallography and molecular modeling. The amino acids at the interface between an Fc region and an Fc ligand include those amino acids that make a direct contact with an FcγR based on crystallographic and structural analysis of Fc-FcγR interactions such as those disclosed by Sondermann et al., (2000, Nature, 406: 267-273; which is incorporated herein by reference in its entirety). Examples of positions within the Fc region that make a direct contact with FcγR are amino acids 234-239 (hinge region), amino acids 265-269 (B/C loop), amino acids 297-299 (C'/E loop), and amino acids 327-332 (F/G) loop. In some embodiments, the molecules of the invention comprising variant Fc regions comprise modification of at least one residue that does not make a direct contact with an FcγR based on structural and crystallographic analysis, e.g., is not within the Fc-FcγR binding site.

Preferably, the engineering methods of the invention do not modify any of the amino acids as identified by Shields et al., which are located in the CH2 domain of an Fc region proximal to the hinge region, e.g., Leu234-Pro238; Ala327, Pro329, and affect binding of an Fc region to all human FcγRs.

In other embodiments, the invention encompasses Fc variants with altered FcγR affinities and/or altered effector functions, such that the Fc variant does not have an amino acid modification at a position at the interface between an Fc region and the Fc ligand. Preferably, such Fc variants in combination with one or more other amino acid modifications which are at the interface between an Fc region and the Fc ligand have a further impact on the particular altered property, e.g. altered FcγR affinity. Modifying amino acids at the interface between Fc and an Fc ligand may be done using methods known in the art, for example based on structural analysis of Fc-ligand complexes. For example but not by way of limitation by exploring energetically favorable substitutions at Fc positions that impact the binding interface, variants can be engineered that sample new interface conformations, some of which may improve binding to the Fc ligand, some of which may reduce Fc ligand binding, and some of which may have other favorable properties. Such new interface conformations could be the result of, for example, direct interaction with Fc ligand residues that form the interface, or indirect effects caused by the amino acid modifications such as perturbation of side chain or backbone conformations The invention encompasses engineering Fc variants comprising any of the amino acid modifications disclosed herein in combination with other modifications in which the conformation of the Fc carbohydrate at position 297 is altered. The invention encompasses conformational and compositional changes in the N297 carbohydrate that result in a desired property, for example increased or reduced affinity for an FcγR. Such modifications may further enhance the phenotype of the original amino acid modification of the Fc variants of the invention. Although not intending to be bound by a particular mechanism of actions such a strategy is supported by the observation that the carbohydrate structure and conformation dramatically affect Fc-FcγR and Fc/C1q binding (Umaha et aL, 1999, Nat Biotechnol 17:176-180; Davies et aL, 2001, Biotechnol Bioeng 74:288-294; Mimura et aL, 2001, J Biol Chem 276:45539; Radaev et aL, 2001, J Biol Chem 276:16478-16483; Shields et al. 2002, J Biol Chem 277:26733-26740; Shinkawa et aL, 2003, J Biol Chem 278:3466-3473).

Another design strategy for generating Fc variants in accordance with the invention is provided in which the Fc region is reengineered to eliminate the structural and functional dependence on glycosylation. This design strategy involves the optimization of Fc structure, stability, solubility, and/or Fc function (for example affinity of Fc for one or more Fc ligands) in the absence of the N297 carbohydrate. In one approach, positions that are exposed to solvent in the absence of glycosylation are engineered such that they are stable, structurally consistent with Fc structure, and have no tendency to aggregate. Approaches for optimizing aglycosylated Fc may involve but are not limited to designing amino acid modifications that enhance aglycoslated Fc stability and/or solubility by incorporating polar and/or charged residues that face inward towards the Cg2-Cg2 dimer axis, and by designing amino acid modifications that directly enhance the aglycosylated Fc-FcγR interface or the interface of aglycosylated Fc with some other Fc ligand.

The Fc variants of the present invention may be combined with other Fc modifications, including but not limited to modifications that alter effector function. The invention encompasses combining an Fc variant of the invention with other Fc modifications to provide additive, synergistic, or novel properties in antibodies or Fc fusions. Such modifications may be in the CH1, CH2, or CH3 domains or a combination thereof. Preferably the Fc variants of the invention enhance the property of the modification with which they are combined. For example, if an Fc variant of the invention is combined with a mutant known to bind FcγRIIIA with a higher affinity than a comparable molecule comprising a wild type Fc region; the combination with a mutant of the invention results in a greater fold enhancement in FcγRIIIA affinity.

In one embodiment, the Fc variants of the present invention may be combined with other known Fc variants such as those disclosed in Duncan et al, 1988, Nature 332:563-564; Lund et al., 1991, J. Immunol 147:2657-2662; Lund et al, 1992, Mol Immunol 29:53-59; Alegre et al, 1994, Transplantation 57:1537-1543; Hutchins et al., 1995, Proc Natl. Acad Sci USA 92:11980-11984; Jefferis et al, 1995, Immunol Lett. 44:111-117; Lund et al., 1995, Faseb J 9:115-119; Jefferis et al, 1996, Immunol Lett 54:101-104; Lund et al, 1996, J Immunol 157:49634969; Armour et aL, 1999, Eur J Immunol 29:2613-2624; Idusogie et al, 2000, J Immunol 164:41784184; Reddy et al, 2000, J Immunol 164:1925-

1933; Xu et al., 2000, Cell Immunol 200:16-26; Idusogie et al, 2001, J Immunol 166:2571-2575; Shields et al., 2001, J Biol Chem 276:6591-6604; Jefferis et al, 2002, Immunol Lett 82:57-65; Presta et al., 2002, Biochem Soc Trans 30:487-490); U.S. Pat. Nos. 5,624,821; 5,885,573; 6,194,551; PCT WO 00/42072; PCT WO 99/58572; each of which is incorporated herein by reference in its entirety.

7.2.2 Functional Assays of Molecules with Variant Fc Regions

The invention encompasses characterization of the molecules of the invention (e.g., an antibody comprising a variant Fc region identified by the yeast display technology and FcγR-Fc binding assays disclosed in U.S Patent Application Publications 2005/0037000 and 2005/0064514, and International Patent Application Publication WO 04/063351 (each of which is hereby incorporated by reference in its entirety); or therapeutic monoclonal antibodies engineered according to the methods of the invention) using assays known to those skilled in the art for identifying the effector cell function of the molecules. In particular, the invention encompasses characterizing the molecules of the invention for FcγR-mediated effector cell function. Examples of effector cell functions that can be assayed in accordance with the invention, include but are not limited to, antibody-dependent cell mediated cytotoxicity, phagocytosis, opsonization, opsonophagocytosis, C1q binding, and complement dependent cell mediated cytotoxicity. Any cell-based or cell free assay known to those skilled in the art for determining effector cell function activity can be used (For effector cell assays, see Perussia et al., 2000, *Methods Mol. Biol.* 121: 179-92; Baggiolini et al., 1998 *Experientia*, 44(10): 841-8; Lehmann et al., 2000 *J. Immunol. Methods*, 243(1-2): 229-42; Brown E J. 1994, *Methods Cell Biol.*, 45: 147-64; Munn et al., 1990 *J. Exp. Med.*, 172: 231-237, Abdul-Majid et al., 2002 *Scand. J. Immunol.* 55: 70-81; Ding et al., 1998, *Immunity* 8:403-411, each of which is incorporated by reference herein in its entirety).

In one embodiment, the molecules of the invention can be assayed for FcγR-mediated phagocytosis in human monocytes. Alternatively, the FcγR-mediated phagocytosis of the molecules of the invention may be assayed in other phagocytes, e.g., neutrophils (polymorphonuclear leuckocytes; PMN); human peripheral blood monocytes, monocyte-derived macrophages, which can be obtained using standard procedures known to those skilled in the art (e.g., see Brown E J. 1994, *Methods Cell Biol.*, 45: 147-164). In one embodiment, the function of the molecules of the invention is characterized by measuring the ability of THP-1 cells to phagocytose fluoresceinated IgG-opsonized sheep red blood cells (SRBC) by methods previously described (Tridandapani et al., 2000, *J. Biol. Chem.* 275: 20480-7). For example, an exemplary assay for measuring phagocytosis of the molecules of the invention comprising variant Fc regions with enhanced affinities for FcγRIIIA, comprises of: treating THP-1 cells with a molecule of the invention or with a control antibody that does not bind to FcγRIIIA, comparing the activity levels of said cells, wherein a difference in the activities of the cells (e.g., rosetting activity (the number of THP-1 cells binding IgG-coated SRBC), adherence activity (the total number of SRBC bound to THP-1 cells), and phagocytic rate) would indicate the functionality of the molecule of the invention. It can be appreciated by one skilled in the art that this exemplary assay can be used to assay any of the molecules identified by the methods of the invention.

Another exemplary assay for determining the phagocytosis of the molecules of the invention is an antibody-dependent opsonophagocytosis assay (ADCP) which can comprise the following: coating a target bioparticle such as *Escherichia coli*-labeled FITC (Molecular Probes) or *Staphylococcus aureus*-FITC with (i) wild-type 4-4-20 antibody, an antibody to fluorescein (See Bedzyk et al., 1989, *J. Biol. Chem*, 264(3): 1565-1569, which is incorporated herein by reference in its entirety), as the control antibody for FcγR-dependent ADCP; or (ii) 4-4-20 antibody harboring the D265A mutation that knocks out binding to FcγRIII, as a background control for FcγR-dependent ADCP (iii) 4-4-20 antibody carrying variant Fc regions identified by the methods of the invention and produced as exemplified in Example 7.6; and forming the opsonized particle; adding any of the opsonized particles described (i-iii) to THP-1 effector cells (a monocytic cell line available from ATCC) in a 60:1 ratio to allow FcγR-mediated phagocytosis to occur; preferably incubating the cells and *E. coli*-FITC/antibody at 37° C. for 1.5 hour; adding trypan blue after incubation (preferably at room temperature for 2-3 min.) to the cells to quench the fluorescence of the bacteria that are adhered to the outside of the cell surface without being internalized; transferring cells into a FACS buffer (e.g., 0.1%, BSA in PBS, 0.1%, sodium azide), analyzing the fluorescence of the THP1 cells using FACS (e.g., BD FACS Calibur). Preferably, the THP-1 cells used in the assay are analyzed by FACS for expression of FcγR on the cell surface. THP-1 cells express both CD32A and CD64. CD64 is a high affinity FcγR that is blocked in conducting the ADCP assay in accordance with the methods of the invention. The THP-1 cells are preferably blocked with 100 μg/mL soluble IgG1 or 10% human serum. To analyze the extent of ADCP, the gate is preferably set on THP-1 cells and median fluorescence intensity is measured. The ADCP activity for individual mutants is calculated and reported as a normalized value to the wild type chMab 4-4-20 obtained. The opsonized particles are added to THP-1 cells such that the ratio of the opsonized particles to THP-1 cells is 30:1 or 60:1. In most preferred embodiments, the ADCP assay is conducted with controls, such as *E. coli*-FITC in medium, *E. coli*-FITC and THP-1 cells (to serve as FcγR-independent ADCP activity), *E. coli*-FITC, THP-1 cells and wild-type 4-4-20 antibody (to serve as FcγR-dependent ADCP activity), *E. coli*-FITC, THP-1 cells, 4-4-20 D265A (to serve as the background control for FcγR-dependent ADCP activity).

In another embodiment, the molecules of the invention can be assayed for FcγR-mediated ADCC activity in effector cells, e.g., natural killer cells, using any of the standard methods known to those skilled in the art (See e.g., Perussia et al., 2000, Methods Mol. Biol. 121: 179-92). An exemplary assay for determining ADCC activity of the molecules of the invention is based on a $^{51}$Cr release assay comprising of: labeling target cells with [$^{51}$Cr]Na$_2$CrO$_4$ (this cell-membrane permeable molecule is commonly used for labeling since it binds cytoplasmic proteins and although spontaneously released from the cells with slow kinetics, it is released massively following target cell necrosis); opsonizing the target cells with the molecules of the invention comprising variant Fc regions; combining the opsonized radiolabeled target cells with effector cells in a microtitre plate at an appropriate ratio of target cells to effector cells; incubating the mixture of cells for 16-18 hours at 37° C.; collecting supernatants; and analyzing radioactivity. The cytotoxicity of the molecules of the invention can then be determined, for example using the following formula: % lysis=(experimental cpm−target leak cpm)/(detergent lysis cpm−target leak cpm)×100%. Alternatively, % lysis=(ADCC−AICC)/(maximum release-spontaneous release). Specific lysis can be calculated using the formula: specific lysis=% lysis with the molecules of the invention−% lysis in the absence of the molecules of the invention. A graph can be generated by varying either the target: effector cell ratio or antibody concentration.

In yet another embodiment, the molecules of the invention are characterized for antibody dependent cellular cytotoxicity (ADCC) see, e.g., Ding et al., *Immunity*, 1998, 8:403-11; which is incorporated herein by reference in its entirety.

Preferably, the effector cells used in the ADCC assays of the invention are peripheral blood mononuclear cells (PBMC) that are preferably purified from normal human blood, using standard methods known to one skilled in the art, e.g., using Ficoll-Paque density gradient centrifugation. Preferred effector cells for use in the methods of the invention express different FcγR activating receptors. The invention encompasses, effector cells, THP-1, expressing FcγRI, FcγRIIA and FcγRIIB, and monocyte derived primary macrophages derived from whole human blood expressing both FcγRIIIA and FcγRIIB, to determine if Fc antibody mutants show increased ADCC activity and phagocytosis relative to wild type IgG1 antibodies.

The human monocyte cell line, THP-1, activates phagocytosis through expression of the high affinity receptor FcγRI and the low affinity receptor FcγRIIA (Fleit et al., 1991, J. Leuk. Biol. 49: 556). THP-1 cells do not constitutively express FcγRIIA or FcγRIIB. Stimulation of these cells with cytokines effects the FcR expression pattern (Pricop et al., 2000 J. Immunol. 166: 531-7). Growth of THP-1 cells in the presence of the cytokine IL4 induces FcγRIIB expression and causes a reduction in FcγRIIA and FcγRI expression. FcγRIIB expression can also be enhanced by increased cell density (Tridandapani et al., 2002, *J. Biol Chem.* 277: 5082-9). In contrast, it has been reported that IFNγ can lead to expression of FcγRIIIA (Pearse et al., 1993 *PNAS USA* 90: 4314-8). The presence or absence of receptors on the cell surface can be determined by FACS using common methods known to one skilled in the art. Cytokine induced expression of FcγR on the cell surface provides a system to test both activation and inhibition in the presence of FcγRIIB. If THP-1 cells are unable to express the FcγRIIB the invention also encompasses another human monocyte cell line, U937. These cells have been shown to terminally differentiate into macrophages in the presence of IFNγ and TNF (Koren et al., 1979, *Nature* 279: 328-331).

FcγR dependent tumor cell killing is mediated by macrophage and NK cells in mouse tumor models (Clynes et al., 1998, *PNAS USA* 95: 652-656). The invention encompasses the use of elutriated monocytes from donors as effector cells to analyze the efficiency Fc mutants to trigger cell cytotoxicity of target cells in both phagocytosis and ADCC assays. Expression patterns of FcγRI, FcγRIIIA, and FcγRIIB are affected by different growth conditions. FcγR expression from frozen elutriated monocytes, fresh elutriated monocytes, monocytes maintained in 10% FBS, and monocytes cultured in FBS+GM-CSF and or in human serum may be determined using common methods known to those skilled in the art. For example, cells can be stained with FcγR specific antibodies and analyzed by FACS to determine FcR profiles. Conditions that best mimic macrophage in vivo FcγR expression is then used for the methods of the invention.

In some embodiments, the invention encompasses the use of mouse cells especially when human cells with the right FcγR profiles are unable to be obtained. In some embodiments, the invention encompasses the mouse macrophage cell line RAW264.7 (ATCC) which can be transfected with human FcγRIIIA and stable transfectants isolated using methods known in the art, see, e.g., Ralph et al., *J. Immunol.* 119: 950-4). Transfectants can be quantitated for FcγRIIIA expression by FACS analysis using routine experimentation and high expressors can be used in the ADCC assays of the invention. In other embodiments, the invention encompasses isolation of spleen peritoneal macrophage expressing human FcγR from knockout transgenic mice such as those disclosed herein.

Lymphocytes may be harvested from peripheral blood of donors (PBM) using a Ficoll-Paque gradient (Pharmacia). Within the isolated mononuclear population of cells the majority of the ADCC activity occurs via the natural killer cells (NK) containing FcγRIIIA but not FcγRIIB on their surface. Results with these cells indicate the efficacy of the mutants on triggering NK cell ADCC and establish the reagents to test with elutriated monocytes.

Target cells used in the ADCC assays of the invention include, but are not limited to, breast cancer cell lines, e.g., SK-BR-3 with ATCC accession number HTB-30 (see, e.g., Tremp et al., 1976, *Cancer Res.* 33-41); B-lymphocytes; cells derived from Burkitts lymphoma, e.g., Raji cells with ATCC accession number CCL-86 (see, e.g., Epstein et al., 1965, *J. Natl. Cancer Inst.* 34: 231-240), and Daudi cells with ATCC accession number CCL-213 (see, e.g., Klein et al., 1968, *Cancer Res.* 28: 1300-10). The target cells must be recognized by the antigen binding site of the immunoglobulin to be assayed.

The ADCC assay is based on the ability of NK cells to mediate cell death via an apoptotic pathway. NK cells mediate cell death in part by FcγRIIIA's recognition of IgG bound to an antigen on a cell surface. The ADCC assays used in accordance with the methods of the invention may be radioactive based assays or fluorescence based assays. The ADCC assay used to characterize the molecules of the invention comprising variant Fc regions comprises labeling target cells, e.g., SK-BR-3, MCF-7, OVCAR3, Raji, Daudi cells, opsonizing target cells with an antibody that recognizes a cell surface receptor on the target cell via its antigen binding site; combining the labeled opsonized target cells and the effector cells at an appropriate ratio, which can be determined by routine experimentation; harvesting the cells; detecting the label in the supernatant of the lysed target cells, using an appropriate detection scheme based on the label used. The target cells may be labeled either with a radioactive label or a fluorescent label, using standard methods known in the art. For example the labels include, but are not limited to, [$^{51}$Cr]Na$_2$CrO$_4$; and the acetoxymethyl ester of the fluorescence enhancing ligand, 2,2':6',2"-terpyridine-6-6"-dicarboxylate (TDA).

In a specific preferred embodiment, a time resolved fluorimetric assay is used for measuring ADCC activity against target cells that have been labeled with the acetoxymethyl ester of the fluorescence enhancing ligand, 2,2':6', 2"-terpyridine-6-6"-dicarboxylate (TDA). Such fluorimetric assays are known in the art, e.g., see, Blomberg et al., 1996, *Journal of Immunological Methods,* 193: 199-206; which is incorporated herein by reference in its entirety. Briefly, target cells are labeled with the membrane permeable acetoxymethyl diester of TDA (bis(acetoxymethyl) 2,2':6', 2"-terpyridine-6-6"-dicarboxylate, (BATDA), which rapidly diffuses across the cell membrane of viable cells. Intracellular esterases split off the ester groups and the regenerated membrane impermeable TDA molecule is trapped inside the cell. After incubation of effector and target cells, e.g., for at least two hours, up to 3.5 hours, at 37° C., under 5% CO$_2$, the TDA released from the lysed target cells is chelated with Eu3+ and the fluorescence of the Europium-TDA chelates formed is quantitated in a time-resolved fluorometer (e.g., Victor 1420, Perkin Elmer/Wallac).

In another specific embodiment, the ADCC assay used to characterize the molecules of the invention comprising variant Fc regions comprises the following steps: Preferably $4$-$5 \times 10^6$ target cells (e.g., SK-BR-3, MCF-7, OVCAR3, Raji cells) are labeled with bis(acetoxymethyl) 2,2':6',2"-terpyridine-t-6"-dicarboxylate (DELFIA BATDA Reagent, Perkin Elmer/Wallac). For optimal labeling efficiency, the number of target cells used in the ADCC assay should preferably not exceed $5 \times 10^6$. BATDA reagent is added to the cells and the mixture is incubated at 37° C. preferably under 5% CO2, for at least 30 minutes. The cells are then washed with a physiological buffer, e.g., PBS with 0.125 mM sulfinpyrazole, and media containing 0.125 mM sulfinpyrazole. The labeled target cells are then opsonized (coated) with a molecule of the invention comprising a variant Fc region, i.e., an immunoglobulin comprising a variant Fc region of the invention, including, but not limited to, a polyclonal antibody, a monoclonal antibody, a bispecific antibody, a multi-specific antibody, a humanized antibody, or a chimeric antibody. In preferred embodiments, the immunoglobulin comprising a variant Fc region used in the ADCC assay is specific for a cell surface receptor, a tumor antigen, or a cancer antigen. The immunoglobulin into which a variant Fc region of the invention is introduced may specifically bind any cancer or tumor antigen, such as those listed in Section 6.4. Additionally, the immunoglobulin into which a variant Fc region of the invention is introduced may be any therapeutic antibody specific for a cancer antigen, such as those listed in Section 6.4. In some embodiments, the immunoglobulin comprising a variant Fc region used in the ADCC assay is an anti-fluoresceine monoclonal antibody, 4-4-20 (Kranz et al., 1982 *J. Biol. Chem.* 257(12): 6987-6995) a mouse-human chimeric anti-CD20 monoclonal antibody 2H7 (Liu et al., 1987, Journal of Immunology, 139: 3521-6); or a humanized antibody (Ab4D5) against the human epidermal growth factor receptor 2 (p185 HER2) (Carter et al. 1992, *Proc. Natl. Acad. Sci. USA* 89: 4285-9). The target cells in the ADCC assay are chosen according to the immunoglobulin into which a variant Fc region of the invention has been introduced so that the immunoglobulin binds a cell surface receptor of the target cell specifically. Preferably, the ADCC assays of the invention are performed using more than one engineered antibody, e.g., anti Her2/neu, 4-4-20, 2B6, Rittman, and 2H7, harboring the Fc variants of the invention. In a most preferred embodiment, the Fc variants of the invention are introduced into at least 3 antibodies and their ADCC activities are tested. Although not intending to be bound by a particular mechanism of action, examining at least 3 antibodies in these functional assays will diminish the chance of eliminating a viable Fc mutation erroneously.

Opsonized target cells are added to effector cells, e.g., PBMC, to produce effector:target ratios of approximately 50:1, 75:1, or 100:1. In a specific embodiment, when the immunoglobulin comprising a variant Fc region has the variable domain of 4-4-20, the effector:target is 75:1. The effector and target cells are incubated for at least two hours, up to 3.5 hours, at 37° C., under 5% CO2. Cell supernatants are harvested and added to an acidic europium solution (e.g., DELFIA Europium Solution, Perkin Elmer/Wallac). The fluorescence of the Europium-TDA chelates formed is quantitated in a time-resolved fluorometer (e.g., Victor 1420, Perkin Elmer/Wallac). Maximal release (MR) and spontaneous release (SR) are determined by incubation of target cells with 1% TX-100 and media alone, respectively. Antibody independent cellular cytotoxicity (AICC) is measured by incubation of target and effector cells in the absence of antibody. Each assay is preferably performed in triplicate. The mean percentage specific lysis is calculated as: Experimental release (ADCC)–AICC)/(MR–SR)×100.

The invention encompasses characterization of the Fc variants in both NK-dependent and macrophage dependent ADCC assays. Fc variants of the invention have altered phenotypes such as an altered effector function as assayed in an NK dependent or macrophage dependent assay.

The invention encompasses assays known in the art and exemplified herein, to bind C1q and mediate complement dependent cytotoxicity (CDC). To determine C1q binding, a C1q binding ELISA may be performed. An exemplary assay may comprise the following: assay plates may be coated overnight at 4 C with polypeptide variant or starting polypeptide (control) in coating buffer. The plates may then be washed and blocked. Following washing, an aliquot of human C1q may be added to each well and incubated for 2 hrs at room temperature. Following a further wash, 100 uL of a sheep anti-complement C1q peroxidase conjugated antibody may be added to each well and incubated for 1 hour at room temperature. The plate may again be washed with wash buffer and 100 ul of substrate buffer containing OPD (O-phenylenediamine dihydrochloride (Sigma)) may be added to each well. The oxidation reaction, observed by the appearance of a yellow color, may be allowed to proceed for 30 minutes and stopped by the addition of 100 ul of 4.5 NH2 SO4. The absorbance may then read at (492-405) nm.

A preferred variant in accordance with the invention is one that displays a significant reduction in C1q binding, as detected and measured in this assay or a similar assay. Preferably the molecule comprising an Fc variant displays about 50 fold reduction, about 60 fold, about 80 fold, or about 90 fold reduction in C1q binding compared to a control antibody having a nonmutated IgG1 Fc region. In the most preferred embodiment, the molecule comprising an Fc variant does not bind C1q, i.e. the variant displays about 100 fold or more reduction in C1q binding compared to the control antibody.

Another exemplary variant is one which has a better binding affinity for human C1q than the molecule comprising wild type Fc region. Such a molecule may display, for example, about two-fold or more, and preferably about five-fold or more, improvement in human C1q binding compared to the parent molecule comprising wild type Fc region. For example, human C1q binding may be about two-fold to about 500-fold, and preferably from about two-fold or from about five-fold to about 1000-fold improved compared to the molecule comprising wild type Fc region.

To assess complement activation, a complement dependent cytotoxicity (CDC) assay may be performed, e.g. as described in Gazzano-Santoro et al., J. Immunol. Methods 202:163 (1996), which is incorporated herein by reference in its entirety. Briefly, various concentrations of the molecule comprising a variant Fc region and human complement may be diluted with buffer. Cells which express the antigen to which the molecule comprising a variant Fc region binds may be diluted to a density of about $1 \times 10^6$ cells/ml. Mixtures of the molecule comprising a variant Fc region, diluted human complement and cells expressing the antigen may be added to a flat bottom tissue culture 96 well plate and allowed to incubate for 2 hrs at 37 C and 5% CO2 to facilitate complement mediated cell lysis. 50 μL of alamar blue (Accumed International) may then be added to each well and incubated overnight at 37 C. The absorbance is measured using a 96-well fluorometer with excitation at 530 nm and emission at 590 nm. The results may be expressed in relative fluorescence units (RFU). The sample concentrations may be computed from a standard curve and the percent activity as compared to nonvariant molecule, i.e., a molecule comprising wild type Fc region, is reported for the variant of interest.

In some embodiments, an Fc variant of the invention does not activate complement. Preferably, the variant does not appear to have any CDC activity in the above CDC assay. The invention also pertains to a variant with enhanced CDC compared to a parent molecule (a molecule comprising wild type Fc region), e.g., displaying about two-fold to about 100-fold improvement in CDC activity in vitro or in vivo (e.g., at the IC50 values for each molecule being compared). Complement assays may be performed with guinea pig, rabbit or human serum. Complement lysis of target cells may be detected by monitoring the release of intracellular enzymes such as lactate dehydrogenase (LDH), as described in Korzeniewski et al., 1983 Immunol. Methods 64(3): 313-20; and Decker et al., 1988 J. Immunol Methods 115(1): 61-9, each of which is incorporated herein by reference in its entirety; or the release of an intracellular lable such as europium, chromium 51 or indium 111 in which target cells are labeled as described herein.

7.2.3 Other Assays

The molecules of the invention comprising variant Fc regions may also be assayed using any surface plasmon resonance based assays known in the art for characterizing the kinetic parameters of Fc-FcγR interaction binding. Any SPR instrument commercially available including, but not limited to, BIAcore Instruments, available from Biacore AB (Uppsala, Sweden); IAsys instruments available from Affinity Sensors (Franklin, Mass.); IBIS system available from Windsor Scientific Limited (Berks, UK), SPR-CELLIA systems available from Nippon Laser and Electronics Lab (Hokkaido, Japan), and SPR Detector Spreeta available from Texas Instruments (Dallas, Tex.) can be used in the instant invention. For a review of SPR-based technology see Mullet et al., 2000, *Methods* 22: 77-91; Dong et al., 2002, *Review in Mol. Biotech.*, 82: 303-23; Fivash et al., 1998, *Current Opinion in Biotechnology* 9: 97-101; Rich et al., 2000, *Current Opinion in Biotechnology* 11: 54-61; all of which are incorporated herein by reference in their entirety. Additionally, any of the SPR instruments and SPR based methods for measuring protein-protein interactions described in U.S. Pat. Nos. 6,373,577; 6,289,286; 5,322,798; 5,341,215; 6,268,125 are contemplated in the methods of the invention, all of which are incorporated herein by reference in their entirety.

Briefly, SPR based assays involve immobilizing a member of a binding pair on a surface, and monitoring its interaction with the other member of the binding pair in solution in real time. SPR is based on measuring the change in refractive index of the solvent near the surface that occurs upon complex formation or dissociation. The surface onto which the immobilization occurs is the sensor chip, which is at the heart of the SPR technology; it consists of a glass surface coated with a thin layer of gold and forms the basis for a range of specialized surfaces designed to optimize the binding of a molecule to the surface. A variety of sensor chips are commercially available especially from the companies listed supra, all of which may be used in the methods of the invention. Examples of sensor chips include those available from BIAcore AB, Inc., e.g., Sensor Chip CMS, SA, NTA, and HPA. A molecule of the invention may be immobilized onto the surface of a sensor chip using any of the immobilization methods and chemistries known in the art, including but not limited to, direct covalent coupling via amine groups, direct covalent coupling via sulfhydryl groups, biotin attachment to avidin coated surface, aldehyde coupling to carbohydrate groups, and attachment through the histidine tag with NTA chips.

In some embodiments, the kinetic parameters of the binding of molecules of the invention comprising variant Fc regions, e.g., immunoglobulins comprising variant Fc region, to an FcγR may be determined using a BIAcore instrument (e.g., BIAcore instrument 1000, BIAcore Inc., Piscataway, N.J.). Any FcγR can be used to assess the interaction with the molecules of the invention comprising variant Fc regions. In a specific embodiment the FcγR is FcγRIIIA, preferably a soluble monomeric FcγRIIIA. For example, in one embodiment, the soluble monomeric FcγRIIIA is the extracellular region of FcγRIIIA joined to the linker-AVITAG sequence (see, U.S. Provisional Application No. 60/439,498, filed on Jan. 9, 2003 and U.S. Provisional Application No. 60/456,041 filed on Mar. 19, 2003, which are incorporated herein by reference in their entireties). In another specific embodiment, the FcγR is FcγRIIB, preferably a soluble dimeric FcγRIIB. For example in one embodiment, the soluble dimeric FcγRIIB protein is prepared in accordance with the methodology described in U.S. Provisional application No. 60/439,709 filed on Jan. 13, 2003, which is incorporated herein by reference in its entirety.

An exemplary assay for determining the kinetic parameters of a molecule comprising a variant Fc region, wherein the molecule is the 4-4-20 antibody, to an FcγR using a BIAcore instrument comprises the following: BSA-FITC is immobilized on one of the four flow cells of a sensor chip surface, preferably through amine coupling chemistry such that about 5000 response units (RU) of BSA-FITC is immobilized on the surface. Once a suitable surface is prepared, 4-4-20 antibodies carrying the Fc mutations are passed over the surface, preferably by one minute injections of a 20 µg/mL solution at a 5 µL/mL flow rate. The level of 4-4-20 antibodies bound to the surface ranges between 400 and 700 RU. Next, dilution series of the receptor (FcγRIIA and FcγRIIB-Fc fusion protein) in HBS-P buffer (20 mM HEPES, 150 mM NaCl, 3 mM EDTA, pH 7.5) are injected onto the surface at 100 4/min. Antibody regeneration between different receptor dilutions is carried out preferably by single 5 second injections of 100 mM NaHCO$_3$ pH 9.4; 3M NaCl. Any regeneration technique known in the art is contemplated in the method of the invention.

Once an entire data set is collected, the resulting binding curves are globally fitted using computer algorithms supplied by the SPR instrument manufacturer, e.g., BIAcore, Inc. (Piscataway, N.J.). These algorithms calculate both the $K_{on}$ and $K_{off}$, from which the apparent equilibrium binding constant, $K_d$ is deduced as the ratio of the two rate constants (i.e., $K_{off}/K_{on}$). More detailed treatments of how the individual rate constants are derived can be found in the BIAevaluaion Software Handbook (BIAcore, Inc., Piscataway, N.J.). The analysis of the generated data may be done using any method known in the art. For a review of the various methods of interpretation of the kinetic data generated see Myszka, 1997, *Current Opinion in Biotechnology* 8: 50-7; Fisher et al., 1994, *Current Opinion in Biotechnology* 5: 389-95; O'Shannessy, 1994, *Current Opinion in Biotechnology*, 5:65-71; Chaiken et al., 1992, *Analytical Biochemistry*, 201: 197-210; Morton et al., 1995, *Analytical Bio-*

*chemistry* 227: 176-85; O'Shannessy et al., 1996, *Analytical Biochemistry* 236: 275-83; all of which are incorporated herein by reference in their entirety.

In preferred embodiments, the kinetic parameters determined using an SPR analysis, e.g., BIAcore, may be used as a predictive measure of how a molecule of the invention will function in a functional assay, e.g., ADCC. An exemplary method for predicting the efficacy of a molecule of the invention based on kinetic parameters obtained from an SPR analysis may comprise the following: determining the $K_{off}$ values for binding of a molecule of the invention to FcγRIIIA and FcγRIIB; plotting (1) $K_{off}$(wt)/$K_{off}$(mut) for FcγRIIIA; (2) $K_{off}$(mut)/$K_{off}$(wt) for FcγRIIB against the ADCC data. Numbers higher than one show a decreased dissociation rate for FcγRIIIA and an increased dissociation rate for FcγRIIB relative to wild type; and possess and enhanced ADCC function.

7.3 Methods of Recombinantly Producing Molecules of the Invention 7.3.1 Polynucleotides Encoding Molecules of the Invention The present invention also includes polynucleotides that encode the molecules, including the polypeptides and antibodies, of the invention identified by the methods of the invention. The polynucleotides encoding the molecules of the invention may be obtained, and the nucleotide sequence of the polynucleotides determined, by any method known in the art.

Once the nucleotide sequence of the molecules (e.g., antibodies) that are identified by the methods of the invention is determined, the nucleotide sequence may be manipulated using methods well known in the art, e.g., recombinant DNA techniques, site directed mutagenesis, PCR, etc. (see, for example, the techniques described in Sambrook et al., 2001, *Molecular Cloning, A Laboratory Manual,* 3rd Ed., Cold Spring Harbor Laboratory, Cold Spring Harbor, N.Y.; and Ausubel et al., eds., 1998, *Current Protocols in Molecular Biology,* John Wiley & Sons, NY, which are both incorporated by reference herein in their entireties), to generate, for example, antibodies having a different amino acid sequence, for example by generating amino acid substitutions, deletions, and/or insertions.

In a specific embodiment, when the nucleic acids encode antibodies, one or more of the CDRs are inserted within framework regions using routine recombinant DNA techniques. The framework regions may be naturally occurring or consensus framework regions, and preferably human framework regions (see, e.g., Chothia et al., 1998, *J. Mol. Biol.* 278: 457-479 for a listing of human framework regions).

In another embodiment, human libraries or any other libraries available in the art, can be screened by standard techniques known in the art, to clone the nucleic acids encoding the molecules of the invention.

7.3.2 Recombinant Expression of Molecules of the Invention

Once a nucleic acid sequence encoding molecules of the invention (i.e., antibodies) has been obtained, the vector for the production of the molecules may be produced by recombinant DNA technology using techniques well known in the art. Methods which are well known to those skilled in the art can be used to construct expression vectors containing the coding sequences for the molecules of the invention and appropriate transcriptional and translational control signals. These methods include, for example, in vitro recombinant DNA techniques, synthetic techniques, and in vivo genetic recombination. (See, for example, the techniques described in Sambrook et al., 1990, *Molecular Cloning, A Laboratory Manual,* 2d Ed., Cold Spring Harbor Laboratory, Cold Spring Harbor, N.Y. and Ausubel et al. eds., 1998, *Current Protocols in Molecular Biology,* John Wiley & Sons, NY).

An expression vector comprising the nucleotide sequence of a molecule identified by the methods of the invention (i.e., an antibody) can be transferred to a host cell by conventional techniques (e.g., electroporation, liposomal transfection, and calcium phosphate precipitation) and the transfected cells are then cultured by conventional techniques to produce the molecules of the invention. In specific embodiments, the expression of the molecules of the invention is regulated by a constitutive, an inducible or a tissue, specific promoter.

The host cells used to express the molecules identified by the methods of the invention may be either bacterial cells such as *Escherichia coli,* or, preferably, eukaryotic cells, especially for the expression of whole recombinant immunoglobulin molecule. In particular, mammalian cells such as Chinese hamster ovary cells (CHO), in conjunction with a vector such as the major intermediate early gene promoter element from human cytomegalovirus is an effective expression system for immunoglobulins (Foecking et al., 1998, *Gene* 45:101; Cockett et al., 1990, *Bio/Technology* 8:2).

A variety of host-expression vector systems may be utilized to express the molecules identified by the methods of the invention. Such host-expression systems represent vehicles by which the coding sequences of the molecules of the invention may be produced and subsequently purified, but also represent cells which may, when transformed or transfected with the appropriate nucleotide coding sequences, express the molecules of the invention in situ. These include, but are not limited to, microorganisms such as bacteria (e.g., *E. coli* and *B. subtilis*) transformed with recombinant bacteriophage DNA, plasmid DNA or cosmid DNA expression vectors containing coding sequences for the molecules identified by the methods of the invention; yeast (e.g., *Saccharomyces Pichia*) transformed with recombinant yeast expression vectors containing sequences encoding the molecules identified by the methods of the invention; insect cell systems infected with recombinant virus expression vectors (e.g., baculovirus) containing the sequences encoding the molecules identified by the methods of the invention; plant cell systems infected with recombinant virus expression vectors (e.g., cauliflower mosaic virus (CaMV) and tobacco mosaic virus (TMV) or transformed with recombinant plasmid expression vectors (e.g., Ti plasmid) containing sequences encoding the molecules identified by the methods of the invention; or mammalian cell systems (e.g., COS, CHO, BHK, 293, 293T, 3T3 cells, lymphotic cells (see U.S. Pat. No. 5,807,715), Per C.6 cells (human retinal cells developed by Crucell) harboring recombinant expression constructs containing promoters derived from the genome of mammalian cells (e.g., metallothionein promoter) or from mammalian viruses (e.g., the adenovirus late promoter; the vaccinia virus 7.5K promoter).

In bacterial systems, a number of expression vectors may be advantageously selected depending upon the use intended for the molecule being expressed. For example, when a large quantity of such a protein is to be produced, for the generation of pharmaceutical compositions of an antibody, vectors which direct the expression of high levels of fusion protein products that are readily purified may be desirable. Such vectors include, but are not limited, to the *E. coli* expression vector pUR278 (Ruther et al., 1983, *EMBO J.* 2:1791), in which the antibody coding sequence may be ligated individually into the vector in frame with the lac Z coding region so that a fusion protein is produced; pIN vectors (Inouye & Inouye, 1985, *Nucleic Acids Res.* 13:3101-3109; Van Heeke & Schuster, 1989, *J. Biol. Chem.* 24:5503-5509); and the like. pGEX vectors may also be used to express foreign polypeptides as fusion proteins with glutathione S-transferase (GST). In general, such fusion proteins are soluble and can easily be purified from lysed cells by adsorption and binding to a matrix glutathione-agarose beads followed by elution in the presence of free gluta-thione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (e.g., the polyhedrin gene) of the virus and placed under control of an AcNPV promoter (e.g., the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the immunoglobulin molecule in infected hosts (e.g., see Logan & Shenk, 1984, *Proc. Natl. Acad. Sci. USA* 81:355-359). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, *Methods in Enzymol.* 153:51-544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 293T, 3T3, WI38, BT483, Hs578T, HTB2, BT20 and T47D, CRL7030 and Hs578Bst.

For long-term, high-yield production of recombinant proteins, stable expression is preferred. For example, cell lines which stably express an antibody of the invention may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibodies of the invention. Such engineered cell lines may be particularly useful in screening and evaluation of compounds that interact directly or indirectly with the antibodies of the invention.

A number of selection systems may be used, including but not limited to the herpes simplex virus thymidine kinase (Wigler et al., 1977, *Cell* 11: 223), hypoxanthine-guanine phosphoribosyltransferase (Szybalska & Szybalski, 1992, *Proc. Natl. Acad. Sci. USA* 48: 202), and adenine phosphoribosyltransferase (Lowy et al., 1980, *Cell* 22: 817) genes can be employed in tk–, hgprt– or aprt– cells, respectively. Also, antimetabolite resistance can be used as the basis of selection for the following genes: dhfr, which confers resistance to methotrexate (Wigler et al., 1980, *Proc. Natl. Acad. Sci. USA* 77:357; O'Hare et al., 1981, *Proc. Natl. Acad. Sci. USA* 78: 1527); gpt, which confers resistance to mycophenolic acid (Mulligan & Berg, 1981, *Proc. Natl. Acad. Sci. USA* 78: 2072); neo, which confers resistance to the aminoglycoside G-418 Clinical Pharmacy 12: 488-505; Wu and Wu, 1991, 3:87-95; Tolstoshev, 1993, *Ann. Rev. Pharmacol. Toxicol.* 32:573-596; Mulligan, 1993, *Science* 260:926-932; and Morgan and Anderson, 1993, *Ann. Rev. Biochem.* 62:191-217; May, 1993, *TIB TECH* 11(5):155-215). Methods commonly known in the art of recombinant DNA technology which can be used are described in Ausubel et al. (eds.), 1993, *Current Protocols in Molecular Biology*, John Wiley & Sons, NY; Kriegler, 1990, *Gene Transfer and Expression, A Laboratory Manual*, Stockton Press, NY; and in Chapters 12 and 13, Dracopoli et al. (eds), 1994, *Current Protocols in Human Genetics*, John Wiley & Sons, NY.; Colberre-Garapin et al., 1981, *J. Mol. Biol.* 150:1; and hygro, which confers resistance to hygromycin (Santerre et al., 1984, *Gene* 30:147).

The expression levels of an antibody of the invention can be increased by vector amplification (for a review, see Bebbington and Hentschel, *The use of vectors based on gene amplification for the expression of cloned genes in mammalian cells in DNA cloning*, Vol. 3 (Academic Press, New York, 1987). When a marker in the vector system expressing an antibody is amplifiable, increase in the level of inhibitor present in culture of host cell will increase the number of copies of the marker gene. Since the amplified region is associated with the nucleotide sequence of the antibody, production of the antibody will also increase (Crouse et al., 1983, *Mol. Cell. Biol.* 3:257).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes both heavy and light chain polypeptides. In such situations, the light chain should be placed before the heavy chain to avoid an excess of toxic free heavy chain (Proudfoot, 1986, *Nature* 322:52; Kohler, 1980, *Proc. Natl. Acad. Sci. USA* 77:2197). The coding sequences for the heavy and light chains may comprise cDNA or genomic DNA.

Once a molecule of the invention (i.e., antibodies) has been recombinantly expressed, it may be purified by any method known in the art for purification of polypeptides or antibodies, for example, by chromatography (e.g., ion exchange, affinity, particularly by affinity for the specific antigen after Protein A, and sizing column chromatography), centrifugation, differential solubility, or by any other standard technique for the purification of polypeptides or antibodies.

7.4 Prophylactic and Therapeutic Methods

The present invention encompasses administering one or more of the molecules of the invention (e.g., antibodies) to an animal, preferably a mammal, and most preferably a human, for preventing, treating, or ameliorating one or more symptoms associated with a disease, disorder, or infection. The molecules of the invention are particularly useful for the treatment or prevention of a disease or disorder where an enhanced efficacy of effector cell function (e.g., ADCC) mediated by FcγR is desired. The methods and compositions of the invention are particularly useful for the treatment or prevention of primary or metastatic neoplastic disease (i.e., cancer), and infectious diseases. Molecules of the invention may be provided in pharmaceutically acceptable compositions as known in the art or as described herein. As detailed below, the molecules of the invention can be used in methods of treating or preventing cancer (particularly in passive immunotherapy), autoimmune disease, inflammatory disorders or infectious diseases.

The molecules of the invention may also be advantageously utilized in combination with other therapeutic agents known in the art for the treatment or prevention of a cancer, autoimmune disease, inflammatory disorders or infectious diseases. In a specific embodiment, molecules of the invention may be used in combination with monoclonal or chimeric antibodies, lymphokines, or hematopoietic growth factors (such as, e.g., IL-2, IL-3 and IL-7), which, for example, serve to increase the number or activity of effector cells which interact with the molecules and, increase immune response. The molecules of the invention may also be advantageously utilized in combination with one or more drugs used to treat a disease, disorder, or infection such as, for example anti-cancer agents, anti-inflammatory agents or anti-viral agents, e.g., as detailed in Sections 6.4.1.2 and 6.4.2.1 below.

7.4.1 Cancers

The invention encompasses methods and composition for treatment or prevention of cancer or metastasis in a subject comprising administering to the subject a therapeutically effective amount of one or more molecules comprising a variant Fc region.

Molecules of the invention (i.e., polypeptides, antibodies) comprising variant Fc regions can be used to prevent, inhibit or reduce the growth of primary tumors or metastasis of cancerous cells. In one embodiment, the molecule of the invention comprises a variant Fc that binds FcγRIIIA and/or FcγRIIA with a greater affinity than a comparable polypeptide comprising a wild type Fc region binds FcγRIIIA and/or FcγRIIA, and/or said variant Fc region has an enhanced effector function, e.g., ADCC, CDC, phagocytosis, opsonization, etc. Such molecules can be used alone to treat or prevent cancer. In another embodiment, the molecule of the invention comprises a variant Fc region that binds FcγRIIIA and/or FcγRIIA with a greater affinity than a comparable polypeptide comprising a wild type Fc region binds FcγRIIIA and/or FcγRIIA, and further binds FcγRIIB with a lower affinity than a comparable polypeptide comprising a wild-type Fc region binds FcγRIIB, and/or said variant Fc region has an enhanced effector function, e.g., ADCC, CDC, phagocytosis, opsonization, etc. Such molecules can also be used alone to treat or prevent cancer.

In some embodiments, the invention encompasses methods and compositions for the treatment or prevention of cancer in a subject with FcγR polymorphisms such as those homozygous for the FγRIIIA-158V or FcγRIIIA-158F alleles. In some embodiments, the invention encompasses engineering therapeutic antibodies, e.g., tumor specific monoclonal antibodies in accordance with the methods of the invention such that the engineered antibodies have enhanced efficacy in patients homozygous for the low affinity allele of FcγRIIIA (158F). In other embodiments, the invention encompasses engineering therapeutic antibodies, e.g., tumor specific monoclonal antibodies in accordance with the methods of the invention such that the engineered antibodies have enhanced efficacy in patients homozygous for the high affinity allele of FcγRIIIA (158V).

In some embodiments, the engineered antibodies of the invention are particularly effective in treating and/or preventing non-Hodgkin's lymphoma (NHL). The engineered antibodies of the invention are therapeutically more effective than current therapeutic regimens for NHL, including but not limited to chemotherapy, and immunotherapy using anti-CD20 mAb, Rituximab. The efficacy of anti-CD20 monoclonal antibodies however depends on the FcγR polymorphism of the subject (Carton et al., 2002 Blood, 99: 754-8; Weng et al., 2003 J Clin Oncol. 21(21):3940-7 both of which are incorporated hrein by reference in their entireties). These receptors are expressed on the surface of the effector cells and mediate ADCC. High affinity alleles, of the low affinity activating receptors, improve the effector cells' ability to mediate ADCC. The methods of the invention allow engineering anti-CD20 antibodies harboring Fc mutations to enhance their affinity to FcγR on effector cells via their altered Fc domains. The engineered antibodies of the invention provide better immunotherapy reagents for patients regardless of their FcγR polymorphism.

An exemplary method for determining the efficacy of the engineered anti-CD20 antibodies in a subject may include the following: Plasmids harboring chimeric anti-HER2/neu heavy chain genes with Fc mutations that show substantially increased killing in ADCC can be be used as a backbone to transfer in the variable domain from the Rituximab heavy chain gene. The variable region from the anti-HER2/neu Fc variant is replaced with the variable region from Rituximab. Plasmids containing wild type Fc domains or a D265A mutation to abrogate FcR binding, or the anti-CD20 Fc variants are transiently cotransfected with the Rituximab light chain gene into 293H cells, conditioned media and the antibody is purified over a protein G column using routine methods.

Anti-CD20 mAbs harboring the Fc variants are tested by ADCC using a cultured B cell line to determine the ability of the Fc mutations to enhance ADCC. Standard ADCC is performed using methods disclosed herein. Lymphocytes are harvested from peripheral blood using a Ficoll-Paque gradient (Pharmacia). Target Daudi cells, a B-cell line expressing CD20, are loaded with Europium (PerkinElmer) and incubated with effectors for 4 hrs at 37° C. Released Europium is detected using a fluorescent plate reader (Wallac). The resulting ADCC data indicates the efficacy of the Fc variants to trigger NK cell mediated cytotoxicity and establish which anti-CD20 Fc variants can be tested with both patient samples and elutriated monocytes. Fc variants showing the greatest potential for enhancing the efficacy of the anti-CD20 antibody are then tested in an ADCC assay using PBMCs from patients. PBMC from healthy donors are used as effector cells. In vitro ADCC assays using anti-CD20 variants and Rituximab are performed in primary lymphoma cells from patients with follicular lymphoma. The specific FcγR polymorphism of the donors is determined and cataloged using methods known in the art. ADCC assay is performed by effector cells from patients with different FcγRIIIA and FcγRIIA genotypes.

According to an aspect of the invention, molecules (e.g., antibodies) of the invention comprising variant Fc regions enhance the efficacy of cancer immunotherapy by increasing the potency of the antibody effector function relative to a molecule containing the wild-type Fc region, e.g., ADCC, CDC, phagocytosis, opsonization, etc. In a specific embodiment, antibody dependent cellular toxicity and/or phagocytosis of tumor cells is enhanced using the molecules of the invention with variant Fc regions. Molecules of the invention may enhance the efficacy of immunotherapy cancer treatment by enhancing at least one antibody-mediated effector function. In one particular embodiment, a molecule of the invention comprising a variant Fc region enhances the efficacy of immunotherapy treatment by enhancing the complement dependent cascade. In another embodiment of the invention, the molecule of the invention comprising a variant Fc region enhances the efficacy of immunotherapy treatment by enhancing the phagocytosis and/or opsonization of the targeted tumor cells. In another embodiment of the invention, the molecule of the invention comprising a variant Fc region enhances the efficacy of treatment by enhancing antibody-dependent cell-mediated cytotoxicity ("ADCC") in destruction of the targeted tumor cells.

The invention further contemplates engineering therapeutic antibodies (e.g., tumor specific monoclonal antibodies) for enhancing the therapeutic efficacy of the therapeutic antibody, for example, by enhancing the effector function of the therapeutic antibody (e.g., ADCC). Preferably the therapeutic antibody is a cytotoxic and/or opsonizing antibody. It will be appreciated by one of skill in the art, that once molecules of the invention with desired binding properties (e.g., molecules with variant Fc regions with at least one amino acid modification, which modification enhances the affinity of the variant Fc region for FcγRIIIA and/or FcγRIIA relative to a comparable molecule, comprising a wild-type Fc region) have been identified (See Section 6.2 and Table 10) according to the methods of the invention, therapeutic antibodies may be engineered using standard recombinant DNA techniques and any known mutagenesis techniques, as described in Section 6.2.2 to produce engineered therapeutic carrying the identified mutation sites with the desired binding properties. Any of the therapeutic antibodies listed in Table 11 that have demonstrated therapeutic utility in cancer treatment, may be engineered according to the methods of the invention, for example, by modifying the Fc region to have an enhanced affinity for FcγRIIIA and/or FcγRIIA compared to a therapeutic antibody having a wild-type Fc region, and used for the treatment and or prevention of a cancer characterized by a cancer antigen. Other therapeutic antibodies include those against pathogenic agents such as those against *Streptococcus pneumoniae* Serotype 6B, see, e.g., Sun et al., 1999, Infection and Immunity, 67(3): 1172-9.

The Fc variants of the invention may be incorporated into therapeutic antibodies such as those disclosed herein or other Fc fusion clinical candidates, i.e., a molecule comprising an Fc regions which has been approved for us in clinical trials or any other molecule that may benefit from the Fc variants of the instant invention, humanized, affinity matured, modified or engineered versions thereof.

The invention also encompasses engineering any other polypeptide comprising an Fc region which has therapeutic utility, including but not limited to ENBREL, according to the methods of the invention, in order to enhance the therapeutic efficacy of such polypeptides, for example, by enhancing the effector function of the polypeptide comprising an Fc region.

TABLE 11

THERAPEUTIC ANTIBODIES THAT CAN BE ENGINEERED ACCORDING TO THE METHODS OF THE INVENTION

| Company | Product | Disease | Target |
| --- | --- | --- | --- |
| Abgenix | ABX-EGF | Cancer | EGF receptor |
| AltaRex | OvaRex | ovarian cancer | tumor antigen CA125 |
|  | BravaRex | metastatic cancers | tumor antigen MUC1 |
| Antisoma | Theragyn (pemtumomabytrrium-90) | ovarian cancer | PEM antigen |
|  | Therex | breast cancer | PEM antigen |
| Boehringer Ingelheim | Blvatuzumab | head & neck cancer | CD44 |
| Centocor/J&J | Panorex | Colorectal cancer | 17-1A |
|  | ReoPro | PTCA | gp IIIb/IIIa |
|  | ReoPro | Acute MI | gp IIIb/IIIa |
|  | ReoPro | Ischemic stroke | gp IIIb/IIIa |
| Corixa | Bexocar | NHL | CD20 |
| CRC Technology | MAb, idiotypic 105AD7 | colorectal cancer vaccine | gp72 |
| Crucell | Anti-EpCAM | cancer | Ep-CAM |
| Cytoclonal | MAb, lung cancer | non-small cell lung cancer | NA |
| Genentech | Herceptin | metastatic breast cancer | HER-2 |
|  | Herceptin | early stage breast cancer | HER-2 |
|  | Rituxan | Relapsed/refractory low-grade or follicular NHL | CD20 |
|  | Rituxan | intermediate & high-grade NHL | CD20 |
|  | MAb-VEGF | NSCLC, metastatic | VEGF |

TABLE 11-continued

THERAPEUTIC ANTIBODIES THAT CAN BE ENGINEERED ACCORDING TO
THE METHODS OF THE INVENTION

| Company | Product | Disease | Target |
|---|---|---|---|
| | MAb-VEGF | Colorectal cancer, metastatic | VEGF |
| | AMD Fab | age-related macular degeneration | CD18 |
| | E-26 (2$^{nd}$ gen. IgE) | allergic asthma & rhinitis | IgE |
| IDEC | Zevalin (Rituxan + yttrium-90) | low grade of follicular, relapsed or refractory, CD20-positive, B-cell NHL and Rituximab-refractory NHL | CD20 |
| ImClone | Cetuximab + innotecan | refractory colorectal carcinoma | EGF receptor |
| | Cetuximab + cisplatin & radiation | newly diagnosed or recurrent head & neck cancer | EGF receptor |
| | Cetuximab + gemcitabine | newly diagnosed metastatic pancreatic carcinoma | EGF receptor |
| | Cetuximab + cisplatin + 5FU or Taxol | recurrent or metastatic head & neck cancer | EGF receptor |
| | Cetuximab + carboplatin + paclitaxel | newly diagnosed non-small cell lung carcinoma | EGF receptor |
| | Cetuximab + cisplatin | head & neck cancer (extensive incurable local-regional disease & distant metasteses) | EGF receptor |
| | Cetuximab + radiation | locally advanced head & neck carcinoma | EGF receptor |
| | BEC2 + Bacillus Calmette Guerin | small cell lung carcinoma | mimics ganglioside GD3 |
| | BEC2 + Bacillus Calmette Guerin | melanoma | mimics ganglioside GD3 |
| | IMC-1C11 | colorectal cancer with liver metasteses | VEGF-receptor |
| ImmonoGen | nuC242-DM1 | Colorectal, gastric, and pancreatic cancer | nuC242 |
| ImmunoMedics | LymphoCide | Non-Hodgkins lymphoma | CD22 |
| | LymphoCide Y-90 | Non-Hodgkins lymphoma | CD22 |
| | CEA-Cide | metastatic solid tumors | CEA |
| | CEA-Cide Y-90 | metastatic solid tumors | CEA |
| | CEA-Scan (Tc-99m-labeled arcitumomab) | colorectal cancer (radioimaging) | CEA |
| | CEA-Scan (Tc-99m-labeled arcitumomab) | Breast cancer (radioimaging) | CEA |
| | CEA-Scan (Tc-99m-labeled arcitumomab) | lung cancer (radioimaging) | CEA |
| | CEA-Scan (Tc-99m-labeled arcitumomab) | intraoperative tumors (radio imaging) | CEA |
| | LeukoScan (Tc-99m-labeled sulesomab) | soft tissue infection (radioimaging) | CEA |
| | LymphoScan (Tc-99m-labeled) | lymphomas (radioimaging) | CD22 |
| | AFP-Scan (Tc-99m-labeled) | liver 7 gem-cell cancers (radioimaging) | AFP |
| Intracel | HumaRAD-HN (+ yttrium-90) | head & neck cancer | NA |
| | HumaSPECT | colorectal imaging | NA |

TABLE 11-continued

THERAPEUTIC ANTIBODIES THAT CAN BE ENGINEERED ACCORDING TO THE METHODS OF THE INVENTION

| Company | Product | Disease | Target |
|---|---|---|---|
| Medarex | MDX-101 (CTLA-4) | Prostate and other cancers | CTLA-4 |
| | MDX-210 (her-2 overexpression) | Prostate cancer | HER-2 |
| | MDX-210/MAK | Cancer | HER-2 |
| MedImmune | Vitaxin | Cancer | $\alpha v \beta_3$ |
| Merck KGaA | MAb 425 | Various cancers | EGF receptor |
| | IS-IL-2 | Various cancers | Ep-CAM |
| Millennium | Campath (alemtuzumab) | chronic lymphocytic leukemia | CD52 |
| NeoRx | CD20-streptavidin (+ biotin-yttrium 90) | Non-Hodgkins lymphoma | CD20 |
| | Avidicin (albumin + NRLU13) | metastatic cancer | NA |
| Peregrine | Oncolym (+ iodine-131) | Non-Hodgkins lymphoma | HLA-DR 10 beta |
| | Cotara (+ iodine-131) | unresectable malignant glioma | DNA-associated proteins |
| Pharmacia Corporation | C215 (+ staphylococcal enterotoxin) | pancreatic cancer | NA |
| | MAb, lung/kidney cancer | lung & kidney cancer | NA |
| | nacolomab tafenatox (C242 + staphylococcal enterotoxin) | colon & pancreatic cancer | NA |
| Protein Design Labs | Nuvion | T cell malignancies | CD3 |
| | SMART M195 | AML | CD33 |
| | SMART 1D10 | NHL | HLA-DR antigen |
| Titan | CEAVac | colorectal cancer, advanced | CEA |
| | TriGem | metastatic melanoma & small cell lung cancer | GD2-ganglioside |
| | TriAb | metastatic breast cancer | MUC-1 |
| Trilex | CEAVac | colorectal cancer, advanced | CEA |
| | TriGem | metastatic melanoma & small cell lung cancer | GD2-ganglioside |
| | TriAb | metastatic breast cancer | MUC-1 |
| Viventia Biotech | NovoMAb-G2 radiolabeled | Non-Hodgkins lymphoma | NA |
| | Monopharm C | colorectal & pancreatic carcinoma | SK-1 antigen |
| | GlioMAb-H (+ gelonin toxin) | glioma, melanoma & neuroblastoma | NA |
| Xoma | Rituxan | Relapsed/refractory low-grade or follicular NHL | CD20 |
| | Rituxan | intermediate & high-grade NHL | CD20 |
| | ING-1 | adenomcarcinoma | Ep-CAM |

Accordingly, the invention provides methods of preventing or treating cancer characterized by a cancer antigen, using a therapeutic antibody that binds a cancer antigen and is cytotoxic and has been modified at one or more sites in the Fc region, according to the invention, to bind FcγRIIIA and/or FcγRIIA with a higher affinity than the parent therapeutic antibody, and/or mediates effector function (e.g., ADCC, phagocytosis) more effectively. In another embodiment, the invention provides methods of preventing or treating cancer characterized by a cancer antigen, using a therapeutic antibody that binds a cancer antigen and is cytotoxic, and has been engineered according to the invention to bind FcγRIIIA and/or FcγRIIA with a higher affinity and bind FcγRIIB with a lower affinity than the parent therapeutic antibody, and/or mediates effector function (e.g., ADCC, phagocytosis) more effectively. The therapeutic antibodies that have been engineered according to the invention are useful for prevention or treatment of cancer, since they have an enhanced cytotoxic activity (e.g., enhanced tumor cell killing and/or enhanced for example, ADCC activity or CDC activity).

Cancers associated with a cancer antigen may be treated or prevented by administration of a therapeutic antibody that binds a cancer antigen and is cytotoxic, and has been engineered according to the methods of the invention to have, for example, an enhanced effector function. In one particular embodiment, the therapeutic antibodies engineered according to the methods of the invention enhance the antibody-mediated cytotoxic effect of the antibody directed at the particular cancer antigen. For example, but not by way of limitation, cancers associated with the following cancer antigens may be treated or prevented by the methods and compositions of the invention: KS 1/4 pancarcinoma antigen (Perez and Walker, 1990, *J. Immunol.* 142:32-37; Bumal, 1988, *Hybridoma* 7(4):407-415), ovarian carcinoma antigen (CA125) (Yu et al., 1991, *Cancer Res.* 51(2):48-475), prostatic acid phosphate (Tailor et al., 1990, *Nucl. Acids Res.* 18(1):4928), prostate specific antigen (Henttu and Vihko, 1989, *Biochem. Biophys. Res. Comm.* 10(2):903-910; Israeli et al., 1993, *Cancer Res.* 53:227-230), melanoma-associated antigen p97 (Estin et al., 1989, *J. Natl. Cancer Instit.* 81(6):445-44), melanoma antigen gp75 (Vijayasardahl et al., 1990, *J Exp. Med.* 171(4):1375-1380), high molecular weight melanoma antigen (HMW-MAA) (Natali et al., 1987, *Cancer* 59:55-3; Mittelman et al., 1990, *J Clin. Invest.* 86:2136-2144)), prostate specific membrane antigen, carcinoembryonic antigen (CEA) (Foon et al., 1994, *Proc. Am. Soc. Clin. Oncol.* 13:294), polymorphic epithelial mucin antigen, human milk fat globule antigen, Colorectal tumor-associated antigens such as: CEA, TAG-72 (Yokata et al., 1992, *Cancer Res.* 52:3402-3408), C017-1A (Ragnhammar et al., 1993, *Int. J. Cancer* 53:751-758); GICA 19-9 (Herlyn et al., 1982, *J. Clin. Immunol.* 2:135), CTA-1 and LEA, Burkitt's lymphoma antigen-38.13, CD19 (Ghetie et al., 1994, *Blood* 83:1329-1336), human B-lymphoma antigen-CD20 (Reff et al., 1994, *Blood* 83:435-445), CD33 (Sgouros et al., 1993, *J. Nucl. Med.* 34:422-430), melanoma specific antigens such as ganglioside GD2 (Saleh et al., 1993, *J. Immunol.*, 151, 3390-3398), ganglioside GD3 (Shitara et al., 1993, *Cancer Immunol. Immunother.* 36:373-380), ganglioside GM2 (Livingston et al., 1994, *J. Clin. Oncol.* 12:1036-1044), ganglioside GM3 (Hoon et al., 1993, *Cancer Res.* 53:5244-5250), tumor-specific transplantation type of cell-surface antigen (TSTA) such as virally-induced tumor antigens including T-antigen DNA tumor viruses and envelope antigens of RNA tumor viruses, oncofetal antigen-alpha-fetoprotein such as CEA of colon, bladder tumor oncofetal antigen (Hellstrom et al., 1985, *Cancer. Res.* 45:2210-2188), differentiation antigen such as human lung carcinoma antigen L6, L20 (Hellstrom et al., 1986, *Cancer Res.* 46:3917-3923), antigens of fibrosarcoma, human leukemia T cell antigen-Gp37 (Bhattacharya-Chatterjee et al., 1988, *J of Immun.* 141:1398-1403), neoglycoprotein, sphingolipids, breast cancer antigen such as EGFR (Epidermal growth factor receptor), HER2 antigen (p185$^{HER2}$), polymorphic epithelial mucin (PEM) (Hilkens et al., 1992, *Trends in Bio. Chem. Sci.* 17:359), malignant human lymphocyte antigen-APO-1 (Bernhard et al., 1989, *Science* 245:301-304), differentiation antigen (Feizi, 1985, *Nature* 314:53-57) such as I antigen found in fetal erthrocytes and primary endoderm, I(Ma) found in gastric adencarcinomas, M18 and M39 found in breast epithelium, SSEA-1 found in myeloid cells, VEP8, VEP9, Myl, VIM-DS, and D156-22 found in colorectal cancer, TRA-1-85 (blood group H), C14 found in colonic adenocarcinoma, F3 found in lung adenocarcinoma, AH6 found in gastric cancer, Y hapten, Le$^y$ found in embryonal carcinoma cells, TL5 (blood group A), EGF receptor found in A431 cells, E$_1$ series (blood group B) found in pancreatic cancer, FC10.2 found in embryonal carcinoma cells, gastric adenocarcinoma, CO-514 (blood group Le$^a$) found in adenocarcinoma, NS-10 found in adenocarcinomas, CO-43 (blood group Le$^b$), G49, EGF receptor, (blood group ALe$^b$/Le$^y$) found in colonic adenocarcinoma, 19.9 found in colon cancer, gastric cancer mucins, T$_5$A$_7$ found in myeloid cells, R24 found in melanoma, 4.2, GD3, D1.1, OFA-1, GM2, OFA-2, GD2, M1:22: 25:8 found in embryonal carcinoma cells and SSEA-3, SSEA-4 found in 4-8-cell stage embryos. In another embodiment, the antigen is a T cell receptor derived peptide from a cutaneous T cell lymphoma (see Edelson, 1998, *The Cancer Journal* 4:62).

Cancers and related disorders that can be treated or prevented by methods and compositions of the present invention include, but are not limited to, the following: Leukemias including, but not limited to, acute leukemia, acute lymphocytic leukemia, acute myelocytic leukemias such as myeloblastic, promyelocytic, myelomonocytic, monocytic, erythroleukemia leukemias and myelodysplastic syndrome, chronic leukemias such as but not limited to, chronic myelocytic (granulocytic) leukemia, chronic lymphocytic leukemia, hairy cell leukemia; polycythemia vera; lymphomas such as but not limited to Hodgkin's disease, non-Hodgkin's disease; multiple myelomas such as but not limited to smoldering multiple myeloma, nonsecretory myeloma, osteosclerotic myeloma, plasma cell leukemia, solitary plasmacytoma and extramedullary plasmacytoma; Waldenström's macroglobulinemia; monoclonal gammopathy of undetermined significance; benign monoclonal gammopathy; heavy chain disease; bone and connective tissue sarcomas such as but not limited to bone sarcoma, osteosarcoma, chondrosarcoma, Ewing's sarcoma, malignant giant cell tumor, fibrosarcoma of bone, chordoma, periosteal sarcoma, soft-tissue sarcomas, angiosarcoma (hemangiosarcoma), fibrosarcoma, Kaposi's sarcoma, leiomyosarcoma, liposarcoma, lymphangiosarcoma, neurilemmoma, rhabdomyosarcoma, synovial sarcoma; brain tumors including but not limited to, glioma, astrocytoma, brain stem glioma, ependymoma, oligodendroglioma, nonglial tumor, acoustic neurinoma, craniopharyngioma, medulloblastoma, meningioma, pineocytoma, pineoblastoma, primary brain lymphoma; breast cancer including, but not limited to, adenocarcinoma, lobular (small cell) carcinoma, intraductal carcinoma, medullary breast cancer, mucinous breast cancer, tubular breast cancer, papillary breast cancer, Paget's disease, and inflammatory breast cancer; adrenal cancer, including but not limited to, pheochromocytom and adrenocortical carcinoma; thyroid cancer such as but not limited to papillary or follicular thyroid cancer, medullary thyroid cancer and anaplastic thyroid cancer; pancreatic cancer, including but not limited to, insulinoma, gastrinoma, glucagonoma, vipoma, somatostatin-secreting tumor, and carcinoid or islet cell tumor; pituitary cancers including but not limited to, Cushing's disease, prolactin-secreting tumor, acromegaly, and diabetes insipius; eye cancers including but not limited to, ocular melanoma such as iris melanoma, choroidal melanoma, and cilliary body melanoma, and retinoblastoma; vaginal cancers, including but not limited to, squamous cell carcinoma, adenocarcinoma, and melanoma; vulvar cancer, including but not limited to, squamous cell carcinoma, melanoma, adenocarcinoma, basal cell carcinoma, sarcoma, and Paget's disease; cervical cancers including but not limited to, squamous cell carcinoma, and adenocarcinoma; uterine cancers including but not limited to, endometrial carcinoma and uterine sarcoma; ovarian cancers including but not limited to, ovarian epithelial carcinoma, borderline tumor, germ cell tumor, and stromal tumor; esophageal cancers including but not limited to, squamous cancer, adenocarcinoma, adenoid cyctic carcinoma, mucoepidermoid carcinoma, adenosquamous carcinoma, sarcoma, melanoma, plasmacytoma, verrucous carcinoma, and oat cell (small cell) carcinoma; stomach cancers including but not limited to, adenocarcinoma, fungating (polypoid), ulcerating, superficial spreading, diffusely spreading, malignant lymphoma, liposarcoma, fibrosarcoma, and carcinosarcoma; colon cancers; rectal cancers; liver cancers including but not limited to hepatocellular carcinoma and hepatoblastoma, gallbladder cancers including but not limited to, adenocarcinoma; cholangiocarcinomas including but not limited to, pappillary, nodular, and diffuse; lung cancers including but not limited to, non-small cell lung cancer, squamous cell carcinoma (epidermoid carcinoma), adenocarcinoma, large-cell carcinoma and small-cell lung cancer; testicular cancers including but not limited to, germinal tumor, seminoma, anaplastic, classic (typical), spermatocytic, nonseminoma, embryonal carcinoma, teratoma carcinoma, choriocarcinoma (yolk-sac tumor), prostate cancers including but not limited to, adenocarcinoma, leiomyosarcoma, and rhabdomyosarcoma; penal cancers; oral cancers including but not limited to, squamous cell carcinoma; basal cancers; salivary gland cancers including but not limited to, adenocarcinoma, mucoepidermoid carcinoma, and adenoidcystic carcinoma; pharynx cancers including but not limited to, squamous cell cancer, and verrucous; skin cancers including but not limited to, basal cell carcinoma, squamous cell carcinoma and melanoma, superficial spreading melanoma, nodular melanoma, lentigo malignant melanoma, acral lentiginous melanoma; kidney cancers including but not limited to, renal cell cancer, adenocarcinoma, hypernephroma, fibrosarcoma, transitional cell cancer (renal pelvis and/or uterer); Wilms' tumor; bladder cancers including but not limited to, transitional cell carcinoma, squamous cell cancer, adenocarcinoma, carcinosarcoma. In addition, cancers include myxosarcoma, osteogenic sarcoma, endotheliosarcoma, lymphangioendotheliosarcoma, mesothelioma, synovioma, hemangioblastoma, epithelial carcinoma, cystadenocarcinoma, bronchogenic carcinoma, sweat gland carcinoma, sebaceous gland carcinoma, papillary carcinoma and papillary adenocarcinomas (for a review of such disorders, see Fishman et al., 1985, *Medicine*, 2d Ed., J.B. Lippincott Co., Philadelphia and Murphy et al., 1997, *Informed Decisions: The Complete Book of Cancer Diagnosis, Treatment, and Recovery*, Viking Penguin, Penguin Books U.S.A., Inc., United States of America).

Accordingly, the methods and compositions of the invention are also useful in the treatment or prevention of a variety of cancers or other abnormal proliferative diseases, including (but not limited to) the following: carcinoma, including that of the bladder, breast, colon, kidney, liver, lung, ovary, pancreas, stomach, prostate, cervix, thyroid and skin; including squamous cell carcinoma; hematopoietic tumors of lymphoid lineage, including leukemia, acute lymphocytic leukemia, acute lymphoblastic leukemia, B-cell lymphoma, T-cell lymphoma, Burketts lymphoma; hematopoietic tumors of myeloid lineage, including acute and chronic myelogenous leukemias and promyelocytic leukemia; tumors of mesenchymal origin, including fibrosarcoma and rhabdomyoscarcoma; other tumors, including melanoma, seminoma, tetratocarcinoma, neuroblastoma and glioma; tumors of the central and peripheral nervous system, including astrocytoma, neuroblastoma, glioma, and schwannomas; tumors of mesenchymal origin, including fibrosafcoma, rhabdomyoscarama, and osteosarcoma; and other tumors, including melanoma, xenoderma pegmentosum, keratoactanthoma, seminoma, thyroid follicular cancer and teratocarcinoma. It is also contemplated that cancers caused by aberrations in apoptosis would also be treated by the methods and compositions of the invention. Such cancers may include but not be limited to follicular lymphomas, carcinomas with p53 mutations, hormone dependent tumors of the breast, prostate and ovary, and precancerous lesions such as familial adenomatous polyposis, and myelodysplastic syndromes. In specific embodiments, malignancy or dysproliferative changes (such as metaplasias and dysplasias), or hyperproliferative disorders, are treated or prevented by the methods and compositions of the invention in the ovary, bladder, breast, colon, lung, skin, pancreas, or uterus. In other specific embodiments, sarcoma, melanoma, or leukemia is treated or prevented by the methods and compositions of the invention.

In a specific embodiment, a molecule of the invention (e.g., an antibody comprising a variant Fc region, or a therapeutic monoclonal antibody engineered according to the methods of the invention) inhibits or reduces the growth of primary tumor or metastasis of cancerous cells by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the growth of primary tumor or metastasis in the absence of said molecule of the invention.

7.4.1.1 Combination Therapy

The invention further encompasses administering the molecules of the invention in combination with other therapies known to those skilled in the art for the treatment or prevention of cancer, including but not limited to, current standard and experimental chemotherapies, hormonal therapies, biological therapies, immunotherapies, radiation therapies, or surgery. In some embodiments, the molecules of the invention may be administered in combination with a therapeutically or prophylactically effective amount of one or more anti-cancer agents, therapeutic antibodies (e.g., antibodies listed in Table 11), or other agents known to those skilled in the art for the treatment and/or prevention of cancer (See Section 6.4.1.2).

In certain embodiments, one or more molecule of the invention is administered to a mammal, preferably a human, concurrently with one or more other therapeutic agents useful for the treatment of cancer. The term "concurrently" is not limited to the administration of prophylactic or therapeutic agents at exactly the same time, but rather it is meant that a molecule of the invention and the other agent are administered to a mammal in a sequence and within a time interval such that the molecule of the invention can act together with the other agent to provide an increased benefit than if they were administered otherwise. For example, each prophylactic or therapeutic agent (e.g., chemotherapy, radiation therapy, hormonal therapy or biological therapy) may be administered at the same time or sequentially in any order at different points in time; however, if not administered at the same time, they should be administered sufficiently close in time so as to provide the desired therapeutic or prophylactic effect. Each therapeutic agent can be administered separately, in any appropriate form and by any suitable route. In various embodiments, the prophylactic or therapeutic agents are administered less than 1 hour apart, at about 1 hour apart, at about 1 hour to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, no more than 24 hours apart or no more than 48 hours apart. In preferred embodiments, two or more components are administered within the same patient visit.

In other embodiments, the prophylactic or therapeutic agents are administered at about 2 to 4 days apart, at about 4 to 6 days apart, at about 1 week part, at about 1 to 2 weeks apart, or more than 2 weeks apart. In preferred embodiments, the prophylactic or therapeutic agents are administered in a time frame where both agents are still active. One skilled in the art would be able to determine such a time frame by determining the half life of the administered agents.

In certain embodiments, the prophylactic or therapeutic agents of the invention are cyclically administered to a subject. Cycling therapy involves the administration of a first agent for a period of time, followed by the administration of a second agent and/or third agent for a period of time and repeating this sequential administration. Cycling therapy can reduce the development of resistance to one or more of the therapies, avoid or reduce the side effects of one of the therapies, and/or improves the efficacy of the treatment.

In certain embodiments, prophylactic or therapeutic agents are administered in a cycle of less than about 3 weeks, about once every two weeks, about once every 10 days or about once every week. One cycle can comprise the administration of a therapeutic or prophylactic agent by infusion over about 90 minutes every cycle, about 1 hour every cycle, about 45 minutes every cycle. Each cycle can comprise at least 1 week of rest, at least 2 weeks of rest, at least 3 weeks of rest. The number of cycles administered is from about 1 to about 12 cycles, more typically from about 2 to about 10 cycles, and more typically from about 2 to about 8 cycles.

In yet other embodiments, the therapeutic and prophylactic agents of the invention are administered in metronomic dosing regimens, either by continuous infusion or frequent administration without extended rest periods. Such metronomic administration can involve dosing at constant intervals without rest periods. Typically the therapeutic agents, in particular cytotoxic agents, are used at lower doses. Such dosing regimens encompass the chronic daily administration of relatively low doses for extended periods of time. In preferred embodiments, the use of lower doses can minimize toxic side effects and eliminate rest periods. In certain embodiments, the therapeutic and prophylactic agents are delivered by chronic low-dose or continuous infusion ranging from about 24 hours to about 2 days, to about 1 week, to about 2 weeks, to about 3 weeks to about 1 month to about 2 months, to about 3 months, to about 4 months, to about 5 months, to about 6 months. The scheduling of such dose regimens can be optimized by the skilled oncologist.

In other embodiments, courses of treatment are administered concurrently to a mammal, i.e., individual doses of the therapeutics are administered separately yet within a time interval such that molecules of the invention can work together with the other agent or agents. For example, one component may be administered one time per week in combination with the other components that may be administered one time every two weeks or one time every three weeks. In other words, the dosing regimens for the therapeutics are carried out concurrently even if the therapeutics are not administered simultaneously or within the same patient visit.

When used in combination with other prophylactic and/or therapeutic agents, the molecules of the invention and the prophylactic and/or therapeutic agent can act additively or, more preferably, synergistically. In one embodiment, a molecule of the invention is administered concurrently with one or more therapeutic agents in the same pharmaceutical composition. In another embodiment, a molecule of the invention is administered concurrently with one or more other therapeutic agents in separate pharmaceutical compositions. In still another embodiment, a molecule of the invention is administered prior to or subsequent to administration of another prophylactic or therapeutic agent. The invention contemplates administration of a molecule of the invention in combination with other prophylactic or therapeutic agents by the same or different routes of administration, e.g., oral and parenteral. In certain embodiments, when a molecule of the invention is administered concurrently with another prophylactic or therapeutic agent that potentially produces adverse side effects including, but not limited to, toxicity, the prophylactic or therapeutic agent can advantageously be administered at a dose that falls below the threshold that the adverse side effect is elicited.

The dosage amounts and frequencies of administration provided herein are encompassed by the terms therapeutically effective and prophylactically effective. The dosage and frequency further will typically vary according to factors specific for each patient depending on the specific therapeutic or prophylactic agents administered, the severity and type of cancer, the route of administration, as well as age, body weight, response, and the past medical history of the patient. Suitable regimens can be selected by one skilled in the art by considering such factors and by following, for example, dosages reported in the literature and recommended in the *Physician's Desk Reference* (56$^{th}$ ed., 2002).

7.4.1.2 Other Therapeutic/Prophylactic Agents

In a specific embodiment, the methods of the invention encompass the administration of one or more molecules of the invention with one or more therapeutic agents used for the treatment and/or prevention of cancer. In one embodiment, angiogenesis inhibitors may be administered in combination with the molecules of the invention. Angiogenesis inhibitors that can be used in the methods and compositions of the invention include but are not limited to: Angiostatin (plasminogen fragment); antiangiogenic antithrombin III; Angiozyme; ABT-627; Bay 12-9566; Benefin; Bevacizumab; BMS-275291; cartilage-derived inhibitor (CDI); CAI; CD59 complement fragment; CEP-7055; Col 3; Combretastatin A-4; Endostatin (collagen XVIII fragment); Fibronectin fragment; Gro-beta; Halofuginone; Heparinases; Heparin hexasaccharide fragment; HMV833; Human chorionic gonadotropin (hCG); IM-862; Interferon alpha/beta/gamma; Interferon inducible protein (IP-10); Interleukin-12; Kringle 5 (plasminogen fragment); Marimastat; Metalloproteinase inhibitors (TIMPs); 2-Methoxyestradiol; MMI 270 (CGS 27023A); MoAb IMC-1C11; Neovastat; NM-3; Panzem; PI-88; Placental ribonuclease inhibitor; Plasminogen activator inhibitor; Platelet factor-4 (PF4); Prinomastat; Prolactin 16 kD fragment; Proliferin-related protein (PRP); PTK 787/ZK 222594; Retinoids; Solimastat; Squalamine; SS 3304; SU 5416; SU6668; SU11248; Tetrahydrocortisol-S; tetrathiomolybdate; thalidomide; Thrombospondin-1 (TSP-1); TNP-470; Transforming growth factor-beta (TGF-b); Vasculostatin; Vasostatin (calreticulin fragment); ZD6126; ZD 6474; farnesyl transferase inhibitors (FTI); and bisphosphonates.

Anti-cancer agents that can be used in combination with the molecules of the invention in the various embodiments of the invention, including pharmaceutical compositions and dosage forms and kits of the invention, include, but are not limited to: acivicin; aclarubicin; acodazole hydrochloride; acronine; adozelesin; aldesleukin; altretamine; ambomycin; ametantrone acetate; aminoglutethimide; amsacrine; anastrozole; anthramycin; asparaginase; asperlin; azacitidine; azetepa; azotomycin; batimastat; benzodepa; bicalutamide;

bisantrene hydrochloride; bisnafide dimesylate; bizelesin; bleomycin sulfate; brequinar sodium; bropirimine; busulfan; cactinomycin; calusterone; caracemide; carbetimer; carboplatin; carmustine; carubicin hydrochloride; carzelesin; cedefingol; chlorambucil; cirolemycin; cisplatin; cladribine; crisnatol mesylate; cyclophosphamide; cytarabine; dacarbazine; dactinomycin; daunorubicin hydrochloride; decitabine; dexormaplatin; dezaguanine; dezaguanine mesylate; diaziquone; docetaxel; doxorubicin; doxorubicin hydrochloride; droloxifene; droloxifene citrate; dromostanolone propionate; duazomycin; edatrexate; eflornithine hydrochloride; elsamitrucin; enloplatin; enpromate; epipropidine; epirubicin hydrochloride; erbulozole; esorubicin hydrochloride; estramustine; estramustine phosphate sodium; etanidazole; etoposide; etoposide phosphate; etoprine; fadrozole hydrochloride; fazarabine; fenretinide; floxuridine; fludarabine phosphate; fluorouracil; flurocitabine; fosquidone; fostriecin sodium; gemcitabine; gemcitabine hydrochloride; hydroxyurea; idarubicin hydrochloride; ifosfamide; ilmofosine; interleukin II (including recombinant interleukin II, or rIL2), interferon alfa-2a; interferon alfa-2b; interferon alfa-n1; interferon alfa-n3; interferon beta-I a; interferon gamma-I b; iproplatin; irinotecan hydrochloride; lanreotide acetate; letrozole; leuprolide acetate; liarozole hydrochloride; lometrexol sodium; lomustine; losoxantrone hydrochloride; masoprocol; maytansine; mechlorethamine hydrochloride; megestrol acetate; melengestrol acetate; melphalan; menogaril; mercaptopurine; methotrexate; methotrexate sodium; metoprine; meturedepa; mitindomide; mitocarcin; mitocromin; mitogillin; mitomalcin; mitomycin; mitosper; mitotane; mitoxantrone hydrochloride; mycophenolic acid; nocodazole; nogalamycin; ormaplatin; oxisuran; paclitaxel; pegaspargase; peliomycin; pentamustine; peplomycin sulfate; perfosfamide; pipobroman; piposulfan; piroxantrone hydrochloride; plicamycin; plomestane; porfimer sodium; porfiromycin; prednimustine; procarbazine hydrochloride; puromycin; puromycin hydrochloride; pyrazofurin; riboprine; rogletimide; safingol; safingol hydrochloride; semustine; simtrazene; sparfosate sodium; sparsomycin; spirogermanium hydrochloride; spiromustine; spiroplatin; streptonigrin; streptozocin; sulofenur; talisomycin; tecogalan sodium; tegafur; teloxantrone hydrochloride; temoporfin; teniposide; teroxirone; testolactone; thiamiprine; thioguanine; thiotepa; tiazofurin; tirapazamine; toremifene citrate; trestolone acetate; triciribine phosphate; trimetrexate; trimetrexate glucuronate; triptorelin; tubulozole hydrochloride; uracil mustard; uredepa; vapreotide; verteporfin; vinblastine sulfate; vincristine sulfate; vindesine; vindesine sulfate; vinepidine sulfate; vinglycinate sulfate; vinleurosine sulfate; vinorelbine tartrate; vinrosidine sulfate; vinzolidine sulfate; vorozole; zeniplatin; zinostatin; zorubicin hydrochloride. Other anti-cancer drugs include, but are not limited to: 20-epi-1,25 dihydroxyvitamin D3; 5-ethynyluracil; abiraterone; aclarubicin; acylfulvene; adecypenol; adozelesin; aldesleukin; ALL-TK antagonists; altretamine; ambamustine; amidox; amifostine; aminolevulinic acid; amrubicin; amsacrine; anagrelide; anastrozole; andrographolide; angiogenesis inhibitors; antagonist D; antagonist G; antarelix; anti-dorsalizing morphogenetic protein-1; antiandrogen, prostatic carcinoma; antiestrogen; antineoplaston; antisense oligonucleotides; aphidicolin glycinate; apoptosis gene modulators; apoptosis regulators; apurinic acid; ara-CDP-DL-PTBA; arginine deaminase; asulacrine; atamestane; atrimustine; axinastatin 1; axinastatin 2; axinastatin 3; azasetron; azatoxin; azatyrosine; baccatin III derivatives; balanol; batimastat; BCR/ABL antagonists; benzochlorins; benzoylstaurosporine; beta lactam derivatives; beta-alethine; betaclamycin B; betulinic acid; bFGF inhibitor; bicalutamide; bisantrene; bisaziridinylspermine; bisnafide; bistratene A; bizelesin; breflate; bropirimine; budotitane; buthionine sulfoximine; calcipotriol; calphostin C; camptothecin derivatives; canarypox IL-2; capecitabine; carboxamide-amino-triazole; carboxyamidotriazole; CaRest M3; CARN 700; cartilage derived inhibitor; carzelesin; casein kinase inhibitors (ICOS); castanospermine; cecropin B; cetrorelix; chlorins; chloroquinoxaline sulfonamide; cicaprost; cis-porphyrin; cladribine; clomifene analogues; clotrimazole; collismycin A; collismycin B; combretastatin A4; combretastatin analogue; conagenin; crambescidin 816; crisnatol; cryptophycin 8; cryptophycin A derivatives; curacin A; cyclopentanthraquinones; cycloplatam; cypemycin; cytarabine ocfosfate; cytolytic factor; cytostatin; dacliximab; decitabine; dehydrodidemnin B; deslorelin; dexamethasone; dexifosfamide; dexrazoxane; dexverapamil; diaziquone; didemnin B; didox; diethylnorspermine; dihydro-5-azacytidine; dihydrotaxol, 9-; dioxamycin; diphenyl spiromustine; docetaxel; docosanol; dolasetron; doxifluridine; droloxifene; dronabinol; duocarmycin SA; ebselen; ecomustine; edelfosine; edrecolomab; eflornithine; elemene; emitefur; epirubicin; epristeride; estramustine analogue; estrogen agonists; estrogen antagonists; etanidazole; etoposide phosphate; exemestane; fadrozole; fazarabine; fenretinide; filgrastim; finasteride; flavopiridol; flezelastine; fluasterone; fludarabine; fluorodaunorunicin hydrochloride; forfenimex; formestane; fostriecin; fotemustine; gadolinium texaphyrin; gallium nitrate; galocitabine; ganirelix; gelatinase inhibitors; gemcitabine; glutathione inhibitors; hepsulfam; heregulin; hexamethylene bisacetamide; hypericin; ibandronic acid; idarubicin; idoxifene; idramantone; ilmofosine; ilomastat; imidazoacridones; imiquimod; immunostimulant peptides; insulin-like growth factor-1 receptor inhibitor; interferon agonists; interferons; interleukins; iobenguane; iododoxorubicin; ipomeanol, 4-; iroplact; irsogladine; isobengazole; isohomohalicondrin B; itasetron; jasplakinolide; kahalalide F; lamellarin-N triacetate; lanreotide; leinamycin; lenograstim; lentinan sulfate; leptolstatin; letrozole; leukemia inhibiting factor; leukocyte alpha interferon; leuprolide+estrogen+progesterone; leuprorelin; levamisole; liarozole; linear polyamine analogue; lipophilic disaccharide peptide; lipophilic platinum compounds; lissoclinamide 7; lobaplatin; lombricine; lometrexol; lonidamine; losoxantrone; lovastatin; loxoribine; lurtotecan; lutetium texaphyrin; lysofylline; lytic peptides; maitansine; mannostatin A; marimastat; masoprocol; maspin; matrilysin inhibitors; matrix metalloproteinase inhibitors; menogaril; merbarone; meterelin; methioninase; metoclopramide; MIF inhibitor; mifepristone; miltefosine; mirimostim; mismatched double stranded RNA; mitoguazone; mitolactol; mitomycin analogues; mitonafide; mitotoxin fibroblast growth factor-saporin; mitoxantrone; mofarotene; molgramostim; monoclonal antibody, human chorionic gonadotrophin; monophosphoryl lipid A+myobacterium cell wall sk; mopidamol; multiple drug resistance gene inhibitor; multiple tumor suppressor 1-based therapy; mustard anticancer agent; mycaperoxide B; mycobacterial cell wall extract; myriaporone; N-acetyldinaline; N-substituted benzamides; nafarelin; nagrestip; naloxone+pentazocine; napavin; naphterpin; nartograstim; nedaplatin; nemorubicin; neridronic acid; neutral endopeptidase; nilutamide; nisamycin; nitric oxide modulators; nitroxide antioxidant; nitrullyn; O6-benzylguanine; octreotide; okicenone; oligonucleotides; onapristone; ondansetron; ondansetron; oracin; oral cytokine inducer; ormaplatin; osaterone; oxaliplatin; oxaunomycin; paclitaxel; paclitaxel analogues; paclitaxel derivatives;

palauamine; palmitoylrhizoxin; pamidronic acid; panaxytriol; panomifene; parabactin; pazelliptine; pegaspargase; peldesine; pentosan polysulfate sodium; pentostatin; pentrozole; perflubron; perfosfamide; pennyl alcohol; phenazinomycin; phenylacetate; phosphatase inhibitors; picibanil; pilocarpine hydrochloride; pirarubicin; piritrexim; placetin A; placetin B; plasminogen activator inhibitor; platinum complex; platinum compounds; platinum-triamine complex; porfimer sodium; porfiromycin; prednisone; propyl bis-acridone; prostaglandin J2; proteasome inhibitors; protein A-based immune modulator; protein kinase C inhibitor; protein kinase C inhibitors, microalgal; protein tyrosine phosphatase inhibitors; purine nucleoside phosphorylase inhibitors; purpurins; pyrazoloacridine; pyridoxylated hemoglobin polyoxyethylene conjugate; raf antagonists; raltitrexed; ramosetron; ras farnesyl protein transferase inhibitors; ras inhibitors; ras-GAP inhibitor; retelliptine demethylated; rhenium Re 186 etidronate; rhizoxin; ribozymes; RH retinamide; rogletimide; rohitukine; romurtide; roquinimex; rubiginone B1; ruboxyl; safingol; saintopin; SarCNU; sarcophytol A; sargramostim; Sdi 1 mimetics; semustine; senescence derived inhibitor 1; sense oligonucleotides; signal transduction inhibitors; signal transduction modulators; single chain antigen binding protein; sizofiran; sobuzoxane; sodium borocaptate; sodium phenylacetate; solverol; somatomedin binding protein; sonermin; sparfosic acid; spicamycin D; spiromustine; splenopentin; spongistatin 1; squalamine; stem cell inhibitor; stem-cell division inhibitors; stipiamide; stromelysin inhibitors; sulfinosine; superactive vasoactive intestinal peptide antagonist; suradista; suramin; swainsonine; synthetic glycosaminoglycans; tallimustine; tamoxifen methiodide; tauromustine; tazarotene; tecogalan sodium; tegafur; tellurapyrylium; telomerase inhibitors; temoporfin; temozolomide; teniposide; tetrachlorodecaoxide; tetrazomine; thaliblastine; thiocoraline; thrombopoietin; thrombopoietin mimetic; thymalfasin; thymopoietin receptor agonist; thymotrinan; thyroid stimulating hormone; tin ethyl etiopurpurin; tirapazamine; titanocene bichloride; topsentin; toremifene; totipotent stem cell factor; translation inhibitors; tretinoin; triacetyluridine; triciribine; trimetrexate; triptorelin; tropisetron; turosteride; tyrosine kinase inhibitors; tyrphostins; UBC inhibitors; ubenimex; urogenital sinus-derived growth inhibitory factor; urokinase receptor antagonists; vapreotide; variolin B; vector system, erythrocyte gene therapy; velaresol; veramine; verdins; verteporfin; vinorelbine; vinxaltine; vitaxin; vorozole; zanoterone; zeniplatin; zilascorb; and zinostatin stimalamer. Preferred additional anti-cancer drugs are 5-fluorouracil and leucovorin.

Examples of therapeutic antibodies that can be used in methods of the invention include but are not limited to ZENAPAX® (daclizumab) (Roche Pharmaceuticals, Switzerland) which is an immunosuppressive, humanized anti-CD25 monoclonal antibody for the prevention of acute renal allograft rejection; PANOREX™ which is a murine anti-17-IA cell surface antigen IgG2a antibody (Glaxo Wellcome/Centocor); BEC2 which is a murine anti-idiotype (GD3 epitope) IgG antibody (ImClone System); IMC-C225 which is a chimeric anti-EGFR IgG antibody (ImClone System); VITAXIN™ which is a humanized anti-αVβ3 integrin antibody (Applied Molecular Evolution/MedImmune); Smart M195 which is a humanized anti-CD33 IgG antibody (Protein Design Lab/Kanebo); LYMPHOCIDE™ which is a humanized anti-CD22 IgG antibody (Immunomedics); ICM3 is a humanized anti-ICAM3 antibody (ICOS Pharm); IDEC-114 is a primatized anti-CD80 antibody (IDEC Pharm/Mitsubishi); IDEC-131 is a humanized anti-CD40L antibody (IDEC/Eisai); IDEC-151 is a primatized anti-CD4 antibody (IDEC); IDEC-152 is a primatized anti-CD23 antibody (IDEC/Seikagaku); SMART anti-CD3 is a humanized anti-CD3 IgG (Protein Design Lab); 5G1.1 is a humanized anti-complement factor 5 (C5) antibody (Alexion Pharm); D2E7 is a humanized anti-TNF-α antibody (CAT/BASF); CDP870 is a humanized anti-TNF-α Fab fragment (Celltech); IDEC-151 is a primatized anti-CD4 IgG1 antibody (IDEC Pharm/SmithKline Beecham); MDX-CD4 is a human anti-CD4 IgG antibody (Medarex/Eisai/Genmab); CDP571 is a humanized anti-TNF-α IgG4 antibody (Celltech); LDP-02 is a humanized anti-α4β7 antibody (LeukoSite/Genentech); OrthoClone OKT4A is a humanized anti-CD4 IgG antibody (Ortho Biotech); ANTOVA™ is a humanized anti-CD40L IgG antibody (Biogen); ANTEGREN™ is a humanized anti-VLA-4 IgG antibody (Elan); and CAT-152 is a human anti-TGF-β$_2$ antibody (Cambridge Ab Tech). Other examples of therapeutic antibodies that can be used in accordance with the invention are presented in Table 11.

7.4.2 Autoimmune Disease and Inflammatory Diseases

In some embodiments, molecules of the invention comprise a variant Fc region, having one or more amino acid modifications in one or more regions, which modification increases the affinity of the variant Fc region for FcγRIIB but decreases the affinity of the variant Fc region for FcγRIIIA and/or FcγRIIA. Molecules of the invention with such binding characteristics are useful in regulating the immune response, e.g., in inhibiting the immune response in connection with autoimmune diseases or inflammatory diseases. Although not intending to be bound by any mechanism of action, molecules of the invention with an enhanced affinity for FcγRIIB and a decreased affinity for FcγRIIIA and/or FcγRIIA may lead to dampening of the activating response to FcγR and inhibition of cellular responsiveness.

In some embodiments, a molecule of the invention comprising a variant Fc region is not an immunoglobulin, and comprises at least one amino acid modification which modification increases the affinity of the variant Fc region for FcγRIIB relative to a molecule comprising a wild-type Fc region. In other embodiments, said molecule further comprises one or more amino acid modifications, which modifications decreases the affinity of the molecule for an activating FcγR. In some embodiments, the molecule is a soluble (i.e., not membrane bound) Fc region. The invention contemplates other amino acid modifications within the soluble Fc region which modulate its affinity for various Fc receptors, including those known to one skilled in the art as described herein. In other embodiments, the molecule (e.g., the Fc region comprising at least one or more amino acid modification) is modified using techniques known to one skilled in the art and as described herein to increase the in vivo half life of the Fc region. Such molecules have therapeutic utility in treating and/or preventing an autoimmune disorder. Although not intending to be bound by any mechanism of actions, such molecules with enhanced affinity for FcγRIIB will lead to a dampening of the activating receptors and thus a dampening of the immune response and have therapeutic efficacy for treating and/or preventing an autoimmune disorder.

In certain embodiments, the one or more amino acid modifications, which increase the affinity of the variant Fc region for FcγRIIB but decrease the affinity of the variant Fc region for FcγRIIIA comprise a substitution at position 246 with threonine and at position 396 with histidine; or a substitution at position 268 with aspartic acid and at position 318 with aspartic acid; or a substitution at position 217 with serine, at position 378 with valine, and at position 408 with arginine; or a substitution at position 375 with cysteine and at position 396 with leucine; or a substitution at position 246 with isoleucine and at position 334 with asparagine. In one embodiment, the one or more amino acid modifications, which increase the affinity of the variant Fc region for FcγRIIB but decrease the affinity of the variant Fc region for FcγRIIIA comprise a substitution at position 247 with leucine. In another embodiment, the one or more amino acid modification, which increases the affinity of the variant Fc region for FcγRIIB but decreases the affinity of the variant Fc region for FcγRIIIA comprise a substitution at position 372 with tyrosine. In yet another embodiment, the one or more amino acid modification, which increases the affinity of the variant Fc region for FcγRIIB but decreases the affinity of the variant Fc region for FcγRIIIA comprise a substitution at position 326 with glutamic acid. In one embodiment, the one or more amino acid modification, which increases the affinity of the variant Fc region for FcγRIIB but decreases the affinity of the variant Fc region for FcγRIIIA comprise a substitution at position 224 with leucine.

The variant Fc regions that have an enhanced affinity for FcγRIIB and a decreased affinity for FcγRIIIA and/or FcγRIIA relative to a comparable molecule comprising a wild-type Fc region, may be used to treat or prevent autoimmune diseases or inflammatory diseases. The present invention provides methods of preventing, treating, or managing one or more symptoms associated with an autoimmune or inflammatory disorder in a subject, comprising administering to said subject a therapeutically or prophylactically effective amount of one or more molecules of the invention with variant Fc regions that have an enhanced affinity for FcγRIIB and a decreased affinity for FcγRIIIA and or FcγRIIA relative to a comparable molecule comprising a wild type Fc region.

The invention also provides methods for preventing, treating, or managing one or more symptoms associated with an inflammatory disorder in a subject further comprising, administering to said subject a therapeutically or prophylactically effective amount of one or more anti-inflammatory agents. The invention also provides methods for preventing, treating, or managing one or more symptoms associated with an autoimmune disease further comprising, administering to said subject a therapeutically or prophylactically effective amount of one or more immunomodulatory agents. Section 6.4.2.1 provides non-limiting examples of anti-inflammatory agents and immunomodulatory agents.

Examples of autoimmune disorders that may be treated by administering the molecules of the present invention include, but are not limited to, alopecia areata, ankylosing spondylitis, antiphospholipid syndrome, autoimmune Addison's disease, autoimmune diseases of the adrenal gland, autoimmune hemolytic anemia, autoimmune hepatitis, autoimmune oophoritis and orchitis, autoimmune thrombocytopenia, Behcet's disease, bullous pemphigoid, cardiomyopathy, celiac sprue-dermatitis, chronic fatigue immune dysfunction syndrome (CFIDS), chronic inflammatory demyelinating polyneuropathy, Churg-Strauss syndrome, cicatrical pemphigoid, CREST syndrome, cold agglutinin disease, Crohn's disease, discoid lupus, essential mixed cryoglobulinemia, fibromyalgia-fibromyositis, glomerulonephritis, Graves' disease, Guillain-Barre, Hashimoto's thyroiditis, idiopathic pulmonary fibrosis, idiopathic thrombocytopenia purpura (ITP), IgA neuropathy, juvenile arthritis, lichen planus, lupus erthematosus, Ménière's disease, mixed connective tissue disease, multiple sclerosis, type 1 or immune-mediated diabetes mellitus, myasthenia gravis, pemphigus vulgaris, pernicious anemia, polyarteritis *nodosa*, polychrondritis, polyglandular syndromes, polymyalgia rheumatica, polymyositis and dermatomyositis, primary agammaglobulinemia, primary biliary cirrhosis, psoriasis, psoriatic arthritis, Raynauld's phenomenon, Reiter's syndrome, Rheumatoid arthritis, sarcoidosis, scleroderma, Sjögren's syndrome, stiff-man syndrome, systemic lupus erythematosus, lupus erythematosus, takayasu arteritis, temporal arteristis/giant cell arteritis, ulcerative colitis, uveitis, vasculitides such as dermatitis herpetiformis vasculitis, vitiligo, and Wegener's granulomatosis. Examples of inflammatory disorders include, but are not limited to, asthma, encephilitis, inflammatory bowel disease, chronic obstructive pulmonary disease (COPD), allergic disorders, septic shock, pulmonary fibrosis, undifferentitated spondyloarthropathy, undifferentiated arthropathy, arthritis, inflammatory osteolysis, and chronic inflammation resulting from chronic viral or bacteria infections. As described herein in Section 3.2.2, some autoimmune disorders are associated with an inflammatory condition. Thus, there is overlap between what is considered an autoimmune disorder and an inflammatory disorder. Therefore, some autoimmune disorders may also be characterized as inflammatory disorders. Examples of inflammatory disorders which can be prevented, treated or managed in accordance with the methods of the invention include, but are not limited to, asthma, encephilitis, inflammatory bowel disease, chronic obstructive pulmonary disease (COPD), allergic disorders, septic shock, pulmonary fibrosis, undifferentiated spondyloarthropathy, undifferentiated arthropathy, arthritis, inflammatory osteolysis, and chronic inflammation resulting from chronic viral or bacteria infections.

Molecules of the invention with variant Fc regions that have an enhanced affinity for FcγRIIB and a decreased affinity for FcγRIIIA relative to a comparable molecule comprising a wild-type Fc region can also be used to reduce the inflammation experienced by animals, particularly mammals, with inflammatory disorders. In a specific embodiment, a molecule of the invention reduces the inflammation in an animal by at least 99%, at least 95%, at least 90%, at least 85%, at least 80%, at least 75%, at least 70%, at least 60%, at least 50%, at least 45%, at least 40%, at least 45%, at least 35%, at least 30%, at least 25%, at least 20%, or at least 10% relative to the inflammation in an animal, which is not administered the said molecule.

Molecules of the invention with variant Fc regions that have an enhanced affinity for FcγRIIB and a decreased affinity for FcγRIIIA relative to a comparable molecule comprising a wild-type Fc region can also be used to prevent the rejection of transplants.

The invention further contemplates engineering any of the antibodies known in the art for the treatment and/or prevention of autoimmune disease or inflammatory disease, so that the antibodies comprise a variant Fc region comprising one or more amino acid modifications, which have been identified by the methods of the invention to have an enhanced affinity for FcγRIIB and a decreased affinity for FcγRIIIA relative to a comparable molecule comprising a wild type Fc region. A non-limiting example of the antibodies that are used for the treatment or prevention of inflammatory disorders which can be engineered according to the invention is presented in Table 12A, and a non-limiting example of the antibodies that are used for the treatment or prevention of autoimmune disorder is presented in Table 12B.

TABLE 12A

ANTIBODIES FOR INFLAMMATORY DISEASES AND AUTOIMMUNE DISEASES THAT CAN ENGINEERED IN ACCORDANCE WITH THE INVENTION.

| Antibody Name | Target Antigen | Product Type | Isotype | Sponsors | Indication |
|---|---|---|---|---|---|
| 5G1.1 | Complement (C5) | Humanized | IgG | Alexion Pharm Inc | Rheumatoid Arthritis |
| 5G1.1 | Complement (C5) | Humanized | IgG | Alexion Pharm Inc | SLE |
| 5G1.1 | Complement (C5) | Humanized | IgG | Alexion Pharm Inc | Nephritis |
| 5G1.1-SC | Complement (C5) | Humanized | ScFv | Alexion Pharm Inc | Cardiopulmonary Bypass |
| 5G1.1-SC | Complement (C5) | Humanized | ScFv | Alexion Pharm Inc | Myocardial Infarction |
| 5G1.1-SC | Complement (C5) | Humanized | ScFv | Alexion Pharm Inc | Angioplasty |
| ABX-CBL | CBL | Human | | Abgenix Inc | GvHD |
| ABX-CBL | CD 147 | Murine | IgG | Abgenix Inc | Allograft rejection |
| ABX-IL8 | IL-8 | Human | IgG2 | Abgenix Inc | Psoriasis |
| Antegren | VLA-4 | Humanized | IgG | Athena/Elan | Multiple Sclerosis |
| Anti-CD11a | CD11a | Humanized | IgG1 | Genentech Inc/Xoma | Psoriasis |
| Anti-CD18 | CD18 | Humanized | Fab'2 | Genentech Inc | Myocardial infarction |
| Anti-LFA1 | CD18 | Murine | Fab'2 | Pasteur-Merieux/Immunotech | Allograft rejection |
| Antova | CD40L | Humanized | IgG | Biogen | Allograft rejection |
| Antova | CD40L | Humanized | IgG | Biogen | SLE |
| BTI-322 | CD2 | Rat | IgG | Medimmune Inc | GvHD, Psoriasis |
| CDP571 | TNF-alpha | Humanized | IgG4 | Celltech | Crohn's |
| CDP571 | TNF-alpha | Humanized | IgG4 | Celltech | Rheumatoid Arthritis |
| CDP850 | E-selectin | Humanized | | Celltech | Psoriasis |
| Corsevin M | Fact VII | Chimeric | | Centocor | Anticoagulant |
| D2E7 | TNF-alpha | Human | | CAT/BASF | Rheumatoid Arthritis |
| Hu23F2G | CD11/18 | Humanized | | ICOS Pharm Inc | Multiple Sclerosis |
| Hu23F2G | CD11/18 | Humanized | IgG | ICOS Pharm Inc | Stroke |
| IC14 | CD14 | | | ICOS Pharm Inc | Toxic shock |
| ICM3 | ICAM-3 | Humanized | | ICOS Pharm Inc | Psoriasis |
| IDEC-114 | CD80 | Primatised | | IDEC Pharm/Mitsubishi | Psoriasis |
| IDEC-131 | CD40L | Humanized | | IDEC Pharm/Eisai | SLE |
| IDEC-131 | CD40L | Humanized | | IDEC Pharm/Eisai | Multiple Sclerosis |
| IDEC-151 | CD4 | Primatised | IgG1 | IDEC Pharm/GlaxoSmithKline | Rheumatoid Arthritis |
| IDEC-152 | CD23 | Primatised | | IDEC Pharm | Asthma/Allergy |
| Infliximab | TNF-alpha | Chimeric | IgG1 | Centocor | Rheumatoid Arthritis |
| Infliximab | TNF-alpha | Chimeric | IgG1 | Centocor | Crohn's |
| LDP-01 | beta2-integrin | Humanized | IgG | Millennium Inc (Leuko Site Inc.) | Stroke |
| LDP-01 | beta2-integrin | Humanized | IgG | Millennium Inc (Leuko Site Inc.) | Allograft rejection |
| LDP-02 | alpha4beta7 | Humanized | | Millennium Inc (Leuko Site Inc.) | Ulcerative Colitis |
| MAK-195F | TNF alpha | Murine | Fab'2 | Knoll Pharm, BASF | Toxic shock |
| MDX-33 | CD64 (FcR) | Human | | Medarex/Centeon | Autoimmune haematogical disorders |
| MDX-CD4 | CD4 | Human | IgG | Medarex/Eisai/Genmab | Rheumatoid Arthritis |
| MEDI-507 | CD2 | Humanized | | Medimmune Inc | Psoriasis |
| MEDI-507 | CD2 | Humanized | | Medimmune Inc | GvHD |
| OKT4A | CD4 | Humanized | IgG | Ortho Biotech | Allograft rejection |
| OrthoClone OKT4A | CD4 | Humanized | IgG | Ortho Biotech | Autoimmune disease |
| Orthoclone/anti-CD3 OKT3 | CD3 | Murine | mIgG2a | Ortho Biotech | Allograft rejection |
| RepPro/Abciximab | gpIIbIIIa | Chimeric | Fab | Centocor/Lilly | Complications of coronary angioplasty |
| rhuMab-E25 | IgE | Humanized | IgG1 | Genentech/Novartis/Tanox Biosystems | Asthma/Allergy |
| SB-240563 | IL5 | Humanized | | GlaxoSmithKline | Asthma/Allergy |
| SB-240683 | IL-4 | Humanized | | GlaxoSmithKline | Asthma/Allergy |

TABLE 12A-continued

ANTIBODIES FOR INFLAMMATORY DISEASES AND AUTOIMMUNE DISEASES THAT CAN ENGINEERED IN ACCORDANCE WITH THE INVENTION.

| Antibody Name | Target Antigen | Product Type | Isotype | Sponsors | Indication |
|---|---|---|---|---|---|
| SCH55700 | IL-5 | Humanized | | Celltech/Schering | Asthma/Allergy |
| Simulect | CD25 | Chimeric | IgG1 | Novartis Pharm | Allograft rejection |
| SMART a-CD3 | CD3 | Humanized | | Protein Design Lab | Autoimmune disease |
| SMART a-CD3 | CD3 | Humanized | | Protein Design Lab | Allograft rejection |
| SMART a-CD3 | CD3 | Humanized IgG | | Protein Design Lab | Psoriasis |
| Zenapax | CD25 | Humanized IgG1 | | Protein Design Lab/Hoffman-La Roche | Allograft rejection |

TABLE 12B

ANTIBODIES FOR AUTOIMMUNE DISORDERS THAT CAN BE ENGINEERED IN ACCORDANCE WITH THE INVENTION

| Antibody | Indication | Target Antigen |
|---|---|---|
| ABX-RB2 | | antibody to CBL antigen on T cells, B cells and NK cells fully human antibody from the Xenomouse |
| 5c8 (Anti CD-40 ligand antibody) | Phase II trials were halted in October 99 examine "adverse events" | CD-40 |
| IDEC 131 | systemic lupus erythematous (SLE) | anti CD40 humanized |
| IDEC 151 | rheumatoid arthritis | primatized; anti-CD4 |
| IDEC 152 | Asthma | primatized; anti-CD23 |
| IDEC 114 | Psoriasis | primatized anti-CD80 |
| MEDI-507 | rheumatoid arthritis; multiple sclerosis Crohn's disease Psoriasis | anti-CD2 |
| LDP-02 (anti-b7 mAb) | inflammatory bowel disease Chron's disease ulcerative colitis | a4b7 integrin receptor on white blood cells (leukocytes) |
| SMART Anti-Gamma Interferon antibody | autoimmune disorders | Anti-Gamma Interferon |
| Verteportin | rheumatoid arthritis | |
| MDX-33 | blood disorders caused by autoimmune reactions Idiopathic Thrombocytopenia Purpurea (ITP) autoimmune hemolytic anemia | monoclonal antibody against FcRI receptors |
| MDX-CD4 | treat rheumatoid arthritis and other autoimmunity | monoclonal antibody against CD4 receptor molecule |
| VX-497 | autoimmune disorders multiple sclerosis rheumatoid arthritis inflammatory bowel disease lupus psoriasis | inhibitor of inosine monophosphate dehydrogenase (enzyme needed to make new RNA and DNA used in production of nucleotides needed for lymphocyte proliferation) |
| VX-740 | rheumatoid arthritis | inhibitor of ICE interleukin-1 beta (converting enzyme controls pathways leading to aggressive immune response) |
| VX-745 | specific to inflammation involved in chemical signalling of immune response onset and progression of inflammation | inhibitor of P38MAP kinase mitogen activated protein kinase |
| Enbrel (etanercept) | | targets TNF (tumor necrosis factor) |
| IL-8 | | fully human monoclonal antibody against IL-8 (interleukin 8) |
| Apogen MP4 | | recombinant antigen selectively destroys disease associated T-cells induces apoptosis T-cells eliminated by programmed cell death no longer attack body's own cells specific apogens target specific T-cells |

7.4.2.1 Immunomodulatory Agents and Anti-Inflammatory Agents

The present invention provides methods of treatment for autoimmune diseases and inflammatory diseases comprising administration of the molecules with variant Fc regions having an enhanced affinity for FcγRIIB and a decreased affinity for FcγRIIIA and/or FcγRIIA in conjunction with other treatment agents. Examples of immunomodulatory agents include, but are not limited to, methothrexate, ENBREL, REMICADE™, leflunomide, cyclophosphamide, cyclosporine A, and macrolide antibiotics (e.g., FK506 (tacrolimus)), methylprednisolone (MP), corticosteroids, steriods, mycophenolate mofetil, rapamycin (sirolimus), mizoribine, deoxyspergualin, brequinar, malononitriloamindes (e.g., leflunamide), T cell receptor modulators, and cytokine receptor modulators.

Anti-inflammatory agents have exhibited success in treatment of inflammatory and autoimmune disorders and are now a common and a standard treatment for such disorders. Any anti-inflammatory agent well-known to one of skill in the art can be used in the methods of the invention. Non-limiting examples of anti-inflammatory agents include non-steroidal anti-inflammatory drugs (NSAIDs), steroidal anti-inflammatory drugs, beta-agonists, antichlingeric agents, and methyl xanthines. Examples of NSAIDs include, but are not limited to, aspirin, ibuprofen, celecoxib (CELEBREX™), diclofenac (VOLTAREN™), etodolac (LODINE™), fenoprofen (NALFON™), indomethacin (INDOCIN™), ketorolac (TORADOL™), oxaprozin (DAYPRO™), nabumentone (RELAFEN™), sulindac (CLINORIL™), tolmentin (TOLECTIN™), rofecoxib (VIOXX™), naproxen (ALEVE™ NAPROSYN™), ketoprofen (ACTRON™) and nabumetone (RELAFEN™). Such NSAIDs function by inhibiting a cyclooxgenase enzyme (e.g., COX-1 and/or COX-2). Examples of steroidal antiinflammatory drugs include, but are not limited to, glucocorticoids, dexamethasone (DECADRON™), cortisone, hydrocortisone, prednisone (DELTASONE™), prednisolone, triamcinolone, azulfidine, and eicosanoids such as prostaglandins, thromboxanes, and leukotrienes.

7.4.3 Infectious Disease

The invention also encompasses methods for treating or preventing an infectious disease in a subject comprising administering a therapeutically or prophylatically effective amount of one or more molecules of the invention. Infectious diseases that can be treated or prevented by the molecules of the invention are caused by infectious agents including but not limited to viruses, bacteria, fungi, protozae, and viruses.

Viral diseases that can be treated or prevented using the molecules of the invention in conjunction with the methods of the present invention include, but are not limited to, those caused by hepatitis type A, hepatitis type B, hepatitis type C, influenza, varicella, adenovirus, herpes simplex type I (HSV-I), herpes simplex type II (HSV-II), rinderpest, rhinovirus, echovirus, rotavirus, respiratory syncytial virus, papilloma virus, papova virus, cytomegalovirus, echinovirus, arbovirus, huntavirus, coxsackie virus, mumps virus, measles virus, rubella virus, polio virus, small pox, Epstein Barr virus, human immunodeficiency virus type I (HIV-I), human immunodeficiency virus type II (HIV-II), and agents of viral diseases such as viral meningitis, encephalitis, dengue or small pox.

Bacterial diseases that can be treated or prevented using the molecules of the invention in conjunction with the methods of the present invention, that are caused by bacteria include, but are not limited to, mycobacteria *rickettsia, mycoplasma, neisseria, S. pneumonia, Borrelia burgdorferi* (Lyme disease), *Bacillus* anthracia (anthrax), tetanus, *streptococcus, staphylococcus, mycobacterium*, tetanus, pertissus, cholera, plague, diptheria, *chlamydia, S. aureus* and *legionella*.

Protozoal diseases that can be treated or prevented using the molecules of the invention in conjunction with the methods of the present invention, that are caused by protozoa include, but are not limited to, *leishmania*, kokzidioa, *trypanosoma* or malaria.

Parasitic diseases that can be treated or prevented using the molecules of the invention in conjunction with the methods of the present invention, that are caused by parasites include, but are not limited to, *chlamydia* and *rickettsia*.

According to one aspect of the invention, molecules of the invention comprising variant Fc regions have an enhanced antibody effector function towards an infectious agent, e.g., a pathogenic protein, relative to a comparable molecule comprising a wild-type Fc region. Examples of infectious agents include but are not limited to bacteria (e.g., *Escherichia coli, Klebsiella pneumoniae, Staphylococcus aureus, Enterococcus faecials, Candida albicans, Proteus vulgaris, Staphylococcus viridans*, and *Pseudomonas aeruginosa*), a pathogen (e.g., B-lymphotropic papovavirus (LPV); Bordatella pertussis; Borna Disease virus (BDV); Bovine coronavirus; Choriomeningitis virus; Dengue virus; a virus, *E. coli*; Ebola; Echovirus 1; Echovirus-11 (EV); Endotoxin (LPS); Enteric bacteria; Enteric Orphan virus; Enteroviruses; Feline leukemia virus; Foot and mouth disease virus; Gibbon ape leukemia virus (GALV); Gram-negative bacteria; Heliobacter *pylori*; Hepatitis B virus (HBV); Herpes Simplex Virus; HIV-1; Human cytomegalovirus; Human coronovirus; Influenza A, B & C; *Legionella; Leishmania mexicana; Listeria monocytogenes*; Measles virus; Meningococcus; Morbilliviruses; Mouse hepatitis virus; Murine leukemia virus; Murine gamma herpes virus; Murine retrovirus; Murine coronavirus mouse hepatitis virus; *Mycobacterium avium*-M; *Neisseria gonorrhoeae*; Newcastle disease virus; Parvovirus B19; *Plasmodium falciparum*; Pox Virus; *Pseudomonas*; Rotavirus; Samonella typhiurium; *Shigella*; Streptococci; T-cell lymphotropic virus 1; Vaccinia virus).

In a specific embodiment, molecules of the invention enhance the efficacy of treatment of an infectious disease by enhancing phagocytosis and/or opsonization of the infectious agent causing the infectious disease. In another specific embodiment, molecules of the invention enhance the efficacy of treatment of an infectious disease by enhancing ADCC of infected cells causing the infectious disease.

In some embodiments, the molecules of the invention may be administered in combination with a therapeutically or prophylactically effective amount of one or additional therapeutic agents known to those skilled in the art for the treatment and/or prevention of an infectious disease. The invention contemplates the use of the molecules of the invention in combination with antibiotics known to those skilled in the art for the treatment and or prevention of an infectious disease. Antibiotics that can be used in combination with the molecules of the invention include, but are not limited to, macrolide (e.g., tobramycin (Tobi®)), a cephalosporin (e.g., cephalexin (Keflex®), cephradine (Velosef®), cefuroxime (Ceftin®), cefprozil (Cefzil®), cefaclor (Ceclor®), cefixime (Suprax®) or cefadroxil (Duricef®)), a clarithromycin (e.g., clarithromycin (Biaxin®)), an erythromycin (e.g., erythromycin (EMycin®)), a penicillin (e.g., penicillin V (V-Cillin K® or Pen Vee K®)) or a quinolone (e.g., ofloxacin (Floxin®), ciprofloxacin (Cipro®) or norfloxacin (Noroxin®)), aminoglycoside antibiotics (e.g., apramycin, arbekacin, bambermycins, butirosin, dibekacin, neomycin, neomycin, undecylenate, netilmicin, paromomycin, ribostamycin, sisomicin, and spectinomycin), amphenicol antibiotics (e.g., azidamfenicol, chloramphenicol, florfenicol, and thiamphenicol), ansamycin antibiotics (e.g., rifamide and rifampin), carbacephems (e.g., loracarbef), carbapenems (e.g., biapenem and imipenem), cephalosporins (e.g., cefaclor, cefadroxil, cefamandole, cefatrizine, cefazedone, cefozopran, cefpimizole, cefpiramide, and cefpirome), cephamycins (e.g., cefbuperazone, cefmetazole, and cefminox), monobactams (e.g., aztreonam, carumonam, and tigemonam), oxacephems (e.g., flomoxef, and moxalactam), penicillins (e.g., amdinocillin, amdinocillin pivoxil, amoxicillin, bacampicillin, benzylpenicillinic acid, benzylpenicillin sodium, epicillin, fenbenicillin, floxacillin, penamccillin, penethamate hydriodide, penicillin o-benethamine, penicillin 0, penicillin V, penicillin V benzathine, penicillin V hydrabamine, penimepicycline, and phencihicillin potassium), lincosamides (e.g., clindamycin, and lincomycin), amphomycin, bacitracin, capreomycin, colistin, enduracidin, enviomycin, tetracyclines (e.g., apicycline, chlortetracycline, clomocycline, and demeclocycline), 2,4-diaminopyrimidines (e.g., brodimoprim), nitrofurans (e.g., furaltadone, and furazolium chloride), quinolones and analogs thereof (e.g., cinoxacin, clinafloxacin, flumequine, and grepagloxacin), sulfonamides (e.g., acetyl sulfamethoxypyrazine, benzylsulfamide, noprylsulfamide, phthalylsulfacetamide, sulfachrysoidine, and sulfacytine), sulfones (e.g., diathymosulfone, glucosulfone sodium, and solasulfone), cycloserine, mupirocin and tuberin.

In certain embodiments, the molecules of the invention can be administered in combination with a therapeutically or prophylactically effective amount of one or more antifungal agents. Antifungal agents that can be used in combination with the molecules of the invention include but are not limited to amphotericin B, itraconazole, ketoconazole, fluconazole, intrathecal, flucytosine, miconazole, butoconazole, clotrimazole, nystatin, terconazole, tioconazole, ciclopirox, econazole, haloprogrin, naftifine, terbinafine, undecylenate, and griseofuldin.

In some embodiments, the molecules of the invention can be administered in combination with a therapeutically or prophylactically effective amount of one or more anti-viral agent. Useful anti-viral agents that can be used in combination with the molecules of the invention include, but are not limited to, protease inhibitors, nucleoside reverse transcriptase inhibitors, non-nucleoside reverse transcriptase inhibitors and nucleoside analogs. Examples of antiviral agents include but are not limited to zidovudine, acyclovir, gangcyclovir, vidarabine, idoxuridine, trifluridine, and ribavirin, as well as foscarnet, amantadine, rimantadine, saquinavir, indinavir, amprenavir, lopinavir, ritonavir, the alpha-interferons; adefovir, clevadine, entecavir, pleconaril.

7.5 Vaccine Therapy

The invention further encompasses using a composition of the invention to induce an immune response against an antigenic or immunogenic agent, including but not limited to cancer antigens and infectious disease antigens (examples of which are disclosed infra). The vaccine compositions of the invention comprise one or more antigenic or immunogenic agents to which an immune response is desired, wherein the one or more antigenic or immunogenic agents is coated with a variant antibody of the invention that has an enhanced affinity to FcγRIIIA. Although not intending to be bound by a particular mechanism of action, coating an antigenic or immunogenic agent with a variant antibody of the invention that has an enhanced affinity to FcγRIIIA, enhances the immune response to the desired antigenic or immunogenic agent by inducing humoral and cell-mediated responses. The vaccine compositions of the invention are particularly effective in eliciting an immune response, preferably a protective immune response against the antigenic or immunogenic agent.

In some embodiments, the antigenic or immunogenic agent in the vaccine compositions of the invention comprises a virus against which an immune response is desired. The viruses may be recombinant or chimeric, and are preferably attenuated. Production of recombinant, chimeric, and attenuated viruses may be performed using standard methods known to one skilled in the art. The invention encompasses a live recombinant viral vaccine or an inactivated recombinant viral vaccine to be formulated in accordance with the invention. A live vaccine may be preferred because multiplication in the host leads to a prolonged stimulus of similar kind and magnitude to that occurring in natural infections, and therefore, confers substantial, long-lasting immunity. Production of such live recombinant virus vaccine formulations may be accomplished using conventional methods involving propagation of the virus in cell culture or in the allantois of the chick embryo followed by purification.

In a specific embodiment, the recombinant virus is non-pathogenic to the subject to which it is administered. In this regard, the use of genetically engineered viruses for vaccine purposes may require the presence of attenuation characteristics in these strains. The introduction of appropriate mutations (e.g., deletions) into the templates used for transfection may provide the novel viruses with attenuation characteristics. For example, specific missense mutations which are associated with temperature sensitivity or cold adaption can be made into deletion mutations. These mutations should be more stable than the point mutations associated with cold or temperature sensitive mutants and reversion frequencies should be extremely low. Recombinant DNA technologies for engineering recombinant viruses are known in the art and encompassed in the invention. For example, techniques for modifying negative strand RNA viruses are known in the art, see, e.g., U.S. Pat. No. 5,166,057, which is incorporated herein by reference in its entirety.

Alternatively, chimeric viruses with "suicide" characteristics may be constructed for use in the intradermal vaccine formulations of the invention. Such viruses would go through only one or a few rounds of replication within the host. When used as a vaccine, the recombinant virus would go through limited replication cycle(s) and induce a sufficient level of immune response but it would not go further in the human host and cause disease. Alternatively, inactivated (killed) virus may be formulated in accordance with the invention. Inactivated vaccine formulations may be prepared using conventional techniques to "kill" the chimeric viruses. Inactivated vaccines are "dead" in the sense that their infectivity has been destroyed. Ideally, the infectivity of the virus is destroyed without affecting its immunogenicity. In order to prepare inactivated vaccines, the chimeric virus may be grown in cell culture or in the allantois of the chick embryo, purified by zonal ultracentrifugation, inactivated by formaldehyde or β-propiolactone, and pooled.

In certain embodiments, completely foreign epitopes, including antigens derived from other viral or non-viral pathogens can be engineered into the virus for use in the intradermal vaccine formulations of the invention. For example, antigens of non-related viruses such as HIV (gp160, gp120, gp41) parasite antigens (e.g., malaria), bacterial or fungal antigens or tumor antigens can be engineered into the attenuated strain.

Virtually any heterologous gene sequence may be constructed into the chimeric viruses of the invention for use in the intradermal vaccine formulations. Preferably, heterologous gene sequences are moieties and peptides that act as biological response modifiers. Preferably, epitopes that induce a protective immune response to any of a variety of pathogens, or antigens that bind neutralizing antibodies may be expressed by or as part of the chimeric viruses. For example, heterologous gene sequences that can be constructed into the chimeric viruses of the invention include, but are not limited to, influenza and parainfluenza hemagglutinin neuraminidase and fusion glycoproteins such as the HN and F genes of human PIV3. In yet another embodiment, heterologous gene sequences that can be engineered into the chimeric viruses include those that encode proteins with immuno-modulating activities. Examples of immuno-modulating proteins include, but are not limited to, cytokines, interferon type 1, gamma interferon, colony stimulating factors, interleukin-1, -2, -4, -5, -6, -12, and antagonists of these agents.

In yet other embodiments, the invention encompasses pathogenic cells or viruses, preferably attenuated viruses, which express the variant antibody on their surface.

In alternative embodiments, the vaccine compositions of the invention comprise a fusion polypeptide wherein an antigenic or immunogenic agent is operatively linked to a variant antibody of the invention that has an enhanced affinity for FcγRIIIA. Engineering fusion polypeptides for use in the vaccine compositions of the invention is performed using routine recombinant DNA technology methods and is within the level of ordinary skill.

The invention further encompasses methods to induce tolerance in a subject by administering a composition of the invention. Preferably a composition suitable for inducing tolerance in a subject, comprises an antigenic or immunogenic agent coated with a variant antibody of the invention, wherein the variant antibody has a higher affinity to FcγRIIB. Although not intending to be bound by a particular mechanism of action, such compositions are effective in inducing tolerance by activating the FcγRIIB meditated inhibitory pathway.

7.6 Compositions and Methods of Administering

The invention provides methods and pharmaceutical compositions comprising molecules of the invention (i.e., antibodies, polypeptides) comprising variant Fc regions. The invention also provides methods of treatment, prophylaxis, and amelioration of one or more symptoms associated with a disease, disorder or infection by administering to a subject an effective amount of a fusion protein or a conjugated molecule of the invention, or a pharmaceutical composition comprising a fusion protein or a conjugated molecule of the invention. In a preferred aspect, an antibody, a fusion protein, or a conjugated molecule, is substantially purified (i.e., substantially free from substances that limit its effect or produce undesired side-effects). In a specific embodiment, the subject is an animal, preferably a mammal such as non-primate (e.g., cows, pigs, horses, cats, dogs, rats etc.) and a primate (e.g., monkey such as, a cynomolgous monkey and a human). In a preferred embodiment, the subject is a human. In yet another preferred embodiment, the antibody of the invention is from the same species as the subject.

Various delivery systems are known and can be used to administer a composition comprising molecules of the invention (i.e., antibodies, polypeptides), comprising variant Fc regions, e.g., encapsulation in liposomes, microparticles, microcapsules, recombinant cells capable of expressing the antibody or fusion protein, receptor-mediated endocytosis (See, e.g., Wu and Wu, 1987*, J Biol. Chem.* 262:4429-4432), construction of a nucleic acid as part of a retroviral or other vector, etc. Methods of administering a molecule of the invention include, but are not limited to, parenteral administration (e.g., intradermal, intramuscular, intraperitoneal, intravenous and subcutaneous), epidural, and mucosal (e.g., intranasal and oral routes). In a specific embodiment, the molecules of the invention are administered intramuscularly, intravenously, or subcutaneously. The compositions may be administered by any convenient route, for example, by infusion or bolus injection, by absorption through epithelial or mucocutaneous linings (e.g., oral mucosa, rectal and intestinal mucosa, etc.) and may be administered together with other biologically active agents. Administration can be systemic or local. In addition, pulmonary administration can also be employed, e.g., by use of an inhaler or nebulizer, and formulation with an aerosolizing agent. See, e.g., U.S. Pat. Nos. 6,019,968; 5,985,320; 5,985,309; 5,934,272; 5,874,064; 5,855,913; 5,290,540; and 4,880,078; and PCT Publication Nos. WO 92/19244; WO 97/32572; WO 97/44013; WO 98/31346; and WO 99/66903, each of which is incorporated herein by reference in its entirety.

The invention also provides that the molecules of the invention (i.e., antibodies, polypeptides) comprising variant Fc regions, are packaged in a hermetically sealed container such as an ampoule or sachette indicating the quantity of antibody. In one embodiment, the molecules of the invention are supplied as a dry sterilized lyophilized powder or water free concentrate in a hermetically sealed container and can be reconstituted, e.g., with water or saline to the appropriate concentration for administration to a subject. Preferably, the molecules of the invention are supplied as a dry sterile lyophilized powder in a hermetically sealed container at a unit dosage of at least 5 mg, more preferably at least 10 mg, at least 15 mg, at least 25 mg, at least 35 mg, at least 45 mg, at least 50 mg, or at least 75 mg. The lyophilized molecules of the invention should be stored at between 2 and 8° C. in their original container and the molecules should be administered within 12 hours, preferably within 6 hours, within 5 hours, within 3 hours, or within 1 hour after being reconstituted. In an alternative embodiment, molecules of the invention are supplied in liquid form in a hermetically sealed container indicating the quantity and concentration of the molecule, fusion protein, or conjugated molecule. Preferably, the liquid form of the molecules of the invention are supplied in a hermetically sealed container at least 1 mg/ml, more preferably at least 2.5 mg/ml, at least 5 mg/ml, at least 8 mg/ml, at least 10 mg/ml, at least 15 mg/kg, at least 25 mg/ml, at least 50 mg/ml, at least 100 mg/ml, at least 150 mg/ml, at least 200 mg/ml of the molecules.

The amount of the composition of the invention which will be effective in the treatment, prevention or amelioration of one or more symptoms associated with a disorder can be determined by standard clinical techniques. The precise dose to be employed in the formulation will also depend on the route of administration, and the seriousness of the condition, and should be decided according to the judgment of the practitioner and each patient's circumstances. Effective doses may be extrapolated from dose-response curves derived from in vitro or animal model test systems.

For antibodies encompassed by the invention, the dosage administered to a patient is typically 0.0001 mg/kg to 100 mg/kg of the patient's body weight. Preferably, the dosage administered to a patient is between 0.0001 mg/kg and 20 mg/kg, 0.0001 mg/kg and 10 mg/kg, 0.0001 mg/kg and 5 mg/kg, 0.0001 and 2 mg/kg, 0.0001 and 1 mg/kg, 0.0001 mg/kg and 0.75 mg/kg, 0.0001 mg/kg and 0.5 mg/kg, 0.0001 mg/kg to 0.25 mg/kg, 0.0001 to 0.15 mg/kg, 0.0001 to 0.10 mg/kg, 0.001 to 0.5 mg/kg, 0.01 to 0.25 mg/kg or 0.01 to 0.10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention or fragments thereof may be reduced by enhancing uptake and tissue penetration of the antibodies by modifications such as, for example, lipidation.

In one embodiment, the dosage of the molecules of the invention administered to a patient are 0.01 mg to 1000 mg/day, when used as single agent therapy. In another embodiment the molecules of the invention are used in combination with other therapeutic compositions and the dosage administered to a patient are lower than when said molecules are used as a single agent therapy.

In a specific embodiment, it may be desirable to administer the pharmaceutical compositions of the invention locally to the area in need of treatment; this may be achieved by, for example, and not by way of limitation, local infusion, by injection, or by means of an implant, said implant being of a porous, non-porous, or gelatinous material, including membranes, such as sialastic membranes, or fibers. Preferably, when administering a molecule of the invention, care must be taken to use materials to which the molecule does not absorb.

In another embodiment, the compositions can be delivered in a vesicle, in particular a liposome (See Langer, Science 249:1527-1533 (1990); Treat et al., in *Liposomes in the Therapy of Infectious Disease and Cancer*, Lopez-Berestein and Fidler (eds.), Liss, New York, pp. 353-365 (1989); Lopez-Berestein, ibid., pp. 3 17-327; see generally ibid.).

In yet another embodiment, the compositions can be delivered in a controlled release or sustained release system. Any technique known to one of skill in the art can be used to produce sustained release formulations comprising one or more molecules of the invention. See, e.g., U.S. Pat. No. 4,526,938; PCT publication WO 91/05548; PCT publication WO 96/20698; Ning et al., 1996, "Intratumoral Radioimmunotheraphy of a Human Colon Cancer Xenograft Using a Sustained-Release Gel," *Radiotherapy & Oncology* 39:179-189, Song et al., 1995, "Antibody Mediated Lung Targeting of Long-Circulating Emulsions," *PDA Journal of Pharmaceutical Science & Technology* 50:372-397; Cleek et al., 1997, "Biodegradable Polymeric Carriers for a bFGF Antibody for Cardiovascular Application," *Pro. Intl. Symp. Control. Rel. Bioact. Mater.* 24:853-854; and Lam et al., 1997, "Microencapsulation of Recombinant Humanized Monoclonal Antibody for Local Delivery," *Proc. Intl. Symp. Control Rel. Bioact. Mater.* 24:759-760, each of which is incorporated herein by reference in its entirety. In one embodiment, a pump may be used in a controlled release system (See Langer, supra; Sefton, 1987, *CRC Crit. Ref. Biomed. Eng.* 14:20; Buchwald et al., 1980, *Surgery* 88:507; and Saudek et al., 1989, *N Engl. J. Med.* 321:574). In another embodiment, polymeric materials can be used to achieve controlled release of antibodies (see e.g., *Medical Applications of Controlled Release*, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, 1983, *J., Macromol. Sci. Rev. Macromol. Chem.* 23:61; See also Levy et al., 1985, *Science* 228:190; During et al., 1989, *Ann. Neurol.* 25:351; Howard et al., 1989, *J. Neurosurg.* 7 1:105); U.S. Pat. Nos. 5,679,377; 5,916,597; 5,912,015; 5,989,463; 5,128,326; PCT Publication No. WO 99/15154; and PCT Publication No. WO 99/20253). Examples of polymers used in sustained release formulations include, but are not limited to, poly(2-hydroxy ethyl methacrylate), poly (methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In yet another embodiment, a controlled release system can be placed in proximity of the therapeutic target (e.g., the lungs), thus requiring only a fraction of the systemic dose (see, e.g., Goodson, in Medical Applications of Controlled Release, supra, vol. 2, pp. 115-138 (1984)). In another embodiment, polymeric compositions useful as controlled release implants are used according to Dunn et al. (See U.S. Pat. No. 5,945,155). This particular method is based upon the therapeutic effect of the in situ controlled release of the bioactive material from the polymer system. The implantation can generally occur anywhere within the body of the patient in need of therapeutic treatment. In another embodiment, a non-polymeric sustained delivery system is used, whereby a non-polymeric implant in the body of the subject is used as a drug delivery system. Upon implantation in the body, the organic solvent of the implant will dissipate, disperse, or leach from the composition into surrounding tissue fluid, and the non-polymeric material will gradually coagulate or precipitate to form a solid, microporous matrix (See U.S. Pat. No. 5,888,533).

Controlled release systems are discussed in the review by Langer (1990, *Science* 249:1527-1533). Any technique known to one of skill in the art can be used to produce sustained release formulations comprising one or more therapeutic agents of the invention. See, e.g., U.S. Pat. No. 4,526,938; International Publication Nos. WO 91/05548 and WO 96/20698; Ning et al., 1996, *Radiotherapy & Oncology* 39:179-189; Song et al., 1995, *PDA Journal of Pharmaceutical Science & Technology* 50:372-397; Cleek et al., 1997, *Pro. Int'l. Symp. Control. Rel. Bioact. Mater.* 24:853-854; and Lam et al., 1997, *Proc. Int'l. Symp. Control Rel. Bioact. Mater.* 24:759-760, each of which is incorporated herein by reference in its entirety.

In a specific embodiment where the composition of the invention is a nucleic acid encoding an antibody, the nucleic acid can be administered in vivo to promote expression of its encoded antibody, by constructing it as part of an appropriate nucleic acid expression vector and administering it so that it becomes intracellular, e.g., by use of a retroviral vector (See U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (See e.g., Joliot et al., 1991, *Proc. Natl. Acad. Sci. USA* 88:1864-1868), etc. Alternatively, a nucleic acid can be introduced intracellularly and incorporated within host cell DNA for expression by homologous recombination.

For antibodies, the therapeutically or prophylactically effective dosage administered to a subject is typically 0.1 mg/kg to 200 mg/kg of the subject's body weight. Preferably, the dosage administered to a subject is between 0.1 mg/kg and 20 mg/kg of the subject's body weight and more preferably the dosage administered to a subject is between 1 mg/kg to 10 mg/kg of the subject's body weight. The dosage and frequency of administration of antibodies of the invention may be reduced also by enhancing uptake and tissue penetration (e.g., into the lung) of the antibodies or fusion proteins by modifications such as, for example, lipidation.

Treatment of a subject with a therapeutically or prophylactically effective amount of molecules of the invention can include a single treatment or, preferably, can include a series of treatments. In a preferred example, a subject is treated with molecules of the invention in the range of between about 0.1 to 30 mg/kg body weight, one time per week for between about 1 to 10 weeks, preferably between 2 to 8 weeks, more preferably between about 3 to 7 weeks, and even more preferably for about 4, 5, or 6 weeks. In other embodiments, the pharmaceutical compositions of the invention are administered once a day, twice a day, or three times a day. In other embodiments, the pharmaceutical compositions are administered once a week, twice a week, once every two weeks, once a month, once every six weeks, once every two months, twice a year or once per year. It will also be appreciated that the effective dosage of the molecules used for treatment may increase or decrease over the course of a particular treatment.

7.6.1 Pharmaceutical Compositions

The compositions of the invention include bulk drug compositions useful in the manufacture of pharmaceutical compositions (e.g., impure or non-sterile compositions) and pharmaceutical compositions (i.e., compositions that are suitable for administration to a subject or patient) which can be used in the preparation of unit dosage forms. Such compositions comprise a prophylactically or therapeutically effective amount of a prophylactic and/or therapeutic agent disclosed herein or a combination of those agents and a pharmaceutically acceptable carrier. Preferably, compositions of the invention comprise a prophylactically or therapeutically effective amount of one or more molecules of the invention and a pharmaceutically acceptable carrier.

In one particular embodiment, the pharmaceutical composition comprises a therapeutically effective amount of one or more molecules of the invention comprising a variant Fc region, wherein said variant Fc region binds FcγRIIIA and/or FcγRIIA with a greater affinity than a comparable molecule comprising a wild-type Fc region binds FcγRIIIA and/or FcγRIIA and/or said variant Fc region mediates an effector function at least 2-fold more effectively than a comparable molecule comprising a wild-type Fc region, and a pharmaceutically acceptable carrier. In another embodiment, the pharmaceutical composition comprises a therapeutically effective amount of one or more molecules of the invention comprising a variant Fc region, wherein said variant Fc region binds FcγRIIIA with a greater affinity than a comparable molecule comprising a wild-type Fc region binds FcγRIIIA, and said variant Fc region binds FcγRIIB with a lower affinity than a comparable molecule comprising a wild-type Fc region binds FcγRIIB, and/or said variant Fc region mediates an effector function at least 2-fold more effectively than a comparable molecule comprising a wild-type Fc region, and a pharmaceutically acceptable carrier. In another embodiment, said pharmaceutical compositions further comprise one or more anti-cancer agents.

The invention also encompasses pharmaceutical compositions comprising a therapeutic antibody (e.g., tumor specific monoclonal antibody) that is specific for a particular cancer antigen, comprising one or more amino acid modifications in the Fc region as determined in accordance with the instant invention, and a pharmaceutically acceptable carrier.

In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant (e.g., Freund's adjuvant (complete and incomplete), excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like.

Generally, the ingredients of compositions of the invention are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compositions of the invention can be formulated as neutral or salt forms. Pharmaceutically acceptable salts include, but are not limited to those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

7.6.2 Kits

The invention provides a pharmaceutical pack or kit comprising one or more containers filled with the molecules of the invention (i.e., antibodies, polypeptides comprising variant Fc regions). Additionally, one or more other prophylactic or therapeutic agents useful for the treatment of a disease can also be included in the pharmaceutical pack or kit. The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The present invention provides kits that can be used in the above methods. In one embodiment, a kit comprises one or more molecules of the invention. In another embodiment, a kit further comprises one or more other prophylactic or therapeutic agents useful for the treatment of cancer, in one or more containers. In another embodiment, a kit further comprises one or more cytotoxic antibodies that bind one or more cancer antigens associated with cancer. In certain embodiments, the other prophylactic or therapeutic agent is a chemotherapeutic. In other embodiments, the prophylactic or therapeutic agent is a biological or hormonal therapeutic.

7.7 Characterization and Demonstration of Therapeutic Utility

Several aspects of the pharmaceutical compositions, prophylactic, or therapeutic agents of the invention are preferably tested in vitro, in a cell culture system, and in an animal model organism, such as a rodent animal model system, for the desired therapeutic activity prior to use in humans. For example, assays which can be used to determine whether administration of a specific pharmaceutical composition is desired, include cell culture assays in which a patient tissue sample is grown in culture, and exposed to or otherwise contacted with a pharmaceutical composition of the invention, and the effect of such composition upon the tissue sample is observed. The tissue sample can be obtained by biopsy from the patient. This test allows the identification of the therapeutically most effective prophylactic or therapeutic molecule(s) for each individual patient. In various specific embodiments, in vitro assays can be carried out with representative cells of cell types involved in an autoimmune or inflammatory disorder (e.g., T cells), to determine if a pharmaceutical composition of the invention has a desired effect upon such cell types.

Combinations of prophylactic and/or therapeutic agents can be tested in suitable animal model systems prior to use in humans. Such animal model systems include, but are not limited to, rats, mice, chicken, cows, monkeys, pigs, dogs, rabbits, etc. Any animal system well-known in the art may be used. In a specific embodiment of the invention, combinations of prophylactic and/or therapeutic agents are tested in a mouse model system. Such model systems are widely used and well-known to the skilled artisan. Prophylactic and/or therapeutic agents can be administered repeatedly. Several aspects of the procedure may vary. Said aspects include the temporal regime of administering the prophylactic and/or therapeutic agents, and whether such agents are administered separately or as an admixture.

Preferred animal models for use in the methods of the invention are, for example, transgenic mice expressing human FcγRs on mouse effector cells, e.g., any mouse model described in U.S. Pat. No. 5,877,396 (which is incorporated herein by reference in its entirety) can be used in the present invention. Transgenic mice for use in the methods of the invention include, but are not limited to, mice carrying human FcγRIIIA; mice carrying human FcγRIIA; mice carrying human FcγRIIB and human FcγRIIIA; mice carrying human FcγRIIB and human FcγRIIA.

Preferably, mutations showing the highest levels of activity in the functional assays described above will be tested for use in animal model studies prior to use in humans. Antibodies harboring the Fc mutants identified using the methods of the invention and tested in ADCC assays, including ch4D5 and ch520C9, two anti-Erb-B2 antibodies, and chCC49, an anti-TAG72 antibody, are preferred for use in animal models since they have been used previously in xenograft mouse model (Hudsiak et al., 1989, *Mol. Cell Biol.* 9: 1165-72; Lewis et al., 1993, *Cancer Immunol. Immunother.* 37: 255-63; Bergman et al., 2001 *Clin. Cancer Res.* 7: 2050-6; Johnson et al., 1995, *Anticancer Res.* 1387-93). Sufficient quantities of antibodies may be prepared for use in animal models using methods described supra, for example using mammalian expression systems and IgG purification methods disclosed and exemplified herein. A typical experiment requires at least about 5.4 mg of mutant antibody. This calculation is based on average quantities of wild type antibody required to protect 8-10 30 g mice following a loading dose of 4 µg/g and a weekly maintenance dose, 2 µg/g, for ten weeks. invention encompasse tumor cell lines as a source for xenograft tumors, such as SK-BR-3, BT474 and HT29 cells which are derived from patients with breast adenocarcinoma. These cells have both Erb-B2 and the prolactin receptors on their surface. The SK-BR-3 cells have been used successfully in both ADCC and xenograft tumor models. In other assays OVCAR3 cells derived from a human ovarian adenocarcinoma may be used. These cells express the antigen TAG72 on the cell surface and can be used in conjunction with the chCC49 antibody. The use of different antibodies and multiple tumor models will circumvent loss of any specific mutations due to an antibody specific Fc mutant incompatibility.

Mouse xenograft models may be used for examining efficacy of mouse antibodies generated against a tumor specific target based on the affinity and specificity of the CDR regions of the antibody molecule and the ability of the Fc region of the antibody to elicit an immune response (Wu et al., 2001, *Trends Cell Biol.* 11: S2-9). Transgenic mice expressing human FcγRs on mouse effector cells are unique and are tailor-made animal models to test the efficacy of human Fc-FcγR interactions. Pairs of FcγRIIIA, FcγRIIIB and FcγRIIA transgenic mouse lines generated in the lab of Dr. Jeffrey Ravetch (Through a licensing agreement with Rockefeller U. and Sloan Kettering Cancer center) can be used such as those listed in the Table 13 below.

TABLE 13

| Mice Strains | |
| --- | --- |
| Strain Background | Human FcR |
| Nude/CD16A KO | none |
| Nude/CD16A KO | FcγRIIIA |
| Nude/CD16A KO | FcγR IIA |
| Nude/CD16A KO | FcγR IIA and IIIA |
| Nude/CD32B KO | none |
| Nude/CD32B KO | FcγR IIB |

Preferably Fc mutants showing both enhanced binding to FcγRIIIA and reduced binding to FcγRIIB, increased activity in ADCC and phagocytosis assays are tested in animal model experiments. The animal model experiments examine the increase in efficacy of Fc mutant bearing antibodies in FcγRIIIA transgenic, nude mCD16A knockout mice compared to a control which has been administered native antibody. Preferably, groups of 8-10 mice are examined using a standard protocol. An exemplary animal model experiment may comprise the following steps: in a breast cancer model, ~2×10$^6$ SK-BR-3 cells are injected subcutaneously on day 1 with 0.1 mL PBS mixed with Matrigel (Becton Dickinson). Initially a wild type chimeric antibody and isotype control are administered to establish a curve for the predetermined therapeutic dose, intravenous injection of 4D5 on day 1 with an initial dose of 4 µg/g followed by weekly injections of 2 µg/g. Tumor volume is monitored for 6-8 weeks to measure progress of the disease. Tumor volume should increase linearly with time in animals injected with the isotype control. In contrast very little tumor growth should occur in the group injected with 4D5. Results from the standard dose study are used to set an upper limit for experiments testing the Fc mutants. These studies are done using subtherapeutic doses of the Fc mutant containing antibodies. A one tenth dose was used on xenograft models in experiments done in FcγRIIB knockout mice, see, Clynes et al., 2000, *Nat. Med.* 6: 443-6, with a resultant block in tumor cell growth. Since the mutants of the invention preferrably show an increase in FcγRIIIA activation and reduction in FcγRIIB binding the mutants are examined at one tenth therapeutic dose. Examination of tumor size at different intervals indicates the efficacy of the antibodies at the lower dose. Statistical analysis of the data using t test provides a way of determining if the data is significant. Fc mutants that show increased efficacy are tested at incrementally lower doses to determine the smallest possible dose as a measure of their efficacy.

The anti-inflammatory activity of the combination therapies of invention can be determined by using various experimental animal models of inflammatory arthritis known in the art and described in Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993). Experimental and spontaneous animal models of inflammatory arthritis and autoimmune rheumatic diseases can also be used to assess the anti-inflammatory activity of the combination therapies of invention. The following are some assays provided as examples, and not by limitation.

The principle animal models for arthritis or inflammatory disease known in the art and widely used include: adjuvant-induced arthritis rat models, collagen-induced arthritis rat and mouse models and antigen-induced arthritis rat, rabbit and hamster models, all described in Crofford L. J. and Wilder R. L., "Arthritis and Autoimmunity in Animals", in Arthritis and Allied Conditions: A Textbook of Rheumatology, McCarty et al. (eds.), Chapter 30 (Lee and Febiger, 1993), incorporated herein by reference in its entirety.

The anti-inflammatory activity of the combination therapies of invention can be assessed using a carrageenan-induced arthritis rat model. Carrageenan-induced arthritis has also been used in rabbit, dog and pig in studies of chronic arthritis or inflammation. Quantitative histomorphometric assessment is used to determine therapeutic efficacy. The methods for using such a carrageenan-induced arthritis model is described in Hansra P. et al., "Carrageenan-Induced Arthritis in the Rat," *Inflammation*, 24(2): 141-155, (2000). Also commonly used are zymosan-induced inflammation animal models as known and described in the art.

The anti-inflammatory activity of the combination therapies of invention can also be assessed by measuring the inhibition of carrageenan-induced paw edema in the rat, using a modification of the method described in Winter C. A. et al., "Carrageenan-Induced Edema in Hind Paw of the Rat as an Assay for Anti-inflammatory Drugs" *Proc. Soc. Exp. Biol Med.* 111, 544-547, (1962). This assay has been used as a primary in vivo screen for the anti-inflammatory activity of most NSAIDs, and is considered predictive of human efficacy. The anti-inflammatory activity of the test prophylactic or therapeutic agents is expressed as the percent inhibition of the increase in hind paw weight of the test group relative to the vehicle dosed control group.

Additionally, animal models for inflammatory bowel disease can also be used to assess the efficacy of the combination therapies of invention (Kim et al., 1992, Scand. J. Gastroenterol. 27:529-537; Strober, 1985, *Dig. Dis. Sci.* 30 (12 Suppl):3S-10S). Ulcerative cholitis and Crohn's disease are human inflammatory bowel diseases that can be induced in animals. Sulfated polysaccharides including, but not limited to amylopectin, carrageen, amylopectin sulfate, and dextran sulfate or chemical irritants including but not limited to trinitrobenzenesulphonic acid (TNBS) and acetic acid can be administered to animals orally to induce inflammatory bowel diseases.

Animal models for autoimmune disorders can also be used to assess the efficacy of the combination therapies of invention. Animal models for autoimmune disorders such as type 1 diabetes, thyroid autoimmunity, sytemic lupus eruthematosus, and glomerulonephritis have been developed (Flanders et al., 1999, *Autoimmunity* 29:235-246; Krogh et al., 1999, *Biochimie* 81:511-515; Foster, 1999, *Semin. Nephrol.* 19:12-24).

Further, any assays known to those skilled in the art can be used to evaluate the prophylactic and/or therapeutic utility of the combinatorial therapies disclosed herein for autoimmune and/or inflammatory diseases.

Toxicity and efficacy of the prophylactic and/or therapeutic protocols of the instant invention can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$.

Prophylactic and/or therapeutic agents that exhibit large therapeutic indices are preferred. While prophylactic and/or therapeutic agents that exhibit toxic side effects may be used, care should be taken to design a delivery system that targets such agents to the site of affected tissue in order to minimize potential damage to uninfected cells and, thereby, reduce side effects.

The data obtained from the cell culture assays and animal studies can be used in formulating a range of dosage of the prophylactic and/or therapeutic agents for use in humans. The dosage of such agents lies preferably within a range of circulating concentrations that include the $ED_{50}$ with little or no toxicity. The dosage may vary within this range depending upon the dosage form employed and the route of administration utilized. For any agent used in the method of the invention, the therapeutically effective dose can be estimated initially from cell culture assays. A dose may be formulated in animal models to achieve a circulating plasma concentration range that includes the IC50 (i.e., the concentration of the test compound that achieves a half-maximal inhibition of symptoms) as determined in cell culture. Such information can be used to more accurately determine useful doses in humans. Levels in plasma may be measured, for example, by high performance liquid chromatography.

The anti-cancer activity of the therapies used in accordance with the present invention also can be determined by using various experimental animal models for the study of cancer such as the SCID mouse model or transgenic mice or nude mice with human xenografts, animal models, such as hamsters, rabbits, etc. known in the art and described in *Relevance of Tumor Models for Anticancer Drug Development* (1999, eds. Fiebig and Burger); *Contributions to Oncology* (1999, Karger); *The Nude Mouse in Oncology Research* (1991, eds. Boven and Winograd); and *Anticancer Drug Development Guide* (1997 ed. Teicher), herein incorporated by reference in their entireties.

Preferred animal models for determining the therapeutic efficacy of the molecules of the invention are mouse xenograft models. Tumor cell lines that can be used as a source for xenograft tumors include but are not limited to, SKBR3 and MCF7 cells, which can be derived from patients with breast adenocarcinoma. These cells have both erbB2 and prolactin receptors. SKBR3 cells have been used routinely in the art as ADCC and xenograft tumor models. Alternatively, OVCAR3 cells derived from a human ovarian adenocarcinoma can be used as a source for xenograft tumors.

The protocols and compositions of the invention are preferably tested in vitro, and then in vivo, for the desired therapeutic or prophylactic activity, prior to use in humans. Therapeutic agents and methods may be screened using cells of a tumor or malignant cell line. Many assays standard in the art can be used to assess such survival and/or growth; for example, cell proliferation can be assayed by measuring $^3$H-thymidine incorporation, by direct cell count, by detecting changes in transcriptional activity of known genes such as proto-oncogenes (e.g., fos, myc) or cell cycle markers; cell viability can be assessed by trypan blue staining, differentiation can be assessed visually based on changes in morphology, decreased growth and/or colony formation in soft agar or tubular network formation in three-dimensional basement membrane or extracellular matrix preparation, etc.

Compounds for use in therapy can be tested in suitable animal model systems prior to testing in humans, including but not limited to in rats, mice, chicken, cows, monkeys, rabbits, hamsters, etc., for example, the animal models described above. The compounds can then be used in the appropriate clinical trials.

Further, any assays known to those skilled in the art can be used to evaluate the prophylactic and/or therapeutic utility of the combinatorial therapies disclosed herein for treatment or prevention of cancer, inflammatory disorder, or autoimmune disease.

Having now generally described the invention, the same will be more readily understood through reference to the following examples, which are provided by way of illustration and are not intended to be limiting of the present invention unless specified.

8. EXAMPLES

8.1 Analysis of Kinetic Parameters of Fc Mutants

Fc mutants exhibiting altered affinity to FcγRIIIA and FcγRIIB were determined from yeast display technology and FcγR-Fc interaction assays as disclosed in U.S Patent Application Publications 2005/0037000 and 2005/0064514, and International Patent Application Publication WO 04/063351, each of which is hereby incorporated by reference in its entirety. Effects of the mutant in in vitro assays was assessed by determining kinetic parameters of the binding of ch4-4-20 antibodies harboring the Fc mutants using a BIAcore assay (BIAcore instrument 1000, BIAcore Inc., Piscataway, N.J.). The FcγRIIIA used in this assay was a soluble monomeric protein, the extracellular region of FcγRIIIA joined to the linker-AVITAG sequence, while the FcγRIIB used in this assay was a soluble dimeric protein, both were prepared as described in U.S Patent Application Publications 2005/0037000 and 2005/0064514, and International Patent Application Publication WO 04/063351. Briefly, the FcγRIIB used was the extracellular domain of FcγRIIB fused to the hinge-CH2-CH3 domain of human IgG2.

BSA-FITC (36 μg/mL in 10 mM Acetate Buffer at pH 5.0) was immobilized on one of the four flow cells (flow cell 2) of a sensor chip surface through amine coupling chemistry (by modification of carboxymethyl groups with mixture of NHS/EDC) such that about 5000 response units (RU) of BSA-FITC was immobilized on the surface. Following this, the unreacted active esters were "capped off" with an injection of 1M Et-NH2. Once a suitable surface was prepared, ch 4-4-20 antibodies carrying the Fc mutations were passed over the surface by one minute injections of a 20 μg/mL solution at a 5 μL/mL flow rate. The level of ch-4-4-20 antibodies bound to the surface ranged between 400 and 700 RU. Next, dilution series of the receptor (FcγRIIIA and FcγRIIB-Fc fusion protein) in HBS-P buffer (10 mM HEPES, 150 mM NaCl, 0.005% Surfactant P20, 3 mM EDTA, pH 7.4) were injected onto the surface at 100 μL/min. Antibody regeneration between different receptor dilutions was carried out by single 5 second injections of 100 mM NaHCO$_3$ pH 9.4; 3M NaCl.

The same dilutions of the receptor were also injected over a BSA-FITC surface without any ch-4-4-20 antibody at the beginning and at the end of the assay as reference injections.

Once an entire data set was collected, the resulting binding curves were globally fitted using computer algorithms supplied by the manufacturer, BIAcore, Inc. (Piscataway, N.J.). These algorithms calculate both the K$_{on}$ and K$_{off}$, from which the apparent equilibrium binding constant, K$_D$ is deduced as the ratio of the two rate constants (i.e., K$_{off}$/K$_{on}$). More detailed treatments of how the individual rate constants are derived can be found in the BIAevaluaion Software Handbook (BIAcore, Inc., Piscataway, N.J.).

Binding curves for two different concentrations (200 nM and 800 nM for FcγRIIIA and 200 nM and 400 nM for FcγRIIB fusion protein) were aligned and responses adjusted to the same level of captured antibodies, and the reference curves were subtracted from the experimental curves. Association and dissociation phases were fitted separately. Dissociation rate constant was obtained for interval 32-34 sec of the dissociation phase; association phase fit was obtained by a 1:1 Langmuir model and base fit was selected on the basis R$_{max}$ and chi$^t$ criteria.

Results

Figure 4:
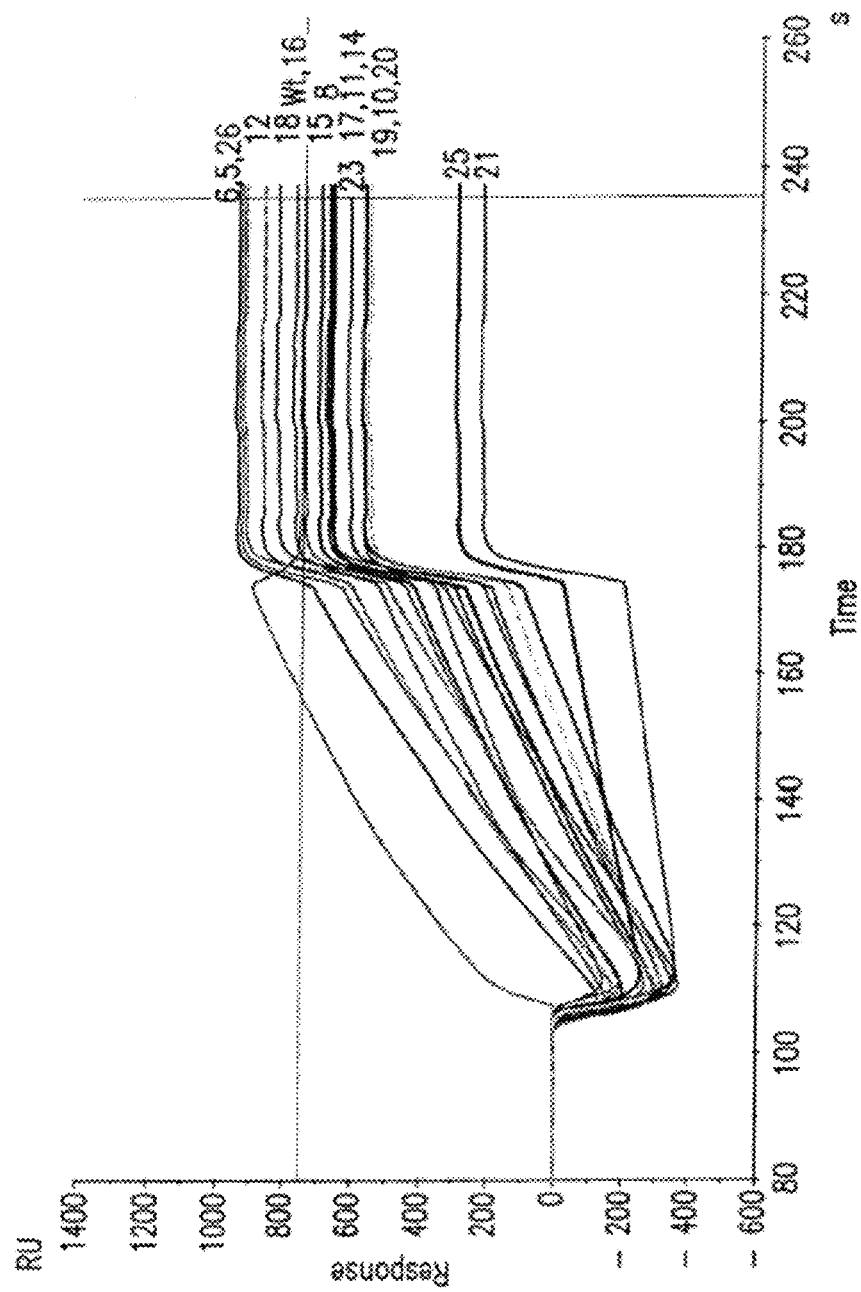

FIG. 4 shows the capture of ch 4-4-20 antibodies with mutant Fc regions on the BSA-FTIC-immobilized sensor chip. 6 μL of antibodies at a concentration of about 20 μg/mL were injected at 5 μL/min over the BSA-FITC surface. FIG. 5 is a sensogram of real time binding of FcγRIIIA to ch-4-4-20 antibodies carrying variant Fc regions. Binding of FcγRIIIA was analyzed at 200 nM concentration and resonance signal responses were normalized at the level of the response obtained for the wild type ch-4-4-20 antibody. Kinetic parameters for the binding of FcγRIIIA to ch-4-4-20 antibodies were obtained by fitting the data obtained at two different FcγRIIIA concentrations, 200 and 800 nM (FIG. 6). The solid line represents the association fit which was obtained based on the K$_{off}$ values calculated for the dissociation curves in interval 32-34 seconds. K$_D$ and K$_{off}$ represent the average calculated from the two different FcγRIIIA concentrations used. FIG. 7 is a sensogram of real time binding of FcγRIIB-Fc fusion protein to ch-4-4-20 antibodies carrying variant Fc regions. Binding of FcγRIIB-Fc fusion protein was analyzed at 200 nM concentration and resonance signal responses were normalized at the level of the response obtained for the wild type ch-4-4-20 antibody. Kinetic parameters for the binding of FcγRIIB-Fc fusion protein to ch-4-4-20 antibodies were obtained by fitting the data obtained at two different FcγRIIB-Fc fusion protein concentrations, 200 and 800 nM (FIG. 8). The solid line represents the association fit which was obtained based on the K$_{off}$ calculated for the dissociation curves in interval 32-34 seconds. K$_D$ and K$_{off}$ represent the average from the two different FcγRIIB-Fc fusion protein concentrations used.

The kinetic parameters (K$_{on}$ and K$_{off}$) that were determined from the BIAcore analysis correlated with the binding characteristic of the mutants as determined by an ELISA assay and the functional activity of the mutants as determined in an ADCC assay. Specifically, as seen in Table 14, mutants that had an enhanced ADCC activity relative to the wild-type protein, and had an enhanced binding to FcγRIIIA as determined by an ELISA assay had an improved K$_{off}$ for FcγRIIIA (i.e., a lower K$_{off}$). Therefore, a lower K$_{off}$ value for FcγRIIIA for a mutant Fc protein relative to a wild type protein may be likely to have an enhanced ADCC function. On the other hand, as seen in Table 15, mutants that had an enhanced ADCC activity relative to the wild-type protein, and had a reduced binding for FcγRIIB-Fc fusion protein as determined by an ELISA assay had a higher K$_{off}$ for FcγRIIB-Fc fusion protein.

Thus, the K$_{off}$ values for FcγRIIIA and FcγRIIB can be used as predictive measures of how a mutant will behave in a functional assay such as an ADCC assay. In fact, ratios of K$_{off}$ values for FcγRIIIA and FcγRIIB-Fc fusion protein of the mutants to the wild type protein were plotted against ADCC data (FIG. 9). Specifically, in the case of K$_{off}$ values for FcγRIIIA, the ratio of K$_{off}$(wt)/K$_{off}$(mutant) was plotted against the ADCC data; and in the case of K$_{off}$ values for FcγRIIB, the ratio of K$_{off}$(mut)/K$_{off}$(wt) was plotted against the ADCC data. Numbers higher than one (1) show a decreased dissociation rate for FcγRIIIA and an increased dissociation rate for FcγRIIB-Fc relative to wild type. Mutants that fall within the indicated box have a lower off rate for FcγRIIIA binding and a higher off-rate for FcγRIIB-Fc binding, and possess an enhanced ADCC function.

TABLE 14

Kinetic parameters of FcRIIIA binding to ch4-4-20Ab obtained by "separate fit" of 200 nM and 800 nM binding curves

| Ch4-4-20Ab | BIAcore Kd, nM | $K_{on}$ 1/Ms | $K_{off}$, 1/s | ELISA, OD | ADCC, % |
|---|---|---|---|---|---|
| Wt(0225) | 319 | $6.0 \times 10^5$ | 0.170 | 0.5 | 17.5 |
| Mut11(0225) | 90 | $\mathbf{8.22 \times 10^5}$ | 0.075 | 0.37 | 32 |
| Mut5(0225) | 214 | $8.2 \times 10^5$ | 0.172 | 0.75 | 26 |
| Mut6(0225) | 264 | $6.67 \times 10^5$ | 0.175 | 0.6 | 23 |
| Mut8(0225) | 234 | $8.3 \times 10^5$ | 0.196 | 0.5 | 22 |
| Mut10(0225) | 128 | $9.04 \times 10^5$ | 0.115 | 1.0 | 41 |
| Mut12(0225) | 111 | $1.04 \times 10^6$ | 0.115 | 1.0 | 37 |
| Mut15(0225) | 67.9 | $\mathbf{1.97 \times 10^6}$ | 0.133 | 1.0 | 15 |
| Mut16(0225) | 84.8 | $\mathbf{1.60 \times 10^6}$ | 0.133 | 1.0 | 15 |
| Mut18(0225) | 92 | $1.23 \times 10^6$ | 0.112 | 1.0 | 28 |
| Mut25(0225) | 48.6 | $2.05 \times 10^6$ | 0.1 | 1.0 | 41 |
| Mut14(0225) | 75.4 | $1.37 \times 10^6$ | 0.1 | 1.1 | 28 |
| Mut17(0225) | 70.5 | $1.42 \times 10^6$ | 0.1 | 1.25 | 30 |
| Mut19(0225) | 100 | $\mathbf{1.20 \times 10^6}$ | 0.120 | 0.75 | 11 |
| Mut20(0225) | 71.5 | $\mathbf{1.75 \times 10^6}$ | 0.126 | 0.5 | 10 |
| Mut23(0225) | 70.2 | $1.43 \times 10^6$ | 0.105 | 1.25 | 25 |

Bolded mutants do not fit to the grow by ELISA or ADCC data.

TABLE 15

Kinetic parameters of FcRIIB-Fc binding to wild type and mutant ch4-4-20Ab obtained by "separate fit" of 200 nM and 800 nM binding curves.

| Ch4-4-20Ab | BIAcore Kd, nM | $K_{on}$ 1/Ms | $K_{off}$, 1/s | ELISA, OD | ADCC, % |
|---|---|---|---|---|---|
| Wt(0225) | 61.4 | | 0.085 | 0.4 | 17.5 |
| Mut11(0225) | 82.3 | | 0.1 | 0.08 | 32 |
| Mut5(0225) | 50 | | 0.057 | 0.6 | 26 |
| Mut6(0225) | 66.5 | | 0.060 | 0.35 | 23 |
| Mut8(0225) | 44.2 | | 0.068 | 0.25 | 22 |
| Mut10(0225) | 41.3 | | 0.05 | 1.2 | 41 |
| Mut12(0225) | 40.1 | | 0.051 | 0.4 | 37 |
| Mut15(0225) | 37.8 | | 0.040 | 1.55 | 15 |
| Mut16(0225) | 40 | | 0.043 | 1.55 | 15 |
| Mut18(0225) | 51.7 | | 0.043 | 1.25 | 28 |
| Mut25(0225) | | | 0.112 | 0.08 | 41 |
| Mut14(0225) | 95.6 | | 0.089 | 0.13 | 28 |
| Mut17(0225) | 55.3 | | 0.056 | 0.38 | 30 |
| Mut19(0225) | 45.3 | | 0.046 | 1.0 | 11 |
| Mut20(0225) | 24.1 | | 0.028 | 0.8 | 10 |
| Mut23(0225) | 108 | | 0.107 | 0.1 | 25 |

8.2 Screening for Fc Mutants Using Multiple Rounds of Enrichment Using a Solid Phase Assay The following mutant screens were aimed at identifying additional sets of mutants that show improved binding to FcγRIIIA and reduced binding to FcγRIIB. Secondary screening of selected Fc variants was performed by ELISA followed by testing for ADCC in the 4-4-20 system. Mutants were than selected primarily based on their ability to mediate ADCC via 4-4-20 using Fluorescein coated SK-BR3 cells as targets and isolated PBMC from human donors as the effector cell population. Fc mutants that showed a relative increase in ADCC, e.g., an enhancement by a factor of 2 were than cloned into anti-HER2/neu or anti-CD20 chAbs and tested in an ADCC assay using the appropriate tumor cells as targets. The mutants were also analyzed by BIAcore and their relative $K_{off}$ were determined.

Screen 1: Sequential solid phase depletion and selection using Magnetic beads coated with FcγRIIB followed by selection with magnetic beads coated with FcγRIIIA. The aim of this screen was identification of Fc mutants that either no longer bind FcγRIIB or show reduced binding to FcγRIIB. A 10-fold excess of the naïve library (~$10^7$ cells) was incubated with magnetic beads ("My One", Dynal) coated with FcγRIIB. Yeast bound to beads were separated from the non-bound fraction by placing the tube containing the mixture in a magnetic field. Those yeast cells that were not bound to the beads were removed and placed in fresh media. They were next bound to beads that were coated with FcγRIIIA. Yeast bound to beads were separated from the nonbound fraction by placing the tube containing the mixture in a magnetic field. Nonbound yeast were removed and the bound cells were removed by vigorous vortexing. The recovered cells were regrown in glucose containing media and reinduced in selective media containing galactose. The selection process was repeated. The final culture was than used to harvest DNA. Inserts containing the Fc domain were amplified by PCR and cloned into 4-4-20. Approximately 90 Fc mutants were screened by 4-4-20 ELISA and ADCC assays and the resultant positive mutants are shown in Table 16.

TABLE 16

Mutants selected by sequential solid phase depletion and selection using Magnetic beads coated with FcγRIIB followed by selection with magnetic beads coated with FcγRIIIA.

| Mutant | Amino Acid changes |
|---|---|
| MgFc37 | K248M |
| MgFc38 | K392T, P396L |
| MgFc39 | E293V, Q295E, A327T |
| MgFc41 | H268N, P396LN |
| MgFc43 | Y319F, P352L, P396L |
| MgFc42 | D221E, D270E, V308A, Q311H, P396L, G402D |

Screens 2&3: Mutants Selected by FACS, Equilibrium and Kinetic Screening:

The first library screen identified a mutation at position 396, changing the amino acid from Proline to Leucine (P396L). This Fc variant showed increased binding to both FcγRIIIA and FcγRIIB. A second library was constructed using P396L as a base line. PCR mutagenesis was used to generate ~$10^7$ mutants each of which contained the P396L mutation and contained additional nucleotide changes. The P396L library was screened using two sets of conditions.

An equilibrium screen was performed using biotinylated FcγRIIIA-linker-avitag as a monomer, using methods already described. Approximately 10-fold excess of library ($10^8$ cells) was incubated in a 0.5 mL of approximately 7 nM FcγRIIIA for 1 hr. The mixture was sorted by FACS, selecting top 1.2% of binders. Selected yeast cells were grown in selective media containing glucose and reinduced in selective media containing galactose. The equilibrium screen was repeated a second time and the sort gate was set to collect the top 0.2% of binders. The selected yeast cells were then grown under selective conditions in glucose. This culture was than used to harvest DNA. Inserts containing the Fc domain were amplified by PCR and cloned into the nucleotide sequence encoding 4-4-20 variable domain using methods already described. Approximately 90 Fc mutants were screened by 4-4-20 ELISA and ADCC and the resultant positive mutants are shown in Table 17.

TABLE 17

Mutants selected by FACS using an Equilibrium screen with concentrations of FcRIIIA of approximately 7 nM.

| Mutant | Amino Acid changes |
| --- | --- |
| MgFc43b | K288R, T307A, K344E, P396L |
| MgFc44 | K334N, P396L |
| MgFc46 | P217S, P396L |
| MgFc47 | K210M, P396L |
| MgFc48 | V379M, P396L |
| MgFc49 | K261N, K210M, P396L |
| MgFc60 | P217S, P396L |

A kinetic screen was also implemented to identify mutants with improved $K_{off}$ in binding FcγRIIIA. Conditions were established for screening the P396L library using a strain with the P396L Fc variant displayed on the yeast surface. Briefly cells grown under inducing conditions were incubated with 0.1 µM biotinylated FcγRIIIA-linker-avitag monomer for 1 hr. The cells were washed to remove the labeled ligand. Labeled cells were then incubated for different times with 0.1 µM unlabeled FcγRIIIA-linker-avitag monomer, washed and then stained with SA:PE for FACS analysis (FIG. 10). Cells were also stained with goat anti-human Fc to show that the Fc display was maintained during the experiment.

Based on the competition study it was determined that a 1 minute incubation resulted in approximately 50% loss of cell staining. This time point was chosen for the kinetic screen using the P396L library. Approximately 10-fold excess of library ($10^8$ cells) was incubated with 0.1 µM biotinylated FcγRIIIA-linker-avitag monomer in a 0.5 mL volume. Cells were washed and then incubated for 1 minute with unlabeled ligand. Subsequently the cells were washed and labeled with SA:PE. The mixture was sorted by FACS, selecting the top 0.3% of binders. Selected yeast cells were grown in selective media containing glucose and reinduced in selective media containing galactose. The kinetic screen was repeated a second time and the sort gate was set to collect the top 0.2% of binders. The nonselected P396L library was compared to the yeast cells selected for improved binding by FACS (FIG. 11). The histograms show the percentage of cells that are costained with both FcγRIIIA/PE and goat anti-human Fc/FITC (upper right).

The selected yeast cells from the second sort were then grown under selective conditions in glucose. This culture was than used to harvest DNA. Inserts containing the Fc domain were amplified by PCR and cloned into the nucleotide sequence encoding 4-4-20 variable domain using methods described above. Approximately 90 Fc mutants were screened by 4-4-20 ELISA and ADCC and the resultant positive mutants are shown in Table 18.

TABLE 18

Mutants selected by FACS using a Kinetic screen using equimolar amounts of unlabeled CD16A for 1 minute.

| Mutants | Amino Acid changes |
| --- | --- |
| MgFc50 | P247S, P396L |
| MgFc51 | Q419H, P396L |
| MgFc52 | V240A, P396L |
| MgFc53 | L410H, P396L |
| MgFc54 | F243L, V305I, A378D, F404S, P396L |
| MgFc55 | R255I, P396L |
| MgFc57 | L242F, P396L |
| MgFc59 | K370E, P396L |

Screens 4 and 5: Combining the Solid Phase FcγRIIB Depletion Step with FcγRIIIA Selection by FACs Sort, Using the FcγRIIIA 158V Allele Analysis of Fc variants from Screen 1 showed that the mutations that were selected from the secondary screen had improved binding to both FcγRIIIA and FcγRIIB. Therefore, the data suggested that sequential depletion and selection using magnetic beads (solid phase) under the established conditions did not efficiently select for differential binding of FcγRIIIA and FcγRIIB. Therefore, in order to screen more effectively for mutants that bind FcγRIIIA, while having reduced or no binding to FcγRIIB, the solid phase FcγRIIB depletion step was combined with FcγRIIIA selection by FACs sort. This combination identified Fc variants that bind FcγRIIIA with greater or equal affinity than wild-type Fc.

A 10-fold excess of the naïve library (~$10^7$) was incubated with magnetic beads coated with FcγRIIB. Yeast bound to beads were separated from the non-bound fraction by placing the tube containing the mixture in a magnetic field. Those yeast cells that were not bound to the beads were removed and placed in fresh media and subsequently reinduced in media containing galactose. The FcγRIIB depletion by magnetic beads was repeated 5 times. The resulting yeast population was analyzed and found to show greater than 50% cell staining with goat anti-human Fc and a very small percentage of cells were stained with FcγRIIIA. These cells were then selected twice by a FACS sort using 0.1 µM biotinylated FcγRIIIA linker-avitag (data not shown). The FcγRIIIA was the 158V allotype. Yeast cells were analyzed for both FcγRIIIA and FcγRIIB binding after each sort and compared to binding by wild-type Fc domain (FIG. 12 A-L).

The selected yeast cells from the second sort were then grown under selective conditions in glucose. This culture was then used to harvest DNA. Inserts containing the Fc domain were amplified by PCR and cloned into the nucleotide sequence encoding 4-4-20 variable domain. Approximately 90 Fc mutants were screened by 4-4-20 ELISA and ADCC and the resultant positive mutants are shown in Table 19 (mutants 61-66).

TABLE 19

Mutants selected by magnetic bead depletion using beads coated with CD32B and final selection by FACS using FcγRIIIA 158Valine or 158Phenylalanine

| Mutants | Amino Acid Changes |
| --- | --- |
| MgFc61 | A330V |
| MgFc62 | R292G |
| MgFc63 | S298N, K360R, N361D |
| MgFc64 | E233G |
| MgFc65 | N276Y |
| MgFc66 | A330V, V427M |
| MgFc67 | V284M, S298N, K334E, R355W, R416T |

Screening of Fc Mutants Using the 158F Allele of FcγRIIIA:

Two different alleles of FcγRIIIA receptor exist that have different binding affinities for the IgG1 Fc domain (Koene et al., 1997, Blood 90: 1109-1114; Wu et al., 1997, J. Clin. Invest. 100: 1059-70). The 158F allele binds to the Fc domain with a binding constant 5-10 fold lower than the 158V allele. Previously all of the Fc screens using yeast display were done using the high binding 158V allele as a ligand. In this experiment, Fc mutants were selected from the FcγRIIB depleted yeast population using biotinylated FcγRIIIA158F-linker-avitag monomer as a ligand. The sort gate was set to select the top 0.25 percent FcγRIIIA 158F binders. The resulting enriched population was analyzed by FACS (FIG. 12 G-J). Individual clones were then isolated and their binding to different FcγRs were analyzed by FACS (FIG. 12 G-J). Analysis of individual clones from the population resulted in the identification of a single mutant harboring 5 mutations MgFc67 (V284M, S298N, K334E, R355W, R416S), which had an enhanced binding to FcγRIIIA and a reduced binding to FcγRIIB.

Secondary Screen of Mutants by an ADCC Assay for Screens 1, 2, and 3:

Mutants that were selected in the above screens were then analyzed using a standard ADCC assay to determine the relative rates of lysis mediated by ch4-4-20 harboring the Fc mutants. ch4-4-20 antibodies carrying the Fc variants were constructed using methods already described above. SK-BR3 cells were used as targets and effector cells were PBMC that were isolated from donors using a Ficoll gradient, as described supra (Section 7.7). The ADCC activity results for the mutants are summarized in Table 20.

As seen in Table 23, mutants isolated using the above primary and secondary screens based on FcγRIIB depletion and FcγRIIIA selection showed enhanced ADCC activity relative to wild-type.

TABLE 20

Analysis of ADCC mediated by 4-4-20 anti-Fluorescein antibody on SKBR3 cells coated with fluorescein.

| Mutant | Amino Acid Change | Relative rate of lysis |
|---|---|---|
| MgFc37 | K248M | 3.83 |
| MgFc38 | K392T, P396L | 3.07 |
| MgFc39 | E293V, Q295E, A327T | 4.29 |
| MgFc41 | H268N, P396LN | 2.24 |
| MgFc43 | Y319F, P352L, P396L | 1.09 |
| MgFc42 | D221E, D270E, V308A, Q311H, P396L, G402D | 3.17 |
| MgFc43b | K288R, T307A, K344E, P396L | 3.3 |
| MgFc44 | K334N, P396L | 2.43 |
| MgFc46 | P217S, P396L | 2.04 |
| MgFc47 | K210M, P396L | 2.02 |
| MgFc48 | V379M, P396L | 2.01 |
| MgFc49 | K261N, K210M, P396L | 2.06 |
| MgFc50 | P247S, P396L | 2.1 |
| MgFc51 | Q419H, P396L | 2.24 |
| MgFc52 | V240A, P396L | 2.35 |
| MgFc53 | L410H, P396L | 2 |
| MgFc54 | F243L, V305I, A378D, F404S, P396L | 3.59 |
| MgFc55 | R255I, P396L | 2.79 |
| MgFc57 | L242F, P396L | 2.4 |
| MgFc59 | K370E, P396L | 2.47 |
| MgFc60 | P217S, P396L | 1.44 |

Mutants 37, 38, 39, 41, 43 were analyzed using 0.5 μg/mL ch4-4-20. All other antibodies were tested at 1 μg/mL. All rates were normalized to wild type ch4-4-20 (IgG1).

Mutants were additionally cloned into the heavy chain of antitumor monoclonal antibody 4D5 (anti-HER2/neu) and anti-CD20 monoclonal antibody 2H7 by replacing the Fc domain of these monoclonal antibodies. These chimeric monoclonal antibodies were expressed and purified and tested in an ADCC assay using standard methods by transient transfection into 293H cells and purification over protein G column. The chimeric 4D5 antibodies were tested in an ADCC assay using SK-BR3 cells as targets (FIG. 13), whereas the chimeric 2H7 antibodies were tested in an ADCC assay using Daudi cells as targets (FIG. 14).

Secondary Screen of Mutants Via BIAcore:

Mutants that were selected in the above screens were then analyzed by BIAcore to determine the kinetic parameters for binding FcγRIIIA (158V) and FcγRIIB. The method used was similar to that disclosed in Section 7.1, supra.

The data displayed are $K_{off}$ values relative to wild type off rates as determined from experiments using the Fc mutants in the ch4-4-20 monoclonal antibody. Relative numbers greater than one indicate a decrease in $K_{off}$ rate. Numbers less than one indicate an increase in off rate.

Mutants that showed a decrease in off rates for FcγRIIIA were MgFc38 (K392, P396L), MgFc43 (Y319F, P352L, P396L), MgFc42 (D221E, D270E, V308A, Q311H, P396L, G402D), MgFc43b (K288R, T307A, K344E, P396L), MgFc44 (K334N, P396L), MgFc46 (P217S, P396L), MgFc49 (K261N, K210M, P396L). Mutants that showed a decrease in off rate for FcγRIIB were, MgFc38 (K392, P396L), MgFc39 (E293V, Q295E, A327T), MgFc43 (K288R, T307A, K344E, P396L), MgFc44 (K334N, P396L). The Biacore data is summarized in Table 21.

TABLE 21

BIAcore data

| Fc mutant | AA residues | FcγRIIIA158V (Koff WT/Mut) | FcγRIIB (Koff WT/Mut) |
|---|---|---|---|
| MgFc37 | K248M | 0.977 | 1.03 |
| MgFc38 | K392T, P396L | 1.64 | 2.3 |
| MgFc39 | E293V, Q295E, A327T | 0.86 | 1.3 |
| MgFc41 | H268N, P396LN | 0.92 | 1.04 |
| MgFc43 | Y319F, P352L, P396L | 1.23 | 2.29 |
| MgFc42 | D221E, D270E, V308A, Q311H, P396L, G402D | 1.38 | |
| MgFc43b | K288R, T307A, K344E, P396L | 1.27 | 0.89 |
| MgFc44 | K334N, P396L | 1.27 | 1.33 |
| MgFc46 | P217S, P396L | 1.17 | 0.95 |
| MgFc47 | K210M, P396L | | |
| MgFc48 | V379M, P396L | | |
| MgFc49 | K261N, K210M, P396L | 1.29 | 0.85 |
| MgFc50 | P247S, P396L | | |
| MgFc51 | Q419H, P396L | | |
| MgFc52 | V240A, P396L | | |
| MgFc53 | L410H, P396L | | |
| MgFc54 | F243L, V305I, A378D, F404S, P396L | | |
| MgFc55 | R255I, P396L | | |
| MgFc57 | L242F, P396L | | |
| MgFc59 | K370E, P396L | | |
| MgFc60 | P217S, P396L | | |
| MgFc61 | A330V | 1 | 0.61 |
| MgFc62 | R292G | 1 | 0.67 |
| MgFc63 | S298N, K360R, N361D | 1 | 0.67 |
| MgFc64 | E233G | 1 | 0.54 |
| MgFc65 | N276Y | 1 | 0.64 |
| MgFc66 | A330V, G427M, | 1 | 0.62 |
| MgFc67 | V284M, S298N, K334E, R355W, R416T | | |

8.3 PBMC Mediated ADCC Assays

Materials and Methods

Fc variants that show improved binding to FcγRIIIA were tested by PBMC based ADCC using 60:1 effector:target ratio. Two different tumor model systems were used as targets, SK-BR3 (anti-HER2/neu) and Daudi (anti-CD20). Percent specific Lysis was quantitated for each mutant. Linear regression analysis was used to plot the data setting the maximal percent lysis at 100%.

ADCC is activated on immune system effector cells via a signal transduction pathway that is triggered by an interaction between low affinity FcγR and an immune complex. Effector cell populations were derived from either primary blood or activated monocyte derived macrophages (MDM). Target cells were loaded with europium and incubated with chimeric MAb and subsequently incubated with effector cell populations. Europium works the same way as $^{51}Cr$, but it is non-radioactive and the released europium is detected in a fluorescent plate reader. Lymphocytes harvested from peripheral blood of donors (PBM) using a Ficoll-Paque gradient (Pharmacia) contain primarily natural killer cells (NK). The majority of the ADCC activity will occur via the NK containing FcγRIIIA but not FcγRIIB on their surface.

Experiments were performed using two different target cell populations, SK-BR-3 and Daudi, expressing HER2/neu and CD20, respectively. ADCC assays were set up using Ch4-4-20/FITC coated SK-BR-3, Ch4D5/SKBR3, and Rituxan/Daudi (data not shown). Chimeric MAbs were modified using Fc mutations identified. Fc mutants were cloned into Ch4D5. Purified Ab was used to opsonize SK-BR-3 cells or Daudi cells. Fc mutants were cloned into Ch4D5.

Results.

Fc mutants showed improved PBMC mediated ADCC activity in SK BR3 cells (FIG. 13). The plot shows linear regression analysis of a standard ADCC assay. Antibody was titrated over 3 logs using an effector to target ratio of 75:1. % lysis=(Experimental release−SR)/(MR−SR)*100.

Fc mutants showed improved PBMC mediated ADCC activity in Daudi cells (FIG. 14).

8.4 Monocyte Derived Macrophage (MDM) Based ADCC Assays

FcγR dependent tumor cell killing is mediated by macrophage and NK cells in mouse tumor models (Clynes et al., 1998, PNAS USA, 95: 652-6). Elutriated monocytes from donors were used as effector cells to analyze the efficiency Fc mutants to trigger cell cytotoxicity of target cells in ADCC assays. Expression patterns of FcγRI, FcγR3A, and FcγR2B are affected by different growth conditions. FcγR expression from frozen monocytes cultured in media containing different combinations of cytokines and human serum were examined by FACS using FcR specific MAbs. (FIG. 15 A-O). Cultured cells were stained with FcγR specific antibodies and analyzed by FACS to determine MDM FcγR profiles. Conditions that best mimic macrophage in vivo FcγR expression, i.e., showed the greatest fraction of cells expressing CD16 and CD32B were used in a monocyte derived macrophage (MDM) based ADCC assay. For the experiment in FIG. 15 A-O, frozen elutriated monocytes were grown for 8 days in DMEM and 20% FBS containing either M-CSF (condition 1) or GM-CSF (condition 2). For the experiment in FIG. 16, frozen elutriated monocytes were cultured for 2 days in DMEM and 20% FBS containing GM-CSF, IL-2 and IFNγ prior to ADCC assay. Serum free conditions have also been developed which allow for high levels of CD16 and CD32B expression (data not shown). Briefly, purified monocytes were grown for 6-8 days in Macrophage-SFM (Invitrogen) containing GM-CSF, M-CSF, IL-6, IL-10, and IL-1β. While the incidence of CD32B+/CD16+ cells in these cultures is highest using a mixture of cytokines, combinations of two of more cytokines will also enhance FcγR expression (M-CSF/IL-6, M-CSF/IL-10; or M-CSF/IL-1β). For ADCC assays, IFNγ is added for the final 24-48 hours.

MDM based ADCC required incubation times of >16 hrs to observe target cell killing. Target cells were loaded with Indium-111 which is retained for long incubations within the target cells. Indium release was quantitated using a gamma counter. All other reagents, Abs and target cells, were similar to the PBMC based ADCC assay. ADCC activity due to FcγRI can be efficiently blocked using the anti-FcRI blocking antibody (M21, Ancell). The assay conditions differ slightly from the PBMC based assay. 20:1 target to effector; 18-14 hr incubation at 37 C.

Fc mutants that show improved PBMC ADCC, increased binding to FcγRIIIA, or decreased binding to FcγRIIB were tested (FIG. 16).

8.5 Effect of Fc Mutants on Complement Activity

Fc mutants were originally identified based on their increased binding to FcγRIIIA. These mutants were subsequently validated for their improved affinity for all low affinity receptors and in many cases improved activity in ADCC mediated by PBMC. In vivo antibody mediated cytotoxicity can occur through multiple mechanisms. In addition to ADCC other possible mechanisms include complement dependent cytotoxicity (CDC) and apoptosis. The binding of C1q to the Fc region of an immunoglobulin initiates as cascade resulting in cell lysis by CDC. The interaction between C1q and the Fc has been studied in a series of Fc mutants. The results of these experiments indicate that C1q and the low affinity FcR bind to overlapping regions of the Fc, however the exact contact residues within the Fc vary.

Mutants that showed improved ADCC in the PBMC based assay were examined for their effect in CDC. Antibodies were analyzed in the anti CD20 Ch-mAb, 2H7. We detected improved CDC for each mutant ch-mAb tested. Interestingly even though these mutants were selected for their improved ADCC they also show enhanced CDC Materials and Methods.

Figure 17:
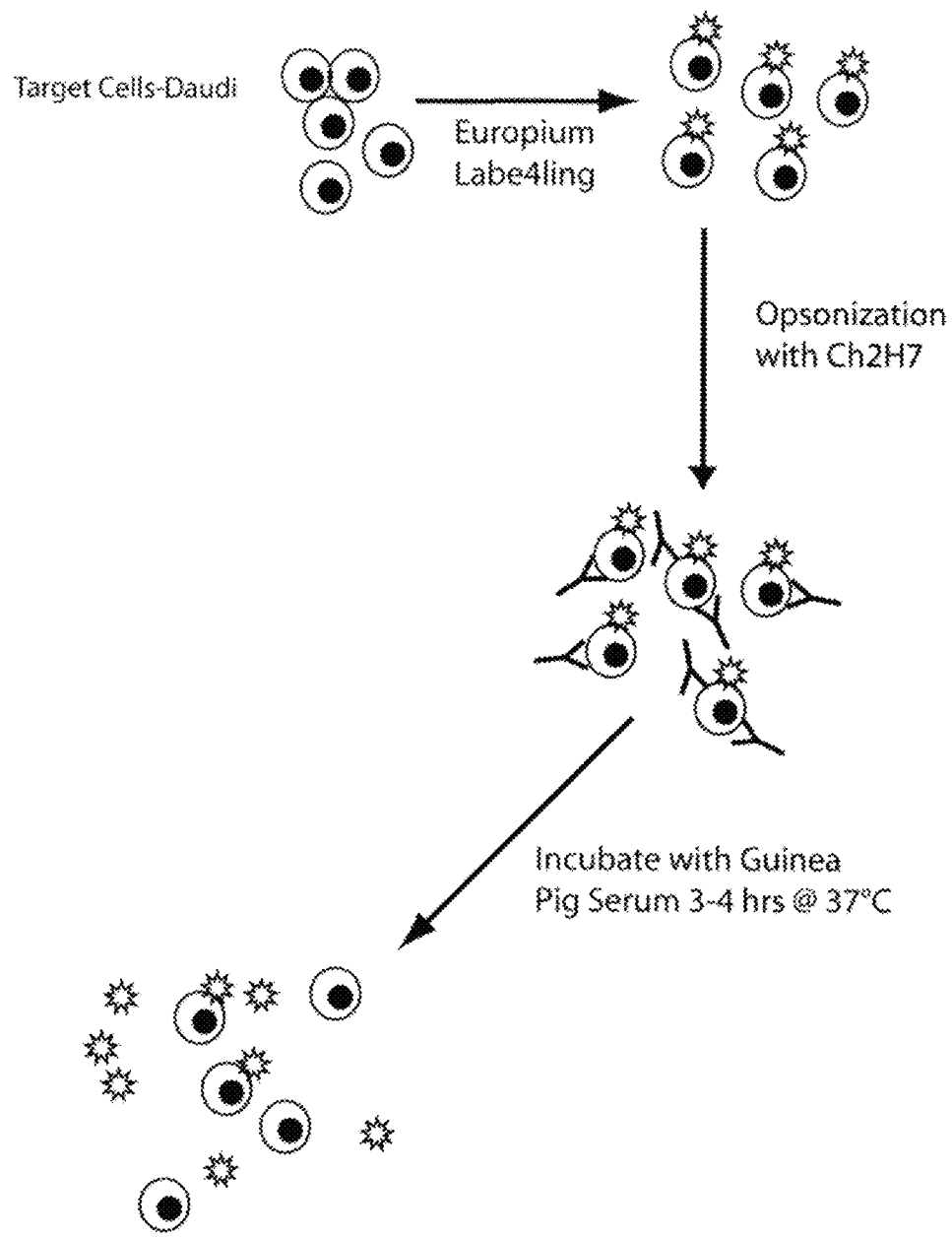

CDC assay was used to test the Fc mutants using anti-CD20 and Daudi cells as targets. Guinea Pig Serum was used as the source for complement (US Biological). The CDC assay was similar to PBMC based ADCC. Target cells were loaded with europium and opsonized with ChMAb. However complement, guinea pig serum, was added instead of effector cells. FIG. 17 shows a flow chart of the assay. Anti-CD20 ChMab over 3 orders of magnitude was titrated. % lysis was calculated. Daudi cells, ($3\times10^6$) were labeled with BADTA reagent. $1\times10^4$ cells were aliquoted into wells in a 96 well plate. Antibodies were titrated into the wells using 3 fold dilutions. The opsonization reaction was allowed to proceed for 30-40 minutes at 37° C. in 5% CO2. Guinea pig serum was added to a final conc. of 20%. The reaction was allowed to proceed for 3.5 hrs at 37° C. in 5% CO2. Subsequently, 100 uls of cell media was added to the reaction and cells were spun down. For detection 20 uls of the supernatant was added to 200 uls of the Europium solution and the plates were read in the Victor2 (Wallac).

Figure 18:
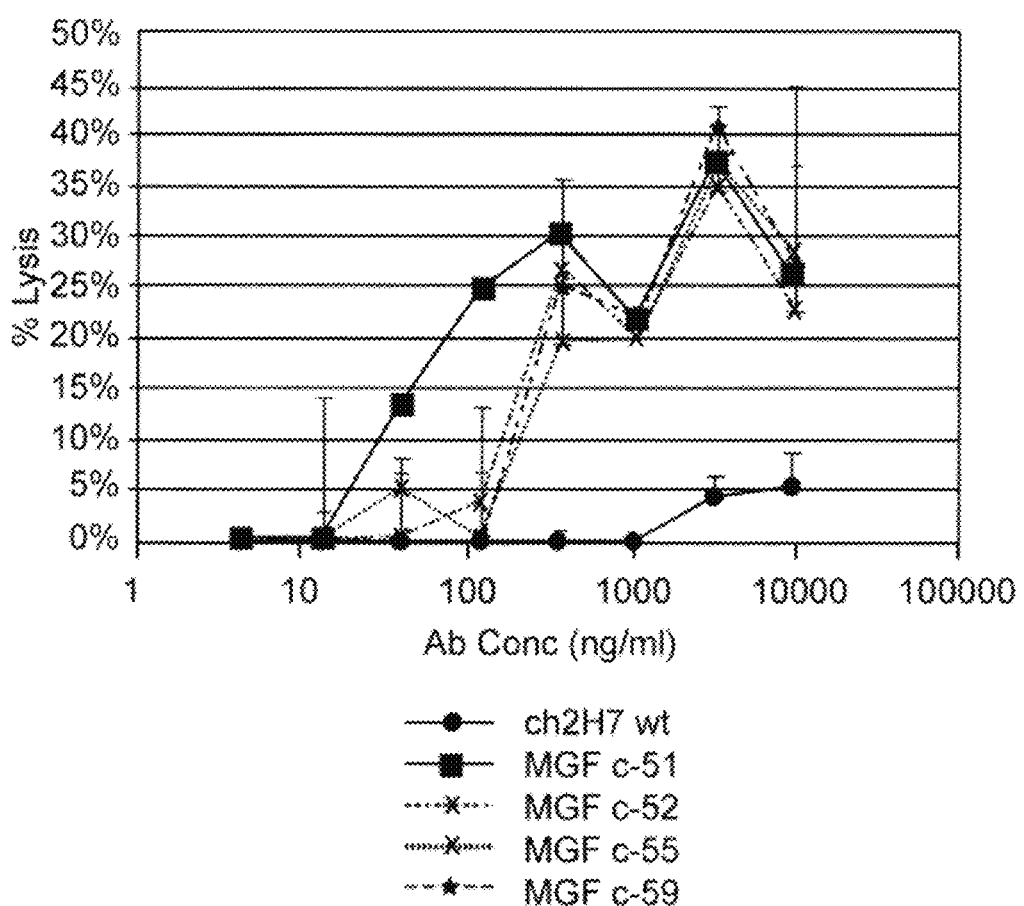

Results:

All mutants that show improved binding for either activating FcR or C1q were placed in the CDC assay (FIG. 18). Fc mutants that showed enhanced binding to FcγRIIIA also showed improved complement activity Each of the mutants show enhanced complement activity compared to wild type. The mutants tested are double mutants. In each case one of the mutations present is P396L.

To determine whether the increase in CDC correlated with increased binding of C1q to IgG1 Fc binding between the two proteins was measured in realtime using surface plasmon resonance. In order to examine the binding between C1q and an IgG1 Fc the Fc variants were cloned into an anti-CD32B ch-mAb, 2B6. This allowed us to capture the wt and mutant antibodies to the glass slide via soluble CD32B protein (FIG. 19A). Three of the four mutants tested in CDC were also examined in the Biacore. All 3 showed greatly enhanced $K_{off}$ compare to wild type Fc (FIG. 19 B-C). BIAcore format for C1q binding to 2B6 mutants demonstrate enhanced binding of mutants with P396L mutation (FIG. 20). Mutation D270E can reduce C1q binding at different extent. A summary of the kinetic analysis of FcγR and C1q binding is depicted in the Table 22 below.

TABLE 22

KINETIC ANALYSIS OF FcgR and C1q binding to mutant 2B6

| 2B6Mutants | 3aV158 | 3aF158 | 2bfcag1 | 2aR131Fcag1 | 2aH131Fcag1 | C1q |
|---|---|---|---|---|---|---|
| WT | 0.192 | 0.434 | 0.056 | 0.070 | 0.053 | 0.124 |
| MgFc38 (K392T, P396L) | 0.114 | 0.243 | 0.024 | 0.028 | 0.024 | 0.096 |
| MgFc51 (Q419H, P396L) | 0.142 | 0.310 | 0.030 | 0.036 | 0.028 | 0.074 |
| MgFc55 (R255I, P396L) | 0.146 | 0.330 | 0.030 | 0.034 | 0.028 | 0.080 |
| MgFc59 (K370E, P396L) | 0.149 | 0.338 | 0.028 | 0.033 | 0.028 | 0.078 |
| MgFc31/60 | 0.084 | 0.238 | 0.094 | 0.127 | 0.034 | 0.210 |
| MgFc51/60 | 0.112 | 0.293 | 0.077 | 0.089 | 0.028 | 0.079 |
| MgFc55/60 | 0.113 | 0.288 | 0.078 | 0.099 | 0.025 | 0.108 |
| MgFc59/60 | 0.105 | 0.296 | 0.078 | 0.095 | 0.024 | 0.107 |

8.6 Designing Fc Variants with Decreased Binding to FcγRIIB

Based on a selection for Fc mutants that reduce binding to FcγRIIB and increase binding to FcγRIIA 131H a number of mutations including D270E were identified. Each mutation was tested individually for binding to the low affinity Fc receptors and their allelic variants.

D270E had the binding characteristics that suggested it would specifically reduce FcγRIIB binding. D270E was tested in combination with mutations that were previously identified based on their improved binding to all FcR.

Results.

As shown in Tables 23 and 24 and FIGS. 21 and 22 addition of D270E mutation enhances FcγRIIIA and FcγRIIA H131 binding and reduces binding to FcγRIIB. FIG. 23 shows the plot of MDM ADCC data against the $K_{off}$ as determined for CD32A H131H binding for select mutants.

TABLE 23

OFF RATE (1/s) of FcγFR BINDING TO WILD TYPE AND MUTANT CHIMERIC 4D5 Ab OBTAINED BY BIACORE ANALYSIS

| 4D5 Mutants | 3aV158 | 3aF158 | 2bfragl | 2aR131Fcagl | 2aH131Fcagl |
|---|---|---|---|---|---|
| Wt pure | 0.175 | 0.408 | 0.078 | 0.067 | 0.046 |
| MgFc55 | 0.148 | 0.381 | 0.036 | 0.033 | 0.029 |
| MgFc55/60 | 0.120 | 0.320 | 0.092 | 0.087 | 0.013 |
| MgFc55/60 + R292G | 0.116 | 0.405 | 0.124 | 0.112 | 0.037 |
| MgFc55/60 + Y300L | 0.106 | 0.304 | 0.092 | 0.087 | 0.015 |
| MgFc52 | 0.140 | 0.359 | 0.038 | 0.040 | 0.026 |
| MgFc52/60 | 0.122 | 0.315 | 0.094 | 0.087 | 0.013 |
| MgFc59 | 0.145 | 0.378 | 0.039 | 0.047 | 0.033 |

TABLE 23-continued

OFF RATE (1/s) of FcγFR BINDING TO WILD TYPE AND MUTANT CHIMERIC 4D5 Ab OBTAINED BY BIACORE ANALYSIS

| 4D5 Mutants | 3aV158 | 3aF158 | 2bfragl | 2aR131Fcagl | 2aH131Fcagl |
|---|---|---|---|---|---|
| MgFc59/60 | 0.117 | 0.273 | 0.088 | 0.082 | 0.012 |
| MgFc31 | 0.125 | 0.305 | 0.040 | 0.043 | 0.030 |
| MgFc31/60 | 0.085 | 0.215 | 0.139 | 0.132 | 0.020 |
| MgFc51 | 0.135 | 0.442 | 0.060 | 0.047 | 0.062 |

TABLE 23-continued

OFF RATE (1/s) of FcγFR BINDING TO WILD TYPE AND MUTANT CHIMERIC 4D5 Ab OBTAINED BY BIACORE ANALYSIS

| 4D5 Mutants | 3aV158 | 3aF158 | 2bfragl | 2aR131Fcagl | 2aH131Fcagl |
|---|---|---|---|---|---|
| MgFc51/60 | 0.098 | 0.264 | 0.118 | 0.106 | 0.023 |
| MgFc38 | 0.108 | 0.292 | 0.034 | 0.025 | 0.032 |
| MgFc38/60 | 0.089 | 0.232 | 0.101 | 0.093 | 0.021 |

TABLE 24

KINETIC CHARACTERISTICS OF 4D5 MUTANTS

| 4D5Mutants | 3aV158 | 3aF158 | 2bfcagl | 2aR131Fcagl | 2aH131Fcagl |
|---|---|---|---|---|---|
| MgFc70 | 0.101 | 0.250 | 0.030 | 0.025 | 0.025 |
| MgFc71 | 0.074 | 0.212 | 0.102 | 0.094 | 0.020 |
| MgFc73 | 0.132 | 0.306 | 0.190 | — | 0.024 |
| MgFc74 | 0.063 | 0.370 | n.b. | 0.311 | 0.166 |
| WT023stable | 0.150 | 0.419 | 0.071 | 0.068 | 0.043 |

8.7 Analysis of Kinetic Parameters of Fc Mutants

Kinetic parameters of binding of chimeric 4D5 antibodies harboring Fc mutants to the two allotypes of FcγRIIIA, FcγRIIA 131H and FcγRIIB were analyzed by BIAcore using a method similar to that disclosed in Section 7.8 supra. The two allotypes of FcγRIIIA, FcγRIIIA 158V and FcγRIIIA 158F, are described in further detail in Section 7.9 supra.

Materials and Methods

Both allotypes of FcγRIIIA used in this assay were soluble monomeric proteins, the extracellular region of FcγRIIIA joined to the linker-AVITAG sequence as described in Section 7.1. The FcγRIIB and FcγRIIA used in this assay were soluble dimeric proteins, i.e. the extracellular domain of FcγRIIB or FcγRIIA fused to the hinge-CH2-CH3 domain of human IgG2 as described in Section 7.1 supra.

Details of BIAcore methodology and analysis are found in Section 7.1. In this assay, variant Fc regions were cloned into a chimeric 4D5 antibody, which is specific for human epidermal growth factor receptor 2 (HER2/neu). The antigen, HER2/neu, was immobilized on one of the flow cells of the sensor chip. The chimeric 4D5 antibodies carrying the Fc mutations were then passed over the surface by 3 minute injections of a 300 nM solution at 5 µl/min flow rate. Next, dilution series of the receptor in HBS-P buffer (10 mM HEPES, 150 mM NaCL, 0.005% Surfactant P20, 3 mMEDTA, pH7.4) were injected onto the surface at 100 µl/min.

Binding curves for two different concentrations of receptor (400 nM and 800 nM for both FcγRIIIA V158 and FcγRIIIA 158F; 100 nM and 200 nM for both FcγRIIA and FcγRIIB) were aligned and responses adjusted to the same levels of captured antibodies, and reference curves subtracted from experimental curves. Association and dissociation phases were separately fitted.

Results

Binding of FcγRIIIA, allotype 158 V and 158F, FcγRIIB and FcγRIIA 131H were analyzed and resonance responses were normalized at the level of response obtained for a wild type chimeric 4D5 antibody. Kinetic parameters for the binding of the FcγRs to the chimeric 4D5 antibody were obtained by fitting the data at two different FcγR concentrations: 400 nM and 800 nM for both FcγRIIIA V158 and FcγRIIIA 158F; 100 nM and 200 nM for both FcγRIIA and FcγRIIB.

Table 25 presents the off rate for each of the four receptors analyzed in association with the indicated variant Fc regions.

TABLE 26

Relative Off-Rate of ch4D5 antibodies obtained by BIAcore analysis

| | FcγR Receptor Relative Off Rate ($K_{off}$WT/$K_{off}$MUT) | | | |
|---|---|---|---|---|
| Chimeric 4D5 Fc Region | 3A 158V | 3A 158 F | 2B | 2A 131H |
| F243L, R292P, Y300L, V305I, P396L | 10.06 | 8.25 | 1.38 | 1.11 |
| F243L, R292P, Y300L | 6.69 | 2.3 | 0.32 | 0.65 |
| F243L, R292P, P396L | 5.37 | 3.52 | 0.32 | 0.65 |
| F243L, R292P, Y300L, P396L | 10.06 | 5.62 | 1.07 | 0.89 |
| F243L, R292P, V305I | 2.56 | 1.43 | nb* | 0.23 |
| F243L | 4.79 | 3.44 | 0.84 | 0.57 |

*nb, no binding 8.8 ADCC Assay of Fc Mutants

Fc mutations identified in Example 7.7 as comprising increased affinity for FcγIIIA and/or FcγIIA were analyzed for their relative ADCC activity.

Materials and Methods

Details regarding ADCC assays are found in Section 7.1 and in U.S Patent Application Publications 2005/0037000 and 2005/0064514, and International Patent Application Publication WO 04/063351, each of which is hereby incorporated by reference in its entirety. In this assay, HT29 colon carcinoma cells (ATCC Accession No. HTB-38) loaded with Indium-111 were used as targets and effector cells were PBMC that were isolated from donors using a Ficoll gradient. Target cells were opsonized with chimeric 4D5 anti-

TABLE 25

Off rate (1/s) of FcγR binding to wild type and mutant chimeric 4D5 Ab obtained by BIAcore analysis

| Chimeric 4D5 Fc Region | Amino Acid at Position | | | | | FcγR Receptor | | | |
|---|---|---|---|---|---|---|---|---|---|
| | 243 | 292 | 300 | 305 | 396 | 3A 158V | 3A 158F | 2B | 2A 131H |
| Wild Type | F | R | Y | V | P | 0.186 | 0.294 | 0.096 | 0.073 |
| MgFc0088 | L | P | L | I | L | 0.016 | 0.064 | 0.058 | 0.035 |
| MGFc0143 Quadruple | I | P | L | I | L | 0.017 | 0.094 | 0.091 | 0.049 |
| MGFc0088A | L | P | L | | L | 0.016 | 0.094 | 0.075 | 0.044 |
| MGFc0084 | L | P | | I | L | 0.048 | 0.133 | 0.278 | 0.083 |
| MGFc0142 Triple | L | | L | I | L | | | | |
| MGFc0155 | L | P | L | | | 0.029 | 0.135 | 0.155 | 0.057 |
| MGFc0074 | L | P | | I | | 0.063 | 0.37 | NB | 0.166 |
| MGFc0093 Double | | P | | I | L | 0.080 | 0.197 | 0.125 | 0.190 |
| MGFc0162 | L | P | | | | 0.041 | 0.515 | 0.900 | 0.18 |
| MGFc0091 | L | | | | L | 0.108 | 0.330 | 0.036 | 0.026 |
| MGFc0070 Single | | P | | I | | 0.101 | 0.250 | 0.030 | 0.025 |
| SV12/F243L | L | | | | | 0.048 | 0.255 | 0.112 | 0.100 |
| MGFc0161 | | P | | | | 0.067 | 0.485 | 0.421 | 0.117 |
| | | G | | | | 0.124 | NT | 0.384 | NT |
| MGFc0092 | | | L | | | 0.211 | NT | 0.058 | 0.02 |
| MGFc0089 | | | | | L | 0.127 | 0.306 | 0.031 | 0.039 |

Table 26 presents the results of an duplicate study wherein the $K_{off}$ values of the chimeric 4D5 antibodies were computed relative to wild type off rates. Relative numbers greater than one indicate a decrease in $K_{off}$ rate. Numbers less than one indicate an increase in $K_{off}$ rate.

bodies comprising the variant Fc regions at final concentrations of 2-5000 ng/ml. Opsonized target cells were then added to effector cells to produce an effector:target ratio of 50:1 and incubated for 18 hours at 37° C., 5% $CO_2$. After incubation, cells were centrifuged at ~220×g for five minutes at 10° C. The level of Indium-111 in the supernatant was recorded by a gamma counter.

Results

Chimeric 4D5 antibodies comprising variant Fc regions MGFc88 (F243L,R292P,Y300L,V305I,P396L), MGFc88A (F243L,R292P,Y300L, P396L) and MGFc155 (F243L, R292P,Y300L) were selected based on enhanced affinity for FcγRIIIA and/or FcγIIA and tested for their ADCC activity. FIGS. 24 A & B show that the Fc variants tested exhibit enhanced ADCC activity relative to wild type antibody at opsonization concentrations above 20 ng/ml in a concentration dependent manner. The data indicate that Fc mutants identified as comprising increased affinity for FcγRIIIA are also likely to exhibit enhanced ADCC activity.

8.9 Fc Mutant Mediated Tumor Growth Control in an In Vivo Tumor Model

Fc mutations identified as comprising enhanced affinity for FcγIIIA and/or FcγIIA were further analyzed for relative efficacy of tumor control using an in vivo tumor model system.

Materials and Methods

Antibodies harboring Fc mutants were tested for anti-tumor activity in a murine xenograft system. Balbc/nude mice are subcutaneously injected with $5 \times 10^6$ Daudi cells and subsequently monitored for general signs of illness, e.g. weight gain/loss and grooming activity. Without treatment, this model system results in 100% mortality with an average survival time of approximately 2 weeks post tumor cell inoculation. Treatment consists of doses of wild-type antibody or antibody comprising a variant Fc region administered at weekly intervals. Animals administered buffer alone at the same intervals serve as a control. Tumor weight is calculated based on the estimated volume of the subcutaneous tumor according to the formula (width$^2 \times$length)/2.

Results

At weekly intervals, mice inoculated with Daudi cells received wild-type humanized 2B6 ("h2B6"), humanized 2B6 comprising mutant FcMG0088 (F243L, R292P, Y300L, V305I P396L) ("h2B6 0088") or buffer alone. Wild-type and Fc mutant h2B6 antibody showed similar levels of tumor suppression at the highest dose schedule tested, weekly doses of 25 µg (FIGS. 25 A and B). However, significant differences in antibody efficacy were observed when dosages were reduced. 100 and 10 fold reduction in wild-type h2B6 dosages provided no greater tumor control than administration of buffer alone (FIG. 42 A). In contrast, h2B6 0088 provided significant protection at weekly doses of 2.5 µg and at least limited protection at weekly doses of 0.25 µg (FIG. 25 B).

The protection conferred by even the lowest dose of Fc mutant antibody was confirmed in survival comparisons. At 11 weeks, 4 out of 7 mice remained alive in the group treated with 0.25 µg doses of h2B6 0088 compared to only 1 out of 7 in the group treated with the same dose of wild-type h2B6 (FIGS. 26 A & B)

8.10 Fc Mutant Mediated Tumor Growth Control in a Human Fc Receptor Expressing Transgenic Mouse Tumor Model Fc mutations identified as comprising enhanced affinity for FcγIIIA and/or FcγIIA were further analyzed for relative efficacy of tumor control using an in vivo xenograft human Fc receptor transgenic mouse tumor model system.

Materials and Methods

Humanized antibodies against human CD32B (h2B6) or HER2/neu (h4D5) harboring Fc mutations were tested for anti-tumor activity in a murine xenograft system, in which mouse FcγIIIA (CD16) was replaced with its human ortho-logue, CD16A (huCD16A). Immunodeficient mice were injected with $5 \times 10^6$ tumor cells and subsequently monitored for general signs of illness, e.g. weight gain/loss and grooming activity. Treatment consists of doses of wild-type antibody or antibody comprising a variant Fc region administered at daily or weekly intervals (as stated). Animals administered buffer alone or antibody comprising mutation N297Q (which abrogates binding to any FcγR) at the same intervals serve as a control. Tumor weight was calculated based on the estimated volume of the subcutaneous tumor according to the formula (width$^2 \times$length)/2.

Results h2B6: Humanized anti-CD32B and Fc variants

At weekly intervals beginning two weeks subsequent to tumor injection, RAG1−/− C57BI/6 mice subcutaneously injected with Raji cells (CD32B-expressing tumor cells) received wild-type humanized 2B6 ("h2B6"; Rituxan), humanized 2B6 comprising mutant FcMG0088 (F243L, R292P, Y300L, V305I P396L) ("h2B6 0088"; "FcMg88", or MGA321) or buffer alone. Wild-type and Fc mutant h2B6 antibody showed similar levels of tumor growth suppression at weekly doses of 250 µg and 25 µg (FIG. 27). However, significant differences in antibody efficacy were observed when the dosage was reduced to 2.5 µg: At this dosage, wild-type h2B6 provided limited tumor growth control compared with administration of buffer alone; in contrast, the 2.5 µg dosage of h2B6 0088 delayed tumor progression by as much as one week (FIG. 27). In another experiment, the efficacy of the lower dosages of Fc-optimized MGA321 tested were equivalent to controls (PBS or Rituxin at equivalent dosages); however, administration of the highest dosage (250 µg) of Fc-optimized h2B6 antibody provided significant tumor growth control compared with wild-type h2B6- and buffer alone-treated mice (FIGS. 28A-2B).

The protection conferred by the Fc mutant antibody was confirmed in survival comparisons. Nude (FoxN1) mice were intraperitoneally injected with EL4-CD32B cells and then treated on days 0, 1, 2, 3, and 6 with IP administered humanized 2B6 1.3 or humanized 2B6 1.3 comprising mutant 31/60 (P247L, D270E, N421K) ("h2B6 1.3 3160"). At 14 weeks, at least 90% of mice treated with h2B6 1.3 3160 survived compared with 55% or less in the group treated with the same dose of wild-type h2B6 1.3 (FIG. 29 and FIG. 30).

In a further survival experiments in the same system, mice were treated with IP administered humanized 2B6 3.5, humanized 2B6 3.5 comprising mutant FcMG0088 (F243L, R292P, Y300L, V305I, P396L) ("h2B6 3.5 0088"), humanized 2B6 3.5 N297Q (negative control) or buffer alone. At 14 weeks, all mice treated with h2B6 3.5 0088 survived compared with 30% in the group treated with the same dose of wild-type h2B6 3.5 and <20% in the groups treated with the N297Q mutant or PBS (FIG. 31A; treatment on day 0, 1, 2, 3); the same result was achieved for a dose as low as 4 µg/g body weight (FIG. 31B; treatment on day 0, 1, 2, 3, 4)

The protective effects of antibodies comprising variant Fc regions was further tested in transgenic mice carrying human CD32A in addition to the mCD16 −/− huCD16A+ genotype using the EL4-CD32B model described supra. Treatment with wild-type h2B6 or negative control, h2B6 3.5 N297Q, resulted in only 20% at 100 days post tumor inoculation; treatment with Fc optimized antibody, h2B6 3.5

0088, increased survival by 10%, with 30% survival at 100 days post inoculation (FIG. 32).

The effect of the expression of hCD16A and/or hCD32A in the transgenic murine EL4-CD32B tumor model on treatment with h2B6 antibodies was further investigated using nude (FoxN1) mice positive for hCD16A, positive for both hCD16A and hCD32A, or positive for hCD32A, each on a mCD16 −/− background. Transgenic were intraperitoneally injected with EL4-CD32B cells and then treated at day 0, 1, 2, and 3 with wild-type humanized 2B6 3.5 ("h2B6 3.5"), humanized 2B6 3.5 comprising mutant FcMG0088 (F243L, R292P, Y300L, V305I, P396L) ("h2B6 3.5 88"), h2B6 N297Q ("h2B6 3.5 N297Q;" negative control) or buffer alone. At 100 days post tumor inoculation, all CD16A positive mice treated with h2B6 3.5 88 survived compared with 50% or less survival in the groups treated with the same dose of wild-type h2B6 3.5 or controls (FIG. 33A). In mice harboring human CD32A in addition to the mCD16 −/− huCD16A+ genotype, survival was not more than 25% at 100 days post inoculation regardless of treatment (FIG. 33B). In mice expressing hCD32A but not hCD16, only mice in the Fc-optimized treatment group, treated with h2B6 3.5 88, survived longer than 1 month, with 25% survival at 100 days post inoculation (FIG. 33C).

The effect of different time courses of treatment with Fc-optimized antibodies (h2B6 0088; "MGA321") on mouse survival was also investigated. Intraperitoneal injection of mice with MGA321 immediately after tumor injection conferred survival on 75%-100% of mice, either at a single or multiple doses over consecutive days or weeks (FIG. 34). When MGA321 was first administered a day or later subsequent to tumor introduction, it conferred a maximum of 40% survival, even when administered in multiple doses over days or weeks (FIG. 34).

ch4D5: Chimeric Anti-HER2/Neu and Fc Variants

A HER2/neu positive tumor model was established by IP injection of mSKOV3 cells (HER2/neu-expressing ovarian tumor cells) into mCD16 knockout nude (FoxN1) mice that also carried, and expressed, human CD16A or both human CD16A and human CD32A. At 8 weekly intervals, starting at time 0, inoculated mice were subcutaneously injected with "wild type" chimeric antibody against human HER2/neu (ch4D5), ch4D5 comprising FcMG0088 (F243L, R292P, Y300L, V305I P396L) ("ch4D5 0088"), ch4D5 comprising N297Q (aglycosylated negative control; "ch4D5 N297Q"), or buffer alone. Treatment with ch4D5 0088 suppressed tumor growth for the entire course of the experiment (10 weeks) in transgenic mice positive for human CD16A on the mCD16−/− background or in transgenic mice harboring human CD32A in addition to the mCD16 −/− huCD16A+ genotype (FIG. 35A or 35B, respectively).

The protection conferred by the Fc mutant ch4D5 antibody was confirmed in survival comparisons. Knockout mCD16 (mCD16 −/−) nude (N/N) mice transgenic for human CD16A were intraperitoneally injected with mSKOV3 cells and then treated with wild-type chimeric 4D5 ("ch4D5"), ch4D5 comprising FcMG0088 (F243L, R292P, Y300L, V305I P396L), ch4D5 N297Q (negative control), or buffer alone. Tumor inoculated mice received six doses beginning at day 0 (day of tumor inoculation) of 100 µg or 1 µg of the antibody delivered IP (FIGS. 36A and 36B, respectively). At 14 weeks, ~60% of mice treated with 100 µg ch4D5 0088 survived compared with ~40% in the group treated with the same dose of wild-type ch4D5 and <10% of mice treated with ch4D5 N297Q or buffer alone (FIG. 36A). At doses of 1 µg, the overall duration of survival of mice treated with wild-type or Fc-optimized antibodies was reduced relative to those treated with 100 µg. However, at six weeks, more than 80% of ch4D5 0088-treated mice were still alive, compared with ~10% of mice that received the other treatments (FIG. 36B), confirming that a moderate dose of Fc-optimized ch4D5 confers a significant improvement over the wild-type antibody in enhancing viability.

Other Fc variants of ch4D5 were tested in similar survival experiments.

A chimeric 4D5 comprising mutant MGFc0155 (F243L, R292P, Y300L) ("ch4D5 0155") or mutant MCFc3160 (P247L, D270E, N421K) ("ch4D5 3160") were tested alongside wild-type ch4D5, ch4D5 N297Q, and ch4D5 0088 as described supra. Mice received eight weekly intraperitoneal treatments, starting at day 0 (tumor inoculation), with 100 µg antibody. In mice receiving doses of 100 µg, 100% of the group treated with ch4D5 0155 were alive at 130 days post inoculation, compared with ~85% of those treated with ch4D5 0088 and 50% of those treated with ch4D5 3160. In contrast, only approximately 30% of mice given wild-type ch4D5 were still alive at day 130. All mice treated with buffer alone or ch4D5 N297Q died within 14 weeks and 10 weeks, respectively, after tumor injection (FIG. 37A). At a 10-fold lower dosage, Fc-optimized antibodies were less efficacious in enhancing survival compared with wild-type ch4D5. While ch4D5 0155 was most effective at enhancing survival at earlier time points, at 18 weeks, ~60% of mice in the group treated with ch4D5 0155 or ch4D5 0088 survived, compared with 50% of wild-type-treated and 25% of ch 4D5 3160-treated (FIG. 37B).

In another set of survival experiments, Knockout mCD16 (mCD16 −/−) nude (N/N) mice transgenic for human CD16A or transgenic for both human CD16A ("hCD16") and human CD32A ("hCD32A") were intraperitoneally injected with mSKOV3 cells and then, starting at day 0, given eight weekly treatments with wild-type ch4D5, ch4D5 0088, ch4D5 N297Q or buffer alone. At seven weeks post-tumor injection, all ch4D5 0088-treated and hCD16 positive mice were alive, whereas only ~30% of Ch4D5 N297Q and −10% of buffer-treated hCD16 positive mice survived (FIG. 38A). In nude mice harboring human CD32A in addition to the mCD16 −/− huCD16A+ genotype, 50% or the mice treated with ch4D5 0088 were alive after eight weeks, compared with those that received ch4D5 N297Q (15% alive at eight weeks) or buffer alone (all dead before six weeks) (FIG. 38B).

8.11 Fc Variants Exhibiting Altered Ratios of Affinities

Immunoglobulins whose Fc regions had been mutated in the manner described above are screened for Fc variants having altered Ratios of Affinities to FcγRIII and FcγRII by assessing the $K_{off}$ of the variants and their wild-type immunoglobulin progenitors. Testing is done using both the V158 and F158 isotypes of FcγRIII, and against FcγRIIB and FcγRIIAH131. The results are summarized in Table 27.

TABLE 27

COMPARISON OF $K_{OFF}$ OF FC MUTANTS TO WILD TYPE ANTIBODY
($K_{OFF}$ WT/$K_{OFF}$ MUTANT)

| Fc sequence | CD16A V158 | CD16A F158 | CD32B | CD32A H131 | Ratio of Affinities CD16A/CD32B V158 | F158 |
|---|---|---|---|---|---|---|
| WT | 1.00 | 1.00 | 1.00 | 1.00 | 1.00 | 1.00 |
| F243L | 4.79 | 3.44 | 0.84 | 0.57 | 5.70 | 4.10 |
| D270E | 1.25 | 1.48 | 0.39 | 2.24 | 3.21 | 3.79 |
| R292P | 2.90 | 0.64 | 0.25 | 0.53 | 11.60 | 2.56 |
| R292G | 1.54 | — | 0.25 | 0.14 | 6.2 | — |
| Y300L | 1.01 | 1.17 | 1.18 | 1.86 | 0.86 | 0.99 |
| P396L | 1.27 | 1.73 | 2.58 | 1.63 | 0.49 | 0.67 |
| P396L D270E | 1.38 | 1.65 | 0.89 | 2.44 | 1.55 | 1.85 |
| P396L F243L | 1.49 | 1.60 | 2.22 | 1.50 | 0.67 | 0.72 |
| P247L N421K | 1.29 | 1.73 | 2.00 | 1.30 | 0.65 | 0.87 |
| P247L N421K D270E | 1.89 | 2.46 | 0.58 | 1.95 | 3.26 | 4.24 |
| P247L N421K F243L | 1.89 | 1.71 | 0.17 | 0.39 | 11.12 | 10.06 |
| P247L N421K D270E F243L | 2.30 | 3.45 | 0.32 | 0.98 | 7.19 | 10.78 |
| P247L N421K D270E Y300L | 2.44 | 1.16 | 0.8 | 1.84 | 3.05 | 1.45 |
| R255L P396L | 1.09 | 1.39 | 2.22 | 1.34 | 0.49 | 0.63 |
| R255L P396L D270E | 1.34 | 1.65 | 0.87 | 3.00 | 1.54 | 1.90 |
| R255L P396L D270E F243L | 1.75 | 1.64 | 0.38 | 1.44 | 4.61 | 4.32 |
| R255L P396L D270E R292G | 1.39 | 1.30 | 0.65 | 1.05 | 2.14 | 2.00 |
| R255L P396L D270E Y300L | 1.52 | 1.74 | 0.87 | 2.60 | 1.75 | 2.00 |
| K392T P396L | 1.49 | 1.81 | 2.35 | 1.22 | 0.63 | 0.77 |
| K392T P396L D270E | 1.81 | 2.28 | 0.79 | 1.86 | 2.29 | 2.89 |
| K392T P396L D270E F243L | 3.16 | 2.44 | 0.44 | 1.70 | 7.18 | 5.55 |
| Q419H P396L | 1.19 | 1.19 | 1.33 | 0.63 | 0.89 | 0.89 |
| Q419H P396L D270E | 1.64 | 2.00 | 0.68 | 1.70 | 2.41 | 2.94 |
| Q419H P396L D270E F243L | 1.46 | 1.15 | 0.26 | 1.11 | 5.62 | 4.42 |
| R292P F243L | 4.73 | 0.6 | 0.12 | 0.34 | 39.4 | 5.00 |
| R292P F243L | 4 | 1.67 | 0.16 | 0.52 | 25 | 10.44 |
| R292P V284M K370N | 1.14 | 1.37 | 0.37 | 1.79 | 3.1 | 3.7 |
| R292P V305I | 1.59 | 2.11 | 2.67 | 1.56 | 0.60 | 0.79 |
| R292P V305I | 1.32 | 1.28 | 0.37 | 0.75 | 3.6 | 3.46 |
| R292P V305I F243L | 2.56 | 1.43 | ND | 0.23 | >25 | >25 |
| R292P V305I F243L P396L | 5.37 | 2.53 | 0.40 | 0.78 | 13.43 | 6.33 |
| R292P V305I F243L P396L Y300L | 10.06 | 8.25 | 1.38 | 1.11 | 7.29 | 5.98 |
| R292P V305I F243L P396L Y300L | 10.9 | 3.12 | 1.05 | 1.49 | 10.4 | 2.97 |
| R292P F243L P396L Y300L | 10.06 | 5.62 | 1.07 | 0.89 | 9.40 | 5.25 |
| R292P F243L P300L | 6.69 | 2.3 | 0.32 | 0.65 | 20.9 | 7.19 |
| R292P V305I P396L | 1.85 | 1.90 | 0.92 | 1.50 | 2.01 | 2.07 |
| R292P V305I P396L F243L | 5.37 | 2.53 | 0.40 | 0.78 | 13.43 | 6.33 |
| G316D R416G D270E | 2.18 | 2.49 | 0.78 | 1.95 | 2.79 | 3.19 |
| G316D R416G D270E F243L | 1.50 | 1.34 | 0.20 | 1.22 | 7.50 | 6.70 |
| G316D R416G D270E P396L | 1.22 | 0.94 | 1.07 | 0.95 | 1.14 | 0.88 |

Fc mutants analyzed in this study are shown in the left hand column. The dissociation rate constants for binding of the Fc to the different FcR were determined by Biacore analysis. ND = no detectable binding The results show that the methods of the present invention are capable of producing both molecules that possess Fc regions having a Ratio of Affinities greater than wild-type (i.e., >1) as well as molecules that possess Fc regions having a Ratio of Affinities less than wild-type (i.e., >1). An analysis of the Fc variants shows that the variant Fc-containing molecules fall into various classes, as shown in Table 28.

TABLE 28

| Fc sequence | CD16A V158 | CD16A F158 | CD32B | Ratio of Affinities CD16A/CD32B V158 | F158 |
|---|---|---|---|---|---|
| Ratio of Affinities >1 Class I: Increased Binding to CD16; Decreased Binding to CD32B | | | | | |
| F243L | 4.79 | 3.44 | 0.84 | 5.70 | 4.10 |
| D270E | 1.25 | 1.48 | 0.39 | 3.21 | 3.79 |
| R292P | 2.90 | | 0.25 | 11.60 | |
| R292G | 1.54 | | 0.25 | 6.2 | |
| P396L D270E | 1.38 | 1.65 | 0.89 | 1.55 | 1.85 |
| P247L N421K D270E | 1.89 | 2.46 | 0.58 | 3.26 | 4.24 |

TABLE 28-continued

| P247L N421K F243L | 1.89 | 1.71 | 0.17 | 11.12 | 10.06 |
|---|---|---|---|---|---|
| P247L N421K D270E F243L | 2.30 | 3.45 | 0.32 | 7.19 | 10.78 |
| R255L P396L D270E | 1.34 | 1.65 | 0.87 | 1.54 | 1.90 |
| R255L P396L D270E F243L | 1.75 | 1.64 | 0.38 | 4.61 | 4.32 |
| R255L P396L D270E R292G | 1.39 | 1.30 | 0.65 | 2.14 | 2.00 |
| R255L P396L D270E Y300L | 1.52 | 1.74 | 0.87 | 1.75 | 2.00 |
| K392T P396L D270E | 1.81 | 2.28 | 0.79 | 2.29 | 2.89 |
| K392T P396L D270E F243L | 3.16 | 2.44 | 0.44 | 7.18 | 5.55 |
| Q419H P396L D270E | 1.64 | 2.00 | 0.68 | 2.41 | 2.94 |
| Q419H P396L D270E F243L | 1.46 | 1.15 | 0.26 | 5.62 | 4.42 |
| R292P F243L | 4.73 | | 0.12 | 39.4 | |
| R292P F243L | 4 | 1.67 | 0.16 | 25 | 10.44 |
| R292P V284M K370N | 1.14 | 1.37 | 0.37 | 3.1 | 3.7 |
| R292P V305I | 1.32 | 1.28 | 0.37 | 3.6 | 3.46 |
| R292P V305I F243L | 2.56 | 1.43 | ND | >25 | >25 |
| R292P V305I F243L P396L | 5.37 | 2.53 | 0.40 | 13.43 | 6.33 |
| R292P F243L P300L | 6.69 | 2.3 | 0.32 | 20.9 | 7.19 |

TABLE 28-continued

| | | | | | |
|---|---|---|---|---|---|
| R292P V305I P396L F243L | 5.37 | 2.53 | 0.40 | 13.43 | 6.33 |
| G316D R416G D270E | 2.18 | 2.49 | 0.78 | 2.79 | 3.19 |
| G316D R416G D270E F243L | 1.50 | 1.34 | 0.20 | 7.50 | 6.70 |
| G316D R416G D270E P396L | 1.22 | | 1.07 | | 1.14 |
| Class II: Decreased Binding to CD16; Greatly Decreased Binding to CD32B | | | | | |
| R292P | | 0.64 | 0.25 | | 2.56 |
| R292P F243L | | 0.6 | 0.12 | | 5.00 |
| Class III: Increased Binding to CD16; Unchanged Binding to CD32B | | | | | |
| R292P V305I F243I P396L Y300L | 10.9 | 3.12 | 1.05 | 10.4 | 2.97 |
| R292P F243L P396L Y300L | 10.06 | 5.62 | 1.07 | 9.40 | 5.25 |
| R292P V305I P396L | 1.85 | 1.90 | 0.92 | 2.01 | 2.07 |
| Class IV: Greatly Increased Binding to CD16; Increased Binding to CD32B | | | | | |
| R292P V305I F243L P396L Y300L | 10.06 | 8.25 | 1.38 | 7.29 | 5.98 |
| G316D R416G D270E P396L | 1.22 | | 1.07 | | 1.14 |
| Ratio of Affinities <1 | | | | | |
| Class V: Unchanged Binding to CD16; Increased Binding to CD32B | | | | | |
| Y300L | | 1.01 | 1.18 | | 0.99 |
| R255L P396L | | 1.09 | 2.22 | 0.49 | |
| Class VI: Increased Binding to CD16; Greatly Increased Binding to CD32B | | | | | |
| P396L | 1.27 | 1.73 | 2.58 | 0.49 | 0.67 |
| R255L P396L | | 1.39 | 2.22 | | 0.63 |
| P396L F243L | 1.49 | 1.60 | 2.22 | 0.67 | 0.72 |
| P247L N421K | 1.29 | 1.73 | 2.00 | 0.65 | 0.87 |
| R255L P396L | | 1.39 | 2.22 | 0.49 | 0.63 |
| K392T P396L | 1.49 | 1.81 | 2.35 | 0.63 | 0.77 |
| Q419H P396L | 1.19 | 1.19 | 1.33 | 0.89 | 0.89 |
| R292P V305I | 1.59 | 2.11 | 2.67 | 0.60 | 0.79 |
| Class VII: Decreased Binding to CD16; Increased/Unchanged Binding to CD32B | | | | | |
| G316D R416G D270E P396L | | 0.94 | 1.07 | | 0.88 |

8.12 Predictive Efficacy of Ratios of Affinities

Fc domains of Fc variants that exhibited improved Ratios of Affinities in the context of the spectrum of murine FcγRs are evaluated to determine their in vivo efficacy. For such purpose, the Fc domains were incorporated into a prototype therapeutic antibody and tested in xenograft mouse models of B-cell lymphoma and in tumor models in FcγRIII-knockout mice that express the low-binding allele of human CD16A. The impact of Fc engineering on tumor clearance was investigated by using WT or human FcγR-transgenic mice. Hu2B6 was used as the model mAb, since this antibody does not induce complement lysis or apoptosis, but inhibits tumor growth in mice by mechanisms that are exquisitely Fcγ dependent (Rankin, C. T. et al. 2006 Blood 108:2384-2391). Because hu2B6 does not cross-react with murine (m) FcγRII or other endogenous murine proteins, there is no antibody target other than the implanted CD32B-positive tumor cells in this model (Rankin, C. T. et al. 2006 Blood 108:2384-2391). Furthermore, hu2B6 completely blocks human CD32B, thus eliminating binding of the hu2B6 Fc region to the target cells as a confounding factor. Fc variants 088, 3160, 5660, 3860 and 0071 were selected for this purpose.

Fc variants 088 and 3160 are tested for treatment of B cell tumors in 16A tg mice. Fc variants 088, 3160, 5660, 3860 and 0071 were tested for treatment of B cell tumors in Balb/c mice.

Mouse Tumor Models

Xenograft Models:

Female athymic Balb/c nude (nu/nu) mice, 8-10 weeks old, are purchased from Taconic. Daudi cells ($5 \times 10^6$ per mouse) are suspended in PBS+Matrigel and injected subcutaneously into the right flank of Balb/c nude mice. Tumor development is monitored twice per week, using calipers, and tumor weight is estimated by the following formula: tumor weight=(length×width$^2$)/2. Intraperitoneal (IP) injections of antibodies at various concentrations (1 µg/g, or 0.1 µg/g) are performed weekly for 6 weeks, starting at day 0.

EL4/CD32B Model:

Male and female athymic mFcγRIII$^{-/-}$, hCD16A$^+$ nude mice, are bred in MacroGenics, Inc. animal facility. EL4/CD32B cells ($1 \times 10^4$ per mouse) are suspended in PBS and injected IP at day 0. IP injections of antibodies (10 µg/g or 4 µg/g) are performed on Days 0, 1, 2, and 3. Mouse body weight is measured twice a week. Mice showing excessive body weight gain as well as signs of ascites tumors are sacrificed by CO2 asphyxiation. Survival was recorded accordingly. Data is analyzed using PRISM (Graphpad Software, San Diego Calif.) for calculation of standard deviation (ADCC, tumor model) and statistical significance using T-tests and log rank analysis (tumor models).

For a complete mechanistic interpretation of the data, the binding profiles of the engineered Fcγ to the mouse (m) FcγRs were fully characterized. Of the mFcγR, mFcγRII is structurally and functionally homologous to human CD32B, while mFcγRIII and mFcγRIV are receptors functionally related to human activating FcγRs expressed on NK cells and monocyte/macrophages, respectively (Nimmerjahn, F. et al. 2005 Science 310:1510-1512; Nimmerjahn, F. 2005 Immunity 23:41-51). Since the ratio of Fcγ-binding to activating and inhibitory FcγRs is shown to be important in determining antibody-dependent outcomes in vivo (Nimmerjahn, F. et al. 2005 Science 310:1510-1512; Nimmerjahn, F. 2005 Immunity 23:41-51), mutants are selected based on their binding profiles (Table 29) using human FcRs. Data in Table 29 is expressed as fold changes relative to wild-type affinities.

TABLE 29

| MGFc No. | Fc Mutant | CD16A$^H$ | CD16A$^L$ | CD32A$^H$ | CD32B | CD16 CD32B |
|---|---|---|---|---|---|---|
| 0193 | F243L | +3.8 | +2.4 | −0.8 | −0.2 | 5.7 |
| 0089 | P396L | +0.3 | +0.7 | +0.6 | +1.6 | 0.5 |
| 3160 | P247L D270E N421K | +0.9 | +1.5 | +1.0 | −0.7 | 3.3 |
| 5560 | R255L D270E: P396L | +0.3 | +0.7 | +2.0 | −0.1 | 1.5 |
| 3860 | D270E K392T P396L | +0.8 | +1.3 | +0.9 | −0.3 | 2.3 |
| 0074 | F243L R292P v3051 | +1.6 | +0.4 | −3.3 | −13.3 | 36.6 |
| 0071 | D270E G316D R416G | +0.4 | +0.1 | +0.4 | −1.7 | 3.8 |
| 0155 | F243L R292P Y300L | +6.4 | +3.6 | 0.0 | −0.7 | 12.3 |
| 0031 | P247L N421K | +0.3 | +0.7 | +0.3 | +1.0 | 0.6 |

TABLE 29-continued

| MGFc No. | Fc Mutant | CD16A$^H$ | CD16A$^L$ | CD32A$^H$ | CD32B | CD16 CD32B |
|---|---|---|---|---|---|---|
| 0161 | R292P | +1.4 | +0.6 | −0.5 | −2.7 | 8.7 |
| 0162 | F243L R292P | +3.0 | +0.7 | −0.9 | −5.3 | 24.7 |
| 0170 | F243L R292P P396L | +5.3 | +2.4 | +0.4 | −1.6 | 16.0 |
| 0092 | Y300L | 0.0 | +0.2 | +1.9 | +0.2 | 0.9 |
| 0088 | F243L R292F Y300L V305I P396L | +9.1 | +7.3 | +2:2 | +0.4 | 7.3 |
| 0084 | F243L R292P V305I P396L | −3.0 | +1.3 | −0.3 | −1.6 | 10.6 |
| Controls | | | | | | |
| Wild-Type | | 0.0 | 0.0 | 0.0 | 0.0 | 1.0 |
| AAA* | E333A K334A S298A | +0.6 | +0.1 | −3.3 | −2.5 | 5.7 |
| XmAb** | S239D I332E 330L | +13.9 | +8.1 | 0.0 | +0.74 | 8.5 |

Bolding indicates Fc versions tested in mouse tumor models.
*see, Presta, L., U. S. Pat. No. 6,737,056; Shields et al. 2002, J Biol Chem 277:26733-26740
**see, Lazar, G. A. et al. Proc. Natl. Acad. Sci. (USA) 103:4005-4010 (2006)

Mutants MGFc3160 (P247E/D270E/N421K) and MGFc0088 showed increased binding to mFcγRIII and mFcγRIV, respectively. MGFc3160, however, showed concomitantly increased mFcγRII binding, while MFc0088 exhibited a more favorable activating-to-inhibitory profile, with no increase in binding to the inhibitory receptor. Mutant MGFc0071 (D270E/G316D/R416G) demonstrated WT Fcγ-level binding to all mFcγRs (Table 29) and was included as a control.

Sub-cutaneous inoculation of Daudi cells in nude mice produces localized, progressively expanding tumors whose growth is significantly reduced by weekly intra-peritoneally (i.p.) injections of 1 μg/g WT hu2B6 (FIG. 39 A-C). Weekly 0.1 μg/g doses, however, are ineffective. At the higher dose, treatment with hu2B6-MGFc3160 is indistinguishable from that with WT hu2B6, but a modest improvement over WT hu2B6 is detectable at the lower dose. hu2B6-MGFc0088, however, resulted in a significant reduction in tumor growth at all doses tested, consistent with its enhanced mFcγRIV binding and highly favorable activating-to-inhibitory ratio due to no corresponding increase in mFcγRII binding. Hu2B6-MGFc0071, which showed WT level binding to all mFcγRs, behaved similarly to WT hu2B6 (FIG. 39D).

Enhanced Tumor Clearance in Human CD16A Transgenic Mice

Figure 39A:
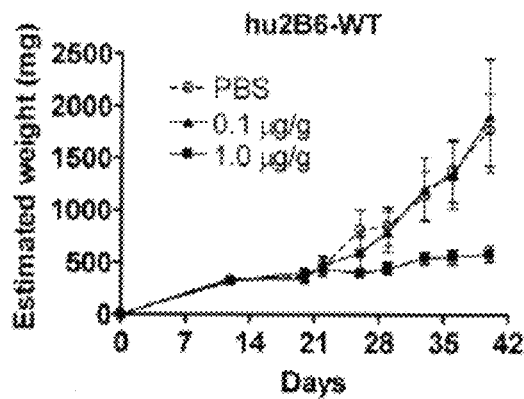
Figure 39D:
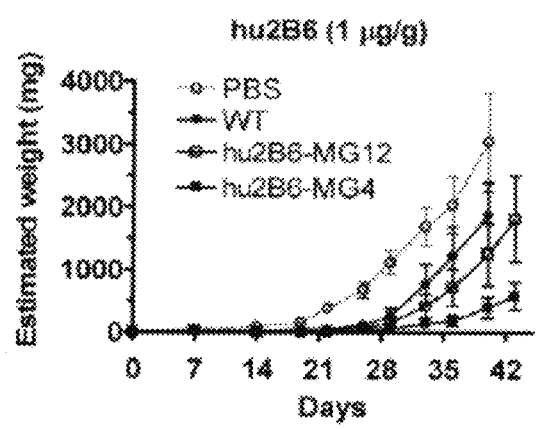
Figure 39B:
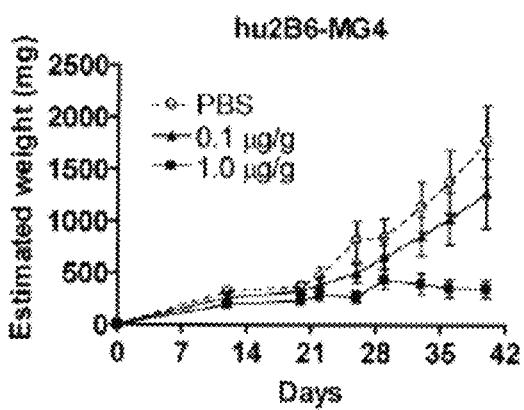
Figure 39E:
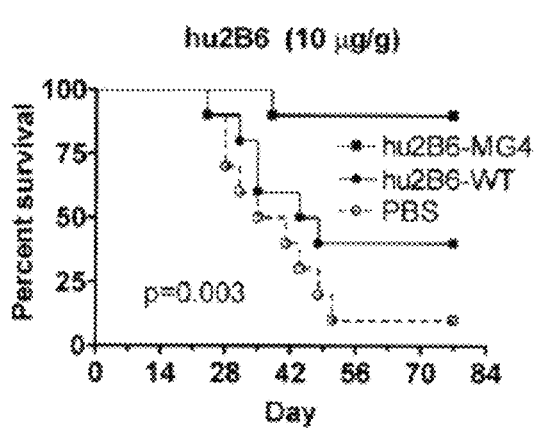
Figure 39C:
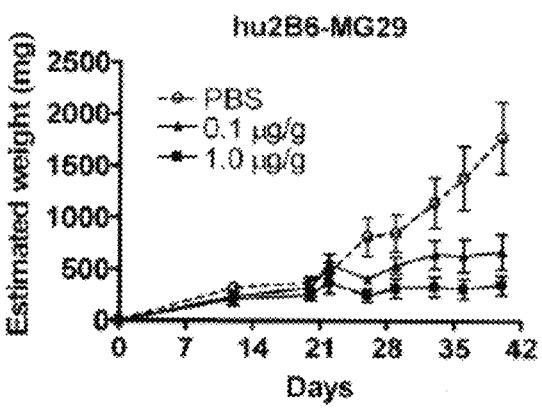
Figure 39F:
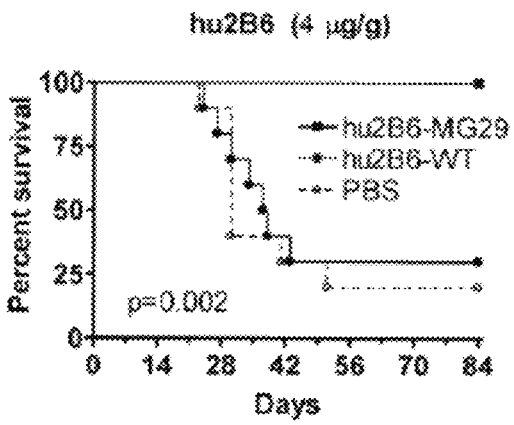

The activity of Fc-engineered mAbs is further analyzed in mFcγRIII-knockout mice expressing the transgene for the low-affinity allele of human CD16A (Li, M. et al. 1996 *J. Exp. Med.* 183:1259-1263). In these mice, human CD16A-158$^{phe}$ is expressed by NK cells and mononuclear phagocytes, similarly to its cell-type specific expression in humans (Perussia, B. et al. *Eur. J. Immunol.* 21:425-429). The murine cell line, EL4 (Gorer, P. A. (1950) *Brit. J. Canc.* 4(4):372-379), was transduced with human CD32B and used in place of Daudi cells, whose tumor take was poor in these transgenic mice. Knock-out transgenic mice, mFcγRIII$^{−/−}$/CD16A-158$^{phe+}$, injected i.p. with CD32B-EL4 cells, died eight weeks after inoculation. Treatment with hu2B6-WT rescued 40% of the animals, whereas 90% survived after receiving hu2B6-MGFc3160 (FIG. 39E). In a separate experiment, a regimen of hu2B6-MGFc0088 that did not prevent tumor growth as a WT Fcγ showed 100% mouse survival for the duration of the experiment (FIG. 39F). Therefore, the potency of hu2B6-MGFc3160 and hu2B6-MGFc0088 in vivo ranks consistently with their relative improvement in binding to FcγRs expressed in the mice (Table 29).

Thus, the Ratio of Affinities of an Fc variant is found to be predictive of the in vivo efficacy of molecules comprising the Fc variant region. Both hu2B6-MGFc3160 and hu2B6-MGFc0088 showed enhanced inhibition of tumor cell growth compared to WT mAb. Since MGFc3160 showed an isolated enhancement in mFcγRIII binding in the absence of improved mFcγRIV interaction, the increased activity could be attributable to both NK cells and mononuclear phagocytes. On the contrary, the properties of MGFc0088, an Fcγ domain with substantially increased affinity to mFcγRIV but mFcγRIII binding properties similar to those of WT, were consistent with the notion that mononuclear phagocytes are the critical cells for improved tumor elimination. In the huFcγR transgenic mouse, the substitution of mFcγRIII with huCD16A-158$^{phe}$ on both NK cells and monocytes resulted in an increase in the activating-to-inhibitory binding ratio for MGFc0088. Again, the greater increase in mouse survival with hu2B6-MGFc0088 correlated with its increased affinity for the second activating receptor, mFcγRIV, expressed by monocytes/macrophages (Nimmerjahn, F. et al. 2005 *Immunity* 23:41-51). The ability of Fc variants to bind mixed human/murine FcγRIII and FcγRII receptors was determined. The results (Table 30) indicate that the variants bind to chimeric receptors with substantial equivalence.

TABLE 30

| No. | Fc Mutant | hCD16 mCD32 | hCD16 mCD32 | hCD16 mCD32 |
|---|---|---|---|---|
| 0071 | D270E G316D R416G | | 1.0 | 1.1 |
| 3160 | P247L D270E N421K | 1.7 | 0.6 | 2.2 |
| 5560 | R255L D270E P396L | | 0.7 | 1.5 |
| 3860 | D270E K392T P396L | | 0.7 | 1.5 |
| 0088 | F243L R292F Y300L V305I P396L | 10.7 | 17.3 | 1.4 |

The binding of selected Fc variants to Fc receptors, and their Ratios of Affinities is shown in Table 31.

TABLE 31

| wt | 3aV1 | 3aF1 | 2bFcag1 1 | 2aRFcag1 1 | 2aHFcag1 1 | 32A-131H:32B 1 | 16A-158V:32B 1 | 16A-158F:32B 1 |
|---|---|---|---|---|---|---|---|---|
| L234F, F243L, R292P, Y300L | 1.7 | 1.6 | 0.2 | 0.2 | 0.3 | 1.5 | 8.5 | 8 |
| L235I, F243L, R292P, Y300L | 2.6 | 3.3 | 0.2 | 0.1 | 0.5 | 2.5 | 13 | 16.5 |
| L235Q, F243L, R292P, Y300L | 1.8 | 1.3 | n.d. | n.d. | 0.2 | n.d. | n.d. | n.d. |
| L235V, F243L, R292P, Y300L, P396L | 6.1 | 4.8 | 0.4 | 0.4 | 1.3 | 3.3 | 15 | 12 |
| L235P, F243L, R292P, Y300L, P396L | 5.4 | 2.5 | 0.2 | 0.2 | 0.7 | 3.5 | 27 | 12.5 |

All publications and patents mentioned in this specification are herein incorporated by reference to the same extent as if each individual publication or patent application was specifically and individually indicated to be incorporated by reference in its entirety.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth.

What is claimed is:

1. An isolated nucleic acid molecule comprising a nucleotide sequence encoding an antibody which comprises an antigen binding region and a variant Fc region, wherein said variant Fc region is a variant of a human IgG Fc region, and said variant Fc region comprises the following amino acid modifications relative to a wild-type Fc region: F243L, R292P and Y300L, wherein the positions are numbered according to the EU index as in Kabat.

2. An isolated vector comprising the nucleic acid molecule of claim 1.

3. The vector of claim 2 which is an expression vector.

4. An isolated host cell comprising the expression vector of claim 3.

5. The nucleic acid molecule of claim 1, wherein said variant Fc region:
   (i) exhibits an increased binding affinity for FcγRIIA or FcγRIIIA relative to an Fc region of a wild-type immunoglobulin; and/or
   (ii) exhibits a decreased binding affinity for FcγRIIB relative to an Fc region of a wild-type immunoglobulin.

6. The nucleic acid molecule of claim 1, wherein said human IgG Fc region is a human IgG1, IgG2, IgG3, or IgG4 Fc region.

7. The nucleic acid molecule of claim 6, wherein said human IgG Fc region is a human IgG1 Fc region.

8. The nucleic acid molecule of claim 1, wherein said antibody is a monoclonal antibody, a chimeric antibody, a humanized antibody, or a human antibody.

9. The nucleic acid molecule of claim 8, wherein said antibody is a humanized antibody.

10. The nucleic acid molecule of claim 9, wherein said antibody comprises a variable domain which binds to CD16A, CD32B, HER2/neu, A33, CD5, CD11c, CD19, CD20, CD22, CD23, CD27, CD40, CD45, CD79a, CD79b, CD103, CTLA4, ErbB1, ErbB3, ErbB4, VEGF receptor, TNF-α receptor, TNF-β receptor, or TNF-γ receptor.

11. The nucleic acid molecule of claim 10, wherein said variable domain binds CD32B and said antibody is produced by hybridoma clone: 2B6 (ATCC Accession No. PTA-4591), 8B5 (ATCC Accession No. PTA-7610), 3H7 (ATCC Accession No. PTA-4592), or 1F2 (ATCC Accession No. PTA- 5959), or is a chimerized or humanized form of said antibody produced by said hybridoma clone 2B6, 8B5, 3H7, or 1F2.

12. The nucleic acid molecule of claim 1, wherein said antibody immunospecifically binds to a cancer antigen selected from the group consisting of: A33; Cyclin B1 (B1); BAGE; beta-catenin; CA125; CD5; CD19; CD20; CD22; CD23; CD25; CD27; CD28; CD36; CD40; CD45; CD56, CD79a; CD79b; CD103, CD154; CDK4; CEA; CTLA4; EGF-R; ErbB1; ErbB3; ErbB4; GAGE-1; GAGE-2; GD2; GD3; GM2; gp100; HER-2/neu; human papillomavirus-E6; human papillomavirus-E7; KSA (17-1A); MAGE-1; MAGE-3; melanoma antigen recognized by T cells (MART); MUC-1; MUM-1; N-acetylglucosaminyltransferase; p15; prostate specific antigen (PSA); prostate-specific membrane antigen (PSMA); squamous cell carcinoma antigen recognized by T cells (SART); siatyl-Tn (sTn); TNF-α receptor; TNF-β receptor; TNF-γ receptor; and VEGF receptor.

13. A composition comprising a therapeutically effective amount of the nucleic acid molecule of claim 1, and a pharmaceutically acceptable carrier.

14. A method for recombinantly producing an antibody, comprising:
(i) culturing in a medium a host cell comprising a nucleic acid molecule encoding an antibody under conditions suitable for expression of said antibody;
wherein said antibody comprises an antigen binding region and a variant Fc region, wherein said variant Fc region is a variant of a human IgG Fc region, said variant Fc region comprising the following amino acid modifications relative to a wild-type Fc region: F243L, R292P and Y300L, wherein the positions are numbered according to the EU index as in Kabat; and
(ii) recovering said antibody from said medium.

15. The method of claim 14, wherein said human IgG Fc region is a human IgG1, IgG2, IgG3, or IgG4 Fc region.

16. The method of claim 15, wherein said human IgG Fc region is a human IgG1 Fc region.

17. The method of claim 16, wherein said antibody is a monoclonal antibody, a chimeric antibody, a humanized antibody, or a human antibody.

18. The method of claim 17, wherein said antibody is a humanized antibody.

19. The method of claim 18, wherein said antibody comprises a variable domain which binds to CD16A, CD32B, HER2/neu, A33, CD5, CD11c, CD19, CD20, CD22, CD23, CD27, CD40, CD45, CD79a, CD79b, CD103, CTLA4, ErbB1, ErbB3, ErbB4, VEGF receptor, TNF-α receptor, TNF-β receptor, or TNF-γ receptor.

20. The method of claim 18, wherein said antibody immunospecifically binds to a cancer antigen selected from the group consisting of: A33; B1; BAGE; beta-catenin; CA125; CD5; CD19; CD20; CD22; CD23; CD25; CD27; CD28; CD36; CD40; CD45; CD56, CD79a; CD79b; CD103, CD154; CDK4; CEA; CTLA4; EGF-R; ErbB1; ErbB3; ErbB4; GAGE-1; GAGE-2; GD2; GD3; GM2; gp100; HER-2/neu; human papillomavirus-E6; human papillomavirus-E7; KSA (17-1A); MAGE-1; MAGE-3; MART; MUC-1; MUM-1; N-acetylglucosaminyltransferase; p15; PSA; PSMA; SART; sTn; TNF-α receptor; TNF-β receptor; TNF-γ receptor; and VEGF receptor.

\* \* \* \* \*